(12) United States Patent
Coelho et al.

(10) Patent No.: US 8,993,262 B2
(45) Date of Patent: Mar. 31, 2015

(54) IN VIVO AND IN VITRO OLEFIN CYCLOPROPANATION CATALYZED BY HEME ENZYMES

(71) Applicant: California Institute of Technology, Pasadena, CA (US)

(72) Inventors: Pedro S. Coelho, Los Angeles, CA (US); Eric M. Brustad, Durham, NC (US); Frances H. Arnold, La Canada, CA (US); Zhan Wang, San Jose, CA (US); Jared C. Lewis, Chicago, IL (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/185,861

(22) Filed: Feb. 20, 2014

(65) Prior Publication Data
US 2014/0242647 A1 Aug. 28, 2014

Related U.S. Application Data

(63) Continuation of application No. PCT/US2013/063577, filed on Oct. 4, 2013.

(60) Provisional application No. 61/711,640, filed on Oct. 9, 2012, provisional application No. 61/740,247, filed on Dec. 20, 2012, provisional application No. 61/784,917, filed on Mar. 14, 2013, provisional application No. 61/838,167, filed on Jun. 21, 2013, provisional application No. 61/815,997, filed on Apr. 25, 2013, provisional application No. 61/818,329, filed on May 1, 2013, provisional application No. 61/856,493, filed on Jul. 19, 2013.

(51) Int. Cl.
*C12P 1/00* (2006.01)
*C12P 13/02* (2006.01)
*C12P 7/62* (2006.01)

(52) U.S. Cl.
CPC .. *C12P 13/02* (2013.01); *C12P 7/62* (2013.01)
USPC .............................. 435/41; 435/119; 435/166

(58) Field of Classification Search
CPC ..................................... C12P 7/04; C12P 1/00
USPC ............................................ 435/41, 119, 166
See application file for complete search history.

(56) References Cited

U.S. PATENT DOCUMENTS

| | | | |
|---|---|---|---|
| 3,965,204 A | 6/1976 | Lukas et al. | |
| 5,296,595 A | 3/1994 | Doyle | |
| 5,703,246 A | 12/1997 | Aggarwal et al. | |
| 7,267,949 B2 | 9/2007 | Richards et al. | |
| 7,625,642 B2 | 12/2009 | Matsutani et al. | |
| 7,662,969 B2 | 2/2010 | Doyle et al. | |
| 7,863,030 B2 | 1/2011 | Arnold et al. | |
| 8,247,430 B2 | 8/2012 | Yuan | |
| 2006/0030718 A1* | 2/2006 | Zhang et al. ................... 548/954 |
| 2006/0111347 A1 | 5/2006 | Askew, Jr. et al. | |
| 2007/0276013 A1 | 11/2007 | Ebbinghaus et al. | |
| 2009/0238790 A2 | 9/2009 | Sommadossi et al. | |
| 2010/0056806 A1 | 3/2010 | Warren | |
| 2010/0168463 A1 | 7/2010 | Hirata et al. | |
| 2010/0240106 A1 | 9/2010 | Wong et al. | |
| 2011/0196086 A1 | 8/2011 | Matsushita et al. | |
| 2012/0237591 A1 | 9/2012 | Cullis et al. | |

FOREIGN PATENT DOCUMENTS

| | | |
|---|---|---|
| EP | 0 200 638 B1 | 4/1986 |
| WO | 2007/144599 A2 | 12/2007 |
| WO | 2011/159550 A3 | 12/2011 |

OTHER PUBLICATIONS

Adams, P.D. et al., "PHENIX: a comprehensive Python-based system for macromolecular structure solution," Acta Crystallogr., Sect. D, Biol. Crystallogr., 2010, D66(2):213-221.
Ajikumar, P.K. et al., "Isoprenoid pathway optimization for taxol precursor overproduction in *Escherichia coli*," Science, 2010, 330:70-74.
Alliot, J. et al., "Enantioselective synthesis of levomilnacipran," Chem. Commun., 2012, 48(65):8111-8113.
Altschul, S.F. et al., "Basic local alignment search tool," J. Mol. Biol., 1990, 215(3):403-10.
Bailey, S., "The CCP4 suite: programs for protein crystallography," Acta Cryst., Sect. D Biol. Crystallogr., 1994, D50(5):760-763.
Bergman, R.G., "Organometallic chemistry: C-H activation," Nature, 2007, 446(7134):391-393.
Bloom, J.D. et al., "Protein stability promotes evolvability," Proc. Natl. Acad. Sci. U. S. A., 2006, 103(15):5869-5874.
Bonnaud, B. et al., "1-Aryl-2-(aminomethyl)cyclopropanecarboxylic acid derivatives. A new series of potential antidepressants," J. Med. Chem., 1987, 30(2):318-25.
Bornscheuer, U.T. and R.J. Kazlauskas, "Reaction specificity of enzymes: Catalytic promiscuity in biocatalysis: Using old enzymes to form new bonds and follow new pathways," Angew. Chem., Int. Ed., 2004, 43(45):6032-6040.
Boyce, M. and C.R. Bertozzi, "Bringing chemistry to life," Nat. Methods, 2011, 8(8):638-642.

(Continued)

*Primary Examiner* — Fereydoun G Sajjadi
*Assistant Examiner* — Pancham Bakshi
(74) *Attorney, Agent, or Firm* — Kilpatrick Townsend & Stockton LLP

(57) ABSTRACT

The present invention provides methods for catalyzing the conversion of an olefin to any compound containing one or more cyclopropane functional groups using heme enzymes. In certain aspects, the present invention provides a method for producing a cyclopropanation product comprising providing an olefinic substrate, a diazo reagent, and a heme enzyme; and admixing the components in a reaction for a time sufficient to produce a cyclopropanation product. In other aspects, the present invention provides heme enzymes including variants and fragments thereof that are capable of carrying out in vivo and in vitro olefin cyclopropanation reactions. Expression vectors and host cells expressing the heme enzymes are also provided by the present invention.

30 Claims, 46 Drawing Sheets

(56) References Cited

OTHER PUBLICATIONS

Breslow, R., "Biomimetic chemistry: Biology as an inspiration," J. Biol. Chem., 2009, 284(3):1337-1342.

Caballero, A. et al., "Metal-catalyzed olefin cyclopropanation with ethyl diazoacetate: control of the diastereoselectivity," Eur. J. Inorg. Chem., 2009(9):1137-1144.

Chen, M.S. and M.C. White, "A predictably selective aliphatic C-H oxidation reaction for complex molecule synthesis," Science, 2007, 318(5851):783-787.

Chen, Y. and X.P. Zhang, "Asymmetric cyclopropanation of styrenes catalyzed by metal complexes of $D_2$-symmetrical chiral porphyrin: Superiority of cobalt over iron," J. Org. Chem., 2007, 72(15):5931-5934.

Cirino, P.C. and F.H. Arnold, "A self-sufficient peroxide-driven hydroxylation biocatalyst," Angew. Chem., Int. Ed., 2003, 42(28):3299-3301.

Clark, J.P., et al., "The role of Thr268 and Phe393 in cytochrome P 450 BM3," J. Inorg. Biochem., 2006, 100(5-6):1075-1090.

Coelho, P.S. et al., "A serine-substituted P450 catalyzes highly efficient carbene transfer to olefins in vivo," Nat. Chem. Biol., 2013, 9(8):485-487.

Coelho, P.S. et al., "Olefin cyclopropanation via carbene transfer catalyzed by engineered cytochrome P450 enzymes," Science, 2013, 339(6117):307-310.

Davies, H.M.L. and C. Venkataramani, "Dirhodium tetraprolinate-catalyzed asymmetric cyclopropanations with high turnover numbers," Org. Lett., 2003, 5(9):1403-1406.

Davies, H.M.L. and J.R. Manning, "Catalytic C-H functionalization by metal carbenoid and nitrenoid insertion," Nature, 2008, 451(7177):417-424.

Davies, H.M.L. and R.E.J. Beckwith, "Catalytic enantioselective C-H activation by means of metal-carbenoid-induced C-H insertion," Chem. Rev., 2003, 103(8):2861-2903.

Dawson, J.H., "Probing structure-function relations in heme-containing oxygenases and peroxidases," Science, 1988, 240(4851):433-9.

Donaldson, W.A., "Synthesis of cyclopropane containing natural products," Tetrahedron, 2001, 57(41):8589-8627.

Doyle, M.P. et al., "Dirhodium(II) tetrakis[methyl 2-oxaazetidine-4-carboxylate]: a chiral dirhodium(II) carboxamidate of exceptional reactivity and selectivity," Org. Lett., 2000, 2(8):1145-7.

Dunford, A.J. et al., "Probing the molecular determinants of coenzyme selectivity in the P450 BM3 FAD/NADPH domain," Biochimica Biophysica Acta, 2009, 1794(8):1181-1189.

Emsley, P. and K. Cowtan, "Coot: model-building tools for molecular graphics," Acta Crystallogr., Sect. D, Biol. Crystallogr., 2004, D60(12, Pt. 1):2126-2132.

Evans, D.A. et al., "Bis(oxazolines) as chiral ligands in metal-catalyzed asymmetric reactions. Catalytic, asymmetric cyclopropanation of olefins," J. Am. Chem. Soc., 1991, 113(2):726-8.

Evans, P., "Scaling and assessment of data quality," Acta Crystallogr., Sect. D, Biol. Crystallogr., 2006, D62(1):72-82.

Green, M.T., "C-H bond activation in heme proteins: the role of thiolate ligation in cytochrome P 450," Curr. Opin. Chem. Biol., 2009, 13(1):84-88.

Groves, J.T., "The bioinorganic chemistry of iron in oxygenases and supramolecular assemblies," Proc. Natl. Acad. Sci. U. S. A., 2003, 100(7):3569-3574.

Haines, D.C. et al., "Pivotal Role of Water in the Mechanism of P450BM-3," Biochemistry, 2001, 40(45):13456-13465.

Hiraga, K. and F.H. Arnold, "General method for sequence-independent site-directed chimeragenesis," J. Mol. Biol., 2003, 330(2):287-96.

Hüettinger, K., "Semi-synthetic proteins for catalytic and analytical applications," in *Chemistry and Biochemistry*, May 2009, Georgia Institute of Technology.

Hyster, T.K. et al., "Biotinylated Rh(III) complexes in engineered streptavidin for accelerated asymmetric c-h activation," Science, 2012, 338(6106):500-503.

Isin, E.M. and F.P. Guengerich, "Complex reactions catalyzed by cytochrome P450 enzymes," Biochim. Biophys. Acta, Gen. Subj., 2007, 1770(3):314-329.

Kabsch, W., "Integration, scaling, space-group assignment and post-refinement," Acta Crystallogr., Sect. D, Biol. Crystallogr., 2010, D66(2):133-144.

Kataoka, M. et al., "Novel bioreduction system for the production of chiral alcohols," Appl. Microbiol. Biotechnol., 2003, 62(5-6):437-45.

Lebel, H. et al., "Stereoselective cyclopropanation reactions," Chem. Rev., 2003, 103(4):977-1050.

Lewis, J.C. and F.H. Arnold, "Catalysts on demand: selective oxidations by laboratory-evolved cytochrome P450 BM3," Chimia, 2009, 63(6):309-312.

Lewis, J.C. et al., "Chemoenzymatic elaboration of monosaccharides using engineered cytochrome $P450_{BM3}$ demethylases," Proc. Natl. Acad. Sci. U. S. A., 2009, 106(39):16550-16555.

Lewis, J.C. et al., "Combinatorial alanine substitution enables rapid optimization of cytochrome $P450_{BM3}$ for selective hydroxylation of large substrates," Chembiochem, 2010, 11(18):2502-05.

Maas, G., "Ruthenium-catalyzed carbenoid cyclopropanation reactions with diazo compounds," Chem. Soc. Rev., 2004, 33(3):183-190.

Mansuy, D. et al., "Reaction of carbon tetrachloride with 5,10,15,20-tetraphenyl-porphinato iron(II) [(TPP)$Fe^{II}$]: evidence for the formation of the carbene complex [(TPP)$Fe^{II}(CCl_2)$]," J. Chem. Soc., Chem. Commun., 1977(18):648-9.

Meinhold, P. et al., "Engineering cytochrome P450 BM3 for terminal alkane hydroxylation," Adv. Synth. Catal., 2006, 348(6):763-772.

Morandi, B. and E.M. Carreira, "Iron-catalyzed cyclopropanation in 6 M KOH with in situ generation of diazomethane," Science, 2012, 335(6075):1471-1474.

Mouzin, G. et al., "A convenient synthesis of bifunctional vicinal cyclopropanes," Synthesis, 1978, 4:304-305.

Murshudov, G.N. et al., "Refinement of macromolecular structures by the maximum-likelihood method," Acta Cryst., Sect. D, Biol. Crystallogr., 1997, D53(3):240-255.

Nakagawa, S. et al., "Construction of catalase deficient *Escherichia coli* strains for the production of uricase," Biosci. Biotechnol. Biochem., 1996, 60(3):415-20.

Narhi, L.O. and A.J. Fulco, "Characterization of a catalytically self-sufficient 119,000-dalton cytochrome P-450 monooxygenase induced by barbiturates in *Bacillus megaterium*," J. Biol. Chem., 1986, 261(16):7160-9.

Nelson, D.R., "The cytochrome P450 homepage," Hum. Genomics, 2009, 4(1):59-65.

Nicolas, I. et al., "Asymmetric catalytic cyclopropanation reactions in water," Coord. Chem. Rev., 2008, 252(5-7):727-735.

Omura, T. and R. Sato, "The carbon monoxide-binding pigment of liver microsomes. I. Evidence for its hemoprotein nature," J. Biol. Chem., 1964, 239(7):2370-8.

Ost, T.W.B. et al., "Phenylalanine 393 exerts thermodynamic control over the heme of flavocytochrome P450 BM3," Biochemistry, 2001, 40(45):13421-13429.

Otey, C.R. et al., "Structure-guided recombination creates an artificial family of cytochromes P450," PLoS Biol., 2006, 4(5):789-798.

Pellissier, H., "Recent developments in asymmetric cyclopropanation," Tetrahedron, 2008, 64(30-31):7041-7095.

Penoni, A. et al., "Cyclopropanation of olefins with diazoalkanes, catalyzed by $Co^{II}$(porphyrin) complexes—A synthetic and mechanistic investigation and the molecular structure of $Co^{III}(TPP)(CH_2CO_2Et)$ (TPP=dianion of meso-tetraphenylporphyrin)," Eur. J. Inorg. Chem., 2003(7):1452-1460.

Perera, R. et al., "Molecular basis for the inability of an oxygen atom donor ligand to replace the natural sulfur donor heme axial ligand in cytochrome P450 catalysis. Spectroscopic characterization of the Cys436Ser CYP2B4 mutant," Arch. Biochem. Biophys., 2011, 507(1):119-125.

Pineiro-Nunez, M., "Dual Selective Serotonin and Norepinephrine Reuptake Inhibitors (SSNRIs) for Depression: 14.3 Synthesis of Milnacipran," in *The Art of Drug Synthesis*, D.S. Johnson and J.J. Li (Eds.), 2007, Wiley: Hoboken, N. J., p. 205-207.

(56) References Cited

OTHER PUBLICATIONS

Preissner, S. et al., "SuperCYP: a comprehensive database on Cytochrome P450 enzymes including a tool for analysis of CYP-drug interactions," Nucleic Acids Res., 2010, 38(Database issue):D237-43.
Raphael, A.L. and H.B. Gray, "Semisynthesis of axial-ligand (position 80) mutants of cytochrome c," J. Am. Chem. Soc., 1991, 113(3):1038-40.
Reedy, C.J. et al., "Development of a heme protein structure—electrochemical function database," Nucleic Acids Res., 2008, 36(Database Iss):D307-D313.
Rosenberg, M.L. et al., "Highly cis-selective cyclopropanations with ethyl diazoacetate using a novel Rh(I) catalyst with a chelating N-heterocyclic iminocarbene ligand," Org. Lett., 2009, 11(3):547-50.
Ruppel, J.V. et al., "Cobalt-catalyzed intramolecular C-H amination with arylsulfonyl azides," Org. Lett., 2007, 9(23):4889-4892.
Sanders, C.J. et al., "Catalyst structure and the enantioselective cyclopropanation of alkenes by copper complexes of biaryldiimines: the importance of ligand acceleration," Tetrahedron Asymmetry, 2001, 12(7):1055-1061.
Setsune, J.I. and D. Dolphin, "Organometallic aspects of cytochrome P-450 metabolism," Can. J. Chem., 1987, 65(3):459-67.
Shuto, S. et al., "(+/−)-(Z)-2-(Aminomethyl)-1-phenylcyclopropanecarboxamide derivatives as a new prototype of NMDA receptor antagonists," J. Med. Chem., 1995, 38(15):2964-8.
Siegel, J.B. et al., "Computational design of an enzyme catalyst for a stereoselective bimolecular Diels-Alder reaction," Science, 2010, 329(5989):309-313.
Sirim, D. et al., "The cytochrome P450 engineering database: integration of biochemical properties," BMC Biochem., 2009, 10:27.
Vagin, A. and A. Teplyakov, "MOLREP: an automated program for molecular replacement," J. Appl. Cryst., 1997, 30(6):1022-1025.
Vatsis, K.P. et al., "Replacement of active-site cysteine-436 by serine converts cytochrome P450 2B4 into an NADPH oxidase with negligible monooxygenase activity," J. Inorg. Biochem., 2002, 91(4):542-553.
Watanabe, N. et al., "Dirhodium(II) tetrakis[3(S)-phthalimido-2-piperidinonate]: a novel dirhodium(II) carboxamidate catalyst for asymmetric cyclopropanation," Heterocycles, 1996, 42(2):537-42.
Wessjohann, L.A. et al., "Biosynthesis and metabolism of cyclopropane rings in natural compounds," Chem. Rev., 2003, 103(4):1625-1647.
Westfall, P.J. et al., "Production of amorphadiene in yeast, and its conversion to dihydroartemisinic acid, precursor to the antimalarial agent artemisinin," Proc. Natl. Acad. Sci. U.S.A., 2012, 109(3):E111-E118.
Whitehouse, C.J.C. et al., "$450_{BM3}$ (CYP102A1): connecting the dots," Chem. Soc. Rev., 2012, 41(3)1218-1260.
Wolf, J.R. et al., "Shape and stereoselective cyclopropanation of alkenes catalyzed by iron porphyrins," J. Am. Chem. Soc., 1995, 117(36):9194-9.
Wuttke, D.S. and H.B. Gray, "Protein engineering as a tool for understanding electron transfer," Curr. Opin. Struct. Biol., 1993, 3(4):555-63.
Yoshioka, S. et al., "Roles of the proximal hydrogen bonding network in cytochrome $P450_{cam}$-catalyzed oxygenation," J. Am. Chem. Soc., 2002, 124(49):14571-14579.
Zhang, M.X. and P.E. Eaton, "BuMgNiPr$_2$: a new base for stoichiometric, position-selective deprotonation of cyclopropane carboxamides and other weak CH acids," Angew Chem. Int. Ed. Engl., 2002, 41(12):2169-71.
Girvan et al., "Glutamate-Heme Ester Bond Formation Is Disfavoured in Flavocytochrome P450 BM3," Biochemical Journal, 2010, pp. 455-466.
Yeom et al., "The Role of Thr268 in Oxygen Activation of Cytochrome $P450_{BM-3}$," Biochemistry, 1995, vol. 34, pp. 14733-14740.

* cited by examiner

Monooxygenation (Oxene transfer)
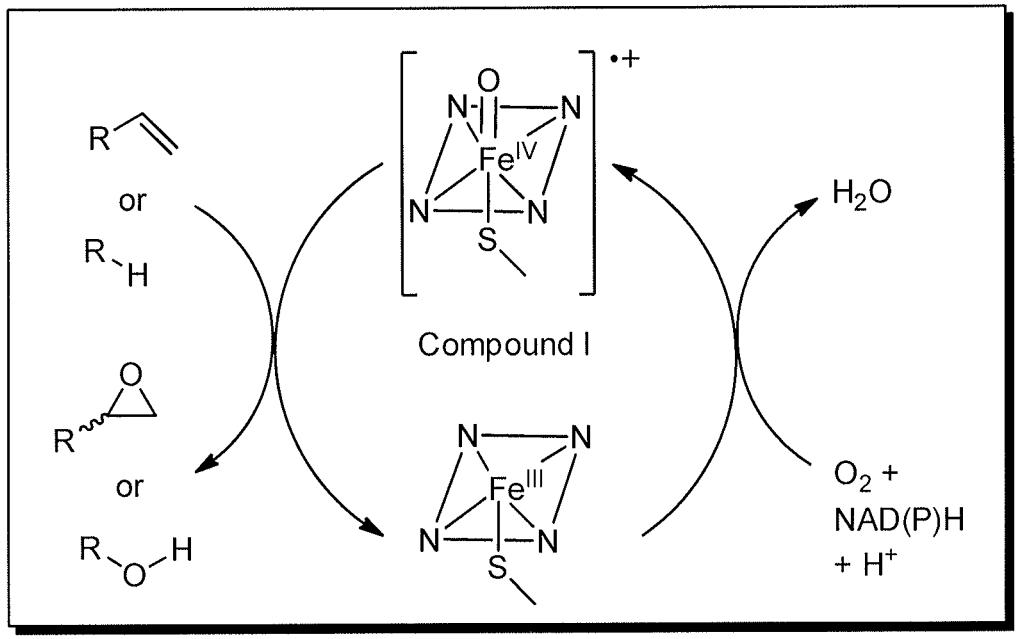
Cyclopropanation (carbene transfer)
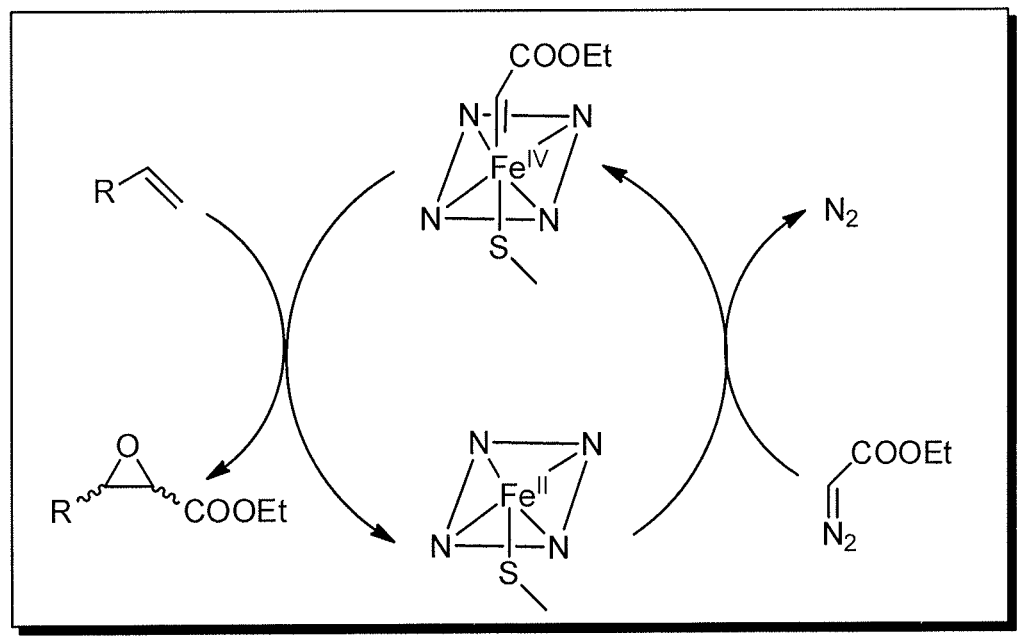
*FIG. 1*

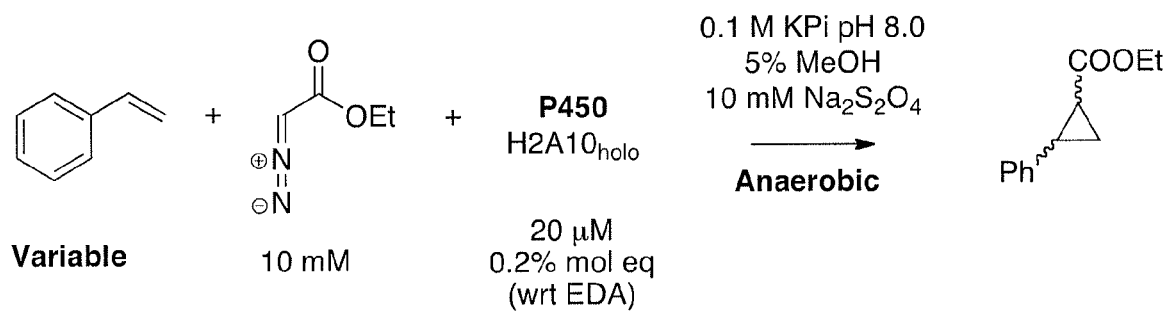
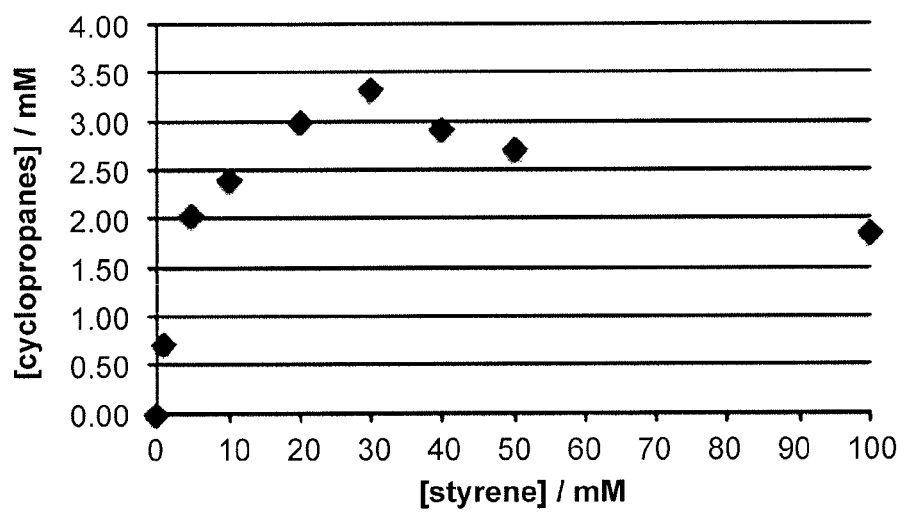
FIG. 3

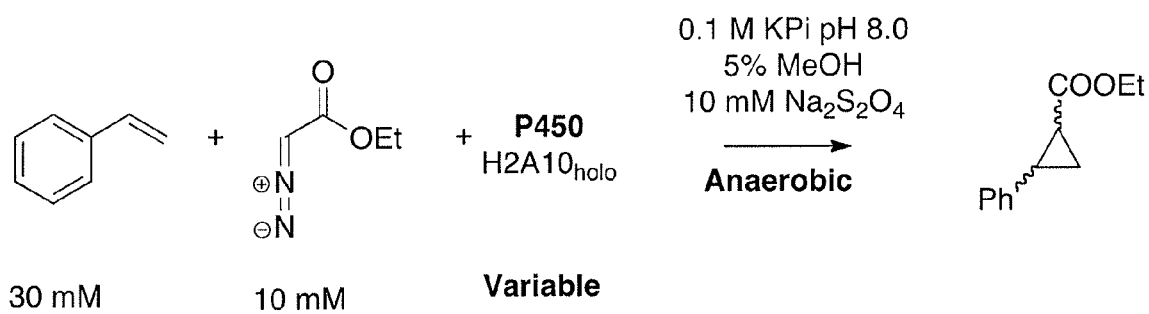
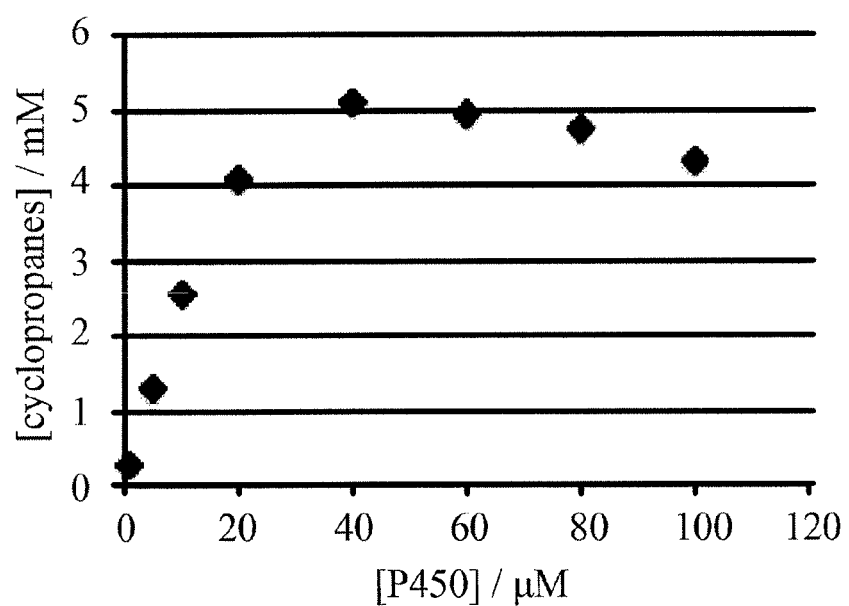
FIG. 4

FIG. 5A
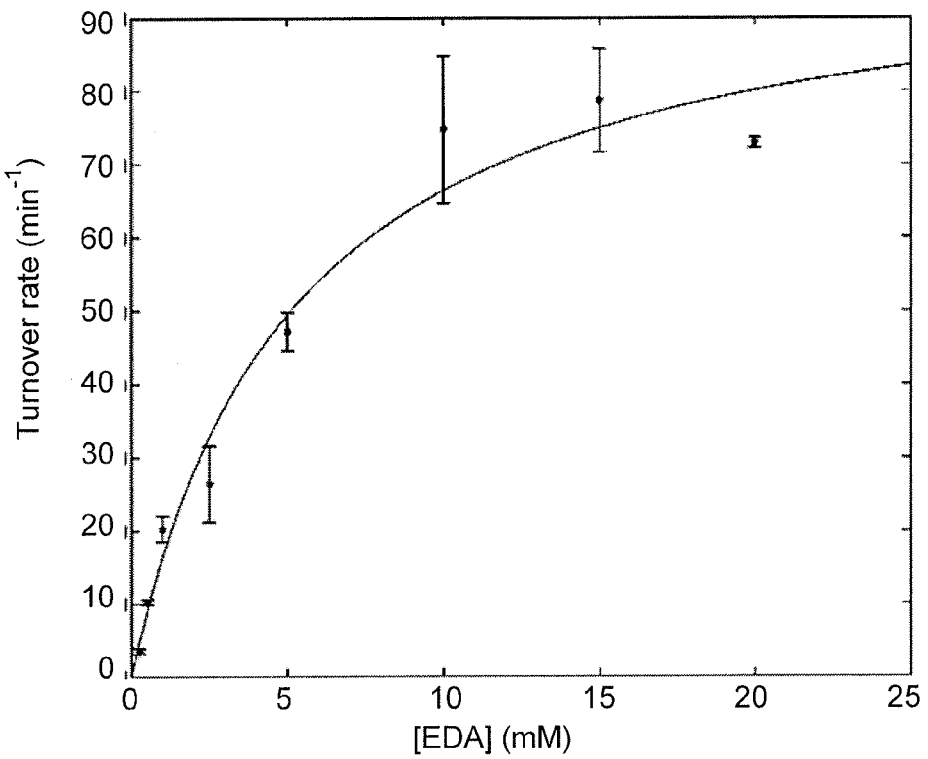
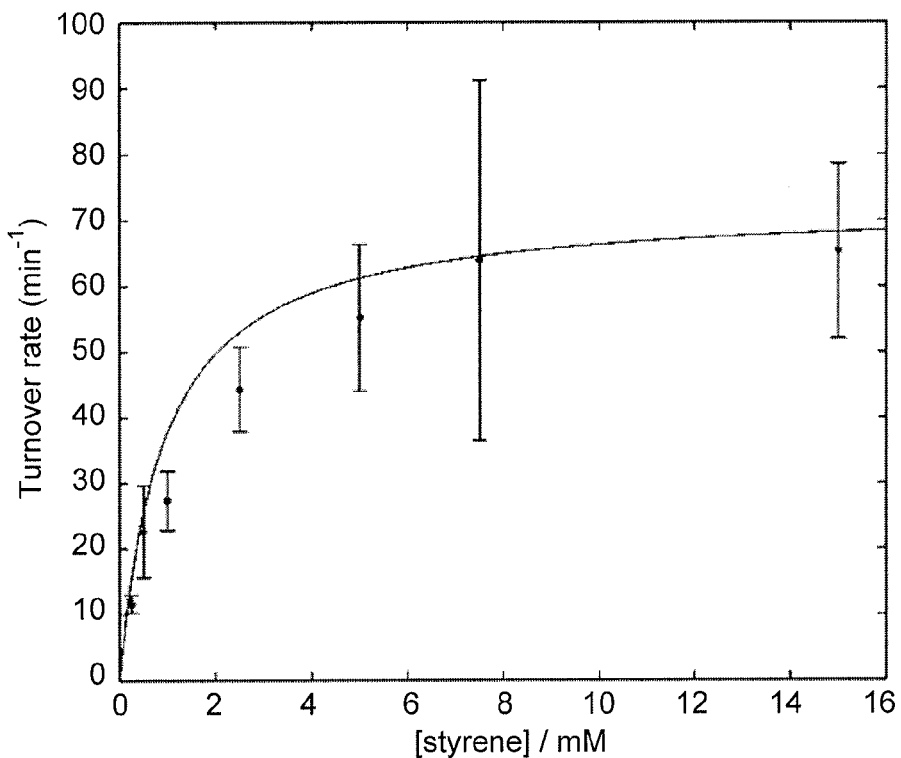
FIG. 5B

FIG. 8A
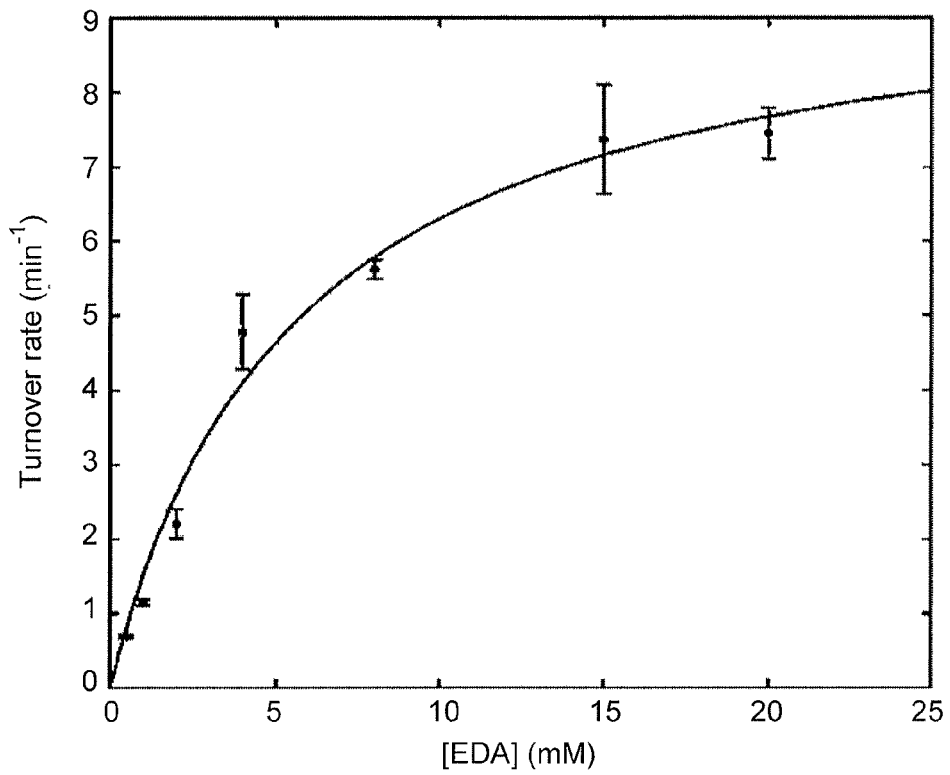
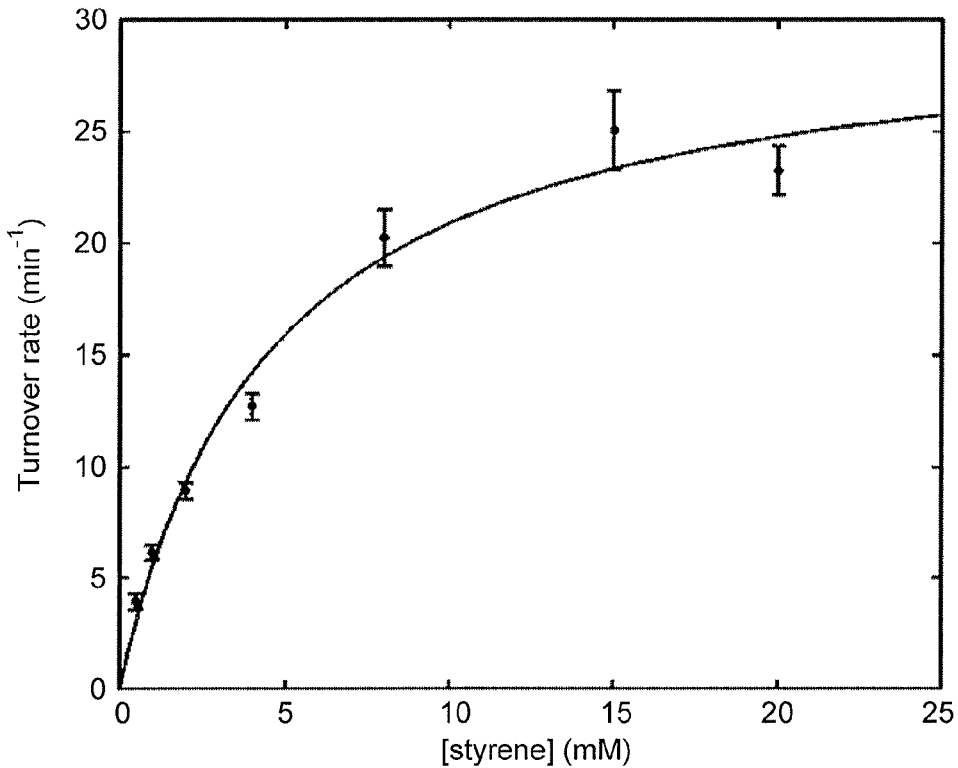
FIG. 8B

| Catalyst | Conditions | Total turnovers (mmol / g cdw) | Yield (%) | O$_2$ inhibition (%) | cis : trans[a] | %ee cis[b] | %ee trans[c] |
|---|---|---|---|---|---|---|---|
| ABC | Anaerobic | 0.842 ± 0.053 | 54 | - | 60 : 40 | -93 | -8 |
| ABC | Aerobic | 0.152 ± 0.008 | 10 | -81 | 41 : 59 | -80 | -11 |
| BM3-CIS$_{holo}$ | Anaerobic | 0.259 ± 0.003 | 14 | - | 27 : 73 | -69 | -12 |
| BM3-CIS$_{holo}$ | Aerobic | 0.139 ± 0.058 | 8 | -43 | 21 : 79 | -49 | -12 |

[a] Diastereomeric ratios and enantiomeric excess were determined by GC analysis. [b] (R,S) – (S,R). [c] (R,R) – (S,S)

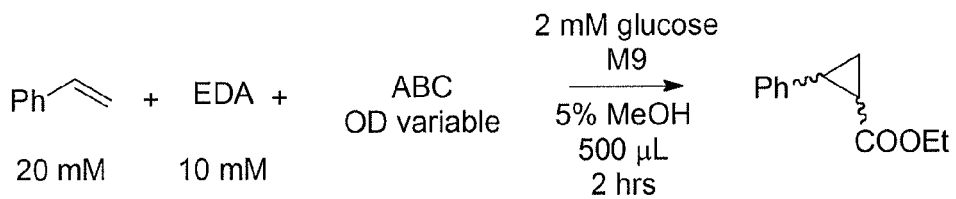
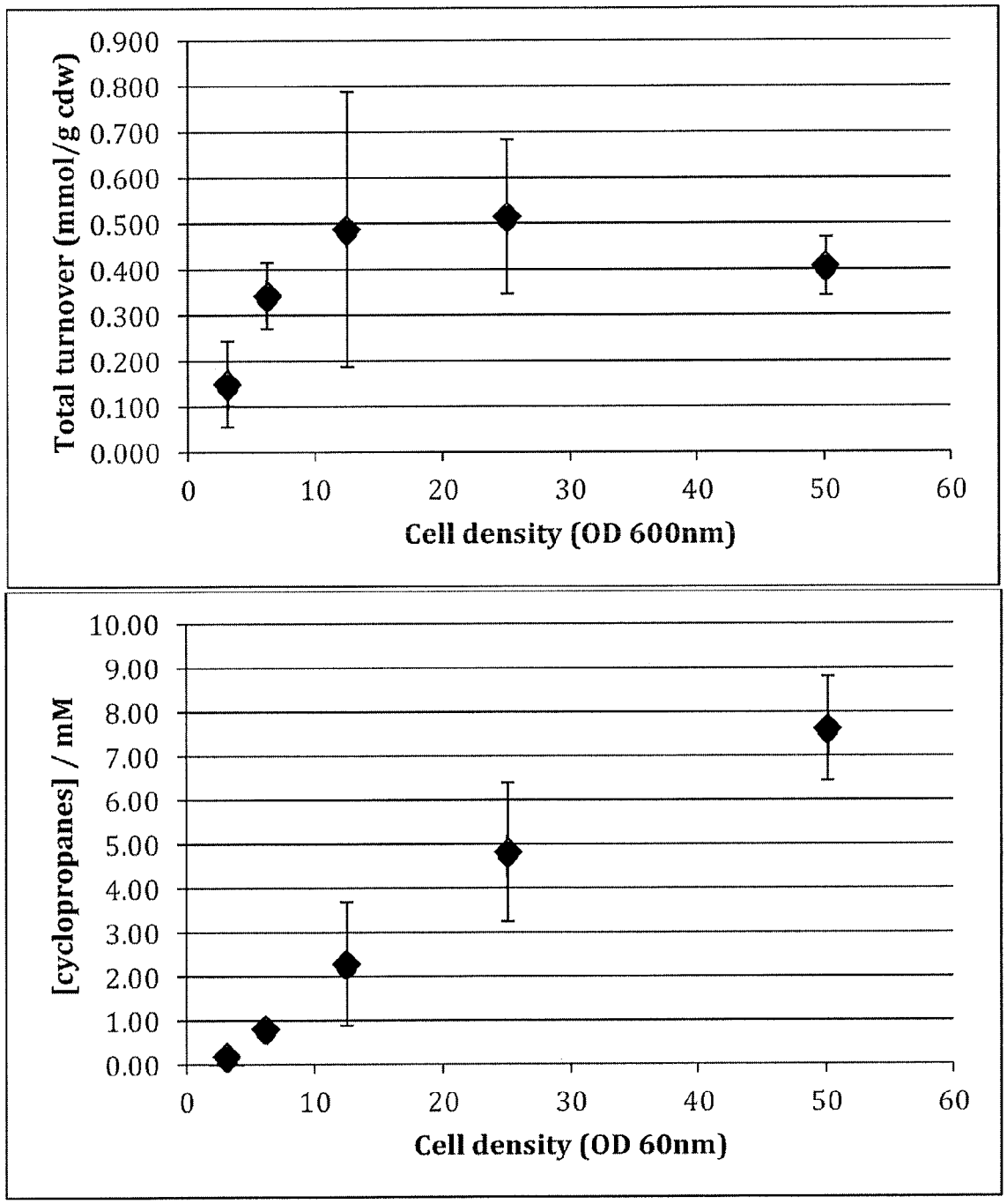
*FIG. 13*

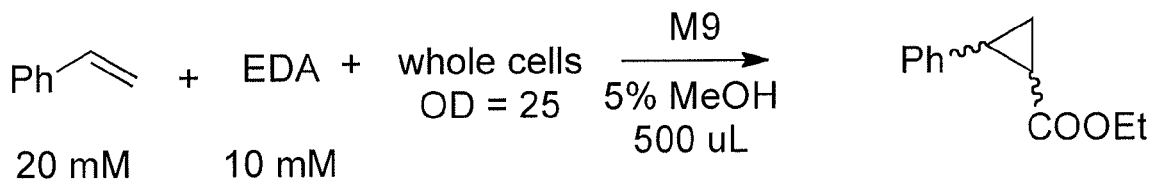
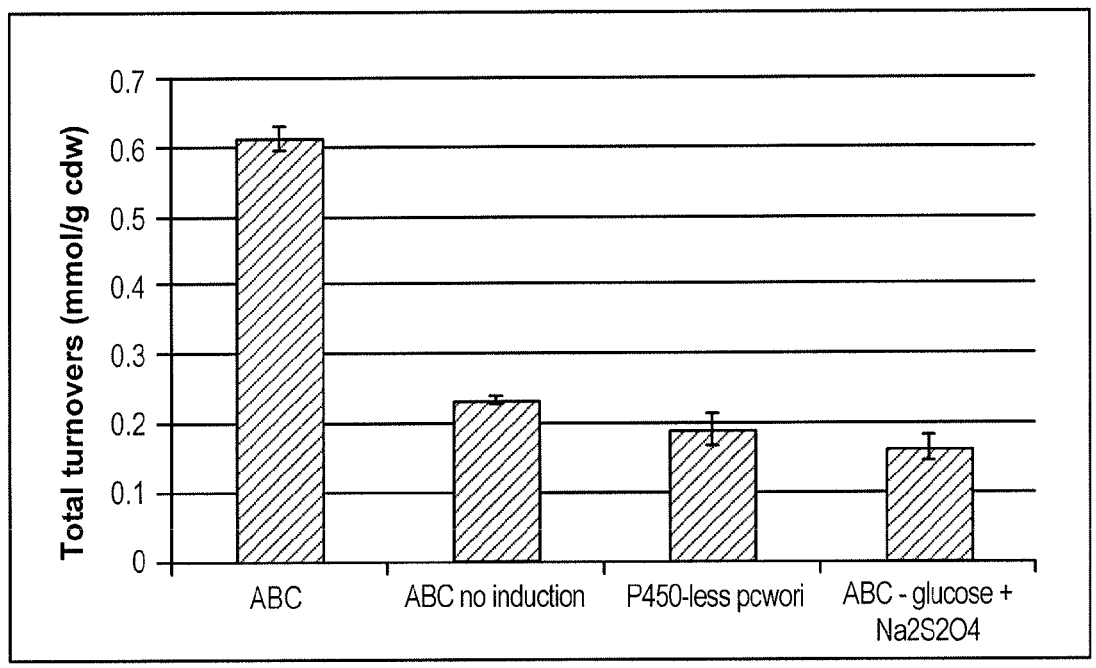
| Catalyst | %cis | %trans | %ee cis | %ee trans | %yield |
|---|---|---|---|---|---|
| ABC + glucose | 60 | 40 | -93 | -9 | 49 |
| ABC no induction | 17 | 83 | -50 | -9 | 16 |
| P450-less pcwori | 11 | 89 | -10 | -12 | 15 |
| ABC + $Na_2S_2O_4$ | 46 | 54 | -87 | -5 | 13 |
*FIG. 15*

FIG. 23A
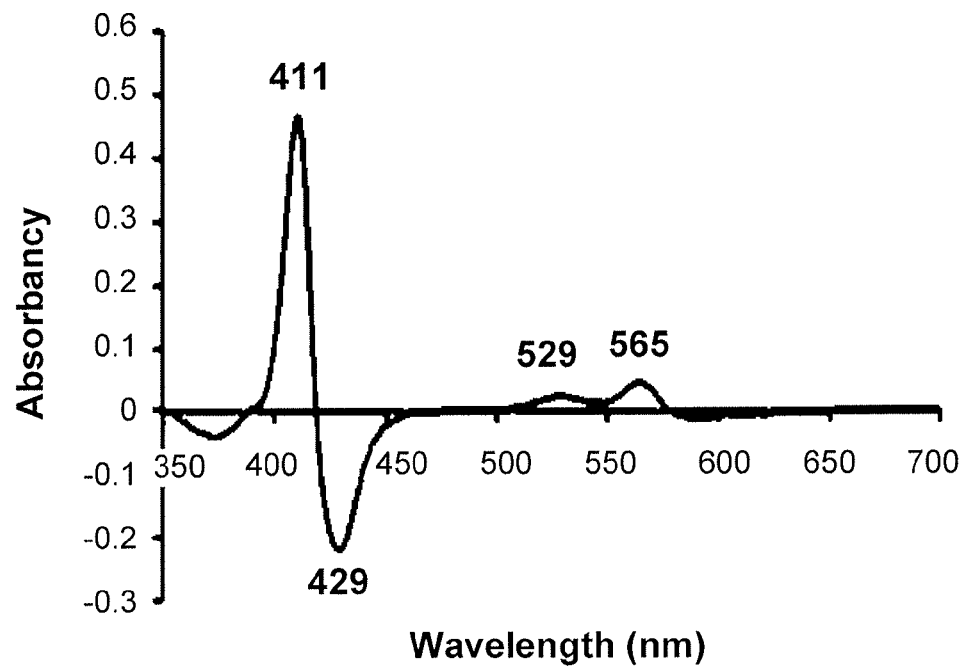
Wavelength (nm)
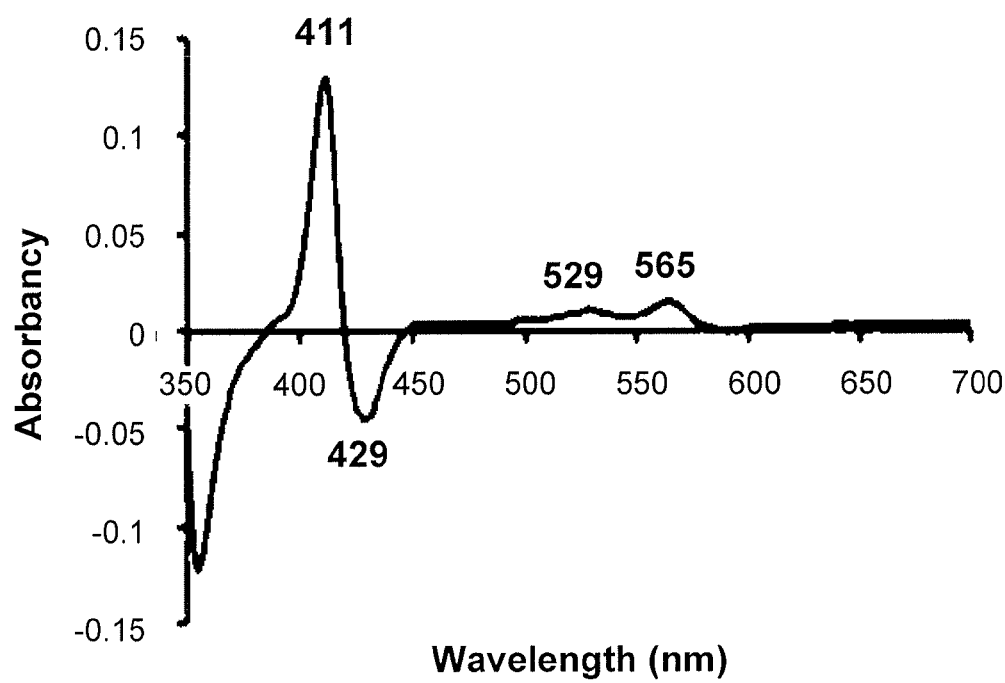
Wavelength (nm)
FIG. 23B

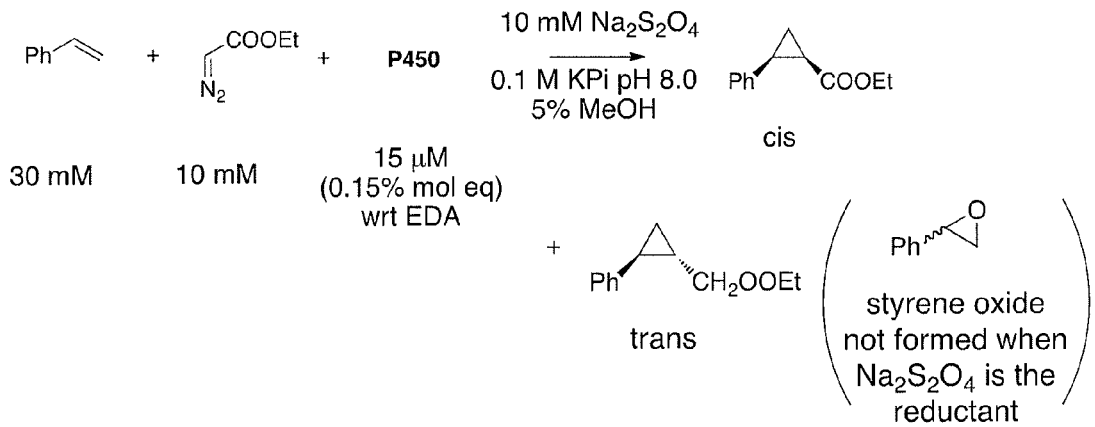
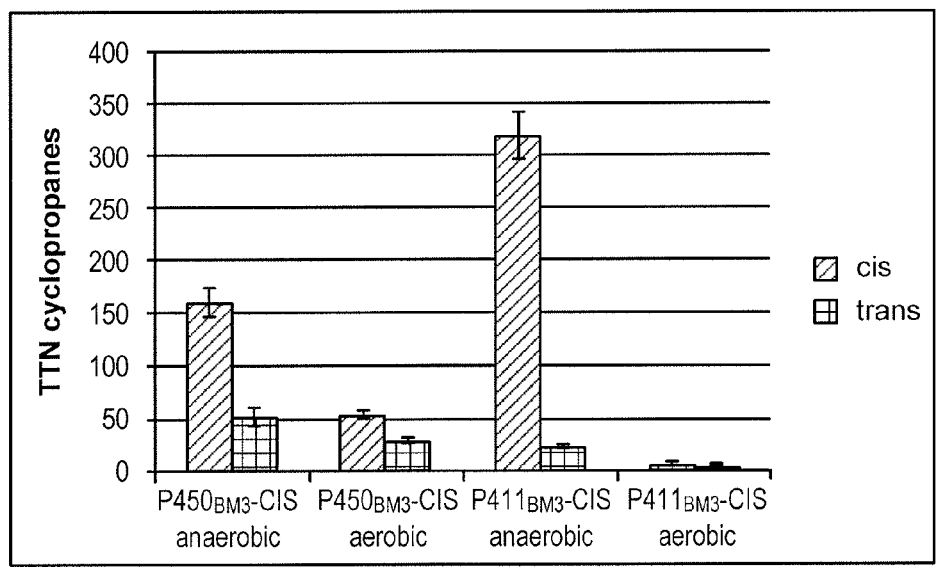
| Catalyst | Conditions | Yield (%)* | TTN | O$_2$ inhibition (%) | cis:trans† | %ee cis‡ | %ee trans§ |
|---|---|---|---|---|---|---|---|
| BM3-CIS$_{heme}$ | Anaerobic | 32 | 212 ± 20 | - | 77:23 | -94 | -91 |
| BM3-CIS$_{heme}$ | Aerobic | 12 | 83 ± 5 | -61 | 65:35 | -87 | -86 |
| ABC-CIS$_{heme}$ | Anaerobic | 51 | 342 ± 21 | - | 93:7 | -99 | -51 |
| ABC-CIS$_{heme}$ | Aerobic | 2 | 10 ± 1 | -97 | 45:55 | -79 | -31 |
\* Based on EDA. † Diastereomeric ratios and enantiomeric excess were determined by GC analysis. ‡ $(2R,1S) - (2S,1R)$. § $(2R,1R) - (2S,1S)$
*FIG. 28*

| Whole-Cell Catalyst | [Glucose] (mM) | Yield (%)* | Total Turnover (mmol $g_{cdw}^{-1}$) | Effect of glucose addition (%) | Cell density ($g_{cdw}$ $L^{-1}$) | cis : trans† | %ee cis‡ | %ee trans § |
|---|---|---|---|---|---|---|---|---|
| BM3-CIS ($P450_{BM3}$-CIS) | 0 | 7 | 0.120 ± 0.03 | - | 5.53 | 34 : 66 | -73 | -22 |
| BM3-CIS ($P450_{BM3}$-CIS) | 2 | 13 | 0.240 ± 0.02 | +98 | 5.53 | 48 : 52 | -86 | -30 |
| ABC-CIS ($P411_{BM3}$-CIS) | 0 | 35 | 0.550 ± 0.06 | - | 6.38 | 70 : 30 | -95 | -11 |
| ABC-CIS ($P411_{BM3}$-CIS) | 2 | 48 | 0.760 ± 0.01 | +37 | 6.38 | 76 : 24 | -96 | -14 |

* Based on EDA. † Diastereomeric ratios and enantiomeric excess were determined by GC analysis. ‡ (2R,1S) − (2S,1R). § (2R,1R) − (2S,1S).

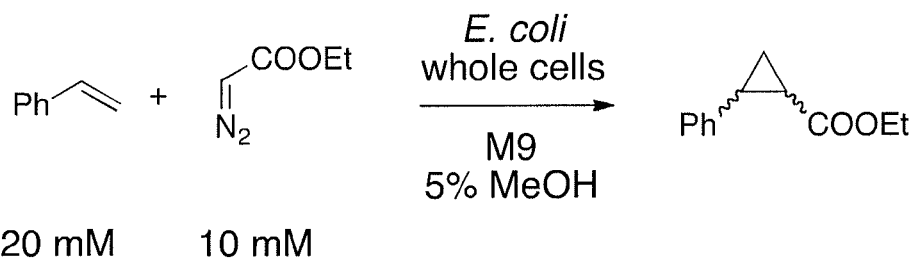
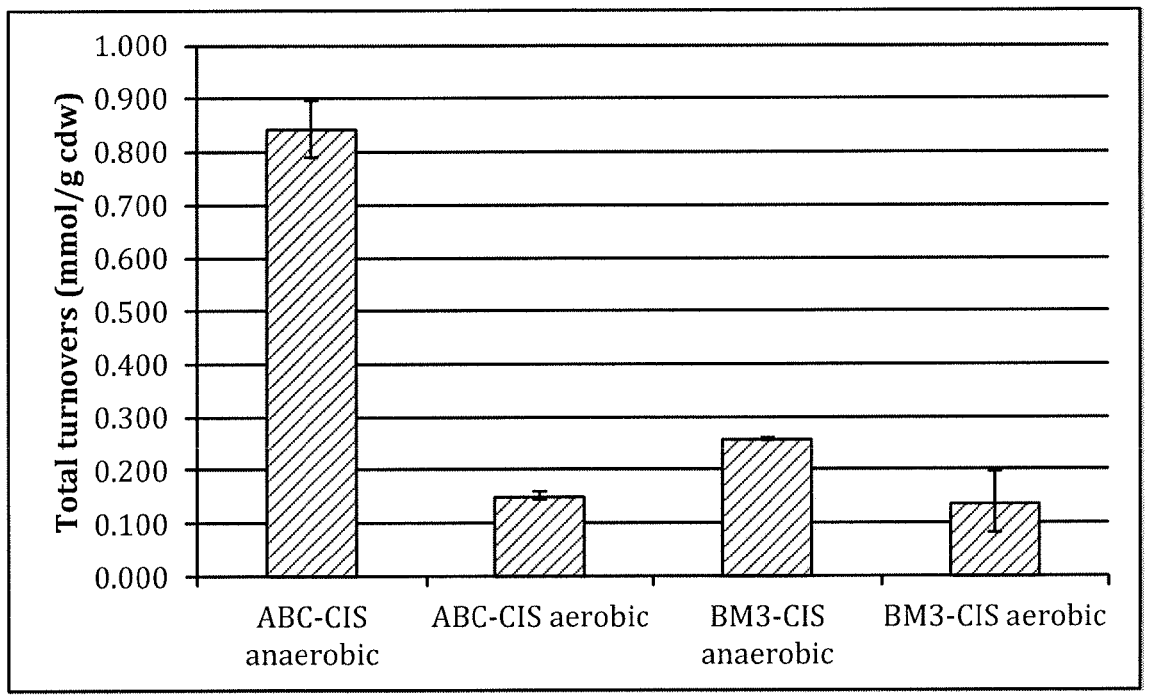
FIG. 31

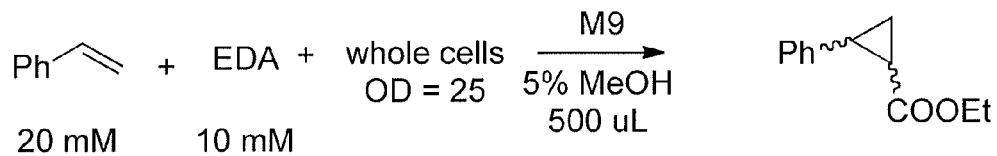
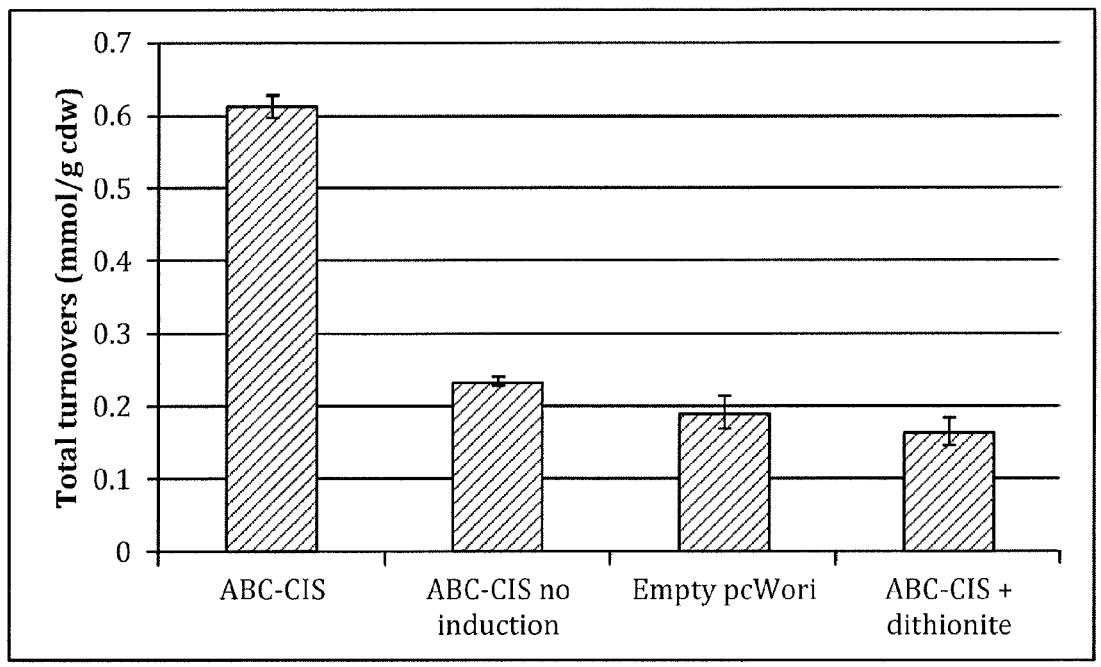
| Catalyst | Yield (%)* | cis:trans† | %ee cis‡ | %ee trans§ |
|---|---|---|---|---|
| ABC-CIS (P411$_{BM3}$-CIS) | 49 | 60:40 | -93 | -9 |
| ABC-CIS (P411$_{BM3}$-CIS) no induction | 16 | 17:83 | -50 | -9 |
| Empty pcWori | 15 | 11:89 | -10 | -12 |
| ABC-CIS (P411$_{BM3}$-CIS) + dithionite | 13 | 46:54 | -87 | -5 |
* Based on EDA. †Diastereomeric ratios and enantiomeric excess were determined by GC analysis. ‡ (2R,1S) – (2S,1R). § (2R,1R) – (2S,1S)
FIG. 32

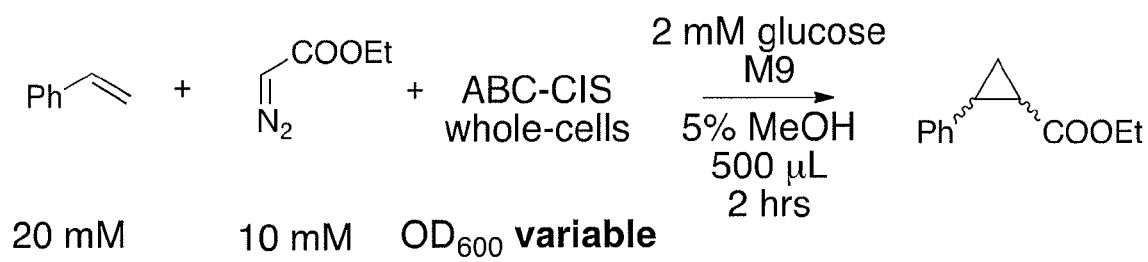
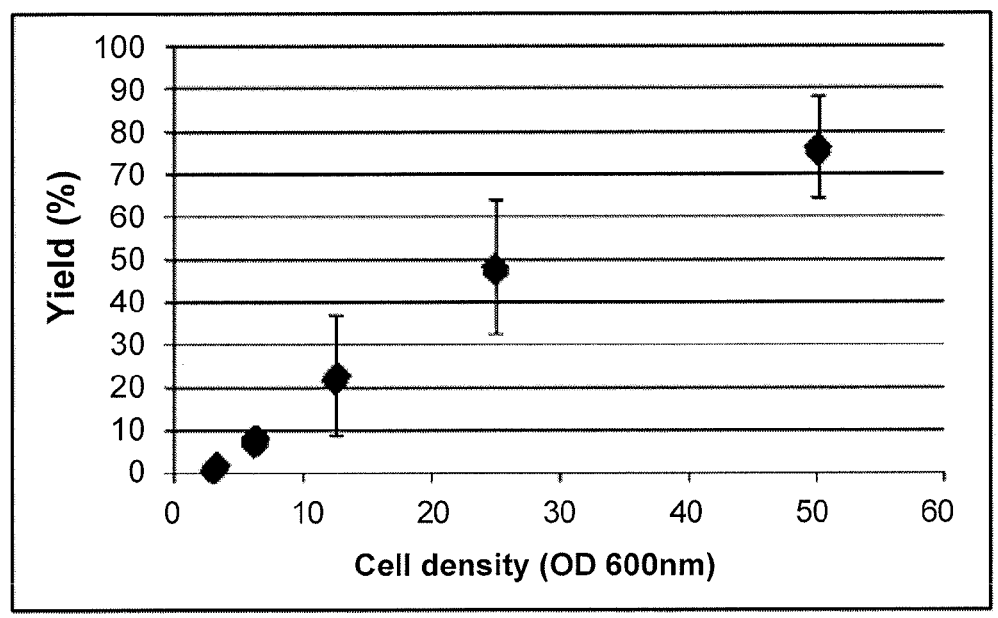
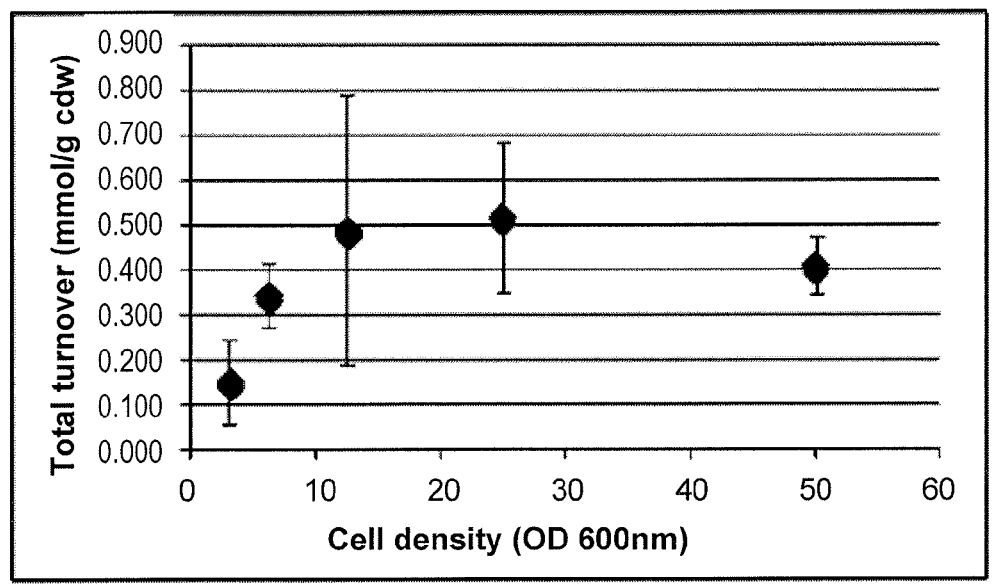
FIG. 33

FIG. 35A
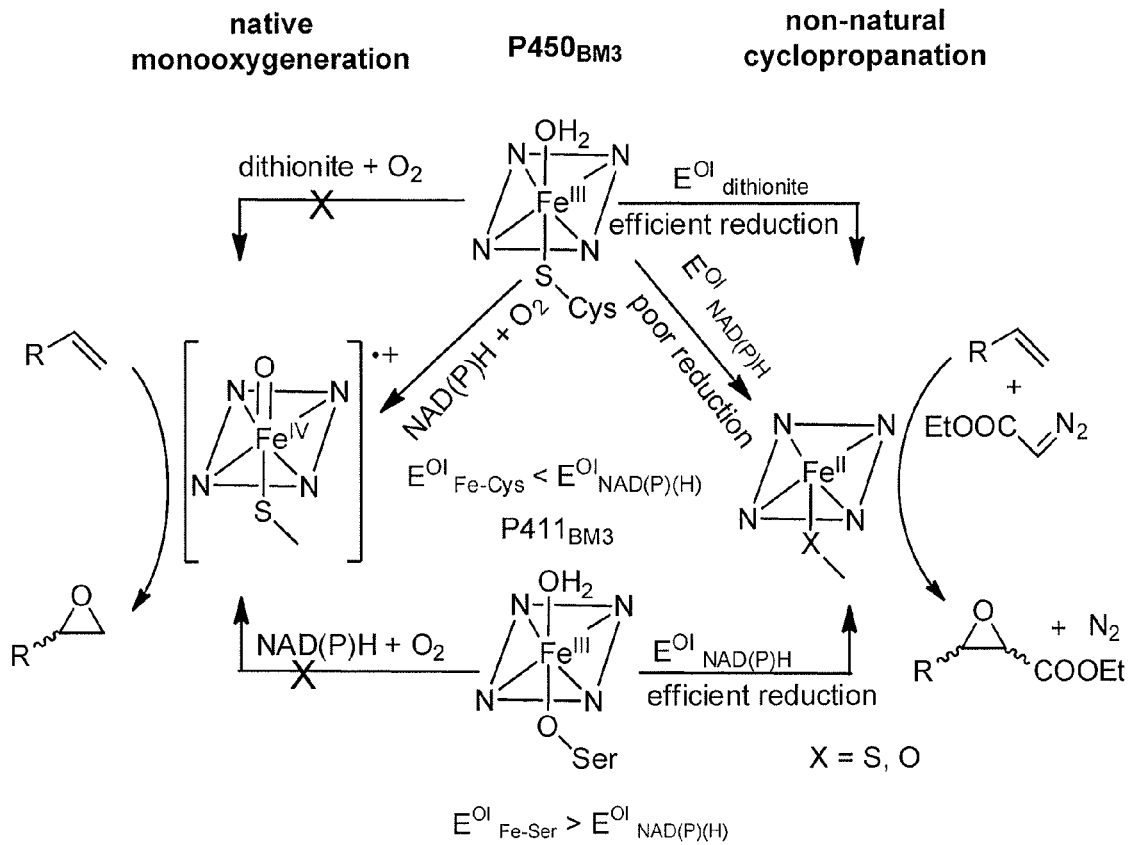
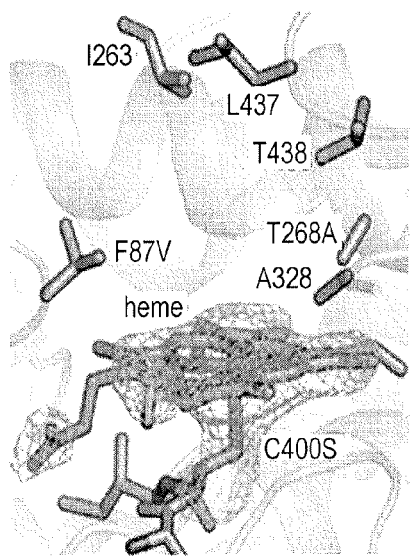
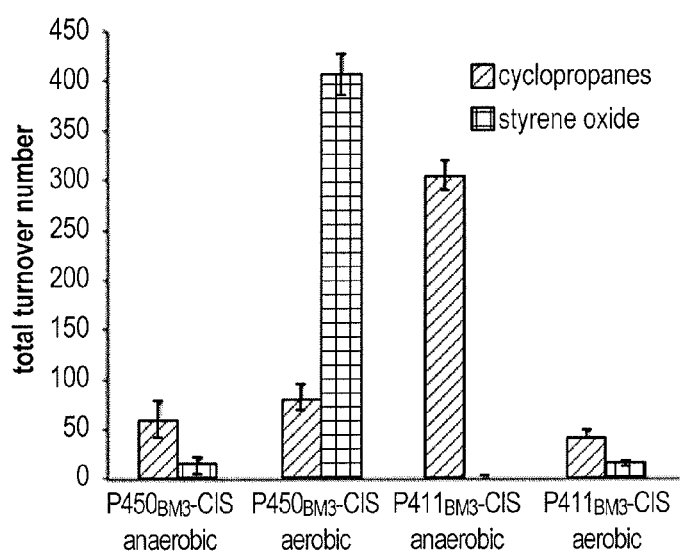
FIG. 35B
FIG. 35C

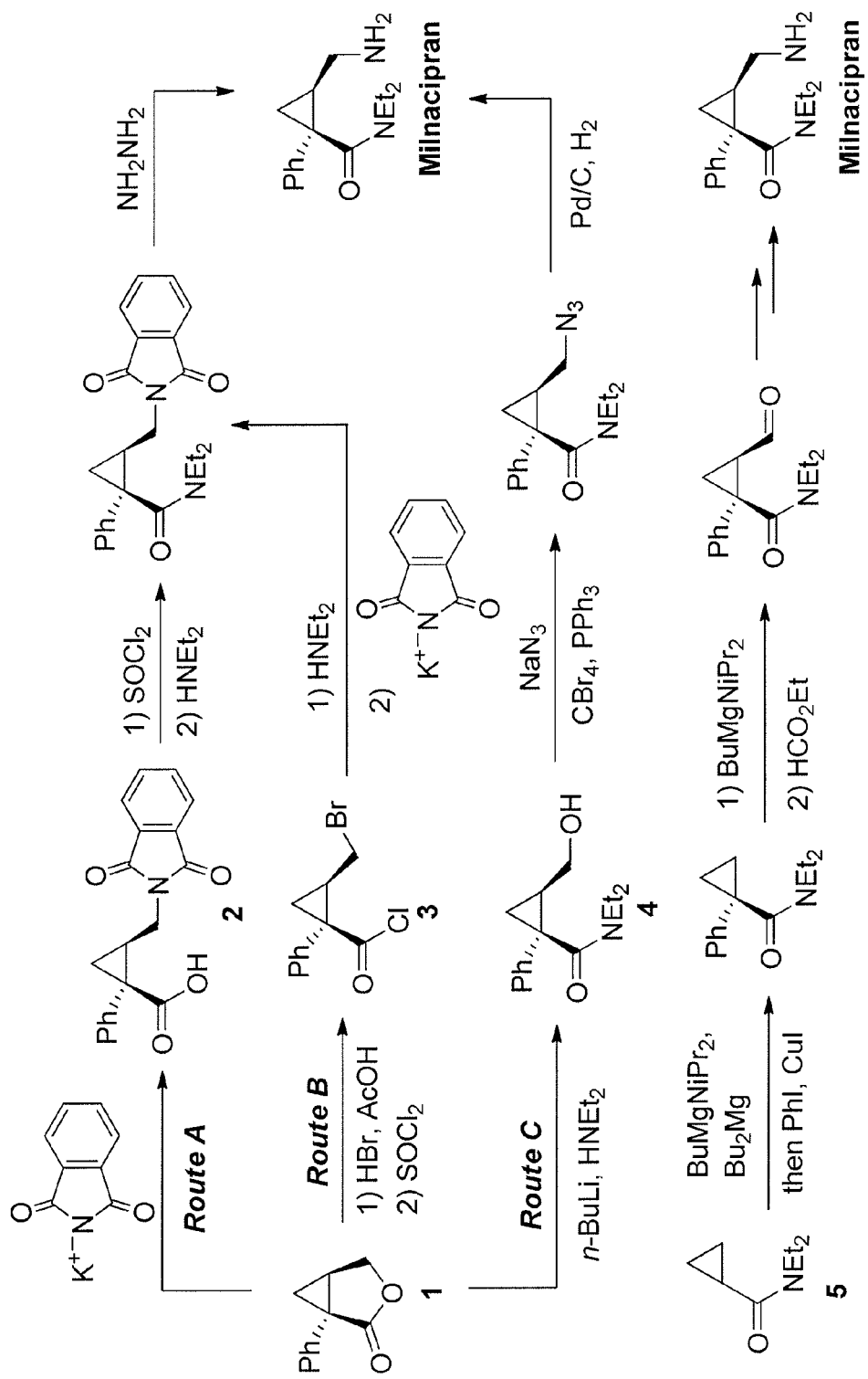
FIG. 36A
FIG. 36B
FIG. 36C

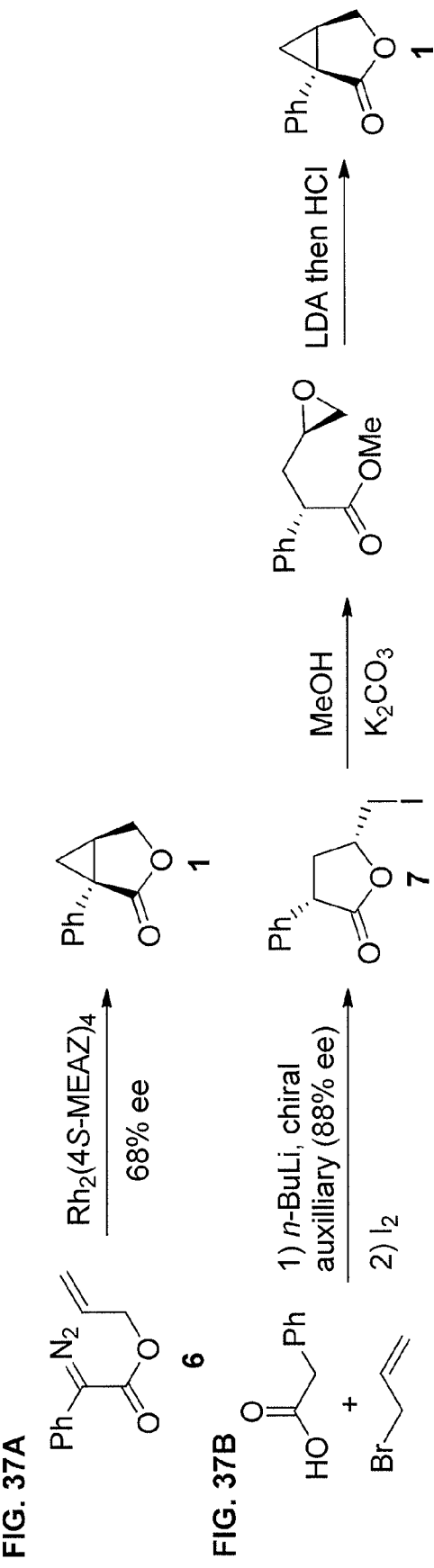

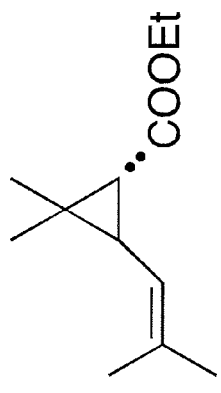
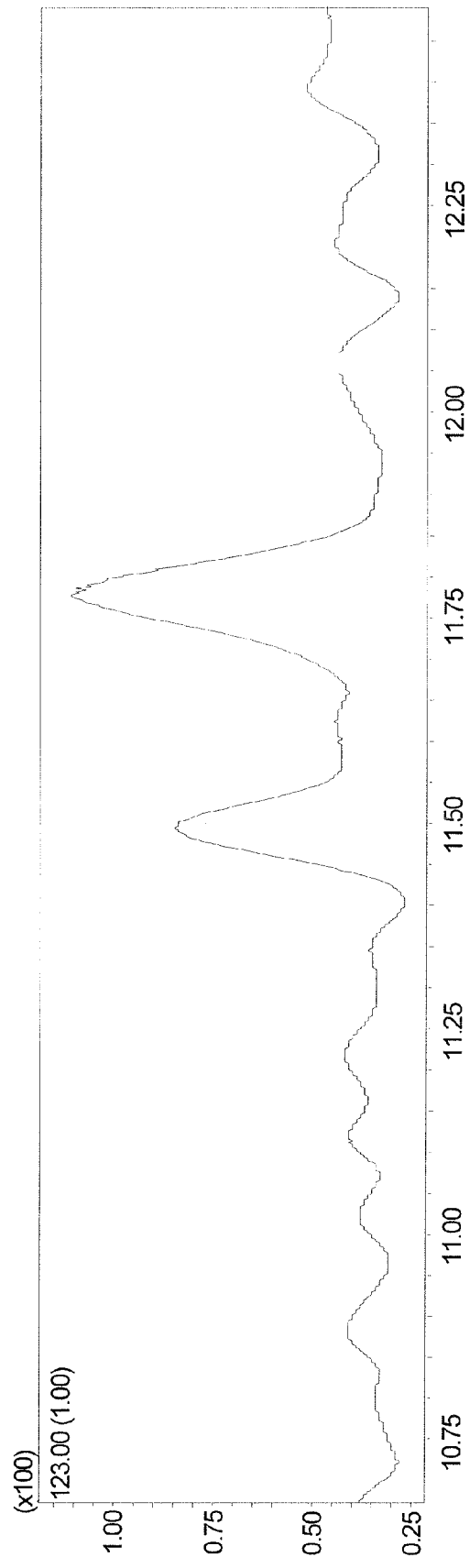
FIG. 43

Range 1: 181 to 424 Graphics    ▼ Next Match ▲ Previous Match

| Score | Expect | Method | Identities | Positives | Gaps |
|---|---|---|---|---|---|
| 59.3 bits(142) | 1e-13 | Compositional matrix adjust. | 63/272(23%) | 104/272(38%) | 33/272(12%) |

```
Query  219  LREVLNAVP-VLPHIPALAGKVLRFQ---KAFLTQLDELLTEHRMTWDPAQPPRDLTEAF  274
            L E +N +   P  PA        +FQ   K   +D+++ + + + +        DL
Sbjct  181  LDEAMNKLQRANPDDPAYDENKRQFQEDIKVMNDLVDKIIADRKASGEQSD---DLLTHM  237

Query  275  LAKKEKAKGSPESSFNDENLRIVVGNLFLAGMVTLTTLAKGLLLMILHLDVQRGRRVSP  334
            L K+   G P  +    +DEN+R +    +AG TT    GLL L+   V+    +
Sbjct  238  LNGKDPETGEP---LDDENIRYQIITPLIAGHETTS-----GLLSFALYFLVKNPHVLQK  289

Query  335  GCSPIVGTHVCPVRVQQEIDDVIGQVRRPEMGDQVHMPYTTAVIHEVQRFGDIVPLGVTH  394
              V PV                      P    + Y   V++E  R  P   +
Sbjct  290  AAEEAARVLVDPV----------PSYKQVKQLKYVGMVLNEALRLWPTAPAFSLY  334

Query  395  MTSRDIEVQGFRIPKGTTLITNLSSVLKDEAVW-EKPFRFHPEHFLDAQGHFVKPEAFLP  453
            +   ++ +    + KG    L+ + + + +D+ +W +     F PE F +  +  AF P
Sbjct  335  AKEDTVLGGEYPLEKGDELMVLIPQLHRDKTIWGDDVEEFRPERFENPSA---IPQHAFKP  392

Query  454  FSAGRRACLGEPLARMELFLFFTSLLQHFSFS  485
            F  G+RAC+G+   A E L  +L+HF F
Sbjct  393  FGNGQRACIGQOFALHEATLVLGMLKHFDFE  424
```

FIG. 45A

Range 1: 115 to 422 Graphics                              ▼ Next Match  ▲ Previous Match

| Score | Expect | Method | Identities | Positives | Gaps |
|---|---|---|---|---|---|
| 74.3 bits(181) | 2e-18 | Compositional matrix adjust. | 84/320(26%) | 144/320(45%) | 42/320(13%) |

```
Query  211  YHLALEAICYILFEK--RVGCLEP-SIPED-TATFIRSVGLMPKNSVYTFLPKWSRPLL    266
            YH + I  L +K   R+  E   +PED T  + ++GL M +++   P +
Sbjct  115  YHAMMVDIAVQLVQKWERLNADEHIEVPEDKTRLTLDTIGLCGFNYRFNSFYRDQPHPPI  174

Query  267  PFWRYMNW----------------DNIFSFGE--KMIBQKVQEIEAQLQAAGPDGVQVS   309
            R ++                     +N  F E K+++  V +I A +A+G   Q
Sbjct  175  TSMVRALDEAMNKLQRANPDDPAYDENKRQFQEDIKYMNDLVDKIIADRKASGE----QSD  231

Query  310  GYLBFLI-------TKELLSPQETVGTFPELILAGVDTTSNTLTWALYHLSKNPEIQEALH  363
              L +L        T E L +          ++AG +TTS  L++ALY L KNP + +
Sbjct  232  DLITHMLNGKDPETGEPLDDENIRYQIITFLIAGHETTSGLLSFALYFLVKNPHVLQRAA   291

Query  364  KEVTGVVPEGKVPQNKDFAHMPLLKAVIKETLRLYPVVPTNSRIITEKETEINGFLFP---  421
            +E   V+   V P  K    +  + +  + V + E LRL+P P S  + KE +P
Sbjct  292  EEAARVL--VDPVPSYKQVFKQLKYVGMVLNEALRLWPTAPAFS---LYAKEDTVLGGEYPLE  348

Query  422  KNTQFVLCTYVVSRDPSVFPEP-ESFQPHRWLRKREDDNSGIQHPFGSVPFGYGVRSCLG   480
            K + ++  ++     + RD +++   QH F  PFG G R+C+G
Sbjct  349  KGDELMVLIPQLHRDKTIWGDDVEEFRPERF-----ENPSAIPQHAFK--PFGNGQRACIG  402

Query  481  RRIAELEMQLLISRLIQKYE   500
            ++ A  E  L+L  +++ ++
Sbjct  403  QQFALSEATLVLGMMLKBFD   422
```

FIG. 45B

```
                        SEQUENCE LISTING

<160> NUMBER OF SEQ ID NOS: 78

<210> SEQ ID NO 1
<211> LENGTH: 1048
<212> TYPE: PRT
<213> ORGANISM: Bacillus megaterium
<220> FEATURE:
<223> OTHER INFORMATION: Bacillus megaterium isolate Fulco PB85
      cytochrome P450:NADPH-P-450 reductase precursor, cytochrome P450
      (BM3), CYP102A1

<400> SEQUENCE: 1

Thr Ile Lys Glu Met Pro Gln Pro Lys Thr Phe Gly Glu Leu Lys Asn
 1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Arg Val
         35                  40                  45

Thr Arg Tyr Leu Ser Ser Gln Arg Leu Ile Lys Glu Ala Cys Asp Glu
     50                  55                  60

Ser Arg Phe Asp Lys Asn Leu Ser Gln Ala Leu Lys Phe Val Arg Asp
 65                  70                  75                  80

Phe Ala Gly Asp Gly Leu Phe Thr Ser Trp Thr His Glu Lys Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
    290                 295                 300
```

-continued

```
Tyr Lys Gln Val Lys Gln Leu Lys Tyr Val Gly Met Val Leu Asn Glu
305                 310                 315                 320
Ala Leu Arg Leu Trp Pro Thr Ala Pro Ala Phe Ser Leu Tyr Ala Lys
                325                 330                 335
Glu Asp Thr Val Leu Gly Gly Glu Tyr Pro Leu Glu Lys Gly Asp Glu
            340                 345                 350
Leu Met Val Leu Ile Pro Gln Leu His Arg Asp Lys Thr Ile Trp Gly
        355                 360                 365
Asp Asp Val Glu Glu Phe Arg Pro Glu Arg Phe Glu Asn Pro Ser Ala
370                 375                 380
Ile Pro Gln His Ala Phe Lys Pro Phe Gly Asn Gly Gln Arg Ala Cys
385                 390                 395                 400
Ile Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
                420                 425                 430
Ile Lys Glu Thr Leu Thr Leu Lys Pro Glu Gly Phe Val Val Lys Ala
        435                 440                 445
Lys Ser Lys Lys Ile Pro Leu Gly Gly Ile Pro Ser Pro Ser Thr Glu
450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
                500                 505                 510
Val Ala Thr Leu Asp Ser His Ala Gly Asn Leu Pro Arg Glu Gly Ala
                515                 520                 525
Val Leu Ile Val Thr Ala Ser Tyr Asn Gly His Pro Pro Asp Asn Ala
        530                 535                 540
Lys Gln Phe Val Asp Trp Leu Asp Gln Ala Ser Ala Asp Glu Val Lys
545                 550                 555                 560
Gly Val Arg Tyr Ser Val Phe Gly Cys Gly Asp Lys Asn Trp Ala Thr
                565                 570                 575
Thr Tyr Gln Lys Val Pro Ala Phe Ile Asp Glu Thr Leu Ala Ala Lys
            580                 585                 590
Gly Ala Glu Asn Ile Ala Asp Arg Gly Glu Ala Asp Ala Ser Asp Asp
        595                 600                 605
Phe Glu Gly Thr Tyr Glu Glu Trp Arg Glu His Met Trp Ser Asp Val
610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Ala Asp Met Pro Leu Ala
                645                 650                 655
Lys Met His Gly Ala Phe Ser Thr Asn Val Val Ala Ser Lys Glu Leu
                660                 665                 670
Gln Gln Pro Gly Ser Ala Arg Ser Thr Arg His Leu Glu Ile Glu Leu
        675                 680                 685
Pro Lys Glu Ala Ser Tyr Gln Glu Gly Asp His Leu Gly Val Ile Pro
690                 695                 700
Arg Asn Tyr Glu Gly Ile Val Asn Arg Val Thr Ala Arg Phe Gly Leu
705                 710                 715                 720
Asp Ala Ser Gln Gln Ile Arg Leu Glu Ala Glu Glu Glu Lys Leu Ala
```

```
                725                 730                 735
His Leu Pro Leu Ala Lys Thr Val Ser Val Glu Glu Leu Leu Gln Tyr
            740                 745                 750
Val Glu Leu Gln Asp Pro Val Thr Arg Thr Gln Leu Arg Ala Met Ala
        755                 760                 765
Ala Lys Thr Val Cys Pro His Lys Val Glu Leu Glu Ala Leu Leu
    770                 775                 780
Glu Lys Gln Ala Tyr Lys Glu Gln Val Leu Ala Lys Arg Leu Thr Met
785                 790                 795                 800
Leu Glu Leu Leu Glu Lys Tyr Pro Ala Cys Glu Met Lys Phe Ser Glu
                805                 810                 815
Phe Ile Ala Leu Leu Pro Ser Ile Arg Pro Arg Tyr Tyr Ser Ile Ser
            820                 825                 830
Ser Ser Pro Arg Val Asp Glu Lys Gln Ala Ser Ile Thr Val Ser Val
        835                 840                 845
Val Ser Gly Glu Ala Trp Ser Gly Tyr Gly Glu Tyr Lys Gly Ile Ala
    850                 855                 860
Ser Asn Tyr Leu Ala Glu Leu Gln Glu Gly Asp Thr Ile Thr Cys Phe
865                 870                 875                 880
Ile Ser Thr Pro Gln Ser Glu Phe Thr Leu Pro Lys Asp Pro Glu Thr
                885                 890                 895
Pro Leu Ile Met Val Gly Pro Gly Thr Gly Val Ala Pro Phe Arg Gly
            900                 905                 910
Phe Val Gln Ala Arg Lys Gln Leu Lys Glu Gln Gly Gln Ser Leu Gly
        915                 920                 925
Glu Ala His Leu Tyr Phe Gly Cys Arg Ser Pro His Glu Asp Tyr Leu
    930                 935                 940
Tyr Gln Glu Glu Leu Glu Asn Ala Gln Ser Glu Gly Ile Ile Thr Leu
945                 950                 955                 960
His Thr Ala Phe Ser Arg Met Pro Asn Gln Pro Lys Thr Tyr Val Gln
                965                 970                 975
His Val Met Glu Gln Asp Gly Lys Lys Leu Ile Glu Leu Leu Asp Gln
            980                 985                 990
Gly Ala His Phe Tyr Ile Cys Gly Asp Gly Ser Gln Met Ala Pro Ala
        995                 1000                1005
Val Glu Ala Thr Leu Met Lys Ser Tyr Ala Asp Val His Gln Val Ser
    1010                1015                1020
Glu Ala Asp Ala Arg Leu Trp Leu Gln Gln Leu Glu Glu Lys Gly Arg
1025                1030                1035                1040
Tyr Ala Lys Asp Val Trp Ala Gly
                1045

<210> SEQ ID NO 2
<211> LENGTH: 1049
<212> TYPE: PRT
<213> ORGANISM: Bacillus megaterium
<220> FEATURE:
<223> OTHER INFORMATION: Bacillus megaterium strain ATCC 21916
      NADPH-cytochrome P450 reductase 102A1V9, CYP102A1, CYP102A1V9

<400> SEQUENCE: 2

Met Thr Ile Lys Glu Met Pro Gln Pro Lys Thr Phe Gly Glu Leu Lys
1               5                   10                  15
Asn Leu Pro Leu Leu Asn Thr Asp Lys Pro Ile Gln Thr Leu Met Lys
            20                  25                  30
```

```
Ile Ala Asp Glu Leu Gly Glu Ile Phe Lys Phe Glu Ala Pro Gly Arg
             35                  40                  45

Val Thr Arg Tyr Leu Ser Ser Gln Arg Leu Ile Lys Glu Ala Cys Asp
 50                  55                  60

Glu Ser Arg Phe Asp Lys Asn Leu Ser Gln Ala Leu Lys Phe Val Arg
 65                  70                  75                  80

Asp Phe Ala Gly Asp Gly Leu Phe Thr Ser Thr His Glu Lys Asn
                 85                  90                  95

Trp Lys Lys Ala His Asn Ile Leu Leu Pro Ser Phe Ser Gln Gln Ala
                100                 105                 110

Met Lys Gly Tyr His Ala Met Met Val Asp Ile Ala Val Gln Leu Ile
                115                 120                 125

Gln Lys Trp Glu Arg Leu Asn Thr Asp Glu His Ile Glu Val Pro Glu
        130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
                180                 185                 190

Asn Pro Asp Asp Pro Ala Tyr Asp Glu Asn Lys Arg Gln Phe Gln Glu
                195                 200                 205

Asp Ile Lys Val Met Asn Asp Leu Val Asp Lys Ile Ile Ala Asp Arg
                210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
                275                 280                 285

Gln Lys Ala Ala Glu Glu Ala Ala Arg Val Leu Val Asp Pro Val Pro
        290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Leu Met Val Leu Ile Pro Gln Leu His Arg Asp Lys Thr Ile Trp
                355                 360                 365

Gly Asp Asp Val Glu Glu Phe Arg Pro Glu Arg Phe Glu Asn Pro Ser
        370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
                435                 440                 445

Ala Lys Ser Lys Gln Ile Pro Leu Gly Gly Ile Pro Ser Pro Ser Arg
```

-continued

```
            450                 455                 460
Glu Gln Ser Ala Lys Lys Glu Arg Lys Thr Val Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
                515                 520                 525

Ala Val Leu Ile Val Thr Ala Ser Tyr Asn Gly His Pro Pro Asp Asn
                530                 535                 540

Ala Lys Glu Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
                580                 585                 590

Lys Gly Ala Glu Asn Ile Ala Glu Arg Gly Glu Ala Asp Ala Ser Asp
                595                 600                 605

Asp Phe Glu Gly Thr Tyr Glu Glu Trp Arg Glu His Met Trp Ser Asp
                610                 615                 620

Leu Ala Ala Tyr Phe Asn Leu Asp Ile Glu Asn Ser Glu Glu Asn Ala
625                 630                 635                 640

Ser Thr Leu Ser Leu Gln Phe Val Asp Ser Ala Ala Asp Met Pro Leu
                645                 650                 655

Ala Lys Met His Arg Ala Phe Ser Ala Asn Val Val Ala Ser Lys Glu
                660                 665                 670

Leu Gln Lys Pro Gly Ser Ala Arg Ser Thr Arg His Leu Glu Ile Glu
                675                 680                 685

Leu Pro Lys Glu Ala Ser Tyr Gln Glu Gly Asp His Leu Gly Val Ile
                690                 695                 700

Pro Arg Asn Tyr Glu Gly Ile Val Asn Arg Val Ala Thr Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Gly Lys Thr Val Ser Val Glu Glu Leu Leu Gln
                740                 745                 750

Tyr Val Glu Leu Gln Asp Pro Val Thr Arg Thr Gln Leu Arg Ala Met
                755                 760                 765

Ala Ala Lys Thr Val Cys Pro Pro His Lys Val Glu Leu Glu Val Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Glu Phe Ser
                805                 810                 815

Glu Phe Ile Ala Leu Leu Pro Ser Met Arg Pro Arg Tyr Tyr Ser Ile
                820                 825                 830

Ser Ser Ser Pro Arg Val Asp Glu Lys Gln Ala Ser Ile Thr Val Ser
                835                 840                 845

Val Val Ser Gly Glu Ala Trp Ser Gly Tyr Gly Glu Tyr Lys Gly Ile
                850                 855                 860

Ala Ser Asn Tyr Leu Ala Asn Leu Gln Glu Gly Asp Thr Ile Thr Cys
865                 870                 875                 880
```

```
Phe Val Ser Thr Pro Gln Ser Gly Phe Thr Leu Pro Lys Gly Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
                915                 920                 925

Gly Glu Ala His Leu Tyr Phe Gly Cys Arg Ser Pro His Glu Asp Tyr
    930                 935                 940

Leu Tyr Gln Lys Glu Leu Glu Asn Ala Gln Asn Glu Gly Ile Ile Thr
945                 950                 955                 960

Leu His Thr Ala Phe Ser Arg Val Pro Asn Gln Pro Lys Thr Tyr Val
                965                 970                 975

Gln His Val Met Glu Gln Asp Gly Lys Lys Leu Ile Glu Leu Leu Asp
                980                 985                 990

Gln Gly Ala His Phe Tyr Ile Cys Gly Asp Gly Ser Gln Met Ala Pro
            995                 1000                1005

Asp Val Glu Ala Thr Leu Met Lys Ser Tyr Ala Glu Val His Gln Val
        1010                1015                1020

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
                1045

<210> SEQ ID NO 3
<211> LENGTH: 1049
<212> TYPE: PRT
<213> ORGANISM: Bacillus megaterium
<220> FEATURE:
<223> OTHER INFORMATION: Bacillus megaterium strain ATCC 19213
      NADPH-cytochrome P450 reductase 102A1V10, CYP102A1, CYP102A1V10

<400> SEQUENCE: 3

Met Thr Ile Lys Glu Met Pro Gln Pro Lys Thr Phe Gly Glu Leu Lys
  1               5                  10                  15

Asn Leu Pro Leu Leu Asn Thr Asp Lys Pro Ile Gln Thr Leu Met Lys
                 20                  25                  30

Ile Ala Asp Glu Leu Gly Glu Ile Phe Lys Phe Glu Ala Pro Gly Arg
             35                  40                  45

Val Thr Arg Tyr Leu Ser Ser Gln Arg Leu Ile Lys Glu Ala Cys Asp
         50                  55                  60

Glu Ser Arg Phe Asp Lys Asn Leu Ser Gln Ala Leu Lys Phe Val Arg
 65                  70                  75                  80

Asp Phe Ala Gly Asp Gly Leu Phe Thr Ser Trp Thr His Glu Lys Asn
                 85                  90                  95

Trp Lys Lys Ala His Asn Ile Leu Leu Pro Ser Phe Ser Gln Gln Ala
                100                 105                 110

Met Lys Gly Tyr His Ala Met Met Val Asp Ile Ala Val Gln Leu Ile
            115                 120                 125

Gln Lys Trp Glu Arg Leu Asn Thr Asp Glu His Ile Glu Val Pro Glu
        130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
```

-continued

```
            180                 185                 190
Asn Pro Asp Asp Pro Ala Tyr Asp Glu Asn Lys Arg Gln Phe Gln Glu
            195                 200                 205
Asp Ile Lys Val Met Asn Asp Leu Val Asp Lys Ile Ile Ala Asp Arg
            210                 215                 220
Lys Ala Ser Gly Glu Gln Ser Asp Asp Leu Leu Thr His Met Leu Asn
225                 230                 235                 240
Gly Lys Asp Pro Glu Thr Gly Glu Pro Leu Asp Asp Glu Asn Ile Arg
            245                 250                 255
Tyr Gln Ile Ile Thr Phe Leu Ile Ala Gly His Glu Thr Thr Ser Gly
            260                 265                 270
Leu Leu Ser Phe Ala Leu Tyr Phe Leu Val Lys Asn Pro His Val Leu
            275                 280                 285
Gln Lys Ala Ala Glu Glu Ala Ala Arg Val Leu Val Asp Pro Val Pro
            290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
            325                 330                 335
Lys Glu Asp Thr Val Leu Gly Gly Glu Tyr Pro Leu Glu Lys Gly Asp
            340                 345                 350
Glu Leu Met Val Leu Ile Pro Gln Leu His Arg Asp Lys Thr Ile Trp
            355                 360                 365
Gly Asp Asp Val Glu Glu Phe Arg Pro Glu Arg Phe Glu Asn Pro Ser
            370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
            405                 410                 415
Met Met Leu Lys His Phe Asp Phe Glu Asp His Thr Asn Tyr Glu Leu
            420                 425                 430
Asp Ile Lys Glu Thr Leu Thr Leu Lys Pro Glu Gly Phe Val Val Lys
            435                 440                 445
Ala Lys Ser Lys Gln Ile Pro Leu Gly Gly Ile Pro Ser Pro Ser Arg
            450                 455                 460
Glu Gln Ser Ala Lys Lys Glu Arg Lys Thr Val Glu Asn Ala His Asn
465                 470                 475                 480
Thr Pro Leu Leu Val Leu Tyr Gly Ser Asn Met Gly Thr Ala Glu Gly
            485                 490                 495
Thr Ala Arg Asp Leu Ala Asp Ile Ala Met Ser Lys Gly Phe Ala Pro
            500                 505                 510
Gln Val Ala Thr Leu Asp Ser His Ala Gly Asn Leu Pro Arg Glu Gly
            515                 520                 525
Ala Val Leu Ile Val Thr Ala Ser Tyr Asn Gly His Pro Pro Asp Asn
            530                 535                 540
Ala Lys Glu Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
            565                 570                 575
Thr Thr Tyr Gln Lys Val Pro Ala Phe Ile Asp Glu Thr Phe Ala Ala
            580                 585                 590
Lys Gly Ala Glu Asn Ile Ala Glu Arg Gly Glu Ala Asp Ala Ser Asp
            595                 600                 605
```

```
Asp Phe Glu Gly Thr Tyr Glu Glu Trp Arg Glu His Met Trp Ser Asp
    610                 615                 620

Leu Ala Ala Tyr Phe Asn Leu Asp Ile Glu Asn Ser Glu Glu Asn Ala
625                 630                 635                 640

Ser Thr Leu Ser Leu Gln Phe Val Asp Ser Ala Ala Asp Met Pro Leu
                645                 650                 655

Ala Lys Met His Arg Ala Phe Ser Ala Asn Val Val Ala Ser Lys Glu
            660                 665                 670

Leu Gln Lys Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Ala Thr Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Gly Lys Thr Val Ser Val Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Val Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Glu Phe Ser
                805                 810                 815

Glu Phe Ile Ala Leu Leu Pro Ser Met Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Asn Leu Gln Glu Gly Asp Thr Ile Thr Cys
865                 870                 875                 880

Phe Val Ser Thr Pro Gln Ser Gly Phe Thr Leu Pro Lys Gly Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Lys Glu Leu Glu Asn Ala Gln Asn Glu Gly Ile Ile Thr
945                 950                 955                 960

Leu His Thr Ala Phe Ser Arg Val Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Asp Val Glu Ala Thr Leu Met Lys Ser Tyr Ala Glu Val His Gln Val
    1010                1015                1020
```

```
Ser Glu Ala Asp Ala Arg Leu Trp Leu Gln Gln Leu Glu Glu Lys Gly
1025                1030                1035                1040

Arg Tyr Ala Lys Asp Val Trp Ala Gly
                1045
```

<210> SEQ ID NO 4
<211> LENGTH: 1049
<212> TYPE: PRT
<213> ORGANISM: Bacillus megaterium
<220> FEATURE:
<223> OTHER INFORMATION: Bacillus megaterium strain ATCC 15451
      NADPH-cytochrome P450 reductase 102A1V4, CYP102A1, CYP102A1V4

<400> SEQUENCE: 4

```
Met Thr Ile Lys Glu Met Pro Gln Pro Lys Thr Phe Gly Glu Leu Lys
 1               5                   10                  15

Asn Leu Pro Leu Leu Asn Thr Asp Lys Pro Ile Gln Thr Leu Met Lys
                20                  25                  30

Ile Ala Asp Glu Leu Gly Glu Ile Phe Lys Phe Glu Ala Pro Gly Arg
            35                  40                  45

Val Thr Arg Tyr Leu Ser Ser Gln Arg Leu Ile Lys Glu Ala Cys Asp
 50                  55                  60

Glu Ser Arg Phe Asp Lys Asn Leu Ser Gln Ala Leu Lys Phe Val Arg
 65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Ile
        115                 120                 125

Gln Lys Trp Glu Arg Leu Asn Thr Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Thr Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335
```

```
Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
            355                 360                 365

Gly Glu Asp Val Glu Glu Phe Arg Pro Glu Arg Phe Glu Asn Pro Ser
            370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
            450                 455                 460

Glu Gln Ser Ala Lys Lys Val Arg Lys Lys Val Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
            530                 535                 540

Ala Lys Gln Phe Val Asp Trp Leu Asp Gln Ala Ser Ala Asp Asp Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
            610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Ala Asn Val Val Ala Ser Lys Glu
            660                 665                 670

Leu Gln Gln Pro Gly Ser Glu Arg Ser Thr Arg His Leu Glu Ile Ala
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Gly Lys Thr Val Ser Val Glu Glu Leu Leu Gln
            740                 745                 750
```

-continued

```
Tyr Val Glu Leu Gln Asp Pro Val Thr Arg Thr Gln Leu Arg Ala Met
            755                 760                 765
Ala Ala Lys Thr Val Cys Pro His Lys Val Glu Leu Glu Ala Leu
770                 775                 780
Leu Glu Lys Gln Ala Tyr Lys Glu Gln Val Leu Ala Lys Arg Leu Thr
    785                 790                 795                 800
Met Leu Glu Leu Leu Glu Lys Tyr Pro Ala Cys Glu Met Glu Phe Ser
                805                 810                 815
Glu Phe Ile Ala Leu Leu Pro Ser Ile Arg Pro Arg Tyr Tyr Ser Ile
            820                 825                 830
Ser Ser Ser Pro Arg Val Asp Glu Lys Gln Ala Ser Ile Thr Val Ser
        835                 840                 845
Val Val Ser Gly Glu Ala Trp Ser Gly Tyr Gly Glu Tyr Lys Gly Ile
    850                 855                 860
Ala Ser Asn Tyr Leu Ala Asn Leu Gln Glu Gly Asp Thr Ile Thr Cys
865                 870                 875                 880
Phe Val Ser Thr Pro Gln Ser Gly Phe Thr Leu Pro Lys Asp Ser Glu
                885                 890                 895
Thr Pro Leu Ile Met Val Gly Pro Gly Thr Gly Val Ala Pro Phe Arg
            900                 905                 910
Ser Phe Val Gln Ala Arg Lys Gln Leu Lys Glu Gln Gly Gln Ser Leu
        915                 920                 925
Gly Glu Ala His Leu Tyr Phe Gly Cys Arg Ser Pro His Glu Asp Tyr
    930                 935                 940
Leu Tyr Gln Glu Glu Leu Glu Asn Ala Gln Asn Glu Gly Ile Ile Thr
945                 950                 955                 960
Leu His Thr Ala Phe Ser Arg Val Pro Asn Gln Pro Lys Thr Tyr Val
                965                 970                 975
Gln His Val Met Glu Gln Asp Gly Lys Lys Leu Ile Glu Leu Leu Asp
            980                 985                 990
Gln Gly Ala His Phe Tyr Ile Cys Gly Asp Gly Ser Gln Met Ala Pro
        995                 1000                1005
Asp Val Glu Ala Thr Leu Met Lys Ser Tyr Ala Asp Val Tyr Glu Val
    1010                1015                1020
Ser Glu Ala Asp Ala Arg Leu Trp Leu Gln Gln Leu Glu Glu Lys Gly
1025                1030                1035                1040
Arg Tyr Ala Lys Asp Val Trp Ala Gly
                1045
```

<210> SEQ ID NO 5
<211> LENGTH: 1049
<212> TYPE: PRT
<213> ORGANISM: Bacillus megaterium
<220> FEATURE:
<223> OTHER INFORMATION: Bacillus megaterium strain ATCC 14945
      NADPH-cytochrome P450 reductase 102A1V8, CYP102A1, CYP102A1V8

<400> SEQUENCE: 5

```
Met Thr Ile Lys Glu Met Pro Gln Pro Lys Thr Phe Gly Glu Leu Lys
1               5                   10                  15
Asn Leu Pro Leu Leu Asn Thr Asp Lys Pro Ile Gln Thr Leu Met Lys
            20                  25                  30
Ile Ala Asp Glu Leu Gly Glu Ile Phe Lys Phe Glu Ala Pro Gly Arg
        35                  40                  45
Val Thr Arg Tyr Leu Ser Ser Gln Arg Leu Ile Lys Glu Ala Cys Asp
    50                  55                  60
```

```
Glu Ser Arg Phe Asp Lys Asn Leu Ser Gln Ala Leu Lys Phe Val Arg
 65                  70                  75                  80

Asp Phe Ala Gly Asp Gly Leu Phe Thr Ser Trp Thr His Glu Lys Asn
                 85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Ile
            115                 120                 125

Gln Lys Trp Glu Arg Leu Asn Thr Asp Glu His Ile Glu Val Pro Glu
            130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
                180                 185                 190

Asn Pro Asp Asp Pro Ala Tyr Asp Glu Asn Lys Arg Gln Phe Gln Glu
            195                 200                 205

Asp Ile Lys Val Met Asn Asp Leu Val Asp Lys Ile Ile Ala Asp Arg
210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
            245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
            275                 280                 285

Gln Lys Ala Ala Glu Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
            325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
            370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
            405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Gln Ile Pro Leu Gly Gly Ile Pro Ser Pro Ser Arg
            450                 455                 460

Glu Gln Ser Ala Lys Lys Glu Arg Lys Thr Val Glu Asn Ala His Asn
465                 470                 475                 480
```

-continued

Thr Pro Leu Leu Val Leu Tyr Gly Ser Asn Met Gly Thr Ala Glu Gly
            485                 490                 495

Thr Ala Arg Asp Leu Ala Asp Ile Ala Met Ser Lys Gly Phe Ala Pro
        500                 505                 510

Arg Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Glu Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
            565                 570                 575

Thr Thr Tyr Gln Lys Val Pro Ala Phe Ile Asp Glu Thr Leu Ala Ala
        580                 585                 590

Lys Gly Ala Glu Asn Ile Ala Glu Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Leu Ala Ala Tyr Phe Asn Leu Asp Ile Glu Asn Ser Glu Glu Asn Ala
625                 630                 635                 640

Ser Thr Leu Ser Leu Gln Phe Val Asp Ser Ala Ala Asp Met Pro Leu
            645                 650                 655

Ala Lys Met His Arg Ala Phe Ser Ala Asn Val Val Ala Ser Lys Glu
        660                 665                 670

Leu Gln Lys Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Ala Thr Arg Phe Gly
705                 710                 715                 720

Leu Asp Ala Ser Gln Gln Ile Arg Leu Glu Ala Glu Glu Lys Leu
            725                 730                 735

Ala His Leu Pro Leu Gly Lys Thr Val Ser Val Glu Glu Leu Leu Gln
        740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Val Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Glu Phe Ser
            805                 810                 815

Glu Phe Ile Ala Leu Leu Pro Ser Met Arg Pro Arg Tyr Tyr Ser Ile
        820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Asn Leu Gln Glu Gly Asp Thr Ile Thr Cys
865                 870                 875                 880

Phe Val Ser Thr Pro Gln Ser Gly Phe Thr Leu Pro Lys Gly Pro Glu
            885                 890                 895

Thr Pro Leu Ile Met Val Gly Pro Gly Thr Gly Val Ala Pro Phe Arg

```
                    900                 905                 910
Gly Phe Val Gln Ala Arg Lys Gln Leu Lys Glu Gln Gly Gln Ser Leu
                915                 920                 925

Gly Glu Ala His Leu Tyr Phe Gly Cys Arg Ser Pro His Glu Asp Tyr
            930                 935                 940

Leu Tyr Gln Lys Glu Leu Glu Asn Ala Gln Asn Glu Gly Ile Ile Thr
945                 950                 955                 960

Leu His Thr Ala Phe Ser Arg Val Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Asp Val Glu Ala Thr Leu Met Lys Ser Tyr Ala Glu Val His Gln Val
        1010                1015                1020

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
                1045

<210> SEQ ID NO 6
<211> LENGTH: 1049
<212> TYPE: PRT
<213> ORGANISM: Bacillus megaterium
<220> FEATURE:
<223> OTHER INFORMATION: Bacillus megaterium strain KCCM 12503
      NADPH-cytochrome P450 reductase 102A1V3, CYP102A1, CYP102A1V3

<400> SEQUENCE: 6

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205
```

```
Asp Ile Lys Val Met Asn Asp Leu Val Asp Lys Ile Ile Ala Asp Arg
210                 215                 220
Lys Ala Ser Gly Glu Gln Ser Asp Asp Leu Leu Thr His Met Leu Asn
225                 230                 235                 240
Gly Lys Asp Pro Glu Thr Gly Glu Pro Leu Asp Asp Glu Asn Ile Arg
                245                 250                 255
Tyr Gln Ile Ile Thr Phe Leu Ile Ala Gly His Glu Thr Thr Ser Gly
                260                 265                 270
Leu Leu Ser Phe Ala Leu Tyr Phe Leu Val Lys Asn Pro His Val Leu
                275                 280                 285
Gln Lys Ala Ala Glu Glu Ala Ala Arg Val Leu Val Asp Pro Val Pro
290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Glu Tyr Pro Leu Glu Lys Gly Asp
                340                 345                 350
Glu Leu Met Val Leu Ile Pro Gln Leu His Arg Asp Lys Thr Ile Trp
                355                 360                 365
Gly Asp Asp Val Glu Glu Phe Arg Pro Glu Arg Phe Glu Asn Pro Ser
370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
                420                 425                 430
Asp Ile Lys Glu Thr Leu Thr Leu Lys Pro Glu Gly Phe Val Val Lys
                435                 440                 445
Ala Lys Ser Lys Lys Ile Pro Leu Gly Gly Ile Pro Ser Pro Ser Thr
450                 455                 460
Glu Gln Ser Ala Lys Lys Val Arg Lys Lys Val Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
                500                 505                 510
Gln Val Ala Thr Leu Asp Ser His Ala Gly Asn Leu Pro Arg Glu Gly
                515                 520                 525
Ala Val Leu Ile Val Thr Ala Ser Tyr Asn Gly His Pro Pro Asp Asn
530                 535                 540
Ala Lys Gln Phe Val Asp Trp Leu Asp Gln Ala Ser Ala Asp Asp Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
                580                 585                 590
Lys Gly Ala Glu Asn Ile Ala Asp Arg Gly Glu Ala Asp Ala Ser Asp
                595                 600                 605
Asp Phe Glu Gly Thr Tyr Glu Glu Trp Arg Glu His Met Trp Ser Asp
610                 615                 620
Val Ala Ala Tyr Phe Asn Leu Asp Ile Glu Asn Ser Glu Asp Asn Lys
```

-continued

```
625                 630                 635                 640
Ser Thr Leu Ser Leu Gln Phe Val Asp Ser Ala Ala Asp Met Pro Leu
                    645                 650                 655

Ala Lys Met His Gly Ala Phe Ser Ala Asn Val Val Ala Ser Lys Glu
                660                 665                 670

Leu Gln Gln Leu Gly Ser Glu Arg Ser Thr Arg His Leu Glu Ile Ala
                675                 680                 685

Leu Pro Lys Glu Ala Ser Tyr Gln Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Gly Lys Thr Val Ser Val Glu Glu Leu Leu Gln
                740                 745                 750

Tyr Val Glu Leu Gln Asp Pro Val Thr Arg Thr Gln Leu Arg Ala Met
                755                 760                 765

Ala Ala Lys Thr Val Cys Pro Pro His Lys Val Glu Leu Glu Ala Leu
                770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Glu Phe Ser
                    805                 810                 815

Glu Phe Ile Ala Leu Leu Pro Ser Ile Ser Pro Arg Tyr Tyr Ser Ile
                820                 825                 830

Ser Ser Ser Pro His Val Asp Glu Lys Gln Ala Ser Ile Thr Val Ser
                835                 840                 845

Val Val Ser Gly Glu Ala Trp Ser Gly Tyr Gly Glu Tyr Lys Gly Ile
                850                 855                 860

Ala Ser Asn Tyr Leu Ala Asn Leu Gln Glu Gly Asp Thr Ile Thr Cys
865                 870                 875                 880

Phe Val Ser Thr Pro Gln Ser Gly Phe Thr Leu Pro Lys Asp Ser Glu
                    885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
                915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Asn Glu Gly Ile Ile Thr
945                 950                 955                 960

Leu His Thr Ala Phe Ser Arg Val Pro Asn Gln Pro Lys Thr Tyr Val
                    965                 970                 975

Gln His Val Met Glu Arg Asp Gly Lys Lys Leu Ile Glu Leu Leu Asp
                980                 985                 990

Gln Gly Ala His Phe Tyr Ile Cys Gly Asp Gly Ser Gln Met Ala Pro
                995                 1000                1005

Asp Val Glu Ala Thr Leu Met Lys Ser Tyr Ala Asp Val Tyr Glu Val
                1010                1015                1020

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
                1045
```

<210> SEQ ID NO 7
<211> LENGTH: 1049
<212> TYPE: PRT
<213> ORGANISM: Bacillus megaterium
<220> FEATURE:
<223> OTHER INFORMATION: Bacillus megaterium strain KCCM 11776
      NADPH-cytochrome P450 reductase 102A1V7, CYP102A1, CYP102A1V7

<400> SEQUENCE: 7

| Met | Thr | Ile | Lys | Glu | Met | Pro | Gln | Pro | Lys | Thr | Phe | Gly | Glu | Leu | Lys |
|---|---|---|---|---|---|---|---|---|---|---|---|---|---|---|---|
| 1 | | | | 5 | | | | | 10 | | | | | 15 | |

| Asn | Leu | Pro | Leu | Leu | Asn | Thr | Asp | Lys | Pro | Ile | Gln | Thr | Leu | Met | Lys |
|---|---|---|---|---|---|---|---|---|---|---|---|---|---|---|---|
| | | 20 | | | | | 25 | | | | | 30 | | | |

| Ile | Ala | Asp | Glu | Leu | Gly | Glu | Ile | Phe | Lys | Phe | Glu | Ala | Pro | Gly | Arg |
| | | 35 | | | | | 40 | | | | 45 | | | | |

| Val | Thr | Arg | Tyr | Leu | Ser | Ser | Gln | Arg | Leu | Ile | Lys | Glu | Ala | Cys | Asp |
| 50 | | | | | 55 | | | | | 60 | | | | | |

| Glu | Ser | Arg | Phe | Asp | Lys | Asn | Leu | Ser | Gln | Ala | Leu | Lys | Phe | Val | Arg |
| 65 | | | | 70 | | | | | 75 | | | | | 80 | |

| Asp | Phe | Ala | Gly | Asp | Gly | Leu | Phe | Thr | Ser | Trp | Thr | His | Glu | Lys | Asn |
| | | | | 85 | | | | | 90 | | | | | 95 | |

| Trp | Lys | Lys | Ala | His | Asn | Ile | Leu | Leu | Pro | Ser | Phe | Ser | Gln | Gln | Ala |
| | | 100 | | | | | 105 | | | | | 110 | | | |

| Met | Lys | Gly | Tyr | His | Ala | Met | Met | Val | Asp | Ile | Ala | Val | Gln | Leu | Ile |
| | | 115 | | | | | 120 | | | | | 125 | | | |

| Gln | Lys | Trp | Glu | Arg | Leu | Asn | Thr | Asp | Glu | His | Ile | Glu | Val | Pro | Glu |
| 130 | | | | | 135 | | | | | 140 | | | | | |

| Asp | Met | Thr | Arg | Leu | Thr | Leu | Asp | Thr | Ile | Gly | Leu | Cys | Gly | Phe | Asn |
| 145 | | | | | 150 | | | | | 155 | | | | | 160 |

| Tyr | Arg | Phe | Asn | Ser | Phe | Tyr | Arg | Asp | Gln | Pro | His | Pro | Phe | Ile | Thr |
| | | | | 165 | | | | | 170 | | | | | 175 | |

| Ser | Met | Val | Arg | Ala | Leu | Asp | Glu | Ala | Met | Asn | Lys | Leu | Gln | Arg | Ala |
| | | | 180 | | | | | 185 | | | | | 190 | | |

| Asn | Pro | Asp | Asp | Pro | Ala | Tyr | Asp | Glu | Asn | Lys | Arg | Gln | Phe | Gln | Glu |
| | | | 195 | | | | | 200 | | | | | 205 | | |

| Asp | Ile | Lys | Val | Met | Asn | Asp | Leu | Val | Asp | Lys | Ile | Ile | Ala | Asp | Arg |
| 210 | | | | | 215 | | | | | 220 | | | | | |

| Lys | Ala | Ser | Gly | Glu | Gln | Ser | Asp | Asp | Leu | Leu | Thr | His | Met | Leu | Asn |
| 225 | | | | | 230 | | | | | 235 | | | | | 240 |

| Gly | Lys | Asp | Pro | Glu | Thr | Gly | Glu | Pro | Leu | Asp | Asp | Glu | Asn | Ile | Arg |
| | | | | 245 | | | | | 250 | | | | | 255 | |

| Tyr | Gln | Ile | Ile | Thr | Phe | Leu | Ile | Ala | Gly | His | Glu | Thr | Thr | Ser | Gly |
| | | | | 260 | | | | | 265 | | | | | 270 | |

| Leu | Leu | Ser | Phe | Ala | Leu | Tyr | Phe | Leu | Val | Lys | Asn | Pro | His | Val | Leu |
| | | 275 | | | | | 280 | | | | | 285 | | | |

| Gln | Lys | Ala | Ala | Glu | Glu | Ala | Ala | Arg | Val | Leu | Val | Asp | Pro | Val | Pro |
| | | 290 | | | | | 295 | | | | | 300 | | | |

| Ser | Tyr | Lys | Gln | Val | Lys | Gln | Leu | Lys | Tyr | Val | Gly | Met | Val | Leu | Asn |
| 305 | | | | | 310 | | | | | 315 | | | | | 320 |

| Glu | Ala | Leu | Arg | Leu | Trp | Pro | Thr | Ala | Pro | Ala | Phe | Ser | Leu | Tyr | Ala |
| | | | | 325 | | | | | 330 | | | | | 335 | |

| Lys | Glu | Asp | Thr | Val | Leu | Gly | Gly | Glu | Tyr | Pro | Leu | Glu | Lys | Gly | Asp |
| | | | 340 | | | | | 345 | | | | | 350 | | |

| Glu | Leu | Met | Val | Leu | Ile | Pro | Gln | Leu | His | Arg | Asp | Lys | Thr | Ile | Trp |

-continued

```
            355                 360                 365
Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                    405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
            435                 440                 445

Ala Lys Ser Lys Gln Ile Pro Leu Gly Gly Ile Pro Ser Pro Ser Arg
450                 455                 460

Glu Gln Ser Ala Lys Lys Glu Arg Lys Thr Val Glu Asn Ala His Asn
465                 470                 475                 480

Thr Pro Leu Leu Val Leu Tyr Gly Ser Asn Met Gly Thr Ala Glu Gly
                    485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Pro Glu Gly
            515                 520                 525

Ala Val Leu Ile Val Thr Ala Ser Tyr Asn Gly His Pro Pro Asp Asn
530                 535                 540

Ala Lys Glu Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                    565                 570                 575

Thr Thr Tyr Gln Lys Val Pro Ala Phe Ile Asp Glu Thr Leu Ala Ala
                580                 585                 590

Lys Gly Ala Glu Asn Ile Ala Glu Arg Gly Glu Ala Asp Ala Ser Asp
            595                 600                 605

Asp Phe Glu Gly Thr Tyr Glu Glu Trp Arg Glu His Met Trp Ser Asp
610                 615                 620

Leu Ala Ala Tyr Phe Asn Leu Asp Ile Glu Asn Ser Glu Glu Asn Ala
625                 630                 635                 640

Ser Thr Leu Ser Leu Gln Phe Val Asp Ser Ala Ala Asp Met Pro Leu
                    645                 650                 655

Ala Lys Met His Arg Ala Phe Ser Ala Asn Val Val Ala Ser Lys Glu
                660                 665                 670

Leu Gln Lys Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
690                 695                 700

Pro Arg Asn Tyr Glu Gly Ile Val Asn Arg Val Ala Thr Arg Phe Gly
705                 710                 715                 720

Leu Asp Ala Ser Gln Gln Ile Arg Leu Glu Ala Glu Glu Lys Leu
                    725                 730                 735

Ala His Leu Pro Leu Gly Lys Thr Val Ser Val Glu Glu Leu Leu Gln
                740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Val Leu
770                 775                 780
```

-continued

```
Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Glu Phe Ser
                805                 810                 815

Glu Phe Ile Ala Leu Leu Pro Ser Met Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
850                 855                 860

Ala Ser Asn Tyr Leu Ala Asn Leu Gln Glu Gly Asp Thr Ile Thr Cys
865                 870                 875                 880

Phe Val Ser Thr Pro Gln Ser Gly Phe Thr Leu Pro Lys Gly Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
930                 935                 940

Leu Tyr Gln Lys Glu Leu Glu Asn Ala Gln Asn Glu Gly Ile Ile Thr
945                 950                 955                 960

Leu His Thr Ala Phe Ser Arg Val Pro Asn Glu Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Asp Val Glu Ala Thr Leu Met Lys Ser Tyr Ala Glu Val His Gln Val
    1010                1015                1020

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
                1045

<210> SEQ ID NO 8
<211> LENGTH: 1049
<212> TYPE: PRT
<213> ORGANISM: Bacillus megaterium
<220> FEATURE:
<223> OTHER INFORMATION: Bacillus megaterium strain KCCM 3712
      NADPH-cytochrome P450 reductase 102A1V2, CYP102A1, CYP102A1V2

<400> SEQUENCE: 8

Met Thr Ile Lys Glu Met Pro Gln Pro Lys Thr Phe Gly Glu Leu Lys
1               5                   10                  15

Asn Leu Pro Leu Leu Asn Thr Asp Lys Pro Ile Gln Thr Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
```

```
                85                  90                  95
Trp Lys Lys Ala His Asn Ile Leu Leu Pro Ser Phe Ser Gln Gln Ala
            100                 105                 110
Met Lys Gly Tyr His Ala Met Met Val Asp Ile Ala Val Gln Leu Ile
            115                 120                 125
Gln Lys Trp Glu Arg Leu Asn Thr Asp Glu His Ile Glu Val Pro Glu
            130                 135                 140
Asp Met Thr Arg Leu Thr Leu Asp Thr Ile Gly Leu Cys Gly Phe Asn
145                 150                 155                 160
Tyr Arg Phe Asn Ser Phe Tyr Arg Asp Gln Pro His Pro Phe Ile Thr
                165                 170                 175
Ser Met Val Arg Ala Leu Asp Glu Ala Met Asn Lys Leu Gln Arg Ala
            180                 185                 190
Asn Pro Asp Asp Pro Ala Tyr Asp Glu Asn Lys Arg Gln Phe Gln Glu
            195                 200                 205
Asp Ile Lys Val Met Asn Asp Leu Val Asp Lys Ile Ile Ala Asp Arg
            210                 215                 220
Lys Ala Ser Gly Glu Gln Ser Asp Asp Leu Leu Thr His Met Leu Asn
225                 230                 235                 240
Gly Lys Asp Pro Glu Thr Gly Glu Pro Leu Asp Asp Glu Asn Ile Arg
                245                 250                 255
Tyr Gln Ile Ile Thr Phe Leu Ile Ala Gly His Glu Thr Thr Ser Gly
                260                 265                 270
Leu Leu Ser Phe Ala Leu Tyr Phe Leu Val Lys Asn Pro His Val Leu
            275                 280                 285
Gln Lys Ala Ala Glu Glu Ala Thr Arg Val Leu Val Asp Pro Val Pro
            290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Glu Tyr Pro Leu Glu Lys Gly Asp
            340                 345                 350
Glu Leu Met Val Leu Ile Pro Gln Leu His Arg Asp Lys Thr Ile Trp
            355                 360                 365
Gly Glu Asp Val Glu Glu Phe Arg Pro Glu Arg Phe Glu Asn Pro Ser
            370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
            420                 425                 430
Asp Ile Lys Glu Thr Leu Thr Leu Lys Pro Glu Gly Phe Val Val Lys
            435                 440                 445
Ala Lys Ser Lys Lys Ile Pro Leu Gly Gly Ile Pro Ser Pro Ser Thr
            450                 455                 460
Glu Gln Ser Ala Lys Lys Val Arg Lys Lys Val Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
            500                 505                 510
```

Gln Val Ala Thr Leu Asp Ser His Ala Gly Asn Leu Pro Arg Glu Gly
             515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Asp Val
545                 550                 555                 560

Lys Gly Val Arg Tyr Ser Val Phe Gly Cys Gly Asp Lys Asn Trp Ala
             565                 570                 575

Thr Thr Tyr Gln Lys Val Pro Ala Phe Ile Asp Glu Thr Leu Ala Ala
             580                 585                 590

Lys Gly Ala Glu Asn Ile Ala Asp Arg Gly Glu Ala Asp Ala Ser Asp
             595                 600                 605

Asp Phe Glu Gly Thr Tyr Glu Glu Trp Arg His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
             645                 650                 655

Ala Lys Met His Gly Ala Phe Ser Ala Asn Val Val Ala Ser Lys Glu
             660                 665                 670

Leu Gln Gln Leu Gly Ser Glu Arg Ser Thr Arg His Leu Glu Ile Ala
             675                 680                 685

Leu Pro Lys Glu Ala Ser Tyr Gln Glu Gly Asp His Leu Gly Val Ile
             690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
             725                 730                 735

Ala His Leu Pro Leu Gly Lys Thr Val Ser Val Glu Glu Leu Leu Gln
             740                 745                 750

Tyr Val Glu Leu Gln Asp Pro Val Thr Arg Thr Gln Leu Arg Ala Met
             755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Glu Phe Ser
             805                 810                 815

Glu Phe Ile Ala Leu Leu Pro Ser Ile Ser Pro Arg Tyr Tyr Ser Ile
             820                 825                 830

Ser Ser Ser Pro His Val Asp Glu Lys Gln Ala Ser Ile Thr Val Ser
             835                 840                 845

Val Val Ser Gly Glu Ala Trp Ser Gly Tyr Gly Glu Tyr Lys Gly Ile
             850                 855                 860

Ala Ser Asn Tyr Leu Ala Asn Leu Gln Glu Gly Asp Thr Ile Thr Cys
865                 870                 875                 880

Phe Val Ser Thr Pro Gln Ser Gly Phe Thr Leu Pro Lys Asp Ser Glu
             885                 890                 895

Thr Pro Leu Ile Met Val Gly Pro Gly Thr Gly Val Ala Pro Phe Arg
             900                 905                 910

Gly Phe Val Gln Ala Arg Lys Gln Leu Lys Glu Gln Gly Gln Ser Leu
             915                 920                 925

```
Gly Glu Ala His Leu Tyr Phe Gly Cys Arg Ser Pro His Glu Asp Tyr
        930                 935                 940

Leu Tyr Gln Glu Glu Leu Glu Asn Ala Gln Asn Glu Gly Ile Ile Thr
945                 950                 955                 960

Leu His Thr Ala Phe Ser Arg Val Pro Asn Gln Pro Lys Thr Tyr Val
                965                 970                 975

Gln His Val Met Glu Arg Asp Gly Lys Lys Leu Ile Glu Leu Leu Asp
            980                 985                 990

Gln Gly Ala His Phe Tyr Ile Cys Gly Asp Gly Ser Gln Met Ala Pro
                995                1000                1005

Asp Val Glu Ala Thr Leu Met Lys Ser Tyr Ala Asp Val Tyr Glu Val
       1010                1015                1020

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
                1045
```

```
<210> SEQ ID NO 9
<211> LENGTH: 1049
<212> TYPE: PRT
<213> ORGANISM: Bacillus megaterium
<220> FEATURE:
<223> OTHER INFORMATION: Bacillus megaterium strain KCTC 2194 cytochrome
      P450:NADPH P450 reductase, CYP102A1

<400> SEQUENCE: 9
```

```
Met Thr Ile Lys Glu Met Pro Gln Pro Lys Thr Phe Gly Glu Leu Lys
 1               5                  10                  15

Asn Leu Pro Leu Leu Asn Thr Asp Lys Pro Ile Gln Thr Leu Met Lys
             20                  25                  30

Ile Ala Asp Glu Leu Gly Glu Ile Phe Lys Phe Glu Ala Pro Gly Arg
         35                  40                  45

Val Thr Arg Tyr Leu Ser Ser Gln Arg Leu Ile Lys Glu Ala Cys Asp
 50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                 85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Ile
        115                 120                 125

Gln Lys Trp Glu Arg Leu Asn Thr Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240
```

```
Gly Lys Asp Pro Glu Thr Gly Glu Pro Leu Asp Asp Glu Asn Ile Arg
            245                 250                 255
Tyr Gln Ile Ile Thr Phe Leu Ile Ala Gly His Glu Thr Thr Ser Gly
        260                 265                 270
Leu Leu Ser Phe Ala Leu Tyr Phe Leu Val Lys Asn Pro His Val Leu
    275                 280                 285
Gln Lys Ala Ala Glu Glu Ala Ala Arg Val Leu Val Asp Pro Val Pro
290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Glu Tyr Pro Leu Glu Lys Gly Asp
            340                 345                 350
Glu Leu Met Val Leu Ile Pro Gln Leu His Arg Asp Lys Thr Ile Trp
        355                 360                 365
Gly Asp Asp Val Glu Glu Phe Arg Pro Glu Arg Phe Glu Asn Pro Ser
    370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
            420                 425                 430
Asp Ile Lys Glu Thr Leu Thr Leu Lys Pro Glu Gly Phe Val Val Lys
        435                 440                 445
Ala Lys Ser Lys Gln Ile Pro Leu Gly Gly Ile Pro Ser Pro Ser Arg
    450                 455                 460
Glu Gln Ser Ala Lys Lys Glu Arg Lys Thr Val Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
            500                 505                 510
Gln Val Ala Thr Leu Asp Ser His Ala Gly Asn Leu Pro Arg Glu Gly
        515                 520                 525
Ala Val Leu Ile Val Thr Ala Ser Tyr Asn Gly His Pro Pro Asp Asn
    530                 535                 540
Ala Lys Glu Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
            580                 585                 590
Lys Gly Ala Glu Asn Ile Ala Glu Arg Gly Glu Ala Asp Ala Ser Asp
        595                 600                 605
Asp Phe Glu Gly Thr Tyr Glu Glu Trp Arg Glu His Met Trp Ser Asp
    610                 615                 620
Leu Ala Ala Tyr Phe Asn Leu Asp Ile Glu Asn Ser Glu Glu Asn Ala
625                 630                 635                 640
Ser Thr Leu Ser Leu Gln Phe Val Asp Ser Ala Asp Met Pro Leu
                645                 650                 655
```

```
Ala Lys Met His Arg Ala Phe Ser Ala Asn Val Val Ala Ser Lys Glu
            660                 665                 670

Leu Gln Lys Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Ala Thr Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Gly Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Val Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Glu Phe Ser
                805                 810                 815

Glu Phe Ile Ala Leu Leu Pro Ser Met Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Asn Leu Gln Glu Gly Asp Thr Ile Thr Cys
865                 870                 875                 880

Phe Val Ser Thr Pro Gln Ser Gly Phe Thr Leu Pro Lys Gly Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Lys Glu Leu Glu Asn Ala Gln Asn Glu Gly Ile Ile Thr
945                 950                 955                 960

Leu His Thr Ala Phe Ser Arg Val Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Asp Val Glu Ala Thr Leu Met Lys Ser Tyr Ala Glu Val His Gln Val
    1010                1015                1020

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
                1045

<210> SEQ ID NO 10
<211> LENGTH: 1049
<212> TYPE: PRT
```

<213> ORGANISM: Bacillus megaterium
<220> FEATURE:
<223> OTHER INFORMATION: Bacillus megaterium strain KCCM 11761
      NADPH-cytochrome P450 reductase 102A1V6, CYP102A1, CYP102A1V6

<400> SEQUENCE: 10

| Met | Thr | Ile | Lys | Glu | Met | Pro | Gln | Pro | Lys | Thr | Phe | Gly | Glu | Leu | Lys |
|---|---|---|---|---|---|---|---|---|---|---|---|---|---|---|---|
| 1 | | | | 5 | | | | | 10 | | | | | 15 | |

Asn Leu Pro Leu Leu Asn Thr Asp Lys Pro Val Gln Ala Leu Met Lys
                20                  25                  30

Ile Ala Asp Glu Leu Gly Glu Ile Phe Lys Phe Glu Ala Pro Gly Arg
            35                  40                  45

Val Thr Arg Tyr Leu Ser Ser Gln Arg Leu Ile Lys Glu Ala Cys Asp
 50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
                100                 105                 110

Met Lys Gly Tyr His Ala Met Met Val Asp Ile Ala Val Gln Leu Ile
                115                 120                 125

Gln Lys Trp Glu Arg Leu Asn Ala Asp Glu His Ile Glu Val Pro Glu
130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
                180                 185                 190

Asn Pro Asp Asp Pro Ala Tyr Asp Glu Asn Lys Arg Gln Phe Gln Asp
                195                 200                 205

Asp Ile Lys Val Met Asn Asp Leu Val Asp Lys Ile Ile Ala Asp Arg
            210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
            275                 280                 285

Gln Lys Ala Ala Glu Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Leu Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
370                 375                 380

```
Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
            405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Gln Ile Pro Leu Gly Gly Ile Pro Ser Pro Ser Arg
450                 455                 460

Glu Gln Ser Ala Lys Lys Glu Arg Lys Thr Val Glu Asn Ala His Asn
465                 470                 475                 480

Thr Pro Leu Leu Val Leu Tyr Gly Ser Asn Met Gly Thr Ala Glu Gly
            485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
            565                 570                 575

Thr Thr Tyr Gln Lys Val Pro Ala Phe Ile Asp Glu Thr Leu Ser Ala
            580                 585                 590

Lys Gly Ala Glu Asn Ile Ala Glu Arg Gly Glu Ala Asp Ala Ser Asp
            595                 600                 605

Asp Phe Glu Gly Thr Tyr Glu Glu Trp Arg Glu His Met Trp Ser Asp
            610                 615                 620

Leu Ala Ala Tyr Phe Asn Leu Asn Ile Glu Asn Ser Glu Asp Asn Ala
625                 630                 635                 640

Ser Thr Leu Ser Leu Gln Phe Val Asp Ser Ala Ala Asp Met Pro Leu
            645                 650                 655

Ala Lys Met His Gly Ala Phe Ser Ala Asn Val Val Ala Ser Lys Glu
            660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Arg Phe Gly
705                 710                 715                 720

Leu Asp Ala Ser Gln Gln Ile Arg Leu Glu Ala Glu Glu Lys Leu
            725                 730                 735

Ala His Leu Pro Leu Gly Lys Thr Val Ser Val Glu Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
            770                 775                 780

Leu Glu Lys Gln Ala Tyr Lys Glu Gln Val Leu Thr Lys Arg Leu Thr
785                 790                 795                 800

Met Leu Glu Leu Leu Glu Lys Tyr Pro Ala Cys Glu Met Glu Phe Ser
```

```
                        805                 810                 815
Glu Phe Ile Ala Leu Leu Pro Ser Met Arg Pro Arg Tyr Tyr Ser Ile
                820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
        850                 855                 860

Ala Ser Asn Tyr Leu Ala Glu Leu Gln Glu Gly Asp Thr Ile Thr Cys
865                 870                 875                 880

Phe Val Ser Thr Pro Gln Ser Gly Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Asn Glu Gly Ile Ile Thr
945                 950                 955                 960

Leu His Thr Ala Phe Ser Arg Val Pro Asn Gln Pro Lys Thr Tyr Val
                965                 970                 975

Gln His Val Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                1000                1005

Asp Val Glu Ala Thr Leu Met Lys Ser Tyr Ala Glu Val His Lys Val
    1010                1015                1020

Ser Glu Ala Asp Ala Arg Leu Trp Leu Gln Gln Leu Glu Glu Lys Ser
1025                1030                1035                1040

Arg Tyr Ala Lys Asp Val Trp Ala Gly
                1045

<210> SEQ ID NO 11
<211> LENGTH: 1049
<212> TYPE: PRT
<213> ORGANISM: Bacillus megaterium
<220> FEATURE:
<223> OTHER INFORMATION: Bacillus megaterium strain ATCC 10778
      NADPH-cytochrome P450 reductase 102A1V5, CYP102A1, CYP102A1V5

<400> SEQUENCE: 11

Met Thr Ile Lys Glu Met Pro Gln Pro Lys Thr Phe Gly Glu Leu Lys
 1               5                  10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110
```

```
Met Lys Gly Tyr His Ala Met Met Val Asp Ile Ala Val Gln Leu Ile
            115                 120                 125
Gln Lys Trp Glu Arg Leu Asn Ala Asp Glu His Ile Glu Val Pro Glu
130                 135                 140
Asp Met Thr Arg Leu Thr Leu Asp Thr Ile Gly Leu Cys Gly Phe Asn
145                 150                 155                 160
Tyr Arg Phe Asn Ser Phe Tyr Arg Asp Gln Pro His Pro Phe Ile Thr
                165                 170                 175
Ser Met Val Arg Ala Leu Asp Glu Ala Met Asn Lys Leu Gln Arg Ala
            180                 185                 190
Asn Pro Asp Asp Pro Ala Tyr Asp Glu Asn Lys Arg Gln Phe Gln Asp
        195                 200                 205
Asp Ile Lys Val Met Asn Asp Leu Val Asp Lys Ile Ile Ala Asp Arg
    210                 215                 220
Lys Ala Ser Gly Glu Gln Ser Asp Asp Leu Leu Thr His Met Leu Asn
225                 230                 235                 240
Gly Lys Asp Pro Glu Thr Gly Glu Pro Leu Asp Asp Gly Asn Ile Arg
                245                 250                 255
Tyr Gln Ile Ile Thr Phe Leu Ile Ala Gly His Glu Thr Thr Ser Gly
            260                 265                 270
Leu Leu Ser Phe Ala Leu Tyr Phe Leu Val Lys Asn Pro His Val Leu
        275                 280                 285
Gln Lys Ala Ala Glu Glu Ala Ala Arg Val Leu Val Asp Pro Val Pro
    290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Glu Tyr Pro Leu Glu Lys Gly Asp
            340                 345                 350
Glu Leu Met Val Leu Ile Pro Gln Leu His Arg Asp Lys Thr Ile Trp
        355                 360                 365
Gly Asp Asp Val Glu Glu Phe Arg Pro Glu Arg Phe Glu Asn Pro Ser
    370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
            420                 425                 430
Asp Ile Lys Glu Thr Leu Thr Leu Lys Pro Glu Gly Phe Val Val Lys
        435                 440                 445
Ala Lys Ser Lys Gln Ile Pro Leu Gly Gly Ile Pro Ser Pro Ser Arg
    450                 455                 460
Glu Gln Ser Ala Lys Lys Glu Arg Lys Thr Val Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
            500                 505                 510
Gln Val Ala Thr Leu Asp Ser His Ala Gly Asn Leu Pro Arg Glu Gly
        515                 520                 525
Ala Val Leu Ile Val Thr Ala Ser Tyr Asn Gly His Pro Pro Asp Asn
```

```
                530             535             540
Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ser Ala
            580                 585                 590

Lys Gly Ala Glu Asn Ile Ala Glu Arg Gly Glu Ala Asp Ala Ser Asp
            595                 600                 605

Asp Phe Glu Gly Thr Tyr Glu Glu Trp Arg Glu His Met Trp Ser Asp
        610                 615                 620

Leu Ala Ala Tyr Phe Asn Leu Asn Ile Glu Asn Ser Glu Asp Asn Ala
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Ala Asn Val Val Ala Ser Lys Glu
                660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Thr Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Gly Lys Thr Val Ser Val Glu Glu Leu Leu Gln
                740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
            770                 775                 780

Leu Glu Lys Gln Ala Tyr Lys Glu Gln Val Leu Thr Lys Arg Leu Thr
785                 790                 795                 800

Met Leu Glu Leu Leu Glu Lys Tyr Pro Ala Cys Glu Met Glu Phe Ser
                805                 810                 815

Glu Phe Ile Ala Leu Leu Pro Ser Met Arg Pro Arg Tyr Tyr Ser Ile
            820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Val Ser Thr Pro Gln Ser Gly Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
        930                 935                 940

Leu Tyr Gln Glu Glu Leu Glu Asn Ala Gln Asn Glu Gly Ile Ile Thr
945                 950                 955                 960
```

Leu His Thr Ala Phe Ser Arg Val Pro Asn Gln Pro Lys Thr Tyr Val
              965                 970                 975

Gln His Val Val Glu Gln Asp Gly Lys Lys Leu Ile Glu Leu Leu Asp
              980                 985                 990

Gln Gly Ala His Phe Tyr Ile Cys Gly Asp Gly Ser Gln Met Ala Pro
              995                1000                1005

Asp Val Glu Ala Thr Leu Met Lys Ser Tyr Ala Glu Val His Lys Val
         1010                1015                1020

Ser Glu Ala Asp Ala Arg Leu Trp Leu Gln Gln Leu Glu Glu Lys Ser
1025                1030                1035                1040

Arg Tyr Ala Lys Asp Val Trp Ala Gly
              1045

<210> SEQ ID NO 12
<211> LENGTH: 420
<212> TYPE: PRT
<213> ORGANISM: Mycobacterium sp. HXN-1500
<220> FEATURE:
<223> OTHER INFORMATION: cytochrome P450 alkane hydroxylase, CYP153A6,
      ahpG

<400> SEQUENCE: 12

Met Thr Glu Met Thr Val Ala Ala Ser Asp Ala Thr Asn Ala Ala Tyr
1               5                  10                  15

Gly Met Ala Leu Glu Asp Ile Asp Val Ser Asn Pro Val Leu Phe Arg
             20                  25                  30

Asp Asn Thr Trp His Pro Tyr Phe Lys Arg Leu Arg Glu Glu Asp Pro
             35                  40                  45

Val His Tyr Cys Lys Ser Ser Met Phe Gly Pro Tyr Trp Ser Val Thr
         50                  55                  60

Lys Tyr Arg Asp Ile Met Ala Val Glu Thr Asn Pro Lys Val Phe Ser
65                  70                  75                  80

Ser Glu Ala Lys Ser Gly Gly Ile Thr Ile Met Asp Asp Asn Ala Ala
                 85                  90                  95

Ala Ser Leu Pro Met Phe Ile Ala Met Asp Pro Pro Lys His Asp Val
            100                 105                 110

Gln Arg Lys Thr Val Ser Pro Ile Val Ala Pro Glu Asn Leu Ala Thr
            115                 120                 125

Met Glu Ser Val Ile Arg Gln Arg Thr Ala Asp Leu Leu Asp Gly Leu
        130                 135                 140

Pro Ile Asn Glu Glu Phe Asp Trp Val His Arg Val Ser Ile Glu Leu
145                 150                 155                 160

Thr Thr Lys Met Leu Ala Thr Leu Phe Asp Phe Pro Trp Asp Asp Arg
                165                 170                 175

Ala Lys Leu Thr Arg Trp Ser Asp Val Thr Thr Ala Leu Pro Gly Gly
            180                 185                 190

Gly Ile Ile Asp Ser Glu Glu Gln Arg Met Ala Glu Leu Met Glu Cys
            195                 200                 205

Ala Thr Tyr Phe Thr Glu Leu Trp Asn Gln Arg Val Asn Ala Glu Pro
        210                 215                 220

Lys Asn Asp Leu Ile Ser Met Met Ala His Ser Glu Ser Thr Arg His
225                 230                 235                 240

Met Ala Pro Glu Glu Tyr Leu Gly Asn Ile Val Leu Leu Ile Val Gly
                245                 250                 255

Gly Asn Asp Thr Thr Arg Asn Ser Met Thr Gly Gly Val Leu Ala Leu

```
                260                 265                 270
Asn Glu Phe Pro Asp Glu Tyr Arg Lys Leu Ser Ala Asn Pro Ala Leu
            275                 280                 285

Ile Ser Ser Met Val Ser Glu Ile Ile Arg Trp Gln Thr Pro Leu Ser
        290                 295                 300

His Met Arg Arg Thr Ala Leu Glu Asp Ile Glu Phe Gly Gly Lys His
305                 310                 315                 320

Ile Arg Gln Gly Asp Lys Val Val Met Trp Tyr Val Ser Gly Asn Arg
                325                 330                 335

Asp Pro Glu Ala Ile Asp Asn Pro Asp Thr Phe Ile Ile Asp Arg Ala
            340                 345                 350

Lys Pro Arg Gln His Leu Ser Phe Gly Phe Gly Ile His Arg Cys Val
        355                 360                 365

Gly Asn Arg Leu Ala Glu Leu Gln Leu Asn Ile Leu Trp Glu Glu Ile
    370                 375                 380

Leu Lys Arg Trp Pro Asp Pro Leu Gln Ile Gln Val Leu Gln Glu Pro
385                 390                 395                 400

Thr Arg Val Leu Ser Pro Phe Val Lys Gly Tyr Glu Ser Leu Pro Val
                405                 410                 415

Arg Ile Asn Ala
            420

<210> SEQ ID NO 13
<211> LENGTH: 496
<212> TYPE: PRT
<213> ORGANISM: Tetrahymena thermophile
<220> FEATURE:
<223> OTHER INFORMATION: Tetrahymena thermophile strain SB210 cytochrome
      P450 monooxygenase CYP5013C2

<400> SEQUENCE: 13

Met Ile Phe Glu Leu Ile Leu Ile Ala Val Ala Leu Phe Ala Tyr Phe
1               5                   10                  15

Lys Ile Ala Lys Pro Tyr Phe Ser Tyr Leu Lys Tyr Arg Lys Tyr Gly
            20                  25                  30

Lys Gly Phe Tyr Tyr Pro Ile Leu Gly Glu Met Ile Glu Gln Glu Gln
        35                  40                  45

Asp Leu Lys Gln His Ala Asp Ala Asp Tyr Ser Val His His Ala Leu
    50                  55                  60

Asp Lys Asp Pro Asp Gln Lys Leu Phe Val Thr Asn Leu Gly Thr Lys
65                  70                  75                  80

Val Lys Leu Arg Leu Ile Glu Pro Glu Ile Ile Lys Asp Phe Phe Ser
                85                  90                  95

Lys Ser Gln Tyr Tyr Gln Lys Asp Gln Thr Phe Ile Gln Asn Ile Thr
            100                 105                 110

Arg Phe Leu Lys Asn Gly Ile Val Phe Ser Glu Gly Asn Thr Trp Lys
        115                 120                 125

Glu Ser Arg Lys Leu Phe Ser Pro Ala Phe His Tyr Glu Tyr Ile Gln
    130                 135                 140

Lys Leu Thr Pro Leu Ile Asn Asp Ile Thr Asp Thr Ile Phe Asn Leu
145                 150                 155                 160

Ala Val Lys Asn Gln Glu Leu Lys Asn Phe Asp Pro Ile Ala Gln Ile
                165                 170                 175

Gln Glu Ile Thr Gly Arg Val Ile Ile Ala Ser Phe Phe Gly Glu Val
            180                 185                 190
```

Ile Glu Gly Glu Lys Phe Gln Gly Leu Thr Ile Ile Gln Cys Leu Ser
195                 200                 205

His Ile Ile Asn Thr Leu Gly Asn Gln Thr Tyr Ser Ile Met Tyr Phe
210                 215                 220

Leu Phe Gly Ser Lys Tyr Phe Glu Leu Gly Val Thr Glu Glu His Arg
225                 230                 235                 240

Lys Phe Asn Lys Phe Ile Ala Glu Phe Asn Lys Tyr Leu Leu Gln Lys
                245                 250                 255

Ile Asp Gln Gln Ile Glu Ile Met Ser Asn Glu Leu Gln Thr Lys Gly
            260                 265                 270

Tyr Ile Gln Asn Pro Cys Ile Leu Ala Gln Leu Ile Ser Thr His Lys
        275                 280                 285

Ile Asp Glu Ile Thr Arg Asn Gln Leu Phe Gln Asp Phe Lys Thr Phe
290                 295                 300

Tyr Ile Ala Gly Met Asp Thr Thr Gly His Leu Leu Gly Met Thr Ile
305                 310                 315                 320

Tyr Tyr Val Ser Gln Asn Lys Asp Ile Tyr Thr Lys Leu Gln Ser Glu
                325                 330                 335

Ile Asp Ser Asn Thr Asp Gln Ser Ala His Gly Leu Ile Lys Asn Leu
            340                 345                 350

Pro Tyr Leu Asn Ala Val Ile Lys Glu Thr Leu Arg Tyr Tyr Gly Pro
        355                 360                 365

Gly Asn Ile Leu Phe Asp Arg Ile Ala Ile Lys Asp His Glu Leu Ala
    370                 375                 380

Gly Ile Pro Ile Lys Lys Gly Thr Ile Val Thr Pro Tyr Ala Met Ser
385                 390                 395                 400

Met Gln Arg Asn Ser Lys Tyr Tyr Gln Asp Pro His Lys Tyr Asn Pro
                405                 410                 415

Ser Arg Trp Leu Glu Lys Gln Ser Ser Asp Leu His Pro Asp Ala Asn
            420                 425                 430

Ile Pro Phe Ser Ala Gly Gln Arg Lys Cys Ile Gly Glu Gln Leu Ala
        435                 440                 445

Leu Leu Glu Ala Arg Ile Ile Leu Asn Lys Phe Ile Lys Met Phe Asp
450                 455                 460

Phe Thr Cys Pro Gln Asp Tyr Lys Leu Met Met Asn Tyr Lys Phe Leu
465                 470                 475                 480

Ser Glu Pro Val Asn Pro Leu Pro Leu Gln Leu Thr Leu Arg Lys Gln
                485                 490                 495

<210> SEQ ID NO 14
<211> LENGTH: 394
<212> TYPE: PRT
<213> ORGANISM: Nonomuraea dietziae
<220> FEATURE:
<223> OTHER INFORMATION: Nonomuraea dietziae strain Sebekia benihana
      cytochrome P450 hydroxylase sb8

<400> SEQUENCE: 14

Val Asn Ile Asp Leu Val Asp Gln Asp His Tyr Ala Thr Phe Gly Pro
1               5                   10                  15

Pro His Glu Gln Met Arg Trp Leu Arg Glu His Ala Pro Val Tyr Trp
                20                  25                  30

His Glu Gly Glu Pro Gly Phe Trp Ala Val Thr Arg His Glu Asp Val
            35                  40                  45

Val His Val Ser Arg His Ser Asp Leu Phe Ser Ser Ala Arg Arg Leu
        50                  55                  60

Ala Leu Phe Asn Glu Met Pro Glu Glu Gln Arg Leu Gln Arg Met
 65                  70                  75                  80

Met Met Leu Asn Gln Asp Pro Pro Glu His Thr Arg Arg Ser Leu
                 85                  90                  95

Val Asn Arg Gly Phe Thr Pro Thr Ile Arg Ala Leu Glu Gln His
            100                 105                 110

Ile Arg Asp Ile Cys Asp Asp Leu Leu Asp Gln Cys Ser Gly Glu Gly
        115                 120                 125

Asp Phe Val Thr Asp Leu Ala Ala Pro Leu Pro Leu Tyr Val Ile Cys
130                 135                 140

Glu Leu Leu Gly Ala Pro Val Ala Asp Arg Asp Lys Ile Phe Ala Trp
145                 150                 155                 160

Ser Asn Arg Met Ile Gly Ala Gln Asp Pro Asp Tyr Ala Ala Ser Pro
                165                 170                 175

Glu Glu Gly Gly Ala Ala Ala Met Glu Val Tyr Ala Tyr Ala Ser Glu
            180                 185                 190

Leu Ala Ala Gln Arg Arg Ala Pro Arg Asp Asp Ile Val Thr Lys
195                 200                 205

Leu Leu Gln Ser Asp Glu Asn Gly Glu Ser Leu Thr Glu Asn Glu Phe
210                 215                 220

Glu Leu Phe Val Leu Leu Val Val Ala Gly Asn Glu Thr Thr Arg
225                 230                 235                 240

Asn Ala Ala Ser Gly Gly Met Leu Thr Leu Phe Glu His Pro Asp Gln
                245                 250                 255

Trp Asp Arg Leu Val Ala Asp Pro Ser Leu Ala Ala Thr Ala Ala Asp
            260                 265                 270

Glu Ile Val Arg Trp Val Ser Pro Val Asn Leu Phe Arg Arg Thr Ala
        275                 280                 285

Thr Ala Asp Leu Thr Leu Gly Gly Gln Gln Val Lys Ala Asp Asp Lys
290                 295                 300

Val Val Val Phe Tyr Ser Ser Ala Asn Arg Asp Ala Ser Val Phe Ser
305                 310                 315                 320

Asp Pro Glu Val Phe Asp Ile Gly Arg Ser Pro Asn Pro His Ile Gly
                325                 330                 335

Phe Gly Gly Gly Gly Ala His Phe Cys Leu Gly Asn His Leu Ala Lys
            340                 345                 350

Leu Glu Leu Arg Val Leu Phe Glu Gln Leu Ala Arg Arg Phe Pro Arg
        355                 360                 365

Met Arg Gln Thr Gly Glu Ala Arg Leu Arg Ser Asn Phe Ile Asn
370                 375                 380

Gly Ile Lys Thr Leu Pro Val Thr Leu Gly
385                 390

<210> SEQ ID NO 15
<211> LENGTH: 501
<212> TYPE: PRT
<213> ORGANISM: Homo sapiens
<220> FEATURE:
<223> OTHER INFORMATION: human vitamin D 25-hydroxylase, CYP2R1,
      cytochrome P450, family 2, subfamily R, polypeptide 1, cytochrome
      P450 2R1

<400> SEQUENCE: 15

Met Trp Lys Leu Trp Arg Ala Glu Glu Gly Ala Ala Ala Leu Gly Gly
 1               5                  10                  15

```
Ala Leu Phe Leu Leu Phe Ala Leu Gly Val Arg Gln Leu Lys
            20              25                  30

Gln Arg Arg Pro Met Gly Phe Pro Pro Gly Pro Gly Leu Pro Phe
        35              40              45

Ile Gly Asn Ile Tyr Ser Leu Ala Ala Ser Ser Glu Leu Pro His Val
50              55                  60

Tyr Met Arg Lys Gln Ser Gln Val Tyr Gly Glu Ile Phe Ser Leu Asp
65                  70              75                  80

Leu Gly Gly Ile Ser Thr Val Val Leu Asn Gly Tyr Asp Val Val Lys
                85                  90                  95

Glu Cys Leu Val His Gln Ser Glu Ile Phe Ala Asp Arg Pro Cys Leu
    100                 105                 110

Pro Leu Phe Met Lys Met Thr Lys Met Gly Gly Leu Leu Asn Ser Arg
        115                 120                 125

Tyr Gly Arg Gly Trp Val Asp His Arg Arg Leu Ala Val Asn Ser Phe
    130                 135                 140

Arg Tyr Phe Gly Tyr Gly Gln Lys Ser Phe Glu Ser Lys Ile Leu Glu
145                 150                 155                 160

Glu Thr Lys Phe Phe Asn Asp Ala Ile Glu Thr Tyr Lys Gly Arg Pro
                    165                 170                 175

Phe Asp Phe Lys Gln Leu Ile Thr Asn Ala Val Ser Asn Ile Thr Asn
            180                 185                 190

Leu Ile Ile Phe Gly Glu Arg Phe Thr Tyr Glu Asp Thr Asp Phe Gln
        195                 200                 205

His Met Ile Glu Leu Phe Ser Glu Asn Val Leu Ala Ala Ser Ala
    210                 215                 220

Ser Val Phe Leu Tyr Asn Ala Phe Pro Trp Ile Gly Ile Leu Pro Phe
225                 230                 235                 240

Gly Lys His Gln Gln Leu Phe Arg Asn Ala Ala Val Val Tyr Asp Phe
                    245                 250                 255

Leu Ser Arg Leu Ile Glu Lys Ala Ser Val Asn Arg Lys Pro Gln Leu
            260                 265                 270

Pro Gln His Phe Val Asp Ala Tyr Leu Asp Glu Met Asp Gln Gly Lys
        275                 280                 285

Asn Asp Pro Ser Ser Thr Phe Ser Lys Glu Asn Leu Ile Phe Ser Val
290                 295                 300

Gly Glu Leu Ile Ile Ala Gly Thr Glu Thr Thr Asn Val Leu Arg
305                 310                 315                 320

Trp Ala Ile Leu Phe Met Ala Leu Tyr Pro Asn Ile Gln Gly Gln Val
                325                 330                 335

Gln Lys Glu Ile Asp Leu Ile Met Gly Pro Asn Gly Lys Pro Ser Trp
            340                 345                 350

Asp Asp Lys Cys Lys Met Pro Tyr Thr Glu Ala Val Leu His Glu Val
        355                 360                 365

Leu Arg Phe Cys Asn Ile Val Pro Leu Gly Ile Phe His Ala Thr Ser
    370                 375                 380

Glu Asp Ala Val Val Arg Gly Tyr Ser Ile Pro Lys Gly Thr Thr Val
385                 390                 395                 400

Ile Thr Asn Leu Tyr Ser Val His Phe Asp Glu Lys Tyr Trp Arg Asp
                    405                 410                 415

Pro Glu Val Phe His Pro Glu Arg Phe Leu Asp Ser Ser Gly Tyr Phe
            420                 425                 430

Ala Lys Lys Glu Ala Leu Val Pro Phe Ser Leu Gly Arg Arg His Cys
```

```
                435                 440                 445
Leu Gly Glu His Leu Ala Arg Met Glu Met Phe Leu Phe Phe Thr Ala
        450                 455                 460

Leu Leu Gln Arg Phe His Leu His Phe Pro His Glu Leu Val Pro Asp
465                 470                 475                 480

Leu Lys Pro Arg Leu Gly Met Thr Leu Gln Pro Gln Pro Tyr Leu Ile
                485                 490                 495

Cys Ala Glu Arg Arg
            500

<210> SEQ ID NO 16
<211> LENGTH: 501
<212> TYPE: PRT
<213> ORGANISM: Macaca mulatta
<220> FEATURE:
<223> OTHER INFORMATION: Rhesus monkey vitamin D 25-hydroxylase, CYP2R1,
      cytochrome P450, family 2, subfamily R, polypeptide 1

<400> SEQUENCE: 16

Met Trp Lys Leu Trp Gly Gly Glu Glu Gly Ala Ala Leu Gly Gly
1               5                   10                  15

Ala Leu Phe Leu Leu Phe Ala Leu Gly Val Arg Gln Leu Leu Lys
            20                  25                  30

Leu Arg Arg Pro Met Gly Phe Pro Pro Gly Pro Pro Gly Leu Pro Phe
            35                  40                  45

Ile Gly Asn Ile Tyr Ser Leu Ala Ala Ser Ala Glu Leu Pro His Val
        50                  55                  60

Tyr Met Arg Lys Gln Ser Gln Val Tyr Gly Glu Ile Phe Ser Leu Asp
65                  70                  75                  80

Leu Gly Gly Ile Ser Thr Val Val Leu Asn Gly Tyr Asp Val Val Lys
                85                  90                  95

Glu Cys Leu Val His Gln Ser Gly Ile Phe Ala Asp Arg Pro Cys Leu
            100                 105                 110

Pro Leu Phe Met Lys Met Thr Lys Met Gly Gly Leu Leu Asn Ser Arg
        115                 120                 125

Tyr Gly Gln Gly Trp Val Glu His Arg Arg Leu Ala Val Asn Ser Phe
    130                 135                 140

Arg Tyr Phe Gly Tyr Gly Gln Lys Ser Phe Glu Ser Lys Ile Leu Glu
145                 150                 155                 160

Glu Thr Lys Phe Phe Thr Asp Ala Ile Glu Thr Tyr Lys Gly Arg Pro
                165                 170                 175

Phe Asp Phe Lys Gln Leu Ile Thr Ser Ala Val Ser Asn Ile Thr Asn
            180                 185                 190

Leu Ile Ile Phe Gly Glu Arg Phe Thr Tyr Glu Asp Thr Asp Phe Gln
        195                 200                 205

His Met Ile Glu Leu Phe Ser Glu Asn Val Glu Leu Ala Ala Ser Ala
    210                 215                 220

Ser Val Phe Leu Tyr Asn Ala Phe Pro Trp Ile Gly Ile Leu Pro Phe
225                 230                 235                 240

Gly Lys His Gln Gln Leu Phe Arg Asn Ala Ser Val Val Tyr Asp Phe
                245                 250                 255

Leu Ser Arg Leu Ile Glu Lys Ala Ser Val Asn Arg Lys Pro Gln Leu
            260                 265                 270

Pro Gln His Phe Val Asp Ala Tyr Phe Asp Glu Met Asp Gln Gly Lys
        275                 280                 285
```

```
Asn Asp Pro Ser Ser Thr Phe Ser Lys Glu Asn Leu Ile Phe Ser Val
    290                 295                 300

Gly Glu Leu Ile Ile Ala Gly Thr Glu Thr Thr Asn Val Leu Arg
305                 310                 315                 320

Trp Ala Ile Leu Phe Met Ala Leu Tyr Pro Asn Ile Gln Gly Gln Val
                325                 330                 335

Gln Lys Glu Ile Asp Leu Ile Met Gly Pro Asn Gly Lys Pro Ser Trp
            340                 345                 350

Asp Asp Lys Phe Lys Met Pro Tyr Thr Glu Ala Val Leu His Glu Val
355                 360                 365

Leu Arg Phe Cys Asn Ile Val Pro Leu Gly Ile Phe His Ala Thr Ser
370                 375                 380

Glu Asp Ala Val Val Arg Gly Tyr Ser Ile Pro Lys Gly Thr Thr Val
385                 390                 395                 400

Ile Thr Asn Leu Tyr Ser Val His Phe Asp Glu Lys Tyr Trp Arg Asp
                405                 410                 415

Pro Glu Val Phe His Pro Glu Arg Phe Leu Asp Ser Ser Gly Tyr Phe
                420                 425                 430

Ala Lys Lys Glu Ala Leu Val Pro Phe Ser Leu Gly Arg Arg His Cys
            435                 440                 445

Leu Gly Glu Gln Leu Ala Arg Met Glu Met Phe Leu Phe Phe Thr Ala
450                 455                 460

Leu Leu Gln Arg Phe His Leu His Phe Pro His Glu Leu Val Pro Asp
465                 470                 475                 480

Leu Lys Pro Arg Leu Gly Met Thr Leu Gln Pro Gln Pro Tyr Leu Ile
                485                 490                 495

Cys Ala Glu Arg Arg
            500

<210> SEQ ID NO 17
<211> LENGTH: 501
<212> TYPE: PRT
<213> ORGANISM: Canis familiaris
<220> FEATURE:
<223> OTHER INFORMATION: dog breed boxer vitamin D 25-hydroxylase,
      CYP2R1, cytochrome P450, family 2, subfamily R, polypeptide 1

<400> SEQUENCE: 17

Met Arg Gly Pro Pro Gly Ala Glu Ala Cys Ala Ala Gly Leu Gly Ala
1               5                   10                  15

Ala Leu Leu Leu Leu Leu Phe Val Leu Gly Val Arg Gln Leu Leu Lys
            20                  25                  30

Gln Arg Arg Pro Ala Gly Phe Pro Pro Gly Pro Ser Gly Leu Pro Phe
        35                  40                  45

Ile Gly Asn Ile Tyr Ser Leu Ala Ala Ser Gly Glu Leu Ala His Val
    50                  55                  60

Tyr Met Arg Lys Gln Ser Arg Val Tyr Gly Glu Ile Phe Ser Leu Asp
65                  70                  75                  80

Leu Gly Gly Ile Ser Ala Val Val Leu Asn Gly Tyr Asp Val Lys
                85                  90                  95

Glu Cys Leu Val His Gln Ser Glu Ile Phe Ala Asp Arg Pro Cys Leu
            100                 105                 110

Pro Leu Phe Met Lys Met Thr Lys Met Gly Gly Leu Leu Asn Ser Arg
        115                 120                 125

Tyr Gly Arg Gly Trp Val Asp His Arg Lys Leu Ala Val Asn Ser Phe
    130                 135                 140
```

```
Arg Cys Phe Gly Tyr Gly Gln Lys Ser Phe Glu Ser Lys Ile Leu Glu
145                 150                 155                 160

Glu Thr Asn Phe Phe Ile Asp Ala Ile Glu Thr Tyr Lys Gly Arg Pro
            165                 170                 175

Phe Asp Leu Lys Gln Leu Ile Thr Asn Ala Val Ser Asn Ile Thr Asn
        180                 185                 190

Leu Ile Ile Phe Gly Glu Arg Phe Thr Tyr Glu Asp Thr Asp Phe Gln
    195                 200                 205

His Met Ile Glu Leu Phe Ser Glu Asn Val Glu Leu Ala Ala Ser Ala
210                 215                 220

Ser Val Phe Leu Tyr Asn Ala Phe Pro Trp Ile Gly Ile Pro Phe
225                 230                 235                 240

Gly Lys His Gln Gln Leu Phe Arg Asn Ala Ala Val Val Tyr Asp Phe
                245                 250                 255

Leu Ser Arg Leu Ile Glu Lys Ala Ser Ile Asn Arg Lys Pro Gln Ser
            260                 265                 270

Pro Gln His Phe Val Asp Ala Tyr Leu Asn Glu Met Asp Gln Gly Lys
        275                 280                 285

Asn Asp Pro Ser Cys Thr Phe Ser Lys Glu Asn Leu Ile Phe Ser Val
290                 295                 300

Gly Glu Leu Ile Ile Ala Gly Thr Glu Thr Thr Thr Asn Val Leu Arg
305                 310                 315                 320

Trp Ala Ile Leu Phe Met Ala Leu Tyr Pro Asn Ile Gln Gly Gln Val
                325                 330                 335

Gln Lys Glu Ile Asp Leu Ile Met Gly Pro Thr Gly Lys Pro Ser Trp
            340                 345                 350

Asp Asp Lys Cys Lys Met Pro Tyr Thr Glu Ala Val Leu His Glu Val
        355                 360                 365

Leu Arg Phe Cys Asn Ile Val Pro Leu Gly Ile Phe His Ala Thr Ser
370                 375                 380

Glu Asp Ala Val Val Arg Gly Tyr Ser Ile Pro Lys Gly Thr Thr Val
385                 390                 395                 400

Ile Thr Asn Leu Tyr Ser Val His Phe Asp Lys Tyr Trp Arg Asn
                405                 410                 415

Pro Glu Ile Phe Tyr Pro Glu Arg Phe Leu Asp Ser Ser Gly Tyr Phe
            420                 425                 430

Ala Lys Lys Glu Ala Leu Val Pro Phe Ser Leu Gly Lys Arg His Cys
        435                 440                 445

Leu Gly Glu Gln Leu Ala Arg Met Glu Met Phe Leu Phe Thr Ala
450                 455                 460

Leu Leu Gln Arg Phe His Leu His Phe Pro His Gly Leu Val Pro Asp
465                 470                 475                 480

Leu Lys Pro Arg Leu Gly Met Thr Leu Gln Pro Gln Pro Tyr Leu Ile
                485                 490                 495

Cys Ala Glu Arg Arg
            500

<210> SEQ ID NO 18
<211> LENGTH: 222
<212> TYPE: PRT
<213> ORGANISM: Mus musculus
<220> FEATURE:
<223> OTHER INFORMATION: mouse Cyp2r1 protein, CYP2R1, cytochrome P450,
      family 2, subfamily r, polypeptide 1, cytochrome P450 2r1, clone
      IMAGE:40046633
```

<400> SEQUENCE: 18

```
Met Gly Asp Glu Met Asp Gln Gly Gln Asn Asp Pro Leu Ser Thr Phe
1               5                   10                  15

Ser Lys Glu Asn Leu Ile Phe Ser Val Gly Glu Leu Ile Ile Ala Gly
            20                  25                  30

Thr Glu Thr Thr Thr Asn Val Leu Arg Trp Ala Ile Leu Phe Met Ala
        35                  40                  45

Leu Tyr Pro Asn Ile Gln Gly Gln Val His Lys Glu Ile Asp Leu Ile
    50                  55                  60

Val Gly His Asn Arg Arg Pro Ser Trp Glu Tyr Lys Cys Lys Met Pro
65                  70                  75                  80

Tyr Thr Glu Ala Val Leu His Glu Val Leu Arg Phe Cys Asn Ile Val
                85                  90                  95

Pro Leu Gly Ile Phe His Ala Thr Ser Glu Asp Ala Val Val Arg Gly
            100                 105                 110

Tyr Ser Ile Pro Lys Gly Thr Val Ile Thr Asn Leu Tyr Ser Val
        115                 120                 125

His Phe Asp Glu Lys Tyr Trp Lys Asp Pro Asp Met Phe Tyr Pro Glu
    130                 135                 140

Arg Phe Leu Asp Ser Asn Gly Tyr Phe Thr Lys Lys Glu Ala Leu Ile
145                 150                 155                 160

Pro Phe Ser Leu Gly Arg Arg His Cys Leu Gly Glu Gln Leu Ala Arg
                165                 170                 175

Met Glu Met Phe Leu Phe Phe Thr Ser Leu Leu Gln Gln Phe His Leu
            180                 185                 190

His Phe Pro His Glu Leu Val Pro Asn Leu Lys Pro Arg Leu Gly Met
        195                 200                 205

Thr Leu Gln Pro Gln Pro Tyr Leu Ile Cys Ala Glu Arg Arg
    210                 215                 220
```

<210> SEQ ID NO 19
<211> LENGTH: 422
<212> TYPE: PRT
<213> ORGANISM: Bacillus halodurans
<220> FEATURE:
<223> OTHER INFORMATION: Bacillus halodurans strain C-125 fatty acid alpha hydroxylase, CYP152A6

<400> SEQUENCE: 19

```
Met Lys Ser Asn Asp Pro Ile Pro Lys Asp Ser Pro Leu Asp His Thr
1               5                   10                  15

Met Asn Leu Met Arg Glu Gly Tyr Glu Phe Leu Ser His Arg Met Glu
            20                  25                  30

Arg Phe Gln Thr Asp Leu Phe Glu Thr Arg Val Met Gly Gln Lys Val
        35                  40                  45

Leu Cys Ile Arg Gly Ala Glu Ala Val Lys Leu Phe Tyr Asp Pro Glu
    50                  55                  60

Arg Phe Lys Arg His Arg Ala Thr Pro Lys Arg Ile Gln Lys Ser Leu
65                  70                  75                  80

Phe Gly Glu Asn Ala Ile Gln Thr Met Asp Asp Lys Ala His Leu His
                85                  90                  95

Arg Lys Gln Leu Phe Leu Ser Met Met Lys Pro Glu Asp Glu Gln Glu
            100                 105                 110

Leu Ala Arg Leu Thr His Glu Thr Trp Arg Arg Val Ala Glu Gly Trp
        115                 120                 125
```

```
Lys Lys Ser Arg Pro Ile Val Leu Phe Asp Glu Ala Lys Arg Val Leu
130                 135                 140

Cys Gln Val Ala Cys Glu Trp Ala Glu Val Pro Leu Lys Ser Thr Glu
145                 150                 155                 160

Ile Asp Arg Arg Ala Glu Asp Phe His Ala Met Val Asp Ala Phe Gly
                165                 170                 175

Ala Val Gly Pro Arg His Trp Arg Gly Arg Lys Gly Arg Arg Arg Thr
            180                 185                 190

Glu Arg Trp Ile Gln Ser Ile Ile His Gln Val Arg Thr Gly Ser Leu
        195                 200                 205

Gln Ala Arg Glu Gly Ser Pro Leu Tyr Lys Val Ser Tyr His Arg Glu
210                 215                 220

Leu Asn Gly Lys Leu Leu Asp Glu Arg Met Ala Ala Ile Glu Leu Ile
225                 230                 235                 240

Asn Val Leu Arg Pro Ile Val Ala Ile Ala Thr Phe Ile Ser Phe Ala
                245                 250                 255

Ala Ile Ala Leu Gln Glu His Pro Glu Trp Gln Arg Leu Lys Asn
            260                 265                 270

Gly Ser Asn Glu Glu Phe His Met Phe Val Gln Glu Val Arg Arg Tyr
        275                 280                 285

Tyr Pro Phe Ala Pro Leu Ile Gly Ala Lys Val Arg Lys Ser Phe Thr
290                 295                 300

Trp Lys Gly Val Arg Phe Lys Lys Gly Arg Leu Val Phe Leu Asp Met
305                 310                 315                 320

Tyr Gly Thr Asn His Asp Pro Lys Leu Trp Asp Glu Pro Asp Ala Phe
                325                 330                 335

Arg Pro Glu Arg Phe Gln Glu Arg Lys Asp Ser Leu Tyr Asp Phe Ile
            340                 345                 350

Pro Gln Gly Gly Gly Asp Pro Thr Lys Gly His Arg Cys Pro Gly Glu
        355                 360                 365

Gly Ile Thr Val Glu Val Met Lys Thr Thr Met Asp Phe Leu Val Asn
370                 375                 380

Asp Ile Asp Tyr Asp Val Pro Asp Gln Ile Ser Tyr Ser Leu Ser
385                 390                 395                 400

Arg Met Pro Thr Arg Pro Glu Ser Gly Tyr Ile Met Ala Asn Ile Glu
                405                 410                 415

Arg Lys Tyr Glu His Ala
            420

<210> SEQ ID NO 20
<211> LENGTH: 389
<212> TYPE: PRT
<213> ORGANISM: Streptomyces parvus
<220> FEATURE:
<223> OTHER INFORMATION: Streptomyces parvus strain HCCB10043 cytochrome
      P450, aryC

<400> SEQUENCE: 20

Met Tyr Leu Gly Gly Arg Arg Gly Thr Glu Ala Val Gly Glu Ser Arg
1               5                   10                  15

Glu Pro Gly Val Trp Glu Val Phe Arg Tyr Asp Glu Ala Val Gln Val
                20                  25                  30

Leu Gly Asp His Arg Thr Phe Ser Ser Asp Met Asn His Phe Ile Pro
            35                  40                  45

Glu Glu Gln Arg Gln Leu Ala Arg Ala Ala Arg Gly Asn Phe Val Gly
```

```
              50                  55                  60
Ile Asp Pro Pro Asp His Thr Gln Leu Arg Gly Leu Val Ser Gln Ala
 65                  70                  75                  80

Phe Ser Pro Arg Val Thr Ala Ala Leu Glu Pro Arg Ile Gly Arg Leu
                 85                  90                  95

Ala Glu Gln Leu Leu Asp Asp Ile Val Ala Arg Gly Asp Lys Ala
            100                 105                 110

Ser Cys Asp Leu Val Gly Glu Phe Ala Gly Pro Leu Ser Ala Ile Val
            115                 120                 125

Ile Ala Glu Leu Phe Gly Ile Pro Glu Ser Asp His Thr Met Ile Ala
            130                 135                 140

Glu Trp Ala Lys Ala Leu Leu Gly Ser Arg Pro Ala Gly Glu Leu Ser
145                 150                 155                 160

Ile Ala Asp Glu Ala Ala Met Gln Asn Thr Ala Asp Leu Val Arg Arg
                165                 170                 175

Ala Gly Glu Tyr Leu Val His His Ile Thr Glu Arg Arg Ala Arg Pro
            180                 185                 190

Gln Asp Asp Leu Thr Ser Arg Leu Ala Thr Thr Glu Val Asp Gly Lys
            195                 200                 205

Arg Leu Asp Asp Glu Glu Ile Val Gly Val Ile Gly Met Phe Leu Ile
210                 215                 220

Ala Gly Tyr Leu Pro Ala Ser Val Leu Thr Ala Asn Thr Val Met Ala
225                 230                 235                 240

Leu Asp Glu His Pro Ala Ala Leu Ala Glu Val Arg Ser Asp Pro Ala
                245                 250                 255

Leu Leu Pro Gly Ala Ile Glu Glu Val Leu Arg Trp Arg Pro Pro Leu
            260                 265                 270

Val Arg Asp Gln Arg Leu Thr Thr Arg Asp Ala Asp Leu Gly Gly Arg
            275                 280                 285

Thr Val Pro Ala Gly Ser Met Val Cys Val Trp Leu Ala Ser Ala His
            290                 295                 300

Arg Asp Pro Phe Arg Phe Glu Asn Pro Asp Leu Phe Asp Ile His Arg
305                 310                 315                 320

Asn Ala Gly Arg His Leu Ala Phe Gly Lys Gly Ile His Tyr Cys Leu
                325                 330                 335

Gly Ala Pro Leu Ala Arg Leu Glu Ala Arg Ile Ala Val Glu Thr Leu
            340                 345                 350

Leu Arg Arg Phe Glu Arg Ile Glu Ile Pro Arg Asp Glu Ser Val Glu
            355                 360                 365

Phe His Glu Ser Ile Gly Val Leu Gly Pro Val Arg Leu Pro Thr Thr
            370                 375                 380

Leu Phe Ala Arg Arg
385

<210> SEQ ID NO 21
<211> LENGTH: 414
<212> TYPE: PRT
<213> ORGANISM: Pseudomonas putida
<220> FEATURE:
<223> OTHER INFORMATION: camphor 5-monooxygenase, camC, cyp101, locus
      CPXA_PSEPU, CYP101A1, cytochrome P450cam

<400> SEQUENCE: 21

Thr Thr Glu Thr Ile Gln Ser Asn Ala Asn Leu Ala Pro Leu Pro Pro
  1               5                  10                  15
```

His Val Pro Glu His Leu Val Phe Asp Phe Asp Met Tyr Asn Pro Ser
            20                  25                  30

Asn Leu Ser Ala Gly Val Gln Glu Ala Trp Ala Val Leu Gln Glu Ser
        35                  40                  45

Asn Val Pro Asp Leu Val Trp Thr Arg Cys Asn Gly Gly His Trp Ile
    50                  55                  60

Ala Thr Arg Gly Gln Leu Ile Arg Glu Ala Tyr Glu Asp Tyr Arg His
65                  70                  75                  80

Phe Ser Ser Glu Cys Pro Phe Ile Pro Arg Glu Ala Gly Glu Ala Tyr
                85                  90                  95

Asp Phe Ile Pro Thr Ser Met Asp Pro Pro Glu Gln Arg Gln Phe Arg
            100                 105                 110

Ala Leu Ala Asn Gln Val Val Gly Met Pro Val Val Asp Lys Leu Glu
        115                 120                 125

Asn Arg Ile Gln Glu Leu Ala Cys Ser Leu Ile Glu Ser Leu Arg Pro
    130                 135                 140

Gln Gly Gln Cys Asn Phe Thr Glu Asp Tyr Ala Glu Pro Phe Pro Ile
145                 150                 155                 160

Arg Ile Phe Met Leu Leu Ala Gly Leu Pro Glu Glu Asp Ile Pro His
                165                 170                 175

Leu Lys Tyr Leu Thr Asp Gln Met Thr Arg Pro Asp Gly Ser Met Thr
            180                 185                 190

Phe Ala Glu Ala Lys Glu Ala Leu Tyr Asp Tyr Leu Ile Pro Ile Ile
        195                 200                 205

Glu Gln Arg Arg Gln Lys Pro Gly Thr Asp Ala Ile Ser Ile Val Ala
    210                 215                 220

Asn Gly Gln Val Asn Gly Arg Pro Ile Thr Ser Asp Glu Ala Lys Arg
225                 230                 235                 240

Met Cys Gly Leu Leu Leu Val Gly Gly Leu Asp Thr Val Val Asn Phe
                245                 250                 255

Leu Ser Phe Ser Met Glu Phe Leu Ala Lys Ser Pro Glu His Arg Gln
            260                 265                 270

Glu Leu Ile Glu Arg Pro Glu Arg Ile Pro Ala Ala Cys Glu Glu Leu
        275                 280                 285

Leu Arg Arg Phe Ser Leu Val Ala Asp Gly Arg Ile Leu Thr Ser Asp
    290                 295                 300

Tyr Glu Phe His Gly Val Gln Leu Lys Lys Gly Asp Gln Ile Leu Leu
305                 310                 315                 320

Pro Gln Met Leu Ser Gly Leu Asp Glu Arg Glu Asn Ala Cys Pro Met
                325                 330                 335

His Val Asp Phe Ser Arg Gln Lys Val Ser His Thr Thr Phe Gly His
            340                 345                 350

Gly Ser His Leu Cys Leu Gly Gln His Leu Ala Arg Arg Glu Ile Ile
        355                 360                 365

Val Thr Leu Lys Glu Trp Leu Thr Arg Ile Pro Asp Phe Ser Ile Ala
    370                 375                 380

Pro Gly Ala Gln Ile Gln His Lys Ser Gly Ile Val Ser Gly Val Gln
385                 390                 395                 400

Ala Leu Pro Leu Val Trp Asp Pro Ala Thr Thr Lys Ala Val
                405                 410

<210> SEQ ID NO 22
<211> LENGTH: 515
<212> TYPE: PRT

<213> ORGANISM: Homo sapiens
<220> FEATURE:
<223> OTHER INFORMATION: human cytochrome P450, CYP2D7, CYP2D, mono-oxygenase, xenobiotic metabolizing enzyme

<400> SEQUENCE: 22

```
Gly Leu Glu Ala Leu Val Pro Leu Ala Met Ile Val Ala Ile Phe Leu
 1               5                  10                  15
Leu Leu Val Asp Leu Met His Arg His Gln Arg Trp Ala Ala Arg Tyr
             20                  25                  30
Pro Pro Gly Pro Leu Pro Leu Pro Gly Leu Gly Asn Leu Leu His Val
         35                  40                  45
Asp Phe Gln Asn Thr Pro Tyr Cys Phe Asp Gln Leu Arg Arg Arg Phe
 50                  55                  60
Gly Asp Val Phe Asn Leu Gln Leu Ala Trp Thr Pro Val Val Val Leu
 65                  70                  75                  80
Asn Gly Leu Ala Ala Val Arg Glu Ala Met Val Thr Arg Gly Glu Asp
                 85                  90                  95
Thr Ala Asp Arg Pro Pro Ala Pro Ile Tyr Gln Val Leu Gly Phe Gly
            100                 105                 110
Pro Arg Ser Gln Gly Val Ile Leu Ser Arg Tyr Gly Pro Ala Trp Arg
        115                 120                 125
Glu Gln Arg Arg Phe Ser Val Ser Thr Leu Arg Asn Leu Gly Leu Gly
130                 135                 140
Lys Lys Ser Leu Glu Gln Trp Val Thr Glu Glu Ala Ala Cys Leu Cys
145                 150                 155                 160
Ala Ala Phe Ala Asp Gln Ala Gly Arg Pro Phe Arg Pro Asn Gly Leu
                165                 170                 175
Leu Asp Lys Ala Val Ser Asn Val Ile Ala Ser Leu Thr Cys Gly Arg
            180                 185                 190
Arg Phe Glu Tyr Asp Asp Pro Arg Phe Leu Arg Leu Leu Asp Leu Ala
        195                 200                 205
Gln Glu Gly Leu Lys Glu Glu Ser Gly Phe Leu Arg Glu Val Leu Asn
210                 215                 220
Ala Val Pro Val Leu Pro His Ile Pro Ala Leu Ala Gly Lys Val Leu
225                 230                 235                 240
Arg Phe Gln Lys Ala Phe Leu Thr Gln Leu Asp Glu Leu Leu Thr Glu
                245                 250                 255
His Arg Met Thr Trp Asp Pro Ala Gln Pro Pro Arg Asp Leu Thr Glu
            260                 265                 270
Ala Phe Leu Ala Lys Lys Glu Lys Ala Lys Gly Ser Pro Glu Ser Ser
        275                 280                 285
Phe Asn Asp Glu Asn Leu Arg Ile Val Val Gly Asn Leu Phe Leu Ala
290                 295                 300
Gly Met Val Thr Thr Leu Thr Thr Leu Ala Trp Gly Leu Leu Leu Met
305                 310                 315                 320
Ile Leu His Leu Asp Val Gln Arg Gly Arg Arg Val Ser Pro Gly Cys
                325                 330                 335
Ser Pro Ile Val Gly Thr His Val Cys Pro Val Arg Val Gln Gln Glu
            340                 345                 350
Ile Asp Asp Val Ile Gly Gln Val Arg Arg Pro Glu Met Gly Asp Gln
        355                 360                 365
Val His Met Pro Tyr Thr Thr Ala Val Ile His Glu Val Gln Arg Phe
370                 375                 380
```

```
Gly Asp Ile Val Pro Leu Gly Val Thr His Met Thr Ser Arg Asp Ile
385                 390                 395                 400

Glu Val Gln Gly Phe Arg Ile Pro Lys Gly Thr Thr Leu Ile Thr Asn
            405                 410                 415

Leu Ser Ser Val Leu Lys Asp Glu Ala Val Trp Glu Lys Pro Phe Arg
        420                 425                 430

Phe His Pro Glu His Phe Leu Asp Ala Gln Gly His Phe Val Lys Pro
    435                 440                 445

Glu Ala Phe Leu Pro Phe Ser Ala Gly Arg Arg Ala Cys Leu Gly Glu
450                 455                 460

Pro Leu Ala Arg Met Glu Leu Phe Leu Phe Phe Thr Ser Leu Leu Gln
465                 470                 475                 480

His Phe Ser Phe Ser Val Ala Ala Gly Gln Pro Arg Pro Ser His Ser
            485                 490                 495

Arg Val Val Ser Phe Leu Val Thr Pro Ser Pro Tyr Glu Leu Cys Ala
            500                 505                 510

Val Pro Arg
        515

<210> SEQ ID NO 23
<211> LENGTH: 532
<212> TYPE: PRT
<213> ORGANISM: Rattus norvegicus
<220> FEATURE:
<223> OTHER INFORMATION: rat strain Sprague-Dawley cytochrome P450,
      CYPC27, P450C27

<400> SEQUENCE: 23

Ala Val Leu Ser Arg Met Arg Leu Arg Trp Ala Leu Leu Asp Thr Arg
1               5                   10                  15

Val Met Gly His Gly Leu Cys Pro Gln Gly Ala Arg Ala Lys Ala Ala
            20                  25                  30

Ile Pro Ala Ala Leu Arg Asp His Glu Ser Thr Glu Gly Pro Gly Thr
        35                  40                  45

Gly Gln Asp Arg Pro Arg Leu Arg Ser Leu Ala Glu Leu Pro Gly Pro
    50                  55                  60

Gly Thr Leu Arg Phe Leu Phe Gln Leu Phe Leu Arg Gly Tyr Val Leu
65                  70                  75                  80

His Leu His Glu Leu Gln Ala Leu Asn Lys Ala Lys Tyr Gly Pro Met
                85                  90                  95

Trp Thr Thr Thr Phe Gly Thr Arg Thr Asn Val Asn Leu Ala Ser Ala
            100                 105                 110

Pro Leu Leu Glu Gln Val Met Arg Gln Glu Gly Lys Tyr Pro Ile Arg
        115                 120                 125

Asp Ser Met Glu Gln Trp Lys Glu His Arg Asp Lys Gly Leu Ser
    130                 135                 140

Tyr Gly Ile Phe Ile Thr Gln Gly Gln Gln Trp Tyr His Leu Arg His
145                 150                 155                 160

Ser Leu Asn Gln Arg Met Leu Lys Pro Ala Glu Ala Leu Tyr Thr
                165                 170                 175

Asp Ala Leu Asn Glu Val Ile Ser Asp Phe Ile Ala Arg Leu Asp Gln
            180                 185                 190

Val Arg Thr Glu Ser Ala Ser Gly Asp Gln Val Pro Asp Val Ala His
        195                 200                 205

Leu Leu Tyr His Leu Ala Leu Glu Ala Ile Cys Tyr Ile Leu Phe Glu
    210                 215                 220
```

```
Lys Arg Val Gly Cys Leu Glu Pro Ser Ile Pro Glu Asp Thr Ala Thr
225                 230                 235                 240

Phe Ile Arg Ser Val Gly Leu Met Phe Lys Asn Ser Val Tyr Val Thr
                245                 250                 255

Phe Leu Pro Lys Trp Ser Arg Pro Leu Leu Pro Phe Trp Lys Arg Tyr
            260                 265                 270

Met Asn Asn Trp Asp Asn Ile Phe Ser Phe Gly Glu Lys Met Ile His
        275                 280                 285

Gln Lys Val Gln Glu Ile Glu Ala Gln Leu Gln Ala Ala Gly Pro Asp
    290                 295                 300

Gly Val Gln Val Ser Gly Tyr Leu His Phe Leu Leu Lys Glu Leu
305                 310                 315                 320

Leu Ser Pro Gln Glu Thr Val Gly Thr Phe Pro Glu Leu Ile Leu Ala
                325                 330                 335

Gly Val Asp Thr Thr Ser Asn Thr Leu Thr Trp Ala Leu Tyr His Leu
            340                 345                 350

Ser Lys Asn Pro Glu Ile Gln Glu Ala Leu His Lys Glu Val Thr Gly
        355                 360                 365

Val Val Pro Phe Gly Lys Val Pro Gln Asn Lys Asp Phe Ala His Met
    370                 375                 380

Pro Leu Leu Lys Ala Val Ile Lys Glu Thr Leu Arg Leu Tyr Pro Val
385                 390                 395                 400

Val Pro Thr Asn Ser Arg Ile Ile Thr Glu Lys Glu Thr Glu Ile Asn
                405                 410                 415

Gly Phe Leu Phe Pro Lys Asn Thr Gln Phe Val Leu Cys Thr Tyr Val
            420                 425                 430

Val Ser Arg Asp Pro Ser Val Phe Pro Glu Pro Glu Ser Phe Gln Pro
        435                 440                 445

His Arg Trp Leu Arg Lys Arg Glu Asp Asp Asn Ser Gly Ile Gln His
    450                 455                 460

Pro Phe Gly Ser Val Pro Phe Gly Tyr Gly Val Arg Ser Cys Leu Gly
465                 470                 475                 480

Arg Arg Ile Ala Glu Leu Glu Met Gln Leu Leu Ser Arg Leu
                485                 490                 495

Gln Lys Tyr Glu Val Val Leu Ser Pro Gly Met Gly Glu Val Lys Ser
            500                 505                 510

Val Ser Arg Ile Val Leu Val Pro Ser Lys Lys Val Ser Leu Arg Phe
        515                 520                 525

Leu Gln Arg Gln
    530

<210> SEQ ID NO 24
<211> LENGTH: 491
<212> TYPE: PRT
<213> ORGANISM: Oryctolagus cuniculus
<220> FEATURE:
<223> OTHER INFORMATION: rabbit cytochrome P450, CYP2B4

<400> SEQUENCE: 24

Met Glu Phe Ser Leu Leu Leu Leu Ala Phe Leu Ala Gly Leu Leu
 1               5                  10                  15

Leu Leu Leu Phe Arg Gly His Pro Lys Ala His Gly Arg Leu Pro Pro
                20                  25                  30

Gly Pro Ser Pro Leu Pro Val Leu Gly Asn Leu Leu Gln Met Asp Arg
            35                  40                  45
```

```
Lys Gly Leu Leu Arg Ser Phe Leu Arg Leu Arg Glu Lys Tyr Gly Asp
    50                  55                  60
Val Phe Thr Val Tyr Leu Gly Ser Arg Pro Val Val Leu Cys Gly
65                  70                  75                  80
Thr Asp Ala Ile Arg Glu Ala Leu Val Asp Gln Ala Glu Ala Phe Ser
                85                  90                  95
Gly Arg Gly Lys Ile Ala Val Val Asp Pro Ile Phe Gln Gly Tyr Gly
            100                 105                 110
Val Ile Phe Ala Asn Gly Glu Arg Trp Arg Ala Leu Arg Arg Phe Ser
        115                 120                 125
Leu Ala Thr Met Arg Asp Phe Gly Met Gly Lys Arg Ser Val Glu Glu
    130                 135                 140
Arg Ile Gln Glu Glu Ala Arg Cys Leu Val Glu Glu Leu Arg Lys Ser
145                 150                 155                 160
Lys Gly Ala Leu Leu Asp Asn Thr Leu Leu Phe His Ser Ile Thr Ser
                165                 170                 175
Asn Ile Ile Cys Ser Ile Val Phe Gly Lys Arg Phe Asp Tyr Lys Asp
            180                 185                 190
Pro Val Phe Leu Arg Leu Leu Asp Leu Phe Phe Gln Ser Phe Ser Leu
        195                 200                 205
Ile Ser Ser Phe Ser Ser Gln Val Phe Glu Leu Phe Pro Gly Phe Leu
    210                 215                 220
Lys His Phe Pro Gly Thr His Arg Gln Ile Tyr Arg Asn Leu Gln Glu
225                 230                 235                 240
Ile Asn Thr Phe Ile Gly Gln Ser Val Glu Lys His Arg Ala Thr Leu
                245                 250                 255
Asp Pro Ser Asn Pro Arg Asp Phe Ile Asp Val Tyr Leu Leu Arg Met
            260                 265                 270
Glu Lys Asp Lys Ser Asp Pro Ser Ser Glu Phe His His Gln Asn Leu
        275                 280                 285
Ile Leu Thr Val Leu Ser Leu Phe Phe Ala Gly Thr Glu Thr Thr Ser
    290                 295                 300
Thr Thr Leu Arg Tyr Gly Phe Leu Leu Met Leu Lys Tyr Pro His Val
305                 310                 315                 320
Thr Glu Arg Val Gln Lys Glu Ile Glu Gln Val Ile Gly Ser His Arg
                325                 330                 335
Pro Pro Ala Leu Asp Asp Arg Ala Lys Met Pro Tyr Thr Asp Ala Val
            340                 345                 350
Ile His Glu Ile Gln Arg Leu Gly Asp Leu Ile Pro Phe Gly Val Pro
        355                 360                 365
His Thr Val Thr Lys Asp Thr Gln Phe Arg Gly Tyr Val Ile Pro Lys
    370                 375                 380
Asn Thr Glu Val Phe Pro Val Leu Ser Ser Ala Leu His Asp Pro Arg
385                 390                 395                 400
Tyr Phe Glu Thr Pro Asn Thr Phe Asn Pro Gly His Phe Leu Asp Ala
                405                 410                 415
Asn Gly Ala Leu Lys Arg Asn Glu Gly Phe Met Pro Phe Ser Leu Gly
            420                 425                 430
Lys Arg Ile Cys Leu Gly Glu Gly Ile Ala Arg Thr Glu Leu Phe Leu
        435                 440                 445
Phe Phe Thr Thr Ile Leu Gln Asn Phe Ser Ile Ala Ser Pro Val Pro
    450                 455                 460
```

Pro Glu Asp Ile Asp Leu Thr Pro Arg Glu Ser Gly Val Gly Asn Val
465                 470                 475                 480

Pro Pro Ser Tyr Gln Ile Arg Phe Leu Ala Arg
                485                 490

<210> SEQ ID NO 25
<211> LENGTH: 1061
<212> TYPE: PRT
<213> ORGANISM: Bacillus subtilis
<220> FEATURE:
<223> OTHER INFORMATION: Bacillus subtilis subsp. subtilis strain 168
      probable bifunctional P-450/NADPH-P450 reductase 1, cypD, yetO,
      yfnJ, locus CYPD_BACSU, CYP102A2

<400> SEQUENCE: 25

Met Lys Glu Thr Ser Pro Ile Pro Gln Pro Lys Thr Phe Gly Pro Leu
1               5                   10                  15

Gly Asn Leu Pro Leu Ile Asp Lys Asp Lys Pro Thr Leu Ser Leu Ile
            20                  25                  30

Lys Leu Ala Glu Glu Gln Gly Pro Ile Phe Gln Ile His Thr Pro Ala
        35                  40                  45

Gly Thr Thr Ile Val Val Ser Gly His Glu Leu Val Lys Glu Val Cys
    50                  55                  60

Asp Glu Glu Arg Phe Asp Lys Ser Ile Glu Gly Ala Leu Glu Lys Val
65                  70                  75                  80

Arg Ala Phe Ser Gly Asp Gly Leu Phe Thr Ser Trp Thr His Glu Pro
                85                  90                  95

Asn Trp Arg Lys Ala His Asn Ile Leu Met Pro Thr Phe Ser Gln Arg
            100                 105                 110

Ala Met Lys Asp Tyr His Glu Lys Met Val Asp Ile Ala Val Gln Leu
        115                 120                 125

Ile Gln Lys Trp Ala Arg Leu Asn Pro Asn Glu Ala Val Asp Val Pro
    130                 135                 140

Gly Asp Met Thr Arg Leu Thr Leu Asp Thr Ile Gly Leu Cys Gly Phe
145                 150                 155                 160

Asn Tyr Arg Phe Asn Ser Tyr Tyr Arg Glu Thr Pro His Pro Phe Ile
                165                 170                 175

Asn Ser Met Val Arg Ala Leu Asp Glu Ala Met His Gln Met Gln Arg
            180                 185                 190

Leu Asp Val Gln Asp Lys Leu Met Val Arg Thr Lys Arg Gln Phe Arg
        195                 200                 205

His Asp Ile Gln Thr Met Phe Ser Leu Val Asp Ser Ile Ile Ala Glu
    210                 215                 220

Arg Arg Ala Asn Gly Asp Gln Asp Glu Lys Asp Leu Leu Ala Arg Met
225                 230                 235                 240

Leu Asn Val Glu Asp Pro Glu Thr Gly Glu Lys Leu Asp Asp Glu Asn
                245                 250                 255

Ile Arg Phe Gln Ile Ile Thr Phe Leu Ile Ala Gly His Glu Thr Thr
            260                 265                 270

Ser Gly Leu Leu Ser Phe Ala Thr Tyr Phe Leu Leu Lys His Pro Asp
        275                 280                 285

Lys Leu Lys Lys Ala Tyr Glu Glu Val Asp Arg Val Leu Thr Asp Ala
    290                 295                 300

Ala Pro Thr Tyr Lys Gln Val Leu Glu Leu Thr Tyr Ile Arg Met Ile
305                 310                 315                 320

Leu Asn Glu Ser Leu Arg Leu Trp Pro Thr Ala Pro Ala Phe Ser Leu

-continued

```
                325                 330                 335
Tyr Pro Lys Glu Asp Thr Val Ile Gly Gly Lys Phe Pro Ile Thr Thr
            340                 345                 350
Asn Asp Arg Ile Ser Val Leu Ile Pro Gln Leu His Arg Asp Arg Asp
        355                 360                 365
Ala Trp Gly Lys Asp Ala Glu Glu Phe Arg Pro Glu Arg Phe Glu His
    370                 375                 380
Gln Asp Gln Val Pro His His Ala Tyr Lys Pro Phe Gly Asn Gly Gln
385                 390                 395                 400
Arg Ala Cys Ile Gly Met Gln Phe Ala Leu His Glu Ala Thr Leu Val
                405                 410                 415
Leu Gly Met Ile Leu Lys Tyr Phe Thr Leu Ile Asp His Glu Asn Tyr
            420                 425                 430
Glu Leu Asp Ile Lys Gln Thr Leu Thr Leu Lys Pro Gly Asp Phe His
        435                 440                 445
Ile Arg Val Gln Ser Arg Asn Gln Asp Ala Ile His Ala Asp Val Gln
    450                 455                 460
Ala Val Glu Lys Ala Ala Ser Asp Glu Gln Lys Glu Lys Thr Glu Ala
465                 470                 475                 480
Lys Gly Thr Ser Val Ile Gly Leu Asn Asn Arg Pro Leu Leu Val Leu
                485                 490                 495
Tyr Gly Ser Asp Thr Gly Thr Ala Glu Gly Val Ala Arg Glu Leu Ala
            500                 505                 510
Asp Thr Ala Ser Leu His Gly Val Arg Thr Glu Thr Ala Pro Leu Asn
        515                 520                 525
Asp Arg Ile Gly Lys Leu Pro Lys Glu Gly Ala Val Val Ile Val Thr
    530                 535                 540
Ser Ser Tyr Asn Gly Lys Pro Pro Ser Asn Ala Gly Gln Phe Val Gln
545                 550                 555                 560
Trp Leu Gln Glu Ile Lys Pro Gly Glu Leu Glu Gly Val His Tyr Ala
                565                 570                 575
Val Phe Gly Cys Gly Asp His Asn Trp Ala Ser Thr Tyr Gln Tyr Val
            580                 585                 590
Pro Arg Phe Ile Asp Glu Gln Leu Ala Glu Lys Gly Ala Thr Arg Phe
        595                 600                 605
Ser Ala Arg Gly Glu Gly Asp Val Ser Gly Asp Phe Glu Gly Gln Leu
    610                 615                 620
Asp Glu Trp Lys Lys Ser Met Trp Ala Asp Ala Ile Lys Ala Phe Gly
625                 630                 635                 640
Leu Glu Leu Asn Glu Asn Ala Asp Lys Glu Arg Ser Thr Leu Ser Leu
                645                 650                 655
Gln Phe Val Arg Gly Leu Gly Glu Ser Pro Leu Ala Arg Ser Tyr Glu
            660                 665                 670
Ala Ser His Ala Ser Ile Ala Glu Asn Arg Glu Leu Gln Ser Ala Asp
        675                 680                 685
Ser Asp Arg Ser Thr Arg His Ile Glu Ile Ala Leu Pro Pro Asp Val
    690                 695                 700
Glu Tyr Gln Glu Gly Asp His Leu Gly Val Leu Pro Lys Asn Ser Gln
705                 710                 715                 720
Thr Asn Val Ser Arg Ile Leu His Arg Phe Gly Leu Lys Gly Thr Asp
                725                 730                 735
Gln Val Thr Leu Ser Ala Ser Gly Arg Ser Ala Gly His Leu Pro Leu
            740                 745                 750
```

-continued

```
Gly Arg Pro Val Ser Leu His Asp Leu Leu Ser Tyr Ser Val Glu Val
            755                 760                 765

Gln Glu Ala Ala Thr Arg Ala Gln Ile Arg Glu Leu Ala Ala Phe Thr
        770                 775                 780

Val Cys Pro Pro His Arg Arg Glu Leu Glu Glu Leu Ser Ala Glu Gly
785                 790                 795                 800

Val Tyr Gln Glu Gln Ile Leu Lys Lys Arg Ile Ser Met Leu Asp Leu
                805                 810                 815

Leu Glu Lys Tyr Glu Ala Cys Asp Met Pro Phe Glu Arg Phe Leu Glu
            820                 825                 830

Leu Leu Arg Pro Leu Lys Pro Arg Tyr Tyr Ser Ile Ser Ser Ser Pro
        835                 840                 845

Arg Val Asn Pro Arg Gln Ala Ser Ile Thr Val Gly Val Val Arg Gly
    850                 855                 860

Pro Ala Trp Ser Gly Arg Gly Glu Tyr Arg Gly Val Ala Ser Asn Asp
865                 870                 875                 880

Leu Ala Glu Arg Gln Ala Gly Asp Asp Val Val Met Phe Ile Arg Thr
                885                 890                 895

Pro Glu Ser Arg Phe Gln Leu Pro Lys Asp Pro Glu Thr Pro Ile Ile
            900                 905                 910

Met Val Gly Pro Gly Thr Gly Val Ala Pro Phe Arg Gly Phe Leu Gln
        915                 920                 925

Ala Arg Asp Val Leu Lys Arg Glu Gly Lys Thr Leu Gly Glu Ala His
    930                 935                 940

Leu Tyr Phe Gly Cys Arg Asn Asp Arg Asp Phe Ile Tyr Arg Asp Glu
945                 950                 955                 960

Leu Glu Arg Phe Glu Lys Asp Gly Ile Val Thr Val His Thr Ala Phe
                965                 970                 975

Ser Arg Lys Glu Gly Met Pro Lys Thr Tyr Val Gln His Leu Met Ala
            980                 985                 990

Asp Gln Ala Asp Thr Leu Ile Ser Ile Leu Asp Arg Gly Gly Arg Leu
        995                 1000                1005

Tyr Val Cys Gly Asp Gly Ser Lys Met Ala Pro Asp Val Glu Ala Ala
    1010                1015                1020

Leu Gln Lys Ala Tyr Gln Ala Val His Gly Thr Gly Glu Gln Glu Ala
1025                1030                1035                1040

Gln Asn Trp Leu Arg His Leu Gln Asp Thr Gly Met Tyr Ala Lys Asp
                1045                1050                1055

Val Trp Ala Gly Ile
            1060

<210> SEQ ID NO 26
<211> LENGTH: 1054
<212> TYPE: PRT
<213> ORGANISM: Bacillus subtilis
<220> FEATURE:
<223> OTHER INFORMATION: Bacillus subtilis subsp. subtilis strain 168
      probable bifunctional P-450/NADPH-P450 reductase 2, cypE, yrhJ,
      locus BSU27160, locus CYPE_BACSU, CYP102A3

<400> SEQUENCE: 26

Met Lys Gln Ala Ser Ala Ile Pro Gln Pro Lys Thr Tyr Gly Pro Leu
1               5                   10                  15

Lys Asn Leu Pro His Leu Glu Lys Glu Gln Leu Ser Gln Ser Leu Trp
            20                  25                  30
```

-continued

```
Arg Ile Ala Asp Glu Leu Gly Pro Ile Phe Arg Phe Asp Phe Pro Gly
            35                  40                  45

Val Ser Ser Val Phe Val Ser Gly His Asn Leu Val Ala Glu Val Cys
 50                  55                  60

Asp Glu Ser Arg Phe Asp Lys Asn Leu Gly Lys Gly Leu Gln Lys Val
 65                  70                  75                  80

Arg Glu Phe Gly Gly Asp Gly Leu Phe Thr Ser Trp Thr His Glu Pro
                 85                  90                  95

Asn Trp Gln Lys Ala His Arg Ile Leu Leu Pro Ser Phe Ser Gln Lys
             100                 105                 110

Ala Met Lys Gly Tyr His Ser Met Met Leu Asp Ile Ala Thr Gln Leu
             115                 120                 125

Ile Gln Lys Trp Ser Arg Leu Asn Pro Asn Glu Glu Ile Asp Val Ala
 130                 135                 140

Asp Asp Met Thr Arg Leu Thr Leu Asp Thr Ile Gly Leu Cys Gly Phe
145                 150                 155                 160

Asn Tyr Arg Phe Asn Ser Phe Tyr Arg Asp Ser Gln His Pro Phe Ile
                165                 170                 175

Thr Ser Met Leu Arg Ala Leu Lys Glu Ala Met Asn Gln Ser Lys Arg
            180                 185                 190

Leu Gly Leu Gln Asp Lys Met Met Val Lys Thr Lys Leu Gln Phe Gln
            195                 200                 205

Lys Asp Ile Glu Val Met Asn Ser Leu Val Asp Arg Met Ile Ala Glu
            210                 215                 220

Arg Lys Ala Asn Pro Asp Asp Asn Ile Lys Asp Leu Leu Ser Leu Met
225                 230                 235                 240

Leu Tyr Ala Lys Asp Pro Val Thr Gly Glu Thr Leu Asp Asp Glu Asn
                245                 250                 255

Ile Arg Tyr Gln Ile Ile Thr Phe Leu Ile Ala Gly His Glu Thr Thr
            260                 265                 270

Ser Gly Leu Leu Ser Phe Ala Ile Tyr Cys Leu Leu Thr His Pro Glu
            275                 280                 285

Lys Leu Lys Lys Ala Gln Glu Glu Ala Asp Arg Val Leu Thr Asp Asp
            290                 295                 300

Thr Pro Glu Tyr Lys Gln Ile Gln Gln Leu Lys Tyr Thr Arg Met Val
305                 310                 315                 320

Leu Asn Glu Thr Leu Arg Leu Tyr Pro Thr Ala Pro Ala Phe Ser Leu
                325                 330                 335

Tyr Ala Lys Glu Asp Thr Val Leu Gly Gly Glu Tyr Pro Ile Ser Lys
            340                 345                 350

Gly Gln Pro Val Thr Val Leu Ile Pro Lys Leu His Arg Asp Gln Asn
            355                 360                 365

Ala Trp Gly Pro Asp Ala Glu Asp Phe Arg Pro Glu Arg Phe Glu Asp
            370                 375                 380

Pro Ser Ser Ile Pro His His Ala Tyr Lys Pro Phe Gly Asn Gly Gln
385                 390                 395                 400

Arg Ala Cys Ile Gly Met Gln Phe Ala Leu Gln Glu Ala Thr Met Val
                405                 410                 415

Leu Gly Leu Val Leu Lys His Phe Glu Leu Ile Asn His Thr Gly Tyr
            420                 425                 430

Glu Leu Lys Ile Lys Glu Ala Leu Thr Ile Lys Pro Asp Asp Phe Lys
            435                 440                 445

Ile Thr Val Lys Pro Arg Lys Thr Ala Ala Ile Asn Val Gln Arg Lys
```

```
            450               455               460
Glu Gln Ala Asp Ile Lys Ala Glu Thr Lys Pro Lys Glu Thr Lys Pro
465                 470               475               480

Lys His Gly Thr Pro Leu Leu Val Leu Tyr Gly Ser Asn Leu Gly Thr
                    485               490               495

Ala Glu Gly Ile Ala Gly Glu Leu Ala Ala Gln Gly Arg Gln Met Gly
                500               505               510

Phe Thr Ala Glu Thr Ala Pro Leu Asp Asp Tyr Ile Gly Lys Leu Pro
                515               520               525

Glu Glu Gly Ala Val Val Ile Val Thr Ala Ser Tyr Asn Gly Ser Pro
            530               535               540

Pro Asp Asn Ala Ala Gly Phe Val Glu Trp Leu Lys Glu Leu Glu Glu
545               550               555               560

Gly Gln Leu Lys Gly Val Ser Tyr Ala Val Phe Gly Cys Gly Asn Arg
                565               570               575

Ser Trp Ala Ser Thr Tyr Gln Arg Ile Pro Arg Leu Ile Asp Asp Met
                580               585               590

Met Lys Ala Lys Gly Ala Ser Arg Leu Thr Glu Ile Gly Glu Gly Asp
                595               600               605

Ala Ala Asp Asp Phe Glu Ser His Arg Glu Ser Trp Glu Asn Arg Phe
            610               615               620

Trp Lys Glu Thr Met Asp Ala Phe Asp Ile Asn Glu Ile Ala Gln Lys
625               630               635               640

Glu Asp Arg Pro Ser Leu Ser Ile Ala Phe Leu Ser Glu Ala Thr Glu
                645               650               655

Thr Pro Val Ala Lys Ala Tyr Gly Ala Phe Glu Gly Val Val Leu Glu
                660               665               670

Asn Arg Glu Leu Gln Thr Ala Asp Ser Thr Arg Ser Thr Arg His Ile
                675               680               685

Glu Leu Glu Ile Pro Ala Gly Lys Thr Tyr Lys Glu Gly Asp His Ile
                690               695               700

Gly Ile Met Pro Lys Asn Ser Arg Glu Leu Val Gln Arg Val Leu Ser
705               710               715               720

Arg Phe Gly Leu Gln Ser Asn His Val Ile Lys Val Ser Gly Ser Ala
                725               730               735

His Met Ser His Leu Pro Met Asp Arg Pro Ile Lys Val Ala Asp Leu
                740               745               750

Leu Ser Ser Tyr Val Glu Leu Gln Glu Pro Ala Ser Arg Leu Gln Leu
                755               760               765

Arg Glu Leu Ala Ser Tyr Thr Val Cys Pro Pro His Gln Lys Glu Leu
                770               775               780

Glu Gln Leu Val Leu Asp Gly Ile Tyr Lys Glu Gln Val Leu Ala
785               790               795               800

Lys Arg Leu Thr Met Leu Asp Phe Leu Glu Asp Tyr Pro Ala Cys Glu
                805               810               815

Met Pro Phe Glu Arg Phe Leu Ala Leu Leu Pro Ser Leu Lys Pro Arg
                820               825               830

Tyr Tyr Ser Ile Ser Ser Ser Pro Lys Val His Ala Asn Ile Val Ser
                835               840               845

Met Thr Val Gly Val Val Lys Ala Ser Ala Trp Ser Gly Arg Gly Glu
                850               855               860

Tyr Arg Gly Val Ala Ser Asn Tyr Leu Ala Glu Leu Asn Thr Gly Asp
865               870               875               880
```

```
Ala Ala Ala Cys Phe Ile Arg Thr Pro Gln Ser Gly Phe Gln Met Pro
                885                 890                 895

Asp Glu Pro Glu Thr Pro Met Ile Met Val Gly Pro Gly Thr Gly Ile
            900                 905                 910

Ala Pro Phe Arg Gly Phe Ile Gln Ala Arg Ser Val Leu Lys Lys Glu
        915                 920                 925

Gly Ser Thr Leu Gly Glu Ala Leu Leu Tyr Phe Gly Cys Arg Arg Pro
    930                 935                 940

Asp His Asp Asp Leu Tyr Arg Glu Glu Leu Asp Gln Ala Glu Gln Glu
945                 950                 955                 960

Gly Leu Val Thr Ile Arg Arg Cys Tyr Ser Arg Val Glu Asn Glu Ser
                965                 970                 975

Lys Gly Tyr Val Gln His Leu Leu Lys Gln Asp Ser Gln Lys Leu Met
                980                 985                 990

Thr Leu Ile Glu Lys Gly Ala His Ile Tyr Val Cys Gly Asp Gly Ser
            995                 1000                1005

Gln Met Ala Pro Asp Val Glu Lys Thr Leu Arg Trp Ala Tyr Glu Thr
        1010                1015                1020

Glu Lys Gly Ala Ser Gln Glu Glu Ser Ala Asp Trp Leu Gln Lys Leu
1025                1030                1035                1040

Gln Asp Gln Lys Arg Tyr Ile Lys Asp Val Trp Thr Gly Asn
                1045                1050

<210> SEQ ID NO 27
<211> LENGTH: 1049
<212> TYPE: PRT
<213> ORGANISM: Bacillus megaterium
<220> FEATURE:
<223> OTHER INFORMATION: Bacillus megaterium strain DSM 32 bifunctional
      P-450/NADPH-P450 reductase, cyp102A1, locus CPXB_BACME, CYP102A1

<400> SEQUENCE: 27

Met Thr Ile Lys Glu Met Pro Gln Pro Lys Thr Phe Gly Glu Leu Lys
  1               5                  10                  15

Asn Leu Pro Leu Leu Asn Thr Asp Lys Pro Val Gln Ala Leu Met Lys
             20                  25                  30

Ile Ala Asp Glu Leu Gly Glu Ile Phe Lys Phe Glu Ala Pro Gly Arg
         35                  40                  45

Val Thr Arg Tyr Leu Ser Ser Gln Arg Leu Ile Lys Glu Ala Cys Asp
     50                  55                  60

Glu Ser Arg Phe Asp Lys Asn Leu Ser Gln Ala Leu Lys Phe Val Arg
 65                  70                  75                  80

Asp Phe Ala Gly Asp Gly Leu Phe Thr Ser Trp Thr His Glu Lys Asn
                 85                  90                  95

Trp Lys Lys Ala His Asn Ile Leu Leu Pro Ser Phe Ser Gln Gln Ala
                100                 105                 110

Met Lys Gly Tyr His Ala Met Met Val Asp Ile Ala Val Gln Leu Val
            115                 120                 125

Gln Lys Trp Glu Arg Leu Asn Ala Asp Glu His Ile Glu Val Pro Glu
        130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
```

```
                180             185                 190
Asn Pro Asp Asp Pro Ala Tyr Asp Glu Asn Lys Arg Gln Phe Gln Glu
            195                 200                 205
Asp Ile Lys Val Met Asn Asp Leu Val Asp Lys Ile Ile Ala Asp Arg
            210                 215                 220
Lys Ala Ser Gly Glu Gln Ser Asp Asp Leu Leu Thr His Met Leu Asn
225                 230                 235                 240
Gly Lys Asp Pro Glu Thr Gly Glu Pro Leu Asp Asp Glu Asn Ile Arg
            245                 250                 255
Tyr Gln Ile Ile Thr Phe Leu Ile Ala Gly His Glu Thr Thr Ser Gly
            260                 265                 270
Leu Leu Ser Phe Ala Leu Tyr Phe Leu Val Lys Asn Pro His Val Leu
            275                 280                 285
Gln Lys Ala Ala Glu Ala Ala Arg Val Leu Val Asp Pro Val Pro
            290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
            325                 330                 335
Lys Glu Asp Thr Val Leu Gly Gly Glu Tyr Pro Leu Glu Lys Gly Asp
            340                 345                 350
Glu Leu Met Val Leu Ile Pro Gln Leu His Arg Asp Lys Thr Ile Trp
            355                 360                 365
Gly Asp Asp Val Glu Glu Phe Arg Pro Glu Arg Phe Glu Asn Pro Ser
            370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
            405                 410                 415
Met Met Leu Lys His Phe Asp Phe Glu Asp His Thr Asn Tyr Glu Leu
            420                 425                 430
Asp Ile Lys Glu Thr Leu Thr Leu Lys Pro Glu Gly Phe Val Val Lys
            435                 440                 445
Ala Lys Ser Lys Lys Ile Pro Leu Gly Gly Ile Pro Ser Pro Ser Thr
            450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Met Gly Thr Ala Glu Gly
            485                 490                 495
Thr Ala Arg Asp Leu Ala Asp Ile Ala Met Ser Lys Gly Phe Ala Pro
            500                 505                 510
Gln Val Ala Thr Leu Asp Ser His Ala Gly Asn Leu Pro Arg Glu Gly
            515                 520                 525
Ala Val Leu Ile Val Thr Ala Ser Tyr Asn Gly His Pro Pro Asp Asn
            530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
            565                 570                 575
Thr Thr Tyr Gln Lys Val Pro Ala Phe Ile Asp Glu Thr Leu Ala Ala
            580                 585                 590
Lys Gly Ala Glu Asn Ile Ala Asp Arg Gly Glu Ala Asp Ala Ser Asp
            595                 600                 605
```

```
Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln Val
        1010                1015                1020
```

-continued

Ser Glu Ala Asp Ala Arg Leu Trp Leu Gln Gln Leu Glu Glu Lys Gly
1025                1030                1035                1040

Arg Tyr Ala Lys Asp Val Trp Ala Gly
            1045

<210> SEQ ID NO 28
<211> LENGTH: 1065
<212> TYPE: PRT
<213> ORGANISM: Bacillus cereus
<220> FEATURE:
<223> OTHER INFORMATION: Bacillus cereus strain ATCC 14579
      NADPH-cytochrome P450 reductase, CYP102A5, locus BC_3211

<400> SEQUENCE: 28

Met Glu Lys Lys Val Ser Ala Ile Pro Gln Pro Lys Thr Tyr Gly Pro
1               5                   10                  15

Leu Gly Asn Leu Pro Leu Ile Asp Lys Asp Lys Pro Thr Leu Ser Phe
            20                  25                  30

Ile Lys Ile Ala Glu Glu Tyr Gly Pro Ile Phe Gln Ile Gln Thr Leu
        35                  40                  45

Ser Asp Thr Ile Ile Val Val Ser Gly His Glu Leu Val Ala Glu Val
    50                  55                  60

Cys Asp Glu Thr Arg Phe Asp Lys Ser Ile Glu Gly Ala Leu Ala Lys
65                  70                  75                  80

Val Arg Ala Phe Ala Gly Asp Gly Leu Phe Thr Ser Glu Thr His Glu
                85                  90                  95

Pro Asn Trp Lys Lys Ala His Asn Ile Leu Met Pro Thr Phe Ser Gln
            100                 105                 110

Arg Ala Met Lys Asp Tyr His Ala Met Met Val Asp Ile Ala Val Gln
        115                 120                 125

Leu Val Gln Lys Trp Ala Arg Leu Asn Pro Asn Glu Asn Val Asp Val
    130                 135                 140

Pro Glu Asp Met Thr Arg Leu Thr Leu Asp Thr Ile Gly Leu Cys Gly
145                 150                 155                 160

Phe Asn Tyr Arg Phe Asn Ser Phe Tyr Arg Glu Thr Pro His Pro Phe
                165                 170                 175

Ile Thr Ser Met Thr Arg Ala Leu Asp Glu Ala Met His Gln Leu Gln
            180                 185                 190

Arg Leu Asp Ile Glu Asp Lys Leu Met Trp Arg Thr Lys Arg Gln Phe
        195                 200                 205

Gln His Asp Ile Gln Ser Met Phe Ser Leu Val Asp Asn Ile Ile Ala
    210                 215                 220

Glu Arg Lys Ser Ser Gly Asp Gln Glu Glu Asn Asp Leu Leu Ser Arg
225                 230                 235                 240

Met Leu Asn Val Pro Asp Pro Glu Thr Gly Glu Lys Leu Asp Asp Glu
                245                 250                 255

Asn Ile Arg Phe Gln Ile Ile Thr Phe Leu Ile Ala Gly His Glu Thr
            260                 265                 270

Thr Ser Gly Leu Leu Ser Phe Ala Ile Tyr Phe Leu Leu Lys Asn Pro
        275                 280                 285

Asp Lys Leu Lys Lys Ala Tyr Glu Glu Val Asp Arg Val Leu Thr Asp
    290                 295                 300

Pro Thr Pro Thr Tyr Gln Gln Val Met Lys Leu Lys Tyr Met Arg Met
305                 310                 315                 320

Ile Leu Asn Glu Ser Leu Arg Leu Trp Pro Thr Ala Pro Ala Phe Ser
                325                 330                 335

Leu Tyr Ala Lys Glu Asp Thr Val Ile Gly Lys Tyr Pro Ile Lys
                340                 345                 350

Lys Gly Glu Asp Arg Ile Ser Val Leu Ile Pro Gln Leu His Arg Asp
            355                 360                 365

Lys Asp Ala Trp Gly Asp Asn Val Glu Glu Phe Gln Pro Glu Arg Phe
        370                 375                 380

Glu Glu Leu Asp Lys Val Pro His His Ala Tyr Lys Pro Phe Gly Asn
385                 390                 395                 400

Gly Gln Arg Ala Cys Ile Gly Met Gln Phe Ala Leu His Glu Ala Thr
                405                 410                 415

Leu Val Met Gly Met Leu Leu Gln His Phe Glu Leu Ile Asp Tyr Gln
            420                 425                 430

Asn Tyr Gln Leu Asp Val Lys Gln Thr Leu Thr Leu Lys Pro Gly Asp
        435                 440                 445

Phe Lys Ile Arg Ile Leu Pro Arg Lys Gln Thr Ile Ser His Pro Thr
    450                 455                 460

Val Leu Ala Pro Thr Glu Asp Lys Leu Lys Asn Asp Glu Ile Lys Gln
465                 470                 475                 480

His Val Gln Lys Thr Pro Ser Ile Ile Gly Ala Asp Asn Leu Ser Leu
                485                 490                 495

Leu Val Leu Tyr Gly Ser Asp Thr Gly Val Ala Glu Gly Ile Ala Arg
            500                 505                 510

Glu Leu Ala Asp Thr Ala Ser Leu Glu Gly Val Gln Thr Glu Val Val
        515                 520                 525

Ala Leu Asn Asp Arg Ile Gly Ser Leu Pro Lys Glu Gly Ala Val Leu
    530                 535                 540

Ile Val Thr Ser Ser Tyr Asn Gly Lys Pro Pro Ser Asn Ala Gly Gln
545                 550                 555                 560

Phe Val Gln Trp Leu Glu Glu Leu Lys Pro Asp Glu Leu Lys Gly Val
                565                 570                 575

Gln Tyr Ala Val Phe Gly Cys Gly Asp His Asn Trp Ala Ser Thr Tyr
            580                 585                 590

Gln Arg Ile Pro Arg Tyr Ile Asp Glu Gln Met Ala Gln Lys Gly Ala
        595                 600                 605

Thr Arg Phe Ser Lys Arg Gly Glu Ala Asp Ala Ser Gly Asp Phe Glu
    610                 615                 620

Glu Gln Leu Glu Gln Trp Lys Gln Asn Met Trp Ser Asp Ala Met Lys
625                 630                 635                 640

Ala Phe Gly Leu Glu Leu Asn Lys Asn Met Glu Lys Glu Arg Ser Thr
                645                 650                 655

Leu Ser Leu Gln Phe Val Ser Arg Leu Gly Gly Ser Pro Leu Ala Arg
            660                 665                 670

Thr Tyr Glu Ala Val Tyr Ala Ser Ile Leu Glu Asn Arg Glu Leu Gln
        675                 680                 685

Ser Ser Ser Ser Asp Arg Ser Thr Arg His Ile Glu Val Ser Leu Pro
    690                 695                 700

Glu Gly Ala Thr Tyr Lys Glu Gly Asp His Leu Gly Val Leu Pro Val
705                 710                 715                 720

Asn Ser Glu Lys Asn Ile Asn Arg Ile Leu Lys Arg Phe Gly Leu Asn
                725                 730                 735

Gly Lys Asp Gln Val Ile Leu Ser Ala Ser Gly Arg Ser Ile Asn His
            740                 745                 750

Ile Pro Leu Asp Ser Pro Val Ser Leu Ala Leu Leu Ser Tyr Ser
         755                 760                 765

Val Glu Val Gln Glu Ala Ala Thr Arg Ala Gln Ile Arg Glu Met Val
770                 775                 780

Thr Phe Thr Ala Cys Pro Pro His Lys Lys Glu Leu Glu Ala Leu Leu
785                 790                 795                 800

Glu Glu Gly Val Tyr His Glu Gln Ile Leu Lys Arg Ile Ser Met
                805                 810                 815

Leu Asp Leu Leu Glu Lys Tyr Glu Ala Cys Glu Ile Arg Phe Glu Arg
                820                 825                 830

Phe Leu Glu Leu Leu Pro Ala Leu Lys Pro Arg Tyr Tyr Ser Ile Ser
         835                 840                 845

Ser Ser Pro Leu Val Ala His Asn Arg Leu Ser Ile Thr Val Gly Val
850                 855                 860

Val Asn Ala Pro Ala Trp Ser Gly Glu Gly Thr Tyr Glu Gly Val Ala
865                 870                 875                 880

Ser Asn Tyr Leu Ala Gln Arg His Asn Lys Asp Glu Ile Ile Cys Phe
                885                 890                 895

Ile Arg Thr Pro Gln Ser Asn Phe Glu Leu Pro Lys Asp Pro Glu Thr
                900                 905                 910

Pro Ile Ile Met Val Gly Pro Gly Thr Gly Ile Ala Pro Phe Arg Gly
         915                 920                 925

Phe Leu Gln Ala Arg Arg Val Gln Lys Gln Lys Gly Met Asn Leu Gly
         930                 935                 940

Gln Ala His Leu Tyr Phe Gly Cys Arg His Pro Glu Lys Asp Tyr Leu
945                 950                 955                 960

Tyr Arg Thr Glu Leu Glu Asn Asp Glu Arg Asp Gly Leu Ile Ser Leu
                965                 970                 975

His Thr Ala Phe Ser Arg Leu Glu Gly His Pro Lys Thr Tyr Val Gln
                980                 985                 990

His Leu Ile Lys Gln Asp Arg Ile Asn Leu Ile Ser Leu Leu Asp Asn
         995                 1000                1005

Gly Ala His Leu Tyr Ile Cys Gly Asp Gly Ser Lys Met Ala Pro Asp
         1010                1015                1020

Val Glu Asp Thr Leu Cys Gln Ala Tyr Gln Glu Ile His Glu Val Ser
1025                1030                1035                1040

Glu Gln Glu Ala Arg Asn Trp Leu Asp Arg Val Gln Asp Glu Gly Arg
                1045                1050                1055

Tyr Gly Lys Asp Val Trp Ala Gly Ile
                1060                1065

<210> SEQ ID NO 29
<211> LENGTH: 1074
<212> TYPE: PRT
<213> ORGANISM: Bacillus licheniformis
<220> FEATURE:
<223> OTHER INFORMATION: Bacillus licheniformis strain DSM 13 = ATCC
      14580 cytochrome P450/NADPH-ferrihemoprotein reductase, CYP102A7

<400> SEQUENCE: 29

Met Asn Lys Leu Asp Gly Ile Pro Ile Pro Lys Thr Tyr Gly Pro Leu
1               5                   10                  15

Gly Asn Leu Pro Leu Leu Asp Lys Asn Arg Val Ser Gln Ser Leu Trp
            20                  25                  30

Lys Ile Ala Asp Glu Met Gly Pro Ile Phe Gln Phe Lys Phe Ala Asp
        35                  40                  45

```
Ala Ile Gly Val Phe Val Ser His Glu Leu Val Lys Glu Val Ser
    50                  55                  60
Glu Glu Ser Arg Phe Asp Lys Asn Met Gly Lys Gly Leu Leu Lys Val
65                  70                  75                  80
Arg Glu Phe Ser Gly Asp Gly Leu Phe Thr Ser Trp Thr Glu Pro
                85                  90                  95
Asn Trp Arg Lys Ala His Asn Ile Leu Leu Pro Ser Phe Ser Gln Lys
                100                 105                 110
Ala Met Lys Gly Tyr His Pro Met Met Gln Asp Ile Ala Val Gln Leu
                115                 120                 125
Ile Gln Lys Trp Ser Arg Leu Asn Gln Asp Ser Ile Asp Val Pro
    130                 135                 140
Asp Asp Met Thr Arg Leu Thr Leu Asp Thr Ile Gly Leu Cys Gly Phe
145                 150                 155                 160
Asn Tyr Arg Phe Asn Ser Phe Tyr Arg Glu Gly Gln His Pro Phe Ile
                165                 170                 175
Glu Ser Met Val Arg Gly Leu Ser Glu Ala Met Arg Gln Thr Lys Arg
                180                 185                 190
Phe Pro Leu Gln Asp Lys Leu Met Ile Gln Thr Lys Arg Arg Phe Asn
                195                 200                 205
Ser Asp Val Glu Ser Met Phe Ser Leu Val Asp Arg Ile Ile Ala Asp
    210                 215                 220
Arg Lys Gln Ala Glu Ser Glu Ser Gly Asn Asp Leu Leu Ser Leu Met
225                 230                 235                 240
Leu His Ala Lys Asp Pro Glu Thr Gly Glu Lys Leu Asp Asp Glu Asn
                245                 250                 255
Ile Arg Tyr Gln Ile Ile Thr Phe Leu Ile Ala Gly His Glu Thr Thr
                260                 265                 270
Ser Gly Leu Leu Ser Phe Ala Ile Tyr Leu Leu Leu Lys His Pro Asp
                275                 280                 285
Lys Leu Lys Lys Ala Tyr Glu Glu Ala Asp Arg Val Leu Thr Asp Pro
    290                 295                 300
Val Pro Ser Tyr Lys Gln Val Gln Gln Leu Lys Tyr Ile Arg Met Ile
305                 310                 315                 320
Leu Asn Glu Ser Ile Arg Leu Trp Pro Thr Ala Pro Ala Phe Ser Leu
                325                 330                 335
Tyr Ala Lys Glu Glu Thr Val Ile Gly Gly Lys Tyr Leu Ile Pro Lys
                340                 345                 350
Gly Gln Ser Val Thr Val Leu Ile Pro Lys Leu His Arg Asp Gln Ser
                355                 360                 365
Val Trp Gly Glu Asp Ala Glu Ala Phe Arg Pro Glu Arg Phe Glu Gln
    370                 375                 380
Met Asp Ser Ile Pro Ala His Ala Tyr Lys Pro Phe Gly Asn Gly Gln
385                 390                 395                 400
Arg Ala Cys Ile Gly Met Gln Phe Ala Leu His Glu Ala Thr Leu Val
                405                 410                 415
Leu Gly Met Ile Leu Gln Tyr Phe Asp Leu Glu Asp His Ala Asn Tyr
                420                 425                 430
Gln Leu Lys Ile Lys Glu Ser Leu Thr Leu Lys Pro Asp Gly Phe Thr
                435                 440                 445
Ile Arg Val Arg Pro Arg Lys Lys Glu Ala Met Thr Ala Met Pro Gly
    450                 455                 460
```

```
Ala Gln Pro Glu Glu Asn Gly Arg Gln Glu Arg Pro Ser Ala Pro
465                 470                 475                 480

Ala Ala Glu Asn Thr His Gly Thr Pro Leu Leu Val Leu Tyr Gly Ser
            485                 490                 495

Asn Leu Gly Thr Ala Glu Ile Ala Lys Glu Leu Ala Glu Glu Ala
            500                 505                 510

Arg Glu Gln Gly Phe His Ser Arg Thr Ala Glu Leu Asp Gln Tyr Ala
            515                 520                 525

Gly Ala Ile Pro Ala Glu Gly Ala Val Ile Val Thr Ala Ser Tyr
            530                 535                 540

Asn Gly Asn Pro Pro Asp Cys Ala Lys Glu Phe Val Asn Trp Leu Glu
545                 550                 555                 560

His Asp Gln Thr Asp Asp Leu Arg Gly Val Lys Tyr Ala Val Phe Gly
            565                 570                 575

Cys Gly Asn Arg Ser Trp Ala Ser Thr Tyr Gln Arg Ile Pro Arg Leu
            580                 585                 590

Ile Asp Ser Val Leu Glu Lys Lys Gly Ala Gln Arg Leu His Lys Leu
            595                 600                 605

Gly Glu Gly Asp Ala Gly Asp Asp Phe Glu Gly Gln Phe Glu Ser Trp
610                 615                 620

Lys Tyr Asp Leu Trp Pro Leu Leu Arg Thr Glu Phe Ser Leu Ala Glu
625                 630                 635                 640

Pro Glu Pro Asn Gln Thr Glu Thr Asp Arg Gln Ala Leu Ser Val Glu
            645                 650                 655

Phe Val Asn Ala Pro Ala Ala Ser Pro Leu Ala Lys Ala Tyr Gln Val
            660                 665                 670

Phe Thr Ala Lys Ile Ser Ala Asn Arg Glu Leu Gln Cys Glu Lys Ser
            675                 680                 685

Gly Arg Ser Thr Arg His Ile Glu Ile Ser Leu Pro Glu Gly Ala Ala
            690                 695                 700

Tyr Gln Glu Gly Asp His Leu Gly Val Leu Pro Gln Asn Ser Glu Val
705                 710                 715                 720

Leu Ile Gly Arg Val Phe Gln Arg Phe Gly Leu Asn Gly Asn Glu Gln
            725                 730                 735

Ile Leu Ile Ser Gly Arg Asn Gln Ala Ser His Leu Pro Leu Glu Arg
            740                 745                 750

Pro Val His Val Lys Asp Leu Phe Gln His Cys Val Glu Leu Gln Glu
            755                 760                 765

Pro Ala Thr Arg Ala Gln Ile Arg Glu Leu Ala Ala His Thr Val Cys
            770                 775                 780

Pro Pro His Gln Arg Glu Leu Glu Asp Leu Leu Lys Asp Asp Val Tyr
785                 790                 795                 800

Lys Asp Gln Val Leu Asn Lys Arg Leu Thr Met Leu Asp Leu Leu Glu
            805                 810                 815

Gln Tyr Pro Ala Cys Glu Leu Pro Phe Ala Arg Phe Leu Ala Leu Leu
            820                 825                 830

Pro Pro Leu Lys Pro Arg Tyr Tyr Ser Ile Ser Ser Pro Gln Leu
            835                 840                 845

Asn Pro Arg Gln Thr Ser Ile Thr Val Ser Val Ser Gly Pro Ala
            850                 855                 860

Leu Ser Gly Arg Gly His Tyr Lys Gly Val Ala Ser Asn Tyr Leu Ala
865                 870                 875                 880

Gly Leu Glu Pro Gly Asp Ala Ile Ser Cys Phe Ile Arg Glu Pro Gln
```

```
                     885                 890                 895
Ser Gly Phe Arg Leu Pro Glu Asp Pro Glu Thr Pro Val Ile Met Val
                900                 905                 910

Gly Pro Gly Thr Gly Ile Ala Pro Tyr Arg Gly Phe Leu Gln Ala Arg
            915                 920                 925

Arg Ile Gln Arg Asp Ala Gly Val Lys Leu Gly Glu Ala His Leu Tyr
        930                 935                 940

Phe Gly Cys Arg Arg Pro Asn Glu Asp Phe Leu Tyr Arg Asp Glu Leu
945                 950                 955                 960

Glu Gln Ala Glu Lys Asp Gly Ile Val His Leu His Thr Ala Phe Ser
                965                 970                 975

Arg Leu Glu Gly Arg Pro Lys Thr Tyr Val Gln Asp Leu Leu Arg Glu
            980                 985                 990

Asp Ala Ala Leu Leu Ile His Leu Leu Asn Glu Gly Arg Leu Tyr
        995                 1000                1005

Val Cys Gly Asp Gly Ser Arg Met Ala Pro Ala Val Glu Gln Ala Leu
    1010                1015                1020

Cys Glu Ala Tyr Arg Ile Val Gln Gly Ala Ser Arg Glu Ser Gln
1025                1030                1035                1040

Ser Trp Leu Ser Ala Leu Leu Glu Gly Arg Tyr Ala Lys Asp Val
            1045                1050                1055

Trp Asp Gly Gly Val Ser Gln His Asn Val Lys Ala Asp Cys Ile Ala
            1060                1065                1070

Arg Thr
```

<210> SEQ ID NO 30
<211> LENGTH: 1065
<212> TYPE: PRT
<213> ORGANISM: Bacillus thuringiensis
<220> FEATURE:
<223> OTHER INFORMATION: Bacillus thuringiensis serovar konkukian strain 97-27 NADPH-cytochrome P450 reductase, CYPX

<400> SEQUENCE: 30

```
Met Asp Lys Lys Val Ser Ala Ile Pro Gln Pro Lys Thr Tyr Gly Pro
1               5                   10                  15

Leu Gly Asn Leu Pro Leu Ile Asp Lys Asp Lys Pro Thr Leu Ser Phe
            20                  25                  30

Ile Lys Leu Ala Glu Glu Tyr Gly Pro Ile Phe Gln Ile Gln Thr Leu
        35                  40                  45

Ser Asp Thr Ile Ile Val Val Ser Gly His Glu Leu Val Ala Glu Val
    50                  55                  60

Cys Asp Glu Thr Arg Phe Asp Lys Ser Ile Glu Gly Ala Leu Ala Lys
65                  70                  75                  80

Val Arg Ala Phe Ala Gly Asp Gly Leu Phe Thr Ser Glu Thr Asp Glu
                85                  90                  95

Pro Asn Trp Lys Lys Ala His Asn Ile Leu Met Pro Thr Phe Ser Gln
            100                 105                 110

Arg Ala Met Lys Asp Tyr His Ala Met Met Val Asp Ile Ala Val Gln
        115                 120                 125

Leu Val Gln Lys Trp Ala Arg Leu Asn Pro Asn Glu Asn Val Asp Val
    130                 135                 140

Pro Glu Asp Met Thr Arg Leu Thr Leu Asp Thr Ile Gly Leu Cys Gly
145                 150                 155                 160

Phe Asn Tyr Arg Phe Asn Ser Phe Tyr Arg Glu Thr Pro His Pro Phe
```

```
                  165                 170                 175
Ile Thr Ser Met Thr Arg Ala Leu Asp Glu Ala Met His Gln Leu Gln
            180                 185                 190

Arg Leu Asp Ile Glu Asp Lys Leu Met Trp Arg Thr Lys Arg Gln Phe
        195                 200                 205

Gln His Asp Ile Gln Ser Met Phe Ser Leu Val Asp Asn Ile Ile Ala
    210                 215                 220

Glu Arg Lys Ser Ser Glu Asn Gln Glu Asn Asp Leu Leu Ser Arg
225                 230                 235                 240

Met Leu Asn Val Gln Asp Pro Glu Thr Gly Glu Lys Leu Asp Asp Glu
            245                 250                 255

Asn Ile Arg Phe Gln Ile Ile Thr Phe Leu Ile Ala Gly His Glu Thr
        260                 265                 270

Thr Ser Gly Leu Leu Ser Phe Ala Ile Tyr Phe Leu Leu Lys Asn Pro
    275                 280                 285

Asp Lys Leu Lys Lys Ala Tyr Glu Glu Val Asp Arg Val Leu Thr Asp
290                 295                 300

Ser Thr Pro Thr Tyr Gln Gln Val Met Lys Leu Lys Tyr Ile Arg Met
305                 310                 315                 320

Ile Leu Asn Glu Ser Leu Arg Leu Trp Pro Thr Ala Pro Ala Phe Ser
            325                 330                 335

Leu Tyr Ala Lys Glu Asp Thr Val Ile Gly Gly Lys Tyr Pro Ile Lys
        340                 345                 350

Lys Gly Glu Asp Arg Ile Ser Val Leu Ile Pro Gln Leu His Arg Asp
    355                 360                 365

Lys Asp Ala Trp Gly Asp Asp Val Glu Glu Phe Gln Pro Glu Arg Phe
    370                 375                 380

Glu Glu Leu Asp Lys Val Pro His His Ala Tyr Lys Pro Phe Gly Asn
385                 390                 395                 400

Gly Gln Arg Ala Cys Ile Gly Met Gln Phe Ala Leu His Glu Ala Thr
            405                 410                 415

Leu Val Met Gly Met Leu Leu Gln His Phe Glu Phe Ile Asp Tyr Glu
        420                 425                 430

Asp Tyr Gln Leu Asp Val Lys Gln Thr Leu Thr Leu Lys Pro Gly Asp
    435                 440                 445

Phe Lys Ile Arg Ile Val Pro Arg Asn Gln Thr Ile Ser His Thr Thr
    450                 455                 460

Val Leu Ala Pro Thr Glu Glu Lys Leu Lys Lys His Glu Ile Lys Lys
465                 470                 475                 480

Gln Val Gln Lys Thr Pro Ser Ile Ile Gly Ala Asp Asn Leu Ser Leu
            485                 490                 495

Leu Val Leu Tyr Gly Ser Asp Thr Gly Val Ala Glu Gly Ile Ala Arg
        500                 505                 510

Glu Leu Ala Asp Thr Ala Ser Leu Glu Gly Val Gln Thr Glu Val Val
    515                 520                 525

Ala Leu Asn Asp Arg Ile Gly Ser Leu Pro Lys Glu Gly Ala Val Leu
    530                 535                 540

Ile Val Thr Ser Ser Tyr Asn Gly Lys Pro Pro Ser Asn Ala Gly Gln
545                 550                 555                 560

Phe Val Gln Trp Leu Glu Glu Leu Lys Pro Asp Glu Leu Lys Gly Val
            565                 570                 575

Gln Tyr Ala Val Phe Gly Cys Gly Asp His Asn Trp Ala Ser Thr Tyr
        580                 585                 590
```

```
Gln Arg Ile Pro Arg Tyr Ile Asp Glu Gln Met Ala Gln Lys Gly Ala
            595                 600                 605

Thr Arg Phe Ser Thr Arg Gly Glu Ala Asp Ala Ser Gly Asp Phe Glu
610                 615                 620

Glu Gln Leu Glu Gln Trp Lys Gln Ser Met Trp Ser Asp Ala Met Lys
625                 630                 635                 640

Ala Phe Gly Leu Glu Leu Asn Lys Asn Met Glu Lys Glu Arg Ser Thr
                645                 650                 655

Leu Ser Leu Gln Phe Val Ser Arg Leu Gly Ser Pro Leu Ala Arg
            660                 665                 670

Thr Tyr Glu Ala Val Tyr Ala Ser Ile Leu Glu Asn Arg Glu Leu Gln
            675                 680                 685

Ser Ser Ser Ser Glu Arg Ser Thr Arg His Ile Glu Ile Ser Leu Pro
            690                 695                 700

Glu Gly Ala Thr Tyr Lys Glu Gly Asp His Leu Gly Val Leu Pro Ile
705                 710                 715                 720

Asn Asn Glu Lys Asn Val Asn Arg Ile Leu Lys Arg Phe Gly Leu Asn
                725                 730                 735

Gly Lys Asp Gln Val Ile Leu Ser Ala Ser Gly Arg Ser Val Asn His
            740                 745                 750

Ile Pro Leu Asp Ser Pro Val Arg Leu Tyr Asp Leu Leu Ser Tyr Ser
            755                 760                 765

Val Glu Val Gln Glu Ala Ala Thr Arg Ala Gln Ile Arg Glu Met Val
770                 775                 780

Thr Phe Thr Ala Cys Pro Pro His Lys Lys Glu Leu Glu Ser Leu Leu
785                 790                 795                 800

Glu Asp Gly Val Tyr Gln Glu Gln Ile Leu Lys Lys Arg Ile Ser Met
                805                 810                 815

Leu Asp Leu Leu Glu Lys Tyr Glu Ala Cys Glu Ile Arg Phe Glu Arg
            820                 825                 830

Phe Leu Glu Leu Leu Pro Ala Leu Lys Pro Arg Tyr Tyr Ser Ile Ser
            835                 840                 845

Ser Ser Pro Leu Val Ala Gln Asp Arg Leu Ser Ile Thr Val Gly Val
            850                 855                 860

Val Asn Ala Pro Ala Trp Ser Gly Glu Gly Thr Tyr Glu Gly Val Ala
865                 870                 875                 880

Ser Asn Tyr Leu Ala Gln Arg His Asn Lys Asp Glu Ile Ile Cys Phe
                885                 890                 895

Ile Arg Thr Pro Gln Ser Asn Phe Gln Leu Pro Glu Asn Pro Glu Thr
            900                 905                 910

Pro Ile Ile Met Val Gly Pro Gly Thr Gly Ile Ala Pro Phe Arg Gly
            915                 920                 925

Phe Leu Gln Ala Arg Arg Val Gln Lys Gln Lys Gly Met Lys Val Gly
            930                 935                 940

Glu Ala His Leu Tyr Phe Gly Cys Arg His Pro Glu Lys Asp Tyr Leu
945                 950                 955                 960

Tyr Arg Thr Glu Leu Glu Asn Asp Glu Arg Asp Gly Leu Ile Ser Leu
                965                 970                 975

His Thr Ala Phe Ser Arg Leu Glu Gly His Pro Lys Thr Tyr Val Gln
            980                 985                 990

His Val Ile Lys Glu Asp Arg Ile His Leu Ile Ser Leu Leu Asp Asn
            995                 1000                1005
```

-continued

```
Gly Ala His Leu Tyr Ile Cys Gly Asp Gly Ser Lys Met Ala Pro Asp
    1010                1015                1020

Val Glu Asp Thr Leu Cys Gln Ala Tyr Gln Glu Ile His Glu Val Ser
1025                1030                1035                1040

Glu Gln Glu Ala Arg Asn Trp Leu Asp Arg Leu Gln Glu Glu Gly Arg
                1045                1050                1055

Tyr Gly Lys Asp Val Trp Ala Gly Ile
            1060                1065

<210> SEQ ID NO 31
<211> LENGTH: 1064
<212> TYPE: PRT
<213> ORGANISM: Cupriavidus metallidurans
<220> FEATURE:
<223> OTHER INFORMATION: Cupriavidus metallidurans (R. metallidurans)
      strain CH34 putative bifunctional P-450:NADPH-450
      reductase 2, CYP102E1

<400> SEQUENCE: 31

Met Ser Thr Ala Thr Pro Ala Ala Leu Glu Pro Ile Pro Arg Asp
 1               5                  10                  15

Pro Gly Trp Pro Ile Phe Gly Asn Leu Phe Gln Ile Thr Pro Gly Glu
                20                  25                  30

Val Gly Gln His Leu Leu Ala Arg Ser Arg His His Asp Gly Ile Phe
            35                  40                  45

Glu Leu Asp Phe Ala Gly Lys Arg Val Pro Phe Val Ser Ser Val Ala
        50                  55                  60

Leu Ala Ser Glu Leu Cys Asp Ala Thr Arg Phe Arg Lys Ile Ile Gly
65                  70                  75                  80

Pro Pro Leu Ser Tyr Leu Arg Asp Met Ala Gly Asp Gly Leu Phe Thr
                85                  90                  95

Ala His Ser Asp Glu Pro Asn Trp Gly Cys Ala His Arg Ile Leu Met
            100                 105                 110

Pro Ala Phe Ser Gln Arg Ala Met Lys Ala Tyr Phe Asp Val Met Leu
        115                 120                 125

Arg Val Ala Asn Arg Leu Val Asp Lys Trp Asp Arg Gln Gly Pro Asp
130                 135                 140

Ala Asp Ile Ala Val Ala Asp Met Thr Arg Leu Thr Leu Asp Thr
145                 150                 155                 160

Ile Ala Leu Ala Gly Phe Gly Tyr Asp Phe Ala Ser Phe Ala Ser Asp
                165                 170                 175

Glu Leu Asp Pro Phe Val Met Ala Met Val Gly Ala Leu Gly Glu Ala
            180                 185                 190

Met Gln Lys Leu Thr Arg Leu Pro Ile Gln Asp Arg Phe Met Gly Arg
        195                 200                 205

Ala His Arg Gln Ala Ala Glu Asp Ile Ala Tyr Met Arg Asn Leu Val
    210                 215                 220

Asp Asp Val Ile Arg Gln Arg Val Ser Pro Thr Ser Gly Met Asp
225                 230                 235                 240

Leu Leu Asn Leu Met Leu Glu Ala Arg Asp Pro Glu Thr Asp Arg Arg
                245                 250                 255

Leu Asp Asp Ala Asn Ile Arg Asn Gln Val Ile Thr Phe Leu Ile Ala
            260                 265                 270

Gly His Glu Thr Thr Ser Gly Leu Leu Thr Phe Ala Leu Tyr Glu Leu
        275                 280                 285

Leu Arg Asn Pro Gly Val Leu Ala Gln Ala Tyr Ala Glu Val Asp Thr
```

```
            290                 295                 300
Val Leu Pro Gly Asp Ala Leu Pro Val Tyr Ala Asp Leu Ala Arg Met
305                 310                 315                 320

Pro Val Leu Asp Arg Val Leu Lys Glu Thr Leu Arg Leu Trp Pro Thr
                325                 330                 335

Ala Pro Ala Phe Ala Val Ala Pro Phe Asp Asp Val Val Leu Gly Gly
            340                 345                 350

Arg Tyr Arg Leu Arg Lys Asp Arg Ile Ser Val Val Leu Thr Ala
        355                 360                 365

Leu His Arg Asp Pro Lys Val Trp Ala Asn Pro Glu Arg Phe Asp Ile
    370                 375                 380

Asp Arg Phe Leu Pro Glu Asn Glu Ala Lys Leu Pro Ala His Ala Tyr
385                 390                 395                 400

Met Pro Phe Gly Gln Gly Glu Arg Ala Cys Ile Gly Arg Gln Phe Ala
                405                 410                 415

Leu Thr Glu Ala Lys Leu Ala Leu Ala Leu Met Leu Arg Asn Phe Ala
            420                 425                 430

Phe Gln Asp Pro His Asp Tyr Gln Phe Arg Leu Lys Glu Thr Leu Thr
        435                 440                 445

Ile Lys Pro Asp Gln Phe Val Leu Arg Val Arg Arg Arg Pro His
    450                 455                 460

Glu Arg Phe Val Thr Arg Gln Ala Ser Gln Ala Val Ala Asp Ala Ala
465                 470                 475                 480

Gln Thr Asp Val Arg Gly His Gly Gln Ala Met Thr Val Leu Cys Ala
                485                 490                 495

Ser Ser Leu Gly Thr Ala Arg Glu Leu Ala Glu Gln Ile His Ala Gly
            500                 505                 510

Ala Ile Ala Ala Gly Phe Asp Ala Lys Leu Ala Asp Leu Asp Asp Ala
        515                 520                 525

Val Gly Val Leu Pro Thr Ser Gly Leu Val Val Val Ala Ala Thr
    530                 535                 540

Tyr Asn Gly Arg Ala Pro Asp Ser Ala Arg Lys Phe Glu Ala Met Leu
545                 550                 555                 560

Asp Ala Asp Asp Ala Ser Gly Tyr Arg Ala Asn Gly Met Arg Leu Ala
                565                 570                 575

Leu Leu Gly Cys Gly Asn Ser Gln Trp Ala Thr Tyr Gln Ala Phe Pro
            580                 585                 590

Arg Arg Val Phe Asp Phe Phe Ile Thr Ala Gly Ala Val Pro Leu Leu
        595                 600                 605

Pro Arg Gly Glu Ala Asp Gly Asn Gly Asp Phe Asp Gln Ala Ala Glu
    610                 615                 620

Arg Trp Leu Ala Gln Leu Trp Gln Ala Leu Gln Ala Asp Gly Ala Gly
625                 630                 635                 640

Thr Gly Gly Leu Gly Val Asp Val Gln Val Arg Ser Met Ala Ala Ile
                645                 650                 655

Arg Ala Glu Thr Leu Pro Ala Gly Thr Gln Ala Phe Thr Val Leu Ser
            660                 665                 670

Asn Asp Glu Leu Val Gly Asp Pro Ser Gly Leu Trp Asp Phe Ser Ile
        675                 680                 685

Glu Ala Pro Arg Thr Ser Thr Arg Asp Ile Arg Leu Gln Leu Pro Pro
    690                 695                 700

Gly Ile Thr Tyr Arg Thr Gly Asp His Ile Ala Val Trp Pro Gln Asn
705                 710                 715                 720
```

```
Asp Ala Gln Leu Val Ser Glu Leu Cys Glu Arg Leu Asp Leu Asp Pro
            725                 730                 735

Asp Ala Gln Ala Thr Ile Ser Ala Pro His Gly Met Gly Arg Gly Leu
            740                 745                 750

Pro Ile Asp Gln Ala Leu Pro Val Arg Gln Leu Leu Thr His Phe Ile
            755                 760                 765

Glu Leu Gln Asp Val Val Ser Arg Gln Thr Leu Arg Ala Leu Ala Gln
            770                 775                 780

Ala Thr Arg Cys Pro Phe Thr Lys Gln Ser Ile Glu Gln Leu Ala Ser
785                 790                 795                 800

Asp Asp Ala Glu His Gly Tyr Ala Thr Lys Val Val Ala Arg Arg Leu
            805                 810                 815

Gly Ile Leu Asp Val Leu Val Glu His Pro Ala Ile Ala Leu Thr Leu
            820                 825                 830

Gln Glu Leu Leu Ala Cys Thr Val Pro Met Arg Pro Arg Leu Tyr Ser
            835                 840                 845

Ile Ala Ser Ser Pro Leu Val Ser Pro Asp Val Ala Thr Leu Leu Val
            850                 855                 860

Gly Thr Val Cys Ala Pro Ala Leu Ser Gly Arg Gly Gln Phe Arg Gly
865                 870                 875                 880

Val Ala Ser Thr Trp Leu Gln His Leu Pro Pro Gly Ala Arg Val Ser
            885                 890                 895

Ala Ser Ile Arg Thr Pro Asn Pro Pro Phe Ala Pro Asp Pro Asp Pro
            900                 905                 910

Ala Ala Pro Met Leu Leu Ile Gly Pro Gly Thr Gly Ile Ala Pro Phe
            915                 920                 925

Arg Gly Phe Leu Glu Glu Arg Ala Leu Arg Lys Met Ala Gly Asn Ala
            930                 935                 940

Val Thr Pro Ala Gln Leu Tyr Phe Gly Cys Arg His Pro Gln His Asp
945                 950                 955                 960

Trp Leu Tyr Arg Glu Asp Ile Glu Arg Trp Ala Gly Gln Gly Val Val
            965                 970                 975

Glu Val His Pro Ala Tyr Ser Val Val Pro Asp Ala Pro Arg Tyr Val
            980                 985                 990

Gln Asp Leu Leu Trp Gln Arg Arg Glu Gln Val Trp Ala Gln Val Arg
            995                 1000                1005

Asp Gly Ala Thr Ile Tyr Val Cys Gly Asp Gly Arg Arg Met Ala Pro
       1010               1015                1020

Ala Val Arg Gln Thr Leu Ile Glu Ile Gly Met Ala Gln Gly Gly Met
1025                1030                1035                1040

Thr Asp Lys Ala Ala Ser Asp Trp Phe Gly Gly Leu Val Ala Gln Gly
                1045                1050                1055

Arg Tyr Arg Gln Asp Val Phe Asn
            1060

<210> SEQ ID NO 32
<211> LENGTH: 1120
<212> TYPE: PRT
<213> ORGANISM: Aspergillus fumigatus
<220> FEATURE:
<223> OTHER INFORMATION: Aspergillus fumigatus strain Af293 putative
      P450 family fatty acid hydroxylase, CYP505X, locus AFUA_3G09220

<400> SEQUENCE: 32

Met Ser Glu Ser Lys Thr Val Pro Ile Pro Gly Pro Arg Gly Val Pro
```

-continued

```
  1               5                  10                 15
Leu Leu Gly Asn Ile Tyr Asp Ile Glu Gln Glu Val Pro Leu Arg Ser
             20                  25                 30

Ile Asn Leu Met Ala Asp Gln Tyr Gly Pro Ile Tyr Arg Leu Thr Thr
             35                  40                 45

Phe Gly Trp Ser Arg Val Phe Val Ser Thr His Glu Leu Val Asp Glu
             50                  55                 60

Val Cys Asp Glu Glu Arg Phe Thr Lys Val Val Thr Ala Gly Leu Asn
 65                  70                  75                 80

Gln Ile Arg Asn Gly Val His Asp Gly Leu Phe Thr Ala Asn Phe Pro
                 85                  90                 95

Gly Glu Glu Asn Trp Ala Ile Ala His Arg Val Leu Val Pro Ala Phe
                100                 105                110

Gly Pro Leu Ser Ile Arg Gly Met Phe Asp Glu Met Tyr Asp Ile Ala
                115                 120                125

Thr Gln Leu Val Met Lys Trp Ala Arg His Gly Pro Thr Val Pro Ile
                130                 135                140

Met Val Thr Asp Asp Phe Thr Arg Leu Thr Leu Asp Thr Ile Ala Leu
145                 150                 155                160

Cys Ala Met Gly Thr Arg Phe Asn Ser Phe Tyr His Glu Glu Met His
                165                 170                175

Pro Phe Val Glu Ala Met Val Gly Leu Leu Gln Gly Ser Gly Asp Arg
                180                 185                190

Ala Arg Arg Pro Ala Leu Leu Asn Asn Leu Pro Thr Ser Glu Asn Ser
                195                 200                205

Lys Tyr Trp Asp Asp Ile Ala Phe Leu Arg Asn Leu Ala Gln Glu Leu
                210                 215                220

Val Glu Ala Arg Arg Lys Asn Pro Glu Asp Lys Asp Leu Leu Asn
225                 230                 235                240

Ala Leu Ile Leu Gly Arg Asp Pro Lys Thr Gly Lys Gly Leu Thr Asp
                245                 250                255

Glu Ser Ile Ile Asp Asn Met Ile Thr Phe Leu Ile Ala Gly His Glu
                260                 265                270

Thr Thr Ser Gly Leu Leu Ser Phe Leu Phe Tyr Tyr Leu Leu Lys Thr
                275                 280                285

Pro Asn Ala Tyr Lys Lys Ala Gln Glu Glu Val Asp Ser Val Val Gly
                290                 295                300

Arg Arg Lys Ile Thr Val Glu Asp Met Ser Arg Leu Pro Tyr Leu Asn
305                 310                 315                320

Ala Val Met Arg Glu Thr Leu Arg Leu Arg Ser Thr Ala Pro Leu Ile
                325                 330                335

Ala Val His Ala His Pro Glu Lys Asn Lys Glu Asp Pro Val Thr Leu
                340                 345                350

Gly Gly Gly Lys Tyr Val Leu Asn Lys Asp Glu Pro Ile Val Ile Ile
                355                 360                365

Leu Asp Lys Leu His Arg Asp Pro Gln Val Tyr Gly Pro Asp Ala Glu
                370                 375                380

Glu Phe Lys Pro Glu Arg Met Leu Asp Glu Asn Phe Glu Lys Leu Pro
385                 390                 395                400

Lys Asn Ala Trp Lys Pro Phe Gly Asn Gly Met Arg Ala Cys Ile Gly
                405                 410                415

Arg Pro Phe Ala Trp Gln Glu Ala Leu Leu Val Val Ala Ile Leu Leu
                420                 425                430
```

```
Gln Asn Phe Asn Phe Gln Met Asp Asp Pro Ser Tyr Asn Leu His Ile
        435                 440                 445

Lys Gln Thr Leu Thr Ile Lys Pro Lys Asp Phe His Met Arg Ala Thr
    450                 455                 460

Leu Arg His Gly Leu Asp Ala Thr Lys Leu Gly Ile Ala Leu Ser Gly
465                 470                 475                 480

Ser Ala Asp Arg Ala Pro Pro Glu Ser Ser Gly Ala Ala Ser Arg Val
                485                 490                 495

Arg Lys Gln Ala Thr Pro Pro Ala Gly Gln Leu Lys Pro Met His Ile
                500                 505                 510

Phe Phe Gly Ser Asn Thr Gly Thr Cys Glu Thr Phe Ala Arg Arg Leu
            515                 520                 525

Ala Asp Asp Ala Val Gly Tyr Gly Phe Ala Ala Asp Val Gln Ser Leu
        530                 535                 540

Asp Ser Ala Met Gln Asn Val Pro Lys Asp Glu Pro Val Val Phe Ile
545                 550                 555                 560

Thr Ala Ser Tyr Glu Gly Gln Pro Pro Asp Asn Ala Ala His Phe Phe
                565                 570                 575

Glu Trp Leu Ser Ala Leu Lys Glu Asn Glu Leu Glu Gly Val Asn Tyr
            580                 585                 590

Ala Val Phe Gly Cys Gly His His Asp Trp Gln Ala Thr Phe His Arg
        595                 600                 605

Ile Pro Lys Ala Val Asn Gln Leu Val Ala Glu His Gly Gly Asn Arg
    610                 615                 620

Leu Cys Asp Leu Gly Leu Ala Asp Ala Ala Asn Ser Asp Met Phe Thr
625                 630                 635                 640

Asp Phe Asp Ser Trp Gly Glu Ser Thr Phe Trp Pro Ala Ile Thr Ser
                645                 650                 655

Lys Phe Gly Gly Gly Lys Ser Asp Glu Pro Lys Pro Ser Ser Ser Leu
            660                 665                 670

Gln Val Glu Val Ser Thr Gly Met Arg Ala Ser Thr Leu Gly Leu Gln
        675                 680                 685

Leu Gln Glu Gly Leu Val Ile Asp Asn Gln Leu Leu Ser Ala Pro Asp
    690                 695                 700

Val Pro Ala Lys Arg Met Ile Arg Phe Lys Leu Pro Ser Asp Met Ser
705                 710                 715                 720

Tyr Arg Cys Gly Asp Tyr Leu Ala Val Leu Pro Val Asn Pro Thr Ser
                725                 730                 735

Val Val Arg Arg Ala Ile Arg Arg Phe Asp Leu Pro Trp Asp Ala Met
            740                 745                 750

Leu Thr Ile Arg Lys Pro Ser Gln Ala Pro Lys Gly Ser Thr Ser Ile
        755                 760                 765

Pro Leu Asp Thr Pro Ile Ser Ala Phe Glu Leu Leu Ser Thr Tyr Val
    770                 775                 780

Glu Leu Ser Gln Pro Ala Ser Lys Arg Asp Leu Thr Ala Leu Ala Asp
785                 790                 795                 800

Ala Ala Ile Thr Asp Ala Asp Ala Gln Ala Glu Leu Arg Tyr Leu Ala
                805                 810                 815

Ser Ser Pro Thr Arg Phe Thr Glu Glu Ile Val Lys Lys Arg Met Ser
            820                 825                 830

Pro Leu Asp Leu Leu Ile Arg Tyr Pro Ser Ile Lys Leu Pro Val Gly
        835                 840                 845
```

Asp Phe Leu Ala Met Leu Pro Pro Met Arg Val Arg Gln Tyr Ser Ile
850                 855                 860

Ser Ser Ser Pro Leu Ala Asp Pro Ser Glu Cys Ser Ile Thr Phe Ser
865                 870                 875                 880

Val Leu Asn Ala Pro Ala Leu Ala Ala Ala Ser Leu Pro Pro Ala Glu
            885                 890                 895

Arg Ala Glu Ala Glu Gln Tyr Met Gly Val Ala Ser Thr Tyr Leu Ser
            900                 905                 910

Glu Leu Lys Pro Gly Glu Arg Ala His Ile Ala Val Arg Pro Ser His
            915                 920                 925

Ser Gly Phe Lys Pro Pro Met Asp Leu Lys Ala Pro Met Ile Met Ala
            930                 935                 940

Cys Ala Gly Ser Gly Leu Ala Pro Phe Arg Gly Phe Ile Met Asp Arg
945                 950                 955                 960

Ala Glu Lys Ile Arg Gly Arg Ser Ser Val Gly Ala Asp Gly Gln
            965                 970                 975

Leu Pro Glu Val Glu Gln Pro Ala Lys Ala Ile Leu Tyr Val Gly Cys
            980                 985                 990

Arg Thr Lys Gly Lys Asp Asp Ile His Ala Thr Glu Leu Ala Glu Trp
            995                 1000                1005

Ala Gln Leu Gly Ala Val Asp Val Arg Trp Ala Tyr Ser Arg Pro Glu
    1010                1015                1020

Asp Gly Ser Lys Gly Arg His Val Gln Asp Leu Met Leu Glu Asp Arg
1025                1030                1035                1040

Glu Glu Leu Val Ser Leu Phe Asp Gln Gly Ala Arg Ile Tyr Val Cys
            1045                1050                1055

Gly Ser Thr Gly Val Gly Asn Gly Val Arg Gln Ala Cys Lys Asp Ile
            1060                1065                1070

Tyr Leu Glu Arg Arg Arg Gln Leu Arg Gln Ala Ala Arg Glu Arg Gly
        1075                1080                1085

Glu Glu Val Pro Ala Glu Asp Glu Asp Ala Ala Ala Glu Gln Phe
    1090                1095                1100

Leu Asp Asn Leu Arg Thr Lys Glu Arg Tyr Ala Thr Asp Val Phe Thr
1105                1110                1115                1120

<210> SEQ ID NO 33
<211> LENGTH: 1083
<212> TYPE: PRT
<213> ORGANISM: Aspergillus nidulans
<220> FEATURE:
<223> OTHER INFORMATION: Aspergillus nidulans strain FGSC A4
      hypothetical protein AN6835.2, CYP505A8

<400> SEQUENCE: 33

Met Ala Glu Ile Pro Glu Pro Lys Gly Leu Pro Leu Ile Gly Asn Ile
1               5                   10                  15

Gly Thr Ile Asp Gln Glu Phe Pro Leu Gly Ser Met Val Ala Leu Ala
            20                  25                  30

Glu Glu His Gly Glu Ile Tyr Arg Leu Arg Phe Pro Gly Arg Thr Val
        35                  40                  45

Val Val Val Ser Thr His Ala Leu Val Asn Glu Thr Cys Asp Glu Lys
    50                  55                  60

Arg Phe Arg Lys Ser Val Asn Ser Ala Leu Ala His Val Arg Glu Gly
65                  70                  75                  80

Val His Asp Gly Leu Phe Thr Ala Lys Met Gly Glu Val Asn Trp Glu
            85                  90                  95

```
Ile Ala His Arg Val Leu Met Pro Ala Phe Gly Pro Leu Ser Ile Arg
            100                 105                 110

Gly Met Phe Asp Glu Met His Asp Ile Ala Ser Gln Leu Ala Leu Lys
            115                 120                 125

Trp Ala Arg Tyr Gly Pro Asp Cys Pro Ile Met Val Thr Asp Phe
130                 135                 140

Thr Arg Leu Thr Leu Asp Thr Leu Ala Leu Cys Ser Met Gly Tyr Arg
145                 150                 155                 160

Phe Asn Ser Tyr Tyr Ser Pro Val Leu His Pro Phe Ile Glu Ala Met
                165                 170                 175

Gly Asp Phe Leu Thr Glu Ala Gly Glu Lys Pro Arg Arg Pro Pro Leu
            180                 185                 190

Pro Ala Val Phe Phe Arg Asn Arg Asp Gln Lys Phe Gln Asp Asp Ile
            195                 200                 205

Ala Val Leu Arg Asp Thr Ala Gln Gly Val Leu Gln Ala Arg Lys Glu
210                 215                 220

Gly Lys Ser Asp Arg Asn Asp Leu Leu Ser Ala Met Leu Arg Gly Val
225                 230                 235                 240

Asp Ser Gln Thr Gly Gln Lys Met Thr Asp Glu Ser Ile Met Asp Asn
                245                 250                 255

Leu Ile Thr Phe Leu Ile Ala Gly His Glu Thr Thr Ser Gly Leu Leu
            260                 265                 270

Ser Phe Val Phe Tyr Gln Leu Leu Lys His Pro Glu Thr Tyr Arg Thr
            275                 280                 285

Ala Gln Gln Glu Val Asp Asn Val Val Gly Gln Gly Val Ile Glu Val
            290                 295                 300

Ser His Leu Ser Lys Leu Pro Tyr Ile Asn Ser Val Leu Arg Glu Thr
305                 310                 315                 320

Leu Arg Leu Asn Ala Thr Ile Pro Leu Phe Thr Val Glu Ala Phe Glu
                325                 330                 335

Asp Thr Leu Leu Ala Gly Lys Tyr Pro Val Lys Ala Gly Glu Thr Ile
            340                 345                 350

Val Asn Leu Leu Ala Lys Ser His Leu Asp Pro Glu Val Tyr Gly Glu
            355                 360                 365

Asp Ala Leu Glu Phe Lys Pro Glu Arg Met Ser Asp Glu Leu Phe Asn
370                 375                 380

Ala Arg Leu Lys Gln Phe Pro Ser Ala Trp Lys Pro Phe Gly Asn Gly
385                 390                 395                 400

Met Arg Ala Cys Ile Gly Arg Pro Phe Ala Trp Gln Glu Ala Leu Leu
                405                 410                 415

Val Met Ala Met Leu Leu Gln Asn Phe Asp Phe Ser Leu Ala Asp Pro
            420                 425                 430

Asn Tyr Asp Leu Lys Phe Lys Gln Thr Leu Thr Ile Lys Pro Lys Asp
            435                 440                 445

Met Phe Met Lys Ala Arg Leu Arg His Gly Leu Thr Pro Thr Thr Leu
450                 455                 460

Glu Arg Arg Leu Ala Gly Leu Ala Val Glu Ser Ala Thr Gln Asp Lys
465                 470                 475                 480

Ile Val Thr Asn Pro Ala Asp Asn Ser Val Thr Gly Thr Arg Leu Thr
                485                 490                 495

Ile Leu Tyr Gly Ser Asn Ser Gly Thr Cys Glu Thr Leu Ala Arg Arg
            500                 505                 510
```

-continued

Ile Ala Ala Asp Ala Pro Ser Lys Gly Phe His Val Met Arg Phe Asp
515                 520                 525

Gly Leu Asp Ser Gly Arg Ser Ala Leu Pro Thr Asp His Pro Val Val
    530                 535                 540

Ile Val Thr Ser Ser Tyr Glu Gly Gln Pro Pro Glu Asn Ala Lys Gln
545                 550                 555                 560

Phe Val Ser Trp Leu Glu Glu Leu Glu Gln Gln Asn Glu Ser Leu Gln
                565                 570                 575

Leu Lys Gly Val Asp Phe Ala Val Phe Gly Cys Phe Lys Glu Trp Ala
            580                 585                 590

Gln Thr Phe His Arg Ile Pro Lys Leu Val Asp Ser Leu Leu Glu Lys
        595                 600                 605

Leu Gly Gly Ser Arg Leu Thr Asp Leu Gly Leu Ala Asp Val Ser Thr
    610                 615                 620

Asp Glu Leu Phe Ser Thr Phe Glu Thr Trp Ala Asp Asp Val Leu Trp
625                 630                 635                 640

Pro Arg Leu Val Ala Gln Tyr Gly Ala Asp Gly Lys Thr Gln Ala His
                645                 650                 655

Gly Ser Ser Ala Gly His Glu Ala Ala Ser Asn Ala Ala Val Glu Val
            660                 665                 670

Thr Val Ser Asn Ser Arg Thr Gln Ala Leu Arg Gln Asp Val Gly Gln
        675                 680                 685

Ala Met Val Val Glu Thr Arg Leu Leu Thr Ala Glu Ser Glu Lys Glu
    690                 695                 700

Arg Arg Lys Lys His Leu Glu Ile Arg Leu Pro Asp Gly Val Ser Tyr
705                 710                 715                 720

Thr Ala Gly Asp Tyr Leu Ala Val Leu Pro Ile Asn Pro Pro Glu Thr
                725                 730                 735

Val Arg Arg Ala Met Arg Gln Phe Lys Leu Ser Trp Asp Ala Gln Ile
            740                 745                 750

Thr Ile Ala Pro Ser Gly Pro Thr Thr Ala Leu Pro Thr Asp Gly Pro
        755                 760                 765

Ile Ala Ala Asn Asp Ile Phe Ser Thr Tyr Val Glu Leu Ser Gln Pro
    770                 775                 780

Ala Thr Arg Lys Asp Leu Arg Ile Met Ala Asp Ala Thr Thr Asp Pro
785                 790                 795                 800

Asp Val Gln Lys Ile Leu Arg Thr Tyr Ala Asn Glu Thr Tyr Thr Ala
                805                 810                 815

Glu Ile Leu Thr Lys Ser Ile Ser Val Leu Asp Ile Leu Glu Gln His
            820                 825                 830

Pro Ala Ile Asp Leu Pro Leu Gly Thr Phe Leu Leu Met Leu Pro Ser
        835                 840                 845

Met Arg Met Arg Gln Tyr Ser Ile Ser Ser Ser Pro Leu Leu Thr Pro
    850                 855                 860

Thr Thr Ala Thr Ile Thr Ile Ser Val Leu Asp Ala Pro Ser Arg Ser
865                 870                 875                 880

Arg Ser Asn Gly Ser Arg His Leu Gly Val Ala Thr Ser Tyr Leu Asp
                885                 890                 895

Ser Leu Ser Val Gly Asp His Leu Gln Val Thr Val Arg Lys Asn Pro
            900                 905                 910

Ser Ser Gly Phe Arg Leu Pro Ser Glu Pro Glu Thr Thr Pro Met Ile
        915                 920                 925

Cys Ile Ala Ala Gly Ser Gly Ile Ala Pro Phe Arg Ala Phe Leu Gln

```
                   930              935              940
Glu Arg Ala Val Met Met Glu Gln Asp Lys Asp Arg Lys Leu Ala Pro
945                 950                 955                 960

Ala Leu Leu Phe Phe Gly Cys Arg Ala Pro Gly Ile Asp Asp Leu Tyr
                965                 970                 975

Arg Glu Gln Leu Glu Glu Trp Gln Ala Arg Gly Val Val Asp Ala Arg
            980                 985                 990

Trp Ala Phe Ser Arg Gln Ser Asp Asp Thr Lys Gly Cys Arg His Val
        995                1000               1005

Asp Asp Arg Ile Leu Ala Asp Arg Glu Asp Val Val Lys Leu Trp Arg
       1010                1015               1020

Asp Gly Ala Arg Val Tyr Val Cys Gly Ser Gly Ala Leu Ala Gln Ser
1025               1030                1035               1040

Val Arg Ser Ala Met Val Thr Val Leu Arg Asp Glu Met Glu Thr Thr
                1045               1050               1055

Gly Asp Gly Ser Asp Asn Gly Lys Ala Glu Lys Trp Phe Asp Glu Gln
               1060                1065               1070

Arg Asn Val Arg Tyr Val Met Asp Val Phe Asp
       1075                1080

<210> SEQ ID NO 34
<211> LENGTH: 1054
<212> TYPE: PRT
<213> ORGANISM: Aspergillus oryzae
<220> FEATURE:
<223> OTHER INFORMATION: Aspergillus oryzae strain ATCC 42149 cytochrome
      P450, locus AO090020000369, locus Q2U4F1_ASPOR, CYP505A3

<400> SEQUENCE: 34

Met Arg Gln Asn Asp Asn Glu Lys Gln Ile Cys Pro Ile Pro Gly Pro
1               5                  10                  15

Gln Gly Leu Pro Phe Leu Gly Asn Ile Leu Asp Ile Asp Leu Asp Asn
            20                  25                  30

Gly Thr Met Ser Thr Leu Lys Ile Ala Lys Thr Tyr Tyr Pro Ile Phe
        35                  40                  45

Lys Phe Thr Phe Ala Gly Glu Thr Ser Ile Val Ile Asn Ser Val Ala
50                  55                  60

Leu Leu Ser Glu Leu Cys Asp Glu Thr Arg Phe His Lys His Val Ser
65                  70                  75                  80

Phe Gly Leu Glu Leu Leu Arg Ser Gly Thr His Asp Gly Leu Phe Thr
                85                  90                  95

Ala Tyr Asp His Glu Lys Asn Trp Glu Leu Ala His Arg Leu Leu Val
            100                 105                 110

Pro Ala Phe Gly Pro Leu Arg Ile Arg Glu Met Phe Pro Gln Met His
        115                 120                 125

Asp Ile Ala Gln Gln Leu Cys Leu Lys Trp Gln Arg Tyr Gly Pro Arg
130                 135                 140

Arg Pro Leu Asn Leu Val Asp Asp Phe Thr Arg Thr Leu Asp Thr
145                 150                 155                 160

Ile Ala Leu Cys Ala Met Gly Tyr Arg Phe Asn Ser Phe Tyr Ser Glu
                165                 170                 175

Gly Asp Phe His Pro Phe Ile Lys Ser Met Val Arg Phe Leu Lys Glu
            180                 185                 190

Ala Glu Thr Gln Ala Thr Leu Pro Ser Phe Ile Ser Asn Leu Arg Val
        195                 200                 205
```

```
Arg Ala Lys Arg Arg Thr Gln Leu Asp Ile Asp Leu Met Arg Thr Val
    210                 215                 220

Cys Arg Glu Ile Val Thr Glu Arg Arg Gln Thr Asn Leu Asp His Lys
225                 230                 235                 240

Asn Asp Leu Leu Asp Thr Met Leu Thr Ser Arg Asp Ser Leu Ser Gly
                245                 250                 255

Asp Ala Leu Ser Asp Glu Ser Ile Ile Asp Asn Ile Leu Thr Phe Leu
            260                 265                 270

Val Ala Gly His Glu Thr Thr Ser Gly Leu Leu Ser Phe Ala Val Tyr
        275                 280                 285

Tyr Leu Leu Thr Thr Pro Asp Ala Met Ala Lys Ala Ala His Glu Val
    290                 295                 300

Asp Asp Val Val Gly Asp Gln Glu Leu Thr Ile Glu His Leu Ser Met
305                 310                 315                 320

Leu Lys Tyr Leu Asn Ala Ile Leu Arg Glu Thr Leu Arg Leu Met Pro
                325                 330                 335

Thr Ala Pro Gly Phe Ser Val Thr Pro Tyr Lys Pro Glu Ile Ile Gly
            340                 345                 350

Gly Lys Tyr Glu Val Lys Pro Gly Asp Ser Leu Asp Val Phe Leu Ala
        355                 360                 365

Ala Val His Arg Asp Pro Ala Val Tyr Gly Ser Asp Ala Asp Glu Phe
    370                 375                 380

Arg Pro Glu Arg Met Ser Asp Glu His Phe Gln Lys Leu Pro Ala Asn
385                 390                 395                 400

Ser Trp Lys Pro Phe Gly Asn Gly Lys Arg Ser Cys Ile Gly Arg Ala
                405                 410                 415

Phe Ala Trp Gln Glu Ala Leu Met Ile Leu Ala Leu Ile Leu Gln Ser
            420                 425                 430

Phe Ser Leu Asn Leu Val Asp Arg Gly Tyr Thr Leu Lys Leu Lys Glu
        435                 440                 445

Ser Leu Thr Ile Lys Pro Asp Asn Leu Trp Ala Tyr Ala Thr Pro Arg
    450                 455                 460

Pro Gly Arg Asn Val Leu His Thr Arg Leu Ala Leu Gln Thr Asn Ser
465                 470                 475                 480

Thr His Pro Glu Gly Leu Met Ser Leu Lys His Glu Thr Val Glu Ser
                485                 490                 495

Gln Pro Ala Thr Ile Leu Tyr Gly Ser Asn Ser Gly Thr Cys Glu Ala
            500                 505                 510

Leu Ala His Arg Leu Ala Ile Glu Met Ser Ser Lys Gly Arg Phe Val
        515                 520                 525

Cys Lys Val Gln Pro Met Asp Ala Ile Glu His Arg Arg Leu Pro Arg
    530                 535                 540

Gly Gln Pro Val Ile Ile Ile Thr Gly Ser Tyr Asp Gly Arg Pro Pro
545                 550                 555                 560

Glu Asn Ala Arg His Phe Val Lys Trp Leu Gln Ser Leu Lys Gly Asn
                565                 570                 575

Asp Leu Glu Gly Ile Gln Tyr Ala Val Phe Gly Cys Gly Leu Pro Gly
            580                 585                 590

His His Asp Trp Ser Thr Thr Phe Tyr Lys Ile Pro Thr Leu Ile Asp
        595                 600                 605

Thr Ile Met Ala Glu His Gly Gly Ala Arg Leu Ala Pro Arg Gly Ser
    610                 615                 620

Ala Asp Thr Ala Glu Asp Asp Pro Phe Ala Glu Leu Glu Ser Trp Ser
```

```
              625                 630                 635                 640
         Glu Arg Ser Val Trp Pro Gly Leu Glu Ala Ala Phe Asp Leu Val Arg
                         645                 650                 655

His Asn Ser Ser Asp Gly Thr Gly Lys Ser Thr Arg Ile Thr Ile Arg
                         660                 665                 670

Ser Pro Tyr Thr Leu Arg Ala Ala His Glu Thr Ala Val Val His Gln
                         675                 680                 685

Val Arg Val Leu Thr Ser Ala Glu Thr Thr Lys Lys Val His Val Glu
                         690                 695                 700

Leu Ala Leu Pro Asp Thr Ile Asn Tyr Arg Pro Gly Asp His Leu Ala
         705                 710                 715                 720

Ile Leu Pro Leu Asn Ser Arg Gln Ser Val Gln Arg Val Leu Ser Leu
                         725                 730                 735

Phe Gln Ile Gly Ser Asp Thr Ile Leu Tyr Met Thr Ser Ser Ser Ala
                         740                 745                 750

Thr Ser Leu Pro Thr Asp Thr Pro Ile Ser Ala His Asp Leu Leu Ser
                         755                 760                 765

Gly Tyr Val Glu Leu Asn Gln Val Ala Thr Pro Thr Ser Leu Arg Ser
                         770                 775                 780

Leu Ala Ala Lys Ala Thr Asp Glu Lys Thr Ala Glu Tyr Leu Glu Ala
         785                 790                 795                 800

Leu Ala Thr Asp Arg Tyr Thr Thr Glu Val Arg Gly Asn His Leu Ser
                         805                 810                 815

Leu Leu Asp Ile Leu Glu Ser Tyr Ser Val Pro Ser Ile Glu Ile Gln
                         820                 825                 830

His Tyr Ile Gln Met Leu Pro Leu Leu Arg Pro Arg Gln Tyr Thr Ile
                         835                 840                 845

Ser Ser Ser Pro Arg Leu Asn Arg Gly Gln Ala Ser Leu Thr Val Ser
                         850                 855                 860

Val Met Glu Arg Ala Asp Val Gly Gly Pro Arg Asn Cys Ala Gly Val
         865                 870                 875                 880

Ala Ser Asn Tyr Leu Ala Ser Cys Thr Pro Gly Ser Ile Leu Arg Val
                         885                 890                 895

Ser Leu Arg Gln Ala Asn Pro Asp Phe Arg Leu Pro Asp Glu Ser Cys
                         900                 905                 910

Ser His Pro Ile Ile Met Val Ala Ala Gly Ser Gly Ile Ala Pro Phe
                         915                 920                 925

Arg Ala Phe Val Gln Glu Arg Ser Val Arg Gln Lys Glu Gly Ile Ile
                         930                 935                 940

Leu Pro Pro Ala Phe Leu Phe Gly Cys Arg Arg Ala Asp Leu Asp
         945                 950                 955                 960

Asp Leu Tyr Arg Glu Glu Leu Asp Ala Phe Glu Glu Gln Gly Val Val
                         965                 970                 975

Thr Leu Phe Arg Ala Phe Ser Arg Ala Gln Ser Glu Ser His Gly Cys
                         980                 985                 990

Lys Tyr Val Gln Asp Leu Leu Trp Met Glu Arg Val Arg Val Lys Thr
                         995                 1000                1005

Leu Trp Gly Gln Asp Ala Lys Val Phe Val Cys Gly Ser Val Arg Met
                         1010                1015                1020

Asn Glu Gly Val Lys Ala Ile Ile Ser Lys Ile Val Ser Pro Thr Pro
         1025                1030                1035                1040

Thr Glu Glu Leu Ala Arg Arg Tyr Ile Ala Glu Thr Phe Ile
                         1045                1050
```

-continued

<210> SEQ ID NO 35
<211> LENGTH: 1103
<212> TYPE: PRT
<213> ORGANISM: Aspergillus oryzae
<220> FEATURE:
<223> OTHER INFORMATION: Aspergillus oryzae strain ATCC 42149 cytochrome
      P450, locus AO090001000445, locus Q2UNA2_ASPOR, CYPX

<400> SEQUENCE: 35

Met Ser Thr Pro Lys Ala Glu Pro Val Pro Ile Pro Gly Pro Arg Gly
 1               5                  10                  15

Val Pro Leu Met Gly Asn Ile Leu Asp Ile Glu Ser Glu Ile Pro Leu
            20                  25                  30

Arg Ser Leu Glu Met Met Ala Asp Thr Tyr Gly Pro Ile Tyr Arg Leu
        35                  40                  45

Thr Thr Phe Gly Phe Ser Arg Cys Met Ile Ser Ser His Glu Leu Ala
    50                  55                  60

Ala Glu Val Phe Asp Glu Arg Phe Thr Lys Lys Ile Met Ala Gly
65                  70                  75                  80

Leu Ser Glu Leu Arg His Gly Ile His Asp Gly Leu Phe Thr Ala His
                85                  90                  95

Met Gly Glu Glu Asn Trp Glu Ile Ala His Arg Val Leu Met Pro Ala
            100                 105                 110

Phe Gly Pro Leu Asn Ile Gln Asn Met Phe Asp Glu Met His Asp Ile
        115                 120                 125

Ala Thr Gln Leu Val Met Lys Trp Ala Arg Gln Gly Pro Lys Gln Lys
    130                 135                 140

Ile Met Val Thr Asp Asp Phe Thr Arg Leu Thr Leu Asp Thr Ile Ala
145                 150                 155                 160

Leu Cys Ala Met Gly Thr Arg Phe Asn Ser Phe Tyr Ser Glu Glu Met
                165                 170                 175

His Pro Phe Val Asp Ala Met Val Gly Met Leu Lys Thr Ala Gly Asp
            180                 185                 190

Arg Ser Arg Arg Pro Gly Leu Val Asn Asn Leu Pro Thr Thr Glu Asn
        195                 200                 205

Asn Lys Tyr Trp Glu Asp Ile Asp Tyr Leu Arg Asn Leu Cys Lys Glu
    210                 215                 220

Leu Val Asp Thr Arg Lys Lys Asn Pro Thr Asp Lys Lys Asp Leu Leu
225                 230                 235                 240

Asn Ala Leu Ile Asn Gly Arg Asp Pro Lys Thr Gly Lys Gly Met Ser
                245                 250                 255

Tyr Asp Ser Ile Ile Asp Asn Met Ile Thr Phe Leu Ile Ala Gly His
            260                 265                 270

Glu Thr Thr Ser Gly Ser Leu Ser Phe Ala Phe Tyr Asn Met Leu Lys
        275                 280                 285

Asn Pro Gln Ala Tyr Gln Lys Ala Gln Glu Val Asp Arg Val Ile
    290                 295                 300

Gly Arg Arg Ile Thr Val Glu Asp Leu Gln Lys Leu Pro Tyr Ile
305                 310                 315                 320

Thr Ala Val Met Arg Glu Thr Leu Arg Leu Thr Pro Thr Ala Pro Ala
                325                 330                 335

Ile Ala Val Gly Pro His Pro Thr Lys Asn His Glu Asp Pro Val Thr
            340                 345                 350

Leu Gly Asn Gly Lys Tyr Val Leu Gly Lys Asp Glu Pro Cys Ala Leu

```
                355                 360                 365
Leu Leu Gly Lys Ile Gln Arg Asp Pro Lys Val Tyr Gly Pro Asp Ala
370                 375                 380
Glu Glu Phe Lys Pro Glu Arg Met Leu Asp Glu His Phe Asn Lys Leu
385                 390                 395                 400
Pro Lys His Ala Trp Lys Pro Phe Gly Asn Gly Met Arg Ala Cys Ile
                405                 410                 415
Gly Arg Pro Phe Ala Trp Gln Glu Ala Leu Leu Val Ile Ala Met Leu
            420                 425                 430
Leu Gln Asn Phe Asn Phe Gln Met Asp Asp Pro Ser Tyr Asn Ile Gln
        435                 440                 445
Leu Lys Gln Thr Leu Thr Ile Lys Pro Asn His Phe Tyr Met Arg Ala
    450                 455                 460
Ala Leu Arg Glu Gly Leu Asp Ala Val His Leu Gly Ser Ala Leu Ser
465                 470                 475                 480
Ala Ser Ser Ser Glu His Ala Asp His Ala Ala Gly His Gly Lys Ala
                485                 490                 495
Gly Ala Ala Lys Lys Gly Ala Asp Leu Lys Pro Met His Val Tyr Tyr
            500                 505                 510
Gly Ser Asn Thr Gly Thr Cys Glu Ala Phe Ala Arg Arg Leu Ala Asp
        515                 520                 525
Asp Ala Thr Ser Tyr Gly Tyr Ser Ala Glu Val Glu Ser Leu Asp Ser
    530                 535                 540
Ala Lys Asp Ser Ile Pro Lys Asn Gly Pro Val Val Phe Ile Thr Ala
545                 550                 555                 560
Ser Tyr Glu Gly Gln Pro Pro Asp Asn Ala Ala His Phe Phe Glu Trp
                565                 570                 575
Leu Ser Ala Leu Lys Gly Asp Lys Pro Leu Asp Gly Val Asn Tyr Ala
            580                 585                 590
Val Phe Gly Cys Gly His His Asp Trp Gln Thr Thr Phe Tyr Arg Ile
        595                 600                 605
Pro Lys Glu Val Asn Arg Leu Val Gly Glu Asn Gly Ala Asn Arg Leu
    610                 615                 620
Cys Glu Ile Gly Leu Ala Asp Thr Ala Asn Ala Asp Ile Val Thr Asp
625                 630                 635                 640
Phe Asp Thr Trp Gly Glu Thr Ser Phe Trp Pro Ala Val Ala Ala Lys
                645                 650                 655
Phe Gly Ser Asn Thr Gln Gly Ser Gln Lys Ser Ser Thr Phe Arg Val
            660                 665                 670
Glu Val Ser Ser Gly His Arg Ala Thr Thr Leu Gly Leu Gln Leu Gln
        675                 680                 685
Glu Gly Leu Val Val Glu Asn Thr Leu Leu Thr Gln Ala Gly Val Pro
    690                 695                 700
Ala Lys Arg Thr Ile Arg Phe Lys Leu Pro Thr Asp Thr Gln Tyr Lys
705                 710                 715                 720
Cys Gly Asp Tyr Leu Ala Ile Leu Pro Val Asn Pro Ser Thr Val Val
                725                 730                 735
Arg Lys Val Met Ser Arg Phe Asp Leu Pro Trp Asp Ala Val Leu Arg
            740                 745                 750
Ile Glu Lys Ala Ser Pro Ser Ser Lys His Ile Ser Ile Pro Met
        755                 760                 765
Asp Thr Gln Val Ser Ala Tyr Asp Leu Phe Ala Thr Tyr Val Glu Leu
    770                 775                 780
```

```
Ser Gln Pro Ala Ser Lys Arg Asp Leu Ala Val Leu Ala Asp Ala Ala
785                 790                 795                 800

Ala Val Asp Pro Glu Thr Gln Ala Glu Leu Gln Ala Ile Ala Ser Asp
                805                 810                 815

Pro Ala Arg Phe Ala Glu Ile Ser Gln Lys Arg Ile Ser Val Leu Asp
                820                 825                 830

Leu Leu Leu Gln Tyr Pro Ser Ile Asn Leu Ala Ile Gly Asp Phe Val
                835                 840                 845

Ala Met Leu Pro Pro Met Arg Val Arg Gln Tyr Ser Ile Ser Ser Ser
                850                 855                 860

Pro Leu Val Asp Pro Thr Glu Cys Ser Ile Thr Phe Ser Val Leu Lys
865                 870                 875                 880

Ala Pro Ser Leu Ala Ala Leu Thr Lys Glu Asp Glu Tyr Leu Gly Val
                885                 890                 895

Ala Ser Thr Tyr Leu Ser Glu Leu Arg Ser Gly Glu Arg Val Gln Leu
                900                 905                 910

Ser Val Arg Pro Ser His Thr Gly Phe Lys Pro Pro Thr Glu Leu Ser
                915                 920                 925

Thr Pro Met Ile Met Ala Cys Ala Gly Ser Gly Leu Ala Pro Phe Arg
                930                 935                 940

Gly Phe Val Met Asp Arg Ala Glu Lys Ile Arg Gly Arg Arg Ser Ser
945                 950                 955                 960

Gly Ser Met Pro Glu Gln Pro Ala Lys Ala Ile Leu Tyr Ala Gly Cys
                965                 970                 975

Arg Thr Gln Gly Lys Asp Ile His Ala Asp Glu Leu Ala Glu Trp
                980                 985                 990

Glu Lys Ile Gly Ala Val Glu Val Arg Arg Ala Tyr Ser Arg Pro Ser
                995                1000                1005

Asp Gly Ser Lys Gly Thr His Val Gln Asp Leu Met Met Glu Asp Lys
    1010                1015                1020

Lys Glu Leu Ile Asp Leu Phe Glu Ser Gly Ala Arg Ile Tyr Val Cys
1025                1030                1035                1040

Gly Thr Pro Gly Val Gly Asn Ala Val Arg Asp Ser Ile Lys Ser Met
                1045                1050                1055

Phe Leu Glu Arg Arg Glu Glu Ile Arg Arg Ile Ala Lys Glu Lys Gly
                1060                1065                1070

Glu Pro Val Ser Asp Asp Glu Thr Ala Phe Glu Lys Phe Leu
    1075                1080                1085

Asp Asp Met Lys Thr Lys Glu Arg Tyr Thr Thr Asp Ile Phe Ala
    1090                1095                1100

<210> SEQ ID NO 36
<211> LENGTH: 1066
<212> TYPE: PRT
<213> ORGANISM: Fusarium oxysporum
<220> FEATURE:
<223> OTHER INFORMATION: bifunctional P-450:NADPH-P450 reductase,
      cytochrome P450foxy, fatty acid omega-hydrolxylase, cytochrome
      P450 505, CYP505, NADPH-cytochrome P450 reductase, locus
      C505_FUSOX, CYP505A1

<400> SEQUENCE: 36

Met Ala Glu Ser Val Pro Ile Pro Glu Pro Pro Gly Tyr Pro Leu Ile
1               5                   10                  15

Gly Asn Leu Gly Glu Phe Thr Ser Asn Pro Leu Ser Asp Leu Asn Arg
                20                  25                  30
```

```
Leu Ala Asp Thr Tyr Gly Pro Ile Phe Arg Leu Arg Leu Gly Ala Lys
        35                  40                  45

Ala Pro Ile Phe Val Ser Ser Asn Ser Leu Ile Asn Glu Val Cys Asp
 50                  55                  60

Glu Lys Arg Phe Lys Lys Thr Leu Lys Ser Val Leu Ser Gln Val Arg
 65                  70                  75                  80

Glu Gly Val His Asp Gly Leu Phe Thr Ala Phe Glu Asp Glu Pro Asn
                 85                  90                  95

Trp Gly Lys Ala His Arg Ile Leu Val Pro Ala Phe Gly Pro Leu Ser
                100                 105                 110

Ile Arg Gly Met Phe Pro Glu Met His Asp Ile Ala Thr Gln Leu Cys
                115                 120                 125

Met Lys Phe Ala Arg His Gly Pro Arg Thr Pro Ile Asp Thr Ser Asp
130                 135                 140

Asn Phe Thr Arg Leu Ala Leu Asp Thr Leu Ala Leu Cys Ala Met Asp
145                 150                 155                 160

Phe Arg Phe Tyr Ser Tyr Tyr Lys Glu Glu Leu His Pro Phe Ile Glu
                165                 170                 175

Ala Met Gly Asp Phe Leu Thr Glu Ser Gly Asn Arg Asn Arg Arg Pro
                180                 185                 190

Pro Phe Ala Pro Asn Phe Leu Tyr Arg Ala Ala Asn Glu Lys Phe Tyr
                195                 200                 205

Gly Asp Ile Ala Leu Met Lys Ser Val Ala Asp Glu Val Val Ala Ala
                210                 215                 220

Arg Lys Ala Ser Pro Ser Asp Arg Lys Asp Leu Leu Ala Ala Met Leu
225                 230                 235                 240

Asn Gly Val Asp Pro Gln Thr Gly Glu Lys Leu Ser Asp Glu Asn Ile
                245                 250                 255

Thr Asn Gln Leu Ile Thr Phe Leu Ile Ala Gly His Glu Thr Thr Ser
                260                 265                 270

Gly Thr Leu Ser Phe Ala Met Tyr Gln Leu Leu Lys Asn Pro Glu Ala
                275                 280                 285

Tyr Ser Lys Val Gln Lys Glu Val Asp Glu Val Val Gly Arg Gly Pro
                290                 295                 300

Val Leu Val Glu His Leu Thr Lys Leu Pro Tyr Ile Ser Ala Val Leu
305                 310                 315                 320

Arg Glu Thr Leu Arg Leu Asn Ser Pro Ile Thr Ala Phe Gly Leu Glu
                325                 330                 335

Ala Ile Asp Asp Thr Phe Leu Gly Gly Lys Tyr Leu Val Lys Lys Gly
                340                 345                 350

Glu Ile Val Thr Ala Leu Leu Ser Arg Gly His Val Asp Pro Val Val
                355                 360                 365

Tyr Gly Asn Asp Ala Asp Lys Phe Ile Pro Glu Arg Met Leu Asp Asp
                370                 375                 380

Glu Phe Ala Arg Leu Asn Lys Glu Tyr Pro Asn Cys Trp Lys Pro Phe
385                 390                 395                 400

Gly Asn Gly Lys Arg Ala Cys Ile Gly Arg Pro Phe Ala Trp Gln Glu
                405                 410                 415

Ser Leu Leu Ala Met Val Val Leu Phe Gln Asn Phe Asn Phe Thr Met
                420                 425                 430

Thr Asp Pro Asn Tyr Ala Leu Glu Ile Lys Gln Thr Leu Thr Ile Lys
                435                 440                 445
```

```
Pro Asp His Phe Tyr Ile Asn Ala Thr Leu Arg His Gly Met Thr Pro
    450                 455                 460
Thr Glu Leu Glu His Val Leu Ala Gly Asn Gly Ala Thr Ser Ser Ser
465                 470                 475                 480
Thr His Asn Ile Lys Ala Ala Ala Asn Leu Asp Ala Lys Ala Gly Ser
                485                 490                 495
Gly Lys Pro Met Ala Ile Phe Tyr Gly Ser Asn Ser Gly Thr Cys Glu
            500                 505                 510
Ala Leu Ala Asn Arg Leu Ala Ser Asp Ala Pro Ser His Gly Phe Ser
            515                 520                 525
Ala Thr Thr Val Gly Pro Leu Asp Gln Ala Lys Gln Asn Leu Pro Glu
    530                 535                 540
Asp Arg Pro Val Ile Val Thr Ala Ser Tyr Glu Gly Gln Pro Pro
545                 550                 555                 560
Ser Asn Ala Ala His Phe Ile Lys Trp Met Glu Asp Leu Asp Gly Asn
                565                 570                 575
Asp Met Glu Lys Val Ser Tyr Ala Val Phe Ala Cys Gly His His Asp
            580                 585                 590
Trp Val Glu Thr Phe His Arg Ile Pro Lys Leu Val Asp Ser Thr Leu
    595                 600                 605
Glu Lys Arg Gly Gly Thr Arg Leu Val Pro Met Gly Ser Ala Asp Ala
610                 615                 620
Ala Thr Ser Asp Met Phe Ser Asp Phe Glu Ala Trp Glu Asp Ile Val
625                 630                 635                 640
Leu Trp Pro Gly Leu Lys Glu Lys Tyr Lys Ile Ser Asp Glu Glu Ser
                645                 650                 655
Gly Gly Gln Lys Gly Leu Leu Val Glu Val Ser Thr Pro Arg Lys Thr
            660                 665                 670
Ser Leu Arg Gln Asp Val Glu Glu Ala Leu Val Val Ala Glu Lys Thr
            675                 680                 685
Leu Thr Lys Ser Gly Pro Ala Lys Lys His Ile Glu Ile Gln Leu Pro
    690                 695                 700
Ser Ala Met Thr Tyr Lys Ala Gly Asp Tyr Leu Ala Ile Leu Pro Leu
705                 710                 715                 720
Asn Pro Lys Ser Thr Val Ala Arg Val Phe Arg Arg Phe Ser Leu Ala
                725                 730                 735
Trp Asp Ser Phe Leu Lys Ile Gln Ser Glu Gly Pro Thr Thr Leu Pro
            740                 745                 750
Thr Asn Val Ala Ile Ser Ala Phe Asp Val Phe Ser Ala Tyr Val Glu
            755                 760                 765
Leu Ser Gln Pro Ala Thr Lys Arg Asn Ile Leu Ala Leu Ala Glu Ala
    770                 775                 780
Thr Glu Asp Lys Asp Thr Ile Gln Glu Leu Glu Arg Leu Ala Gly Asp
785                 790                 795                 800
Ala Tyr Gln Ala Glu Ile Ser Pro Lys Arg Val Ser Val Leu Asp Leu
                805                 810                 815
Leu Glu Lys Phe Pro Ala Val Ala Leu Pro Ile Ser Ser Tyr Leu Ala
            820                 825                 830
Met Leu Pro Pro Met Arg Val Arg Gln Tyr Ser Ile Ser Ser Ser Pro
            835                 840                 845
Phe Ala Asp Pro Ser Lys Leu Thr Leu Thr Tyr Ser Leu Leu Asp Ala
    850                 855                 860
Pro Ser Leu Ser Gly Gln Gly Arg His Val Gly Val Ala Thr Asn Phe
```

```
                865                 870                 875                 880
Leu Ser His Leu Thr Ala Gly Asp Lys Leu His Val Ser Val Arg Ala
                    885                 890                 895

Ser Ser Glu Ala Phe His Leu Pro Ser Asp Ala Glu Lys Thr Pro Ile
                900                 905                 910

Ile Cys Val Ala Ala Gly Thr Gly Leu Ala Pro Leu Arg Gly Phe Ile
                915                 920                 925

Gln Glu Arg Ala Ala Met Leu Ala Ala Gly Arg Thr Leu Ala Pro Ala
            930                 935                 940

Leu Leu Phe Phe Gly Cys Arg Asn Pro Glu Ile Asp Asp Leu Tyr Ala
945                 950                 955                 960

Glu Glu Phe Glu Arg Trp Glu Lys Met Gly Ala Val Asp Val Arg Arg
                    965                 970                 975

Ala Tyr Ser Arg Ala Thr Asp Lys Ser Glu Gly Cys Lys Tyr Val Gln
                980                 985                 990

Asp Arg Val Tyr His Asp Arg Ala Asp Val Phe Lys Val Trp Asp Gln
            995                 1000                1005

Gly Ala Lys Val Phe Ile Cys Gly Ser Arg Glu Ile Gly Lys Ala Val
        1010                1015                1020

Glu Asp Val Cys Val Arg Leu Ala Ile Glu Lys Ala Gln Gln Asn Gly
1025                1030                1035                1040

Arg Asp Val Thr Glu Glu Met Ala Arg Ala Trp Phe Gly Arg Ser Arg
                    1045                1050                1055

Asn Glu Arg Phe Ala Thr Asp Val Phe Asp
            1060                1065

<210> SEQ ID NO 37
<211> LENGTH: 1115
<212> TYPE: PRT
<213> ORGANISM: Fusarium verticillioides
<220> FEATURE:
<223> OTHER INFORMATION: Fusarium verticillioides strain M-3125
      (Gibberella moniliformis) Fum6p, CYPX, FUM6

<400> SEQUENCE: 37

Met Ser Ala Thr Ala Leu Phe Thr Arg Arg Ser Val Ser Thr Ser Asn
1               5                   10                  15

Pro Glu Leu Arg Pro Ile Pro Gly Pro Lys Pro Leu Pro Leu Leu Gly
                20                  25                  30

Asn Leu Phe Asp Phe Asp Phe Asp Asn Leu Thr Lys Ser Leu Gly Glu
            35                  40                  45

Leu Gly Lys Ile His Gly Pro Ile Tyr Ser Ile Thr Phe Gly Ala Ser
        50                  55                  60

Thr Glu Ile Met Val Thr Ser Arg Glu Ile Ala Gln Glu Leu Cys Asp
65                  70                  75                  80

Glu Thr Arg Phe Cys Lys Leu Pro Gly Gly Ala Leu Asp Val Met Lys
                85                  90                  95

Ala Val Val Gly Asp Gly Leu Phe Thr Ala Glu Thr Ser Asn Pro Lys
                100                 105                 110

Trp Ala Ile Ala His Arg Ile Ile Thr Pro Leu Phe Gly Ala Met Arg
            115                 120                 125

Ile Arg Gly Met Phe Asp Asp Met Lys Asp Ile Cys Glu Gln Met Cys
        130                 135                 140

Leu Arg Trp Ala Arg Phe Gly Pro Asp Glu Pro Leu Asn Val Cys Asp
145                 150                 155                 160
```

-continued

```
Asn Met Thr Lys Leu Thr Leu Asp Thr Ile Ala Leu Cys Thr Ile Asp
            165                 170                 175

Tyr Arg Phe Asn Ser Phe Tyr Arg Glu Asn Gly Ala Ala His Pro Phe
        180                 185                 190

Ala Glu Ala Val Val Asp Val Met Thr Glu Ser Phe Asp Gln Ser Asn
    195                 200                 205

Leu Pro Asp Phe Val Asn Asn Tyr Val Arg Phe Arg Ala Met Ala Lys
210                 215                 220

Phe Lys Arg Gln Ala Ala Glu Leu Arg Arg Gln Thr Glu Glu Leu Ile
225                 230                 235                 240

Ala Ala Arg Arg Gln Asn Pro Val Asp Arg Asp Leu Leu Asn Ala
            245                 250                 255

Met Leu Ser Ala Lys Asp Pro Lys Thr Gly Glu Gly Leu Ser Pro Glu
        260                 265                 270

Ser Ile Val Asp Asn Leu Leu Thr Phe Leu Ile Ala Gly His Glu Thr
    275                 280                 285

Thr Ser Ser Leu Leu Ser Phe Cys Phe Tyr Tyr Leu Leu Glu Asn Pro
    290                 295                 300

His Val Leu Arg Arg Val Gln Gln Glu Val Asp Thr Val Val Gly Ser
305                 310                 315                 320

Asp Thr Ile Thr Val Asp His Leu Ser Ser Met Pro Tyr Leu Glu Ala
            325                 330                 335

Val Leu Arg Glu Thr Leu Arg Leu Arg Asp Pro Gly Pro Gly Phe Tyr
        340                 345                 350

Val Lys Pro Leu Lys Asp Glu Val Val Ala Gly Lys Tyr Ala Val Asn
    355                 360                 365

Lys Asp Gln Pro Leu Phe Ile Val Phe Asp Ser Val His Arg Asp Gln
370                 375                 380

Ser Thr Tyr Gly Ala Asp Ala Asp Glu Phe Arg Pro Glu Arg Met Leu
385                 390                 395                 400

Lys Asp Gly Phe Asp Lys Leu Pro Pro Cys Ala Trp Lys Pro Phe Gly
            405                 410                 415

Asn Gly Val Arg Ala Cys Val Gly Arg Pro Phe Ala Met Gln Gln Ala
        420                 425                 430

Ile Leu Ala Val Ala Met Val Leu His Lys Phe Asp Leu Val Lys Asp
    435                 440                 445

Glu Ser Tyr Thr Leu Lys Tyr His Val Thr Met Thr Val Arg Pro Val
450                 455                 460

Gly Phe Thr Met Lys Val Arg Leu Arg Gln Gly Gln Arg Ala Thr Asp
465                 470                 475                 480

Leu Ala Met Gly Leu His Arg Gly His Ser Gln Glu Ala Ser Ala Ala
            485                 490                 495

Ala Ser Pro Ser Arg Ala Ser Leu Lys Arg Leu Ser Ser Asp Val Asn
        500                 505                 510

Gly Asp Asp Thr Asp His Lys Ser Gln Ile Ala Val Leu Tyr Ala Ser
    515                 520                 525

Asn Ser Gly Ser Cys Glu Ala Leu Ala Tyr Arg Leu Ala Ala Glu Ala
    530                 535                 540

Thr Glu Arg Gly Phe Gly Ile Arg Ala Val Asp Val Asn Asn Ala
545                 550                 555                 560

Ile Asp Arg Ile Pro Val Gly Ser Pro Val Ile Leu Ile Thr Ala Ser
            565                 570                 575

Tyr Asn Gly Glu Pro Ala Asp Asp Ala Gln Glu Phe Val Pro Trp Leu
```

-continued

```
            580                 585                 590
Lys Ser Leu Glu Ser Gly Arg Leu Asn Gly Val Lys Phe Ala Val Phe
        595                 600                 605

Gly Asn Gly His Arg Asp Trp Ala Asn Thr Leu Phe Ala Val Pro Arg
610                 615                 620

Leu Ile Asp Ser Glu Leu Ala Arg Cys Gly Ala Glu Arg Val Ser Leu
625                 630                 635                 640

Met Gly Val Ser Asp Thr Cys Asp Ser Asp Pro Phe Ser Asp Phe
                    645                 650                 655

Glu Arg Trp Ile Asp Glu Lys Leu Phe Pro Glu Leu Glu Thr Pro His
                660                 665                 670

Gly Pro Gly Gly Val Lys Asn Gly Asp Arg Ala Val Pro Arg Gln Glu
        675                 680                 685

Leu Gln Val Ser Leu Gly Gln Pro Pro Arg Ile Thr Met Arg Lys Gly
    690                 695                 700

Tyr Val Arg Ala Ile Val Thr Glu Ala Arg Ser Leu Ser Ser Pro Gly
705                 710                 715                 720

Val Pro Glu Lys Arg His Leu Glu Leu Leu Pro Lys Asp Phe Asn
                    725                 730                 735

Tyr Lys Ala Gly Asp His Val Tyr Ile Leu Pro Arg Asn Ser Pro Arg
                740                 745                 750

Asp Val Val Arg Ala Leu Ser Tyr Phe Gly Leu Gly Glu Asp Thr Leu
            755                 760                 765

Ile Thr Ile Arg Asn Thr Ala Arg Lys Leu Ser Leu Gly Leu Pro Leu
        770                 775                 780

Asp Thr Pro Ile Thr Ala Thr Asp Leu Leu Gly Ala Tyr Val Glu Leu
785                 790                 795                 800

Gly Arg Thr Ala Ser Leu Lys Asn Leu Trp Thr Leu Val Asp Ala Ala
                    805                 810                 815

Gly His Gly Ser Arg Ala Ala Leu Leu Ser Leu Thr Glu Pro Glu Arg
                820                 825                 830

Phe Arg Ala Glu Val Gln Asp Arg His Val Ser Ile Leu Asp Leu Leu
            835                 840                 845

Glu Arg Phe Pro Asp Ile Asp Leu Ser Leu Ser Cys Phe Leu Pro Met
        850                 855                 860

Leu Ala Gln Ile Arg Pro Arg Ala Tyr Ser Phe Ser Ser Ala Pro Asp
865                 870                 875                 880

Trp Lys Pro Gly His Ala Thr Leu Thr Tyr Thr Val Val Asp Phe Ala
                    885                 890                 895

Thr Pro Ala Thr Gln Gly Ile Asn Gly Ser Ser Lys Ser Lys Ala Val
                900                 905                 910

Gly Asp Gly Thr Ala Val Val Gln Arg Gln Gly Leu Ala Ser Ser Tyr
            915                 920                 925

Leu Ser Ser Leu Gly Pro Gly Thr Ser Leu Tyr Val Ser Leu His Arg
        930                 935                 940

Ala Ser Pro Tyr Phe Cys Leu Gln Lys Ser Thr Ser Leu Pro Val Ile
945                 950                 955                 960

Met Val Gly Ala Gly Thr Gly Leu Ala Pro Phe Arg Ala Phe Leu Gln
                    965                 970                 975

Glu Arg Arg Met Ala Ala Glu Gly Ala Lys Gln Arg Phe Gly Pro Ala
                980                 985                 990

Leu Leu Phe Phe Gly Cys Arg Gly Pro Arg Leu Asp Ser Leu Tyr Ser
            995                 1000                1005
```

```
Val Glu Leu Glu Ala Tyr Glu Thr Ile Gly Leu Val Gln Val Arg Arg
        1010                1015                1020

Ala Tyr Ser Arg Asp Pro Ser Ala Gln Asp Ala Gln Gly Cys Lys Tyr
1025                1030                1035                1040

Val Thr Asp Arg Leu Gly Lys Cys Arg Asp Glu Val Ala Arg Leu Trp
            1045                1050                1055

Met Asp Gly Ala Gln Val Leu Val Cys Gly Gly Lys Lys Met Ala Asn
        1060                1065                1070

Asp Val Leu Glu Val Leu Gly Pro Met Leu Leu Glu Ile Asp Gln Lys
            1075                1080                1085

Arg Gly Glu Thr Thr Ala Lys Thr Val Val Glu Trp Arg Ala Arg Leu
        1090                1095                1100

Asp Lys Ser Arg Tyr Val Glu Glu Val Tyr Val
1105                1110                1115

<210> SEQ ID NO 38
<211> LENGTH: 1069
<212> TYPE: PRT
<213> ORGANISM: Gibberella zeae
<220> FEATURE:
<223> OTHER INFORMATION: Gibberella zeae strain PH1, NRRL 31084
      (Fusarium graminearum) bifunctional P-450:NADPH-P450 reductase,
      fatty acid omega-hyroxylase, P450foxy, locus FG01972.1, locus
      C505_FUSOX, CYP505A7

<400> SEQUENCE: 38

Met Ala Glu Ser Val Pro Ile Pro Glu Pro Pro Gly Tyr Pro Leu Ile
1                   5                   10                  15

Gly Asn Leu Gly Glu Phe Lys Thr Asn Pro Leu Asn Asp Leu Asn Arg
            20                  25                  30

Leu Ala Asp Thr Tyr Gly Pro Ile Phe Arg Leu His Leu Gly Ser Lys
        35                  40                  45

Thr Pro Thr Phe Val Ser Ser Asn Ala Phe Ile Asn Glu Val Cys Asp
    50                  55                  60

Glu Lys Arg Phe Lys Lys Thr Leu Lys Ser Val Leu Ser Val Val Arg
65                  70                  75                  80

Glu Gly Val His Asp Gly Leu Phe Thr Ala Phe Glu Asp Glu Pro Asn
                85                  90                  95

Trp Gly Lys Ala His Arg Ile Leu Ile Pro Ala Phe Gly Pro Leu Ser
            100                 105                 110

Ile Arg Asn Met Phe Pro Glu Met His Glu Ile Ala Asn Gln Leu Cys
        115                 120                 125

Met Lys Leu Ala Arg His Gly Pro His Thr Pro Val Asp Ala Ser Asp
    130                 135                 140

Asn Phe Thr Arg Leu Ala Leu Asp Thr Leu Ala Leu Cys Ala Met Asp
145                 150                 155                 160

Phe Arg Phe Asn Ser Tyr Tyr Lys Glu Glu Leu His Pro Phe Ile Glu
                165                 170                 175

Ala Met Gly Asp Phe Leu Leu Glu Ser Gly Asn Arg Asn Arg Arg Pro
            180                 185                 190

Ala Phe Ala Pro Asn Phe Leu Tyr Arg Ala Ala Asn Asp Lys Phe Tyr
        195                 200                 205

Ala Asp Ile Ala Leu Met Lys Ser Val Ala Asp Glu Val Val Ala Thr
    210                 215                 220

Arg Lys Gln Asn Pro Thr Asp Arg Lys Asp Leu Leu Ala Ala Met Leu
225                 230                 235                 240
```

```
Glu Gly Val Asp Pro Gln Thr Gly Glu Lys Leu Ser Asp Asp Asn Ile
                245                 250                 255
Thr Asn Gln Leu Ile Thr Phe Leu Ile Ala Gly His Glu Thr Thr Ser
            260                 265                 270
Gly Thr Leu Ser Phe Ala Met Tyr His Leu Leu Lys Asn Pro Glu Ala
        275                 280                 285
Tyr Asn Lys Leu Gln Lys Glu Ile Asp Glu Val Ile Gly Arg Asp Pro
    290                 295                 300
Val Thr Val Glu His Leu Thr Lys Leu Pro Tyr Leu Ser Ala Val Leu
305                 310                 315                 320
Arg Glu Thr Leu Arg Ile Ser Ser Pro Ile Thr Gly Phe Gly Val Glu
                325                 330                 335
Ala Ile Glu Asp Thr Phe Leu Gly Gly Lys Tyr Leu Ile Lys Lys Gly
            340                 345                 350
Glu Thr Val Leu Ser Val Leu Ser Arg Gly His Val Asp Pro Val Val
        355                 360                 365
Tyr Gly Pro Asp Ala Glu Lys Phe Val Pro Glu Arg Met Leu Asp Asp
    370                 375                 380
Glu Phe Ala Arg Leu Asn Lys Glu Phe Pro Asn Cys Trp Lys Pro Phe
385                 390                 395                 400
Gly Asn Gly Lys Arg Ala Cys Ile Gly Arg Pro Phe Ala Trp Gln Glu
                405                 410                 415
Ser Leu Leu Ala Met Ala Leu Leu Phe Gln Asn Phe Asn Phe Thr Gln
            420                 425                 430
Thr Asp Pro Asn Tyr Glu Leu Gln Ile Lys Gln Asn Leu Thr Ile Lys
        435                 440                 445
Pro Asp Asn Phe Phe Phe Asn Cys Thr Leu Arg His Gly Met Thr Pro
    450                 455                 460
Thr Asp Leu Glu Gly Gln Leu Ala Gly Lys Gly Ala Thr Thr Ser Ile
465                 470                 475                 480
Ala Ser His Ile Lys Ala Pro Ala Ala Ser Lys Gly Ala Lys Ala Ser
                485                 490                 495
Asn Gly Lys Pro Met Ala Ile Tyr Tyr Gly Ser Asn Ser Gly Thr Cys
            500                 505                 510
Glu Ala Leu Ala Asn Arg Leu Ala Ser Asp Ala Ala Gly His Gly Phe
        515                 520                 525
Ser Ala Ser Val Ile Gly Thr Leu Asp Gln Ala Lys Gln Asn Leu Pro
    530                 535                 540
Glu Asp Arg Pro Val Val Ile Val Thr Ala Ser Tyr Glu Gly Gln Pro
545                 550                 555                 560
Pro Ser Asn Ala Ala His Phe Ile Lys Trp Met Glu Asp Leu Ala Gly
                565                 570                 575
Asn Glu Met Glu Lys Val Ser Tyr Ala Val Phe Gly Cys Gly His His
            580                 585                 590
Asp Trp Val Asp Thr Phe Leu Arg Ile Pro Lys Leu Val Asp Thr Thr
        595                 600                 605
Leu Glu Gln Arg Gly Gly Thr Arg Leu Val Pro Met Gly Ser Ala Asp
    610                 615                 620
Ala Ala Thr Ser Asp Met Phe Ser Asp Phe Glu Ala Trp Glu Asp Thr
625                 630                 635                 640
Val Leu Trp Pro Ser Leu Lys Glu Lys Tyr Asn Val Thr Asp Asp Glu
                645                 650                 655
```

```
Ala Ser Gly Gln Arg Gly Leu Leu Val Glu Val Thr Thr Pro Arg Lys
            660                 665                 670

Thr Thr Leu Arg Gln Asp Val Glu Glu Ala Leu Val Val Ser Glu Lys
            675                 680                 685

Thr Leu Thr Lys Thr Gly Pro Ala Lys Lys His Ile Glu Ile Gln Leu
            690                 695                 700

Pro Ser Gly Met Thr Tyr Lys Ala Gly Asp Tyr Leu Ala Ile Leu Pro
705                 710                 715                 720

Leu Asn Pro Arg Lys Thr Val Ser Arg Val Phe Arg Arg Phe Ser Leu
                725                 730                 735

Ala Trp Asp Ser Phe Leu Lys Ile Gln Ser Asp Gly Pro Thr Thr Leu
            740                 745                 750

Pro Ile Asn Ile Ala Ile Ser Ala Phe Asp Val Phe Ser Ala Tyr Val
            755                 760                 765

Glu Leu Ser Gln Pro Ala Thr Lys Arg Asn Ile Leu Ala Leu Ser Glu
            770                 775                 780

Ala Thr Glu Asp Lys Ala Thr Ile Gln Glu Leu Glu Lys Leu Ala Gly
785                 790                 795                 800

Asp Ala Tyr Gln Glu Asp Val Ser Ala Lys Lys Val Ser Val Leu Asp
                805                 810                 815

Leu Leu Glu Lys Tyr Pro Ala Val Ala Leu Pro Ile Ser Ser Tyr Leu
            820                 825                 830

Ala Met Leu Pro Pro Met Arg Val Arg Gln Tyr Ser Ile Ser Ser Ser
            835                 840                 845

Pro Phe Ala Asp Pro Ser Lys Leu Thr Leu Thr Tyr Ser Leu Leu Asp
850                 855                 860

Ala Pro Ser Leu Ser Gly Gln Gly Arg His Val Gly Val Ala Thr Asn
865                 870                 875                 880

Phe Leu Ser Gln Leu Ile Ala Gly Asp Lys Leu His Ile Ser Val Arg
                885                 890                 895

Ala Ser Ser Ala Ala Phe His Leu Pro Ser Asp Pro Glu Thr Thr Pro
            900                 905                 910

Ile Ile Cys Val Ala Ala Gly Thr Gly Leu Ala Pro Phe Arg Gly Phe
            915                 920                 925

Ile Gln Glu Arg Ala Ala Met Leu Ala Ala Gly Arg Lys Leu Ala Pro
            930                 935                 940

Ala Leu Leu Phe Phe Gly Cys Arg Asp Pro Glu Asn Asp Asp Leu Tyr
945                 950                 955                 960

Ala Glu Glu Leu Ala Arg Trp Glu Gln Met Gly Ala Val Asp Val Arg
                965                 970                 975

Arg Ala Tyr Ser Arg Ala Thr Asp Lys Ser Glu Gly Cys Lys Tyr Val
            980                 985                 990

Gln Asp Arg Ile Tyr His Asp Arg Ala Asp Val Phe Lys Val Trp Asp
            995                 1000                1005

Gln Gly Ala Lys Val Phe Ile Cys Gly Ser Arg Glu Ile Gly Lys Ala
            1010                1015                1020

Val Glu Asp Ile Cys Val Arg Leu Ala Met Glu Arg Ser Glu Ala Thr
1025                1030                1035                1040

Gln Glu Gly Lys Gly Ala Thr Glu Glu Lys Ala Arg Glu Trp Phe Glu
                1045                1050                1055

Arg Ser Arg Asn Glu Arg Phe Ala Thr Asp Val Phe Asp
            1060                1065
```

<210> SEQ ID NO 39
<211> LENGTH: 1066
<212> TYPE: PRT
<213> ORGANISM: Gibberella zeae
<220> FEATURE:
<223> OTHER INFORMATION: Gibberella zeae strain PH1a, NRRL 31084
      (Fusarium graminearum) hypothetical protein FG07596.1, CYP505C2

<400> SEQUENCE: 39

```
Met Ala Ile Lys Asp Gly Gly Lys Lys Ser Gly Gln Ile Pro Gly Pro
1               5                   10                  15

Lys Gly Leu Pro Val Leu Gly Asn Leu Phe Asp Leu Asp Leu Ser Asp
            20                  25                  30

Ser Leu Thr Ser Leu Ile Asn Ile Gly Gln Lys Tyr Ala Pro Ile Phe
        35                  40                  45

Ser Leu Glu Leu Gly Gly His Arg Glu Val Met Ile Cys Ser Arg Asp
    50                  55                  60

Leu Leu Asp Glu Leu Cys Asp Glu Thr Arg Phe His Lys Ile Val Thr
65                  70                  75                  80

Gly Gly Val Asp Lys Leu Arg Pro Leu Ala Gly Asp Gly Leu Phe Thr
                85                  90                  95

Ala Gln His Gly Asn His Asp Trp Gly Ile Ala His Arg Ile Leu Met
            100                 105                 110

Pro Leu Phe Gly Pro Leu Lys Ile Arg Glu Met Phe Asp Asp Met Gln
        115                 120                 125

Asp Val Ser Glu Gln Leu Cys Leu Lys Trp Ala Arg Leu Gly Pro Ser
    130                 135                 140

Ala Thr Ile Asp Val Ala Asn Asp Phe Thr Arg Leu Thr Leu Asp Thr
145                 150                 155                 160

Ile Ala Leu Cys Thr Met Gly Tyr Arg Phe Asn Ser Phe Tyr Ser Asn
                165                 170                 175

Asp Lys Met His Pro Phe Val Asp Ser Met Val Ala Ala Leu Ile Asp
            180                 185                 190

Ala Asp Lys Gln Ser Met Phe Pro Asp Phe Ile Gly Ala Cys Arg Val
        195                 200                 205

Lys Ala Leu Ser Ala Phe Arg Lys His Ala Ala Ile Met Lys Gly Thr
    210                 215                 220

Cys Asn Glu Leu Ile Gln Glu Arg Arg Lys Asn Pro Ile Glu Gly Thr
225                 230                 235                 240

Asp Leu Leu Thr Ala Met Met Glu Gly Lys Asp Pro Lys Thr Gly Glu
                245                 250                 255

Gly Met Ser Asp Asp Leu Ile Val Gln Asn Leu Ile Thr Phe Leu Ile
            260                 265                 270

Ala Gly His Glu Thr Thr Ser Gly Leu Leu Ser Phe Ala Phe Tyr Tyr
        275                 280                 285

Leu Leu Glu Asn Pro His Thr Leu Glu Lys Ala Arg Ala Glu Val Asp
    290                 295                 300

Glu Val Val Gly Asp Gln Ala Leu Asn Val Asp His Leu Thr Lys Met
305                 310                 315                 320

Pro Tyr Val Asn Met Ile Leu Arg Glu Thr Leu Arg Leu Met Pro Thr
                325                 330                 335

Ala Pro Gly Phe Phe Val Thr Pro His Lys Asp Glu Ile Ile Gly Gly
            340                 345                 350

Lys Tyr Ala Val Pro Ala Asn Glu Ser Leu Phe Cys Phe Leu His Leu
        355                 360                 365
```

-continued

```
Ile His Arg Asp Pro Lys Val Trp Gly Ala Asp Ala Glu Glu Phe Arg
    370                 375                 380

Pro Glu Arg Met Ala Asp Glu Phe Phe Glu Ala Leu Pro Lys Asn Ala
385                 390                 395                 400

Trp Lys Pro Phe Gly Asn Gly Met Arg Gly Cys Ile Gly Arg Glu Phe
                405                 410                 415

Ala Trp Gln Glu Ala Lys Leu Ile Thr Val Met Ile Leu Gln Asn Phe
            420                 425                 430

Glu Leu Ser Lys Ala Asp Pro Ser Tyr Lys Leu Lys Ile Lys Gln Ser
        435                 440                 445

Leu Thr Ile Lys Pro Asp Gly Phe Asn Met His Ala Lys Leu Arg Asn
    450                 455                 460

Asp Arg Lys Val Ser Gly Leu Phe Lys Ala Pro Ser Leu Ser Ser Gln
465                 470                 475                 480

Gln Pro Ser Leu Ser Ser Arg Gln Ser Ile Asn Ala Ile Asn Ala Lys
                485                 490                 495

Asp Leu Lys Pro Ile Ser Ile Phe Tyr Gly Ser Asn Thr Gly Thr Cys
            500                 505                 510

Glu Ala Leu Ala Gln Lys Leu Ser Ala Asp Cys Val Ala Ser Gly Phe
        515                 520                 525

Met Pro Ser Lys Pro Leu Pro Leu Asp Met Ala Thr Lys Asn Leu Ser
    530                 535                 540

Lys Asp Gly Pro Asn Ile Leu Leu Ala Ala Ser Tyr Asp Gly Arg Pro
545                 550                 555                 560

Ser Asp Asn Ala Glu Glu Phe Thr Lys Trp Ala Glu Ser Leu Lys Pro
                565                 570                 575

Gly Glu Leu Glu Gly Val Gln Phe Ala Val Phe Gly Cys Gly His Lys
            580                 585                 590

Asp Trp Val Ser Thr Tyr Phe Lys Ile Pro Lys Ile Leu Asp Lys Cys
        595                 600                 605

Leu Ala Asp Ala Gly Ala Glu Arg Leu Val Glu Ile Gly Leu Thr Asp
    610                 615                 620

Ala Ser Thr Gly Arg Leu Tyr Ser Asp Phe Asp Asp Trp Glu Asn Gln
625                 630                 635                 640

Lys Leu Phe Thr Glu Leu Ser Lys Arg Gln Gly Val Thr Pro Thr Asp
                645                 650                 655

Asp Ser His Leu Glu Leu Asn Val Thr Val Ile Gln Pro Gln Asn Asn
            660                 665                 670

Asp Met Gly Gly Asn Phe Lys Arg Ala Glu Val Val Glu Asn Thr Leu
        675                 680                 685

Leu Thr Tyr Pro Gly Val Ser Arg Lys His Ser Leu Leu Lys Leu
    690                 695                 700

Pro Lys Asp Met Glu Tyr Thr Pro Gly Asp His Val Leu Val Leu Pro
705                 710                 715                 720

Lys Asn Pro Pro Gln Leu Val Glu Gln Ala Met Ser Cys Phe Gly Val
                725                 730                 735

Asp Ser Asp Thr Ala Leu Thr Ile Ser Ser Lys Arg Pro Thr Phe Leu
            740                 745                 750

Pro Thr Asp Thr Pro Ile Leu Ile Ser Ser Leu Leu Ser Ser Leu Val
        755                 760                 765

Glu Leu Ser Gln Thr Val Ser Arg Thr Ser Leu Lys Arg Leu Ala Asp
    770                 775                 780

Phe Ala Asp Asp Asp Asp Thr Lys Ala Cys Val Glu Arg Ile Ala Gly
```

```
                    785                 790                 795                 800
Asp Asp Tyr Thr Val Glu Val Glu Gln Arg Met Ser Leu Leu Asp
                805                 810                 815

Ile Leu Arg Lys Tyr Pro Gly Ile Asn Met Pro Leu Ser Thr Phe Leu
                820                 825                 830

Ser Met Leu Pro Gln Met Arg Pro Arg Thr Tyr Ser Phe Ala Ser Ala
                835                 840                 845

Pro Glu Trp Lys Gln Gly His Gly Met Leu Leu Phe Ser Val Val Glu
            850                 855                 860

Ala Glu Glu Gly Thr Val Ser Arg Pro Gly Gly Leu Ala Thr Asn Tyr
865                 870                 875                 880

Met Ala Gln Leu Arg Gln Gly Asp Ser Ile Leu Val Glu Pro Arg Pro
                885                 890                 895

Cys Arg Pro Glu Leu Arg Thr Thr Met Met Leu Pro Glu Pro Lys Val
                900                 905                 910

Pro Ile Ile Met Ile Ala Val Gly Ala Gly Leu Ala Pro Phe Leu Gly
            915                 920                 925

Tyr Leu Gln Lys Arg Phe Leu Gln Ala Gln Ser Gln Arg Thr Ala Leu
        930                 935                 940

Pro Pro Cys Thr Leu Leu Phe Gly Cys Arg Gly Ala Lys Met Asp Asp
945                 950                 955                 960

Ile Cys Arg Ala Gln Leu Asp Glu Tyr Ser Arg Ala Gly Val Val Ser
                965                 970                 975

Val His Arg Ala Tyr Ser Arg Asp Pro Asp Ser Gln Cys Lys Tyr Val
            980                 985                 990

Gln Gly Leu Val Thr Lys His Ser Glu Thr Leu Ala Lys Gln Trp Ala
        995                 1000                1005

Gln Gly Ala Ile Val Met Val Cys Ser Gly Lys Lys Val Ser Asp Gly
        1010                1015                1020

Val Met Asn Val Leu Ser Pro Ile Leu Phe Ala Glu Glu Lys Arg Ser
1025                1030                1035                1040

Gly Met Thr Gly Ala Asp Ser Val Asp Val Trp Arg Gln Asn Val Pro
            1045                1050                1055

Lys Glu Arg Met Ile Leu Glu Val Phe Gly
            1060                1065

<210> SEQ ID NO 40
<211> LENGTH: 1130
<212> TYPE: PRT
<213> ORGANISM: Magnaporthe oryzae
<220> FEATURE:
<223> OTHER INFORMATION: Magnaporthe oryzae (M. grisea) strain 70-15
      hypothetical protein MGG_01925, CYP505A5, bifunctional
      unspecific monooxygenase/NADPH-hemoprotein reductase

<400> SEQUENCE: 40

Met Phe Phe Leu Ser Ser Leu Ala Tyr Met Ala Ala Thr Gln Ser
1               5                   10                  15

Arg Asp Trp Ala Ser Phe Gly Val Ser Leu Pro Ser Thr Ala Leu Gly
                20                  25                  30

Arg His Leu Gln Ala Ala Met Pro Phe Leu Ser Glu Glu Asn His Lys
            35                  40                  45

Ser Gln Gly Thr Val Leu Ile Pro Asp Ala Gln Gly Pro Ile Pro Phe
        50                  55                  60

Leu Gly Ser Val Pro Leu Val Asp Pro Glu Leu Pro Ser Gln Ser Leu
65                  70                  75                  80
```

```
Gln Arg Leu Ala Arg Gln Tyr Gly Glu Ile Tyr Arg Phe Val Ile Pro
                85                  90                  95
Gly Arg Gln Ser Pro Ile Leu Val Ser Thr His Ala Leu Val Asn Glu
            100                 105                 110
Leu Cys Asp Glu Lys Arg Phe Lys Lys Val Ala Ala Ala Leu Leu
        115                 120                 125
Gly Leu Arg Glu Ala Ile His Asp Gly Leu Phe Thr Ala His Asn Asp
    130                 135                 140
Glu Pro Asn Trp Gly Ile Ala His Arg Ile Leu Met Pro Ala Phe Gly
145                 150                 155                 160
Pro Met Ala Ile Lys Gly Met Phe Asp Glu Met His Val Ala Ser
                165                 170                 175
Gln Met Ile Leu Lys Trp Ala Arg His Gly Ser Thr Thr Pro Ile Met
            180                 185                 190
Val Ser Asp Asp Phe Thr Arg Leu Thr Leu Asp Thr Ile Ala Leu Cys
        195                 200                 205
Ser Met Gly Tyr Arg Phe Asn Ser Phe Tyr His Asp Ser Met His Glu
    210                 215                 220
Phe Ile Glu Ala Met Thr Cys Trp Met Lys Glu Ser Gly Asn Lys Thr
225                 230                 235                 240
Arg Arg Leu Leu Pro Asp Val Phe Tyr Arg Thr Thr Asp Lys Lys Trp
                245                 250                 255
His Asp Asp Ala Glu Ile Leu Arg Arg Thr Ala Asp Glu Val Leu Lys
            260                 265                 270
Ala Arg Lys Glu Asn Pro Ser Gly Arg Lys Asp Leu Leu Thr Ala Met
        275                 280                 285
Ile Glu Gly Val Asp Pro Lys Thr Gly Gly Lys Leu Ser Asp Ser Ser
    290                 295                 300
Ile Ile Asp Asn Leu Ile Thr Phe Leu Ile Ala Gly His Glu Thr Thr
305                 310                 315                 320
Ser Gly Met Leu Ser Phe Ala Phe Tyr Leu Leu Lys Asn Pro Thr
                325                 330                 335
Ala Tyr Arg Lys Ala Gln Gln Glu Ile Asp Asp Leu Cys Gly Arg Glu
            340                 345                 350
Pro Ile Thr Val Glu His Leu Ser Lys Met Pro Tyr Ile Thr Ala Val
        355                 360                 365
Leu Arg Glu Thr Leu Arg Leu Tyr Ser Thr Ile Pro Ala Phe Val Val
    370                 375                 380
Glu Ala Ile Glu Asp Thr Val Val Gly Gly Lys Tyr Ala Ile Pro Lys
385                 390                 395                 400
Asn His Pro Ile Phe Leu Met Ile Ala Glu Ser His Arg Asp Pro Lys
                405                 410                 415
Val Tyr Gly Asp Asp Ala Gln Glu Phe Glu Pro Glu Arg Met Leu Asp
            420                 425                 430
Gly Gln Phe Glu Arg Arg Asn Arg Glu Phe Pro Asn Ser Trp Lys Pro
        435                 440                 445
Phe Gly Asn Gly Met Arg Gly Cys Ile Gly Arg Ala Phe Ala Trp Gln
    450                 455                 460
Glu Ala Leu Leu Ile Thr Ala Met Leu Leu Gln Asn Phe Asn Phe Val
465                 470                 475                 480
Met His Asp Pro Ala Tyr Gln Leu Ser Ile Lys Glu Asn Leu Thr Leu
                485                 490                 495
```

```
Lys Pro Asp Asn Phe Tyr Met Arg Ala Ile Leu Arg His Gly Met Ser
            500                 505                 510

Pro Thr Glu Leu Glu Arg Ser Ile Ser Gly Val Ala Pro Thr Gly Asn
        515                 520                 525

Lys Thr Pro Pro Arg Asn Ala Thr Arg Thr Ser Ser Pro Asp Pro Glu
    530                 535                 540

Asp Gly Gly Ile Pro Met Ser Ile Tyr Tyr Gly Ser Asn Ser Gly Thr
545                 550                 555                 560

Cys Glu Ser Leu Ala His Lys Leu Ala Val Asp Ala Ser Ala Gln Gly
            565                 570                 575

Phe Lys Ala Glu Thr Val Asp Val Leu Asp Ala Asn Gln Lys Leu
        580                 585                 590

Pro Ala Gly Asn Arg Gly Pro Val Val Leu Ile Thr Ala Ser Tyr Glu
    595                 600                 605

Gly Leu Pro Pro Asp Asn Ala Lys His Phe Val Glu Trp Leu Glu Asn
610                 615                 620

Leu Lys Gly Gly Asp Glu Leu Val Asp Thr Ser Tyr Ala Val Phe Gly
625                 630                 635                 640

Cys Gly His Gln Asp Trp Thr Lys Thr Phe His Arg Ile Pro Lys Leu
            645                 650                 655

Val Asp Glu Lys Leu Ala Glu His Gly Ala Val Arg Leu Ala Pro Leu
        660                 665                 670

Gly Leu Ser Asn Ala Ala His Gly Asp Met Phe Val Asp Phe Glu Thr
    675                 680                 685

Trp Glu Phe Glu Thr Leu Trp Pro Ala Leu Ala Asp Arg Tyr Lys Thr
690                 695                 700

Gly Ala Gly Arg Gln Asp Ala Ala Thr Asp Leu Thr Ala Ala Leu
705                 710                 715                 720

Ser Gln Leu Ser Val Glu Val Ser His Pro Arg Ala Ala Asp Leu Arg
            725                 730                 735

Gln Asp Val Gly Glu Ala Val Val Ala Ala Arg Asp Leu Thr Ala
        740                 745                 750

Pro Gly Ala Pro Pro Lys Arg His Met Glu Ile Arg Leu Pro Lys Thr
    755                 760                 765

Gly Gly Arg Val His Tyr Ser Ala Gly Asp Tyr Leu Ala Val Leu Pro
770                 775                 780

Val Asn Pro Lys Ser Thr Val Glu Arg Ala Met Arg Arg Phe Gly Leu
785                 790                 795                 800

Ala Trp Asp Ala His Val Thr Ile Arg Ser Gly Gly Arg Thr Thr Leu
            805                 810                 815

Pro Thr Gly Ala Pro Val Ser Ala Arg Glu Val Leu Ser Ser Tyr Val
        820                 825                 830

Glu Leu Thr Gln Pro Ala Thr Lys Arg Gly Ile Ala Val Leu Ala Gly
    835                 840                 845

Ala Val Thr Gly Gly Pro Ala Ala Glu Gln Gln Ala Lys Ala Ala
850                 855                 860

Leu Leu Asp Leu Ala Gly Asp Ser Tyr Ala Leu Glu Val Ser Ala Lys
865                 870                 875                 880

Arg Val Gly Val Leu Asp Leu Leu Glu Arg Phe Pro Ala Cys Ala Val
            885                 890                 895

Pro Phe Gly Thr Phe Leu Ala Leu Leu Pro Pro Met Arg Val Arg Gln
        900                 905                 910

Tyr Ser Ile Ser Ser Ser Pro Leu Trp Asn Asp Glu His Ala Thr Leu
```

```
                    915                 920                 925
Thr Tyr Ser Val Leu Ser Ala Pro Ser Leu Ala Asp Pro Ala Arg Thr
    930                 935                 940

His Val Gly Val Ala Ser Ser Tyr Leu Ala Gly Leu Gly Glu Gly Asp
945                 950                 955                 960

His Leu His Val Ala Leu Arg Pro Ser His Val Ala Phe Arg Leu Pro
                965                 970                 975

Ser Pro Glu Thr Pro Val Val Cys Val Cys Ala Gly Ser Gly Met Ala
            980                 985                 990

Pro Phe Arg Ala Phe Ala Gln Glu Arg Ala Ala Leu Val Gly Ala Gly
        995                 1000                1005

Arg Lys Val Ala Pro Leu Leu Leu Phe Phe Gly Cys Arg Glu Pro Gly
    1010                1015                1020

Val Asp Asp Leu Tyr Arg Glu Leu Glu Gly Trp Glu Ala Lys Gly
1025                1030                1035                1040

Val Leu Ser Val Arg Arg Ala Tyr Ser Arg Arg Thr Glu Gln Ser Glu
                1045                1050                1055

Gly Cys Arg Tyr Val Gln Asp Arg Leu Leu Lys Asn Arg Ala Glu Val
            1060                1065                1070

Lys Ser Leu Trp Ser Gln Asp Ala Lys Val Phe Val Cys Gly Ser Arg
        1075                1080                1085

Glu Val Ala Glu Gly Val Lys Glu Ala Met Phe Lys Val Val Ala Gly
    1090                1095                1100

Lys Glu Gly Ser Ser Glu Glu Val Gln Ala Trp Tyr Glu Glu Val Arg
1105                1110                1115                1120

Asn Val Arg Tyr Ala Ser Asp Ile Phe Asp
                1125                1130

<210> SEQ ID NO 41
<211> LENGTH: 1108
<212> TYPE: PRT
<213> ORGANISM: Neurospora crassa
<220> FEATURE:
<223> OTHER INFORMATION: Neurospora crassa strain OR74A bifunctional
      P-450:NADPH-P450 reductase, CYP505A2, locus NCU05185

<400> SEQUENCE: 41

Met Ser Ser Asp Glu Thr Pro Gln Thr Ile Pro Ile Pro Gly Pro Pro
1               5                   10                  15

Gly Leu Pro Leu Val Gly Asn Ser Phe Asp Ile Asp Thr Glu Phe Pro
            20                  25                  30

Leu Gly Ser Met Leu Asn Phe Ala Asp Gln Tyr Gly Glu Ile Phe Arg
        35                  40                  45

Leu Asn Phe Pro Gly Arg Asn Thr Val Phe Val Thr Ser Gln Ala Leu
    50                  55                  60

Val His Glu Leu Cys Asp Glu Lys Arg Phe Gln Lys Thr Val Asn Ser
65                  70                  75                  80

Ala Leu His Glu Ile Arg His Gly Ile His Asp Gly Leu Phe Thr Ala
                85                  90                  95

Arg Asn Asp Glu Pro Asn Trp Gly Ile Ala His Arg Ile Leu Met Pro
            100                 105                 110

Ala Phe Gly Pro Met Ala Ile Gln Asn Met Phe Pro Glu Met His Glu
        115                 120                 125

Ile Ala Ser Gln Leu Ala Leu Lys Trp Ala Arg His Gly Pro Asn Gln
    130                 135                 140
```

-continued

```
Ser Ile Lys Val Thr Asp Asp Phe Thr Arg Leu Thr Leu Asp Thr Ile
145                 150                 155                 160

Ala Leu Cys Ser Met Asp Tyr Arg Phe Asn Ser Tyr Tyr His Asp Asp
                165                 170                 175

Met His Pro Phe Ile Asp Ala Met Ala Ser Phe Leu Val Glu Ser Gly
                180                 185                 190

Asn Arg Ser Arg Arg Pro Ala Leu Pro Ala Phe Met Tyr Ser Lys Val
                195                 200                 205

Asp Arg Lys Phe Tyr Asp Asp Ile Arg Val Leu Arg Glu Thr Ala Glu
210                 215                 220

Gly Val Leu Lys Ser Arg Lys Glu His Pro Ser Glu Arg Lys Asp Leu
225                 230                 235                 240

Leu Thr Ala Met Leu Asp Gly Val Asp Pro Lys Thr Gly Gly Lys Leu
                245                 250                 255

Ser Asp Asp Ser Ile Ile Asp Asn Leu Ile Thr Phe Leu Ile Ala Gly
                260                 265                 270

His Glu Thr Thr Ser Gly Leu Leu Ser Phe Ala Phe Val Gln Leu Leu
                275                 280                 285

Lys Asn Pro Glu Thr Tyr Arg Lys Ala Gln Lys Glu Val Asp Asp Val
290                 295                 300

Cys Gly Lys Gly Pro Ile Lys Leu Glu His Met Asn Lys Leu His Tyr
305                 310                 315                 320

Ile Ala Ala Val Leu Arg Glu Thr Leu Arg Leu Cys Pro Thr Ile Pro
                325                 330                 335

Val Ile Gly Val Glu Ser Lys Glu Asp Thr Val Ile Gly Gly Lys Tyr
                340                 345                 350

Glu Val Ser Lys Gly Gln Pro Phe Ala Leu Leu Phe Ala Lys Ser His
                355                 360                 365

Val Asp Pro Ala Val Tyr Gly Asp Thr Ala Asn Asp Phe Asp Pro Glu
                370                 375                 380

Arg Met Leu Asp Glu Asn Phe Glu Arg Leu Asn Lys Glu Phe Pro Asp
385                 390                 395                 400

Cys Trp Lys Pro Phe Gly Asn Gly Met Arg Ala Cys Ile Gly Arg Pro
                405                 410                 415

Phe Ala Trp Gln Glu Ala Leu Leu Val Met Ala Val Cys Leu Gln Asn
                420                 425                 430

Phe Asn Phe Met Pro Glu Asp Pro Asn Tyr Thr Leu Gln Tyr Lys Gln
                435                 440                 445

Thr Leu Thr Thr Lys Pro Lys Gly Phe Tyr Met Arg Ala Met Leu Arg
450                 455                 460

Asp Gly Met Ser Ala Leu Asp Leu Glu Arg Arg Leu Lys Gly Glu Leu
465                 470                 475                 480

Val Ala Pro Lys Pro Thr Ala Gln Gly Pro Val Ser Gly Gln Pro Lys
                485                 490                 495

Lys Ser Gly Glu Gly Lys Pro Ile Ser Ile Tyr Tyr Gly Ser Asn Thr
                500                 505                 510

Gly Thr Cys Glu Thr Phe Ala Gln Arg Leu Ala Ser Asp Ala Glu Ala
                515                 520                 525

His Gly Phe Thr Ala Thr Ile Ile Asp Ser Leu Asp Ala Ala Asn Gln
                530                 535                 540

Asn Leu Pro Lys Asp Arg Pro Val Val Phe Ile Thr Ala Ser Tyr Glu
545                 550                 555                 560

Gly Gln Pro Pro Asp Asn Ala Ala Leu Phe Val Gly Trp Leu Glu Ser
```

```
                        565                 570                 575
Leu Thr Gly Asn Glu Leu Glu Gly Val Gln Tyr Ala Val Phe Gly Cys
            580                 585                 590
Gly His His Asp Trp Ala Gln Thr Phe His Arg Ile Pro Lys Leu Val
            595                 600                 605
Asp Asn Thr Val Ser Glu Arg Gly Asp Arg Ile Cys Ser Leu Gly
    610                 615                 620
Leu Ala Asp Ala Gly Lys Gly Glu Met Phe Thr Glu Phe Glu Gln Trp
625                 630                 635                 640
Glu Asp Glu Val Phe Trp Pro Ala Met Glu Glu Lys Tyr Glu Val Ser
                645                 650                 655
Arg Lys Glu Asp Asp Asn Glu Ala Leu Leu Gln Ser Gly Leu Thr Val
            660                 665                 670
Asn Phe Ser Lys Pro Arg Ser Ser Thr Leu Arg Gln Asp Val Gln Glu
            675                 680                 685
Ala Val Val Val Asp Ala Lys Thr Ile Thr Ala Pro Gly Ala Pro Pro
    690                 695                 700
Lys Arg His Ile Glu Val Gln Leu Ser Ser Asp Ser Gly Ala Tyr Arg
705                 710                 715                 720
Ser Gly Asp Tyr Leu Ala Val Leu Pro Ile Asn Pro Lys Glu Thr Val
                725                 730                 735
Asn Arg Val Met Arg Arg Phe Gln Leu Ala Trp Asp Thr Asn Ile Thr
            740                 745                 750
Ile Glu Ala Ser Arg Gln Thr Thr Ile Leu Pro Thr Gly Val Pro Met
            755                 760                 765
Pro Val His Asp Val Leu Gly Ala Tyr Val Glu Leu Ser Gln Pro Ala
    770                 775                 780
Thr Lys Lys Asn Ile Leu Ala Leu Ala Glu Ala Ala Asp Asn Ala Glu
785                 790                 795                 800
Thr Lys Ala Thr Leu Arg Gln Leu Ala Gly Pro Glu Tyr Thr Glu Lys
                805                 810                 815
Ile Thr Ser Arg Arg Val Ser Ile Leu Asp Leu Leu Glu Gln Phe Pro
            820                 825                 830
Ser Ile Pro Leu Pro Phe Ser Ser Phe Leu Ser Leu Leu Pro Pro Met
            835                 840                 845
Arg Val Arg Gln Tyr Ser Ile Ser Ser Ser Pro Leu Trp Asn Pro Ser
    850                 855                 860
His Val Thr Leu Thr Tyr Ser Leu Leu Glu Ser Pro Ser Leu Ser Asn
865                 870                 875                 880
Pro Asp Lys Lys His Val Gly Val Ala Thr Ser Tyr Leu Ala Ser Leu
                885                 890                 895
Glu Ala Gly Asp Lys Leu Asn Val Ser Ile Arg Pro Ser His Lys Ala
            900                 905                 910
Phe His Leu Pro Val Asp Ala Asp Lys Thr Pro Leu Ile Met Ile Ala
            915                 920                 925
Ala Gly Ser Gly Leu Ala Pro Phe Arg Gly Phe Val Gln Glu Arg Ala
    930                 935                 940
Ala Gln Ile Ala Ala Gly Arg Ser Leu Ala Pro Ala Met Leu Phe Tyr
945                 950                 955                 960
Gly Cys Arg His Pro Glu Gln Asp Asp Leu Tyr Arg Asp Glu Phe Asp
                965                 970                 975
Lys Trp Glu Ser Ile Gly Ala Val Ser Val Arg Arg Ala Phe Ser Arg
            980                 985                 990
```

```
Cys Pro Glu Ser Gln Glu Thr Lys Gly Cys Lys Tyr Val Gly Asp Arg
        995                 1000                1005

Leu Trp Glu Asp Arg Glu Glu Val Thr Gly Leu Trp Asp Arg Gly Ala
    1010                1015                1020

Lys Val Tyr Val Cys Gly Ser Arg Glu Val Gly Glu Ser Val Lys Lys
1025                1030                1035                1040

Val Val Val Arg Ile Ala Leu Glu Arg Gln Lys Met Ile Val Glu Ala
            1045                1050                1055

Arg Glu Lys Gly Glu Leu Asp Ser Leu Pro Glu Gly Ile Val Glu Gly
        1060                1065                1070

Leu Lys Leu Lys Gly Leu Thr Val Glu Asp Val Glu Val Ser Glu Glu
        1075                1080                1085

Arg Ala Leu Lys Trp Phe Glu Gly Ile Arg Asn Glu Arg Tyr Ala Thr
        1090                1095                1100

Asp Val Phe Asp
1105

<210> SEQ ID NO 42
<211> LENGTH: 561
<212> TYPE: PRT
<213> ORGANISM: Oryza sativa
<220> FEATURE:
<223> OTHER INFORMATION: Oryza sativa Japonica group cultivar Nipponbare
      cytochrome P450 family protein, CYP97C

<400> SEQUENCE: 42

Met Ala Ala Ala Ala Ala Ala Val Pro Cys Val Pro Phe Leu Cys
 1               5                  10                  15

Pro Pro Pro Pro Leu Val Ser Pro Arg Leu Arg Arg Gly His Val
            20                  25                  30

Arg Leu Arg Leu Arg Pro Pro Arg Ser Ser Gly Gly Gly Gly Gly
        35                  40                  45

Gly Ala Gly Gly Asp Glu Pro Pro Ile Thr Thr Ser Trp Val Ser Pro
 50                  55                  60

Asp Trp Leu Thr Ala Leu Ser Arg Ser Val Ala Thr Arg Leu Gly Gly
65                  70                  75                  80

Gly Asp Asp Ser Gly Ile Pro Val Ala Ser Ala Lys Leu Asp Asp Val
                85                  90                  95

Arg Asp Leu Leu Gly Gly Ala Leu Phe Leu Pro Leu Phe Lys Trp Phe
            100                 105                 110

Arg Glu Glu Gly Pro Val Tyr Arg Leu Ala Ala Gly Pro Arg Asp Leu
        115                 120                 125

Val Val Val Ser Asp Pro Ala Val Ala Arg His Val Leu Arg Gly Tyr
130                 135                 140

Gly Ser Arg Tyr Glu Lys Gly Leu Val Ala Glu Val Ser Glu Phe Leu
145                 150                 155                 160

Phe Gly Ser Gly Phe Ala Ile Ala Glu Gly Ala Leu Trp Thr Val Arg
                165                 170                 175

Arg Arg Ser Val Val Pro Ser Leu His Lys Arg Phe Leu Ser Val Met
            180                 185                 190

Val Asp Arg Val Phe Cys Lys Cys Ala Glu Arg Leu Val Glu Lys Leu
        195                 200                 205

Glu Thr Ser Ala Leu Ser Gly Lys Pro Val Asn Met Glu Ala Arg Phe
210                 215                 220

Ser Gln Met Thr Leu Asp Val Ile Gly Leu Ser Leu Phe Asn Tyr Asn
```

```
            225                 230                 235                 240

Phe Asp Ser Leu Thr Ser Asp Ser Pro Val Ile Asp Ala Val Tyr Thr
                        245                 250                 255

Ala Leu Lys Glu Ala Glu Leu Arg Ser Thr Asp Leu Leu Pro Tyr Trp
                        260                 265                 270

Lys Ile Asp Leu Leu Cys Lys Ile Val Pro Arg Gln Ile Lys Ala Glu
                        275                 280                 285

Lys Ala Val Asn Ile Ile Arg Asn Thr Val Glu Asp Leu Ile Thr Lys
                        290                 295                 300

Cys Lys Lys Ile Val Asp Ala Glu Asn Glu Gln Ile Glu Gly Glu Glu
        305                 310                 315                 320

Tyr Val Asn Glu Ala Asp Pro Ser Ile Leu Arg Phe Leu Leu Ala Ser
                        325                 330                 335

Arg Glu Glu Val Thr Ser Val Gln Leu Arg Asp Asp Leu Leu Ser Met
                        340                 345                 350

Leu Val Ala Gly His Glu Thr Thr Gly Ser Val Leu Thr Trp Thr Ile
                        355                 360                 365

Tyr Leu Leu Ser Lys Asp Pro Ala Ala Leu Arg Arg Ala Gln Ala Glu
                        370                 375                 380

Val Asp Arg Val Leu Gln Gly Arg Leu Pro Arg Tyr Glu Asp Leu Lys
        385                 390                 395                 400

Glu Leu Lys Tyr Leu Met Arg Cys Ile Asn Glu Ser Met Arg Leu Tyr
                        405                 410                 415

Pro His Pro Pro Val Leu Ile Arg Arg Ala Ile Val Asp Asp Val Leu
                        420                 425                 430

Pro Gly Asn Tyr Lys Ile Lys Ala Gly Gln Asp Ile Met Ile Ser Val
                        435                 440                 445

Tyr Asn Ile His Arg Ser Pro Glu Val Trp Asp Arg Ala Asp Asp Phe
                        450                 455                 460

Ile Pro Glu Arg Phe Asp Leu Glu Gly Pro Val Pro Asn Glu Thr Asn
        465                 470                 475                 480

Thr Glu Tyr Arg Phe Ile Pro Phe Ser Gly Gly Pro Arg Lys Cys Val
                        485                 490                 495

Gly Asp Gln Phe Ala Leu Leu Glu Ala Ile Val Ala Leu Ala Val Val
                        500                 505                 510

Leu Gln Lys Met Asp Ile Glu Leu Val Pro Asp Gln Lys Ile Asn Met
                        515                 520                 525

Thr Thr Gly Ala Thr Ile His Thr Thr Asn Gly Leu Tyr Met Asn Val
                        530                 535                 540

Ser Leu Arg Lys Val Asp Arg Glu Pro Asp Phe Ala Leu Ser Gly Ser
        545                 550                 555                 560

Arg

<210> SEQ ID NO 43
<211> LENGTH: 467
<212> TYPE: PRT
<213> ORGANISM: Artificial Sequence
<220> FEATURE:
<223> OTHER INFORMATION: synthetic chimeric heme enzyme C2G9, chimeric
      cytochrome P450 enzyme C2G9

<400> SEQUENCE: 43

Met Lys Glu Thr Ser Pro Ile Pro Gln Pro Lys Thr Phe Gly Pro Leu
 1               5                  10                  15

Gly Asn Leu Pro Leu Ile Asp Lys Asp Lys Pro Thr Leu Ser Leu Ile
```

```
            20                  25                  30
Lys Leu Ala Glu Glu Gln Gly Pro Ile Phe Gln Ile His Thr Pro Ala
        35                  40                  45
Gly Thr Thr Ile Val Val Ser Gly His Glu Leu Val Lys Glu Val Cys
 50                  55                  60
Asp Glu Glu Arg Phe Asp Lys Ser Ile Glu Gly Ala Leu Glu Lys Val
 65                  70                  75                  80
Arg Ala Phe Ser Gly Asp Gly Leu Ala Thr Ser Trp Thr His Glu Pro
                85                  90                  95
Asn Trp Arg Lys Ala His Asn Ile Leu Met Pro Thr Phe Ser Gln Arg
                100                 105                 110
Ala Met Lys Asp Tyr His Glu Lys Met Val Asp Ile Ala Val Gln Leu
            115                 120                 125
Ile Gln Lys Trp Ala Arg Leu Asn Pro Asn Glu Ala Val Asp Val Pro
        130                 135                 140
Gly Asp Met Thr Arg Leu Thr Leu Asp Thr Ile Gly Leu Cys Gly Phe
145                 150                 155                 160
Asn Tyr Arg Phe Asn Ser Tyr Tyr Arg Glu Thr Pro His Pro Phe Ile
                165                 170                 175
Asn Ser Met Val Arg Ala Leu Asp Glu Ala Met His Gln Met Gln Arg
            180                 185                 190
Leu Asp Val Gln Asp Lys Leu Met Val Arg Thr Lys Arg Gln Phe Arg
        195                 200                 205
Tyr Asp Ile Gln Thr Met Phe Ser Leu Val Asp Arg Met Ile Ala Glu
    210                 215                 220
Arg Lys Ala Asn Pro Asp Glu Asn Ile Lys Asp Leu Leu Ser Leu Met
225                 230                 235                 240
Leu Tyr Ala Lys Asp Pro Val Thr Gly Glu Thr Leu Asp Asp Glu Asn
                245                 250                 255
Ile Arg Tyr Gln Ile Ile Thr Phe Leu Ile Ala Gly His Glu Thr Thr
            260                 265                 270
Ser Gly Leu Leu Ser Phe Ala Leu Tyr Phe Leu Val Lys Asn Pro His
        275                 280                 285
Val Leu Gln Lys Ala Ala Glu Glu Ala Ala Arg Val Leu Val Asp Pro
    290                 295                 300
Val Pro Ser Tyr Lys Gln Val Lys Gln Leu Lys Tyr Val Gly Met Val
305                 310                 315                 320
Leu Asn Glu Ala Leu Arg Leu Trp Pro Thr Ala Pro Ala Phe Ser Leu
                325                 330                 335
Tyr Ala Lys Glu Asp Thr Val Leu Gly Gly Glu Tyr Pro Ile Ser Lys
            340                 345                 350
Gly Gln Pro Val Thr Val Leu Ile Pro Lys Leu His Arg Asp Gln Asn
        355                 360                 365
Ala Trp Gly Pro Asp Ala Glu Asp Phe Arg Pro Glu Arg Phe Glu Asp
    370                 375                 380
Pro Ser Ser Ile Pro His His Ala Tyr Lys Pro Phe Gly Asn Gly Gln
385                 390                 395                 400
Arg Ala Cys Ile Gly Met Gln Phe Ala Leu His Glu Ala Thr Leu Val
                405                 410                 415
Leu Gly Met Ile Leu Lys Tyr Phe Thr Leu Ile Asp His Glu Asn Tyr
            420                 425                 430
Glu Leu Asp Ile Lys Gln Thr Leu Thr Leu Lys Pro Gly Asp Phe His
        435                 440                 445
```

-continued

Ile Ser Val Gln Ser Arg His Gln Glu Ala Ile His Ala Asp Val Gln
    450                 455                 460

Ala Ala Glu
465

<210> SEQ ID NO 44
<211> LENGTH: 467
<212> TYPE: PRT
<213> ORGANISM: Artificial Sequence
<220> FEATURE:
<223> OTHER INFORMATION: synthetic chimeric heme enzyme X7, chimeric
      cytochrome P450 enzyme X7

<400> SEQUENCE: 44

Met Lys Glu Thr Ser Pro Ile Pro Gln Pro Lys Thr Phe Gly Pro Leu
1               5                   10                  15

Gly Asn Leu Pro Leu Ile Asp Lys Asp Lys Pro Thr Leu Ser Leu Ile
            20                  25                  30

Lys Leu Ala Glu Glu Gln Gly Pro Ile Phe Gln Ile His Thr Pro Ala
        35                  40                  45

Gly Thr Thr Ile Val Val Ser Gly His Glu Leu Val Lys Glu Val Cys
50                  55                  60

Asp Glu Glu Arg Phe Asp Lys Ser Ile Glu Gly Ala Leu Glu Lys Val
65                  70                  75                  80

Arg Ala Phe Ser Gly Asp Gly Leu Ala Thr Ser Trp Thr His Glu Pro
                85                  90                  95

Asn Trp Arg Lys Ala His Asn Ile Leu Met Pro Thr Phe Ser Gln Arg
            100                 105                 110

Ala Met Lys Asp Tyr His Glu Lys Met Val Asp Ile Ala Thr Gln Leu
        115                 120                 125

Ile Gln Lys Trp Ser Arg Leu Asn Pro Asn Glu Glu Ile Asp Val Ala
130                 135                 140

Asp Asp Met Thr Arg Leu Thr Leu Asp Thr Ile Gly Leu Cys Gly Phe
145                 150                 155                 160

Asn Tyr Arg Phe Asn Ser Phe Tyr Arg Asp Gln Pro His Pro Phe Ile
                165                 170                 175

Thr Ser Met Val Arg Ala Leu Asp Glu Ala Met Asn Lys Leu Gln Arg
            180                 185                 190

Ala Asn Pro Asp Asp Pro Ala Tyr Asp Glu Asn Lys Arg Gln Phe Gln
        195                 200                 205

Glu Asp Ile Lys Val Met Asn Asp Leu Val Asp Ser Ile Ile Ala Glu
    210                 215                 220

Arg Arg Ala Asn Gly Asp Gln Asp Glu Lys Asp Leu Leu Ala Arg Met
225                 230                 235                 240

Leu Asn Val Glu Asp Pro Glu Thr Gly Glu Lys Leu Asp Asp Glu Asn
                245                 250                 255

Ile Arg Phe Gln Ile Ile Thr Phe Leu Ile Ala Gly His Glu Thr Thr
            260                 265                 270

Ser Gly Leu Leu Ser Phe Ala Ile Tyr Cys Leu Leu Thr His Pro Glu
        275                 280                 285

Lys Leu Lys Lys Ala Gln Glu Glu Ala Asp Arg Val Leu Thr Asp Asp
    290                 295                 300

Thr Pro Glu Tyr Lys Gln Ile Gln Gln Leu Lys Tyr Ile Arg Met Val
305                 310                 315                 320

Leu Asn Glu Thr Leu Arg Leu Tyr Pro Thr Ala Pro Ala Phe Ser Leu

Tyr Ala Lys Glu Asp Thr Val Leu Gly Gly Glu Tyr Pro Ile Ser Lys
325                 330                 335

Gly Gln Pro Val Thr Val Leu Ile Pro Lys Leu His Arg Asp Gln Asn
        340                 345                 350

Ala Trp Gly Pro Asp Ala Glu Asp Phe Arg Pro Glu Arg Phe Glu Asp
            355                 360                 365

Pro Ser Ser Ile Pro His His Ala Tyr Lys Pro Phe Gly Asn Gly Gln
370                 375                 380

Arg Ala Cys Ile Gly Met Gln Phe Ala Leu Gln Glu Ala Thr Met Val
        385                 390                 395                 400

Leu Gly Leu Val Leu Lys His Phe Glu Leu Ile Asn His Thr Gly Tyr
            405                 410                 415

Glu Leu Lys Ile Lys Glu Ala Leu Thr Ile Lys Pro Asp Asp Phe Lys
                420                 425                 430

Ile Thr Val Lys Pro Arg Lys Thr Ala Ala Ile Asn Val Gln Arg Lys
435                 440                 445

Glu Gln Ala
        450                 455                 460
465

<210> SEQ ID NO 45
<211> LENGTH: 466
<212> TYPE: PRT
<213> ORGANISM: Artificial Sequence
<220> FEATURE:
<223> OTHER INFORMATION: synthetic chimeric heme enzyme X7-12, chimeric
      cytochrome P450 enzyme X7-12

<400> SEQUENCE: 45

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Glu Arg Phe Asp Lys Ser Ile Glu Gly Ala Leu Glu Lys Val Arg
65                  70                  75                  80

Ala Phe Ser Gly Asp Gly Leu Ala Thr Ser Trp Thr His Glu Pro Asn
                85                  90                  95

Trp Arg Lys Ala His Asn Ile Leu Met Pro Thr Phe Ser Gln Arg Ala
            100                 105                 110

Met Lys Asp Tyr His Glu Lys Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

```
Asp Ile Lys Val Met Asn Asp Leu Val Asp Ser Ile Ile Ala Glu Arg
    210                 215                 220

Arg Ala Asn Gly Asp Gln Asp Glu Lys Asp Leu Leu Ala Arg Met Leu
225                 230                 235                 240

Asn Val Glu Asp Pro Glu Thr Gly Lys Leu Asp Asp Glu Asn Ile
            245                 250                 255

Arg Phe Gln Ile Ile Thr Phe Leu Ile Ala Gly His Glu Thr Thr Ser
        260                 265                 270

Gly Leu Leu Ser Phe Ala Ile Tyr Cys Leu Leu Thr His Pro Glu Lys
            275                 280                 285

Leu Lys Lys Ala Gln Glu Glu Ala Asp Arg Val Leu Thr Asp Asp Thr
290                 295                 300

Pro Glu Tyr Lys Gln Ile Gln Gln Leu Lys Tyr Ile Arg Met Val Leu
305                 310                 315                 320

Asn Glu Thr Leu Arg Leu Tyr Pro Thr Ala Pro Ala Phe Ser Leu Tyr
                325                 330                 335

Ala Lys Glu Asp Thr Val Leu Gly Gly Glu Tyr Pro Ile Ser Lys Gly
            340                 345                 350

Gln Pro Val Thr Val Leu Ile Pro Lys Leu His Arg Asp Gln Asn Ala
        355                 360                 365

Trp Gly Pro Asp Ala Glu Asp Phe Arg Pro Glu Arg Phe Glu Asp Pro
    370                 375                 380

Ser Ser Ile Pro His His Ala Tyr Lys Pro Phe Gly Asn Gly Gln Arg
385                 390                 395                 400

Ala Cys Ile Gly Met Gln Phe Ala Leu Gln Glu Ala Thr Met Val Leu
                405                 410                 415

Gly Leu Val Leu Lys His Phe Glu Leu Ile Asn His Thr Gly Tyr Glu
            420                 425                 430

Leu Lys Ile Lys Glu Ala Leu Thr Ile Lys Pro Asp Asp Phe Lys Ile
        435                 440                 445

Thr Val Lys Pro Arg Lys Thr Ala Ala Ile Asn Val Gln Arg Lys Glu
    450                 455                 460

Gln Ala
465

<210> SEQ ID NO 46
<211> LENGTH: 465
<212> TYPE: PRT
<213> ORGANISM: Artificial Sequence
<220> FEATURE:
<223> OTHER INFORMATION: synthetic chimeric heme enzyme C2E6, chimeric
      cytochrome P450 enzyme C2E6

<400> SEQUENCE: 46

Met Thr Ile Lys Glu Met Pro Gln Pro Lys Thr Phe Gly Glu Leu Lys
  1               5                  10                  15

Asn Leu Pro Leu Leu Asn Thr Asp Lys Pro Val Gln Ala Leu Met Lys
                20                  25                  30

Ile Ala Asp Glu Leu Gly Glu Ile Phe Lys Phe Glu Ala Pro Gly Arg
            35                  40                  45

Val Thr Arg Tyr Leu Ser Ser Gln Arg Leu Ile Lys Glu Ala Cys Asp
        50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95
```

Trp Lys Lys Ala His Asn Ile Leu Leu Pro Ser Phe Ser Gln Gln Ala
            100                 105                 110

Met Lys Gly Tyr His Ala Met Val Asp Ile Ala Val Gln Leu Val
            115                 120                 125

Gln Lys Trp Glu Arg Leu Asn Ala Asp Glu His Ile Glu Val Pro Glu
        130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Arg Met Ile Ala Glu Arg
210                 215                 220

Lys Ala Asn Pro Asp Glu Asn Ile Lys Asp Leu Leu Ser Leu Met Leu
225                 230                 235                 240

Tyr Ala Lys Asp Pro Val Thr Gly Glu Thr Leu Asp Asp Glu Asn Ile
                245                 250                 255

Arg Tyr Gln Ile Ile Thr Phe Leu Ile Ala Gly His Glu Thr Thr Ser
            260                 265                 270

Gly Leu Leu Ser Phe Ala Ile Tyr Cys Leu Leu Thr His Pro Glu Lys
            275                 280                 285

Leu Lys Lys Ala Gln Glu Glu Ala Asp Arg Val Leu Thr Asp Asp Thr
        290                 295                 300

Pro Glu Tyr Lys Gln Ile Gln Gln Leu Lys Tyr Ile Arg Met Val Leu
305                 310                 315                 320

Asn Glu Thr Leu Arg Leu Tyr Pro Thr Ala Pro Ala Phe Ser Leu Tyr
                325                 330                 335

Ala Lys Glu Asp Thr Val Leu Gly Gly Glu Tyr Pro Leu Glu Lys Gly
            340                 345                 350

Asp Glu Leu Met Val Leu Ile Pro Gln Leu His Arg Asp Lys Thr Ile
        355                 360                 365

Trp Gly Asp Asp Val Glu Glu Phe Arg Pro Glu Arg Phe Glu Asn Pro
370                 375                 380

Ser Ala Ile Pro Gln His Ala Phe Lys Pro Phe Gly Asn Gly Gln Arg
385                 390                 395                 400

Ala Cys Ile Gly Gln Gln Phe Ala Leu His Glu Ala Thr Leu Val Leu
                405                 410                 415

Gly Met Met Leu Lys His Phe Asp Phe Glu Asp His Thr Asn Tyr Glu
            420                 425                 430

Leu Asp Ile Lys Glu Thr Leu Thr Leu Lys Pro Glu Gly Phe Val Val
        435                 440                 445

Lys Ala Lys Ser Lys Lys Ile Pro Leu Gly Gly Ile Pro Ser Pro Ser
450                 455                 460

Thr
465

<210> SEQ ID NO 47
<211> LENGTH: 467
<212> TYPE: PRT
<213> ORGANISM: Artificial Sequence
<220> FEATURE:

<223> OTHER INFORMATION: synthetic chimeric heme enzyme X7-9, chimeric
      cytochrome P450 enzyme X7-9

<400> SEQUENCE: 47

```
Met Lys Gln Ala Ser Ala Ile Pro Gln Pro Lys Thr Tyr Gly Pro Leu
 1               5                  10                  15

Lys Asn Leu Pro His Leu Glu Lys Glu Gln Leu Ser Gln Ser Leu Trp
            20                  25                  30

Arg Ile Ala Asp Glu Leu Gly Pro Ile Phe Arg Phe Asp Phe Pro Gly
        35                  40                  45

Val Ser Ser Val Phe Val Ser Gly His Asn Leu Val Ala Glu Val Cys
    50                  55                  60

Asp Glu Glu Arg Phe Asp Lys Ser Ile Glu Gly Ala Leu Glu Lys Val
65                  70                  75                  80

Arg Ala Phe Ser Gly Asp Gly Leu Ala Thr Ser Trp Thr His Glu Pro
                85                  90                  95

Asn Trp Arg Lys Ala His Asn Ile Leu Met Pro Thr Phe Ser Gln Arg
            100                 105                 110

Ala Met Lys Asp Tyr His Glu Lys Met Val Asp Ile Ala Thr Gln Leu
        115                 120                 125

Ile Gln Lys Trp Ser Arg Leu Asn Pro Asn Glu Glu Ile Asp Val Ala
    130                 135                 140

Asp Asp Met Thr Arg Leu Thr Leu Asp Thr Ile Gly Leu Cys Gly Phe
145                 150                 155                 160

Asn Tyr Arg Phe Asn Ser Phe Tyr Arg Asp Gln Pro His Pro Phe Ile
                165                 170                 175

Thr Ser Met Val Arg Ala Leu Asp Glu Ala Met Asn Lys Leu Gln Arg
            180                 185                 190

Ala Asn Pro Asp Asp Pro Ala Tyr Asp Glu Asn Lys Arg Gln Phe Gln
        195                 200                 205

Glu Asp Ile Lys Val Met Asn Asp Leu Val Asp Ser Ile Ile Ala Glu
    210                 215                 220

Arg Arg Ala Asn Gly Asp Gln Asp Glu Lys Asp Leu Leu Ala Arg Met
225                 230                 235                 240

Leu Asn Val Glu Asp Pro Glu Thr Gly Glu Lys Leu Asp Asp Glu Asn
                245                 250                 255

Ile Arg Phe Gln Ile Ile Thr Phe Leu Ile Ala Gly His Glu Thr Thr
            260                 265                 270

Ser Gly Leu Leu Ser Phe Ala Ile Tyr Cys Leu Leu Thr His Pro Glu
        275                 280                 285

Lys Leu Lys Lys Ala Gln Glu Glu Ala Asp Arg Val Leu Thr Asp Asp
    290                 295                 300

Thr Pro Glu Tyr Lys Gln Ile Gln Gln Leu Lys Tyr Ile Arg Met Val
305                 310                 315                 320

Leu Asn Glu Thr Leu Arg Leu Tyr Pro Thr Ala Pro Ala Phe Ser Leu
                325                 330                 335

Tyr Ala Lys Glu Asp Thr Val Leu Gly Gly Glu Tyr Pro Ile Ser Lys
            340                 345                 350

Gly Gln Pro Val Thr Val Leu Ile Pro Lys Leu His Arg Asp Gln Asn
        355                 360                 365

Ala Trp Gly Pro Asp Ala Glu Asp Phe Arg Pro Glu Arg Phe Glu Asp
    370                 375                 380

Pro Ser Ser Ile Pro His His Ala Tyr Lys Pro Phe Gly Asn Gly Gln
385                 390                 395                 400
```

```
Arg Ala Cys Ile Gly Met Gln Phe Ala Leu Gln Ala Thr Met Val
            405                 410                 415

Leu Gly Leu Val Leu Lys His Phe Glu Leu Ile Asn His Thr Gly Tyr
            420                 425                 430

Glu Leu Lys Ile Lys Glu Ala Leu Thr Ile Lys Pro Asp Asp Phe Lys
            435                 440                 445

Ile Thr Val Lys Pro Arg Lys Thr Ala Ala Ile Asn Val Gln Arg Lys
            450                 455                 460

Glu Gln Ala
465

<210> SEQ ID NO 48
<211> LENGTH: 467
<212> TYPE: PRT
<213> ORGANISM: Artificial Sequence
<220> FEATURE:
<223> OTHER INFORMATION: synthetic chimeric heme enzyme C2B12, chimeric
      cytochrome P450 enzyme C2B12

<400> SEQUENCE: 48

Met Lys Gln Ala Ser Ala Ile Pro Gln Pro Lys Thr Tyr Gly Pro Leu
  1               5                  10                  15

Lys Asn Leu Pro His Leu Glu Lys Glu Gln Leu Ser Gln Ser Leu Trp
             20                  25                  30

Arg Ile Ala Asp Glu Leu Gly Pro Ile Phe Arg Phe Asp Phe Pro Gly
         35                  40                  45

Val Ser Ser Val Phe Val Ser Gly His Asn Leu Val Ala Glu Val Cys
 50                  55                  60

Asp Glu Glu Arg Phe Asp Lys Ser Ile Glu Gly Ala Leu Glu Lys Val
 65                  70                  75                  80

Arg Ala Phe Ser Gly Asp Gly Leu Ala Thr Ser Trp Thr His Glu Pro
                 85                  90                  95

Asn Trp Arg Lys Ala His Asn Ile Leu Met Pro Thr Phe Ser Gln Arg
            100                 105                 110

Ala Met Lys Asp Tyr His Glu Lys Met Val Asp Ile Ala Thr Gln Leu
            115                 120                 125

Ile Gln Lys Trp Ser Arg Leu Asn Pro Asn Glu Glu Ile Asp Val Ala
            130                 135                 140

Asp Asp Met Thr Arg Leu Thr Leu Asp Thr Ile Gly Leu Cys Gly Phe
145                 150                 155                 160

Asn Tyr Arg Phe Asn Ser Phe Tyr Arg Asp Gln Pro His Pro Phe Ile
                165                 170                 175

Thr Ser Met Val Arg Ala Leu Asp Glu Ala Met Asn Lys Leu Gln Arg
            180                 185                 190

Ala Asn Pro Asp Asp Pro Ala Tyr Asp Glu Asn Lys Arg Gln Phe Gln
            195                 200                 205

Glu Asp Ile Lys Val Met Asn Asp Leu Val Asp Arg Met Ile Ala Glu
            210                 215                 220

Arg Lys Ala Asn Pro Asp Glu Asn Ile Lys Asp Leu Leu Ser Leu Met
225                 230                 235                 240

Leu Tyr Ala Lys Asp Pro Val Thr Gly Glu Thr Leu Asp Asp Glu Asn
                245                 250                 255

Ile Arg Tyr Gln Ile Ile Thr Phe Leu Ile Ala Gly His Glu Thr Thr
            260                 265                 270

Ser Gly Leu Leu Ser Phe Ala Thr Tyr Phe Leu Leu Lys His Pro Asp
```

```
                275                 280                 285
Lys Leu Lys Lys Ala Tyr Glu Glu Val Asp Arg Val Leu Thr Asp Ala
    290                 295                 300
Ala Pro Thr Tyr Lys Gln Val Leu Glu Leu Thr Tyr Ile Arg Met Ile
305                 310                 315                 320
Leu Asn Glu Ser Leu Arg Leu Trp Pro Thr Ala Pro Ala Phe Ser Leu
                325                 330                 335
Tyr Ala Lys Glu Asp Thr Val Leu Gly Gly Glu Tyr Pro Ile Ser Lys
            340                 345                 350
Gly Gln Pro Val Thr Val Leu Ile Pro Lys Leu His Arg Asp Gln Asn
        355                 360                 365
Ala Trp Gly Pro Asp Ala Glu Asp Phe Arg Pro Glu Arg Phe Glu Asp
    370                 375                 380
Pro Ser Ser Ile Pro His His Ala Tyr Lys Pro Phe Gly Asn Gly Gln
385                 390                 395                 400
Arg Ala Cys Ile Gly Met Gln Phe Ala Leu Gln Glu Ala Thr Met Val
                405                 410                 415
Leu Gly Leu Val Leu Lys His Phe Glu Leu Ile Asn His Thr Gly Tyr
            420                 425                 430
Glu Leu Lys Ile Lys Glu Ala Leu Thr Ile Lys Pro Asp Asp Phe Lys
        435                 440                 445
Ile Thr Val Lys Pro Arg Lys Thr Ala Ala Ile Asn Val Gln Arg Lys
    450                 455                 460
Glu Gln Ala
465

<210> SEQ ID NO 49
<211> LENGTH: 467
<212> TYPE: PRT
<213> ORGANISM: Artificial Sequence
<220> FEATURE:
<223> OTHER INFORMATION: synthetic chimeric heme enzyme TSP234, chimeric
      cytochrome P450 enzyme TSP234

<400> SEQUENCE: 49

Met Lys Glu Thr Ser Pro Ile Pro Gln Pro Lys Thr Phe Gly Pro Leu
1               5                   10                  15
Gly Asn Leu Pro Leu Ile Asp Lys Asp Lys Pro Thr Leu Ser Leu Ile
            20                  25                  30
Lys Leu Ala Glu Glu Gln Gly Pro Ile Phe Gln Ile His Thr Pro Ala
        35                  40                  45
Gly Thr Thr Ile Val Val Ser Gly His Glu Leu Val Lys Glu Val Cys
    50                  55                  60
Asp Glu Glu Arg Phe Asp Lys Ser Ile Glu Gly Ala Leu Glu Lys Val
65                  70                  75                  80
Arg Ala Phe Ser Gly Asp Gly Leu Ala Thr Ser Trp Thr His Glu Pro
                85                  90                  95
Asn Trp Arg Lys Ala His Asn Ile Leu Met Pro Thr Phe Ser Gln Arg
            100                 105                 110
Ala Met Lys Asp Tyr His Glu Lys Met Val Asp Ile Ala Thr Gln Leu
        115                 120                 125
Ile Gln Lys Trp Ser Arg Leu Asn Pro Asn Glu Glu Ile Asp Val Ala
    130                 135                 140
Asp Asp Met Thr Arg Leu Thr Leu Asp Thr Ile Gly Leu Cys Gly Phe
145                 150                 155                 160
```

Asn Tyr Arg Phe Asn Ser Phe Tyr Arg Asp Gln Pro His Pro Phe Ile
                165                 170                 175

Thr Ser Met Val Arg Ala Leu Asp Glu Ala Met Asn Lys Leu Gln Arg
            180                 185                 190

Ala Asn Pro Asp Asp Pro Ala Tyr Asp Glu Asn Lys Arg Gln Phe Gln
        195                 200                 205

Glu Asp Ile Lys Val Met Asn Asp Leu Val Asp Arg Met Ile Ala Glu
    210                 215                 220

Arg Lys Ala Asn Pro Asp Glu Asn Ile Lys Asp Leu Leu Ser Leu Met
225                 230                 235                 240

Leu Tyr Ala Lys Asp Pro Val Thr Gly Glu Thr Leu Asp Asp Glu Asn
                245                 250                 255

Ile Arg Tyr Gln Ile Ile Thr Phe Leu Ile Ala Gly His Glu Thr Thr
            260                 265                 270

Ser Gly Leu Leu Ser Phe Ala Ile Tyr Cys Leu Leu Thr His Pro Glu
        275                 280                 285

Lys Leu Lys Lys Ala Gln Glu Glu Ala Asp Arg Val Leu Thr Asp Asp
    290                 295                 300

Thr Pro Glu Tyr Lys Gln Ile Gln Gln Leu Lys Tyr Ile Arg Met Val
305                 310                 315                 320

Leu Asn Glu Thr Leu Arg Leu Tyr Pro Thr Ala Pro Ala Phe Ser Leu
                325                 330                 335

Tyr Ala Lys Glu Asp Thr Val Leu Gly Gly Tyr Pro Ile Ser Lys
            340                 345                 350

Gly Gln Pro Val Thr Val Leu Ile Pro Lys Leu His Arg Asp Gln Asn
        355                 360                 365

Ala Trp Gly Pro Asp Ala Glu Asp Phe Arg Pro Glu Arg Phe Glu Asp
    370                 375                 380

Pro Ser Ser Ile Pro His His Ala Tyr Lys Pro Phe Gly Asn Gly Gln
385                 390                 395                 400

Arg Ala Cys Ile Gly Met Gln Phe Ala Leu Gln Glu Ala Thr Met Val
                405                 410                 415

Leu Gly Leu Val Leu Lys His Phe Glu Leu Ile Asn His Thr Gly Tyr
            420                 425                 430

Glu Leu Lys Ile Lys Glu Ala Leu Thr Ile Lys Pro Asp Asp Phe Lys
        435                 440                 445

Ile Thr Val Lys Pro Arg Lys Thr Ala Ala Ile Asn Val Gln Arg Lys
    450                 455                 460

Glu Gln Ala
465

<210> SEQ ID NO 50
<211> LENGTH: 463
<212> TYPE: PRT
<213> ORGANISM: Artificial Sequence
<220> FEATURE:
<223> OTHER INFORMATION: synthetic cytochrome P450-BM3 variant WT-AxA
      (heme)

<400> SEQUENCE: 50

Thr Ile Lys Glu Met Pro Gln Pro Lys Thr Phe Gly Glu Leu Lys Asn
 1               5                  10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

```
Thr Arg Tyr Leu Ser Ser Gln Arg Leu Ile Lys Glu Ala Cys Asp Glu
 50                  55                  60

Ser Arg Phe Asp Lys Asn Leu Ser Gln Ala Leu Lys Phe Val Arg Asp
 65                  70                  75                  80

Phe Ala Gly Asp Gly Leu Phe Thr Ser Trp Thr His Glu Lys Asn Trp
                     85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
            115                 120                 125

Lys Trp Glu Arg Leu Asn Ala Asp Glu His Ile Glu Val Pro Glu Asp
            130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
            195                 200                 205

Ile Lys Val Met Asn Asp Leu Val Asp Lys Ile Ala Asp Arg Lys
            210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
            275                 280                 285

Lys Ala Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Ala
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Ser Leu Lys Pro Lys Gly Phe Val Val Lys Ala
            435                 440                 445

Lys Ser Lys Lys Ile Pro Leu Gly Gly Ile Pro Ser Pro Ser Thr
450                 455                 460
```

<210> SEQ ID NO 51
<211> LENGTH: 463
<212> TYPE: PRT
<213> ORGANISM: Artificial Sequence
<220> FEATURE:
<223> OTHER INFORMATION: synthetic cytochrome P450-BM3 variant WT-AxD (heme)

<400> SEQUENCE: 51

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Arg Val
         35                  40                  45

Thr Arg Tyr Leu Ser Ser Gln Arg Leu Ile Lys Glu Ala Cys Asp Glu
     50                  55                  60

Ser Arg Phe Asp Lys Asn Leu Ser Gln Ala Leu Lys Phe Val Arg Asp
 65                  70                  75                  80

Phe Ala Gly Asp Gly Leu Phe Thr Ser Trp Thr His Glu Lys Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
        355                 360                 365
```

```
Asp Asp Val Glu Glu Phe Arg Pro Glu Arg Phe Glu Asn Pro Ser Ala
        370                 375                 380

Ile Pro Gln His Ala Phe Lys Pro Phe Gly Asn Gly Gln Arg Ala Asp
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Ser Leu Lys Pro Lys Gly Phe Val Val Lys Ala
            435                 440                 445

Lys Ser Lys Lys Ile Pro Leu Gly Gly Ile Pro Ser Pro Ser Thr
450                 455                 460

<210> SEQ ID NO 52
<211> LENGTH: 463
<212> TYPE: PRT
<213> ORGANISM: Artificial Sequence
<220> FEATURE:
<223> OTHER INFORMATION: synthetic cytochrome P450-BM3 variant WT-AxH
      (heme)

<400> SEQUENCE: 52

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Val Arg Asp
65                  70                  75                  80

Phe Ala Gly Asp Gly Leu Phe Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
```

```
                260                 265                 270
Leu Ser Phe Ala Leu Tyr Phe Leu Val Lys Asn Pro His Val Leu Gln
        275                 280                 285

Lys Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala His
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Ser Leu Lys Pro Lys Gly Phe Val Val Lys Ala
        435                 440                 445

Lys Ser Lys Lys Ile Pro Leu Gly Gly Ile Pro Ser Pro Ser Thr
    450                 455                 460

<210> SEQ ID NO 53
<211> LENGTH: 463
<212> TYPE: PRT
<213> ORGANISM: Artificial Sequence
<220> FEATURE:
<223> OTHER INFORMATION: synthetic cytochrome P450-BM3 variant WT-AxK
      (heme)

<400> SEQUENCE: 53

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Val Arg Asp
65                  70                  75                  80

Phe Ala Gly Asp Gly Leu Phe Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160
```

Arg Phe Asn Ser Phe Tyr Arg Asp Gln Pro His Pro Phe Ile Thr Ser
            165                 170                 175

Met Val Arg Ala Leu Asp Glu Ala Met Asn Lys Leu Gln Arg Ala Asn
        180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Lys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Ser Leu Lys Pro Lys Gly Phe Val Val Lys Ala
        435                 440                 445

Lys Ser Lys Lys Ile Pro Leu Gly Gly Ile Pro Ser Pro Ser Thr
    450                 455                 460

<210> SEQ ID NO 54
<211> LENGTH: 463
<212> TYPE: PRT
<213> ORGANISM: Artificial Sequence
<220> FEATURE:
<223> OTHER INFORMATION: synthetic cytochrome P450-BM3 variant WT-AxM
      (heme)

<400> SEQUENCE: 54

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

```
Ser Arg Phe Asp Lys Asn Leu Ser Gln Ala Leu Lys Phe Val Arg Asp
 65                  70                  75                  80

Phe Ala Gly Asp Gly Leu Phe Thr Ser Trp Thr His Glu Lys Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
            115                 120                 125

Lys Trp Glu Arg Leu Asn Ala Asp Glu His Ile Glu Val Pro Glu Asp
130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
            195                 200                 205

Ile Lys Val Met Asn Asp Leu Val Asp Lys Ile Ile Ala Asp Arg Lys
210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
            275                 280                 285

Lys Ala Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Met
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Ser Leu Lys Pro Lys Gly Phe Val Val Lys Ala
            435                 440                 445

Lys Ser Lys Lys Ile Pro Leu Gly Gly Ile Pro Ser Pro Ser Thr
450                 455                 460
```

<210> SEQ ID NO 55
<211> LENGTH: 463

<212> TYPE: PRT
<213> ORGANISM: Artificial Sequence
<220> FEATURE:
<223> OTHER INFORMATION: synthetic cytochrome P450-BM3 variant WT-AxN (heme)

<400> SEQUENCE: 55

| | | | | | | | | | | | | | | |
|---|---|---|---|---|---|---|---|---|---|---|---|---|---|---|
| Thr | Ile | Lys | Glu | Met | Pro | Gln | Pro | Lys | Thr | Phe | Gly | Glu | Leu | Lys | Asn |
| 1 | | | | 5 | | | | | 10 | | | | | 15 | |
| Leu | Pro | Leu | Leu | Asn | Thr | Asp | Lys | Pro | Val | Gln | Ala | Leu | Met | Lys | Ile |
| | | | 20 | | | | | 25 | | | | | 30 | | |
| Ala | Asp | Glu | Leu | Gly | Glu | Ile | Phe | Lys | Phe | Glu | Ala | Pro | Gly | Arg | Val |
| | | | 35 | | | | | 40 | | | | | 45 | | |
| Thr | Arg | Tyr | Leu | Ser | Ser | Gln | Arg | Leu | Ile | Lys | Glu | Ala | Cys | Asp | Glu |
| | 50 | | | | | 55 | | | | | 60 | | | | |
| Ser | Arg | Phe | Asp | Lys | Asn | Leu | Ser | Gln | Ala | Leu | Lys | Phe | Val | Arg | Asp |
| 65 | | | | | 70 | | | | | 75 | | | | | 80 |
| Phe | Ala | Gly | Asp | Gly | Leu | Phe | Thr | Ser | Trp | Thr | His | Glu | Lys | Asn | Trp |
| | | | | 85 | | | | | 90 | | | | | 95 | |
| Lys | Lys | Ala | His | Asn | Ile | Leu | Leu | Pro | Ser | Phe | Ser | Gln | Gln | Ala | Met |
| | | | | 100 | | | | | 105 | | | | | 110 | |
| Lys | Gly | Tyr | His | Ala | Met | Met | Val | Asp | Ile | Ala | Val | Gln | Leu | Val | Gln |
| | | | 115 | | | | | 120 | | | | | 125 | | |
| Lys | Trp | Glu | Arg | Leu | Asn | Ala | Asp | Glu | His | Ile | Glu | Val | Pro | Glu | Asp |
| | 130 | | | | | 135 | | | | | 140 | | | | |
| Met | Thr | Arg | Leu | Thr | Leu | Asp | Thr | Ile | Gly | Leu | Cys | Gly | Phe | Asn | Tyr |
| 145 | | | | | 150 | | | | | 155 | | | | | 160 |
| Arg | Phe | Asn | Ser | Phe | Tyr | Arg | Asp | Gln | Pro | His | Pro | Phe | Ile | Thr | Ser |
| | | | | 165 | | | | | 170 | | | | | 175 | |
| Met | Val | Arg | Ala | Leu | Asp | Glu | Ala | Met | Asn | Lys | Leu | Gln | Arg | Ala | Asn |
| | | | | 180 | | | | | 185 | | | | | 190 | |
| Pro | Asp | Asp | Pro | Ala | Tyr | Asp | Glu | Asn | Lys | Arg | Gln | Phe | Gln | Glu | Asp |
| | | | 195 | | | | | 200 | | | | | 205 | | |
| Ile | Lys | Val | Met | Asn | Asp | Leu | Val | Asp | Lys | Ile | Ile | Ala | Asp | Arg | Lys |
| | 210 | | | | | 215 | | | | | 220 | | | | |
| Ala | Ser | Gly | Glu | Gln | Ser | Asp | Asp | Leu | Leu | Thr | His | Met | Leu | Asn | Gly |
| 225 | | | | | 230 | | | | | 235 | | | | | 240 |
| Lys | Asp | Pro | Glu | Thr | Gly | Glu | Pro | Leu | Asp | Asp | Glu | Asn | Ile | Arg | Tyr |
| | | | | 245 | | | | | 250 | | | | | 255 | |
| Gln | Ile | Ile | Thr | Phe | Leu | Ile | Ala | Gly | His | Glu | Thr | Thr | Ser | Gly | Leu |
| | | | 260 | | | | | 265 | | | | | 270 | | |
| Leu | Ser | Phe | Ala | Leu | Tyr | Phe | Leu | Val | Lys | Asn | Pro | His | Val | Leu | Gln |
| | | 275 | | | | | 280 | | | | | 285 | | | |
| Lys | Ala | Ala | Glu | Glu | Ala | Ala | Arg | Val | Leu | Val | Asp | Pro | Val | Pro | Ser |
| | 290 | | | | | 295 | | | | | 300 | | | | |
| Tyr | Lys | Gln | Val | Lys | Gln | Leu | Lys | Tyr | Val | Gly | Met | Val | Leu | Asn | Glu |
| 305 | | | | | 310 | | | | | 315 | | | | | 320 |
| Ala | Leu | Arg | Leu | Trp | Pro | Thr | Ala | Pro | Ala | Phe | Ser | Leu | Tyr | Ala | Lys |
| | | | | 325 | | | | | 330 | | | | | 335 | |
| Glu | Asp | Thr | Val | Leu | Gly | Gly | Tyr | Pro | Leu | Glu | Lys | Gly | Asp | Glu |
| | | | 340 | | | | | 345 | | | | | 350 | |
| Leu | Met | Val | Leu | Ile | Pro | Gln | Leu | His | Arg | Asp | Lys | Thr | Ile | Trp | Gly |
| | | | 355 | | | | | 360 | | | | | 365 | | |
| Asp | Asp | Val | Glu | Glu | Phe | Arg | Pro | Glu | Arg | Phe | Glu | Asn | Pro | Ser | Ala |
| | | | 370 | | | | | 375 | | | | | 380 | | |

```
Ile Pro Gln His Ala Phe Lys Pro Phe Gly Asn Gly Gln Arg Ala Asn
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Ser Leu Lys Pro Lys Gly Phe Val Val Lys Ala
                435                 440                 445

Lys Ser Lys Lys Ile Pro Leu Gly Gly Ile Pro Ser Pro Ser Thr
450                 455                 460
```

<210> SEQ ID NO 56
<211> LENGTH: 1047
<212> TYPE: PRT
<213> ORGANISM: Artificial Sequence
<220> FEATURE:
<223> OTHER INFORMATION: synthetic cytochrome P450-BM3 variant BM3-CIS-T438S-AxA

<400> SEQUENCE: 56

```
Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
50                  55                  60

Ser Arg Phe Asp Lys Asn Leu Ser Gln Ala Leu Lys Phe Ala Arg Asp
65                  70                  75                  80

Phe Ala Gly Asp Gly Leu Val Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Ile Ala Asp Arg Lys Ala
210                 215                 220

Arg Gly Glu Gln Ser Asp Asp Leu Leu Thr Gln Met Leu Asn Gly Lys
225                 230                 235                 240

Asp Pro Glu Thr Gly Glu Pro Leu Asp Asp Gly Asn Ile Arg Tyr Gln
                245                 250                 255

Ile Ile Thr Phe Leu Ile Ala Gly His Glu Ala Thr Ser Gly Leu Leu
            260                 265                 270

Ser Phe Ala Leu Tyr Phe Leu Val Lys Asn Pro His Val Leu Gln Lys
```

-continued

```
                275                 280                 285
Val Ala Glu Ala Ala Arg Val Leu Val Asp Pro Val Pro Ser Tyr
290                 295                 300
Lys Gln Val Lys Gln Leu Lys Tyr Val Gly Met Val Leu Asn Glu Ala
305                 310                 315                 320
Leu Arg Leu Trp Pro Thr Ala Pro Ala Phe Ser Leu Tyr Ala Lys Glu
                325                 330                 335
Asp Thr Val Leu Gly Gly Glu Tyr Pro Leu Glu Lys Gly Asp Glu Val
                340                 345                 350
Met Val Leu Ile Pro Gln Leu His Arg Asp Lys Thr Val Trp Gly Asp
                355                 360                 365
Asp Val Glu Glu Phe Arg Pro Glu Arg Phe Glu Asn Pro Ser Ala Ile
370                 375                 380
Pro Gln His Ala Phe Lys Pro Phe Gly Asn Gly Gln Arg Ala Ala Ile
385                 390                 395                 400
Gly Gln Gln Phe Ala Leu His Glu Ala Thr Leu Val Leu Gly Met Met
                405                 410                 415
Leu Lys His Phe Asp Phe Glu Asp His Thr Asn Tyr Glu Leu Asp Ile
                420                 425                 430
Lys Glu Thr Leu Ser Leu Lys Pro Lys Gly Phe Val Val Lys Ala Lys
                435                 440                 445
Ser Lys Lys Ile Pro Leu Gly Gly Ile Pro Ser Pro Ser Thr Glu Gln
450                 455                 460
Ser Ala Lys Lys Val Arg Lys Lys Ala Glu Asn Ala His Asn Thr Pro
465                 470                 475                 480
Leu Leu Val Leu Tyr Gly Ser Asn Met Gly Thr Ala Glu Gly Thr Ala
                485                 490                 495
Arg Asp Leu Ala Asp Ile Ala Met Ser Lys Gly Phe Ala Pro Gln Val
                500                 505                 510
Ala Thr Leu Asp Ser His Ala Gly Asn Leu Pro Arg Glu Gly Ala Val
                515                 520                 525
Leu Ile Val Thr Ala Ser Tyr Asn Gly His Pro Pro Asp Asn Ala Lys
                530                 535                 540
Gln Phe Val Asp Trp Leu Asp Gln Ala Ser Ala Asp Glu Val Lys Gly
545                 550                 555                 560
Val Arg Tyr Ser Val Phe Gly Cys Gly Asp Lys Asn Trp Ala Thr Thr
                565                 570                 575
Tyr Gln Lys Val Pro Ala Phe Ile Asp Glu Thr Leu Ala Ala Lys Gly
                580                 585                 590
Ala Glu Asn Ile Ala Asp Arg Gly Glu Ala Asp Ala Ser Asp Asp Phe
                595                 600                 605
Glu Gly Thr Tyr Glu Glu Trp Arg Glu His Met Trp Ser Asp Val Ala
                610                 615                 620
Ala Tyr Phe Asn Leu Asp Ile Glu Asn Ser Glu Asp Asn Lys Ser Thr
625                 630                 635                 640
Leu Ser Leu Gln Phe Val Asp Ser Ala Ala Asp Met Pro Leu Ala Lys
                645                 650                 655
Met His Gly Ala Phe Ser Thr Asn Val Val Ala Ser Lys Glu Leu Gln
                660                 665                 670
Gln Pro Gly Ser Ala Arg Ser Thr Arg His Leu Glu Ile Glu Leu Pro
                675                 680                 685
Lys Glu Ala Ser Tyr Gln Glu Gly Asp His Leu Gly Val Ile Pro Arg
                690                 695                 700
```

Asn Tyr Glu Gly Ile Val Asn Arg Val Thr Ala Arg Phe Gly Leu Asp
705                 710                 715                 720

Ala Ser Gln Gln Ile Arg Leu Glu Ala Glu Glu Lys Leu Ala His
            725                 730                 735

Leu Pro Leu Ala Lys Thr Val Ser Val Glu Glu Leu Leu Gln Tyr Val
            740                 745                 750

Glu Leu Gln Asp Pro Val Thr Arg Thr Gln Leu Arg Ala Met Ala Ala
            755                 760                 765

Lys Thr Val Cys Pro Pro His Lys Val Glu Leu Glu Ala Leu Leu Glu
770                 775                 780

Lys Gln Ala Tyr Lys Glu Gln Val Leu Ala Lys Arg Leu Thr Met Leu
785                 790                 795                 800

Glu Leu Leu Glu Lys Tyr Pro Ala Cys Glu Met Lys Phe Ser Glu Phe
            805                 810                 815

Ile Ala Leu Leu Pro Ser Ile Arg Pro Arg Tyr Tyr Ser Ile Ser Ser
            820                 825                 830

Ser Pro Arg Val Asp Glu Lys Gln Ala Ser Ile Thr Val Ser Val Val
            835                 840                 845

Ser Gly Glu Ala Trp Ser Gly Tyr Gly Glu Tyr Lys Gly Ile Ala Ser
850                 855                 860

Asn Tyr Leu Ala Glu Leu Gln Glu Gly Asp Thr Ile Thr Cys Phe Ile
865                 870                 875                 880

Ser Thr Pro Gln Ser Glu Phe Thr Leu Pro Lys Asp Pro Glu Thr Pro
            885                 890                 895

Leu Ile Met Val Gly Pro Gly Thr Gly Val Ala Pro Phe Arg Gly Phe
            900                 905                 910

Val Gln Ala Arg Lys Gln Leu Lys Glu Gln Gly Gln Ser Leu Gly Glu
            915                 920                 925

Ala His Leu Tyr Phe Gly Cys Arg Ser Pro His Glu Asp Tyr Leu Tyr
930                 935                 940

Gln Glu Glu Leu Glu Asn Ala Gln Ser Glu Gly Ile Ile Thr Leu His
945                 950                 955                 960

Thr Ala Phe Ser Arg Met Pro Asn Gln Pro Lys Thr Tyr Val Gln His
            965                 970                 975

Val Met Glu Gln Asp Gly Lys Lys Leu Ile Glu Leu Leu Asp Gln Gly
            980                 985                 990

Ala His Phe Tyr Ile Cys Gly Asp Gly Ser Gln Met Ala Pro Ala Val
            995                 1000                1005

Glu Ala Thr Leu Met Lys Ser Tyr Ala Asp Val His Gln Val Ser Glu
            1010                1015                1020

Ala Asp Ala Arg Leu Trp Leu Gln Gln Leu Glu Glu Lys Gly Arg Tyr
1025                1030                1035                1040

Ala Lys Asp Val Trp Ala Gly
            1045

<210> SEQ ID NO 57
<211> LENGTH: 1047
<212> TYPE: PRT
<213> ORGANISM: Artificial Sequence
<220> FEATURE:
<223> OTHER INFORMATION: synthetic cytochrome P450-BM3 variant
      BM3-CIS-T438S-AxD

<400> SEQUENCE: 57

Thr Ile Lys Glu Met Pro Gln Pro Lys Thr Phe Gly Glu Leu Lys Asn

-continued

```
              1               5              10              15
Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
                35                  40                  45

Thr Arg Tyr Leu Ser Ser Gln Arg Leu Ile Lys Glu Ala Cys Asp Glu
                50                  55                  60

Ser Arg Phe Asp Lys Asn Leu Ser Gln Ala Leu Lys Phe Ala Arg Asp
 65                 70                  75                  80

Phe Ala Gly Asp Gly Leu Val Thr Ser Trp Thr His Glu Lys Asn Trp
                85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
                115                 120                 125

Lys Trp Glu Arg Leu Asn Ala Asp Glu His Ile Glu Val Ser Glu Asp
                130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
                180                 185                 190

Pro Asp Asp Pro Ala Tyr Asp Glu Asn Lys Arg Gln Phe Gln Glu Asp
                195                 200                 205

Ile Lys Val Met Asn Asp Leu Val Asp Ile Ile Ala Asp Arg Lys Ala
                210                 215                 220

Arg Gly Glu Gln Ser Asp Asp Leu Leu Thr Gln Met Leu Asn Gly Lys
225                 230                 235                 240

Asp Pro Glu Thr Gly Glu Pro Leu Asp Asp Gly Asn Ile Arg Tyr Gln
                245                 250                 255

Ile Ile Thr Phe Leu Ile Ala Gly His Glu Ala Thr Ser Gly Leu Leu
                260                 265                 270

Ser Phe Ala Leu Tyr Phe Leu Val Lys Asn Pro His Val Leu Gln Lys
                275                 280                 285

Val Ala Glu Glu Ala Ala Arg Val Leu Val Asp Pro Val Pro Ser Tyr
                290                 295                 300

Lys Gln Val Lys Gln Leu Lys Tyr Val Gly Met Val Leu Asn Glu Ala
305                 310                 315                 320

Leu Arg Leu Trp Pro Thr Ala Pro Ala Phe Ser Leu Tyr Ala Lys Glu
                325                 330                 335

Asp Thr Val Leu Gly Gly Glu Tyr Pro Leu Glu Lys Gly Asp Glu Val
                340                 345                 350

Met Val Leu Ile Pro Gln Leu His Arg Asp Lys Thr Val Trp Gly Asp
                355                 360                 365

Asp Val Glu Glu Phe Arg Pro Glu Arg Phe Glu Asn Pro Ser Ala Ile
                370                 375                 380

Pro Gln His Ala Phe Lys Pro Phe Gly Asn Gly Gln Arg Ala Asp Ile
385                 390                 395                 400

Gly Gln Gln Phe Ala Leu His Glu Ala Thr Leu Val Leu Gly Met Met
                405                 410                 415

Leu Lys His Phe Asp Phe Glu Asp His Thr Asn Tyr Glu Leu Asp Ile
                420                 425                 430
```

```
Lys Glu Thr Leu Ser Leu Lys Pro Lys Gly Phe Val Lys Ala Lys
            435                 440                 445

Ser Lys Lys Ile Pro Leu Gly Gly Ile Pro Ser Pro Ser Thr Glu Gln
    450                 455                 460

Ser Ala Lys Lys Val Arg Lys Lys Ala Glu Asn Ala His Asn Thr Pro
465                 470                 475                 480

Leu Leu Val Leu Tyr Gly Ser Asn Met Gly Thr Ala Glu Gly Thr Ala
                485                 490                 495

Arg Asp Leu Ala Asp Ile Ala Met Ser Lys Gly Phe Ala Pro Gln Val
                500                 505                 510

Ala Thr Leu Asp Ser His Ala Gly Asn Leu Pro Arg Glu Gly Ala Val
                515                 520                 525

Leu Ile Val Thr Ala Ser Tyr Asn Gly His Pro Pro Asp Asn Ala Lys
            530                 535                 540

Gln Phe Val Asp Trp Leu Asp Gln Ala Ser Ala Asp Glu Val Lys Gly
545                 550                 555                 560

Val Arg Tyr Ser Val Phe Gly Cys Gly Asp Lys Asn Trp Ala Thr Thr
                565                 570                 575

Tyr Gln Lys Val Pro Ala Phe Ile Asp Glu Thr Leu Ala Ala Lys Gly
            580                 585                 590

Ala Glu Asn Ile Ala Asp Arg Gly Glu Ala Asp Ala Ser Asp Asp Phe
            595                 600                 605

Glu Gly Thr Tyr Glu Glu Trp Arg Glu His Met Trp Ser Asp Val Ala
            610                 615                 620

Ala Tyr Phe Asn Leu Asp Ile Glu Asn Ser Glu Asp Asn Lys Ser Thr
625                 630                 635                 640

Leu Ser Leu Gln Phe Val Asp Ser Ala Ala Asp Met Pro Leu Ala Lys
                645                 650                 655

Met His Gly Ala Phe Ser Thr Asn Val Val Ala Ser Lys Glu Leu Gln
                660                 665                 670

Gln Pro Gly Ser Ala Arg Ser Thr Arg His Leu Glu Ile Glu Leu Pro
            675                 680                 685

Lys Glu Ala Ser Tyr Gln Glu Gly Asp His Leu Gly Val Ile Pro Arg
            690                 695                 700

Asn Tyr Glu Gly Ile Val Asn Arg Val Thr Ala Arg Phe Gly Leu Asp
705                 710                 715                 720

Ala Ser Gln Gln Ile Arg Leu Glu Ala Glu Glu Lys Leu Ala His
                725                 730                 735

Leu Pro Leu Ala Lys Thr Val Ser Val Glu Glu Leu Leu Gln Tyr Val
                740                 745                 750

Glu Leu Gln Asp Pro Val Thr Arg Thr Gln Leu Arg Ala Met Ala Ala
            755                 760                 765

Lys Thr Val Cys Pro Pro His Lys Val Glu Leu Glu Ala Leu Leu Glu
            770                 775                 780

Lys Gln Ala Tyr Lys Glu Gln Val Leu Ala Lys Arg Leu Thr Met Leu
785                 790                 795                 800

Glu Leu Leu Glu Lys Tyr Pro Ala Cys Glu Met Lys Phe Ser Glu Phe
                805                 810                 815

Ile Ala Leu Leu Pro Ser Ile Arg Pro Arg Tyr Tyr Ser Ile Ser Ser
                820                 825                 830

Ser Pro Arg Val Asp Glu Lys Gln Ala Ser Ile Thr Val Ser Val Val
            835                 840                 845
```

```
Ser Gly Glu Ala Trp Ser Gly Tyr Gly Tyr Lys Gly Ile Ala Ser
    850                 855                 860

Asn Tyr Leu Ala Glu Leu Gln Glu Gly Asp Thr Ile Thr Cys Phe Ile
865                 870                 875                 880

Ser Thr Pro Gln Ser Glu Phe Thr Leu Pro Lys Asp Pro Glu Thr Pro
                885                 890                 895

Leu Ile Met Val Gly Pro Gly Thr Gly Val Ala Pro Phe Arg Gly Phe
                900                 905                 910

Val Gln Ala Arg Lys Gln Leu Lys Glu Gln Gly Gln Ser Leu Gly Glu
                915                 920                 925

Ala His Leu Tyr Phe Gly Cys Arg Ser Pro His Glu Asp Tyr Leu Tyr
            930                 935                 940

Gln Glu Glu Leu Glu Asn Ala Gln Ser Glu Gly Ile Ile Thr Leu His
945                 950                 955                 960

Thr Ala Phe Ser Arg Met Pro Asn Gln Pro Lys Thr Tyr Val Gln His
                965                 970                 975

Val Met Glu Gln Asp Gly Lys Lys Leu Ile Glu Leu Leu Asp Gln Gly
                980                 985                 990

Ala His Phe Tyr Ile Cys Gly Asp Gly Ser Gln Met Ala Pro Ala Val
            995                 1000                1005

Glu Ala Thr Leu Met Lys Ser Tyr Ala Asp Val His Gln Val Ser Glu
        1010                1015                1020

Ala Asp Ala Arg Leu Trp Leu Gln Gln Leu Glu Glu Lys Gly Arg Tyr
1025                1030                1035                1040

Ala Lys Asp Val Trp Ala Gly
            1045

<210> SEQ ID NO 58
<211> LENGTH: 1047
<212> TYPE: PRT
<213> ORGANISM: Artificial Sequence
<220> FEATURE:
<223> OTHER INFORMATION: synthetic cytochrome P450-BM3 variant
      BM3-CIS-T438S-AxM

<400> SEQUENCE: 58

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Ala Arg Asp
65                  70                  75                  80

Phe Ala Gly Asp Gly Leu Val Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160
```

```
Arg Phe Asn Ser Phe Tyr Arg Asp Gln Pro His Pro Phe Ile Ile Ser
            165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Phe Gln Glu Asp
            195                 200                 205

Ile Lys Val Met Asn Asp Leu Val Asp Ile Ile Ala Asp Arg Lys Ala
210                 215                 220

Arg Gly Glu Gln Ser Asp Asp Leu Leu Thr Gln Met Leu Asn Gly Lys
225                 230                 235                 240

Asp Pro Glu Thr Gly Glu Pro Leu Asp Asp Gly Asn Ile Arg Tyr Gln
            245                 250                 255

Ile Ile Thr Phe Leu Ile Ala Gly His Glu Ala Thr Ser Gly Leu Leu
            260                 265                 270

Ser Phe Ala Leu Tyr Phe Leu Val Lys Asn Pro His Val Leu Gln Lys
            275                 280                 285

Val Ala Glu Glu Ala Ala Arg Val Leu Val Asp Pro Val Pro Ser Tyr
            290                 295                 300

Lys Gln Val Lys Gln Leu Lys Tyr Val Gly Met Val Leu Asn Glu Ala
305                 310                 315                 320

Leu Arg Leu Trp Pro Thr Ala Pro Ala Phe Ser Leu Tyr Ala Lys Glu
            325                 330                 335

Asp Thr Val Leu Gly Gly Glu Tyr Pro Leu Glu Lys Gly Asp Glu Val
            340                 345                 350

Met Val Leu Ile Pro Gln Leu His Arg Asp Lys Thr Val Trp Gly Asp
            355                 360                 365

Asp Val Glu Glu Phe Arg Pro Glu Arg Phe Glu Asn Pro Ser Ala Ile
370                 375                 380

Pro Gln His Ala Phe Lys Pro Phe Gly Asn Gly Gln Arg Ala Met Ile
385                 390                 395                 400

Gly Gln Gln Phe Ala Leu His Glu Ala Thr Leu Val Leu Gly Met Met
            405                 410                 415

Leu Lys His Phe Asp Phe Glu Asp His Thr Asn Tyr Glu Leu Asp Ile
            420                 425                 430

Lys Glu Thr Leu Ser Leu Lys Pro Lys Gly Phe Val Val Lys Ala Lys
            435                 440                 445

Ser Lys Lys Ile Pro Leu Gly Gly Ile Pro Ser Pro Ser Thr Glu Gln
450                 455                 460

Ser Ala Lys Lys Val Arg Lys Lys Ala Glu Asn Ala His Asn Thr Pro
465                 470                 475                 480

Leu Leu Val Leu Tyr Gly Ser Asn Met Gly Thr Ala Glu Gly Thr Ala
            485                 490                 495

Arg Asp Leu Ala Asp Ile Ala Met Ser Lys Gly Phe Ala Pro Gln Val
            500                 505                 510

Ala Thr Leu Asp Ser His Ala Gly Asn Leu Pro Arg Glu Gly Ala Val
            515                 520                 525

Leu Ile Val Thr Ala Ser Tyr Asn Gly His Pro Pro Asp Asn Ala Lys
            530                 535                 540

Gln Phe Val Asp Trp Leu Asp Gln Ala Ser Ala Asp Glu Val Lys Gly
545                 550                 555                 560

Val Arg Tyr Ser Val Phe Gly Cys Gly Asp Lys Asn Trp Ala Thr Thr
            565                 570                 575
```

-continued

```
Tyr Gln Lys Val Pro Ala Phe Ile Asp Glu Thr Leu Ala Ala Lys Gly
            580                 585                 590

Ala Glu Asn Ile Ala Asp Arg Gly Glu Ala Ala Ser Asp Asp Phe
595                 600                 605

Glu Gly Thr Tyr Glu Glu Trp Arg Glu His Met Trp Ser Asp Val Ala
            610                 615                 620

Ala Tyr Phe Asn Leu Asp Ile Glu Asn Ser Glu Asp Asn Lys Ser Thr
625                 630                 635                 640

Leu Ser Leu Gln Phe Val Asp Ser Ala Ala Asp Met Pro Leu Ala Lys
                645                 650                 655

Met His Gly Ala Phe Ser Thr Asn Val Val Ala Ser Lys Glu Leu Gln
                660                 665                 670

Gln Pro Gly Ser Ala Arg Ser Thr Arg His Leu Glu Ile Glu Leu Pro
            675                 680                 685

Lys Glu Ala Ser Tyr Gln Glu Gly Asp His Leu Gly Val Ile Pro Arg
690                 695                 700

Asn Tyr Glu Gly Ile Val Asn Arg Val Thr Ala Arg Phe Gly Leu Asp
705                 710                 715                 720

Ala Ser Gln Gln Ile Arg Leu Glu Ala Glu Glu Lys Leu Ala His
                725                 730                 735

Leu Pro Leu Ala Lys Thr Val Ser Val Glu Glu Leu Leu Gln Tyr Val
                740                 745                 750

Glu Leu Gln Asp Pro Val Thr Arg Thr Gln Leu Arg Ala Met Ala Ala
            755                 760                 765

Lys Thr Val Cys Pro Pro His Lys Val Glu Leu Glu Ala Leu Leu Glu
770                 775                 780

Lys Gln Ala Tyr Lys Glu Gln Val Leu Ala Lys Arg Leu Thr Met Leu
785                 790                 795                 800

Glu Leu Leu Glu Lys Tyr Pro Ala Cys Glu Met Lys Phe Ser Glu Phe
                805                 810                 815

Ile Ala Leu Leu Pro Ser Ile Arg Pro Arg Tyr Tyr Ser Ile Ser Ser
                820                 825                 830

Ser Pro Arg Val Asp Glu Lys Gln Ala Ser Ile Thr Val Ser Val Val
            835                 840                 845

Ser Gly Glu Ala Trp Ser Gly Tyr Gly Glu Tyr Lys Gly Ile Ala Ser
850                 855                 860

Asn Tyr Leu Ala Glu Leu Gln Glu Gly Asp Thr Ile Thr Cys Phe Ile
865                 870                 875                 880

Ser Thr Pro Gln Ser Glu Phe Thr Leu Pro Lys Asp Pro Glu Thr Pro
                885                 890                 895

Leu Ile Met Val Gly Pro Gly Thr Gly Val Ala Pro Phe Arg Gly Phe
                900                 905                 910

Val Gln Ala Arg Lys Gln Leu Lys Glu Gln Gly Gln Ser Leu Gly Glu
            915                 920                 925

Ala His Leu Tyr Phe Gly Cys Arg Ser Pro His Glu Asp Tyr Leu Tyr
930                 935                 940

Gln Glu Glu Leu Glu Asn Ala Gln Ser Glu Gly Ile Ile Thr Leu His
945                 950                 955                 960

Thr Ala Phe Ser Arg Met Pro Asn Gln Pro Lys Thr Tyr Val Gln His
                965                 970                 975

Val Met Glu Gln Asp Gly Lys Lys Leu Ile Glu Leu Leu Asp Gln Gly
                980                 985                 990

Ala His Phe Tyr Ile Cys Gly Asp Gly Ser Gln Met Ala Pro Ala Val
```

```
                    995                 1000                1005
Glu Ala Thr Leu Met Lys Ser Tyr Ala Asp Val His Gln Val Ser Glu
        1010                1015                1020

Ala Asp Ala Arg Leu Trp Leu Gln Gln Leu Glu Glu Lys Gly Arg Tyr
1025                1030                1035                1040

Ala Lys Asp Val Trp Ala Gly
            1045

<210> SEQ ID NO 59
<211> LENGTH: 1047
<212> TYPE: PRT
<213> ORGANISM: Artificial Sequence
<220> FEATURE:
<223> OTHER INFORMATION: synthetic cytochrome P450-BM3 variant
      BM3-CIS-T438S-AxY

<400> SEQUENCE: 59

Thr Ile Lys Glu Met Pro Gln Pro Lys Thr Phe Gly Glu Leu Lys Asn
 1               5                  10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
50                  55                  60

Ser Arg Phe Asp Lys Asn Leu Ser Gln Ala Leu Lys Phe Ala Arg Asp
65                  70                  75                  80

Phe Ala Gly Asp Gly Leu Val Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Ile Ile Ala Asp Arg Lys Ala
210                 215                 220

Arg Gly Glu Gln Ser Asp Asp Leu Leu Thr Gln Met Leu Asn Gly Lys
225                 230                 235                 240

Asp Pro Glu Thr Gly Glu Pro Leu Asp Asp Gly Asn Ile Arg Tyr Gln
                245                 250                 255

Ile Ile Thr Phe Leu Ile Ala Gly His Glu Ala Thr Ser Gly Leu Leu
            260                 265                 270

Ser Phe Ala Leu Tyr Phe Leu Val Lys Asn Pro His Val Leu Gln Lys
        275                 280                 285

Val Ala Glu Glu Ala Ala Arg Val Leu Val Asp Pro Val Pro Ser Tyr
290                 295                 300
```

```
Lys Gln Val Lys Gln Leu Lys Tyr Val Gly Met Val Leu Asn Glu Ala
305                 310                 315                 320

Leu Arg Leu Trp Pro Thr Ala Pro Ala Phe Ser Leu Tyr Ala Lys Glu
            325                 330                 335

Asp Thr Val Leu Gly Gly Glu Tyr Pro Leu Glu Lys Gly Asp Glu Val
        340                 345                 350

Met Val Leu Ile Pro Gln Leu His Arg Asp Lys Thr Val Trp Gly Asp
    355                 360                 365

Asp Val Glu Glu Phe Arg Pro Glu Arg Phe Glu Asn Pro Ser Ala Ile
370                 375                 380

Pro Gln His Ala Phe Lys Pro Phe Gly Asn Gly Gln Arg Ala Tyr Ile
385                 390                 395                 400

Gly Gln Gln Phe Ala Leu His Glu Ala Thr Leu Val Leu Gly Met Met
                405                 410                 415

Leu Lys His Phe Asp Phe Glu Asp His Thr Asn Tyr Glu Leu Asp Ile
                420                 425                 430

Lys Glu Thr Leu Ser Leu Lys Pro Lys Gly Phe Val Val Lys Ala Lys
            435                 440                 445

Ser Lys Lys Ile Pro Leu Gly Gly Ile Pro Ser Pro Ser Thr Glu Gln
450                 455                 460

Ser Ala Lys Lys Val Arg Lys Lys Ala Glu Asn Ala His Asn Thr Pro
465                 470                 475                 480

Leu Leu Val Leu Tyr Gly Ser Asn Met Gly Thr Ala Glu Gly Thr Ala
                485                 490                 495

Arg Asp Leu Ala Asp Ile Ala Met Ser Lys Gly Phe Ala Pro Gln Val
            500                 505                 510

Ala Thr Leu Asp Ser His Ala Gly Asn Leu Pro Arg Glu Gly Ala Val
            515                 520                 525

Leu Ile Val Thr Ala Ser Tyr Asn Gly His Pro Pro Asp Asn Ala Lys
530                 535                 540

Gln Phe Val Asp Trp Leu Asp Gln Ala Ser Ala Asp Glu Val Lys Gly
545                 550                 555                 560

Val Arg Tyr Ser Val Phe Gly Cys Gly Asp Lys Asn Trp Ala Thr Thr
                565                 570                 575

Tyr Gln Lys Val Pro Ala Phe Ile Asp Glu Thr Leu Ala Ala Lys Gly
            580                 585                 590

Ala Glu Asn Ile Ala Asp Arg Gly Glu Ala Asp Ala Ser Asp Asp Phe
            595                 600                 605

Glu Gly Thr Tyr Glu Glu Trp Arg Glu His Met Trp Ser Asp Val Ala
        610                 615                 620

Ala Tyr Phe Asn Leu Asp Ile Glu Asn Ser Glu Asp Asn Lys Ser Thr
625                 630                 635                 640

Leu Ser Leu Gln Phe Val Asp Ser Ala Ala Asp Met Pro Leu Ala Lys
                645                 650                 655

Met His Gly Ala Phe Ser Thr Asn Val Val Ala Ser Lys Glu Leu Gln
                660                 665                 670

Gln Pro Gly Ser Ala Arg Ser Thr Arg His Leu Glu Ile Glu Leu Pro
            675                 680                 685

Lys Glu Ala Ser Tyr Gln Glu Gly Asp His Leu Gly Val Ile Pro Arg
            690                 695                 700

Asn Tyr Glu Gly Ile Val Asn Arg Val Thr Ala Arg Phe Gly Leu Asp
705                 710                 715                 720

Ala Ser Gln Gln Ile Arg Leu Glu Ala Glu Glu Glu Lys Leu Ala His
```

```
                    725                 730                 735

Leu Pro Leu Ala Lys Thr Val Ser Val Glu Glu Leu Gln Tyr Val
                740                 745                 750

Glu Leu Gln Asp Pro Val Thr Arg Thr Gln Leu Arg Ala Met Ala
            755                 760                 765

Lys Thr Val Cys Pro His Lys Val Glu Leu Glu Ala Leu Leu Glu
        770                 775                 780

Lys Gln Ala Tyr Lys Glu Gln Val Leu Ala Lys Arg Leu Thr Met Leu
785                 790                 795                 800

Glu Leu Leu Glu Lys Tyr Pro Ala Cys Glu Met Lys Phe Ser Glu Phe
                805                 810                 815

Ile Ala Leu Leu Pro Ser Ile Arg Pro Arg Tyr Tyr Ser Ile Ser Ser
                820                 825                 830

Ser Pro Arg Val Asp Glu Lys Gln Ala Ser Ile Thr Val Ser Val Val
            835                 840                 845

Ser Gly Glu Ala Trp Ser Gly Tyr Gly Glu Tyr Lys Gly Ile Ala Ser
        850                 855                 860

Asn Tyr Leu Ala Glu Leu Gln Glu Gly Asp Thr Ile Thr Cys Phe Ile
865                 870                 875                 880

Ser Thr Pro Gln Ser Glu Phe Thr Leu Pro Lys Asp Pro Glu Thr Pro
                885                 890                 895

Leu Ile Met Val Gly Pro Gly Thr Gly Val Ala Pro Phe Arg Gly Phe
                900                 905                 910

Val Gln Ala Arg Lys Gln Leu Lys Glu Gln Gly Gln Ser Leu Gly Glu
            915                 920                 925

Ala His Leu Tyr Phe Gly Cys Arg Ser Pro His Glu Asp Tyr Leu Tyr
        930                 935                 940

Gln Glu Glu Leu Glu Asn Ala Gln Ser Glu Gly Ile Ile Thr Leu His
945                 950                 955                 960

Thr Ala Phe Ser Arg Met Pro Asn Gln Pro Lys Thr Tyr Val Gln His
                965                 970                 975

Val Met Glu Gln Asp Gly Lys Lys Leu Ile Glu Leu Leu Asp Gln Gly
                980                 985                 990

Ala His Phe Tyr Ile Cys Gly Asp Gly Ser Gln Met Ala Pro Ala Val
            995                1000                1005

Glu Ala Thr Leu Met Lys Ser Tyr Ala Asp Val His Gln Val Ser Glu
        1010                1015                1020

Ala Asp Ala Arg Leu Trp Leu Gln Gln Leu Glu Glu Lys Gly Arg Tyr
1025                1030                1035                1040

Ala Lys Asp Val Trp Ala Gly
                1045

<210> SEQ ID NO 60
<211> LENGTH: 1047
<212> TYPE: PRT
<213> ORGANISM: Artificial Sequence
<220> FEATURE:
<223> OTHER INFORMATION: synthetic cytochrome P450-BM3 variant
      BM3-CIS-T438S-AxT

<400> SEQUENCE: 60

Thr Ile Lys Glu Met Pro Gln Pro Lys Thr Phe Gly Glu Leu Lys Asn
 1               5                  10                  15

Leu Pro Leu Leu Asn Thr Asp Lys Pro Val Gln Ala Leu Met Lys Ile
                20                  25                  30
```

Ala Asp Glu Leu Gly Glu Ile Phe Lys Phe Glu Ala Pro Gly Arg Val
 35                  40                  45

Thr Arg Tyr Leu Ser Ser Gln Arg Leu Ile Lys Glu Ala Cys Asp Glu
 50                  55                  60

Ser Arg Phe Asp Lys Asn Leu Ser Gln Ala Leu Lys Phe Ala Arg Asp
 65                  70                  75                  80

Phe Ala Gly Asp Gly Leu Val Thr Ser Trp Thr His Glu Lys Asn Trp
                 85                  90                  95

Lys Lys Ala His Asn Ile Leu Leu Pro Ser Phe Ser Gln Gln Ala Met
             100                 105                 110

Lys Gly Tyr His Ala Met Met Val Asp Ile Ala Val Gln Leu Val Gln
             115                 120                 125

Lys Trp Glu Arg Leu Asn Ala Asp Glu His Ile Glu Val Ser Glu Asp
 130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
             180                 185                 190

Pro Asp Asp Pro Ala Tyr Asp Glu Asn Lys Arg Gln Phe Gln Glu Asp
             195                 200                 205

Ile Lys Val Met Asn Asp Leu Val Asp Ile Ile Ala Asp Arg Lys Ala
             210                 215                 220

Arg Gly Glu Gln Ser Asp Asp Leu Leu Thr Gln Met Leu Asn Gly Lys
225                 230                 235                 240

Asp Pro Glu Thr Gly Glu Pro Leu Asp Asp Gly Asn Ile Arg Tyr Gln
                245                 250                 255

Ile Ile Thr Phe Leu Ile Ala Gly His Glu Ala Thr Ser Gly Leu Leu
             260                 265                 270

Ser Phe Ala Leu Tyr Phe Leu Val Lys Asn Pro His Val Leu Gln Lys
             275                 280                 285

Val Ala Glu Glu Ala Ala Arg Val Leu Val Asp Pro Val Pro Ser Tyr
             290                 295                 300

Lys Gln Val Lys Gln Leu Lys Tyr Val Gly Met Val Leu Asn Glu Ala
305                 310                 315                 320

Leu Arg Leu Trp Pro Thr Ala Pro Ala Phe Ser Leu Tyr Ala Lys Glu
                325                 330                 335

Asp Thr Val Leu Gly Gly Glu Tyr Pro Leu Glu Lys Gly Asp Glu Val
             340                 345                 350

Met Val Leu Ile Pro Gln Leu His Arg Asp Lys Thr Val Trp Gly Asp
             355                 360                 365

Asp Val Glu Glu Phe Arg Pro Glu Arg Phe Glu Asn Pro Ser Ala Ile
             370                 375                 380

Pro Gln His Ala Phe Lys Pro Phe Gly Asn Gly Gln Arg Ala Thr Ile
385                 390                 395                 400

Gly Gln Gln Phe Ala Leu His Glu Ala Thr Leu Val Leu Gly Met Met
                405                 410                 415

Leu Lys His Phe Asp Phe Glu Asp His Thr Asn Tyr Glu Leu Asp Ile
             420                 425                 430

Lys Glu Thr Leu Ser Leu Lys Pro Lys Gly Phe Val Val Lys Ala Lys
             435                 440                 445

Ser Lys Lys Ile Pro Leu Gly Gly Ile Pro Ser Pro Ser Thr Glu Gln

```
                450                 455                 460
Ser Ala Lys Lys Val Arg Lys Lys Ala Glu Asn Ala His Asn Thr Pro
465                 470                 475                 480

Leu Leu Val Leu Tyr Gly Ser Asn Met Gly Thr Ala Glu Gly Thr Ala
                    485                 490                 495

Arg Asp Leu Ala Asp Ile Ala Met Ser Lys Gly Phe Ala Pro Gln Val
                500                 505                 510

Ala Thr Leu Asp Ser His Ala Gly Asn Leu Pro Arg Glu Gly Ala Val
                515                 520                 525

Leu Ile Val Thr Ala Ser Tyr Asn Gly His Pro Pro Asp Asn Ala Lys
        530                 535                 540

Gln Phe Val Asp Trp Leu Asp Gln Ala Ser Ala Asp Glu Val Lys Gly
545                 550                 555                 560

Val Arg Tyr Ser Val Phe Gly Cys Gly Asp Lys Asn Trp Ala Thr Thr
                    565                 570                 575

Tyr Gln Lys Val Pro Ala Phe Ile Asp Glu Thr Leu Ala Ala Lys Gly
                580                 585                 590

Ala Glu Asn Ile Ala Asp Arg Gly Glu Ala Asp Ala Ser Asp Asp Phe
                595                 600                 605

Glu Gly Thr Tyr Glu Glu Trp Arg Glu His Met Trp Ser Asp Val Ala
                610                 615                 620

Ala Tyr Phe Asn Leu Asp Ile Glu Asn Ser Glu Asp Asn Lys Ser Thr
625                 630                 635                 640

Leu Ser Leu Gln Phe Val Asp Ser Ala Ala Asp Met Pro Leu Ala Lys
                    645                 650                 655

Met His Gly Ala Phe Ser Thr Asn Val Val Ala Ser Lys Glu Leu Gln
                660                 665                 670

Gln Pro Gly Ser Ala Arg Ser Thr Arg His Leu Glu Ile Glu Leu Pro
                675                 680                 685

Lys Glu Ala Ser Tyr Gln Glu Gly Asp His Leu Gly Val Ile Pro Arg
                690                 695                 700

Asn Tyr Glu Gly Ile Val Asn Arg Val Thr Ala Arg Phe Gly Leu Asp
705                 710                 715                 720

Ala Ser Gln Gln Ile Arg Leu Glu Ala Glu Glu Lys Leu Ala His
                    725                 730                 735

Leu Pro Leu Ala Lys Thr Val Ser Val Glu Glu Leu Leu Gln Tyr Val
                    740                 745                 750

Glu Leu Gln Asp Pro Val Thr Arg Thr Gln Leu Arg Ala Met Ala Ala
                    755                 760                 765

Lys Thr Val Cys Pro Pro His Lys Val Glu Leu Glu Ala Leu Leu Glu
770                 775                 780

Lys Gln Ala Tyr Lys Glu Gln Val Leu Ala Lys Arg Leu Thr Met Leu
785                 790                 795                 800

Glu Leu Leu Glu Lys Tyr Pro Ala Cys Glu Met Lys Phe Ser Glu Phe
                    805                 810                 815

Ile Ala Leu Leu Pro Ser Ile Arg Pro Arg Tyr Tyr Ser Ile Ser Ser
                820                 825                 830

Ser Pro Arg Val Asp Glu Lys Gln Ala Ser Ile Thr Val Ser Val Val
                835                 840                 845

Ser Gly Glu Ala Trp Ser Gly Tyr Gly Glu Tyr Lys Gly Ile Ala Ser
                850                 855                 860

Asn Tyr Leu Ala Glu Leu Gln Glu Gly Asp Thr Ile Thr Cys Phe Ile
865                 870                 875                 880
```

```
Ser Thr Pro Gln Ser Glu Phe Thr Leu Pro Lys Asp Pro Glu Thr Pro
            885                 890                 895

Leu Ile Met Val Gly Pro Gly Thr Gly Val Ala Pro Phe Arg Gly Phe
            900                 905                 910

Val Gln Ala Arg Lys Gln Leu Lys Glu Gln Gly Gln Ser Leu Gly Glu
            915                 920                 925

Ala His Leu Tyr Phe Gly Cys Arg Ser Pro His Glu Asp Tyr Leu Tyr
            930                 935                 940

Gln Glu Glu Leu Glu Asn Ala Gln Ser Glu Gly Ile Ile Thr Leu His
945                 950                 955                 960

Thr Ala Phe Ser Arg Met Pro Asn Gln Pro Lys Thr Tyr Val Gln His
            965                 970                 975

Val Met Glu Gln Asp Gly Lys Lys Leu Ile Glu Leu Leu Asp Gln Gly
            980                 985                 990

Ala His Phe Tyr Ile Cys Gly Asp Gly Ser Gln Met Ala Pro Ala Val
            995                 1000                1005

Glu Ala Thr Leu Met Lys Ser Tyr Ala Asp Val His Gln Val Ser Glu
        1010                1015                1020

Ala Asp Ala Arg Leu Trp Leu Gln Gln Leu Glu Glu Lys Gly Arg Tyr
1025                1030                1035                1040

Ala Lys Asp Val Trp Ala Gly
            1045

<210> SEQ ID NO 61
<211> LENGTH: 35
<212> TYPE: PRT
<213> ORGANISM: Artificial Sequence
<220> FEATURE:
<223> OTHER INFORMATION: synthetic cytochrome P450-BM3 sequence of
      CYP102A1

<400> SEQUENCE: 61

Glu Asn Pro Ser Ala Ile Pro Gln His Ala Phe Lys Pro Phe Gly Asn
 1               5                  10                  15

Gly Gln Arg Ala Cys Ile Gly Gln Gln Phe Ala Leu His Glu Ala Thr
            20                  25                  30

Leu Val Leu
        35

<210> SEQ ID NO 62
<211> LENGTH: 43
<212> TYPE: PRT
<213> ORGANISM: Artificial Sequence
<220> FEATURE:
<223> OTHER INFORMATION: synthetic cytochrome P450-CAM sequence of
      Pseudomonas putida CYP101A1

<400> SEQUENCE: 62

Glu Arg Glu Asn Ala Cys Pro Met His Val Asp Phe Ser Arg Gln Lys
 1               5                  10                  15

Val Ser His Thr Thr Phe Gly His Gly Ser His Leu Cys Leu Gly Gln
            20                  25                  30

His Leu Ala Arg Arg Glu Ile Ile Val Thr Leu
        35                  40

<210> SEQ ID NO 63
<211> LENGTH: 60
<212> TYPE: PRT
<213> ORGANISM: Artificial Sequence
```

<220> FEATURE:
<223> OTHER INFORMATION: synthetic cytochrome P450-BM3 sequence of
    CYP102A1

<400> SEQUENCE: 63

Gly His Glu Thr Thr Ser Gly Leu Leu Ser Phe Ala Leu Tyr Phe Leu
1               5                   10                  15

Val Lys Asn Pro His Val Leu Gln Lys Ala Ala Glu Glu Ala Ala Arg
            20                  25                  30

Val Leu Val Asp Pro Val Pro Ser Tyr Lys Gln Val Lys Gln Leu Lys
        35                  40                  45

Tyr Val Gly Met Val Leu Asn Glu Ala Leu Arg Leu
    50                  55                  60

<210> SEQ ID NO 64
<211> LENGTH: 42
<212> TYPE: PRT
<213> ORGANISM: Artificial Sequence
<220> FEATURE:
<223> OTHER INFORMATION: synthetic cytochrome P450-CAM sequence of
    Pseudomonas putida CYP101A1

<400> SEQUENCE: 64

Gly Leu Asp Thr Val Val Asn Phe Leu Ser Phe Ser Met Glu Phe Leu
1               5                   10                  15

Ala Lys Ser Pro Glu His Arg Gln Glu Leu Ile Glu Arg Pro Glu Arg
            20                  25                  30

Ile Pro Ala Ala Cys Glu Glu Leu Leu Arg
        35                  40

<210> SEQ ID NO 65
<211> LENGTH: 49
<212> TYPE: PRT
<213> ORGANISM: Artificial Sequence
<220> FEATURE:
<223> OTHER INFORMATION: synthetic cytochrome P450-BM3 sequence of
    CYP102A1

<400> SEQUENCE: 65

Phe Arg Pro Glu Arg Phe Glu Asn Pro Ser Ala Ile Pro Gln His Ala
1               5                   10                  15

Phe Lys Pro Phe Gly Asn Gly Gln Arg Ala Cys Ile Gly Gln Gln Phe
            20                  25                  30

Ala Leu His Glu Ala Thr Leu Val Leu Gly Met Met Leu Lys His Phe
        35                  40                  45

Asp

<210> SEQ ID NO 66
<211> LENGTH: 51
<212> TYPE: PRT
<213> ORGANISM: Artificial Sequence
<220> FEATURE:
<223> OTHER INFORMATION: synthetic cytochrome P450 sequence of
    Oryctolagus cuniculus CYP2B4

<400> SEQUENCE: 66

Phe Asn Pro Gly His Phe Leu Asp Ala Asn Gly Ala Leu Lys Arg Asn
1               5                   10                  15

Glu Gly Phe Met Pro Phe Ser Leu Gly Lys Arg Val Cys Leu Gly Glu
            20                  25                  30

Gly Ile Ala Arg Thr Glu Leu Phe Leu Phe Thr Thr Ile Leu Gln
         35                  40                  45

Asn Phe Ser
     50

<210> SEQ ID NO 67
<211> LENGTH: 59
<212> TYPE: PRT
<213> ORGANISM: Artificial Sequence
<220> FEATURE:
<223> OTHER INFORMATION: synthetic cytochrome P450-BM3 sequence of
      CYP102A1

<400> SEQUENCE: 67

Gln Ile Ile Thr Phe Leu Ile Ala Gly His Glu Thr Thr Ser Gly Leu
1               5                   10                  15

Leu Ser Phe Ala Leu Tyr Phe Leu Val Lys Asn Pro His Val Leu Gln
            20                  25                  30

Lys Ala Ala Glu Glu Ala Ala Arg Val Leu Val Asp Pro Val Pro Ser
        35                  40                  45

Tyr Lys Gln Val Lys Gln Leu Lys Tyr Val Gly
    50                  55

<210> SEQ ID NO 68
<211> LENGTH: 60
<212> TYPE: PRT
<213> ORGANISM: Artificial Sequence
<220> FEATURE:
<223> OTHER INFORMATION: synthetic cytochrome P450 sequence of
      Oryctolagus cuniculus CYP2B4

<400> SEQUENCE: 68

Thr Val Leu Ser Leu Phe Phe Ala Gly Thr Glu Thr Thr Ser Thr Thr
1               5                   10                  15

Leu Arg Tyr Gly Phe Leu Leu Met Leu Lys Tyr Pro His Val Thr Glu
            20                  25                  30

Arg Val Gln Lys Glu Ile Glu Gln Val Ile Gly Ser His Arg Pro Pro
        35                  40                  45

Ala Leu Asp Asp Arg Ala Lys Met Pro Tyr Thr Asp
    50                  55                  60

<210> SEQ ID NO 69
<211> LENGTH: 4
<212> TYPE: PRT
<213> ORGANISM: Artificial Sequence
<220> FEATURE:
<223> OTHER INFORMATION: synthetic P450-BM3 (CYP102A1) and Oryctolagus
      cuniculus (CYP2B4) consensus peptide

<400> SEQUENCE: 69

Glu Thr Thr Ser
1

<210> SEQ ID NO 70
<211> LENGTH: 26
<212> TYPE: DNA
<213> ORGANISM: Artificial Sequence
<220> FEATURE:
<223> OTHER INFORMATION: synthetic standard overlap mutagenesis forward
      primer HFT

<400> SEQUENCE: 70
caggaaacag gatcagctta ctcccc                                    26

<210> SEQ ID NO 71
<211> LENGTH: 36
<212> TYPE: DNA
<213> ORGANISM: Artificial Sequence
<220> FEATURE:
<223> OTHER INFORMATION: synthetic standard overlap mutagenesis forward primer BM3_C400S_F_nheI

<400> SEQUENCE: 71
gaaacggtca gcgtgctagc atcggtcagc agttcg                    36

<210> SEQ ID NO 72
<211> LENGTH: 36
<212> TYPE: DNA
<213> ORGANISM: Artificial Sequence
<220> FEATURE:
<223> OTHER INFORMATION: synthetic standard overlap mutagenesis reverse primer BM3_C400S_R_nheI

<400> SEQUENCE: 72
cgaactgctg accgatgcta gcacgctgac cgtttc                    36

<210> SEQ ID NO 73
<211> LENGTH: 30
<212> TYPE: DNA
<213> ORGANISM: Artificial Sequence
<220> FEATURE:
<223> OTHER INFORMATION: synthetic standard overlap mutagenesis reverse primer pCWori-Rev

<400> SEQUENCE: 73
gcgtatcacg aggccctttc gtcttcaagc                           30

<210> SEQ ID NO 74
<211> LENGTH: 6
<212> TYPE: PRT
<213> ORGANISM: Artificial Sequence
<220> FEATURE:
<223> OTHER INFORMATION: synthetic metal binding affinity tag His6, His6 tag

<400> SEQUENCE: 74

His His His His His His
 1               5

<210> SEQ ID NO 75
<211> LENGTH: 267
<212> TYPE: PRT
<213> ORGANISM: Artificial Sequence
<220> FEATURE:
<223> OTHER INFORMATION: synthetic human cytochrome P450, CYP2D7 amino acids 219-485

<400> SEQUENCE: 75

Leu Arg Glu Val Leu Asn Ala Val Pro Val Leu Pro His Ile Pro Ala
 1               5                  10                  15

Leu Ala Gly Lys Val Leu Arg Phe Gln Lys Ala Phe Leu Thr Gln Leu
             20                  25                  30

Asp Glu Leu Leu Thr Glu His Arg Met Thr Trp Asp Pro Ala Gln Pro
         35                  40                  45

Pro Arg Asp Leu Thr Glu Ala Phe Leu Ala Lys Lys Glu Lys Ala Lys
     50                  55                  60

Gly Ser Pro Glu Ser Ser Phe Asn Asp Glu Asn Leu Arg Ile Val Val
65                  70                  75                  80

```
Gly Asn Leu Phe Leu Ala Gly Met Val Thr Leu Thr Thr Leu Ala
                85                  90                  95

Trp Gly Leu Leu Leu Met Ile Leu His Leu Asp Val Gln Arg Gly Arg
        100                 105                 110

Arg Val Ser Pro Gly Cys Ser Pro Ile Val Gly Thr His Val Cys Pro
            115                 120                 125

Val Arg Val Gln Gln Glu Ile Asp Asp Val Ile Gly Gln Val Arg Arg
    130                 135                 140

Pro Glu Met Gly Asp Gln Val His Met Pro Tyr Thr Thr Ala Val Ile
145                 150                 155                 160

His Glu Val Gln Arg Phe Gly Asp Ile Val Pro Leu Gly Val Thr His
                165                 170                 175

Met Thr Ser Arg Asp Ile Glu Val Gln Gly Phe Arg Ile Pro Lys Gly
            180                 185                 190

Thr Thr Leu Ile Thr Asn Leu Ser Ser Val Leu Lys Asp Glu Ala Val
        195                 200                 205

Trp Glu Lys Pro Phe Arg Phe His Pro Glu His Phe Leu Asp Ala Gln
    210                 215                 220

Gly His Phe Val Lys Pro Glu Ala Phe Leu Pro Phe Ser Ala Gly Arg
225                 230                 235                 240

Arg Ala Cys Leu Gly Glu Pro Leu Ala Arg Met Glu Leu Phe Leu Phe
                245                 250                 255

Phe Thr Ser Leu Leu Gln His Phe Ser Phe Ser
            260                 265

<210> SEQ ID NO 76
<211> LENGTH: 244
<212> TYPE: PRT
<213> ORGANISM: Artificial Sequence
<220> FEATURE:
<223> OTHER INFORMATION: synthetic human cytochrome P450:NADPH-P-450
      reductase precursor, cytochrome P450 (BM3),
      CYP102A1 amino acids 181-424

<400> SEQUENCE: 76

Leu Asp Glu Ala Met Asn Lys Leu Gln Arg Ala Asn Pro Asp Asp Pro
1               5                   10                  15

Ala Tyr Asp Glu Asn Lys Arg Gln Phe Gln Glu Asp Ile Lys Val Met
            20                  25                  30

Asn Asp Leu Val Asp Lys Ile Ile Ala Asp Arg Lys Ala Ser Gly Glu
        35                  40                  45

Gln Ser Asp Asp Leu Leu Thr His Met Leu Asn Gly Lys Asp Pro Glu
    50                  55                  60

Thr Gly Glu Pro Leu Asp Asp Glu Asn Ile Arg Tyr Gln Ile Ile Thr
65                  70                  75                  80

Phe Leu Ile Ala Gly His Glu Thr Thr Ser Gly Leu Leu Ser Phe Ala
                85                  90                  95

Leu Tyr Phe Leu Val Lys Asn Pro His Val Leu Gln Lys Ala Ala Glu
            100                 105                 110

Glu Ala Ala Arg Val Leu Val Asp Pro Val Pro Ser Tyr Lys Gln Val
        115                 120                 125

Lys Gln Leu Lys Tyr Val Gly Met Val Leu Asn Glu Ala Leu Arg Leu
    130                 135                 140

Trp Pro Thr Ala Pro Ala Phe Ser Leu Tyr Ala Lys Glu Asp Thr Val
145                 150                 155                 160
```

```
Leu Gly Gly Glu Tyr Pro Leu Glu Lys Gly Asp Glu Leu Met Val Leu
            165                 170                 175

Ile Pro Gln Leu His Arg Asp Lys Thr Ile Trp Gly Asp Asp Val Glu
        180                 185                 190

Glu Phe Arg Pro Glu Arg Phe Glu Asn Pro Ser Ala Ile Pro Gln His
            195                 200                 205

Ala Phe Lys Pro Phe Gly Asn Gly Gln Arg Ala Cys Ile Gly Gln Gln
        210                 215                 220

Phe Ala Leu His Glu Ala Thr Leu Val Leu Gly Met Met Leu Lys His
225                 230                 235                 240

Phe Asp Phe Glu
```

<210> SEQ ID NO 77
<211> LENGTH: 290
<212> TYPE: PRT
<213> ORGANISM: Artificial Sequence
<220> FEATURE:
<223> OTHER INFORMATION: synthetic rat cytochrome P450, CYPC27, P4502C27
      amino acids 211-500

<400> SEQUENCE: 77

```
Tyr His Leu Ala Leu Glu Ala Ile Cys Tyr Ile Leu Phe Glu Lys Arg
1               5                   10                  15

Val Gly Cys Leu Glu Pro Ser Ile Pro Glu Asp Thr Ala Thr Phe Ile
            20                  25                  30

Arg Ser Val Gly Leu Met Phe Lys Asn Ser Val Tyr Val Thr Phe Leu
        35                  40                  45

Pro Lys Trp Ser Arg Pro Leu Pro Phe Trp Lys Arg Tyr Met Asn
50                  55                  60

Asn Trp Asp Asn Ile Phe Ser Phe Gly Glu Lys Met Ile His Gln Lys
65                  70                  75                  80

Val Gln Glu Ile Glu Ala Gln Leu Gln Ala Ala Gly Pro Asp Gly Val
            85                  90                  95

Gln Val Ser Gly Tyr Leu His Phe Leu Leu Thr Lys Glu Leu Leu Ser
        100                 105                 110

Pro Gln Glu Thr Val Gly Thr Phe Pro Glu Leu Ile Leu Ala Gly Val
    115                 120                 125

Asp Thr Thr Ser Asn Thr Leu Thr Trp Ala Leu Tyr His Leu Ser Lys
130                 135                 140

Asn Pro Glu Ile Gln Glu Ala Leu His Lys Glu Val Thr Gly Val Val
145                 150                 155                 160

Pro Phe Gly Lys Val Pro Gln Asn Lys Asp Phe Ala His Met Pro Leu
                165                 170                 175

Leu Lys Ala Val Ile Lys Glu Thr Leu Arg Leu Tyr Pro Val Val Pro
            180                 185                 190

Thr Asn Ser Arg Ile Ile Thr Glu Lys Glu Thr Glu Ile Asn Gly Phe
        195                 200                 205

Leu Phe Pro Lys Asn Thr Gln Phe Val Leu Cys Thr Tyr Val Val Ser
    210                 215                 220

Arg Asp Pro Ser Val Phe Pro Glu Pro Glu Ser Phe Gln Pro His Arg
225                 230                 235                 240

Trp Leu Arg Lys Arg Glu Asp Asp Asn Ser Gly Ile Gln His Pro Phe
                245                 250                 255

Gly Ser Val Pro Phe Gly Tyr Gly Val Arg Ser Cys Leu Gly Arg Arg
            260                 265                 270
```

```
Ile Ala Glu Leu Glu Met Gln Leu Leu Ser Arg Leu Ile Gln Lys
            275                 280                 285

Tyr Glu
    290

<210> SEQ ID NO 78
<211> LENGTH: 308
<212> TYPE: PRT
<213> ORGANISM: Artificial Sequence
<220> FEATURE:
<223> OTHER INFORMATION: synthetic human cytochrome P450:NADPH-P-450
      reductase precursor, cytochrome P450 (BM3),
      CYP102A1 amino acids 115-422

<400> SEQUENCE: 78

Tyr His Ala Met Met Val Asp Ile Ala Val Gln Leu Val Gln Lys Trp
  1               5                  10                  15

Glu Arg Leu Asn Ala Asp Glu His Ile Glu Val Pro Glu Asp Met Thr
                 20                  25                  30

Arg Leu Thr Leu Asp Thr Ile Gly Leu Cys Gly Phe Asn Tyr Arg Phe
             35                  40                  45

Asn Ser Phe Tyr Arg Asp Gln Pro His Pro Phe Ile Thr Ser Met Val
 50                  55                  60

Arg Ala Leu Asp Glu Ala Met Asn Lys Leu Gln Arg Ala Asn Pro Asp
 65                  70                  75                  80

Asp Pro Ala Tyr Asp Glu Asn Lys Arg Gln Phe Gln Glu Asp Ile Lys
                 85                  90                  95

Val Met Asn Asp Leu Val Asp Lys Ile Ile Ala Asp Arg Lys Ala Ser
            100                 105                 110

Gly Glu Gln Ser Asp Asp Leu Leu Thr His Met Leu Asn Gly Lys Asp
            115                 120                 125

Pro Glu Thr Gly Glu Pro Leu Asp Asp Glu Asn Ile Arg Tyr Gln Ile
            130                 135                 140

Ile Thr Phe Leu Ile Ala Gly His Glu Thr Thr Ser Gly Leu Leu Ser
145                 150                 155                 160

Phe Ala Leu Tyr Phe Leu Val Lys Asn Pro His Val Leu Gln Lys Ala
                165                 170                 175

Ala Glu Glu Ala Ala Arg Val Leu Val Asp Pro Val Pro Ser Tyr Lys
            180                 185                 190

Gln Val Lys Gln Leu Lys Tyr Val Gly Met Val Leu Asn Glu Ala Leu
            195                 200                 205

Arg Leu Trp Pro Thr Ala Pro Ala Phe Ser Leu Tyr Ala Lys Glu Asp
        210                 215                 220

Thr Val Leu Gly Gly Glu Tyr Pro Leu Glu Lys Gly Asp Glu Leu Met
225                 230                 235                 240

Val Leu Ile Pro Gln Leu His Arg Asp Lys Thr Ile Trp Gly Asp Asp
                245                 250                 255

Val Glu Glu Phe Arg Pro Glu Arg Phe Glu Asn Pro Ser Ala Ile Pro
            260                 265                 270

Gln His Ala Phe Lys Pro Phe Gly Asn Gly Gln Arg Ala Cys Ile Gly
            275                 280                 285

Gln Gln Phe Ala Leu His Glu Ala Thr Leu Val Leu Gly Met Met Leu
            290                 295                 300

Lys His Phe Asp
305
```

IN VIVO AND IN VITRO OLEFIN CYCLOPROPANATION CATALYZED BY HEME ENZYMES

CROSS-REFERENCES TO RELATED APPLICATIONS

This application is a continuation of PCT/US2013/063577, filed Oct. 4, 2013, which application claims priority to U.S. Provisional Application No. 61/711,640, filed Oct. 9, 2012, U.S. Provisional Application No. 61/740,247, filed Dec. 20, 2012, U.S. Provisional Application No. 61/784,917, filed Mar. 14, 2013, U.S. Provisional Application No. 61/838,167, filed Jun. 21, 2013, U.S. Provisional Application No. 61/815,997, filed Apr. 25, 2013, U.S. Provisional Application No. 61/818,329, filed May 1, 2013, and U.S. Provisional Application No. 61/856,493, filed Jul. 19, 2013. The disclosures of each of these applications and International Application No. PCT/US2013/63428, filed Oct. 4, 2013, are hereby incorporated by reference in their entirety for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -150-1.TXT, created on May 8, 2014, 2014, 417,792 bytes, machine format IBM-PC, MS-Windows operating system, is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support under Grant No. DE-FG02-06ER15762/T-20 105789 and Grant No. DE-FG02-06ER15762/T-106029 awarded by the Department of Energy and under 1F32b015846-01 and with government support under Grant No. EB015846 awarded by the National Institute of Health. The government's has certain rights in the invention.

BACKGROUND OF THE INVENTION

A considerable challenge in modern synthetic chemistry is the selective direct functionalization of unactivated carbon-hydrogen (C—H) bonds and carbon-carbon (C═C) double bonds (e.g., olefins) (R. G. Bergman, *Nature* 446, 391 (2007); H. Pellissier, *Tetrahedron* 64, 7041 (2008)). Adapting asymmetric catalytic processes to these reactions has important consequences in the stereoselective and regioselective elaboration of molecules for natural product and pharmaceutical synthesis. In recent years, much success has been achieved in the development of catalysts for the select addition of oxygen into molecules (M. S. Chen et al., *Science* 318, 783 (2007)). More challenging is the direct introduction of new carbon-carbon centers into complex structures. A contemporary catalytic approach uses metallocarbenoid intermediates that transfer a reactive carbene into select C—H and C═C bonds, creating new asymmetric highly substituted carbon centers and cyclopropanes, respectively (H. M. L. Davies et al., *Chemical Reviews* 103, 2861 (2003)). However, the most successful catalysts to date often utilize expensive and possibly toxic transition metal complexes, with dirhodium species marking representative examples. Notably, high yield, regioselectivity, and stereoselectivity in these systems remains difficult to achieve and many of these catalysts are hampered by harsh reaction conditions including high temperature and organic solvents.

The asymmetric cyclopropanation of olefins with high-energy carbene precursors is a hallmark reaction that generates up to 3 stereogenic centers in a single step to make the important cyclopropane motif, featured in many natural products and therapeutic agents (H. Lebel et al., *Chemical Reviews* 103, 977 (2003)). Limited to using physiologically accessible reagents, Nature catalyzes intermolecular cyclopropane formation through wholly different strategies, typically involving olefin addition to the methyl cation of S-adenosyl methionine or through cyclization of dimethylallyl pyrophosphate-derived allylic carbenium ions (L. A. Wessjohann et al., *Chemical Reviews* 103, 1625 (2003)). As a result, the diverse cyclopropanation products that can be formed by metallocarbene chemistry cannot be readily accessed by engineering natural cyclopropanation enzymes. As such, there is a need in the art for novel reagents and catalytic schemes that are capable of creating the cyclopropane motif with high yield, regioselectivity, and stereoselectivity, but without the toxicity and harsh reaction conditions associated with current approaches. The present invention satisfies this need by providing novel iron-heme-containing enzyme catalysts for producing cyclopropanation products in vitro and in vivo, and offers related advantages as well.

SUMMARY OF THE INVENTION

The present invention provides methods for catalyzing the conversion of an olefin to any compound (e.g., any intermediate or final compound) containing one or more cyclopropane functional groups using heme enzymes.

In certain aspects, the present invention provides a method for producing a cyclopropanation product, the method comprising:
(a) providing an olefinic substrate, a diazo reagent, and a heme enzyme; and
(b) admixing the components of step (a) in a reaction for a time sufficient to produce a cyclopropanation product.

In some embodiments, the cyclopropanation product is a compound according to Formula I:

wherein:
$R^1$ is independently selected from the group consisting of H, optionally substituted $C_{1-18}$ alkyl, optionally substituted $C_{6-10}$ aryl, optionally substituted 6- to 10-membered heteroaryl, halo, cyano, $C(O)OR^{1a}$, $C(O)N(R^7)_2$, $C(O)R^8$, $C(O)C(O)OR^8$, and $Si(R^8)_3$;
$R^2$ is independently selected from the group consisting of H, optionally substituted $C_{1-18}$ alkyl, optionally substituted $C_{6-10}$ aryl, optionally substituted 6- to 10-membered heteroaryl, halo, cyano, $C(O)OR^{2a}$, $C(O)N(R^7)_2$, $C(O)R^8$, $C(O)C(O)OR^8$, and $Si(R^8)_3$;
wherein:
$R^{1a}$ and $R^{2a}$ are independently selected from the group consisting of H, optionally substituted $C_{1-18}$ alkyl and -L-$R^C$, wherein each L is selected from the group consisting of a bond, —C($R^L$)$_2$—, and —$NR^L$—C($R^L$)$_2$—, each $R^L$ is independently selected from the group consisting of H, $C_{1-6}$ alkyl, halo, —CN, and —$SO_2$, and each $R^C$ is selected from the group consisting of optionally substituted $C_{6-10}$ aryl, optionally substituted 6- to 10-membered heteroaryl, and optionally substituted 6- to 10-membered heterocyclyl; and $R^3$, $R^4$, $R^5$, and $R^6$ are independently selected from the group consisting of H, $C_{1-18}$ alkyl, $C_{2-18}$ alkenyl, $C_{2-18}$ alkynyl, optionally substituted $C_{6-10}$ aryl, optionally substituted $C_1$-$C_6$ alkoxy, halo, hydroxy, cyano, C(O)N($R^7$)$_2$, $NR^7$C(O)$R^8$, C(O)$R^8$, C(O)O$R^8$, and N($R^9$)$_2$, wherein:

each $R^7$ and $R^8$ is independently selected from the group consisting of H, optionally substituted $C_{1-12}$ alkyl, optionally substituted $C_{2-12}$ alkenyl, and optionally substituted $C_{6-10}$ aryl; and each $R^9$ is independently selected from the group consisting of H, optionally substituted $C_{6-10}$ aryl, and optionally substituted 6- to 10-membered heteroaryl, or two $R^9$ moieties, together with the nitrogen atom to which they are attached, can form 6- to 18-membered heterocyclyl;

or $R^3$ forms an optionally substituted 3- to 18-membered ring with $R^4$;

or $R^5$ forms an optionally substituted 3- to 18-membered ring with $R^6$;

or $R^3$ or $R^4$ forms a double bond with $R^5$ or $R^6$;

or $R^3$ or $R^4$ forms an optionally substituted 5- to 6-membered ring with $R^5$ or $R^6$.

In certain embodiments, $R^1$ is C(O)O-L$R^c$; $R^2$ is selected from the group consisting of H and optionally substituted $C_{6-10}$ aryl; and $R^3$, $R^4$, $R^5$, and $R^6$ are independently selected from the group consisting of H, optionally substituted $C_{1-6}$ alkyl, optionally substituted $C_{2-6}$ alkenyl, optionally substituted $C_{2-6}$ alkynyl, optionally substituted $C_{6-10}$ aryl and halo, or $R^3$ forms an optionally substituted 3- to 18-membered ring with $R^4$; or $R^5$ forms an optionally substituted 3- to 18-membered ring with $R^6$.

In certain other embodiments, the cyclopropanation product is a compound according to Formula II:

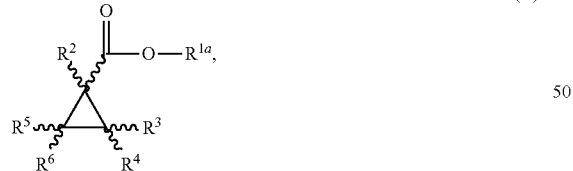

(II)

wherein $R^{1a}$ is $C_{1-6}$ alkyl and $R^2$ is selected from the group consisting of H and optionally substituted $C_{6-10}$ aryl.

In some instances, $R^2$ is H. In other instances, the cyclopropanation product is selected from the group consisting of:

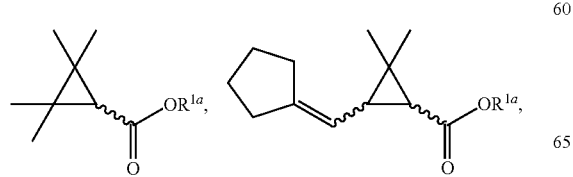

-continued

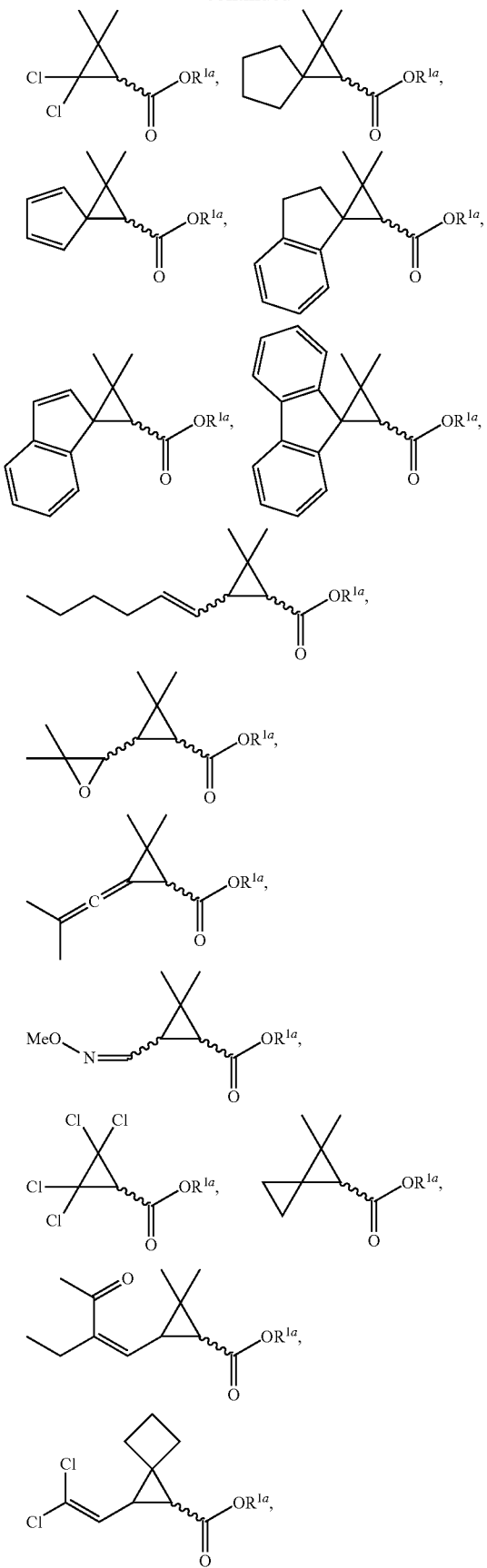

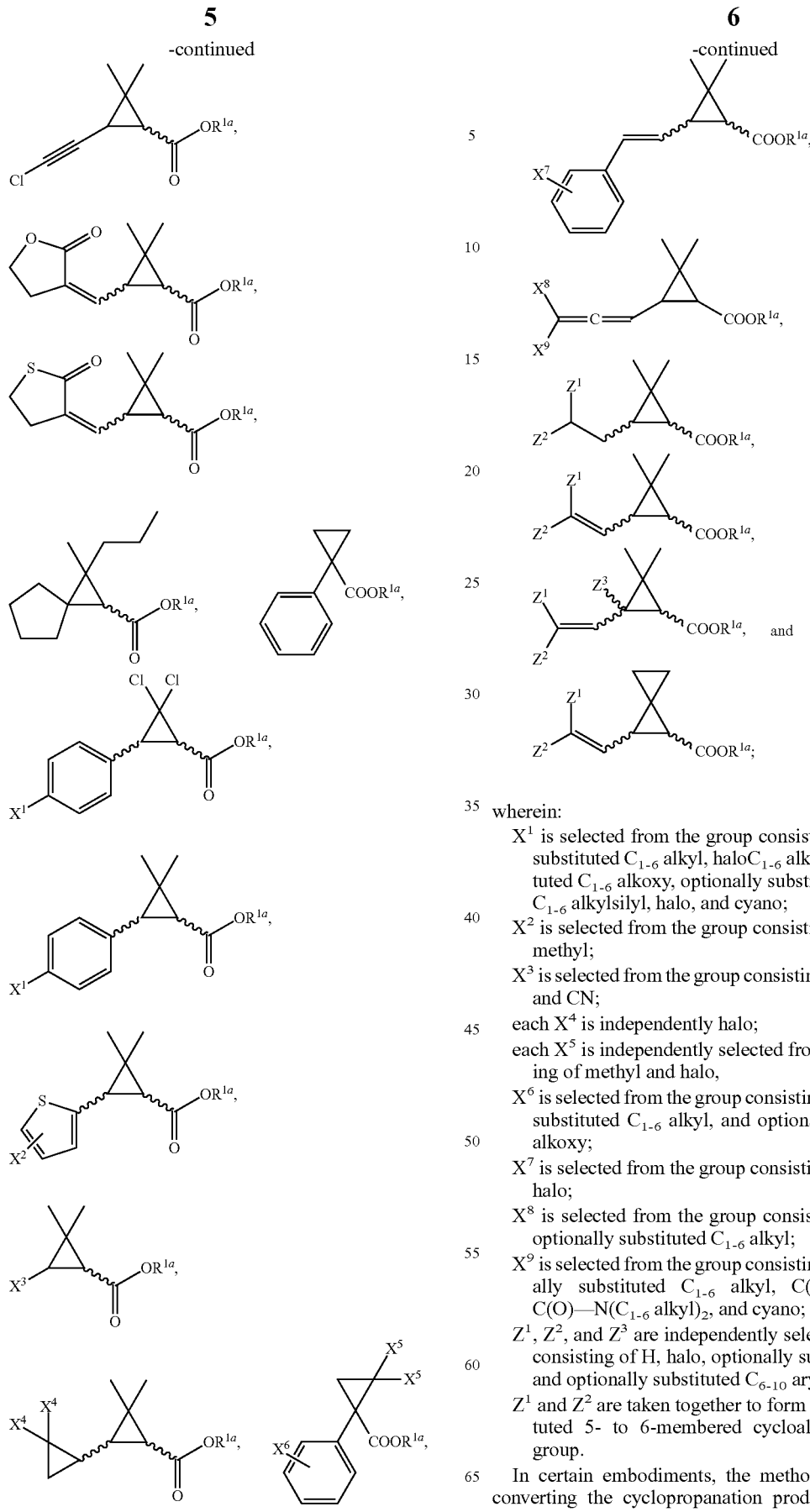

wherein:
X¹ is selected from the group consisting of H, optionally substituted $C_{1-6}$ alkyl, halo$C_{1-6}$ alkyl, optionally substituted $C_{1-6}$ alkoxy, optionally substituted $C_{1-6}$ alkylthio, $C_{1-6}$ alkylsilyl, halo, and cyano;

X² is selected from the group consisting of H, chloro, and methyl;

X³ is selected from the group consisting of H, methyl, halo, and CN;

each X⁴ is independently halo;

each X⁵ is independently selected from the group consisting of methyl and halo,

X⁶ is selected from the group consisting of halo, optionally substituted $C_{1-6}$ alkyl, and optionally substituted $C_{1-6}$ alkoxy;

X⁷ is selected from the group consisting of H, methyl, and halo;

X⁸ is selected from the group consisting of H, halo, and optionally substituted $C_{1-6}$ alkyl;

X⁹ is selected from the group consisting of H, halo, optionally substituted $C_{1-6}$ alkyl, C(O)O—($C_{1-6}$ alkyl), C(O)—N($C_{1-6}$ alkyl)₂, and cyano; and Z¹, Z², and Z³ are independently selected from the group consisting of H, halo, optionally substituted $C_{1-6}$ alkyl, and optionally substituted $C_{6-10}$ aryl; or Z¹ and Z² are taken together to form an optionally substituted 5- to 6-membered cycloalkyl or heterocyclyl group.

In certain embodiments, the method further comprises converting the cyclopropanation product to a compound according to Formula III:

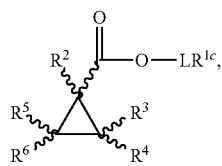
(III)

wherein:
L is selected from the group consisting of a bond, —C(R$^L$)$_2$—, and —NR$^L$—C(R$^L$)$_2$—,
each R$^L$ is independently selected from the group consisting of H, —CN, and —SO$_2$, and
R$^{1c}$ is selected from the group consisting of optionally substituted C$_{6-10}$ aryl, optionally substituted 6- to 10-membered heteroraryl, and optionally substituted 6- to 10-membered heterocyclyl.

In some instances, L is selected from the group consisting of a bond, —CH$_2$—, —CH(CN)—, and —N(SO$_2$)—CH$_2$. In other instances, the moiety L-R$^{1c}$ has a structure selected from the group consisting of:

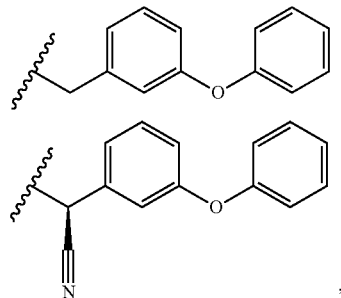
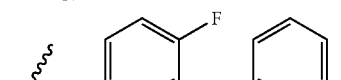
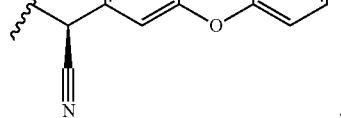
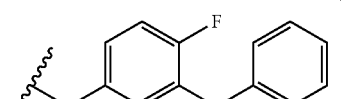
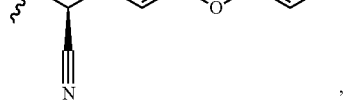
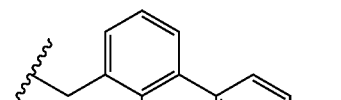
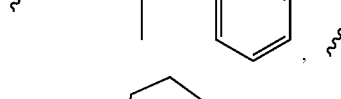
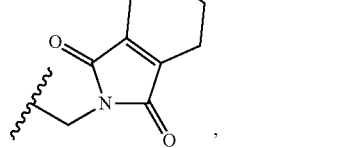

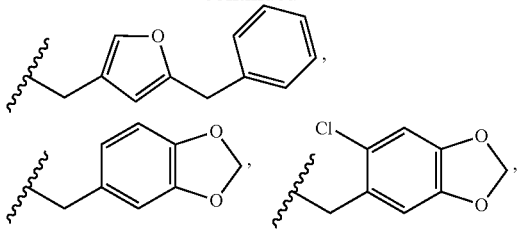
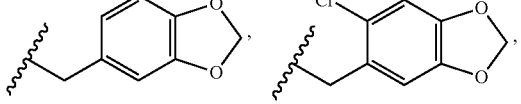
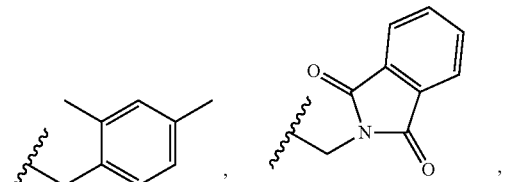
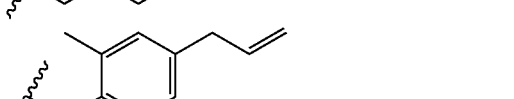
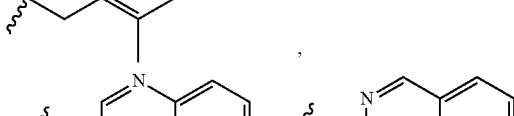
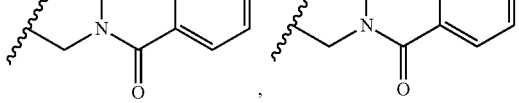
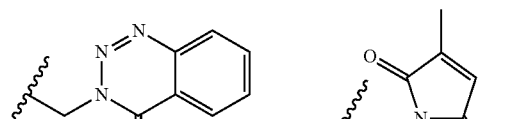
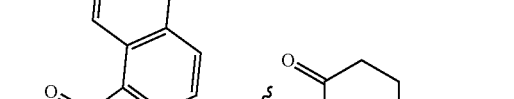
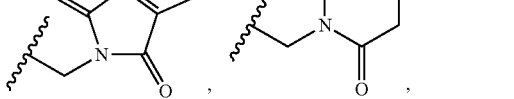
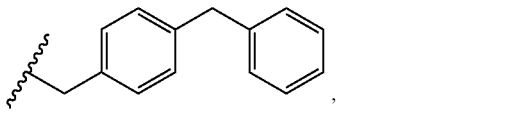
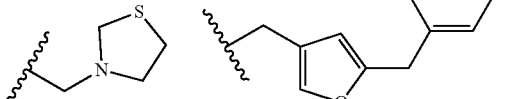
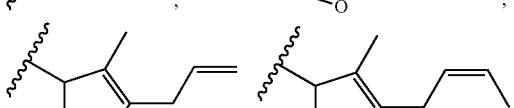

stituted $C_{2-6}$ alkenyl, optionally substituted $C_{2-6}$ alkynyl, phenyl, and (phenyl)$C_{1-6}$ alkoxy;

each $Y^2$ is independently selected from the group consisting of halo, optionally substituted $C_{1-6}$ alkyl, optionally substituted $C_{2-6}$ alkenyl, optionally substituted $C_{1-6}$ alkoxy, and nitro;

each $Y^3$ is independently optionally substituted $C_{1-6}$ alkyl;

each $Y^4$ is independently selected from the group consisting of optionally substituted $C_{1-6}$ alkyl, optionally substituted $C_{2-6}$ alkenyl, optionally substituted $C_{2-6}$ alkynyl, $C_{6-10}$ aryl-$C_{1-6}$ alkyl, furfuryl, $C_{1-6}$ alkoxy, ($C_{2-6}$ alkenyl)oxy, $C_{1-12}$ acyl, and halo;

$Y^5$ is selected from the group consisting of optionally substituted $C_{1-6}$ alkyl, optionally substituted $C_{1-6}$ alkoxy, and halo, the subscript m is an integer from 1 to 3, the subscript n is an integer from 1 to 5, the subscript p is an integer from 1 to 4, the subscript q is an integer from 0 to 3, and the wavy line at the left of the structure represents the point of connection between the moiety -L-$R^{1c}$ and the rest of the compound according to Formula III.

In yet other instances, the compound according to Formula III is resmethrin.

In certain embodiments, the cyclopropanation product is a compound having a structure according to the formula:

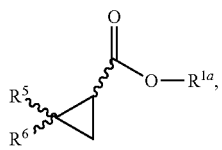

wherein:

$R^{1a}$ is optionally substituted $C_{1-6}$ alkyl, and $R^5$ and $R^6$ are independently selected from the group consisting of H, optionally substituted $C_{1-6}$ alkyl, optionally substituted $C_{6-10}$ aryl, C(O)N($R^7$)$_2$, C(O)O$R^8$ and N$R^7$C(O)$R^8$.

In some instances, the cyclopropanation product has a structure selected from the group consisting of:

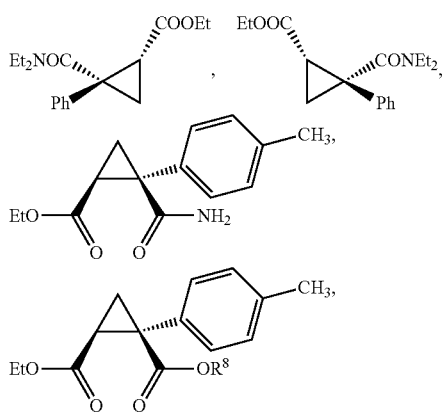

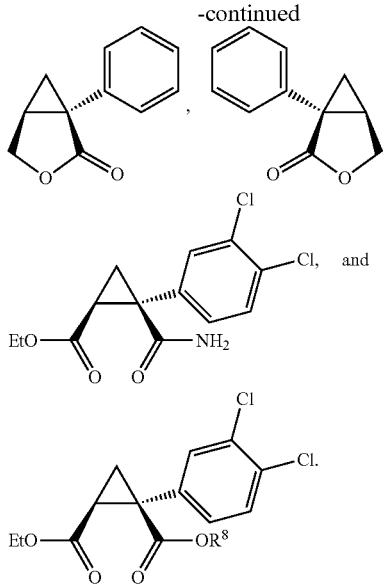

In certain instances, the method further comprises converting the cyclopropanation product to a compound selected from the group consisting of milnacipran, levomilnacipran, bicifadine, and 1-(3,4-dichlorophenyl)-3-azabicyclo[3.1.0]hexane.

In some embodiments, the olefinic substrate is selected from the group consisting of an alkene, a cycloalkene, and an arylalkene. In certain instances, the olefinic substrate comprises an arylalkene. In some instances, the arylalkene is a styrene. In other instances, the styrene has the formula:

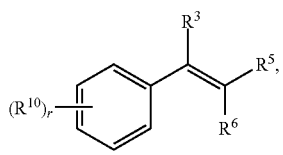

wherein $R^3$ is selected from the group consisting of H, optionally substituted $C_1$-$C_6$ alkyl, optionally substituted $C_1$-$C_6$ alkoxy, $C(O)N(R^7)_2$, $C(O)OR^8$, $N(R^9)_2$, halo, hydroxy, and cyano;

$R^5$ and $R^6$ are independently selected from the group consisting of H, optionally substituted $C_{1-6}$ alkyl, and halo;

$R^{10}$ is selected from the group consisting of optionally substituted $C_1$-$C_6$ alkyl, optionally substituted $C_1$-$C_6$ alkoxy, halo, and haloalkyl; and the subscript r is an integer from 0 to 2.

In some embodiments, the diazo reagent has a structure according to the formula:

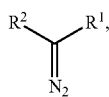

wherein:

$R^1$ is independently selected from the group consisting of H, optionally substituted $C_{1-18}$ alkyl, optionally substituted $C_{6-10}$ aryl, optionally substituted 6- to 10-membered heteroaryl, halo, cyano, $C(O)OR^{1a}$, $C(O)N(R^7)_2$, $C(O)R^8$, $C(O)C(O)OR^8$, and $Si(R^8)_3$; and $R^2$ is independently selected from the group consisting of H, optionally substituted $C_{1-18}$ alkyl, optionally substituted $C_{6-10}$ aryl, optionally substituted 6- to 10-membered heteroaryl, halo, cyano, $C(O)OR^{2a}$, $C(O)N(R^7)_2$, $C(O)R^8$, $C(O)C(O)OR^8$, and $Si(R^8)_3$;

wherein $R^{1a}$ and $R^{2a}$ are independently selected from the group consisting of H, optionally substituted $C_{1-18}$ alkyl and -L-$R^C$, wherein each L is selected from the group consisting of a bond, —C($R^L$)$_2$—, and —N$R^L$—C($R^1$)$_2$—, each $R^L$ is independently selected from the group consisting of H, $C_{1-6}$ alkyl, halo, —CN, and —SO$_2$, and each $R^C$ is selected from the group consisting of optionally substituted $C_{6-10}$ aryl, optionally substituted 6- to 10-membered heteroraryl, and optionally substituted 6- to 10-membered heterocyclyl; and each $R^7$ and $R^8$ is independently selected from the group consisting of H, optionally substituted $C_{1-12}$ alkyl, optionally substituted $C_{2-12}$ alkenyl, and optionally substituted $C_{6-10}$ aryl.

In certain embodiments, the diazo reagent is selected from the group consisting of an α-diazoester, an α-diazoamide, an α-diazonitrile, an α-diazoketone, an α-diazoaldehyde, and an α-diazosilane.

In certain instances, the diazo reagent has a formula selected from the group consisting of:

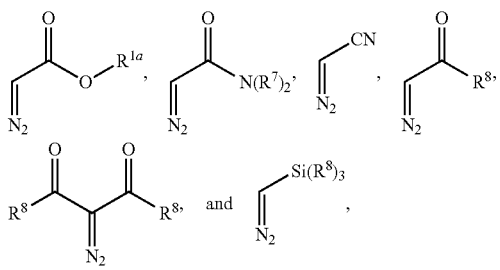

wherein $R^{1a}$ is selected from the group consisting of H and optionally substituted $C_1$-$C_6$ alkyl; and each $R^7$ and $R^8$ is independently selected from the group consisting of H, optionally substituted $C_{1-12}$ alkyl, optionally substituted $C_{2-12}$ alkenyl, and optionally substituted $C_{6-10}$ aryl.

In certain other instances, the diazo reagent is selected from the group consisting of diazomethane, ethyl diazoacetate, and (trimethylsilyl)diazomethane. In yet other instances, the diazo reagent has the formula:

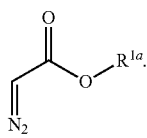

In particular embodiments, the cyclopropanation product has a formula selected from the group consisting of:

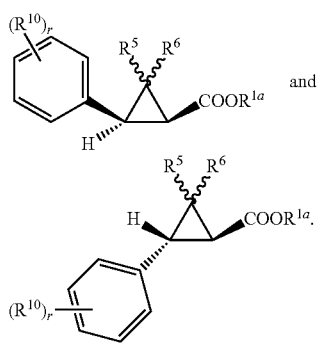

In some embodiments, the method is carried out in vitro. In certain instances, the reaction further comprises a reducing agent. In other embodiments, the heme enzyme is localized within a whole cell and the method is carried out in vivo. In some embodiments, the method is carried out under anaerobic conditions.

In some embodiments, the method produces a plurality of cyclopropanation products. In certain instances, the plurality of cyclopropanation products has a Z:E ratio of from 1:99 to 99:1. In some instances, the plurality of cyclopropanation products has a % $ee_Z$ of from about −90% to about 90%. In other instances, the plurality of cyclopropanation products has a % $ee_E$ of from about −90% to about 90%. In some instances, the cyclopropanation reaction is at least 30% to at least 90% diastereoselective. In other instances, the cyclopropanation reaction is at least 30% to at least 90% enantioselective.

In some embodiments, the heme enzyme is expressed in a bacterial, archaeal, or fungal host organism.

In certain embodiments, the heme enzyme is a fragment thereof comprising the heme domain. In particular embodiments, the heme enzyme is an engineered heme enzyme such as a heme enzyme variant comprising a mutation at the axial position of the heme coordination site. In some instances, the mutation is a substitution of the native residue with Ala, Asp, Arg, Asn, Cys, Glu, Gln, Gly, His, Ile, Lys, Leu, Met, Phe, Pro, Ser, Thr, Trp, Tyr, or Val at the axial position. In certain instances, the mutation is a substitution of Cys with Ser at the axial position. In other embodiments, the heme enzyme variant is a chimeric protein comprising recombined sequences or blocks of amino acids from two, three, or more different heme-containing proteins.

In particular embodiments, the heme enzyme is a cyclochrome P450 enzyme or a variant thereof. In preferred embodiments, the cyclochrome P450 enzyme is a P450 BM3 enzyme or a variant thereof.

In certain embodiments, the cyclochrome P450 enzyme variant comprises a mutation at the axial position of the heme coordination site. In some instances, the mutation is a substitution of Cys with Ala, Asp, Arg, Asn, Glu, Gln, Gly, His, Ile, Lys, Leu, Met, Phe, Pro, Ser, Thr, Trp, Tyr, or Val at the axial position. In certain instances, the mutation is a substitution of Cys with Ser at the axial position. In other embodiments, the cyclochrome P450 variant is a chimeric protein comprising recombined sequences or blocks of amino acids from at least two, three, or more different P450 enzymes (e.g., CYP102A1 (P450 BM3), CYP102A2, and CYP102A3).

In some embodiments, the P450 BM3 enzyme comprises the amino acid sequence set forth in SEQ ID NO:1. In particular embodiments, the P450 BM3 enzyme variant comprises a C400X mutation at the axial position in SEQ ID NO:1, wherein X is any amino acid other than Cys. In other embodiments, the P450 BM3 enzyme variant comprises at least one, two, three, four, five, six, seven, eight, nine, ten, eleven, twelve, or all thirteen of the following amino acid substitutions in SEQ ID NO:1: V78A, F87V, P142S, T175I, A184V, S226R, H236Q, E252G, T268A, A290V, L353V, I366V, and E442K.

In some embodiments, the P450 BM3 enzyme variant comprises at least one, two, or all three of the following amino acid substitutions in SEQ ID NO:1: I263A, A328G, and a T438 mutation. In certain instances, the T438 mutation is T438A, T438S, or T438P.

In some embodiments, the P450 BM3 enzyme variant comprises from one to five alanine substitutions in the active site of SEQ ID NO:1. In certain instances, the active site alanine substitutions are selected from the group consisting of L75A, M177A, L181A, I263A, L437A, and a combination thereof.

In particular embodiments, the P450 BM3 enzyme variant comprises a T268A mutation and/or a C400X mutation in SEQ ID NO:1, wherein X is any amino acid other than Cys.

In some embodiments, the heme enzyme comprises a fragment of the cytochrome P450 enzyme or variant thereof. In certain instances, the fragment comprises the heme domain of the cyclochrome P450 enzyme or variant thereof.

In particular embodiments, the heme enzyme is a P450 enzyme variant selected from Tables 4, 5A, and 5B.

In other aspects, the present invention provides a heme enzyme or a fragment thereof that can cyclopropanate an olefinic substrate.

In particular embodiments, the heme enzyme is an engineered heme enzyme such as a heme enzyme variant comprising a mutation at the axial position of the heme coordination site. In some instances, the mutation is a substitution of the native residue with Ala, Asp, Arg, Asn, Cys, Glu, Gln, Gly, His, Ile, Lys, Leu, Met, Phe, Pro, Ser, Thr, Trp, Tyr, or Val at the axial position. In certain instances, the mutation is a substitution of Cys with Ser at the axial position. In other embodiments, the heme enzyme variant is a chimeric protein comprising recombined sequences or blocks of amino acids from two, three, or more different heme-containing proteins.

In some embodiments, the heme enzyme variant is isolated and/or purified. In other embodiments, the heme enzyme variant is a cyclochrome P450 enzyme variant. In preferred embodiments, the cyclochrome P450 enzyme variant is a P450 BM3 enzyme variant.

In certain embodiments, the cyclochrome P450 enzyme variant comprises a mutation at the axial position of the heme coordination site. In some instances, the mutation is a substitution of Cys with Ala, Asp, Arg, Asn, Glu, Gln, Gly, His, Ile, Lys, Leu, Met, Phe, Pro, Ser, Thr, Trp, Tyr, or Val at the axial position. In certain instances, the mutation is a substitution of Cys with Ser at the axial position. In other embodiments, the cyclochrome P450 variant is a chimeric protein comprising recombined sequences or blocks of amino acids from at least two, three, or more different P450 enzymes (e.g., CYP102A1, CYP102A2, and CYP102A3).

In certain embodiments, the P450 BM3 enzyme variant comprises at least one mutation in the amino acid sequence set forth in SEQ ID NO:1. In particular embodiments, the P450 BM3 enzyme variant comprises a C400X mutation at the axial position in SEQ ID NO:1, wherein X is any amino acid other than Cys. In other embodiments, the P450 BM3 enzyme variant comprises at least one, two, three, four, five, six, seven, eight, nine, ten, eleven, twelve, or all thirteen of the following amino acid substitutions in SEQ ID NO:1: V78A, F87V, P142S, T175I, A184V, S226R, H236Q, E252G, T268A, A290V, L353V, I366V, and E442K.

In some embodiments, the P450 BM3 enzyme variant comprises at least one, two, or all three of the following amino acid substitutions in SEQ ID NO:1: I263A, A328G, and a T438 mutation. In certain instances, the T438 mutation is T438A, T438S, or T438P.

In some embodiments, the P450 BM3 enzyme variant comprises from one to five alanine substitutions in the active site of SEQ ID NO:1. In certain instances, the active site alanine substitutions are selected from the group consisting of L75A, M177A, L181A, I263A, L437A, and a combination thereof.

In particular embodiments, the P450 BM3 enzyme variant comprises a T268A mutation and/or a C400X mutation in SEQ ID NO:1, wherein X is any amino acid other than Cys.

In some embodiments, the heme enzyme variant fragment comprises the heme domain thereof. In particular embodiments, the heme enzyme variant is a P450 enzyme variant selected from Tables 4, 5A, and 5B.

In other embodiments, the heme enzyme variant has a higher total turnover number (TTN) compared to the wild-type sequence. In certain instances, the heme enzyme variant has a TTN greater than about 100.

In some instances, the heme enzyme variant produces a plurality of cyclopropanation products having a Z:E ratio of from 1:99 to 99:1. In some instances, the heme enzyme variant produces a plurality of cyclopropanation products having a % ee$_Z$ of at least −90% to at least 90%. In other instances, the heme enzyme variant produces a plurality of cyclopropanation products having a % ee$_E$ of at least −90% to at least 90%. In some instances, the heme enzyme variant produces a plurality of cyclopropanation products having at least 30% to at least 90% diasteroselectivity. In other instances, the heme enzyme variant produces a plurality of cyclopropanation products having at least 30% to at least 90% enantioselectivity. In yet other instances, the heme enzyme variant is in lyophilized form.

In further aspects, the present invention provides a cell expressing a heme enzyme described herein. In certain embodiments, the cell is a bacterial cell or a yeast cell.

In yet other aspects, the present invention provides an expression vector comprising a nucleic acid sequence encoding a heme enzyme described herein. In related aspects, the present invention provides a cell comprising the expression vector. In certain embodiments, the cell is a bacterial cell or a yeast cell.

Other objects, features, and advantages of the present invention will be apparent to one of skill in the art from the following detailed description and figures.

BRIEF DESCRIPTION OF THE DRAWINGS

FIG. 1 illustrates the canonical mode of reactivity of cytochrome P450s. (Left): monooxygenation of olefins and C—H bonds to epoxides and alcohols catalyzed by the ferryl porphyrin radical intermediate (Compound I). (Right): Artificial mode of formal carbene transfer activity of cytochrome P450s utilizing diazoester reagents as carbene precursors.

FIG. 3 illustrates the effect of styrene concentration on cyclopropane yield.

FIG. 4 illustrates the effect of P450 (H2A10) concentration on cyclopropane yield.

FIGS. 5A-B illustrate the initial velocities plot for variant 9-10A-TS-F87V-T268A (C3C)$_{heme}$. (FIG. 5A) EDA concentration was varied at a saturating concentration of styrene (30 mM). (FIG. 5B) Styrene concentration was varied at a fixed concentration of EDA (20 mM). Initial rates were computed as the slope of a zero-intercept linear fit of three different time points from independent reactions. Error bars correspond to 1-σ (68.3%) confidence intervals for the slope.

FIGS. 8A-B illustrate the initial velocities plot for BM3-CIS-C400S (also called ABC-CIS or P411BM3-CIS)$_{heme}$. (FIG. 8A) EDA concentration was varied at a saturating concentration of styrene (30 mM). (FIG. 8B) Styrene concentration was varied at a fixed concentration of EDA (20 mM). Initial rates were computed as the slope of a zero-intercept linear fit of three different time points from independent reactions. Error bars correspond to 1-σ (68.3%) confidence intervals for the slope.

FIG. 13 illustrates that increasing ABC catalyst loading (cell density) increases cyclopropanes yield up to approximately 80% at $OD_{600}$~50. ABC (BM3-C400S or $P411_{BM3}$).

FIG. 15 illustrates controls for ABC catalyzed cyclopropanation. Variant 9-10A-TS-F87V-T268A=BM3-CIS and ABC=BM3-C400S.

(FIG. 17A) Diazo-compounds that can be used as the carbenoid precursor. (FIG. 17B) Olefin partners for reaction. (FIG. 17C) Cyclopropanation of geranyl acetone for synthesis of anthroplalone and noranthroplone. (FIG. 17D) Cyclopropanation of 2,5-dimethylhexa-2,4-diene in the synthesis of pyrethroid insecticides.

(FIG. 19B) Close-up of the ABC-CIS active site (PDB: 4H24) superimposed with an $F_o$-$F_c$ simulated annealing omit map contoured at 3 σ showing electron density (green mesh) corresponding to the bound heme and C400S mutation. Interconnected density between C400S and the heme iron is consistent with proximal heme ligation by the C400S side chain hydroxyl. The heme, C400S and additional active site amino acid side chains are shown as sticks. (FIG. 19C) Potentiometric redox titrations for BM3 (green circles) and ABC (blue triangles) with overlaid one-electron Nernst curves. Insets show spectral changes between ferric (dashed line) and ferrous (solid line) states. The changes in absorbance near 450-470 nm (BM3) and 420-440 (ABC) were used to determine the $Fe^{II}/Fe^{III}$ ratio after reduction with dithionite. The reduction is reversible, and reoxidation by potassium ferricyanide shows little or no hysteresis. The midpoint potential of the serine-ligated mutant (−293 mV) is shifted 127 mV positive compared to WT (−420 mV).

(FIG. 20A) Stereo image of heme bound to $P411_{BM3}$-CIS viewed from the top of the heme in the active site. (FIG. 20B) Stereo image of heme bound to $P411_{BM3}$-CIS rotated ~90° from panel A shows clear indication of heme-iron ligation by the side chain hydroxyl of C400S. All atoms are shown as sticks. All electron density maps were contoured at σ=1.0. For perspective, in panel B, the main chain atoms of residues 399 and 401 are also shown as sticks.

FIGS. 23A-B illustrate the difference spectra for ferrous carbonyl with respect to ferrous for: (FIG. 23A) ABC-$CIS_{heme}$ and (FIG. 23B) ABC-$CIS_{holo}$.

FIG. 28 illustrates the cyclopropanation activity under anaerobic vs. aerobic conditions with dithionite in variant 9-10A-TS-F87V-T268A (also called BM3-CIS or $P450_{BM3-heme}$-CIS) and BM3-CIS-C400S (also called ABC-CIS or $P411_{BM3-heme}$-CIS). Measurements were taken in triplicate and the error bars represent the standard deviation of the measurements.

FIG. 31 illustrates the effect of dioxygen exposure on whole-cell catalyzed cyclopropanation. ABC-CIS (P411$_{BM3}$-CIS) is strongly inhibited by dioxygen in vivo. All reactions had a cell density equivalent to OD$_{600}$=25. Reactions were conducted in the absence of exogenous glucose. Measurements were taken in triplicate and the error bars represent the standard deviation from the mean value. Product formation is defined as the amount of cyclopropane product (mmol) formed per mass of catalyst (g$_{cdw}$).

FIG. 32 illustrates the empty plasmid, no-induction controls and dithionite addition to whole cells. E. coli cells carrying the ABC-CIS (P411$_{BM3}$-CIS) gene but grown without the addition of IPTG (ABC-CIS no induction); E. coli cells carrying the pcWori plasmid but not the ABC-CIS gene (empty pcWori); ABC-CIS reaction with the addition of exogenous dithionite instead of glucose (ABC-CIS+dithionite). Reactions were left for two hours at 298 K. Measurements were taken in triplicate and the error bars represent the standard deviation from the mean value. Product formation is defined as the amount of cyclopropane product (mmol) formed per mass of catalyst (g$_{cdw}$).

FIG. 33 illustrates that increasing cell density increases cyclopropane yields up ~80%. Total turnovers do not increase for cell densities higher than OD$_{600}$=20. Measurements were taken in triplicate and the error bars represent the standard deviation from the mean value. Product formation is defined as the amount of cyclopropane product (mmol) formed per mass of catalyst (g$_{cdw}$).

FIGS. 35A-C illustrate the contrasting P450- and P411-mediated cyclopropanation. (FIG. 35A) Cytochrome P450s inefficiently catalyze cyclopropanation using NAD(P)H as a reductant because the Fe$^{III}$/Fe$^{II}$ redox potential for the low-spin resting state (E°'$_{Fe-cys}$=−430 mV) is lower than that of NAD(P)$^+$/NAD(P)H (E°'$_1$=−320 mV, right). Mutation of the heme-ligating Cys to Ser allows NAD(P)H-driven cyclopropanation while removing native monooxygenation (left). (FIG. 35B) Close-up of the P411$_{BM3-heme}$-CIS active site (PDB: 4H24) superimposed with an F$_o$-F$_c$ simulated annealing omit map contoured at 3 σ showing electron density (green mesh) corresponding to the bound heme and C400S mutation. Heme, C400S and additional active site amino acid side chains are shown as sticks. (FIG. 35C) In vitro cyclopropanation vs. epoxidation of styrene catalyzed by P450$_{BM3}$-CIS and P411$_{BM3}$-CIS under anaerobic and aerobic conditions. Reaction conditions were as follows: 30 mM styrene, 10 mM EDA, 0.5 mM NADPH, 25 mM glucose, 2 U ml$^{-1}$ glucose dehydrogenase and 20 μg enzyme in aqueous potassium phosphate buffer and 5% MeOH cosolvent for six hours at 25° C. Error bars represent the standard deviation of three independent measurements.

FIGS. 36A-C illustrate the racemic synthesis of milnacipran. (FIG. 36A) Synthesis of key intermediate 1. (FIG. 36B) Routes A-C for conversion of 1 to milnacipran. (FIG. 36C) Route to milnacipran based on selective deprotonation of 5.

FIGS. 37A-B illustrate the enantioselective synthesis of levomilnacipran using (FIG. 37A) Rh-catalyzed intramolecular cyclopropanation or (FIG. 37B) asymmetric alkylation using tetraamine chiral auxiliary.

FIG. 43 illustrates a GC-MS ion chromatogram (m=123) showing the two chrysanthemate diastereomers produced by BM3-T268A-C400S. Top insert shows the fragmentation pattern for ethyl chrysanthemate that gives rise to the molecular ion with m=123. Oven temperature: 90° C. for 2 min, then 2° C./min to 110° C., then 30° C./min to 230° C. HP-5 column (Agilent) 30 m×0.32 mm×0.25 μm.

FIG. 45A shows the sequence alignment between cytochrome P450 BM3 (SEQ ID NO:76) and CYP2D7 (SEQ ID NO:75). The C400 axial ligand in P450 BM3 corresponds to C461 in CYP2D7. FIG. 45B shows the sequence alignment between cytochrome P450 BM3 (SEQ ID NO:78) and P450C27 (SEQ ID NO:77). The C400 axial ligand in P450 BM3 corresponds to C478 in P450C27.

DETAILED DESCRIPTION OF THE INVENTION

I. Introduction

Figure 2:
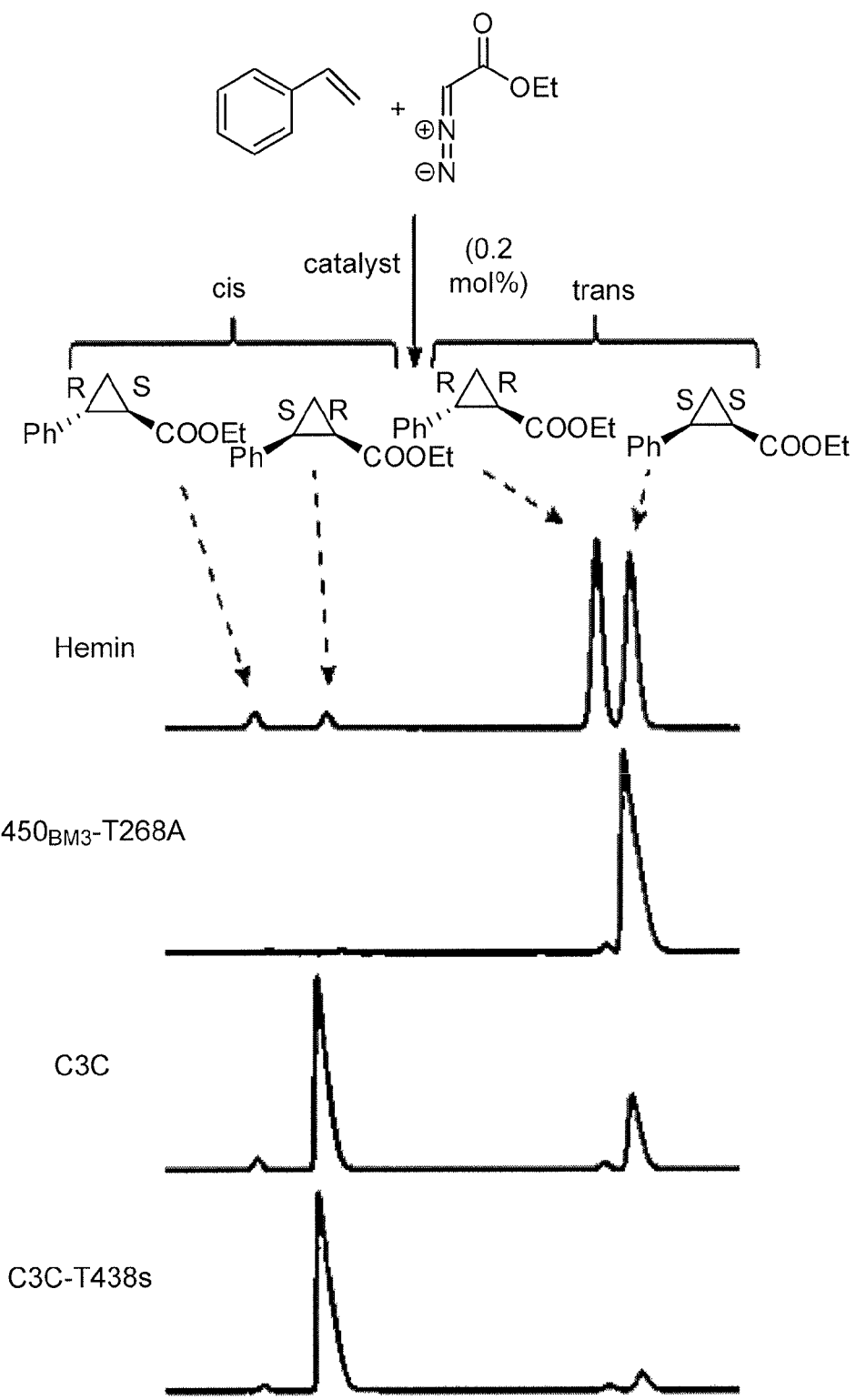
FIG. 2 illustrates the absolute stereoselectivity of select P450$_{BM3}$ cyclopropanation catalysts. Reaction conditions: 20 μM catalyst, 30 mM styrene, 10 mM EDA, 10 mM Na$_2$S$_2$O$_4$, under argon in aqueous potassium phosphate buffer (pH 8.0) and 5% MeOH cosolvent for 2 hours at 298 K. Enzyme loading is 0.2 mol % with respect to EDA. The structures of each product stereoisomer are shown above the reaction gas chromatograms.

The present invention is based on the surprising discovery that heme enzymes can be used to catalyze the conversion of olefins to any product containing one or more cyclopropane functional groups. In some aspects, cytochrome P450 enzymes (e.g., P450 BM3 (CYP102A1)) and variants thereof were identified as having an unexpectedly improved ability to catalyze the formal transfer of carbene equivalents from diazo reagents to various olefinic substrates, thereby making cyclopropane products with high regioselectivity and/or stereoselectivity. In particular embodiments, the present inventors have discovered that variants of P450$_{BM3}$ with at least one or more amino acid mutations such as an axial ligand C400X (e.g., C400S) and/or an T268A amino acid substitution can catalyze cyclopropanation reactions efficiently, displaying increased total turnover numbers (TTN) and demonstrating highly regio- and enantioselective product formation compared to wild-type enzymes.

As a non-limiting example, axial serine heme ligation (C400S in BM3) in cytochrome P450s creates the homologous "cytochrome P411" family, which catalyze the cyclopropanation reaction in vivo in whole cells, providing over 10,000 total turnovers with high stereoselectivity, optical purity and yield, making the cyclopropane product with titers of over 20 g L$^{-1}$. Thus, the cytochrome P411 family is spectroscopically, electrochemically, and catalytically distinct from cytochrome P450s, providing a scaffold for engineering orthogonal heme-enzyme catalysis. As such, the ability to catalyze this non-natural C—C bond forming reaction in vivo advantageously expands the scope of transformations that are accessible to microbial organic synthesis and provides artificial metabolic pathways to complement nature's existing strategies for making cyclopropanes.

II. Definitions

The following definitions and abbreviations are to be used for the interpretation of the invention. The term "invention" or "present invention" as used herein is a non-limiting term and is not intended to refer to any single embodiment but encompasses all possible embodiments.

As used herein, the terms "comprises," "comprising," "includes," "including," "has," "having", "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The term "cyclopropanation (enzyme) catalyst" or "enzyme with cyclopropanation activity" refers to any and all chemical processes catalyzed by enzymes, by which substrates containing at least one carbon-carbon double bond can be converted into cyclopropane products by using diazo reagents as carbene precursors.

The terms "engineered heme enzyme" and "heme enzyme variant" include any heme-containing enzyme comprising at least one amino acid mutation with respect to wild-type and also include any chimeric protein comprising recombined sequences or blocks of amino acids from two, three, or more different heme-containing enzymes.

The terms "engineered cytochrome P450" and "cytochrome P450 variant" include any cytochrome P450 enzyme comprising at least one amino acid mutation with respect to wild-type and also include any chimeric protein comprising recombined sequences or blocks of amino acids from two, three, or more different cytochrome P450 enzymes.

The term "whole cell catalyst" includes microbial cells expressing heme-containing enzymes, wherein the whole cell catalyst displays cyclopropanation activity.

As used herein, the terms "porphyrin" and "metal-substituted porphyrins" include any porphyrin that can be bound by a heme enzyme or variant thereof. In particular embodiments, these porphyrins may contain metals including, but not limited to, Fe, Mn, Co, Cu, Rh, and Ru.

The terms "carbene equivalent" and "carbene precursor" include molecules that can be decomposed in the presence of metal (or enzyme) catalysts to structures that contain at least one divalent carbon with only 6 valence shell electrons and that can be transferred to C═C bonds to form cyclopropanes or to C—H or heteroatom-H bonds to form various carbon ligated products.

The terms "carbene transfer" and "foimal carbene transfer" as used herein include any chemical transformation where carbene equivalents are added to C═C bonds, carbon-heteroatom double bonds or inserted into C—H or heteroatom-H substrates.

As used herein, the terms "microbial," "microbial organism" and "microorganism" include any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. Also included are cell cultures of any species that can be cultured for the production of a chemical.

As used herein, the term "non-naturally occurring", when used in reference to a microbial organism or enzyme activity of the invention, is intended to mean that the microbial organism or enzyme has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary non-naturally occurring microbial organism or enzyme activity includes the cyclopropanation activity described above.

As used herein, the term "anaerobic", when used in reference to a reaction, culture or growth condition, is intended to mean that the concentration of oxygen is less than about 25 μM, preferably less than about 5 μM, and even more preferably less than 1 μM. The term is also intended to include sealed chambers of liquid or solid medium maintained with an atmosphere of less than about 1% oxygen. Preferably, anaerobic conditions are achieved by sparging a reaction mixture with an inert gas such as nitrogen or argon.

As used herein, the term "exogenous" is intended to mean that the referenced molecule or the referenced activity is introduced into the host microbial organism. The term as it is used in reference to expression of an encoding nucleic acid refers to the introduction of the encoding nucleic acid in an expressible form into the microbial organism. When used in reference to a biosynthetic activity, the term refers to an activity that is introduced into the host reference organism.

The term "heterologous" as used herein with reference to molecules, and in particular enzymes and polynucleotides, indicates molecules that are expressed in an organism other than the organism from which they originated or are found in nature, independently of the level of expression that can be lower, equal or higher than the level of expression of the molecule in the native microorganism.

On the other hand, the term "native" or "endogenous" as used herein with reference to molecules, and in particular enzymes and polynucleotides, indicates molecules that are expressed in the organism in which they originated or are found in nature, independently of the level of expression that can be lower equal or higher than the level of expression of the molecule in the native microorganism. It is understood that expression of native enzymes or polynucleotides may be modified in recombinant microorganisms.

The term "homolog," as used herein with respect to an original enzyme or gene of a first family or species, refers to distinct enzymes or genes of a second family or species which are determined by functional, structural or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In particular embodiments, the homology between two proteins is indicative of its shared ancestry, related by evolution.

The terms "analog" and "analogous" include nucleic acid or protein sequences or protein structures that are related to one another in function only and are not from common descent or do not share a common ancestral sequence. Analogs may differ in sequence but may share a similar structure, due to convergent evolution. For example, two enzymes are analogs or analogous if the enzymes catalyze the same reaction of conversion of a substrate to a product, are unrelated in sequence, and irrespective of whether the two enzymes are related in structure.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can refer to alkyl groups having up to 20 carbons atoms, such as, but not limited to heptyl, octyl, nonyl, decyl, etc. Alkyl groups can be optionally substituted with one or more moieties selected from halo, hydroxy, amino, alkylamino, alkoxy, haloalkyl, carboxy, amido, nitro, oxo, and cyano.

As used herein, the term "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl(ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be optionally substituted with one or more moieties selected from halo, hydroxy, amino, alkylamino, alkoxy, haloalkyl, carboxy, amido, nitro, oxo, and cyano.

As used herein, the term "alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be optionally substituted with one or more moieties selected from halo, hydroxy, amino, alkylamino, alkoxy, haloalkyl, carboxy, amido, nitro, oxo, and cyano.

As used herein, the term "aryl" refers to an aromatic carbon ring system having any suitable number of ring atoms and any suitable number of rings. Aryl groups can include any suitable number of carbon ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be optionally substituted with one or more moieties selected from halo, hydroxy, amino, alkylamino, alkoxy, haloalkyl, carboxy, amido, nitro, oxo, and cyano.

As used herein, the term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, and $C_{6-8}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. Cycloalkyl groups can be optionally substituted with one or more moieties selected from halo, hydroxy, amino, alkylamino, alkoxy, haloalkyl, carboxy, amido, nitro, oxo, and cyano.

As used herein, the term "heterocyclyl" refers to a saturated ring system having from 3 to 12 ring members and from 1 to 4 heteroatoms selected from N, O and S. Additional heteroatoms including, but not limited to, B, Al, Si and P can also be present in a heterocycloalkyl group. The heteroatoms can be oxidized to form moieties such as, but not limited to, —S(O)— and —S(O)$_2$—. Heterocyclyl groups can include any number of ring atoms, such as, 3 to 6, 4 to 6, 5 to 6, 4 to 6, or 4 to 7 ring members. Any suitable number of heteroatoms can be included in the heterocyclyl groups, such as 1, 2, 3, or 4, or 1 to 2, 1 to 3, 1 to 4, 2 to 3, 2 to 4, or 3 to 4. Examples of heterocyclyl groups include, but are not limited to, aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. Heterocyclyl groups can be optionally substituted with one or more moieties selected from halo, hydroxy, amino, alkylamino, alkoxy, haloalkyl, carboxy, amido, nitro, oxo, and cyano.

As used herein, the term "heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms including, but not limited to, B, Al, Si and P can also be present in a heteroaryl group. The heteroatoms can be oxidized to form moieties such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. Examples of heteroaryl groups include, but are not limited to, pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. Heteroaryl groups can be optionally substituted with one or more moieties selected from halo, hydroxy, amino, alkylamino, alkoxy, haloalkyl, carboxy, amido, nitro, oxo, and cyano.

As used herein, the term "alkoxy" refers to an alkyl group having an oxygen atom that connects the alkyl group to the point of attachment: i.e., alkyl-O—. As for alkyl group, alkoxy groups can have any suitable number of carbon atoms, such as $C_{1-6}$ or $C_{1-4}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. Alkoxy groups can be optionally substituted with one or more moieties selected from halo, hydroxy, amino, alkylamino, alkoxy, haloalkyl, carboxy, amido, nitro, oxo, and cyano.

As used herein, the term "alkylthio" refers to an alkyl group having a sulfur atom that connects the alkyl group to the point of attachment: i.e., alkyl-S—. As for alkyl groups, alkylthio groups can have any suitable number of carbon atoms, such as $C_{1-6}$ or $C_{1-4}$. Alkylthio groups include, for example, methoxy, ethoxy, propoxy, iso-propoxy, butoxy, 2-butoxy, iso-butoxy, sec-butoxy, tert-butoxy, pentoxy, hexoxy, etc. Alkylthio groups can be optionally substituted with one or more moieties selected from halo, hydroxy, amino, alkylamino, alkoxy, haloalkyl, carboxy, amido, nitro, oxo, and cyano.

As used herein, the terms "halo" and "halogen" refer to fluorine, chlorine, bromine and iodine.

As used herein, the term "haloalkyl" refers to an alkyl moiety as defined above substituted with at least one halogen atom.

As used herein, the term "alkylsilyl" refers to a moiety —SiR$_3$, wherein at least one R group is alkyl and the other R groups are H or alkyl. The alkyl groups can be substituted with one more halogen atoms.

As used herein, the term "acyl" refers to a moiety —C(O)R, wherein R is an alkyl group.

As used herein, the term "oxo" refers to an oxygen atom that is double-bonded to a compound (i.e., O=).

As used herein, the term "carboxy" refers to a moiety —C(O)OH. The carboxy moiety can be ionized to form the carboxylate anion.

As used herein, the term "amino" refers to a moiety —NR$_3$, wherein each R group is H or alkyl.

As used herein, the term "amido" refers to a moiety —NRC(O)R or —C(O)NR$_2$, wherein each R group is H or alkyl.

III. Description of the Embodiments

In some aspects, the present invention provides methods for catalyzing the conversion of an olefin to any compound (e.g., any intermediate or final compound) containing one or more cyclopropane functional groups using heme enzymes. In certain aspects, the present invention provides a method for producing a cyclopropanation product, the method comprising:

(a) providing an olefinic substrate, a diazo reagent, and a heme enzyme; and (b) admixing the components of step (a) in a reaction for a time sufficient to produce a cyclopropanation product.

In certain instances, the cyclopropanation product is produced via an intermolecular cyclopropanation reaction between the olefinic substrate and diazo reagent as separate distinct substrates. In other instances, the cyclopropanation product is produced via an intramolecular cyclopropanation reaction, e.g., wherein the olefinic substrate and diazo reagent are part of the same substrate.

The methods of the invention can be used to provide a vast number of cyclopropanation products. The cyclopropanation products include classes of compounds such as, but not limited to, insecticides (e.g., pyrethroid compounds), active pharmaceutical agents having chiral and/or achiral cyclopropane moieties (e.g., milnacipran, levomilnacipran, and other active ingredients such as antibiotics, antivirals, etc.), commodity and fine chemicals, plant hormones, flavors and scents, and fatty acids. The cyclopropanation products can also serve as intermediates for the synthesis of compounds belonging to these and other classes (e.g., chrysanthemate esters for the synthesis of pyrethroid compounds).

In other aspects, the present invention provides heme enzymes including variants and fragments thereof (e.g., truncated forms) as well as chimeric heme enzymes that are capable of carrying out the cyclopropanation reactions described herein. Expression vectors and host cells expressing the heme enzymes are also provided by the present invention.

The following sections provide a description of exemplary and preferred embodiments including heme enzymes, expression vectors, host cells, cyclopropanation products such as, e.g., compounds comprising one or more cyclopropane functional groups, starting materials such as, e.g., olefinic substrates and diazo reagents, and characteristics and reaction conditions for the in vitro and in vivo cyclopropanation reactions described herein.

A. Heme Enzymes

In certain aspects, the present invention provides compositions comprising one or more heme enzymes that catalyze the conversion of an olefinic substrate to products containing one or more cyclopropane functional groups. In particular embodiments, the present invention provides heme enzyme variants comprising at least one or more amino acid mutations therein that catalyze the formal transfer of carbene equivalents from a diazo reagent (e.g., a diazo ester) to an olefinic substrate, making cyclopropane products with high stereoselectivity. In preferred embodiments, the heme enzyme variants of the present invention have the ability to catalyze cyclopropanation reactions efficiently, display increased total turnover numbers, and/or demonstrate highly regio- and/or enantioselective product formation compared to the corresponding wild-type enzymes.

The terms "heme enzyme" and "heme protein" are used herein to include any member of a group of proteins containing heme as a prosthetic group. Non-limiting examples of heme enzymes include globins, cytochromes, oxidoreductases, any other protein containing a heme as a prosthetic group, and combinations thereof. Heme-containing globins include, but are not limited to, hemoglobin, myoglobin, and combinations thereof. Heme-containing cytochromes include, but are not limited to, cytochrome P450, cytochrome b, cytochrome c1, cytochrome c, and combinations thereof. Heme-containing oxidoreductases include, but are not limited to, a catalase, an oxidase, an oxygenase, a haloperoxidase, a peroxidase, and combinations thereof.

In certain instances, the heme enzymes are metal-substituted heme enzymes containing protoporphyrin 1× or other porphyrin molecules containing metals other than iron, including, but not limited to, cobalt, rhodium, copper, ruthenium, and manganese, which are active cyclopropanation catalysts.

In some embodiments, the heme enzyme is a member of one of the enzyme classes set forth in Table 1. In other embodiments, the heme enzyme is a variant or homolog of a member of one of the enzyme classes set forth in Table 1. In yet other embodiments, the heme enzyme comprises or consists of the heme domain of a member of one of the enzyme classes set forth in Table 1 or a fragment thereof (e.g., a truncated heme domain) that is capable of carrying out the cyclopropanation reactions described herein.

TABLE 1

Heme enzymes identified by their enzyme classification number (EC number) and classification name.

| EC Number | Name |
| --- | --- |
| 1.1.2.3 | L-lactate dehydrogenase |
| 1.1.2.6 | polyvinyl alcohol dehydrogenase (cytochrome) |
| 1.1.2.7 | methanol dehydrogenase (cytochrome c) |
| 1.1.5.5 | alcohol dehydrogenase (quinone) |
| 1.1.5.6 | formate dehydrogenase-N: |
| 1.1.9.1 | alcohol dehydrogenase (azurin): |
| 1.1.99.3 | gluconate 2-dehydrogenase (acceptor) |
| 1.1.99.11 | fructose 5-dehydrogenase |
| 1.1.99.18 | cellobiose dehydrogenase (acceptor) |
| 1.1.99.20 | alkan-1-ol dehydrogenase (acceptor) |
| 1.2.1.70 | glutamyl-tRNA reductase |
| 1.2.3.7 | indole-3-acetaldehyde oxidase |
| 1.2.99.3 | aldehyde dehydrogenase (pyrroloquinoline-quinone) |
| 1.3.1.6 | fumarate reductase (NADH): |
| 1.3.5.1 | succinate dehydrogenase (ubiquinone) |
| 1.3.5.4 | fumarate reductase (menaquinone) |
| 1.3.99.1 | succinate dehydrogenase |
| 1.4.9.1 | methylamine dehydrogenase (amicyanin) |
| 1.4.9.2. | aralkylamine dehydrogenase (azurin) |
| 1.5.1.20 | methylenetetrahydrofolate reductase [NAD(P)H] |
| 1.5.99.6 | spermidine dehydrogenase |
| 1.6.3.1 | NAD(P)H oxidase |
| 1.7.1.1 | nitrate reductase (NADH) |
| 1.7.1.2 | Nitrate reductase [NAD(P)H] |
| 1.7.1.3 | nitrate reductase (NADPH) |
| 1.7.1.4 | nitrite reductase [NAD(P)H] |
| 1.7.1.14 | nitric oxide reductase [NAD(P), nitrous oxide-forming] |
| 1.7.2.1 | nitrite reductase (NO-forming) |
| 1.7.2.2 | nitrite reductase (cytochrome; ammonia-forming) |
| 1.7.2.3 | trimethylamine-N-oxide reductase (cytochrome c) |
| 1.7.2.5 | nitric oxide reductase (cytochrome c) |
| 1.7.2.6 | hydroxylamine dehydrogenase |
| 1.7.3.6 | hydroxylamine oxidase (cytochrome) |
| 1.7.5.1 | nitrate reductase (quinone) |

TABLE 1-continued

Heme enzymes identified by their enzyme classification number (EC number) and classification name.

| EC Number | Name |
| --- | --- |
| 1.7.5.2 | nitric oxide reductase (menaquinol) |
| 1.7.6.1 | nitrite dismutase |
| 1.7.7.1 | ferredoxin-nitrite reductase |
| 1.7.7.2 | ferredoxin-nitrate reductase |
| 1.7.99.4 | nitrate reductase |
| 1.7.99.8 | hydrazine oxidoreductase |
| 1.8.1.2 | sulfite reductase (NADPH) |
| 1.8.2.1 | sulfite dehydrogenase |
| 1.8.2.2 | thiosulfate dehydrogenase |
| 1.8.2.3 | sulfide-cytochrome-c reductase (flavocytochrome c) |
| 1.8.2.4 | dimethyl sulfide:cytochrome c2 reductase |
| 1.8.3.1 | sulfite oxidase |
| 1.8.7.1 | sulfite reductase (ferredoxin) |
| 1.8.98.1 | CoB-CoM heterodisulfide reductase |
| 1.8.99.1 | sulfite reductase |
| 1.8.99.2 | adenylyl-sulfate reductase |
| 1.8.99.3 | hydrogensulfite reductase |
| 1.9.3.1 | cytochrome-c oxidase |
| 1.9.6.1 | nitrate reductase (cytochrome) |
| 1.10.2.2 | ubiquinol-cytochrome-c reductase |
| 1.10.3.1 | catechol oxidase |
| 1.10.3.B1 | caldariellaquinol oxidase (H+-transporting) |
| 1.10.3.3 | L-ascorbate oxidase |
| 1.10.3.9 | photosystem II |
| 1.10.3.10 | ubiquinol oxidase (H+-transporting) |
| 1.10.3.11 | ubiquinol oxidase |
| 1.10.3.12 | menaquinol oxidase (H+-transporting) |
| 1.10.9.1 | plastoquinol-plastocyanin reductase |
| 1.11.1.5 | cytochrome-c peroxidase |
| 1.11.1.6 | catalase |
| 1.11.1.7 | peroxidase |
| 1.11.1.B2 | chloride peroxidase (vanadium-containing) |
| 1.11.1.B7 | bromide peroxidase (heme-containing) |
| 1.11.1.8 | iodide peroxidase |
| 1.11.1.10 | chloride peroxidase |
| 1.11.1.11 | L-ascorbate peroxidase |
| 1.11.1.13 | manganese peroxidase |
| 1.11.1.14 | lignin peroxidase |
| 1.11.1.16 | versatile peroxidase |
| 1.11.1.19 | dye decolorizing peroxidase |
| 1.11.1.21 | catalase-peroxidase |
| 1.11.2.1 | unspecific peroxygenase |
| 1.11.2.2 | myeloperoxidase |
| 1.11.2.3 | plant seed peroxygenase |
| 1.11.2.4 | fatty-acid peroxygenase |
| 1.12.2.1 | cytochrome-c3 hydrogenase |
| 1.12.5.1 | hydrogen:quinone oxidoreductase |
| 1.12.99.6 | hydrogenase (acceptor) |
| 1.13.11.9 | 2,5-dihydroxypyridine 5,6-dioxygenase |
| 1.13.11.11 | tryptophan 2,3-dioxygenase |
| 1.13.11.49 | chlorite O2-lyase |
| 1.13.11.50 | acetylacetone-cleaving enzyme |
| 1.13.11.52 | indoleamine 2,3-dioxygenase |
| 1.13.11.60 | linoleate 8R-lipoxygenase |
| 1.13.99.3 | tryptophan 2'-dioxygenase |
| 1.14.11.9 | flavanone 3-dioxygenase |
| 1.14.12.17 | nitric oxide dioxygenase |
| 1.14.13.39 | nitric-oxide synthase (NADPH dependent) |
| 1.14.13.17 | cholesterol 7alpha-monooxygenase |
| 1.14.13.41 | tyrosine N-monooxygenase |
| 1.14.13.70 | sterol 14alpha-demethylase |
| 1.14.13.71 | N-methylcoclaurine 3'-monooxygenase |
| 1.14.13.81 | magnesium-protoporphyrin IX monomethyl ester (oxidative) cyclase |
| 1.14.13.86 | 2-hydroxyisoflavanone synthase |
| 1.14.13.98 | cholesterol 24-hydroxylase |
| 1.14.13.119 | 5-epiaristolochene 1,3-dihydroxylase |
| 1.14.13.126 | vitamin D3 24-hydroxylase |
| 1.14.13.129 | beta-carotene 3-hydroxylase |
| 1.14.13.141 | cholest-4-en-3-one 26-monooxygenase |
| 1.14.13.142 | 3-ketosteroid 9alpha-monooxygenase |
| 1.14.13.151 | linalool 8-monooxygenase |
| 1.14.13.156 | 1,8-cineole 2-endo-monooxygenase |
| 1.14.13.159 | vitamin D 25-hydroxylase |
| 1.14.14.1 | unspecific monooxygenase |

TABLE 1-continued

Heme enzymes identified by their enzyme classification number (EC number) and classification name.

| EC Number | Name |
|---|---|
| 1.14.15.1 | camphor 5-monooxygenase |
| 1.14.15.6 | cholesterol monooxygenase (side-chain-cleaving) |
| 1.14.15.8 | steroid 15beta-monooxygenase |
| 1.14.15.9 | spheroidene monooxygenase |
| 1.14.18.1 | tyrosinase |
| 1.14.19.1 | stearoyl-CoA 9-desaturase |
| 1.14.19.3 | linoleoyl-CoA desaturase |
| 1.14.21.7 | biflaviolin synthase |
| 1.14.99.1 | prostaglandin-endoperoxide synthase |
| 1.14.99.3 | heme oxygenase |
| 1.14.99.9 | steroid 17alpha-monooxygenase |
| 1.14.99.10 | steroid 21-monooxygenase |
| 1.14.99.15 | 4-methoxybenzoate monooxygenase (O-demethylating) |
| 1.14.99.45 | carotene epsilon-monooxygenase |
| 1.16.5.1 | ascorbate ferrireductase (transmembrane) |
| 1.16.9.1 | iron:rusticyanin reductase |
| 1.17.1.4 | xanthine dehydrogenase |
| 1.17.2.2 | lupanine 17-hydroxylase (cytochrome c) |
| 1.17.99.1 | 4-methylphenol dehydrogenase (hydroxylating) |
| 1.17.99.2 | ethylbenzene hydroxylase |
| 1.97.1.1 | chlorate reductase |
| 1.97.1.9 | selenate reductase |
| 2.7.7.65 | diguanylate cyclase |
| 2.7.13.3 | histidine kinase |
| 3.1.4.52 | cyclic-guanylate-specific phosphodiesterase |
| 4.2.1.B9 | colneleic acid/etheroleic acid synthase |
| 4.2.1.22 | Cystathionine beta-synthase |
| 4.2.1.92 | hydroperoxide dehydratase |
| 4.2.1.212 | colneleate synthase |
| 4.3.1.26 | chromopyrrolate synthase |
| 4.6.1.2 | guanylate cyclase |
| 4.99.1.3 | sirohydrochlorin cobaltochelatase |
| 4.99.1.5 | aliphatic aldoxime dehydratase |
| 4.99.1.7 | phenylacetaldoxime dehydratase |
| 5.3.99.3 | prostaglandin-E synthase |
| 5.3.99.4 | prostaglandin-I synthase |
| 5.3.99.5 | Thromboxane-A synthase |
| 5.4.4.5 | 9,12-octadecadienoate 8-hydroperoxide 8R-isomerase |
| 5.4.4.6 | 9,12-octadecadienoate 8-hydroperoxide 8S-isomerase |
| 6.6.1.2 | cobaltochelatase |

In particular embodiments, the heme enzyme is a variant or a fragment thereof (e.g., a truncated variant containing the heme domain) comprising at least one mutation such as, e.g., a mutation at the axial position of the heme coordination site. In some instances, the mutation is a substitution of the native residue with Ala, Asp, Arg, Asn, Cys, Glu, Gln, Gly, His, Ile, Lys, Leu, Met, Phe, Pro, Ser, Thr, Trp, Tyr, or Val at the axial position. In certain instances, the mutation is a substitution of Cys with any other amino acid such as Ser at the axial position.

In certain embodiments, the in vitro methods for producing a cyclopropanation product comprise providing a heme enzyme, variant, or homolog thereof with a reducing agent such as NADPH or a dithionite salt (e.g., $Na_2S_2O_4$). In certain other embodiments, the in vivo methods for producing a cyclopropanation product comprise providing whole cells such as E. coli cells expressing a heme enzyme, variant, or homolog thereof.

In some embodiments, the heme enzyme, variant, or homolog thereof is recombinantly expressed and optionally isolated and/or purified for carrying out the in vitro cyclopropanation reactions of the present invention. In other embodiments, the heme enzyme, variant, or homolog thereof is expressed in whole cells such as E. coli cells, and these cells are used for carrying out the in vivo cyclopropanation reactions of the present invention.

In certain embodiments, the heme enzyme, variant, or homolog thereof comprises or consists of the same number of amino acid residues as the wild-type enzyme (e.g., a full-length polypeptide). In some instances, the heme enzyme, variant, or homolog thereof comprises or consists of an amino acid sequence without the start methionine (e.g., P450 BM3 amino acid sequence set forth in SEQ ID NO:1). In other embodiments, the heme enzyme comprises or consists of a heme domain fused to a reductase domain. In yet other embodiments, the heme enzyme does not contain a reductase domain, e.g., the heme enzyme contains a heme domain only or a fragment thereof such as a truncated heme domain.

In some embodiments, the heme enzyme, variant, or homolog thereof has an enhanced cyclopropanation activity of at least about 1.5, 2, 3, 4, 5, 6, 7, 8, 9, 10, 15, 20, 25, 30, 35, 40, 45, 50, 55, 60, 65, 70, 75, 80, 85, 90, 95, or 100 fold compared to the corresponding wild-type heme enzyme.

In some embodiments, the heme enzyme, variant, or homolog thereof has a resting state reduction potential higher than that of NADH or NADPH.

In particular embodiments, the heme enzyme comprises a cyclochrome P450 enzyme. Cytochrome P450 enzymes constitute a large superfamily of heme-thiolate proteins involved in the metabolism of a wide variety of both exogenous and endogenous compounds. Usually, they act as the terminal oxidase in multicomponent electron transfer chains, such as P450-containing monooxygenase systems. Members of the cytochrome P450 enzyme family catalyze myriad oxidative transformations, including, e.g., hydroxylation, epoxidation, oxidative ring coupling, heteratom release, and heteroatom oxygenation (E. M. Isin et al., *Biochim. Biophys. Acta* 1770, 314 (2007)). The active site of these enzymes contains an $Fe^{III}$-protoporphyrin IX cofactor (heme) ligated proximally by a conserved cysteine thiolate (M. T. Green, *Current Opinion in Chemical Biology* 13, 84 (2009)). The remaining axial iron coordination site is occupied by a water molecule in the resting enzyme, but during native catalysis, this site is capable of binding molecular oxygen. In the presence of an electron source, typically provided by NADH or NADPH from an adjacent fused reductase domain or an accessory cytochrome P450 reductase enzyme, the heme center of cytochrome P450 activates molecular oxygen, generating a high valent iron (IV)-oxo porphyrin cation radical species intermediate (Compound I, FIG. 1) and a molecule of water.

One skilled in the art will appreciate that the cytochrome P450 enzyme superfamily has been compiled in various databases, including, but not limited to, the P450 homepage (available at http://dmelson.uthsc.edu/CytochromeP450.html; see also, D. R. Nelson, *Hum. Genomics* 4, 59 (2009)), the cytochrome P450 enzyme engineering database (available at http://www.cyped.uni-stuttgart.de/cgi-bin/CYPED5/index.pl; see also, D. Sirim et al., *BMC Biochem* 10, 27 (2009)), and the SuperCyp database (available at http://bioinformatics.charite.de/supercyp/; see also, S. Preissner et al., *Nucleic Acids Res.* 38, D237 (2010)), the disclosures of which are incorporated herein by reference in their entirety for all purposes.

In certain embodiments, the cytochrome P450 enzymes of the invention are members of one of the classes shown in Table 2 (see, http://www.icgeb.org/~p450srv/P450enzymes.html, the disclosure of which is incorporated herein by reference in its entirety for all purposes).

TABLE 2

Cytochrome P450 enzymes classified by their EC number, recommended name, and family/gene name.

| EC | Recommended name | Family/gene |
| --- | --- | --- |
| 1.3.3.9 | secologanin synthase | CYP72A1 |
| 1.14.13.11 | trans-cinnamate 4-monooxygenase | CYP73 |
| 1.14.13.12 | benzoate 4-monooxygenase | CYP53 |
| 1.14.13.13 | calcidiol 1-monooxygenase | CYP27 |
| 1.14.13.15 | cholestanetriol 26-monooxygenase | CYP27 |
| 1.14.13.17 | cholesterol 7α-monooxygenase | CYP7 |
| 1.14.13.21 | flavonoid 3'-monooxygenase | CYP75 |
| 1.14.13.28 | 3,9-dihydroxypterocarpan 6a-monooxygenase | CYP93A1 |
| 1.14.13.30 | leukotriene-B$_4$ 20-monooxygenase | CYP4F |
| 1.14.13.37 | methyltetrahydroprotoberberine 14-monooxygenase | CYP93A1 |
| 1.14.13.41 | tyrosine N-monooxygenase | CYP79 |
| 1.14.13.42 | hydroxyphenylacetonitrile 2-monooxygenase | — |
| 1.14.13.47 | (−)-limonene 3-monooxygenase | — |
| 1.14.13.48 | (−)-limonene 6-monooxygenase | — |
| 1.14.13.49 | (−)-limonene 7-monooxygenase | — |
| 1.14.13.52 | isoflavone 3'-hydroxylase | — |
| 1.14.13.53 | isoflavone 2'-hydroxylase | — |
| 1.14.13.55 | protopine 6-monooxygenase | — |
| 1.14.13.56 | dihydrosanguinarine 10-monooxygenase | — |
| 1.14.13.57 | dihydrochelirubine 12-monooxygenase | — |
| 1.14.13.60 | 27-hydroxycholesterol 7α-monooxygenase | — |
| 1.14.13.70 | sterol 14-demethylase | CYP51 |
| 1.14.13.71 | N-methylcoclaurine 3'-monooxygenase | CYP80B1 |
| 1.14.13.73 | tabersonine 16-hydroxylase | CYP71D12 |
| 1.14.13.74 | 7-deoxyloganin 7-hydroxylase | — |
| 1.14.13.75 | vinorine hydroxylase | — |
| 1.14.13.76 | taxane 10β-hydroxylase | CYP725A1 |
| 1.14.13.77 | taxane 13α-hydroxylase | CYP725A2 |
| 1.14.13.78 | ent-kaurene oxidase | CYP701 |
| 1.14.13.79 | ent-kaurenoic acid oxidase | CYP88A |
| 1.14.14.1 | unspecific monooxygenase | multiple |
| 1.14.15.1 | camphor 5-monooxygenase | CYP101 |
| 1.14.15.3 | alkane 1-monooxygenase | CYP4A |
| 1.14.15.4 | steroid 1β-monooxygenase | CYP11B |
| 1.14.15.5 | corticosterone 18-monooxygenase | CYP11B |
| 1.14.15.6 | cholesterol monooxygenase (side-chain-cleaving) | CYP11A |
| 1.14.21.1 | (S)-stylopine synthase | — |
| 1.14.21.2 | (S)-cheilanthifoline synthase | — |
| 1.14.21.3 | berbamunine synthase | CYP80 |
| 1.14.21.4 | salutaridine synthase | — |
| 1.14.21.5 | (S)-canadine synthase | — |
| 1.14.99.9 | steroid 17α-monooxygenase | CYP17 |
| 1.14.99.10 | steroid 21-monooxygenase | CYP21 |
| 1.14.99.22 | ecdysone 20-monooxygenase | — |
| 1.14.99.28 | linalool 8-monooxygenase | CYP111 |
| 4.2.1.92 | hydroperoxide dehydratase | CYP74 |
| 5.3.99.4 | prostaglandin-I synthase | CYP8 |
| 5.3.99.5 | thromboxane-A synthase | CYP5 |

Table 3 below lists additional cyclochrome P450 enzymes that are suitable for use in the cyclopropanation reactions of the present invention. The accession numbers in Table 3 are incorporated herein by reference in their entirety for all purposes. The cytochrome P450 gene and/or protein sequences disclosed in the following patent documents are hereby incorporated by reference in their entirety for all purposes: WO 2013/076258; CN 103160521; CN 103223219; KR 2013081394; JP 5222410; WO 2013/073775; WO 2013/054890; WO 2013/048898; WO 2013/031975; WO 2013/064411; U.S. Pat. No. 8,361,769; WO 2012/150326, CN 102747053; CN 102747052; JP 2012170409; WO 2013/115484; CN 103223219; KR 2013081394; CN 103194461; JP 5222410; WO 2013/086499; WO 2013/076258; WO 2013/073775; WO 2013/064411; WO 2013/054890; WO 2013/031975; U.S. Pat. No. 8,361,769; WO 2012/156976; WO 2012/150326; CN 102747053; CN 102747052; US 20120258938; JP 2012170409; CN 102399796; JP 2012055274; WO 2012/029914; WO 2012/028709; WO 2011/154523; JP 2011234631; WO 2011/121456; EP 2366782; WO 2011/105241; CN 102154234; WO 2011/093185; WO 2011/093187; WO 2011/093186; DE 102010000168; CN 102115757; CN 102093984; CN 102080069; JP 2011103864; WO 2011/042143; WO 2011/038313; JP 2011055721; WO 2011/025203; JP 2011024534; WO 2011/008231; WO 2011/008232; WO 2011/005786; IN 2009DE01216; DE 102009025996; WO 2010/134096; JP 2010233523; JP 2010220609; WO 2010/095721; WO 2010/064764; US 20100136595; JP 2010051174; WO 2010/024437; WO 2010/011882; WO 2009/108388; US 20090209010; US 20090124515; WO 2009/041470; KR 2009028942; WO 2009/039487; WO 2009/020231; JP 2009005687; CN 101333520; CN 101333521; US 20080248545; JP 2008237110; CN 101275141; WO 2008/118545; WO 2008/115844; CN 101255408; CN 101250506; CN 101250505; WO 2008/098198; WO 2008/096695; WO 2008/071673; WO 2008/073498; WO 2008/065370; WO 2008/067070; JP 2008127301; JP 2008054644; KR 794395; EP 1881066; WO 2007/147827; CN 101078014; JP 2007300852; WO 2007/048235; WO 2007/044688; WO 2007/032540; CN 1900286; CN 1900285; JP 2006340611; WO 2006/126723; KR 2006029792; KR 2006029795; WO 2006/105082; WO 2006/076094; US 2006/0156430; WO 2006/065126; JP 2006129836; CN 1746293; WO 2006/029398; JP 2006034215; JP 2006034214; WO 2006/009334; WO 2005/111216; WO 2005/080572; US 2005/0150002; WO 2005/061699; WO 2005/052152; WO 2005/038033; WO 2005/038018; WO 2005/030944; JP 2005065618; WO 2005/017106; WO 2005/017105; US 20050037411; WO 2005/010166; JP 2005021106; JP 2005021104; JP 2005021105; WO 2004/113527; CN 1472323; JP 2004261121; WO 2004/013339; WO 2004/011648; DE 10234126; WO 2004/003190; WO 2003/087381; WO 2003/078577; US 20030170627; US 20030166176; US 20030150025; WO 2003/057830; WO 2003/052050; CN 1358756; US 20030092658; US 20030078404; US 20030066103; WO 2003/014341; US 20030022334; WO 2003/008563; EP 1270722; US 20020187538; WO 2002/092801; WO 2002/088341; US 20020160950; WO 2002/083868; US 20020142379; WO 2002/072758; WO 2002/064765; US 20020076777; US 20020076774; US 20020076774; WO 2002/046386; WO 2002/044213; US 20020061566; CN 1315335; WO 2002/034922; WO 2002/033057; WO 2002/029018; WO 2002/018558; JP 2002058490; US 20020022254; WO 2002/008269; WO 2001/098461; WO 2001/081585; WO 2001/051622; WO 2001/034780; CN 1271005; WO 2001/011071; WO 2001/007630; WO 2001/007574; WO 2000/078973; U.S. Pat. No. 6,130,077; JP 2000152788; WO 2000/031273; WO 2000/020566; WO 2000/000585; DE 19826821; JP 11235174; U.S. Pat. No. 5,939,318; WO 99/19493; WO 99/18224; U.S. Pat. No. 5,886,157; WO 99/08812; U.S. Pat. No. 5,869,283; JP 10262665; WO 98/40470; EP 776974; DE 19507546; GB 2294692; U.S. Pat. No. 5,516,674; JP 07147975; WO 94/29434; JP 06205685; JP 05292959; JP 04144680; DD 298820; EP 477961; SU 1693043; JP 01047375; EP 281245; JP 62104583; JP 63044888; JP 62236485; JP 62104582; and JP 62019084.

TABLE 3

Additional cytochrome P450 enzymes of the present invention.

| Species | Cyp No. | Accession No. | SEQ ID NO |
| --- | --- | --- | --- |
| Bacillus megaterium | 102A1 | AAA87602 | 1 |
| Bacillus megaterium | 102A1 | ADA57069 | 2 |
| Bacillus megaterium | 102A1 | ADA57068 | 3 |
| Bacillus megaterium | 102A1 | ADA57062 | 4 |
| Bacillus megaterium | 102A1 | ADA57061 | 5 |
| Bacillus megaterium | 102A1 | ADA57059 | 6 |

TABLE 3-continued

Additional cytochrome P450 enzymes of the present invention.

| Species | Cyp No. | Accession No. | SEQ ID NO |
|---|---|---|---|
| Bacillus megaterium | 102A1 | ADA57058 | 7 |
| Bacillus megaterium | 102A1 | ADA57055 | 8 |
| Bacillus megaterium | 102A1 | ACZ37122 | 9 |
| Bacillus megaterium | 102A1 | ADA57057 | 10 |
| Bacillus megaterium | 102A1 | ADA57056 | 11 |
| Mycobacterium sp. HXN-1500 | 153A6 | CAH04396 | 12 |
| Tetrahymena thermophile | 5013C2 | ABY59989 | 13 |
| Nonomuraea dietziae | | AGE14547.1 | 14 |
| Homo sapiens | 2R1 | NP_078790 | 15 |
| Macca mulatta | 2R1 | NP_001180887.1 | 16 |
| Canis familiaris | 2R1 | XP_854533 | 17 |
| Mus musculus | 2R1 | AAI08963 | 18 |
| Bacillus halodurans C-125 | 152A6 | NP_242623 | 19 |
| Streptomyces parvus | aryC | AFM80022 | 20 |
| Pseudomonas putida | 101A1 | P00183 | 21 |
| Homo sapiens | 2D7 | AAO49806 | 22 |
| Rattus norvegicus | C27 | AAB02287 | 23 |
| Oryctolagus cuniculus | 2B4 | AAA65840 | 24 |
| Bacillus subtilis | 102A2 | O08394 | 25 |
| Bacillus subtilis | 102A3 | O08336 | 26 |
| B. megaterium DSM 32 | 102A1 | P14779 | 27 |
| B. cereus ATCC14579 | 102A5 | AAP10153 | 28 |
| B. licheniformis ATTC1458 | 102A7 | YP 079990 | 29 |
| B. thuringiensis serovar konkukian str.97-27 | X | YP 037304 | 30 |
| R. metallidurans CH34 | 102E1 | YP 585608 | 31 |
| A. fumigatus Af293 | 505X | EAL92660 | 32 |
| A. nidulans FGSC A4 | 505A8 | EAA58234 | 33 |
| A. oryzae ATCC42149 | 505A3 | Q2U4F1 | 34 |
| A. oryzae ATCC42149 | X | Q2UNA2 | 35 |
| F. oxysporum | 505A1 | Q9Y8G7 | 36 |
| G. moniliformis | X | AAG27132 | 37 |
| G. zeae PH1 | 505A7 | EAA67736 | 38 |
| G. zeae PH1 | 505C2 | EAA77183 | 39 |
| M. grisea 70-15 syn | 505A5 | XP 365223 | 40 |
| N. crassa OR74 A | 505A2 | XP 961848 | 41 |
| Oryza sativa* | 97A | | |
| Oryza sativa* | 97B | | |
| Oryza sativa | 97C | ABB47954 | 42 |

The start methionine ("M") may be present or absent from these sequences.
*See, M. Z. Lv et al., Plant Cell Physiol., 53(6): 987-1002 (2012).

In certain embodiments, the present invention provides amino acid substitutions that efficiently remove monooxygenation chemistry from cytochrome P450 enzymes. This system permits selective enzyme-driven cyclopropanation chemistry without competing side reactions mediated by native P450 catalysis. The invention also provides P450-mediated catalysis that is competent for cyclopropanation chemistry but not able to carry out traditional P450-mediated monooxygenation reactions as 'orthogonal' P450 catalysis and respective enzyme variants as 'orthogonal' P450s. In some instances, orthogonal P450 variants comprise a single amino acid mutation at the axial position of the heme coordination site (e.g., a C400S mutation in the P450 BM3 enzyme) that alters the proximal heme coordination environment. Accordingly, the present invention also provides P450 variants that contain an axial heme mutation in combination with one or more additional mutations described herein to provide orthogonal P450 variants that show enriched diastereoselective and/or enantioselective product distributions. The present invention further provides a compatible reducing agent for orthogonal P450 cyclopropanation catalysis that includes, but is not limited to, NAD(P)H or sodium dithionite.

In particular embodiments, the cytochrome P450 enzyme is one of the P450 enzymes or enzyme classes set forth in Table 2 or 3. In some embodiments, the cytochrome P450 enzyme is a variant or homolog of one of the P450 enzymes or enzyme classes set forth in Table 2 or 3. In preferred embodiments, the P450 enzyme variant comprises a mutation at the conserved cysteine (Cys or C) residue of the corresponding wild-type sequence that serves as the heme axial ligand to which the iron in protoporphyrin IX is attached. As non-limiting examples, axial mutants of any of the P450 enzymes set forth in Table 2 or 3 can comprise a mutation at the axial position ("AxX") of the heme coordination site, wherein "X" is selected from Ala, Asp, Arg, Asn, Glu, Gln, Gly, His, Ile, Lys, Leu, Met, Phe, Pro, Ser, Thr, Trp, Tyr, and Val.

In certain embodiments, the conserved cysteine residue in a cytochrome P450 enzyme of interest that serves as the heme axial ligand and is attached to the iron in protoporphyrin IX can be identified by locating the segment of the DNA sequence in the corresponding cytochrome P450 gene which encodes the conserved cysteine residue. In some instances, this DNA segment is identified through detailed mutagenesis studies in a conserved region of the protein (see, e.g., Shimizu et al., *Biochemistry* 27, 4138-4141, 1988). In other instances, the conserved cysteine is identified through crystallographic study (see, e.g., Poulos et al., *J. Mol. Biol.* 195:687-700, 1987).

In situations where detailed mutagenesis studies and crystallographic data are not available for a cytochrome P450 enzyme of interest, the axial ligand may be identified through phylogenetic study. Due to the similarities in amino acid sequence between P450 enzymes, standard protein alignment algorithms may show a phylogenetic similarity between a P450 enzyme for which crystallographic or mutagenesis data exist and a new P450 enzyme for which such data do not exist. Thus, the polypeptide sequences of the present invention for which the heme axial ligand is known can be used as a "query sequence" to perform a search against a specifc new cytochrome P450 enzyme of interest or a database comprising cytochrome P450 sequences to identify the heme axial ligand. Such analyses can be performed using the BLAST programs (see, e.g., Altschul et al., *J Mol Biol.* 215(3):403-10 (1990)). Software for performing BLAST analyses publicly available through the National Center for Biotechnology Information (http://ncbi.nlm.nih.gov). BLASTP is used for amino acid sequences.

Exemplary parameters for performing amino acid sequence alignments to identify the heme axial ligand in a P450 enzyme of interest using the BLASTP algorithm include E value=10, word size=3, Matrix=Blosum62, Gap opening=11, gap extension=1, and conditional compositional score matrix adjustment. Those skilled in the art will know what modifications can be made to the above parameters, e.g., to either increase or decrease the stringency of the comparison and/or to determine the relatedness of two or more sequences.

In preferred embodiments, the cytochrome P450 enzyme is a cytochrome P450 BM3 enzyme or a variant, homolog, or fragment thereof. The bacterial cytochrome P450 BM3 from *Bacillus megaterium* is a water soluble, long-chain fatty acid monooxygenase. The native P450 BM3 protein is comprised of a single polypeptide chain of 1048 amino acids and can be divided into 2 functional subdomains (see, L. O, Narhi et al., *J. Biol. Chem.* 261, 7160 (1986)). An N-terminal domain, amino acid residues 1-472, contains the heme-bound active site and is the location for monoxygenation catalysis. The remaining C-terminal amino acids encompass a reductase domain that provides the necessary electron equivalents from NADPH to reduce the heme cofactor and drive catalysis. The presence of a fused reductase domain in P450 BM3 creates a self-sufficient monooxygenase, obviating the need for exogenous accessory proteins for oxygen activation (see, id.). It has been shown that the N-terminal heme domain can be isolated as an individual, well-folded, soluble protein that retains activity in the presence of hydrogen peroxide as a terminal oxidant under appropriate conditions (P. C. Cirino et al., *Angew. Chem., Int. Ed.* 42, 3299 (2003)).

In certain instances, the cytochrome P450 BM3 enzyme comprises or consists of the amino acid sequence set forth in SEQ ID NO:1. In certain other instances, the cytochrome P450 BM3 enzyme is a natural variant thereof as described, e.g., in J. Y. Kang et al., *AMB Express* 1:1 (2011), wherein the natural variants are divergent in amino acid sequence from the wild-type cytochrome P450 BM3 enzyme sequence (SEQ ID NO:1) by up to about 5% (e.g., SEQ ID NOS:2-11).

In particular embodiments, the P450 BM3 enzyme variant comprises or consists of the heme domain of the wild-type P450 BM3 enzyme sequence (e.g., amino acids 1-463 of SEQ ID NO:1) and optionally at least one mutation as described herein. In other embodiments, the P450 BM3 enzyme variant comprises or consists of a fragment of the heme domain of the wild-type P450 BM3 enzyme sequence (SEQ ID NO:1), wherein the fragment is capable of carrying out the cyclopropanation reactions of the present invention. In some instances, the fragment includes the heme axial ligand and at least one, two, three, four, or five of the active site residues.

In certain embodiments, the P450 BM3 enzyme variant comprises a mutation at the axial position ("AxX") of the heme coordination site, wherein "X" is selected from Ala, Asp, Arg, Asn, Glu, Gln, Gly, His, Ile, Lys, Leu, Met, Phe, Pro, Ser, Thr, Trp, Tyr, and Val. The conserved cysteine (Cys or C) residue in the wild-type P450 BM3 enzyme is located at position 400 in SEQ ID NO:1. As used herein, the terms "AxX" and "C400X" refer to the presence of an amino acid substitution "X" located at the axial position (i.e., residue 400) of the wild-type P450 BM3 enzyme (i.e., SEQ ID NO:1). In some instances, X is Ala (A), Asp (D), His (H), Lys (K), Asn (N), Met (M), Thr (T), or Tyr (Y). In some embodiments, the P450 BM3 enzyme variant comprises or consists of the heme domain of the wild-type P450 BM3 enzyme sequence (e.g., amino acids 1-463 of SEQ ID NO:1) or a fragment thereof and an AxX mutation (i.e., "WT-AxX heme").

In other embodiments, the P450 BM3 enzyme variant comprises at least one or more (e.g., at least two, three, four, five, six, seven, eight, nine, ten, eleven, twelve, or all thirteen) of the following amino acid substitutions in SEQ ID NO:1: V78A, F87V, P142S, T175I, A184V, S226R, H236Q, E252G, T268A, A290V, L353V, I366V, and E442K. In certain instances, the P450 BM3 enzyme variant comprises a T268A mutation alone or in combination with one or more additional mutations such as a C400X mutation (e.g., C400S) in SEQ ID NO:1. In other instances, the P450 BM3 enzyme variant comprises all thirteen of these amino acid substitutions (i.e., V78A, F87V, P142S, T175I, A184V, S226R, H236Q, E252G, T268A, A290V, L353V, I366V, and E442K; "BM3-CIS") in combination with a C400X mutation (e.g., C400S) in SEQ ID NO:1. In some instances, the P450 BM3 enzyme variant comprises or consists of the heme domain of the BM3-CIS enzyme sequence (e.g., amino acids 1-463 of SEQ ID NO:1 comprising all thirteen of these amino acid substitutions) or a fragment thereof and an "AxX" mutation (i.e., "BM3-CIS-AxX heme").

In some embodiments, the P450 BM3 enzyme variant further comprises at least one or more (e.g., at least two, or all three) of the following amino acid substitutions in SEQ ID NO:1: I263A, A328G, and a T438 mutation. In certain instances, the T438 mutation is T438A, T438S, or T438P. In some instances, the P450 BM3 enzyme variant comprises a T438 mutation such as T438A, T438S, or T438P alone or in combination with one or more additional mutations such as a C400X mutation (e.g., C400S) in SEQ ID NO:1 or a heme domain or fragment thereof. In other instances, the P450 BM3 enzyme variant comprises a T438 mutation such as T438A, T438S, or T438P in a BM3-CIS backbone alone or in combination with a C400X mutation (e.g., C400S) in SEQ ID NO:1 (i.e., "BM3-CIS-T438S-AxX"). In yet other instances, the P450 BM3 enzyme variant comprises or consists of the heme domain of the BM3-CIS enzyme sequence or a fragment thereof in combination with a T438 mutation and an "AxX" mutation (e.g., "BM3-CIS-T438S-AxX heme").

In other embodiments, the P450 BM3 enzyme variant further comprises from one to five (e.g., one, two, three, four, or five) active site alanine substitutions in the active site of SEQ ID NO:1. In certain instances, the active site alanine substitutions are selected from the group consisting of L75A, M177A, L181A, I263A, L437A, and a combination thereof.

In further embodiments, the P450 BM3 enzyme variant comprises at least one or more (e.g., at least about 2, 3, 4, 5, 6, 7, 8, 9, 10, 11, 12, 13, 14, 15, 16, 17, 18, 19, 20, 21, or 22) of the following amino acid substitutions in SEQ ID NO:1: R47C, L521, I58V, L75R, F81 (e.g., F81L, F81W), A82 (e.g., A82S, A82F, A82G, A82T, etc.), F87A, K94I, I94K, H100R, S106R, F107L, A135S, F162I, A197V, F205C, N239H, R255S, S274T, L324I, A328V, V340M, and K434E. In particular embodiments, the P450 BM3 enzyme variant comprises any one or a plurality of these mutations alone or in combination with one or more additional mutations such as those described above, e.g., an "AxX" mutation and/or at least one or more mutations including V78A, F87V, P142S, T175I, A184V, S226R, H236Q, E252G, T268A, A290V, L353V, I366V, and E442K.

Table 4 below provides non-limiting examples of cytochrome P450 BM3 variants of the present invention. Each P450 BM3 variant comprises one or more of the listed mutations (Variant Nos. 1-31), wherein a "+" indicates the presence of that particular mutation(s) in the variant. Any of the variants listed in Table 4 can further comprise an I263A and/or an A328G mutation and/or at least one, two, three, four, or five of the following alanine substitutions, in any combination, in the P450 BM3 enzyme active site: L75A, M177A, L181A, I263A, and L437A. In particular embodiments, the P450 BM3 variant comprises or consists of the heme domain of any one of Variant Nos. 1-31 listed in Table 4 or a fragment thereof, wherein the fragment is capable of carrying out the cyclopropanation reactions of the present invention.

TABLE 4

Exemplary cytochrome P450 BM3 enzyme variants of the present invention.

| | P450$_{BM3}$ variant | | | | | | | | | | | | | | | |
|---|---|---|---|---|---|---|---|---|---|---|---|---|---|---|---|---|
| Mutation | 1 | 2 | 3 | 4 | 5 | 6 | 7 | 8 | 9 | 10 | 11 | 12 | 13 | 14 | 15 | 16 |
| C400X | + | | | | | + | + | + | + | | | | | | | + |
| T268A | | + | | | | + | | | | + | + | + | | | | + |
| F87V | | | + | | | | + | | | | + | | | + | + | + |

TABLE 4-continued

Exemplary cytochrome P450 BM3 enzyme variants of the present invention.

| Mutation | | | | | | | |
|---|---|---|---|---|---|---|---|
| 9-10A-TS | | + | | + | | + | + | + |
| T438Z | | | + | | + | | + | + | + |

| Mutation | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|
| C400X | + | + | + | + | + | | | | | + | + | + | + | | + |
| T268A | + | + | | | | + | + | + | | + | + | + | | + | + |
| F87V | | | + | + | | + | + | | + | + | + | | + | + | |
| 9-10A-TS | + | | + | | + | + | | + | + | | + | | + | + | + |
| T438Z | | + | | + | + | | + | + | + | | + | + | + | + | + |

Mutations relative to the wild-type P450$_{BM3}$ amino acid sequence (SEQ ID NO: 1);
"X" is selected from Ala, Asp, Arg, Asn, Glu, Gln, Gly, His, Ile, Lys, Leu, Met, Phe, Pro, Ser, Thr, Trp, Tyr, and Val;
"Z" is selected from Ala, Ser, and Pro;
"9-10A-TS" includes the following amino acid substitutions in SEQ ID NO: 1: V78A, P142S, T175I, A184V, S226R, H236Q, E252G, A290V, L353V, I366V, and E442K.

One skilled in the art will understand that any of the mutations listed in Table 4 can be introduced into any cytochrome P450 enzyme of interest by locating the segment of the DNA sequence in the corresponding cytochrome P450 gene which encodes the conserved amino acid residue as described above for identifying the conserved cysteine residue in a cytochrome P450 enzyme of interest that serves as the heme axial ligand. In certain instances, this DNA segment is identified through detailed mutagenesis studies in a conserved region of the protein (see, e.g., Shimizu et al., *Biochemistry* 27, 4138-4141, 1988). In other instances, the conserved amino acid residue is identified through crystallographic study (see, e.g., Poulos et al., *J. Mol. Biol.* 195:687-700, 1987). In yet other instances, protein sequence alignment algorithms can be used to identify the conserved amino acid residue. As non-limiting examples, the use of BLAST alignment with the P450 BM3 amino acid sequence as the query sequence to identify the heme axial ligand site and/or the equivalent T268 residue in other cytochrome P450 enzymes is illustrated in Examples 3 and 9.

Table 5A below provides non-limiting examples of preferred cytochrome P450 BM3 variants of the present invention. Table 5B below provides non-limiting examples of preferred chimeric cytochrome P450 enzymes of the present invention.

TABLE 5A

Exemplary preferred cytochrome P450 BM3 enzyme variants of the invention.

| P450$_{BM3}$ variants | Mutations compared to wild-type P450$_{BM3}$ (SEQ ID NO: 1) |
|---|---|
| P450$_{BM3}$-T268A | T268A |
| P450$_{BM3}$-T268A-C400H | T268A + C400H |
| P411$_{BM3}$ (ABC) | C400S |
| P411$_{BM3}$-T268A | T268A + C400S |
| P450$_{BM3}$-T268A-F87V | T268A + F87V |
| 9-10A TS | V78A, P142S, T175I, A184V, S226R, H236Q, E252G, A290V, L353V, I366V, E442K |
| 9-10A-TS-F87V | 9-10A TS + F87V |
| H2A10 | 9-10A TS + F87V, L75A, L181A, T268A |
| H2A10-C400S | 9-10A TS + F87V, L75A, L181A, T268A, C400S |
| H2A10-C400H | 9-10A TS + F87V, L75A, L181A, T268A, C400H |
| H2A10-C400M | 9-10A TS + F87V, L75A, L181A, T268A, C400M |
| H2-5-F10 | 9-10A TS + F87V, L75A, I263A, T268A, L437A |
| H2-5-F10-C400S | 9-10A TS + F87V, L75A, I263A, T268A, L437A, C400S |
| H2-5-F10-C400H | 9-10A TS + F87V, L75A, I263A, T268A, L437A, C400H |
| H2-5-F10-C400M | 9-10A TS + F87V, L75A, I263A, T268A, L437A, C400M |
| H2-4-D4 | 9-10A TS + F87V, L75A, M177A, L181A, T268A, L437A |
| H2-4-D4-C400S | 9-10A TS + F87V, L75A, M177A, L181A, T268A, L437A, C400S |
| H2-4-D4-C400H | 9-10A TS + F87V, L75A, M177A, L181A, T268A, L437A, C400H |
| H2-2-A1 | 9-10A TS + F87A, L75A, L181A, L437A |
| H2-2-A1-C400S | 9-10A TS + F87A, L75A, L181A, L437A, C400S |
| H2-2-A1-C400H | 9-10A TS + F87A, L75A, L181A, L437A, C400H |
| H2-8-C7 | 9-10A TS + L75A, F87V, L181A |
| H2-5-F10-A75L | 9-10A TS + F87V-I263A-T268A-L437A |
| CH F8 | R47C, V78A, K94I, P142S, T175I, A184V, F205C, S226R, H236Q, E252G, R255S, A290V, L353V, F81W, A82S, F87A, A197V |
| BM3-CIS (P450$_{BM3}$-CIS; C3C) | 9-10A TS + F87V, T268A |
| BM3-CIS-I263A | BM3-CIS + I263A |
| BM3-CIS-A328G | BM3-CIS + A328G |
| BM3-CIS-T438S | BM3-CIS + T438S |
| BM3-CIS-C400S (P411$_{BM3}$-CIS; ABC-CIS) | BM3-CIS + C400S |
| BM3-CIS-C400D (BM3-CIS-AxD) | BM3-CIS + C400D |
| BM3-CIS-C400Y (BM3-CIS-AxY) | BM3-CIS + C400Y |
| BM3-CIS-C400K (BM3-CIS-AxK) | BM3-CIS + C400K |

TABLE 5A-continued

Exemplary preferred cytochrome P450 BM3 enzyme variants of the invention.

| P450$_{BM3}$ variants | Mutations compared to wild-type P450$_{BM3}$ (SEQ ID NO: 1) |
|---|---|
| BM3-CIS-C400H (BM3-CIS-AxH) | BM3-CIS + C400H |
| BM3-CIS-C400M (BM3-CIS-AxM) | BM3-CIS + C400M |
| WT-AxA (heme) | WT heme domain (amino acids 1-463 of SEQ ID NO: 1) + C400A |
| WT-AxD (heme) | WT heme domain (amino acids 1-463 of SEQ ID NO: 1) + C400D |
| WT-AxH (heme) | WT heme domain (amino acids 1-463 of SEQ ID NO: 1) + C400H |
| WT-AxK (heme) | WT heme domain (amino acids 1-463 of SEQ ID NO: 1) + C400K |
| WT-AxM (heme) | WT heme domain (amino acids 1-463 of SEQ ID NO: 1) + C400M |
| WT-AxN (heme) | WT heme domain (amino acids 1-463 of SEQ ID NO: 1) + C400N |
| WT-AxY (heme) | WT heme domain (amino acids 1-463 of SEQ ID NO: 1) + C400Y |
| BM3-CIS-T438S-AxA | BM3-CIS-T438S + C400A |
| BM3-CIS-T438S-AxD | BM3-CIS-T438S + C400D |
| BM3-CIS-T438S-AxM | BM3-CIS-T438S + C400M |
| BM3-CIS-T438S-AxY | BM3-CIS-T438S + C400Y |
| BM3-CIS-T438S-AxT | BM3-CIS-T438S + C400T |
| 7-11D | R47C, V78A, K94I, P142S, T175I, A184V, F205C, S226R, H236Q, E252G, R255S, A290V, L353V, A82F, A328V |
| 7-11D-C400S | R47C, V78A, K94I, P142S, T175I, A184V, F205C, S226R, H236Q, E252G, R255S, A290V, L353V, A82F, A328V, C400S |
| 12-10C | R47C, V78A, A82G, F87V, K94I, P142S, T175I, A184V, F205C, S226R, H236Q, E252G, R255S, A290V, A328V, L353V |
| 22A3 | L52I, I58V, L75R, F87A, H100R, S106R, F107L, A135S, F162I, A184V, N239H, S274T, L324I, V340M, I366V, K434E |
| Man1 | V78A, K94I, P142S, T175I, A184V, F205C, S226R, H236Q, E252G, R255S, A290V, L353V, F81L, A82T, F87A, I94K |

TABLE 5B

Exemplary preferred chimeric cytochrome P450 enzymes of the invention.

| Chimeric P450s | Heme domain block sequence | SEQ ID NO |
|---|---|---|
| C2G9 | 22223132 | 43 |
| X7 | 22312333 | 44 |
| X7-12 | 12112333 | 45 |
| C2E6 | 11113311 | 46 |
| X7-9 | 32312333 | 47 |
| C2B12 | 32313233 | 48 |
| TSP234 | 22313333 | 49 |

In particular embodiments, cytochrome P450 BM3 variants with at least one or more amino acid mutations such as, e.g., C400X (AxX), BM3-CIS, T438, and/or T268A amino acid substitutions catalyze cyclopropanation reactions efficiently, displaying increased total turnover numbers and demonstrating highly regio- and/or enantioselective product formation compared to the wild-type enzyme.

As a non-limiting example, the cytochrome P450 BM3 variants of the present invention are cis-selective catalysts that demonstrate diastereomeric ratios at least comparable to wild-type P450 BM3, e.g., at least 37:63 cis:trans, at least 50:50 cis:trans, at least 60:40 cis:trans, or at least 95:5 cis: trans. Particular mutations for improving cis-selective catalysis include at least one mutation comprising T268A, C400X, and T438S, but preferably one, two, or all three of these mutations in combination with additional mutations comprising V78A, P142S, T175I, A184V, S226R, H236Q, E252G, A290V, L353V, I366V, E442K, and F87V derived from P450 BM3 variant 9-10A-TS. These mutations are isolated to the heme domain of P450 BM3 and are located in various regions of the heme domain structure including the active site and periphery.

As another non-limiting example, the cytochrome P450 BM3 variants of the present invention are trans-selective catalysts that demonstrate diastereomeric ratios at least comparable to wild-type P450 BM3, e.g., at least 37:63 cis:trans, at least 20:80 cis:trans, or at least 1:99 cis:trans. Particular mutations for improving trans-selective catalysis include at least one mutation comprising including T268A and C400X, but preferably one or both of these mutations in the background of wild-type P450 BM3. In certain embodiments, trans-preferential mutations in combination with additional mutations such as V78A, P142S, T175I, A184V, S226R, H236Q, E252G, A290V, L353V, I366V, E442K, and F87V (from 9-10-A-TS) are also tolerated when in the presence of additional mutations including, but not limited to, I263A, L437A, L181A and/or L75A. These mutations are isolated to the heme domain of P450 BM3 and are located in various regions of the heme domain structure including the active site and periphery.

In certain embodiments, the present invention also provides P450 variants that catalyze enantioselective cyclopropanation with enantiomeric excess values of at least 30% (comparable with wild-type P450 BM3), but more preferably at least 80%, and even more preferably at least >95% for preferred product diastereomers.

In other aspects, the present invention provides chimeric heme enzymes such as, e.g., chimeric P450 proteins comprised of recombined sequences from P450 BM3 and at least one, two, or more distantly related P450 enzymes from *Bacillus subtillis* or any other organism that are competent cyclopropanation catalysts using similar conditions to wild-type P450 BM3 and highly active P450 BM3 variants. As a non-limiting example, site-directed recombination of three bacterial cytochrome P450s can be performed with sequence crossover sites selected to minimize the number of disrupted contacts within the protein structure. In some embodiments, seven crossover sites can be chosen, resulting in eight sequence blocks. One skilled in the art will understand that the number of crossover sites can be chosen to produce the desired number of sequence blocks, e.g., 1, 2, 3, 4, 5, 6, 7, 8, or 9 crossover sites for 2, 3, 4, 5, 6, 7, 8, 9, or 10 sequence blocks, respectively. In other embodiments, the numbering used for the chimeric P450 refers to the identity of the parent sequence at each block. For example, "12312312" refers to a sequence containing block 1 from P450 #1, block 2 from P450 #2, block 3 from P450 #3, block 4 from P450 #1, block 5 from P450 #2, and so on. A chimeric library useful for generating the chimeric heme enzymes of the invention can be constructed as described in, e.g., Otey et al., *PLoS Biology*, 4(5):e112 (2006), following the SISDC method (see, Hiraga et al., *J. Mol. Biol.*, 330:287-96 (2003)) using the type IIb restriction endonuclease BsaXI, ligating the full-length library into the pCWori vector and transforming into the catalase-deficient *E. coli* strain SN0037 (see, Nakagawa et al., *Biosci. Biotechnol. Biochem.*, 60:415-420 (1996)); the disclosures of these references are hereby incorporated by reference in their entirety for all purposes.

As a non-limiting example, chimeric P450 proteins comprising recombined sequences or blocks of amino acids from CYP102A1 (Accession No. J04832), CYP102A2 (Accession No. CAB12544), and CYP102A3 (Accession No. U93874) can be constructed. In certain instances, the CYP102A1 parent sequence is assigned "1", the CYP102A2 parent sequence is assigned "2", and the CYP102A3 is parent sequence assigned "3". In some instances, each parent sequence is divided into eight sequence blocks containing the following amino acids (aa): block 1: aa 1-64; block 2: aa 65-122; block 3: aa 123-166; block 4: aa 167-216; block 5: aa 217-268; block 6: aa 269-328; block 7: aa 329-404; and block 8: aa 405-end. Thus, in this example, there are eight blocks of amino acids and three fragments are possible at each block. For instance, "12312312" refers to a chimeric P450 protein of the invention containing block 1 (aa 1-64) from CYP102A1, block 2 (aa 65-122) from CYP102A2, block 3 (aa 123-166) from CYP102A3, block 4 (aa 167-216) from CYP102A1, block 5 (aa 217-268) from CYP102A2, and so on. See, e.g., Otey et al., *PLoS Biology*, 4(5):e112 (2006). Non-limiting examples of chimeric P450 proteins include those set forth in Table 5B (C2G9, X7, X7-12, C2E6, X7-9, C2B12, TSP234) and Table 13. In some embodiments, the chimeric heme enzymes of the invention can comprise at least one or more of the mutations described herein.

In some embodiments, the present invention provides the incorporation of homologous or analogous mutations to C400X (AxX) and/or T268A in other cytochrome P450 enzymes and heme enzymes in order to impart or enhance cyclopropanation activity.

As non-limiting examples, the cytochrome P450 can be a variant of CYP101A1 (SEQ ID NO:25) comprising a C357X (e.g., C357S) mutation, a T252A mutation, or a combination of C357X (e.g., C357S) and T252A mutations, wherein "X" is any amino acid other than Cys, or the cytochrome P450 can be a variant of CYP2B4 (SEQ ID NO:28) comprising a C436X (e.g., C436S) mutation, a T302A mutation, or a combination of C436X (e.g., C436S) and T302A mutations, wherein "X" is any amino acid other than Cys, or the cytochrome P450 can be a variant of CYP2D7 (SEQ ID NO:26) comprising a C461X (e.g., C461S) mutation, wherein "X" is any amino acid other than Cys, or the cytochrome P450 can be a variant of P450C27 (SEQ ID NO:27) comprising a C478X (e.g., C478S) mutation, wherein "X" is any amino acid other than Cys.

An enzyme's total turnover number (or TTN) refers to the maximum number of molecules of a substrate that the enzyme can convert before becoming inactivated. In general, the TTN for the heme enzymes of the invention range from about 1 to about 100,000 or higher. For example, the TTN can be from about 1 to about 1,000, or from about 1,000 to about 10,000, or from about 10,000 to about 100,000, or from about 50,000 to about 100,000, or at least about 100,000. In particular embodiments, the TTN can be from about 100 to about 10,000, or from about 10,000 to about 50,000, or from about 5,000 to about 10,000, or from about 1,000 to about 5,000, or from about 100 to about 1,000, or from about 250 to about 1,000, or from about 100 to about 500, or at least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, or more. In certain embodiments, the variant or chimeric heme enzymes of the present invention have higher TTNs compared to the wild-type sequences. In some instances, the variant or chimeric heme enzymes have TTNs greater than about 100 (e.g., at least about 100, 150, 200, 250, 300, 325, 350, 400, 450, 500, or more) in carrying out in vitro cyclopropanation reactions. In other instances, the variant or chimeric heme enzymes have TTNs greater than about 1000 (e.g., at least about 1000, 2500, 5000, 10,000, 25,000, 50,000, 75,000, 100,000, or more) in carrying out in vivo whole cell cyclopropanation reactions.

When whole cells expressing a heme enzyme are used to carry out a cyclopropanation reaction, the turnover can be expressed as the amount of substrate that is converted to product by a given amount of cellular material. In general, in vivo cyclopropanation reactions exhibit turnovers from at least about 0.01 to at least about 10 mmol·$g_{cdw}^{-1}$, wherein $g_{cdw}$ is the mass of cell dry weight in grams. For example, the turnover can be from about 0.1 to about 10 mmol·$g_{cdw}^{-1}$, or from about 1 to about 10 mmol·$g_{cdw}^{-1}$, or from about 5 to about 10 mmol or from about 0.01 to about 1 mmol·$g_{cdw}^{-1}$, or from about 0.01 to about 0.1 mmol·$g_{cdw}^{-1}$, or from about 0.1 to about 1 mmol·$g_{cdw}^{-1}$, or greater than 1 mmol·$g_{cdw}^{-1}$. The turnover can be about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or about 10 mmol·$g_{cdw}^{-1}$.

When whole cells expressing a heme enzyme are used to carry out a cyclopropanation reaction, the activity can further be expressed as a specific productivity, e.g., concentration of product formed by a given concentration of cellular material per unit time, e.g., in g/L of product per g/L of cellular material per hour (g $g_{cdw}^{-1}$ h$^{-1}$). In general, in vivo cyclopropanation reactions exhibit specific productivities from at least about 0.01 to at least about 0.5 g $g_{cdw}^{-1}$ h$^{-1}$, wherein $g_{cdw}$ is the mass of cell dry weight in grams. For example, the specific productivity can be from about 0.01 to about 0.1 g $g_{cdw}^{-1}$ h$^{-1}$, or from about 0.1 to about 0.5 g $g_{cdw}^{-1}$ h$^{-1}$, or greater than 0.5 g $g_{cdw}^{-1}$ h$^{-1}$. The specific productivity can be about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, or about 0.5 g $g_{cdw}^{-1}$ h$^{-1}$.

In certain embodiments, mutations can be introduced into the target gene using standard cloning techniques (e.g., site-directed mutagenesis) or by gene synthesis to produce the heme enzymes (e.g., cytochrome P450 variants) of the present invention. The mutated gene can be expressed in a host cell (e.g., bacterial cell) using an expression vector under the control of an inducible promoter or by means of chromosomal integration under the control of a constitutive promoter. Cyclopropanation activity can be screened in vivo or in vitro by following product formation by GC or HPLC as described herein.

The expression vector comprising a nucleic acid sequence that encodes a heme enzyme of the invention can be a viral vector, a plasmid, a phage, a phagemid, a cosmid, a fosmid, a bacteriophage (e.g., a bacteriophage P1-derived vector (PAC)), a baculovirus vector, a yeast plasmid, or an artificial chromosome (e.g., bacterial artificial chromosome (BAC), a yeast artificial chromosome (YAC), a mammalian artificial chromosome (MAC), and human artificial chromosome (HAC)). Expression vectors can include chromosomal, non-chromosomal, and synthetic DNA sequences. Equivalent expression vectors to those described herein are known in the art and will be apparent to the ordinarily skilled artisan.

The expression vector can include a nucleic acid sequence encoding a heme enzyme that is operably linked to a promoter, wherein the promoter comprises a viral, bacterial, archaeal, fungal, insect, or mammalian promoter. In certain embodiments, the promoter is a constitutive promoter. In some embodiments, the promoter is an inducible promoter. In other embodiments, the promoter is a tissue-specific promoter or an environmentally regulated or a developmentally regulated promoter.

It is understood that affinity tags may be added to the N- and/or C-terminus of a heme enzyme expressed using an expression vector to facilitate protein purification. Non-limiting examples of affinity tags include metal binding tags such as His6-tags (SEQ ID NO:74) and other tags such as glutathione S-transferase (GST).

Non-limiting expression vectors for use in bacterial host cells include pCWori, pET vectors such as pET22 (EMD Millipore), pBR322 (ATCC37017), pQE™ vectors (Qiagen), pBluescript™ vectors (Stratagene), pNH vectors, lambda-ZAP vectors (Stratagene); ptrc99a, pKK223-3, pDR540, pRIT2T (Pharmacia), pRSET, pCR-TOPO vectors, pET vectors, pSyn_1 vectors, pChlamy_1 vectors (Life Technologies, Carlsbad, Calif.), pGEM1 (Promega, Madison, Wis.), and pMAL (New England Biolabs, Ipswich, Mass.). Non-limiting examples of expression vectors for use in eukaryotic host cells include pXT1, pSG5 (Stratagene), pSVK3, pBPV, pMSG, pSVLSV40 (Pharmacia), pcDNA3.3, pcDNA4/TO, pcDNA6/TR, pLenti6/TR, pMT vectors (Life Technologies), pKLAC1 vectors, pKLAC2 vectors (New England Biolabs), pQE™ vectors (Qiagen), BacPak baculoviral vectors, pAdeno-X™ adenoviral vectors (Clontech), and pBABE retroviral vectors. Any other vector may be used as long as it is replicable and viable in the host cell.

The host cell can be a bacterial cell, an archaeal cell, a fungal cell, a yeast cell, an insect cell, or a mammalian cell.

Suitable bacterial host cells include, but are not limited to, BL21 *E. coli*, DE3 strain *E. coli*, *E. coli* M15, DH5α, DH10β, HB101, T7 Express Competent *E. coli* (NEB), *B. subtilis* cells, *Pseudomonas fluorescens* cells, and cyanobacterial cells such as *Chlamydomonas reinhardtii* cells and *Synechococcus elongates* cells. Non-limiting examples of archaeal host cells include *Pyrococcus furiosus*, *Metallosphera sedula*, *Thermococcus litoralis*, *Methanobacterium thermoautotrophicum*, *Methanococcus jannaschii*, *Pyrococcus abyssi*, *Sulfolobus solfataricus*, *Pyrococcus woesei*, *Sulfolobus shibatae*, and variants thereof. Fungal host cells include, but are not limited to, yeast cells from the genera *Saccharomyces* (e.g., *S. cerevisiae*), *Pichia* (*P. Pastoris*), *Kluyveromyces* (e.g., *K. lactis*), *Hansenula* and *Yarrowia*, and filamentous fungal cells from the genera *Aspergillus*, *Trichoderma*, and *Myceliophthora*. Suitable insect host cells include, but are not limited to, Sf9 cells from *Spodoptera frugiperda*, Sf21 cells from *Spodoptera frugiperda*, Hi-Five cells, BTI-TN-5B1-4 *Trichophusia ni* cells, and Schneider 2 (S2) cells and Schneider 3 (S3) cells from *Drosophila melanogaster*. Non-limiting examples of mammalian host cells include HEK293 cells, HeLa cells, CHO cells, COS cells, Jurkat cells, NSO hybridoma cells, baby hamster kidney (BHK) cells, MDCK cells, NIH-3T3 fibroblast cells, and any other immortalized cell line derived from a mammalian cell.

In certain embodiments, the present invention provides heme enzymes such as the P450 variants described herein that are active cyclopropanation catalysts inside living cells. As a non-limiting example, bacterial cells (e.g., *E. coli*) can be used as whole cell catalysts for the in vivo cyclopropanation reactions of the present invention. In some embodiments, whole cell catalysts containing P450 enzymes with the equivalent C400X mutation are found to significantly enhance the total turnover number (TTN) compared to in vitro reactions using isolated P450 enzymes.

B. Compounds

The methods of the invention can be used to provide a number of cyclopropanation products. The cyclopropanation products include several classes of compound including, but not limited to, commodity and fine chemicals, flavors and scents, insecticides, and active ingredients in pharmaceutical compositions. The cyclopropanation products can also serve as starting materials or intermediates for the synthesis of compounds belonging to these and other classes.

In some embodiments, the cyclopropanation product is a compound according to formula I

(I)

For compounds of Formula I, $R^1$ is independently selected from H, optionally substituted $C_{1-18}$ alkyl, optionally substituted $C_{6-10}$ aryl, optionally substituted 6- to 10-membered heteroaryl, halo, cyano, $C(O)OR^{1a}$, $C(O)N(R^7)_2$, $C(O)R^8$, $C(O)C(O)OR^8$, and $Si(R^8)_3$; and $R^2$ is independently selected from H, optionally substituted $C_{1-18}$ alkyl, optionally substituted $C_{6-10}$ aryl, optionally substituted 6- to 10-membered heteroaryl, halo, cyano, $C(O)OR^{2a}$, $C(O)N(R^7)_2$, $C(O)R^8$, $C(O)C(O)OR^8$, and $Si(R^8)_3$. $R^{1a}$ and $R^{2a}$ are independently selected from H, optionally substituted $C_{1-18}$ alkyl and -L-$R^C$.

When the moiety -L-$R^C$ is present, L is selected from a bond, —$C(R^L)_2$— and —$NR^L$—$C(R^L)_2$—. Each $R^L$ is independently selected from H, $C_{1-6}$ alkyl, halo, —CN, and —$SO_2$, and each $R^C$ is selected from optionally substituted $C_{6-10}$ aryl, optionally substituted 6- to 10-membered heteroaryl, and optionally substituted 6- to 10-membered heterocyclyl.

For compounds of Formula I, $R^3$, $R^4$, $R^5$, and $R^6$ are independently selected from H, $C_{1-18}$ alkyl, $C_{2-18}$ alkenyl, $C_{2-18}$ alkynyl, optionally substituted $C_{6-10}$ aryl, optionally substituted $C_1$-$C_6$ alkoxy, halo, hydroxy, cyano, $C(O)N(R^7)_2$, $NR^7C(O)R^8$, $C(O)R^8$, $C(O)OR^8$, and $N(R^9)_2$. Each $R^7$ and $R^8$ is independently selected from H, optionally substituted $C_{1-12}$ alkyl, optionally substituted $C_{2-12}$ alkenyl, and optionally substituted $C_{6-10}$ aryl. Each $R^9$ is independently selected from H, optionally substituted $C_{6-10}$ aryl, and optionally substituted 6- to 10-membered heteroaryl. Alternatively, two $R^9$ moieties, together with the nitrogen atom to which they are attached, can form 6- to 18-membered heterocyclyl.

Alternatively, $R^3$ forms an optionally substituted 3- to 18-membered ring with $R^4$, or $R^5$ forms an optionally substituted 18-membered ring with $R^6$. $R^3$ or $R^4$ can also form a double bond with $R^5$ or $R^6$. $R^3$ or $R^4$ forms an optionally substituted 5- to 6-membered ring with $R^5$ or $R^6$.

In some embodiments, the cyclopropanation product is a compound of formula I as described above, wherein $R^1$ is $C(O)O\text{-}L12^c$; $R^2$ is selected from H and optionally substituted $C_{6-10}$ aryl; and $R^3$, $R^4$, $R^5$, and $R^6$ are independently selected from H, optionally substituted $C_{1-6}$ alkyl, optionally substituted $C_{2-6}$ alkenyl, optionally substituted $C_{2-6}$ alkynyl, optionally substituted $C_{6-10}$ aryl, and halo. Alternatively, $R^3$ can form an optionally substituted 3.to 18-membered ring with $R^4$, or $R^5$ can form an optionally substituted 3.to 18-membered ring with $R^6$. In such embodiments, the cyclopropanation product can be a pyrethroid or a pyrethroid precursor.

In general, pyrethroids are characterized by an ester core having a structure according to Formula III:

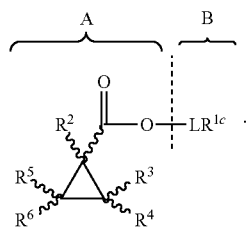
(III)

Formula III is presented above as a cyclopropyl carboxylate moiety ("A") esterified with an $LR^{1c}$ moiety ("B"), with $R^{1c}$ defined as for $R^C$. The methods of the invention can be used to prepare pyrethroids and pyrethroid intermediates having a variety of "A" moieties connected to any of a variety of "B" moieties. For example, the pyrethroids can have an "A" moiety selected from:

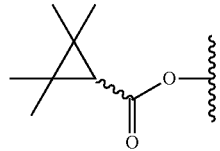
A1

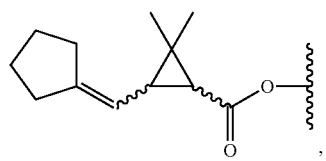
A2

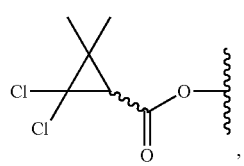
A3

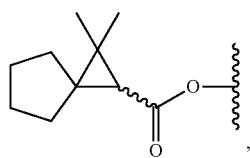
A4

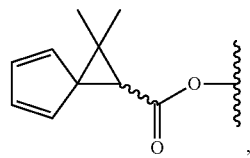
A5

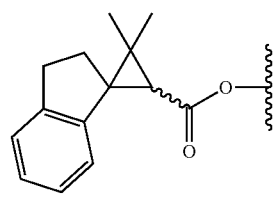
A6

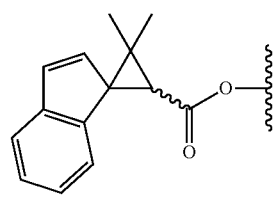
A7

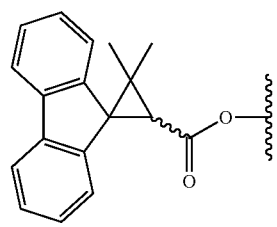
A8

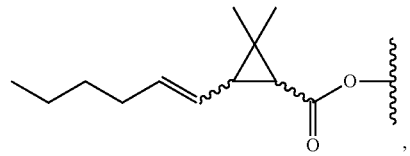
A9

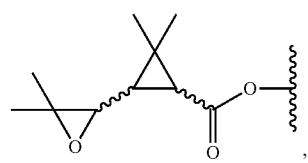
A10

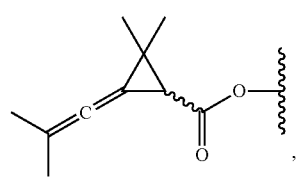
A11

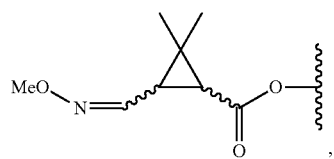
A12

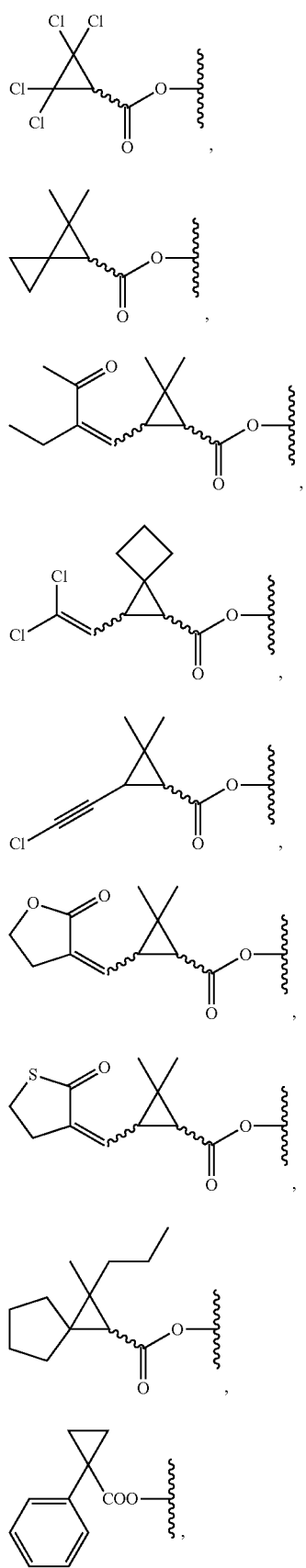
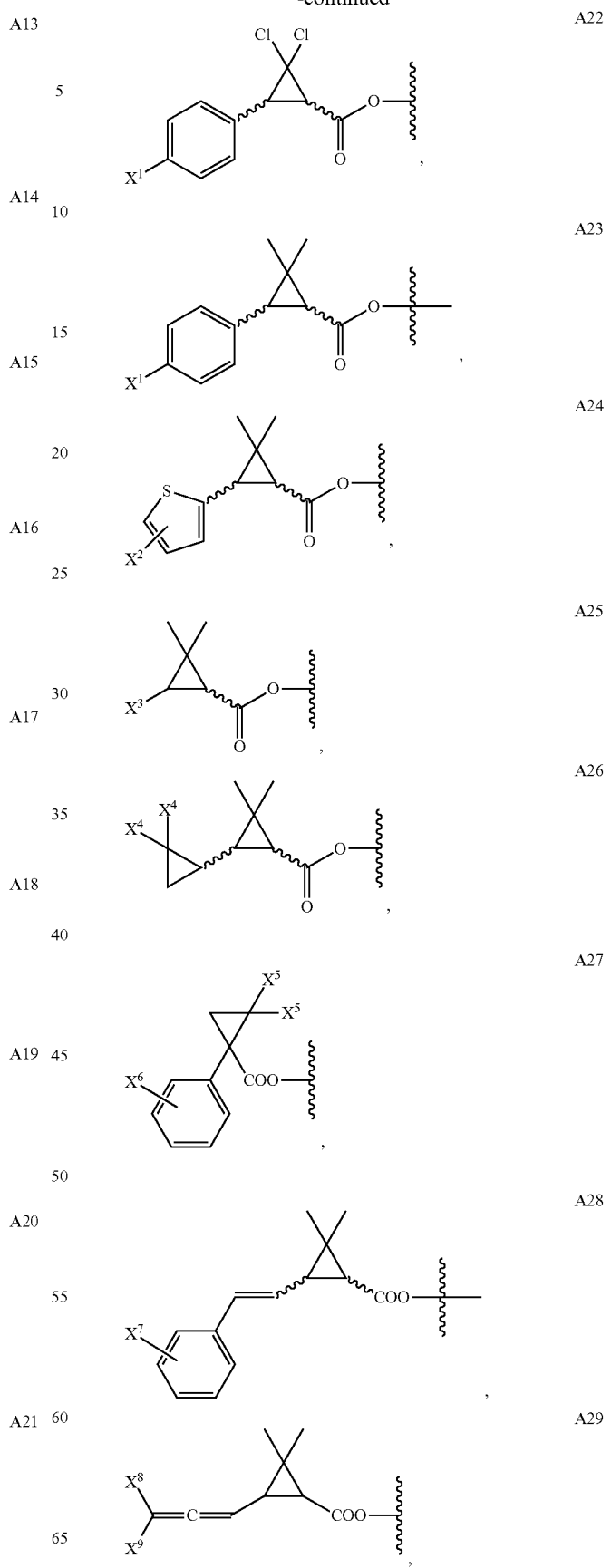

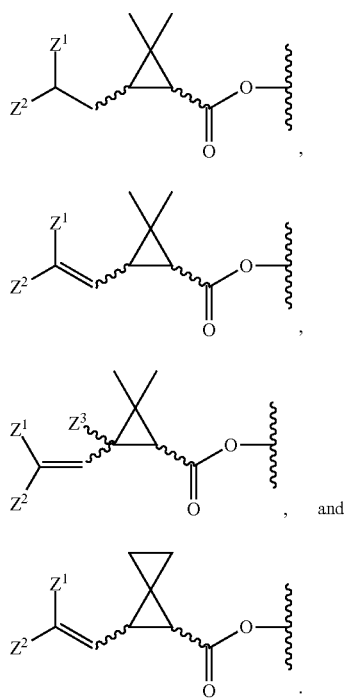

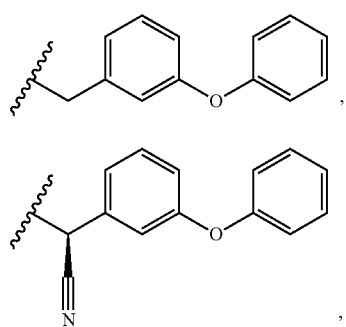

For the A moieties listed above, $X^1$ is selected from H, optionally substituted $C_{1-6}$ alkyl, halo$C_{1-6}$ alkyl, optionally substituted $C_{1-6}$ alkoxy, halo$C_{1-6}$ alkyl, optionally substituted $C_{1-6}$ alkylthio, $C_{1-6}$ alkylsilyl, halo, and cyano. $X^2$ is selected from H, chloro, and methyl. $X^3$ is selected from H, methyl, halo, and CN. Each $X^4$ is independently halo. Each $X^5$ is independently selected from methyl and halo. $X^6$ is selected from halo, optionally substituted $C_{1-6}$ alkyl, and optionally substituted $C_{1-6}$ alkoxy. $X^7$ is selected from H, methyl, and halo. $X^8$ is selected from H, halo, and optionally substituted $C_{1-6}$ alkyl. $X^9$ is selected from H, halo, optionally substituted $C_{1-6}$ alkyl, C(O)O—($C_{1-6}$ alkyl), C(O)—N($C_{1-6}$ alkyl)$_2$, and cyano. $Z^1$, $Z^2$, and $Z^3$ are independently selected from H, halo, optionally substituted $C_{1-6}$ alkyl, and optionally substituted $C_{6-10}$ aryl, or $Z^1$ and $Z^2$ are taken together to form an optionally substituted 5- to 6-membered cycloalkyl or heterocyclyl group. The wavy line at the right of each structure represents the point of connection between the A moiety and a B moiety.

The pyrethroids can have "B" moieties selected from:

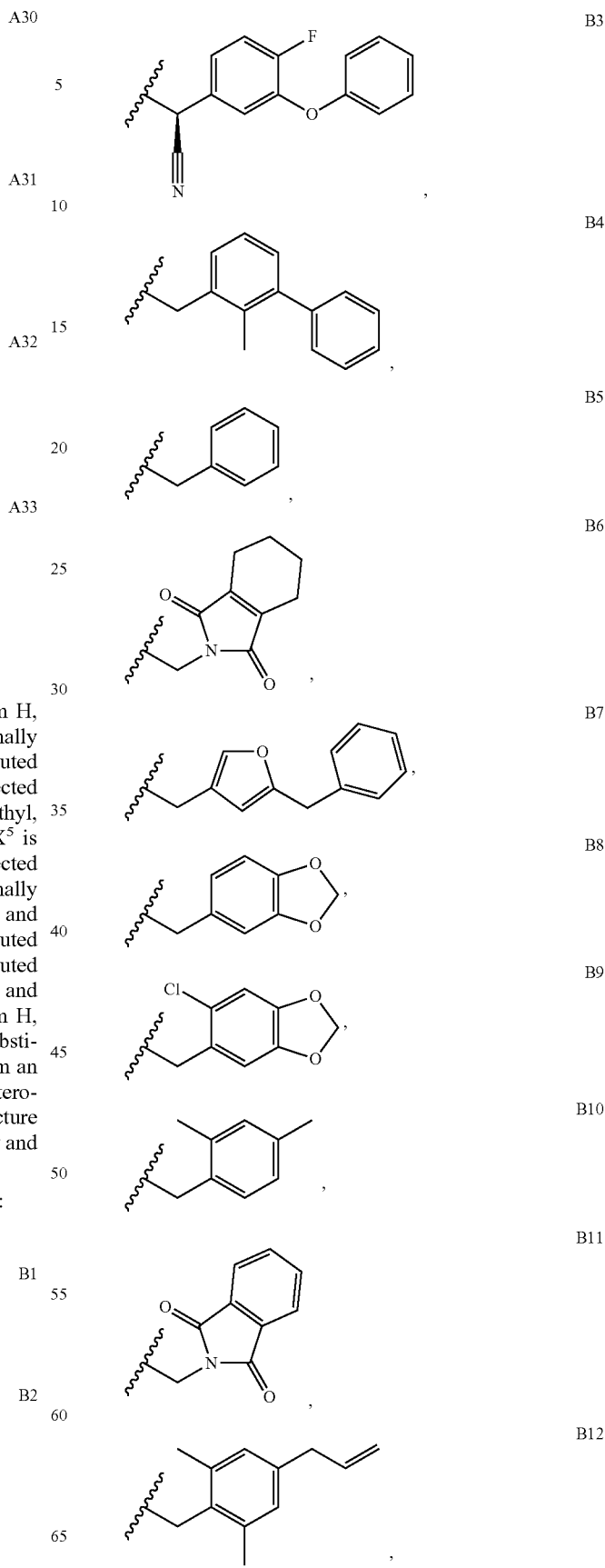

-continued
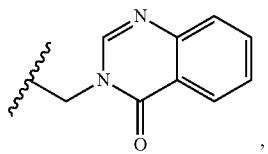, B13
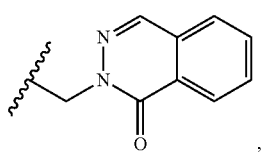, B14
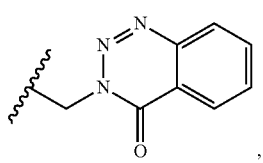, B15
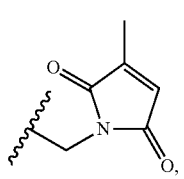, B16
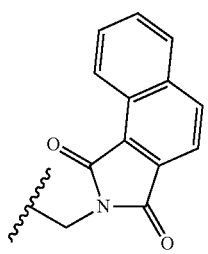, B17
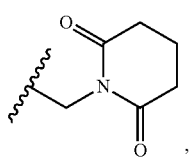, B18
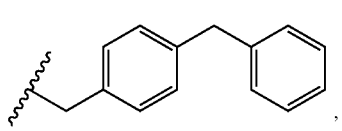, B19
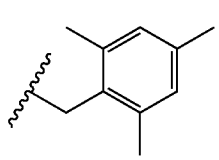, B20
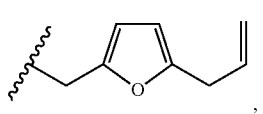, B21
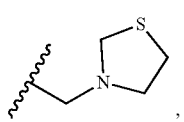, B22
-continued
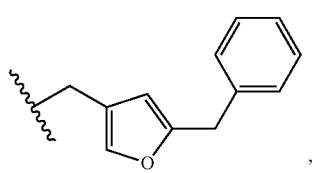, B23
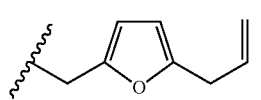, B21
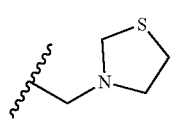, B22
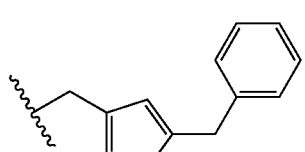, B23
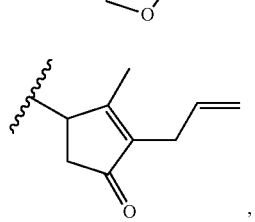, B24
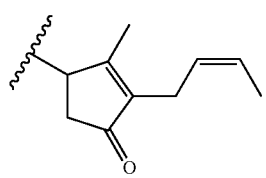, B25
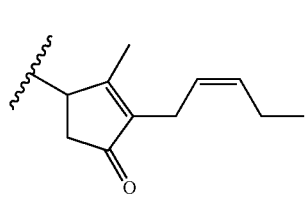, B26
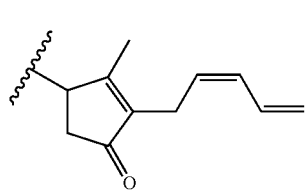, B27
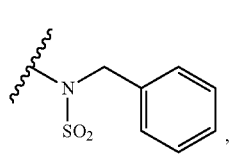, B28
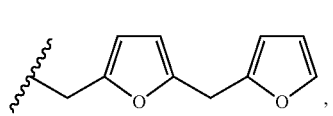, B29

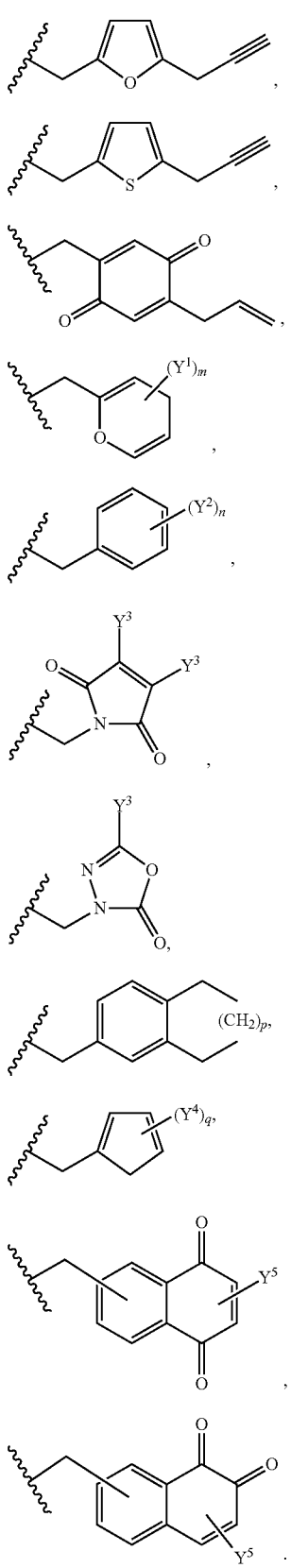

For the B moieties listed above, each Y¹ is independently selected from optionally substituted $C_{1-6}$ alkyl, optionally substituted $C_{2-6}$ alkenyl, optionally substituted $C_{2-6}$ alkynyl, phenyl, and (phenyl)$C_{1-6}$ alkoxy. Each $Y^2$ is independently selected from halo, optionally substituted $C_{1-6}$ alkyl, optionally substituted $C_{2-6}$ alkenyl, optionally substituted $C_{1-6}$ alkoxy, and nitro. Each $Y^3$ is independently optionally substituted $C_{1-6}$ alkyl. Each $Y^4$ is independently selected from optionally substituted $C_{1-6}$ alkyl, optionally substituted $C_{2-6}$ alkenyl, optionally substituted $C_{2-6}$ alkynyl, $C_{6-10}$ aryl-$C_{1-6}$ alkyl, furfuryl, $C_{1-6}$ alkoxy, ($C_{2-6}$ alkenyl)oxy, $C_{1-12}$ acyl, and halo. $Y^5$ is selected from the group consisting of optionally substituted $C_{1-6}$ alkyl, optionally substituted $C_{1-6}$ alkoxy, and halo. The subscript m is an integer from 1 to 3, the subscript n is an integer from 1 to 5, the subscript p is an integer from 1 to 4, and the subscript q is an integer from 0 to 3. The wavy line at the left of each structure represents the point of connection between the B moiety and an A moiety.

The methods of the invention can be used to prepare pyrethroids having any A moiety joined to any B moiety. A given pyrethroid can have a structure selected from: A1-B1, A2-B1, A3-B1, A4-B1, A5-B1, A6-B1, A7-B1, A8-B1, A9-B1, A10-B1, A11-B1, A12-B1, A13-B1, A14-B1, A15-B1, A16-B1, A17-B1, A18-B1, A19-B1, A20-B1, A21-B1, A22-B1, A23-B1, A24-B1, A25-B1, A26-B1, A27-B1, A28-B1, A29-B1, A30-B1, A31-B1, A32-B1, A33-B1, A1-B2, A2-B2, A3-B2, A4-B2, A5-B2, A6-B2, A7-B2, A8-B2, A9-B2, A10-B2, A11-B2, A12-B2, A13-B2, A14-B2, A15-B2, A16-B2, A17-B2, A18-B2, A19-B2, A20-B2, A21-B2, A22-B2, A23-B2, A24-B2, A25-B2, A26-B2, A27-B2, A28-B2, A29-B2, A30-B2, A31-B2, A32-B2, A33-B2, A1-B3, A2-B3, A3-B3, A4-B3, A5-B3, A6-B3, A7-B3, A8-B3, A9-B3, A10-B3, A11-B3, A12-B3, A13-B3, A14-B3, A15-B3, A16-B3, A17-B3, A18-B3, A19-B3, A20-B3, A21-B3, A22-B3, A23-B3, A24-B3, A25-B3, A26-B3, A27-B3, A28-B3, A29-B3, A30-B3, A31-B3, A32-B3, A33-B3, A1-B4, A2-B4, A3-B4, A4-B4, A5-B4, A6-B4, A7-B4, A8-B4, A9-B4, A10-B4, A11-B4, A12-B4, A13-B4, A14-B4, A15-B4, A16-B4, A17-B4, A18-B4, A19-B4, A20-B4, A21-B4, A22-B4, A23-B4, A24-B4, A25-B4, A26-B4, A27-B4, A28-B4, A29-B4, A30-B4, A31-B4, A32-B4, A33-B4, A1-B5, A2-B5, A3-B5, A4-B5, A5-B5, A6-B5, A7-B5, A8-B5, A9-B5, A10-B5, A11-B5, A12-B5, A13-B5, A14-B5, A15-B5, A16-B5, A17-B5, A18-B5, A19-B5, A20-B5, A21-B5, A22-B5, A23-B5, A24-B5, A25-B5, A26-B5, A27-B5, A28-B5, A29-B5, A30-B5, A31-B5, A32-B5, A33-B5, A1-B6, A2-B6, A3-B6, A4-B6, A5-B6, A6-B6, A7-B6, A8-B6, A9-B6, A10-B6, A11-B6, A12-B6, A13-B6, A14-B6, A15-B6, A16-B6, A17-B6, A18-B6, A19-B6, A20-B6, A21-B6, A22-B6, A23-B6, A24-B6, A25-B6, A26-B6, A27-B6, A28-B6, A29-B6, A30-B6, A31-B6, A32-B6, A33-B6, A1-B7, A2-B7, A3-B7, A4-B7, A5-B7, A6-B7, A7-B7, A8-B7, A9-B7, A10-B7, A11-B7, A12-B7, A13-B7, A14-B7, A15-B7, A16-B7, A17-B7, A18-B7, A19-B7, A20-B7, A21-B7, A22-B7, A23-B7, A24-B7, A25-B7, A26-B7, A27-B7, A28-B7, A29-B7, A30-B7, A31-B7, A32-B7, A33-B7, A1-B8, A2-B8, A3-B8, A4-B8, A5-B8, A6-B8, A7-B8, A8-B8, A9-B8, A10-B8, A11-B8, A12-B8, A13-B8, A14-B8, A15-B8, A16-B8, A17-B8, A18-B8, A19-B8, A20-B8, A21-B8, A22-B8, A23-B8, A24-B8, A25-B8, A26-B8, A27-B8, A28-B8, A29-B8, A30-B8, A31-B8, A32-B8, A33-B8, A1-B9, A2-B9, A3-B9, A4-B9, A5-B9, A6-B9, A7-B9, A8-B9, A9-B9, A10-B9, A11-B9, A12-B9, A13-B9, A14-B9, A15-B9, A16-B9, A17-B9, A18-B9, A19-B9, A20-B9, A21-B9, A22-B9, A23-B9, A24-B9, A25-B9, A26-B9, A27-B9, A28-B9, A29-B9, A30-B9, A31-B9, A32-B9, A33-B9, A1-B10, A2-B10, A3-B10, A4-B10, A5-B10, A6-B10, A7-B10, A8-B10, A9-B10, A10-B10, A11-B10, A12-B10, A13-B10, A14-B10, A15-B10, A16-B10, A17-B10, A18-B10, A19-B10, A20-B10, A21-

B10, A22-B10, A23-B10, A24-B10, A25-B10, A26-B10, A27-B10, A28-B10, A29-B10, A30-B10, A31-B10, A32-B10, A33-B10, A1-B11, A2-B11, A3-B11, A4-B11, A5-B11, A6-B11, A7-B11, A8-B11, A9-B11, A10-B11, A11-B11, A12-B11, A13-B11, A14-B11, A15-B11, A16-B11, A17-B11, A18-B11, A19-B11, A20-B11, A21-B11, A22-B11, A23-B11, A24-B11, A25-B11, A26-B11, A27-B11, A28-B11, A29-B11, A30-B11, A31-B11, A32-B11, A33-B11, A1-B12, A2-B12, A3-B12, A4-B12, A5-B12, A6-B12, A7-B12, A8-B12, A9-B12, A10-B12, A11-B12, A12-B12, A13-B12, A14-B12, A15-B12, A16-B12, A17-B12, A18-B12, A19-B12, A20-B12, A21-B12, A22-B12, A23-B12, A24-B12, A25-B12, A26-B12, A27-B12, A28-B12, A29-B12, A30-B12, A31-B12, A32-B12, A33-B12, A1-B13, A2-B13, A3-B13, A4-B13, A5-B13, A6-B13, A7-B13, A8-B13, A9-B13, A10-B13, A11-B13, A12-B13, A13-B13, A14-B13, A15-B13, A16-B13, A17-B13, A18-B13, A19-B13, A20-B13, A21-B13, A22-B13, A23-B13, A24-B13, A25-B13, A26-B13, A27-B13, A28-B13, A29-B13, A30-B13, A31-B13, A32-B13, A33-B13, A1-B14, A2-B14, A3-B14, A4-B14, A5-B14, A6-B14, A7-B14, A8-B14, A9-B14, A10-B14, A11-B14, A12-B14, A13-B14, A14-B14, A15-B14, A16-B14, A17-B14, A18-B14, A19-B14, A20-B14, A21-B14, A22-B14, A23-B14, A24-B14, A25-B14, A26-B14, A27-B14, A28-B14, A29-B14, A30-B14, A31-B14, A32-B14, A33-B14, A1-B15, A2-B15, A3-B15, A4-B15, A5-B15, A6-B15, A7-B15, A8-B15, A9-B15, A10-B15, A11-B15, A12-B15, A13-B15, A14-B15, A15-B15, A16-B15, A17-B15, A18-B15, A19-B15, A20-B15, A21-B15, A22-B15, A23-B15, A24-B15, A25-B15, A26-B15, A27-B15, A28-B15, A29-B15, A30-B15, A31-B15, A32-B15, A33-B15, A1-B16, A2-B16, A3-B16, A4-B16, A5-B16, A6-B16, A7-B16, A8-B16, A9-B16, A10-B16, A11-B16, A12-B16, A13-B16, A14-B16, A15-B16, A16-B16, A17-B16, A18-B16, A19-B16, A20-B16, A21-B16, A22-B16, A23-B16, A24-B16, A25-B16, A26-B16, A27-B16, A28-B16, A29-B16, A30-B16, A31-B16, A32-B16, A33-B16, A1-B17, A2-B17, A3-B17, A4-B17, A5-B17, A6-B17, A7-B17, A8-B17, A9-B17, A10-B17, A11-B17, A12-B17, A13-B17, A14-B17, A15-B17, A16-B17, A17-B17, A18-B17, A19-B17, A20-B17, A21-B17, A22-B17, A23-B17, A24-B17, A25-B17, A26-B17, A27-B17, A28-B17, A29-B17, A30-B17, A31-B17, A32-B17, A33-B17, A1-B18, A2-B18, A3-B18, A4-B18, A5-B18, A6-B18, A7-B18, A8-B18, A9-B18, A10-B18, A11-B18, A12-B18, A13-B18, A14-B18, A15-B18, A16-B18, A17-B18, A18-B18, A19-B18, A20-B18, A21-B18, A22-B18, A23-B18, A24-B18, A25-B18, A26-B18, A27-B18, A28-B18, A29-B18, A30-B18, A31-B18, A32-B18, A33-B18, A1-B19, A2-B19, A3-B19, A4-B19, A5-B19, A6-B19, A7-B19, A8-B19, A9-B19, A10-B19, A11-B19, A12-B19, A13-B19, A14-B19, A15-B19, A16-B19, A17-B19, A18-B19, A19-B19, A20-B19, A21-B19, A22-B19, A23-B19, A24-B19, A25-B19, A26-B19, A27-B19, A28-B19, A29-B19, A30-B19, A31-B19, A32-B19, A33-B19, A1-B20, A2-B20, A3-B20, A4-B20, A5-B20, A6-B20, A7-B20, A8-B20, A9-B20, A10-B20, A11-B20, A12-B20, A13-B20, A14-B20, A15-B20, A16-B20, A17-B20, A18-B20, A19-B20, A20-B20, A21-B20, A22-B20, A23-B20, A24-B20, A25-B20, A26-B20, A27-B20, A28-B20, A29-B20, A30-B20, A31-B20, A32-B20, A33-B20, A1-B21, A2-B21, A3-B21, A4-B21, A5-B21, A6-B21, A7-B21, A8-B21, A9-B21, A10-B21, A11-B21, A12-B21, A13-B21, A14-B21, A15-B21, A16-B21, A17-B21, A18-B21, A19-B21, A20-B21, A21-B21, A22-B21, A23-B21, A24-B21, A25-B21, A26-B21, A27-B21, A28-B21, A29-B21, A30-B21, A31-B21, A32-B21, A33-B21, A1-B22, A2-B22, A3-B22, A4-B22, A5-B22, A6-B22, A7-B22, A8-B22, A9-B22, A10-B22, A11-B22, A12-B22, A13-B22, A14-B22, A15-B22, A16-B22, A17-B22, A18-B22, A19-B22, A20-B22, A21-B22, A22-B22, A23-B22, A24-B22, A25-B22, A26-B22, A27-B22, A28-B22, A29-B22, A30-B22, A31-B22, A32-B22, A33-B22, A1-B23, A2-B23, A3-B23, A4-B23, A5-B23, A6-B23, A7-B23, A8-B23, A9-B23, A10-B23, A11-B23, A12-B23, A13-B23, A14-B23, A15-B23, A16-B23, A17-B23, A18-B23, A19-B23, A20-B23, A21-B23, A22-B23, A23-B23, A24-B23, A25-B23, A26-B23, A27-B23, A28-B23, A29-B23, A30-B23, A31-B23, A32-B23, A33-B23, A1-B24, A2-B24, A3-B24, A4-B24, A5-B24, A6-B24, A7-B24, A8-B24, A9-B24, A10-B24, A11-B24, A12-B24, A13-B24, A14-B24, A15-B24, A16-B24, A17-B24, A18-B24, A19-B24, A20-B24, A21-B24, A22-B24, A23-B24, A24-B24, A25-B24, A26-B24, A27-B24, A28-B24, A29-B24, A30-B24, A31-B24, A32-B24, A33-B24, A1-B25, A2-B25, A3-B25, A4-B25, A5-B25, A6-B25, A7-B25, A8-B25, A9-B25, A10-B25, A11-B25, A12-B25, A13-B25, A14-B25, A15-B25, A16-B25, A17-B25, A18-B25, A19-B25, A20-B25, A21-B25, A22-B25, A23-B25, A24-B25, A25-B25, A26-B25, A27-B25, A28-B25, A29-B25, A30-B25, A31-B25, A32-B25, A33-B25, A1-B26, A2-B26, A3-B26, A4-B26, A5-B26, A6-B26, A7-B26, A8-B26, A9-B26, A10-B26, A11-B26, A12-B26, A13-B26, A14-B26, A15-B26, A16-B26, A17-B26, A18-B26, A19-B26, A20-B26, A21-B26, A22-B26, A23-B26, A24-B26, A25-B26, A26-B26, A27-B26, A28-B26, A29-B26, A30-B26, A31-B26, A32-B26, A33-B26, A1-B27, A2-B27, A3-B27, A4-B27, A5-B27, A6-B27, A7-B27, A8-B27, A9-B27, A10-B27, A11-B27, A12-B27, A13-B27, A14-B27, A15-B27, A16-B27, A17-B27, A18-B27, A19-B27, A20-B27, A21-B27, A22-B27, A23-B27, A24-B27, A25-B27, A26-B27, A27-B27, A28-B27, A29-B27, A30-B27, A31-B27, A32-B27, A33-B27, A1-B28, A2-B28, A3-B28, A4-B28, A5-B28, A6-B28, A7-B28, A8-B28, A9-B28, A10-B28, A11-B28, A12-B28, A13-B28, A14-B28, A15-B28, A16-B28, A17-B28, A18-B28, A19-B28, A20-B28, A21-B28, A22-B28, A23-B28, A24-B28, A25-B28, A26-B28, A27-B28, A28-B28, A29-B28, A30-B28, A31-B28, A32-B28, A33-B28, A1-B29, A2-B29, A3-B29, A4-B29, A5-B29, A6-B29, A7-B29, A8-B29, A9-B29, A10-B29, A11-B29, A12-B29, A13-B29, A14-B29, A15-B29, A16-B29, A17-B29, A18-B29, A19-B29, A20-B29, A21-B29, A22-B29, A23-B29, A24-B29, A25-B29, A26-B29, A27-B29, A28-B29, A29-B29, A30-B29, A31-B29, A32-B29, A33-B29, A1-B30, A2-B30, A3-B30, A4-B30, A5-B30, A6-B30, A7-B30, A8-B30, A9-B30, A10-B30, A11-B30, A12-B30, A13-B30, A14-B30, A15-B30, A16-B30, A17-B30, A18-B30, A19-B30, A20-B30, A21-B30, A22-B30, A23-B30, A24-B30, A25-B30, A26-B30, A27-B30, A28-B30, A29-B30, A30-B30, A31-B30, A32-B30, A33-B30, A1-B31, A2-B31, A3-B31, A4-B31, A5-B31, A6-B31, A7-B31, A8-B31, A9-B31, A10-B31, A11-B31, A12-B31, A13-B31, A14-B31, A15-B31, A16-B31, A17-B31, A18-B31, A19-B31, A20-B31, A21-B31, A22-B31, A23-B31, A24-B31, A25-B31, A26-B31, A27-B31, A28-B31, A29-B31, A30-B31, A31-B31, A32-B31, A33-B31, A1-B32, A2-B32, A3-B32, A4-B32, A5-B32, A6-B32, A7-B32, A8-B32, A9-B32, A10-B32, A11-B32, A12-B32, A13-B32, A14-B32, A15-B32, A16-B32, A17-B32, A18-B32, A19-B32, A20-B32, A21-B32, A22-B32, A23-B32, A24-B32, A25-B32, A26-B32, A27-B32, A28-B32, A29-B32, A30-B32, A31-B32, A32-B32, A33-B32, A1-B33, A2-B33, A3-B33, A4-B33, A5-B33, A6-B33, A7-B33, A8-B33, A9-B33, A10-B33, A11-B33, A12-B33, A13-B33, A14-B33, A15-B33, A16-B33, A17-B33, A18-B33, A19-B33, A20-B33, A21-B33, A22-B33, A23-B33, A24-B33,

A25-B33, A26-B33, A27-B33, A28-B33, A29-B33, A30-B33, A31-B33, A32-B33, A33-B33, A1-B34, A2-B34, A3-B34, A4-B34, A5-B34, A6-B34, A7-B34, A8-B34, A9-B34, A10-B34, A11-B34, A12-B34, A13-B34, A14-B34, A15-B34, A16-B34, A17-B34, A18-B34, A19-B34, A20-B34, A21-B34, A22-B34, A23-B34, A24-B34, A25-B34, A26-B34, A27-B34, A28-B34, A29-B34, A30-B34, A31-B34, A32-B34, A33-B34, A1-B35, A2-B35, A3-B35, A4-B35, A5-B35, A6-B35, A7-B35, A8-B35, A9-B35, A10-B35, A11-B35, A12-B35, A13-B35, A14-B35, A15-B35, A16-B35, A17-B35, A18-B35, A19-B35, A20-B35, A21-B35, A22-B35, A23-B35, A24-B35, A25-B35, A26-B35, A27-B35, A28-B35, A29-B35, A30-B35, A31-B35, A32-B35, A33-B35, A1-B36, A2-B36, A3-B36, A4-B36, A5-B36, A6-B36, A7-B36, A8-B36, A9-B36, A10-B36, A11-B36, A12-B36, A13-B36, A14-B36, A15-B36, A16-B36, A17-B36, A18-B36, A19-B36, A20-B36, A21-B36, A22-B36, A23-B36, A24-B36, A25-B36, A26-B36, A27-B36, A28-B36, A29-B36, A30-B36, A31-B36, A32-B36, A33-B36, A1-B37, A2-B37, A3-B37, A4-B37, A5-B37, A6-B37, A7-B37, A8-B37, A9-B37, A10-B37, A11-B37, A12-B37, A13-B37, A14-B37, A15-B37, A16-B37, A17-B37, A18-B37, A19-B37, A20-B37, A21-B37, A22-B37, A23-B37, A24-B37, A25-B37, A26-B37, A27-B37, A28-B37, A29-B37, A30-B37, A31-B37, A32-B37, A33-B37, A1-B38, A2-B38, A3-B38, A4-B38, A5-B38, A6-B38, A7-B38, A8-B38, A9-B38, A10-B38, A11-B38, A12-B38, A13-B38, A14-B38, A15-B38, A16-B38, A17-B38, A18-B38, A19-B38, A20-B38, A21-B38, A22-B38, A23-B38, A24-B38, A25-B38, A26-B38, A27-B38, A28-B38, A29-B38, A30-B38, A31-B38, A32-B38, A33-B38, A1-B39, A2-B39, A3-B39, A4-B39, A5-B39, A6-B39, A7-B39, A8-B39, A9-B39, A10-B39, A11-B39, A12-B39, A13-B39, A14-B39, A15-B39, A16-B39, A17-B39, A18-B39, A19-B39, A20-B39, A21-B39, A22-B39, A23-B39, A24-B39, A25-B39, A26-B39, A27-B39, A28-B39, A29-B39, A30-B39, A31-B39, A32-B39, and A33-B39. The A moiety is joined to the B moiety to form the ester bond as shown in Formula III above.

A pyrethroid prepared according to the methods of the invention can have, for example, a structure selected from:

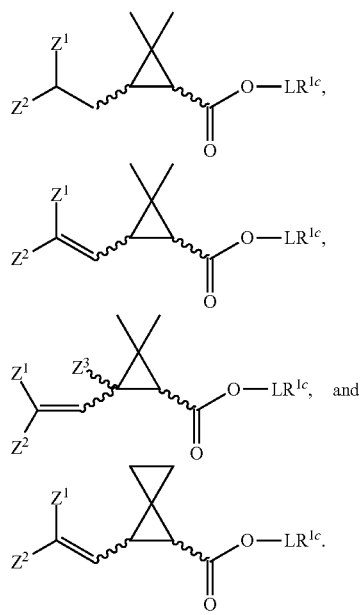

$Z^1$, $Z^2$, and $Z^3$ are independently selected from H, halo, optionally substituted $C_{1-6}$ alkyl, and optionally substituted $C_{6-10}$ aryl. $Z^1$ and $Z^2$ can also be taken together to form an optionally substituted 5- to 6-membered cycloalkyl or heterocyclyl group.

In some embodiments, the methods of the invention can be used to prepare pyrethroid intermediate compounds that can be converted to the pyrethroid compounds described above. Alkyl esters of cyclopropanecarboxylic acid and cyclopropanecarboxylic acid derivatives can be converted to a variety of pyrethroid compounds via reaction with appropriate alcohols.

Accordingly, some embodiments of the invention provide methods as wherein the cyclopropanation product is a compound according to formula II:

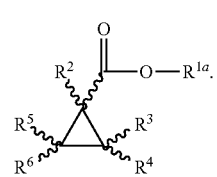

For compounds of formula II: $R^{1a}$ is $C_{1-6}$ alkyl and $R^2$ is selected from H and optionally substituted $C_{6-10}$ aryl. In some embodiments, $R^2$ is H. In some embodiments, the compound of formula II is selected from:

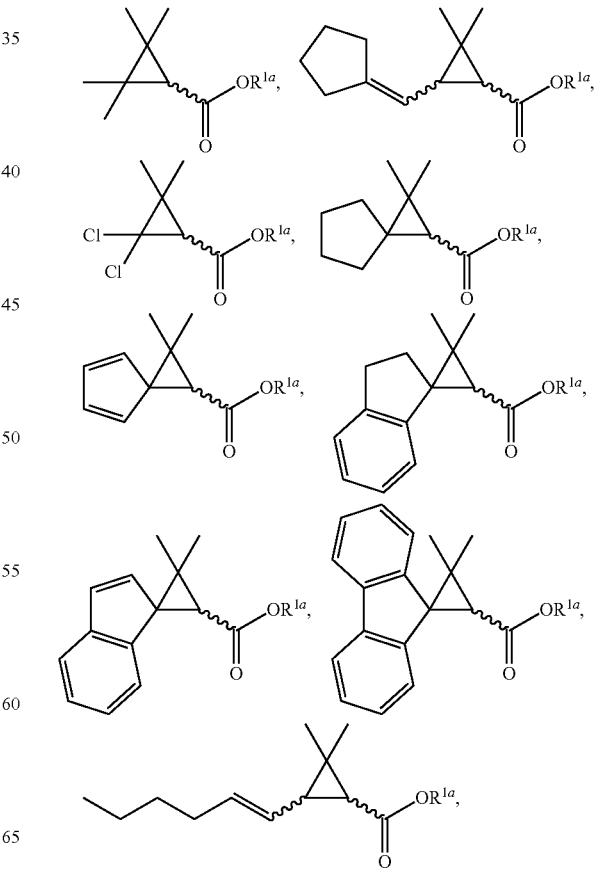

-continued
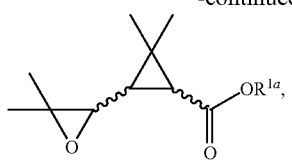
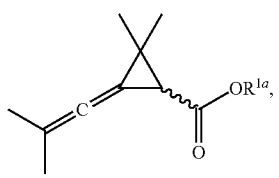
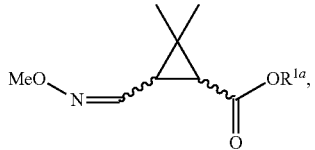
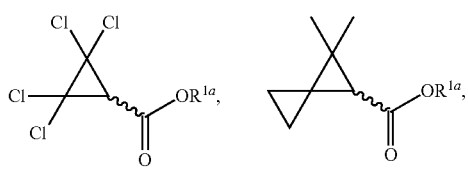
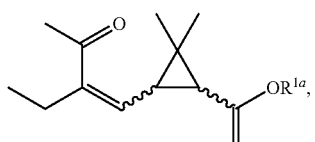
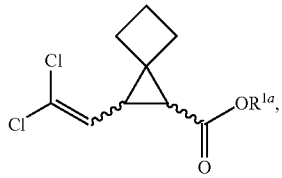
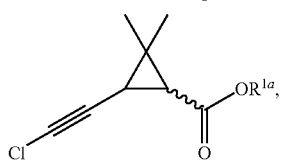
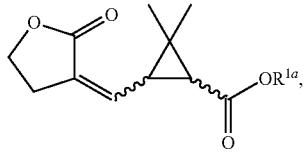
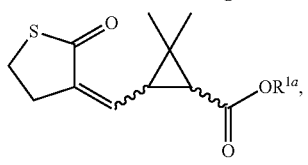
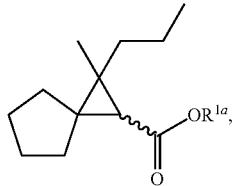 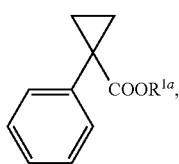
-continued
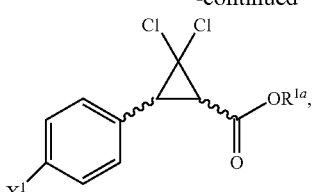
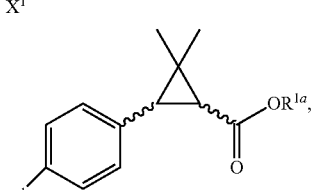
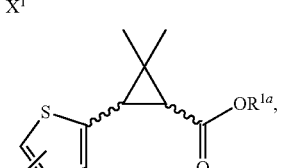
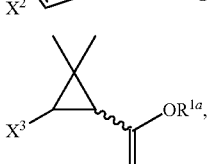
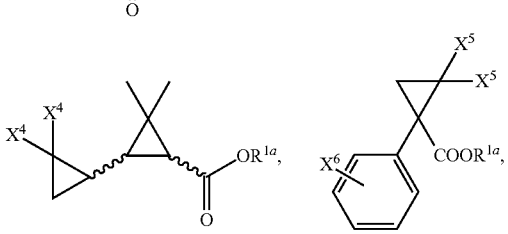
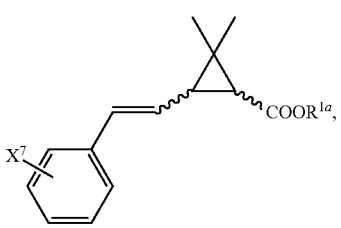
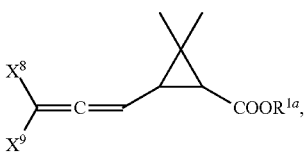
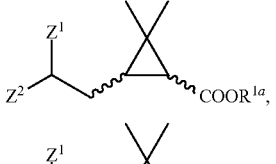
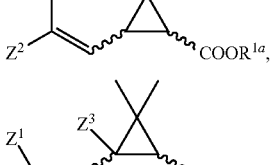
 and -continued

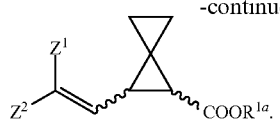

In such embodiments, X' is selected from H, optionally substituted $C_{1-6}$ alkyl, halo$C_{1-6}$ alkyl, optionally substituted $C_{1-6}$ alkoxy, optionally substituted $C_{1-6}$ alkylthio, $C_{1-6}$ alkylsilyl, halo, and cyano. $X^2$ is selected from H, chloro, and methyl. $X^3$ is selected from H, methyl, halo, and CN. Each $X^4$ is independently halo. Each $X^5$ is independently selected from methyl and halo. $X^6$ is selected from halo, optionally substituted $C_{1-6}$ alkyl, and optionally substituted $C_{1-6}$ alkoxy. $X^7$ is selected from H, methyl, and halo. $X^8$ is selected from H, halo, and optionally substituted $C_{1-6}$ alkyl. $X^9$ is selected from H, halo, optionally substituted $C_{1-6}$ alkyl, C(O)O—($C_{1-6}$ alkyl), C(O)—N($C_{1-6}$ alkyl)$_2$, and cyano. Z', $Z^2$, and $Z^3$ are independently selected from H, halo, optionally substituted $C_{1-6}$ alkyl, and optionally substituted $C_{6-10}$ aryl. Z' and $Z^2$ can also be taken together to form an optionally substituted 5- to 6-membered cycloalkyl or heterocyclyl group In some embodiments, the methods of the invention include converting the cyclopropanation product according to formula II to a compound according to formula III:

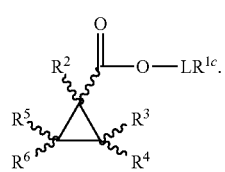

(III)

For compounds of formula III, L is selected from a bond, —C(R$^L$)$_2$—, and —NR$^L$—C(R$^L$)$_2$—. Each R$^L$ is independently selected from H, —CN, and —SO$_2$. R$^{1C}$ is selected from optionally substituted $C_{6-10}$ aryl, optionally substituted 6- to 10-membered heteroraryl, and optionally substituted 6- to 10-membered heterocyclyl. In some embodiments, L in the compounds of formula III is selected from a bond, —CH$_2$—, —CH(CN)—, and —N(SO$_2$)—CH$_2$.

In some embodiments, the moiety L-R$^{1C}$ in the compounds according to formula III has a structure selected from:

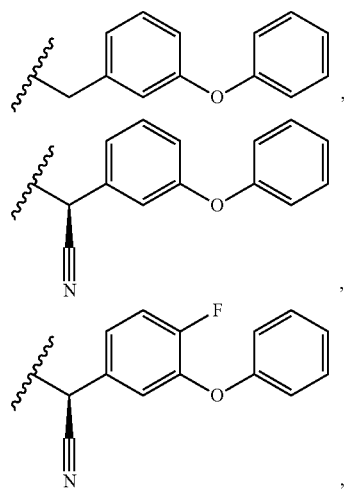

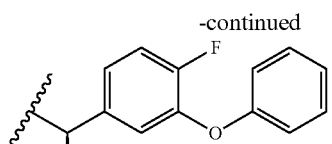

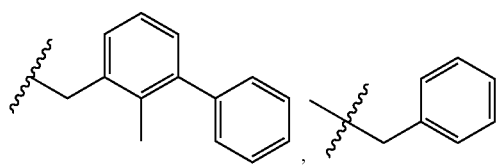

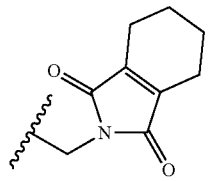

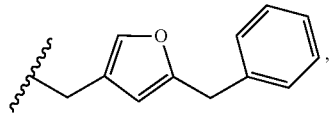

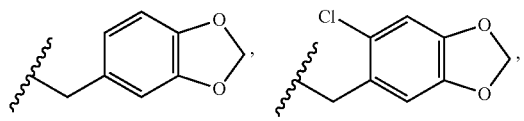

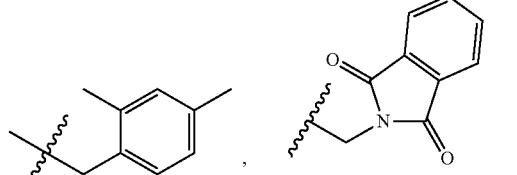

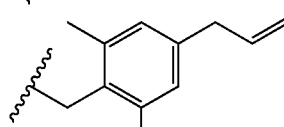

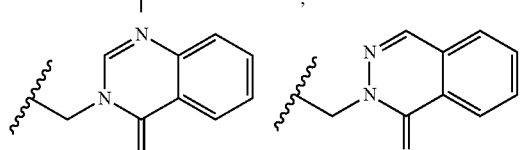

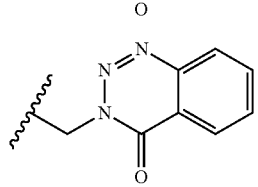

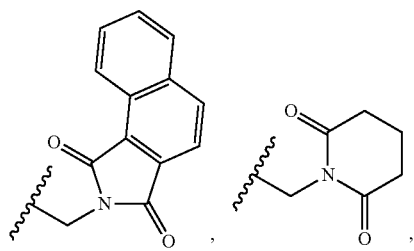

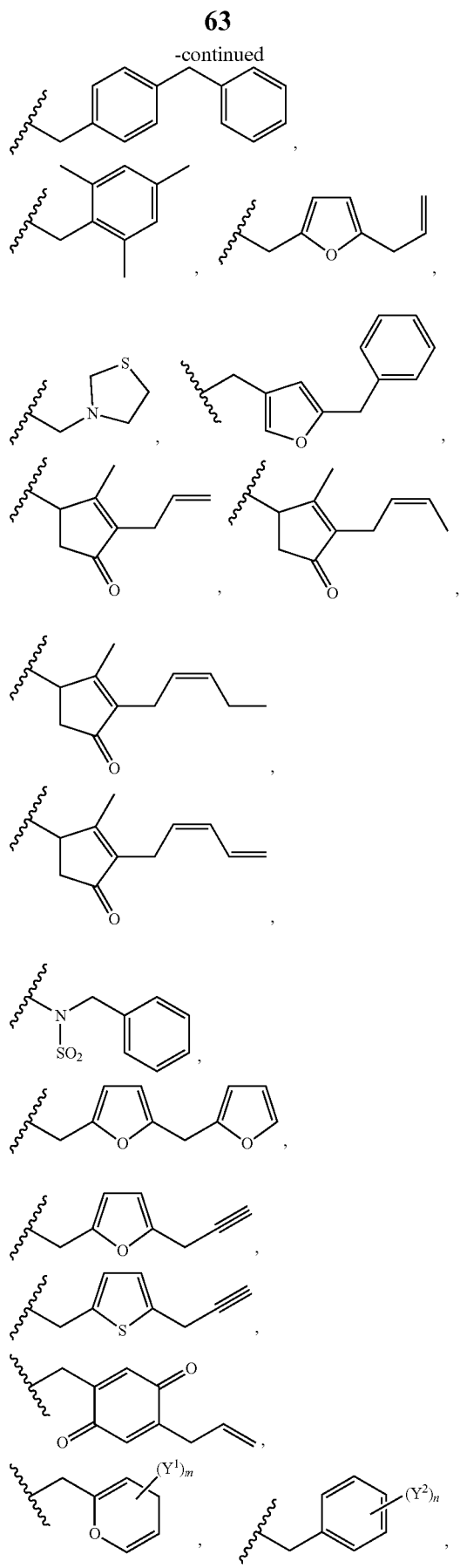

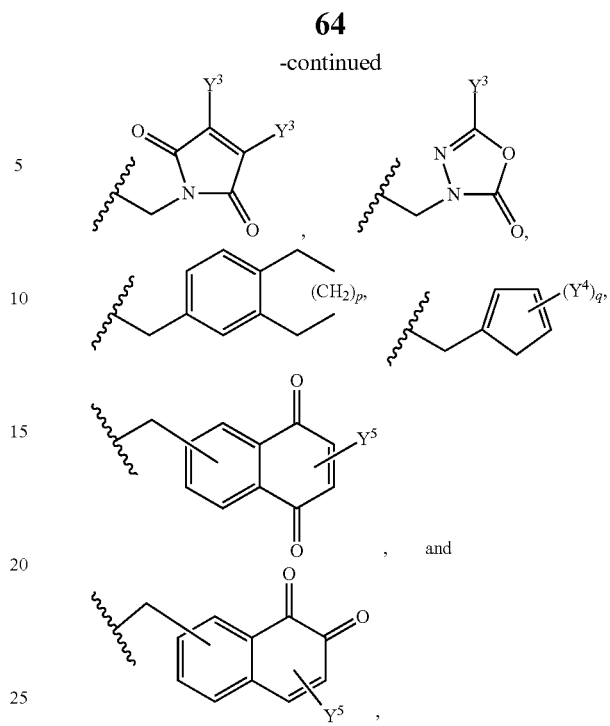

In such embodiments, each $Y^1$ is independently selected from optionally substituted $C_{1-6}$ alkyl, optionally substituted $C_{2-6}$ alkenyl, optionally substituted $C_{2-6}$ alkynyl, phenyl, and (phenyl)$C_{1-6}$ alkoxy. Each $Y^2$ is independently selected from halo, optionally substituted $C_{1-6}$ alkyl, optionally substituted $C_{2-6}$ alkenyl, optionally substituted $C_{1-6}$ alkoxy, and nitro. Each $Y^3$ is independently optionally substituted $C_{1-6}$ alkyl. Each $Y^4$ is independently selected from optionally substituted $C_{1-6}$ alkyl, optionally substituted $C_{2-6}$ alkenyl, optionally substituted $C_{2-6}$ alkynyl, $C_{6-10}$ aryl-$C_{1-6}$ alkyl, furfuryl, $C_{1-6}$ alkoxy, ($C_{2-6}$ alkenyl)oxy, $C_{1-12}$ acyl, and halo. $Y^5$ is selected from the group consisting of optionally substituted $C_{1-6}$ alkyl, optionally substituted $C_{1-6}$ alkoxy, and halo. The subscript m is an integer from 1 to 3, the subscript n is an integer from 1 to 5, the subscript p is an integer from 1 to 4, and the subscript q is an integer from 0 to 3. The wavy line at the left of each structure represents the point of connection between the moiety -L-R$^{1c}$ and the rest of the compound according to formula III.

In some embodiments, the compound of formula III is selected from:

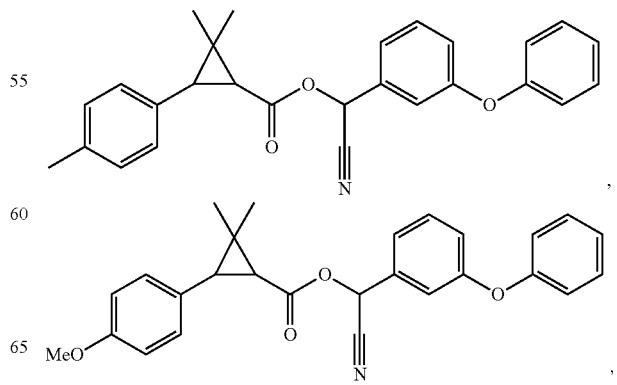

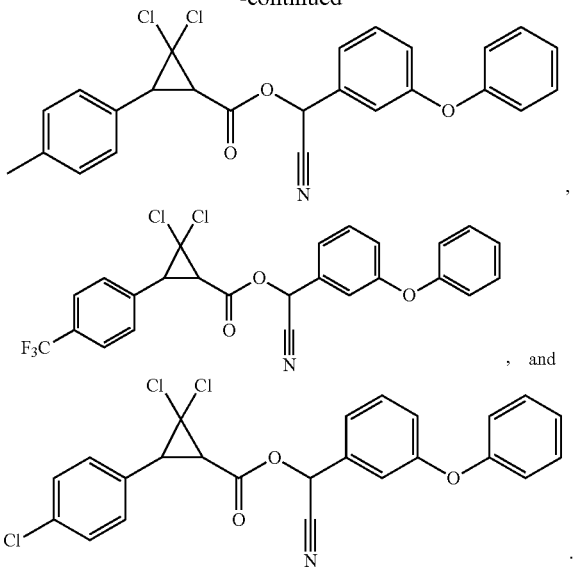

In some embodiments, the compound of formula III is resmethrin.

As for the pyrethroids discussed herein, a number of other compounds can be synthesized via processes that include a cyclopropanation product. Such processes are generalized in Scheme 1 showing the enzyme-catalyzed formation of a cyclopropanation product from an olefinic substrate and a diazo reagent, followed by chemical conversion of to a final product such as a pharmaceutical agent. Depending on the particular final product, the process can include conversion of the cyclopropanation product to one or more synthetic intermediates prior to preparation of the final product. Non-limiting examples of cyclopropanation products useful in such processes are summarized in Table 6.

Scheme 1

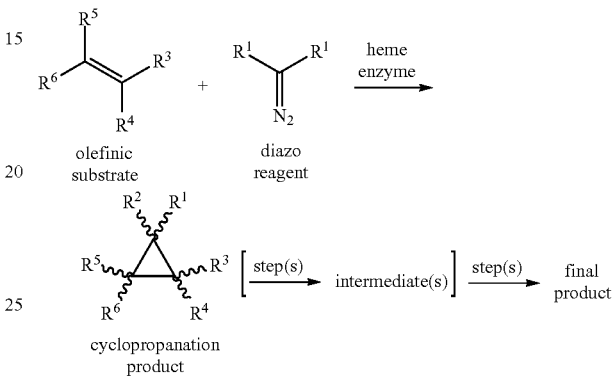

TABLE 6

Cyclopropanation for synthesis of intermediates en route to biologically active compounds.

| Olefinic Substrate | Diazo Reagent | Cyclopropanation Product/Intermediate | Final Product |
|---|---|---|---|
|  |  |  | milnacipran |
|  |  |  | milnacipran |
|  |  |  | milnacipran; bicifidine; 1-(3,4-dichlorophenyl)-3-azabicyclo[3.1.0]hexane |

TABLE 6-continued

Cyclopropanation for synthesis of intermediates en route to biologically active compounds.

| Olefinic Substrate | Diazo Reagent | Cyclopropanation Product/Intermediate | Final Product |
|---|---|---|---|
| | | | milnacipran; bicifidine; 1-(3,4-dichloro-phenyl)-3-azabicyclo[3.1.0]hexane |
| | | | cilastain |
| | | | boceprevir |
| | | | boceprevir |
| | | | boceprevir |
| | | | 1R,2S-fluoro-cyclopropyl-amine, sitafloxacin |
| | | | 1R,2S-fluoro-cyclopropyl-amine, sitafloxacin |

TABLE 6-continued

Cyclopropanation for synthesis of intermediates en route to biologically active compounds.

| Olefinic Substrate | Diazo Reagent | Cyclopropanation Product/Intermediate | Final Product |
|---|---|---|---|
| | | | anthoplalone, norantho-plone |
| | | | odanacatib |
| | | | odanacatib |
| | | | montekulast |
| | | | montekulast |
| | | | carene |
| | | | pyrethrin II |

In some embodiments, the cyclopropanation product is a compound having a structure according to the formula:

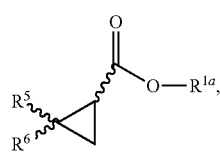

wherein $R^{1a}$ is optionally substituted $C_{1-6}$ alkyl, and $R^5$ and $R^6$ are independently selected from H, optionally substituted $C_{1-6}$ alkyl, optionally substituted $C_{6-10}$ aryl, $C(O)N(R^7)_2$, $C(O)OR^8$ and $NR^7C(O)R^8$.

In some embodiments, the cyclopropanation product has the structure selected from:

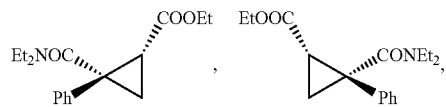

-continued

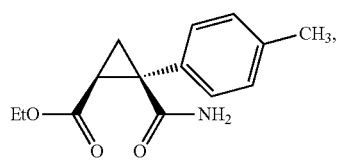

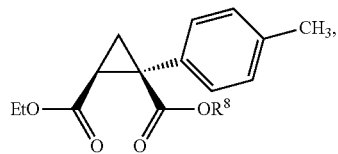

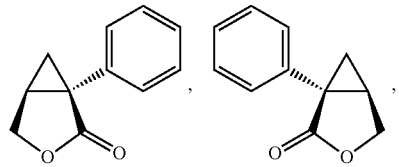

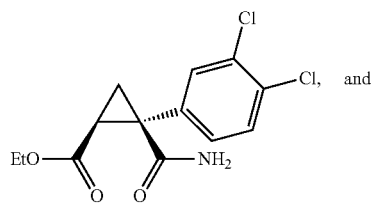

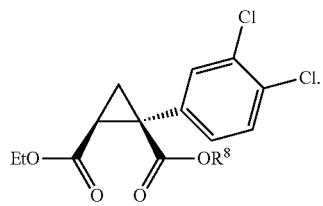

In such embodiments, the methods of the invention can include converting the cyclopropanation product to a compound selected from milcanipran, levomilnacipran, bicifadine, and 1-(3,4-dichlorophenyl)-3-azabicyclo[3.1.0]hexane.

The methods of the invention can be used to prepare several different types of compounds having cyclopropane functional groups. The compounds include, but are not limited to, pharmaceutical agents having chiral cyclopropane moieties, pharmaceutical agents having achiral cyclopropane moieties, insecticides, plant hormones, flavors, scents, and fatty acids.

In some embodiments, the methods of the invention are used to prepare a compound selected from:

,

-continued

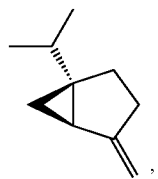,

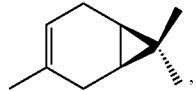,

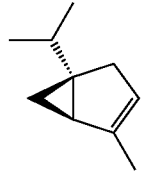,

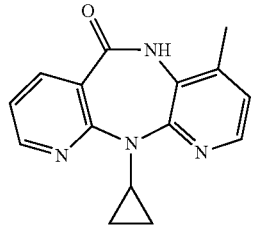,

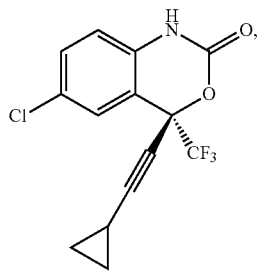,

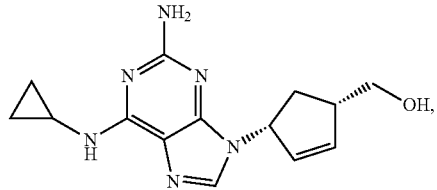,

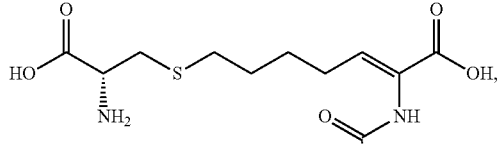,

,

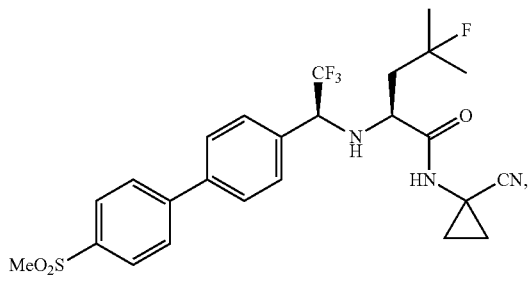

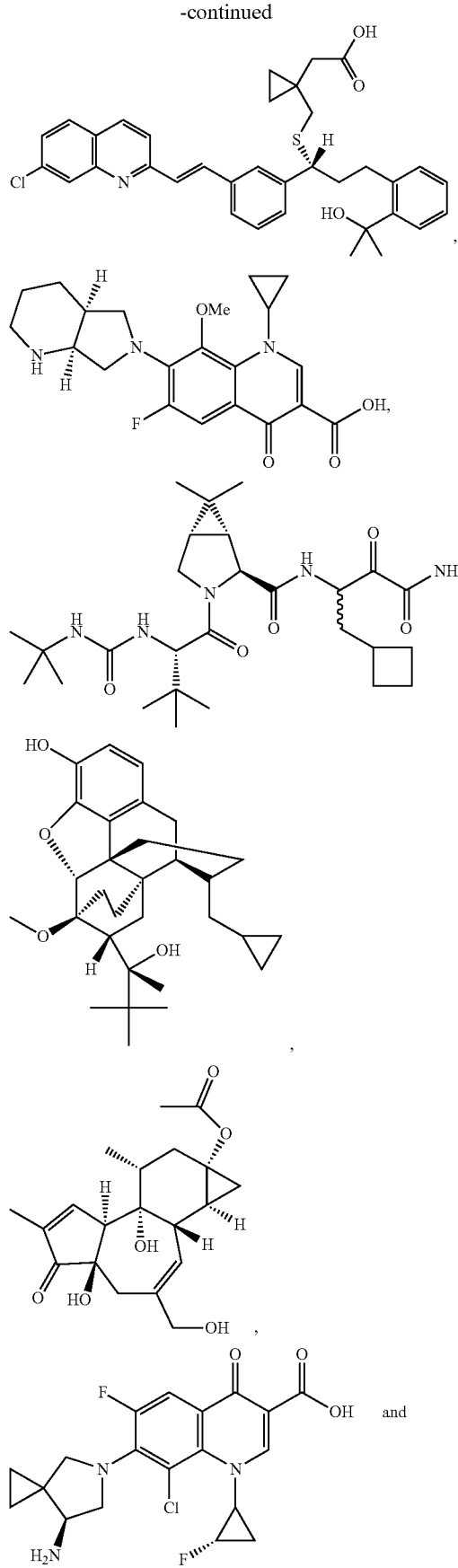
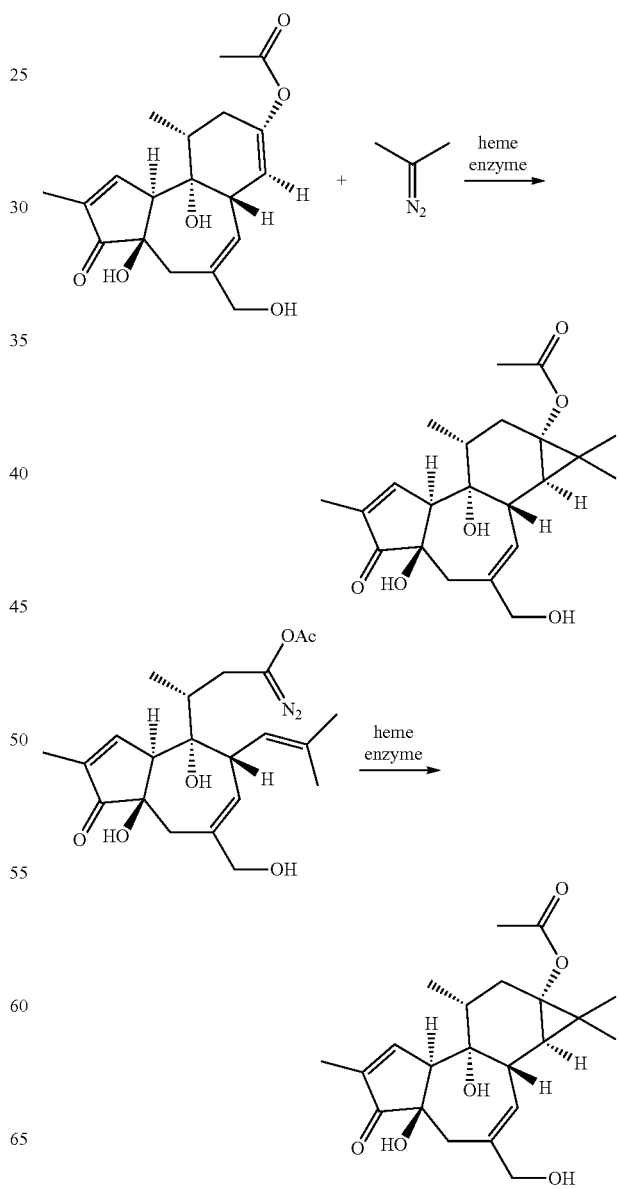
Synthesis of prostratin, a protein kinase C activator, is shown as a non-limiting example in Scheme 2. The prostratin cyclopropane moiety can be installed by heme enzyme-catalyzed intramolecular or intermolecular cyclopropanation reactions.
Scheme 2

Some embodiments of the invention provide a method as described above, wherein the olefinic substrate is selected from the group consisting of an alkene, a cycloalkane, and an arylalkene. In some embodiments, the olefinic substrate is an arylalkene. In some embodiments, the arylalkene is a styrene.

In some embodiments, the styrene has the formula:

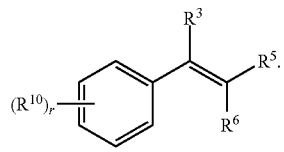

$R^3$ is selected from the H, optionally substituted $C_1$-$C_6$ alkyl, optionally substituted $C_1$-$C_6$ alkoxy, $C(O)N(R^7)_2$, $C(O)OR^8$, $N(R^9)_2$, halo, hydroxy, and cyano. $R^5$ and $R^6$ are independently selected from H, optionally substituted $C_{1-6}$ alkyl, and halo. $R^{10}$ is selected from optionally substituted $C_1$-$C_6$ alkyl, optionally substituted $C_1$-$C_6$ alkoxy, halo, and haloalkyl, and the subscript r is an integer from 0 to 2.

In general, the diazo reagents useful in the methods of the invention have the structure:

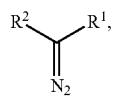

wherein $R^1$ and $R^2$ are defined as for the cyclopropanation products. Any diazoreagent can be added to the reaction as a reagent itself, or the diazoreagent can be prepared in situ.

In some embodiments, the diazo reagent is selected from an α-diazoester, an α-diazoamide, an α-diazonitrile, an α-diazoketone, an α-diazoaldehyde, and an α-diazosilane. In some embodiments, the diazo reagent has a formula selected from:

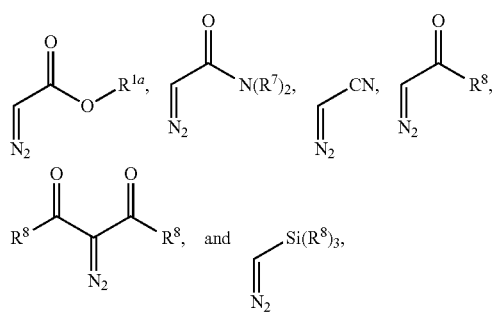

wherein $R^{1a}$ is selected from H and optionally substituted $C_1$-$C_6$ alkyl; and each $R^7$ and $R^8$ is independently selected from H, optionally substituted $C_{1-12}$ alkyl, optionally substituted $C_{2-12}$ alkenyl, and optionally substituted $C_{6-10}$ aryl.

In some embodiments, the diazo reagent is selected from the group consisting of diazomethane, ethyl diazoacetate, and (trimethylsilyl)diazomethane.

In some embodiments, the diazo reagent is an α-diazoester. In some embodiments, the diazo reagent has the formula:

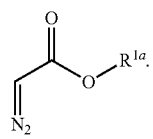

In some embodiments, the cyclopropanation product has a formula selected from:

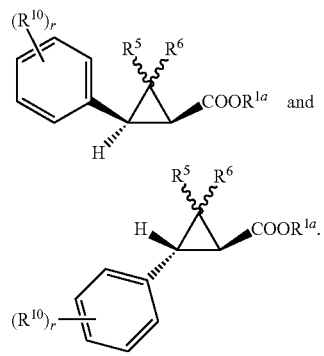

One of skill in the art will appreciate that stereochemical configuration of the cyclopropanation product will be determined in part by the orientation of the diazo reagent with respect to the position of an olefinic substrate such as styrene during the cyclopropanation step. For example, any substituent originating from the olefinic substrate can be positioned on the same side of the cyclopropyl ring as a substituent origination from the diazo reagent. Cyclopropanation products having this arrangement are called "cis" compounds or "Z" compounds. Any substituent originating from the olefinic substrate and any substituent originating from the diazo reagent can also be on opposite sides of the cyclopropyl ring. Cyclopropanation products having this arrangement are called "trans" compounds or "E" compounds. An example of such arrangements is shown in the reaction scheme of FIG. 29.

Figure 29:
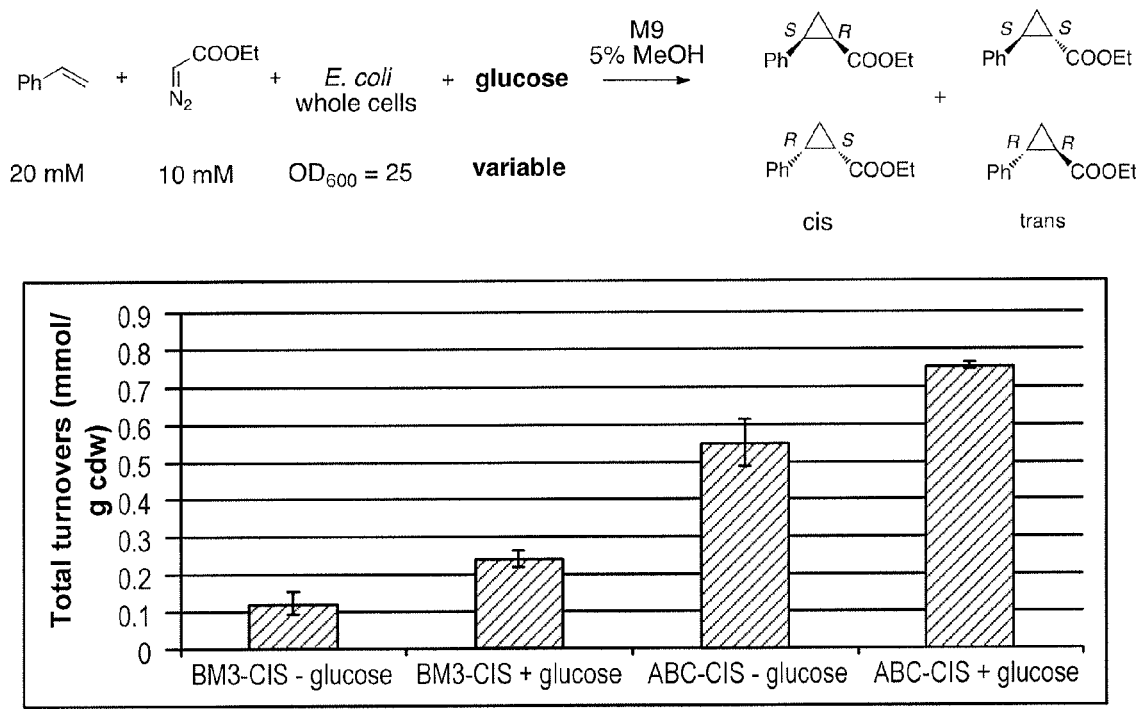
FIG. 29 illustrates the effect of adding exogenous glucose (2 mM) on olefin cyclopropanation catalyzed by E. coli whole cells expressing 9-10A-TS-F87V-T268A (also called BM3-CIS and P450$_{BM3}$-CIS) or BM3-CIS-C400S (also called ABC-CIS and P411$_{BM3}$-CIS).

As shown in FIG. 29, two cis isomers and two trans isomers can arise from the reaction of an olefinic substrate with a diazo reagent. The two cis isomers are enantiomers with respect to one another, in that the structures are non-superimposable mirror images of each other. Similarly, the two trans isomers are enantiomers. One of skill in the art will appreciate that the absolute stereochemistry of a cyclopropanation product—that is, whether a given chiral center exhibits the right-handed "R" configuration or the left-handed "S" configuration—will depend on factors including the structures of the particular olefinic substrate and diazo reagent used in the reaction, as well as the identity of the enzyme. This is also true for the relative stereochemistry—that is, whether a cyclopropanation product exhibits a cis or trans configuration—as well as for the distribution of cyclopropanation product mixtures will also depend on such factors.

In general, cyclopropanation product mixtures have cis:trans ratios ranging from about 1:99 to about 99:1. The cis:trans ratio can be, for example, from about 1:99 to about 1:75, or from about 1:75 to about 1:50, or from about 1:50 to about 1:25, or from about 99:1 to about 75:1, or from about 75:1 to about 50:1, or from about 50:1 to about 25:1. The cis:trans ratio can be from about 1:80 to about 1:20, or from about 1:60 to about 1:40, or from about 80:1 to about 20:1 or from about 60:1 to about 40:1. The cis:trans ratio can be about 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, or about 1:95. The cis:trans ratio can be about 5:1, 10:1, 15:1, 20:1, 25:1, 30:1, 35:1, 40:1, 45:1, 50:1, 55:1, 60:1, 65:1, 70:1, 75:1, 80:1, 85:1, 90:1, or about 95:1.

The distribution of a cyclopropanation product mixture can be assessed in terms of the enantiomeric excess, or "% ee," of the mixture. The enantiomeric excess refers to the difference in the mole fractions of two enantiomers in a mixture. Taking the reaction scheme in FIG. 29 as a non-limiting example, for instance, the enantiomeric excess of the "E" or trans (R,R) and (S,S) enantiomers can be calculated using the formula: % $ee_E = [(\chi_{R,R} - \chi_{S,S})/(\chi_{R,R} + \chi_{S,S})] \times 100\%$, wherein $\chi$ is the mole fraction for a given enantiomer. The enantiomeric excess of the "Z" or cis enantiomers (% $ee_Z$) can be calculated in the same manner.

In general, cyclopropanantion product mixtures exhibit % ee values ranging from about 1% to about 99%, or from about −1% to about −99%. The closer a given % ee value is to 99% (or −99%), the purer the reaction mixture is. The % ee can be, for example, from about −90% to about 90%, or from about −80% to about 80%, or from about −70% to about 70%, or from about −60% to about 60%, or from about −40% to about 40%, or from about −20% to about 20%. The % ee can be from about 1% to about 99%, or from about 20% to about 80%, or from about 40% to about 60%, or from about 1% to about 25%, or from about 25% to about 50%, or from about 50% to about 75%. The % ee can be from about −1% to about −99%, or from about −20% to about −80%, or from about −40% to about −60%, or from about −1% to about −25%, or from about −25% to about −50%, or from about −50% to about −75%. The % ee can be about −99%, −95%, −90%, −85%, −80%, −75%, −70%, −65%, −60%, −55%, −50%, −45%, −40%, −35%, −30%, −25%, −20%, −15%, −10%, 10%, 15%, 20%, 25%, 30%, 35%, 40%, 45%, 50%, 55%, 60%, 65%, 70%, 75%, 80%, 85%, 90%, or about 95%. Any of these values can be % $ee_E$ values or % $ee_Z$ values.

Accordingly, some embodiments of the invention provide methods for producing a plurality of cyclopropanation products having a % $ee_Z$ of from about −90% to about 90%. In some embodiments, the % $ee_Z$ is at least 90%. In some embodiments, the % $ee_Z$ is at least −99%. In some embodiments, the % $ee_E$ is from about −90% to about 90%. In some embodiments, the % $ee_E$ is at least 90%. In some embodiments, the % $ee_E$ is at least −99%.

In a related aspect, certain embodiments of the invention provide cyclopropane-containing compounds according to any of Formulas I, II, III as described herein. The compounds are prepared using the methods of the invention. In some embodiments, the invention provides a pyrethroid prepared according to the methods of the invention. In some embodiments, the invention provides milnacipran, levomilnacipran, bicifadine, or 1-(3,4-dichlorophenyl)-3-azabicyclo[3.1.0]hexane prepared according to the methods of the invention. In some embodiments, the invention provides any of the compounds illustrated in Table 6, which compounds are prepared according to the methods of the invention. The invention can provide other compounds prepared according to the methods described herein.

C. Reaction Conditions

The methods of the invention include forming reaction mixtures that contain the heme enzymes described herein. The heme enzymes can be, for example, purified prior to addition to a reaction mixture or secreted by a cell present in the reaction mixture. The reaction mixture can contain a cell lysate including the enzyme, as well as other proteins and other cellular materials. Alternatively, a heme enzyme can catalyze the reaction within a cell expressing the heme enzyme. Any suitable amount of heme enzyme can be used in the methods of the invention. In general, cyclopropanation reaction mixtures contain from about 0.01 mol % to about 10 mol % heme enzyme with respect to the diazo reagent and/or olefinic substrate. The reaction mixtures can contain, for example, from about 0.01 mol % to about 0.1 mol % heme enzyme, or from about 0.1 mol % to about 1 mol % heme enzyme, or from about 1 mol % to about 10 mol % heme enzyme. The reaction mixtures can contain from about 0.05 mol % to about 5 mol % heme enzyme, or from about 0.05 mol % to about 0.5 mol % heme enzyme. The reaction mixtures can contain about 0.1, 0.2, 0.3, 0.4, 0.5, 0.6, 0.7, 0.8, 0.9, or about 1 mol % heme enzyme.

The concentration of olefinic substrate and diazo reagent are typically in the range of from about 100 µM to about 1 M. The concentration can be, for example, from about 100 µM to about 1 mM, or about from 1 mM to about 100 mM, or from about 100 mM to about 500 mM, or from about 500 mM to 1 M. The concentration can be from about 500 µM to about 500 mM, 500 µM to about 50 mM, or from about 1 mM to about 50 mM, or from about 15 mM to about 45 mM, or from about 15 mM to about 30 mM. The concentration of olefinic substrate or diazo reagent can be, for example, about 100, 200, 300, 400, 500, 600, 700, 800, or 900 µM. The concentration of olefinic substrate or diazo reagent can be about 1, 5, 10, 15, 20, 25, 30, 35, 40, 45, 50, 55, 60, 65, 70, 75, 80, 85, 90, 95, 100, 150, 200, 250, 300, 350, 400, 450, or 500 mM.

Reaction mixtures can contain additional reagents. As non-limiting examples, the reaction mixtures can contain buffers (e.g., 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, isopropanol, glycerol, tetrahydrofuran, acetone, acetonitrile, and acetic acid), salts (e.g., NaCl, KCl, CaCl$_2$, and salts of Mn$^{2+}$ and Mg$^{2+}$), denaturants (e.g., urea and guandinium hydrochloride), detergents (e.g., sodium dodecylsulfate and Triton-X 100), chelators (e.g., ethylene glycol-bis(2-aminoethylether)-N,N,N',N'-tetraacetic acid (EGTA), 2-({2-[Bis(carboxymethyl]amino]ethyl}(carboxymethyl)amino)acetic acid (EDTA), and 1,2-bis(o-aminophenoxy)ethane-N,N,N,N-tetraacetic acid (BAPTA)), sugars (e.g., glucose, sucrose, and the like), and reducing agents (e.g., sodium dithionite, NADPH, dithiothreitol (DTT), β-mercaptoethanol (BME), and tris(2-carboxyethyl)phosphine (TCEP)). Buffers, cosolvents, salts, denaturants, detergents, chelators, sugars, and reducing agents can be used at any suitable concentration, which can be readily determined by one of skill in the art. In general, buffers, cosolvents, salts, denaturants, detergents, chelators, sugars, and reducing agents, if present, are included in reaction mixtures at concentrations ranging from about 1 µM to about 1 M. For example, a buffer, a cosolvent, a salt, a denaturant, a detergent, a chelator, a sugar, or a reducing agent can be included in a reaction mixture at a concentration of about 1 or about 10 µM, or about 100 µM, or about 1 mM, or about 10 mM, or about 25 mM, or about 50 mM, or about 100 mM, or about 250 mM, or about 500 mM, or about 1 M. In some embodiments, a reducing agent is used in a sub-stoichiometric amount with respect to the olefin substrate and the diazo reagent. Cosolvents, in particular, can be included in the reaction mixtures in amounts ranging from about 1% v/v to about 75% v/v, or higher. A cosolvent can be included in the reaction mixture, for example, in an amount of about 5, 10, 20, 30, 40, or 50% (v/v).

Reactions are conducted under conditions sufficient to catalyze the formation of a cyclopropanation product. The reactions can be conducted at any suitable temperature. In general, the reactions are conducted at a temperature of from about 4° C. to about 40° C. The reactions can be conducted, for example, at about 25° C. or about 37° C. The reactions can be conducted at any suitable pH. In general, the reactions are conducted at a pH of from about 6 to about 10. The reactions can be conducted, for example, at a pH of from about 6.5 to about 9. The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. Reactions can be conducted under aerobic conditions or anaerobic conditions. Reactions can be conducted under an inert atmosphere, such as a nitrogen atmosphere or argon atmosphere. In some embodiments, a solvent is added to the reaction mixture. In some embodiments, the solvent forms a second phase, and the cyclopropanation occurs in the aqueous phase. In some embodiments, the heme enzymes is located in the aqueous layer whereas the substrates and/or products occur in an organic layer. Other reaction conditions may be employed in the methods of the invention, depending on the identity of a particular heme enzyme, olefinic substrate, or diazo reagent.

Reactions can be conducted in vivo with intact cells expressing a heme enzyme of the invention. The in vivo reactions can be conducted with any of the host cells used for expression of the heme enzymes, as described herein. A suspension of cells can be formed in a suitable medium supplemented with nutrients (such as mineral micronutrients, glucose and other fuel sources, and the like). Cyclopropanation yields from reactions in vivo can be controlled, in part, by controlling the cell density in the reaction mixtures. Cellular suspensions exhibiting optical densities ranging from about 0.1 to about 50 at 600 nm can be used for cyclopropanation reactions. Other densities can be useful, depending on the cell type, specific heme enzymes, or other factors.

The methods of the invention can be assessed in terms of the diastereoselectivity and/or enantioselectivity of cyclopropanation reaction—that is, the extent to which the reaction produces a particular isomer, whether a diastereomer or enantiomer. A perfectly selective reaction produces a single isomer, such that the isomer constitutes 100% of the product. As another non-limiting example, a reaction producing a particular enantiomer constituting 90% of the total product can be said to be 90% enantioselective. A reaction producing a particular diastereomer constituting 30% of the total product, meanwhile, can be said to be 30% diastereoselective.

In general, the methods of the invention include reactions that are from about 1% to about 99% diastereoselective. The reactions are from about 1% to about 99% enantioselective. The reaction can be, for example, from about 10% to about 90% diastereoselective, or from about 20% to about 80% diastereoselective, or from about 40% to about 60% diastereoselective, or from about 1% to about 25% diastereoselective, or from about 25% to about 50% diastereoselective, or from about 50% to about 75% diastereoselective. The reaction can be about 10%, 15%, 20%, 25%, 30%, 35%, 40%, 45%, 50%, 55%, 60%, 65%, 70%, 75%, 80%, 85%, 90%, or about 95% diastereoselective. The reaction can be from about 10% to about 90% enantioselective, from about 20% to about 80% enantioselective, or from about 40% to about 60% enantioselective, or from about 1% to about 25% enantioselective, or from about 25% to about 50% enantioselective, or from about 50% to about 75% enantioselective. The reaction can be about 10%, 15%, 20%, 25%, 30%, 35%, 40%, 45%, 50%, 55%, 60%, 65%, 70%, 75%, 80%, 85%, 90%, or about 95% enantioselective. Accordingly some embodiments of the invention provide methods wherein the reaction is at least 30% to at least 90% diastereoselective. In some embodiments, the reaction is at least 30% to at least 90% enantioselective.

IV. EXAMPLES

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

C=C Functionalization by Enzyme-Catalyzed Carbenoid Insertion

This example illustrates bacterial cytochrome P450s that are engineered to catalyze highly stereoselective carbene transfers to aryl-substituted olefins, a reaction without a known biological counterpart.

Creating enzymes that catalyze novel reactions, one of the hallmarks of evolution, is a huge challenge and nearly unexplored frontier in protein engineering. Carbene transfers to C=C bonds are powerful catalytic methods that lack biological counterparts. Stereo-control over these transformations currently relies on expensive transition metal catalysts that require toxic organic solvents and are difficult to systematically modify or optimize. This example illustrates variants of cytochrome $P450_{BM3}$ that catalyze an important reaction not previously known for this monooxygenase: the cyclopropanation of styrene from diazoester reagents with exquisite enantio- and diastereocontrol. As such, this example demonstrates that existing enzymes can be adapted for catalysis of synthetically-important reactions not previously observed in Nature.

Introduction

The many strategies for functionalizing C=C bonds that have evolved in the biological world have captivated the imaginations of chemists who attempt to develop 'biomimetic' catalysts (J. T. Groves, *Proc. Natl. Acad. Sci. U.S.A.* 100, 3569 (2003); R. Breslow, *J. Biol. Chem.* 284, 1337 (2009)). The reverse of this, developing new biocatalysts inspired by synthetic chemistry, has received little attention, mainly because we poorly understand how to encode a desired function in a protein sequence. Nature's entire catalyst repertoire has been built with and utilizes physiologically accessible reagents. Not subject to the same limitations, synthetic chemists have developed powerful methods for direct C=C functionalization based on transition metal-catalyzed carbenoid insertions, reactions that are used extensively in the synthesis of natural product intermediates and artificial drugs (H. M. L. Davies et al., *Nature* 451, 417 (2008)). Utilizing high-energy precursors typically in the form of acceptor-substituted diazo reagents, these synthetic systems, upon dinitrogen extrusion, form metallo-carbenoid intermediates that insert into C=C bonds to form new carbon-carbon centers. Synthetic catalysts, however, require expensive transition metals and elaborate ligand designs for stereocontrol; they also often require toxic organic solvents. This example demonstrates combining the high levels of selectivity and 'green' process conditions afforded by enzymes with the synthetic power of carbene transfer strategies enabled by transition metal catalysis.

Results

Members of the diverse cytochrome P450 enzyme family catalyze myriad oxidative transformations, including hydroxylation, epoxidation, oxidative ring coupling, heteratom release, and heteroatom oxygenation (E. M. Isin et al., Biochim. Biophys. Acta 1770, 314 (2007)). The majority of transformations encompassed by this broad catalytic scope are manifestations of the same high-valent iron-oxene intermediate (compound I, FIG. 1). Inspired by the impressive chemo-, regio- and stereo-selectivities with which cytochrome P450s can insert oxygen atoms into C=C bonds, whether these enzymes could be engineered to mimic this chemistry was investigated for isoelectronic carbene transfer reactions via high-valent iron-enoid species (FIG. 1). This example shows that variants of the cytochrome P450 from *Bacillus megaterium* (CYP102A1, or P450$_{BM3}$) are efficient catalysts for the asymmetric metallocarbene-mediated cyclopropanation of styrenes.

Since iron porphyrins are known to catalyze carbene-based cyclopropanations (J. R. Wolf et al., *J. Am. Chem. Soc.* 117, 9194 (1995)), whether some common heme proteins display measurable levels of 'cyclopropanase' activity was first probed. The reaction between styrene and ethyl diazoacetate (EDA, FIG. 2), a well-recognized model system for validating new cyclopropanation catalysts, was investigated. Initial experiments showed that optimal formation of the desired cyclopropanation products occurred in water in the presence of a reducing agent (e.g., sodium dithionite) under anaerobic conditions (Tables 7-10). Horseradish peroxidase (HRP), cytochrome c (cyt c), myoglobin (Mb) and P450$_{BM3}$ all displayed multiple turnovers towards the cyclopropane products, with HRP, cyt c and Mb showing negligible enantio-induction and forming the trans cyclopropane with over 90% selectivity, which is comparable to the diastereoselectivity induced by free hemin (Table 7). Interestingly, P450$_{BM3}$, despite forming the cyclopropane products in low yield, catalyzed the reaction with different diastereoselectivity (cis:trans 37:63) and slight enantio-induction (Table 11), indicating that carbene transfer and selectivity were dictated by the active site-bound heme cofactor rather than by hemin released from the protein.

TABLE 7

Heme catalysts under anaerobic conditions with sodium dithionite (Na$_2$S$_2$O$_4$).

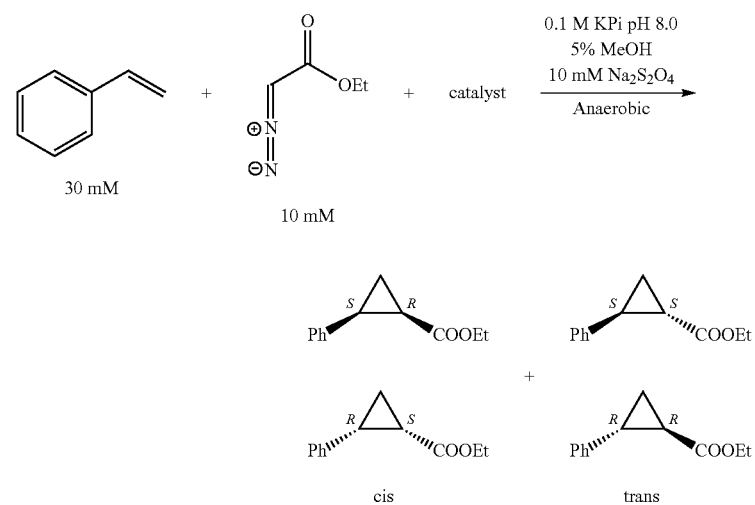

| Catalyst | Axial ligand | Cat. loading (% mol eq) | TTN | cis:trans[a] | % ee cis[b] | % ee trans[c] |
|---|---|---|---|---|---|---|
| Catalase | O-Tyr | 0.16 | 0 | — | — | — |
| CPO[d] | S-Cys | 0.40 | 0 | — | — | — |
| HRP | N-His | 1.00 | 9 | 7:93 | 8 | −7 |
| cyt c | N-His, S-Met | 1.00 | 19 | 6:94 | 0 | 12 |
| Mb | N-His | 1.00 | 43 | 6:94 | −1 | 2 |
| P450$_{BM3}$ | S-Cys | 0.20 | 5 | 37:63 | −27 | −2 |
| Hemin | — | 0.20 | 73 | 6:94 | −1 | 0 |

[a]Diastereomeric ratios and enantiomeric excess were determined by GC analysis.
[b](R,S) - (S,R).
[c](R,R) - (S,S).
[d]Bioconversion conducted at 0.1 M citrate buffer pH = 4.0.

TABLE 8

Heme catalysts under anaerobic conditions without $Na_2S_2O_4$.

| Catalyst | Axial ligand | Cat. loading (% mol eq) | TTN | cis:trans[a] | % ee cis[b] | % ee trans[c] |
|---|---|---|---|---|---|---|
| Catalase | O-Tyr | 0.16 | 0 | — | — | — |
| CPO[d] | S-Cys | 0.40 | 0 | — | — | — |
| HRP | N-His | 1.00 | 0 | — | — | — |
| cyt c | N-His, S-Met | 1.00 | 12 | 8:92 | 8 | −3 |
| Mb | N-His | 1.00 | 0.8 | 11:89 | −2 | 8 |
| P450$_{BM3}$ | S-Cys | 0.20 | 0 | 0 | — | — |
| Hemin | — | 0.20 | 4 | 11:89 | −1 | 3 |

[a]Diastereomeric ratios and enantiomeric excess were determined by GC analysis.
[b](R,S) − (S,R).
[c](R,R) − (S,S).
[d]Bioconversion conducted at 0.1 M citrate buffer pH = 4.0.

TABLE 9

Heme catalysts under aerobic conditions with $Na_2S_2O_4$.

| Catalyst | Axial ligand | Cat. loading (% mol eq) | TTN | cis:trans[a] | % ee cis[b] | % ee trans[c] |
|---|---|---|---|---|---|---|
| Catalse | O-Tyr | 0.16 | 0 | — | — | — |
| CPO[d] | S-Cys | 0.40 | 0 | — | — | — |
| HRP | N-His | 1.00 | 1 | 12:88 | −3 | −7 |
| cyt c | N-His, S-Met | 1.00 | 3 | 9:91 | −6 | 16 |
| Mb | N-His | 1.00 | 6 | 7:93 | −13 | 12 |

TABLE 9-continued

| | | | | | | |
|---|---|---|---|---|---|---|
| P450$_{BM3}$ | S-Cys | 0.20 | 1 | 13:87 | −38 | −8 |
| Hemin | — | 0.20 | 6 | 8:92 | −5 | 1 |

[a]Diastereomeric ratios and enantiomeric excess were determined by GC analysis.
[b](R,S) - (S,R).
[c](R,R) - (S,S).
[d]Bioconversion conducted at 0.1 M citrate buffer pH = 4.0.

TABLE 10

Heme catalysts under aerobic conditions without Na$_2$S$_2$O$_4$.

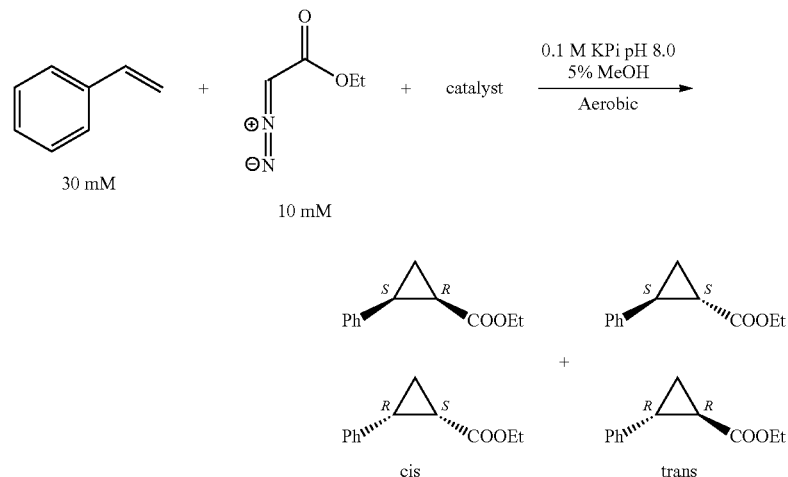

| Catalyst | Axial ligand | Cat. loading (% mol eq) | TTN | cis:trans[a] | % ee cis[b] | % ee trans[c] |
|---|---|---|---|---|---|---|
| Catalase | O-Tyr | 0.16 | 0 | — | — | — |
| CPO[d] | S-Cys | 0.40 | 0 | — | — | — |
| HRP | N-His | 1.00 | 0 | — | — | — |
| cyt c | N-His, S-Met | 1.00 | 0 | — | — | — |
| Mb | N-His | 1.00 | 0 | — | — | — |
| P450$_{BM3}$ | S-Cys | 0.20 | 0.4 | 46:54 | −46 | 36 |
| Hemin | — | 0.20 | 0 | — | — | — |

[a]Diastereomeric ratios and enantiomeric excess were determined by GC analysis.
[b](R,S) - (S,R).
[c](R,R) - (S,S).
[d]Bioconversion conducted at 0.1 M citrate buffer pH = 4.0.

TABLE 11

Stereoselective P450$_{BM3}$ cyclopropanases. Reactions were run in phosphate buffer (pH 8.0) at room temperature under argon with 30 mM styrene, 10 mM EDA, 0.2 mole % catalyst (with respect to EDA), and 10 mM sodium dithionite. Yields, diastereomeric ratios and enantiomeric excess were determined by GC analysis.

| Catalyst | % yield[a] | TTN | cis:trans | % ee$_{cis}$[b] | % ee$_{trans}$[c] |
|---|---|---|---|---|---|
| Hemin | 15 | 73 | 6:94 | −1 | 0 |
| P450$_{BM3}$ | 1 | 5 | 37:63 | −27 | −2 |
| P450$_{BM3}$-F87A | 1 | 6 | 38:62 | 26 | −6 |
| P450$_{BM3}$-T268A | 65 | 323 | 1:99 | −15 | −96 |
| H2-5-F10 | 59 | 294 | 16:84 | −41 | −63 |
| H2A10 | 33 | 167 | 60:40 | −95 | −78 |
| H2-4-D4 | 41 | 206 | 53:47 | −79 | −33 |
| C3C | 40 | 199 | 71:29 | −94 | −91 |
| C3C-I263A | 38 | 190 | 19:81 | −62 | −91 |
| C3C-A328G | 37 | 186 | 83:17 | 52 | −45 |
| C3C-T438S | 59 | 293 | 92:8 | −97 | −66 |

[a]Based on EDA.
[b](R,S)-(S,R).
[c](R,R)-(S,S). Variant 9-10A-TS-F87V-T268A is denoted as C3C. Other sequence identities are described in Table 12.

Whether the activity and selectivity of heme-catalyzed cyclopropanation could be enhanced by engineering the protein sequence was determined. P450$_{BM3}$ is a well-studied, soluble, self-sufficient (heme and diflavin reductase domains are fused in a single polypeptide), long-chain fatty acid monooxygenase. More than a decade of protein engineering attests to the functional plasticity of this biocatalyst (C. J. C. Whitehouse et al., *Chem. Soc. Rev.* 41, 1218 (2012)). Thousands of variants that exhibit monooxygenase activity on a wide range of substrates have been accumulated from using directed evolution to engineer cytochrome P450$_{BM3}$ for synthetic applications (J. C. Lewis et al., *Chimia* 63, 309 (2009)). Some of these variants were tested by chiral gas chromatography for altered cyclopropanation diastero- and enantioselectivity. A panel of 92 P450$_{BM3}$ variants, chosen for diversity of activity and protein sequence, was screened in *E. coli* lysate for the reaction of styrene and EDA under aerobic conditions in the presence of sodium dithionite (Tables 12 and 13). The ten most promising hits were selected for purification and subsequent characterization under standardized anaerobic reaction conditions (Tables 11 and 14).

TABLE 12

Raw data from P450$_{BM3}$ compilation plate screen. Diastereo- and enantioselectivity were determined by gas chromatography using a chiral β-CDX column as the stationary phase.

| P450$_{BM3}$ variants | Mutations compared to wild-type P450$_{BM3}$ (SEQ ID NO: 1) | Absolute activity[a] | de[b] | ee (cis)[c] |
|---|---|---|---|---|
| CYP102A3 | N/A | 0.004053 | −74 | −8 |
| CYP102A2 | N/A | 0.002963 | −76 | −36 |
| CYP102A1 (P450$_{BM3}$) | None | 0.002240 | −81 | 7 |
| WT F87A | F87A | 0.001704 | −28 | 57 |
| WT T88L | T88L | 0.004522 | −78 | 23 |
| WT A328V | A328V | 0.000830 | −100 | N/A |
| J[4] | V78A, T175I, A184V, F205C, S226R, H236Q, E252G, R255S, A290V, L353V | 0.001334 | −100 | N/A |
| 139-3[5] | V78A, H138Y, T175I, V178I, A184V, F205C, S226R, H236Q, E252G, R255S, A290V, L353V | 0.001386 | −86 | 0 |
| 9-10A[4] | R47C, V78A, K94I, P142S, T175I, A184V, F205C, S226R, H236Q, E252G, R255S, A290V, L353V | 0.004292 | −74 | −20 |
| 9-10A L75W[1] | 9-10A L75W | 0.005191 | −83 | −8 |
| 9-10A L75I[1] | 9-10A L75I | 0.002267 | −85 | −3 |
| 9-10A A78F[1] | 9-10A L78F | 0.002008 | −82 | −35 |
| 9-10A A78S[1] | 9-10A A78S | 0.005098 | −81 | −6 |
| 9-10A A82G[1] | 9-10A A82G | 0.002245 | −76 | −7 |
| 9-10A A82F[1] | 9-10A A82F | #VALUE! | N/A | N/A |
| 9-10A A82C[1] | 9-10A A82C | 0.002487 | −74 | 16 |
| 9-10A A82I[1] | 9-10A A82I | 0.001031 | −100 | N/A |
| 9-10A A82S[1] | 9-10A A82S | 0.001483 | −82 | 14 |
| 9-10A A82L[4] | 9-10A A82L | 0.000591 | −100 | N/A |
| 9-10A F87A | 9-10A F87A | 0.001701 | −61 | −10 |
| 9-10A F87V[1] | 9-10A F87V | 0.000000 | N/A | N/A |
| 9-10A F87I[1] | 9-10A F87I | 0.000983 | −100 | N/A |
| 9-10A F87L[1] | 9-10A F87L | 0.000710 | −100 | N/A |
| 9-10A T88C[1] | 9-10A T88C | 0.002516 | −77 | 3 |
| 9-10A T260S[1] | 9-10A T260S | 0.004259 | −82 | −6 |
| 9-10A T260N[1] | 9-10A T260N | 0.003882 | −77 | 15 |
| 9-10A T260L[1] | 9-10A T260L | 0.006173 | −77 | −2 |
| 9-10A A328V[1] | 9-10A A328V | 0.006471 | −68 | −8 |
| 9-10A A328M[1] | 9-10A A328M | 0.005180 | −82 | 6 |
| 9-10A A328F[1] | 9-10A A328F | 0.002009 | −63 | −32 |
| 49-1A | R47C, V78T, A82G, F87V, K94I, P142S, T175I, A184V, F205C, S226R, H236Q, E252G, R255S, A290V, A328L, L353V | 0.001874 | −75 | −32 |
| 35-7F | R47C, V78F, A82S, K94I, P142S, T175I, A184V, F205C, S226R, H236Q, E252G, R255S, A290V, A328L, L353V | 0.004514 | −73 | −52 |
| 53-5H[1] | 9-10A A78F, A82S, A328F | 0.002840 | −80 | 2 |
| 7-11D | 9-10A A82F, A328V | 0.036840 | −24 | −28 |
| 49-9B | R47C, V78A, A82G, F87V, K94I, P142S, T175I, A184V, F205C, S226R, H236Q, E252G, R255S, A290V, A328L, L353V | 0.000000 | N/A | N/A |
| 41-5B | R47C, V78F, A82G, K94I, P142S, T175I, A184V, F205C, S226R, H236Q, E252G, R255S, A290V, A328V, L353V | 0.008391 | −77 | −17 |
| 13-7C[1] | 9-10A A78T, A328L | 0.005493 | −73 | −43 |

TABLE 12-continued

Raw data from P450$_{BM3}$ compilation plate screen. Diastereo- and enantioselectivity were determined by gas chromatography using a chiral β-CDX column as the stationary phase.

| P450$_{BM3}$ variants | Mutations compared to wild-type P450$_{BM3}$ (SEQ ID NO: 1) | Absolute activity[a] | de[b] | ee (cis)[c] |
|---|---|---|---|---|
| 12-10C | R47C, V78A, A82G, F87V, K94I, P142S, T175I, A184V, F205C, S226R, H236Q, E252G, R255S, A290V, A328V, L353V | 0.004566 | −73 | −21 |
| 77-9H[1] | 9-10A A78T, A82G, A328L | 0.003053 | −73 | −34 |
| 11-8E | R47C, V78A, F87V, K94I, P142S, T175I, A184V, F205C, S226R, H236Q, E252G, R255S, A290V, A328L, L353V | 0.001453 | −77 | 15 |
| 1-12G[4] | 9-10A A82L, A328V | 0.003884 | −70 | −19 |
| 29-3E | R47C, V78A, A82F, K94I, P142S, T175I, A184V, F205C, S226R, H236Q, E252G, R255S, A290V, A328F, L353V | 0.003425 | −80 | 15 |
| 29-10E | R47C, V78F, A82G, K94I, P142S, T175I, A184V, F205C, S226R, H236Q, E252G, R255S, A290V, A328F, L353V | 0.001935 | −70 | 16 |
| 68-8F[1] | 9-10A A78F, A82G, A328L | 0.004127 | −72 | −32 |
| 35E11[6] | R47C, V78F, A82S, K94I, P142S, T175I, A184V, F205C, S226R, H236Q, E252G, R255S, A290V, A328F, L353V, E464G, I710T | 0.003600 | −71 | −14 |
| 19A12[6] | 35E11 L52I, L188P, I366V | 0.006909 | −70 | −27 |
| ETS8[6] | 35E11 L52I, I366V | 0.003966 | −79 | −19 |
| (11-3)[6] | 35E11 L52I, A74S, L188P, I366V | 0.005633 | −76 | −39 |
| (7-7)[6] | 35E11 L52I, A74E, S82G, A184V, L188P, I366V | 0.010499 | −77 | −9 |
| H2A10 | 9-10A TS F87V, L75A, L181A, T268A | 0.066422 | −8 | −94 |
| SL2-6F8 | R47C, L52I, V78F, A82S, K94I, P142S, T175I, A184V, F205C, S226R, H236Q, E252G, R255S, A290V, A328L, K349N, L353V, I366V, E464G, I710T | 0.000778 | −100 | N/A |
| A12SL-17-4 | R47C, L52I, A74E, V78F, A82S, K94I, P142S, T175I, A184V, L188P, F205C, S226R, H236Q, E252G, R255S, A290V, A328F, L353V, I366V, E464G, I710T | 0.010935 | −80 | 6 |
| H2-2-A1[2] | 9-10A TS F87V, L75A, L181A, L437A | 0.003042 | −75 | −11 |
| A12RM-2-8 | R47C, L52I, A74E, V78F, A82S, K94I, P142S, T175I, A184S, L188P, F205C, S226R, H236Q, E252G, R255S, A290V, A328F, L353V, I366V, E464G, I710T | 0.007705 | −77 | −13 |
| H2-5-F10 | 9-10A TS F87V, L75A, I263A, T268A, L437A | 0.141237 | −46 | −56 |
| 13C9R1 | L52I, I58V, L75R, F87A, H100R, S106R, F107L, A135S, A184V, N239H, S274T, L324I, V340M, I366V, K434E, E442K, V446I | 0.001980 | −100 | N/A |
| 22A3 | 13C9R1 F162I E434K K442E I446V | 0.004053 | −70 | 4 |
| 2C6[3] | 9-10A A78L, F87A, V184T, G315S, A330V | 0.004257 | −78 | −15 |
| 9C7[3] | 9-10A C47R, A78L, F87G, I94K, A180V, V184T, G315S, A330V, Y345C | 0.007258 | −79 | −5 |
| B1[3] | 9-10A C47R, A78L, F87A, I94K, V184T, I263M, G315S, A330V | 0.002246 | −61 | −14 |

TABLE 12-continued

Raw data from P450$_{BM3}$ compilation plate screen. Diastereo- and enantioselectivity were determined by gas chromatography using a chiral β-CDX column as the stationary phase.

| P450$_{BM3}$ variants | Mutations compared to wild-type P450$_{BM3}$ (SEQ ID NO: 1) | Absolute activity[a] | de[b] | ee (cis)[c] |
|---|---|---|---|---|
| B1SYN[3] | 9-10A C47S, N70Y, A78L, F87A, I174N, I94K, V184T, I263M, G315S, A330V | 0.002705 | −76 | −23 |
| H2-4-D4 | 9-10A TS F87V, L75A, M177A, L181A, T268A, L437A | 0.052439 | 57 | −84 |
| E12 A87V[3] | 9-10A C47R, A78L, F87V, I94K, A111V, V141I, A180V, V184T, G315S, A330V | 0.001990 | −65 | −52 |
| GlcA4 T180A | 9-10A C47R, F81W, A82S, F87A, I94K | 0.004925 | −78 | 12 |
| H2-8-C7[2] | 9-10A TS F87V, L75A, L181A | 0.000808 | −100 | N/A |
| CH-F8 | 9-10A L51A, C47A, F87V, I94K, L181A, C205F, S254R, I366V, L437A, E442K | 0.001126 | −100 | N/A |
| H2-4-H5[2] | 9-10A TS F87V, L75A, M177A, L181A | 0.001229 | −100 | N/A |
| SA9 | 9-10A C47R, F81W, A82I, F87A, I94K, A180T, A197V | 0.004170 | −81 | 11 |
| ManA10 | 9-10A C47R, F81S, A82V, F87A, I94K, A180T, A197V | 0.006340 | −82 | 14 |
| Man1 | 9-10A C47R, F81L, A82T, F87A, I94K | 0.003053 | −73 | 21 |
| MB2 | 9-10A C47R, F81W, A82I, F87A, I94K | 0.003282 | −77 | 10 |
| HA62 | 9-10A C47R, F81A, A82L, F87A, I94K | 0.003375 | −81 | −5 |
| 9-10A TS | V78A, P142S, T175I, A184V, S226R, H236Q, E252G, A290V, L353V, I366V, E442K | 0.001920 | −75 | −54 |
| 9-10A TS F87A | 9-10A TS F87A | 0.001546 | −60 | 5 |
| 25F7 | 9-10A C47R, A74F, A78S, F87A, I282K, C205F, S255R | 0.001829 | −81 | 43 |
| 24C4 | 9-10A C47R, A74I, A78L, F87A, I94K, C205F, S255R | 0.000783 | −100 | N/A |
| 5A1 | 9-10A M30T, C47R, A74F, A78S, I94K, C205F, S255R, Q310L, I366V, E442K | 0.002471 | −80 | 15 |
| 8B3 | 9-10A M30T, C47R, A74F, A78S, I94K, C205F, C255R, L310Q, Q323L, I366V, N381K, R398H, E441K | 0.001315 | −100 | N/A |

Determined by GC analysis on a chiral β-CDX column.
[a]Reported as the sum of the area of the cyclopropane peaks over the area of the internal standard.
[b]Diastereomeric excess = ([cis] − [trans])/([cis] + [trans]).
[c](R,S)-(S,R).
[1]P. Meinhold et al., Adv. Synth. Catal. 348, 763 (2006).
[2]J. C. Lewis et al., Chembiochem: a European journal of chemical biology 11, 2502 (2010).
[3]J. C. Lewis et al., Proceedings of the National Academy of Sciences of the United States of America 106, 16550 (2009).
[4]M. W. Peters et al., J. Am. Chem. Soc. 125, 13442 (2003).
[5]A. Glieder et al., Nat. Biotechnol. 20, 1135 (2002).
[6]R. Fasan et al., Angew. Chem., Int. Ed. 46, 8414 (2007).

TABLE 13

Raw GC screening data for the chimeric P450s in the compilation plate.

| P450 | Chimeric P450s (heme domain block sequence) | Absolute activity[a] | de[b] | ee (cis)[c] |
|---|---|---|---|---|
| CYP102A1 (P450$_{BM3}$) F87A[1] | 11111111 | 0.001704 | −28 | 56 |
| CYP102A2 F88A[1] | 22222222 | N/A | N/A | N/A |
| CYP102A3 F88A[1] | 33333333 | N/A | N/A | N/A |
| 5R1[2] | 32312231 | 0.008625 | 58 | 19 |
| 9R1[2] | 12112333 | 0.0042707 | 58 | 24 |
| 12R1[2] | 12112333 | 0.0701514 | 32 | −49 |
| C1D11R1[2] | 21113312 | 0.007138 | 51 | 9 |
| C2B12R1[2] | 32313233 | 0.005914 | 38 | −5 |
| C2C12R1[2] | 21313111 | 0.006226 | 28 | 9 |
| C2E6R1[2] | 11113311 | 0.008731 | 25 | 6 |
| C2G9R1[2] | 22213132 | 0.007975 | 15 | 31 |

TABLE 13-continued

Raw GC screening data for the chimeric P450s in the compilation plate.

| P450 | Chimeric P450s (heme domain block sequence) | Absolute activity[a] | de[b] | ee (cis)[c] |
|---|---|---|---|---|
| C3D10R1[2] | 22132231 | 0.004898 | −16 | −2 |
| C3E4R1[2] | 21313311 | 0.007893 | 14 | 17 |
| F3H12R1[2] | 21333233 | 0.005586 | −56 | −17 |
| F6D8R1[2] | 22313233 | 0.008088 | −76 | −6 |
| C3B5R1[2] | 23132233 | 0.014722 | −81 | 4 |
| X7R1[2] | 22312333 | 0.017305 | −4 | −34 |

[a]Reported as the sum of the area of the cyclopropane peaks over the area of the internal standard.
[b]Diastereomeric excess = ([cis] − [trans])/([cis] + [trans]).
[c](R,S)-(S,R).
[1]C. R. Otey et al., *PLoS Biol.* 4, 789 (2006).
[2]M. Landwehr et al., *Chem. Biol.* 14, 269 (2007). Site-directed recombination of three bacterial cytochrome P450s was performed with sequence crossover sites chosen to minimize the number of disrupted contacts within the protein structure. Seven crossover sites where chosen resulting in eight sequence blocks. The numbering refers to the identity of the parent sequence at each block. For example, "12312312" refers to a sequence containing block 1 from P450 1, block 2 from P450 2, block 3 from P450 3, etc.

acid substitutions from wild type, catalyzes 294 TTN, equivalent to ~58% yield (with respect to EDA) under these conditions. This represents a 50-fold improvement in TTN over wild type $P450_{BM3}$. Furthermore, mutations affect both the diastereo- and enantioselectivity of cyclopropanation: H2-5-F10 favors the trans cyclopropanation product (cis:trans 16:84) with 63% $ee_{trans}$, while variant H2A10, which catalyzes up to 167 TTN, demonstrates reversed diastereoselectivity (cis:trans 60:40) with high enantioselectivity (95% $ee_{cis}$).

The variant H2A10 was used to verify the role of the enzyme in catalysis and identify optimal conditions (Table 15, FIGS. 3 and 4). Heat inactivation produced diastereo- and enantioselectivities similar to those obtained using free hemin, consistent with protein denaturation and release of the cofactor. Complete inhibition was achieved by pre-incubating the bioconversion with carbon monoxide, which irreversibly binds the reduced P450 heme, confirming that catalysis occurs at the active site. Air inhibited the cyclopropanation reaction by about 50%, showing that dioxygen and EDA compete for reduced $Fe^{II}$. Cyclopropanation was also achieved with NADPH as the reductant, confirming that the novel activity can also be driven by the endogenous electron transport machinery of the diflavin-containing reductase domain. The presence of a reducing agent in sub-stoichiometric amounts proved essential for cyclopropanation (Table 16), implying that the active species is $Fe^{II}$ rather than the resting state $Fe^{III}$.

TABLE 14

Stereoselective $P450_{BM3}$ based cyclopropanases.

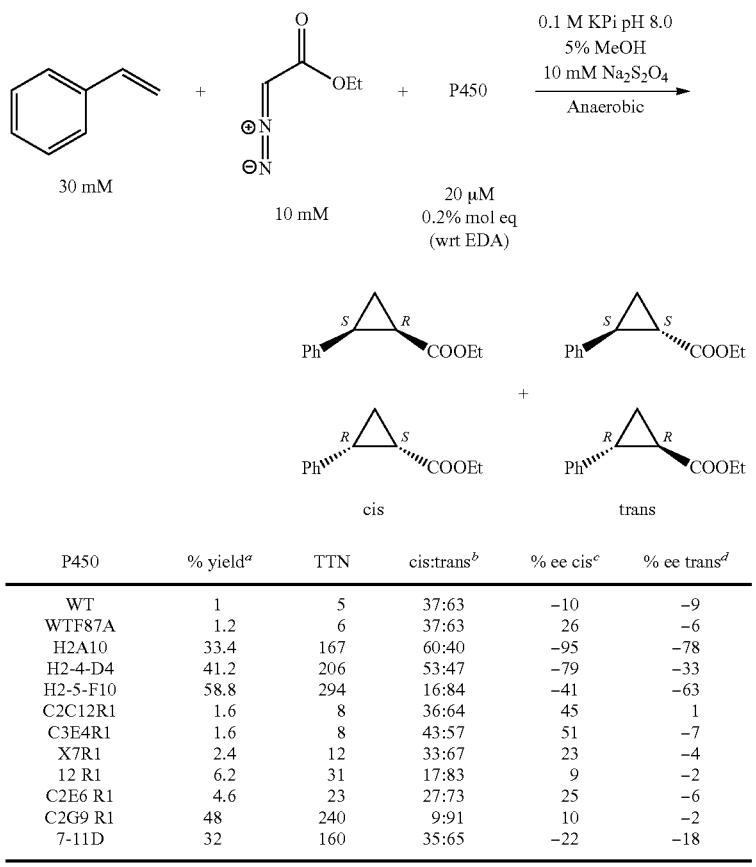

| P450 | % yield[a] | TTN | cis:trans[b] | % ee cis[c] | % ee trans[d] |
|---|---|---|---|---|---|
| WT | 1 | 5 | 37:63 | −10 | −9 |
| WTF87A | 1.2 | 6 | 37:63 | 26 | −6 |
| H2A10 | 33.4 | 167 | 60:40 | −95 | −78 |
| H2-4-D4 | 41.2 | 206 | 53:47 | −79 | −33 |
| H2-5-F10 | 58.8 | 294 | 16:84 | −41 | −63 |
| C2C12R1 | 1.6 | 8 | 36:64 | 45 | 1 |
| C3E4R1 | 1.6 | 8 | 43:57 | 51 | −7 |
| X7R1 | 2.4 | 12 | 33:67 | 23 | −4 |
| 12 R1 | 6.2 | 31 | 17:83 | 9 | −2 |
| C2E6 R1 | 4.6 | 23 | 27:73 | 25 | −6 |
| C2G9 R1 | 48 | 240 | 9:91 | 10 | −2 |
| 7-11D | 32 | 160 | 35:65 | −22 | −18 |

[a]based on EDA.
[b]Diastereomeric ratios and enantiomeric excess were determined by GC analysis.
[c](R,S) − (S,R).
[d](R,R) − (S,S).

Five of the ten selected P450s showed improvements in activity (>100 TTN), a comprehensive range of diastereoselectivities with cis:trans ratios varying from 9:91 to 60:40, and impressive enantioselectivities (up to 95% ee, Table 14). For example, variant H2-5-F10, which contains 16 amino

TABLE 15

Controls for P450 based cyclopropanation using variant H2A10.

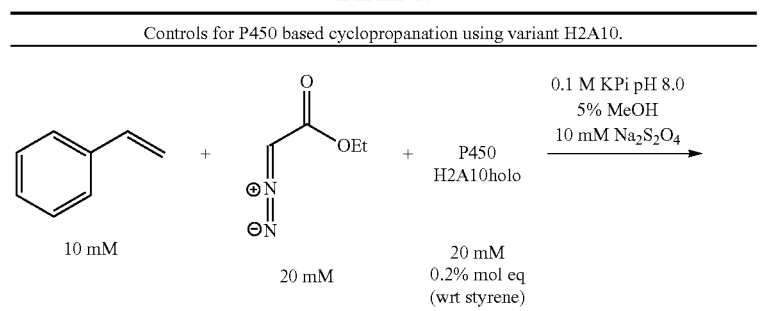

| Conditions | TTN | % inhibition | cis:trans[a] | % ee cis[b] | % ee trans[c] |
|---|---|---|---|---|---|
| Complete System (CS) | 101 | — | 70:30 | −95 | −78 |
| CS−Na$_2$S$_2$O$_4$ + NADPH | 45 | −55 | 61:39 | −87 | −31 |
| CS−Na$_2$S$_2$O$_4$ + NADH | 38 | −62 | 53:47 | −76 | −19 |
| CS−Na$_2$S$_2$O$_4$ | 0 | −100 | — | — | — |
| CS−P450 | 0 | −100 | — | — | — |
| CS + CO | 0 | −100 | — | — | — |
| Boiled P450 | 146 | +45 | 16:84 | 2 | −2 |
| H2A10$_{heme}$ | 85 | −16 | 67:33 | −92 | −67 |
| CS−P450 + Hemin | 16 | −84 | 15:85 | −1 | −2 |
| CS (aerobic) | 43 | −57 | 67:33 | −94 | −76 |

[a]Diastereomeric ratios and enantiomeric excess were determined by GC analysis.
[b](R,S) − (S,R).
[c](R,R) − (S,S).

TABLE 16

Effect of concentration of sodium dithionite on cyclopropane yield.

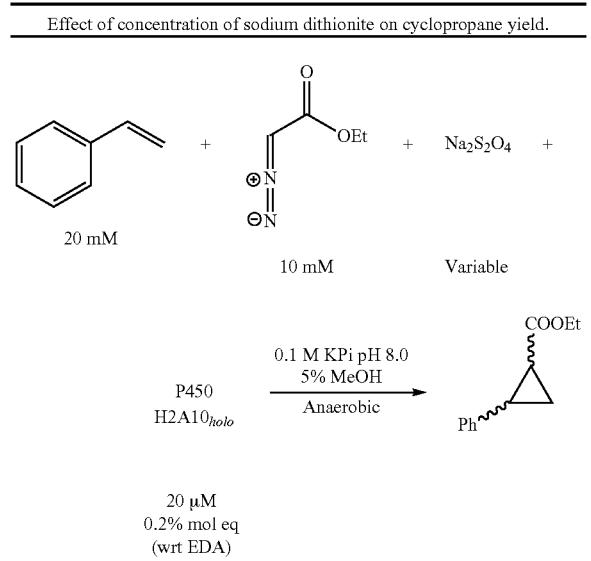

| [Na$_2$S$_2$O$_4$]/mM | [cyclopropanes]/mM | TTN |
|---|---|---|
| 0 | 0 | 0 |
| 1 | 2.59 | 129 |
| 5 | 2.72 | 136 |
| 10 | 3.34 | 167 |
| 20 | 3.13 | 156 |
| 50 | 2.79 | 140 |
| 100 | 2.71 | 136 |

Highly active variants H2A10, H2-5-F10 and H2-4-D4 have three to five active site alanine substitutions with respect to 9-10A-TS-F87V (12 mutations from wild type), which itself shows negligible cyclopropanase activity. These variants demonstrate significant differences in TTN, diastereoselectivity, and enantioselectivity (Table 11). To better understand how protein sequence controls P450-mediated cyclopropanation, 12 new variants were constructed to assess the contributions of individual alanine mutations to catalysis and stability (Table 17). T268A is key for achieving high levels of cyclopropanation activity, and this mutation alone converts inactive 9-10A-TS-F87V into an active cyclopropanase. Variant 9-10A-TS-F87V-T268A (denoted C3C) is a competent cyclopropanase (199 TTN), displays strong preference for the cis product (cis:trans 71:29), forms both diastereomers with over 90% ee, and is as stable as wild-type type 450$_{BM3}$. Other active site alanine mutations tune the product distribution. Notably, the addition of I263A to C3C reverses diastereoselectivity (cis:trans 19:81). The effects of similar mutations introduced in the poorly active wild type P450$_{BM3}$ were also investigated (Table 18). Impressively, P450$_{BM3}$-

T268A, with a single mutation, is an active cyclopropanase (323 TTN, Table 11) with exquisite trans-selectivity (cis:trans 1:99) and high enantioselectivity for the major diastereomer (−96% ee$_{trans}$, FIG. 2). Whereas C3C is a cis-selective cyclopropanase, identical active site mutations in wild type P450$_{BM3}$ result in a trans-selective enzyme (Table 18), demonstrating that mutations outside of the active site can also influence the stereochemical outcome.

TABLE 17

Mutational analysis of alanine substitutions on 9-10A TS F87V.

| P450 (Holo) | L75A | M177A | L181A | I263A | T268A | L437A | TTN | cis:trans$^a$ | % ee cis$^b$ | % ee trans$^c$ | $T_{50}$ (° C.) |
|---|---|---|---|---|---|---|---|---|---|---|---|
| 9-10A TS F87V | No | No | No | No | No | No | 7 | 35:65 | −41 | −8 | 59.5 |
| 9-10A TS F87V L75A | Yes | No | No | No | No | No | 5 | 42:58 | −59 | −11 | 52.3 |
| 9-10ATS F87V L181A | No | No | Yes | No | No | No | 5 | 41:59 | −27 | −7 | 53.3 |
| 9-10A TS F87V I263A | No | No | No | Yes | No | No | 8 | 29:71 | −31 | −39 | 55.4 |
| 9-10A TS F87V T268A (C3C) | No | No | No | No | Yes | No | 199 | 71:29 | −94 | −91 | 55.2 |
| C3C I263A | No | No | No | Yes | Yes | No | 190 | 19:81 | −62 | −91 | 54.0 |
| C3C L181A | No | No | Yes | No | Yes | No | 159 | 56:44 | −92 | −94 | 50.8 |
| H2A10 | Yes | No | Yes | No | Yes | No | 167 | 60:40 | −95 | −78 | 48.9 |
| C3C L181A I263A | No | No | Yes | Yes | Yes | No | 203 | 14:86 | −46 | −95 | 50.9 |
| C3C L181A L437A | No | No | Yes | No | Yes | Yes | 180 | 27:73 | −74 | −98 | 48.4 |
| C3C L181A I263A L437A | No | No | Yes | Yes | Yes | Yes | 218 | 9:91 | −55 | −96 | 48.2 |
| 4H5 | Yes | Yes | Yes | No | No | No | 7 | 32:68 | −9 | 0 | 49.4 |
| C3C I263A L437A | No | No | No | Yes | Yes | Yes | 267 | 16:84 | −59 | −89 | 50.4 |
| H2-5-F10 | Yes | No | No | Yes | Yes | Yes | 294 | 16:84 | −41 | −63 | 47.5 |
| H2-4-D4 | Yes | Yes | Yes | No | Yes | Yes | 206 | 53:47 | −79 | −33 | 46.4 |

$^a$Diastereomeric ratios and enantiomeric excess were determined by GC analysis.
$^b$(R,S) - (S,R).
$^c$(R,S) - (S,S).

TABLE 18

Introducing variant 9-10A-TS-F87V-T268A related active site mutations in wild-type $P450_{BM3}$.

| P450 (Holo) | Mutations relative to wild-type $P450_{BM3}$ | | | | TTN | cis:trans[a] | % ee cis[b] | % ee trans[c] | $T_{50}$ (° C.) |
| --- | --- | --- | --- | --- | --- | --- | --- | --- | --- |
| | V78 | F87 | T268 | I263 | | | | | |
| WT | — | — | — | — | 5 | 37:63 | −10 | −9 | 56.0 |
| WT-F87A | — | A | — | — | 6 | 38:62 | 26 | −6 | 53.0 |
| WT-F87V | — | V | — | — | 9 | 30:70 | −33 | −26 | 52.9 |
| WT-T268A | — | — | A | — | 323 | 1:99 | −15 | −96 | 53.6 |
| WT-F87V/T268A | — | V | A | — | 274 | 32:68 | −77 | −99 | 52.0 |
| WT-V78A/F87V/T268A | A | V | A | — | 190 | 32:68 | −70 | −20 | 50.8 |
| WT-F87V/I263A/T268A | — | V | A | A | 246 | 7:93 | 8 | −94 | 50.0 |

[a] Diastereomeric ratios and enantiomeric excess were determined by GC analysis.
[b] (R,S) - (S,R).
[c] (R,R) - (S,S).

Since the design of cis-selective small-molecule catalysts for diazocarbonyl-mediated cyclopropanations has proven more challenging than their trans counterparts (A. Caballero et al., *European Journal of Inorganic Chemistry*, 1137 (2009)), whether further active site engineering of $P450_{BM3}$ could provide robust cis-selective water-compatible catalysts to complement existing organometallic systems was investigated. Five active site residues (L181, I263, A328, L437, T438) were chosen for individual site-saturation mutagenesis (see, Materials and Methods). Substitutions A328G, T438A, T438S and T438P all afforded enhanced cis-selectivity (Table 19). Notably A328G also reversed the enantioselectivity for the cis-diastereomer (Table 11). C3C-T438S displayed the highest diastereo- and enantioselectivities (cis:trans 92:8 and −97% $ee_{cis}$) and maintained activity comparable to C3C (Table 11).

TABLE 19

Cyclopropanation activity of selected C3C$_{heme}$ active site variants.

| P450$_{heme}$ | Yield (%)[a] | TTN | cis:trans[b] | % ee cis[c] | % ee trans[d] |
|---|---|---|---|---|---|
| 9-10A TS F87V T268A (C3C) | 57 | 286 | 71:29 | −92 | −88 |
| C3C-L181G | 47 | 234 | 59:41 | −89 | −90 |
| C3C-A328G | 37 | 186 | 83:17 | 52 | −45 |
| C3C-L437F | 53 | 265 | 53:47 | −82 | −85 |
| C3C-L437Q | 30 | 148 | 53:47 | −73 | −87 |
| C3C-L437G | 58 | 290 | 54:46 | −88 | −91 |
| C3C-L437A | 39 | 194 | 38:62 | −84 | −11 |
| C3-T438A | 54 | 273 | 91:9 | −92 | −75 |
| C3C-T438G | 15 | 78 | 73:27 | −87 | −59 |
| C3C-T438S | 59 | 293 | 92:8 | −97 | −66 |
| C3C-T438Q | 41 | 206 | 38:62 | 67 | 70 |
| C3C-T438P | 32 | 161 | 90:10 | −91 | −50 |

[a]Based on ED.
[b]Diastereomeric ratios and enantiomeric excess were determined by GC analysis.
[c](R,S) - (S,R).
[d](R,R) - (S,S).
Variant 9-10A-TS-F87V-T268A is denoted as C3C.

C3C exhibits Michaelis-Menten kinetics (FIG. 5 and Table 20) with similar $K_M$ values for the olefin (~1.5 mM) and the diazocarbene (~5 mM). The relatively high $K_M$ values reflect the lack of evolutionary pressure for these enzymes to bind these substrates. C3C exhibits a notable $k_{cat}$ for cyclopropanation of 100 min$^{-1}$, comparable to the $k_{cat}$ of many native P450s for hydroxylation, but about fifty times slower than P450$_{BM3}$-catalyzed fatty acid hydroxylation (Table 21). When used at 0.1 mol % equivalent, C3C-catalyzed cyclopropanations reached completion after 30 minutes. Adding more EDA equivalents leads to enhanced turnovers for cyclopropanes, with preserved C3C stereoselectivity (Table 22), confirming catalyst integrity and implying that the reaction stops because of EDA depletion rather than due to mechanistic inactivation.

TABLE 20

Michaelis-Menten parameters for P450 cyclopropanases variant 9-10A-TS-F87V-T268A (herein called C3C).

| catalyst | $k_{cat}$ (min$^{-1}$) | $K_{M\text{-}EDA}$ (mM) | $K_{M\text{-}styrene}$ (mM) | $k_{cat}/K_{M\text{-}EDA}$ (s$^{-1}$ M$^{-1}$) | $k_{cat}/K_{M\text{-}styrene}$ (s$^{-1}$ M$^{-1}$) | $k_{cat}/(K_{M\text{-}EDA} \times K_{M\text{-}styrene})$ (s$^{-1}$ M$^{-1}$ M$^{-1}$) |
|---|---|---|---|---|---|---|
| C3C$_{heme}$ | 100 ± 24 | 5.2 ± 3.5 | 1.4 ± 0.5 | 320 | 1,100 | 2.1 × 10$^5$ |

TABLE 21

Kinetic parameters for wild-type cytochrome P450s acting on their native substrates and for an engineered variant of P450$_{BM3}$ (propane monooxygenase, PMO) acting on the non-native substrate propane.

| P450 | Substrate | $k_{cat}$ (min$^{-1}$) | $K_{M\text{-}EDA}$ (mM) | $k_{cat}/K_{M\text{-}EDA}$ (s$^{-1}$ M$^{-1}$) |
|---|---|---|---|---|
| CYP153A6[1] | Octane | 75 | 0.32 | 3,900 |
| P450$_{BM3}$[2] | Lauric acid | 5140 | 0.29 | 3.0 × 10$^5$ |
| PMO[3] | Propane | 450 | 0.17 | 4.4 × 10$^4$ |

[1]M. M. Chen et al., *Advanced Synthesis & Catalysis* 354, 964 (2012).
[2]M. A. Noble et al., *Biochemical Journal* 339 (Pt 2), 371 (1999).
[3]R. Fasan et al.,. *J. Mol. Biol.* 383, 1069 (2008).

TABLE 22

Effect of EDA addition at t = 30 min on variant 9-10A-TS-F87V-T268A-catalyzed cyclopropanations.

Ph—CH=CH₂ (30 mM) + N₂=CH-COOEt (Table S17) + C3C_heme (20 µM, 0.2% mol eq (wrt EDA)) → (0.1 M KPi pH 8.0, 5% MeOH, 10 mM Na₂S₂O₄)

cis: Ph(S)—△—(R)COOEt  +  Ph(S)—△—(S)COOEt (trans)
     Ph(R)—△—(S)COOEt       Ph(R)—△—(R)COOEt

| Conditions | TTN | cis:trans$^a$ | % ee cis$^b$ | % ee trans$^c$ |
|---|---|---|---|---|
| 10 mM EDA added at t = 0 | 273 ± 2.5 | 72:28 | −92 | −90 |
| 10 mM EDA added at t = 0 + 10 mM EDA at t = 30 min | 425 ± 17 | 73:27 | −93 | −89 |

TTN values are reported as the mean of triplicates ± standard deviation.
$^a$Diastereomeric ratios and enantiomeric excess were determined by GC analysis.
$^b$(R,S) - (S,R).
$^c$(R,R) - (S,S).

To assess substrate scope of P450$_{BM3}$-catalyzed cyclopropanation, the activities of seven variants against various olefins and diazo compounds were investigated (Tables 23-27). P450 cyclopropanation is robust to both electron-donating (p-vinylanisole, p-vinyltoluene) and electron-withdrawing (p-trifluoromethylstyrene) substitutions on styrene, and 7-11D demonstrated consistent cis-selectivity for these substrates. The P450s were also active on 1,1-disubstituted olefins (e.g., α-methyl styrene), with chimeric P450 C2G9R1 forming cyclopropanes in 77% yield (with respect to EDA). The P450s were only moderately active with t-butyl diazoacetate as substrate (<30 TTN), forming the trans product with >87% selectivity and offering no advantage over free hemin (Table 27). However, for reactions involving EDA and aryl-substituted olefins, the P450s consistently outperformed the free cofactor in both activity and stereoselectivity.

TABLE 23

Substrate scope of P450 cyclopropanases: p-methylstyrene + EDA.

p-methylstyrene (30 mM) + EDA (10 mM) + P450 (20 µM, 0.2 mol %) → (0.1 M KPi pH 8.0, 5% MeOH, 10 mM Na₂S₂O₄, Anaerobic) → p-tolyl-cyclopropane-COOEt

| P450 | % yield | TTN | cis:trans | % ee cis | % ee trans$^a$ |
|---|---|---|---|---|---|
| 7-11D | 21 | 104 | 54:46 | 0.3 | N/A |
| H2-5-F10 | 44 | 222 | 11:89 | 14.9 | N/A |

TABLE 23-continued

| | | | | | |
|---|---|---|---|---|---|
| C2G9 R1 | 18 | 92 | 10:90 | 8.9 | N/A |
| H2A10 | 10 | 50 | 43:57 | −84.3 | N/A |
| 9-10A TS F87V T268A (C3C) | 46 | 228 | 78:22 | −81.4 | N/A |
| Hemin | 7 | 37 | 6:94 | −1.6 | N/A |

GC (cyclosil-B column 30 m × 0.32 mm, 0.25 μm film): oven temperature = 100° C. for 5 min, 5° C./min to 200° C., 20° C./min to 250° C., 250° C. for 5 min. Elution times: cis-cyclopropanes (21.03 and 21.18 min), trans-cyclopropanes (22.71 min).
[a]trans-enantiomers did not resolve.

TABLE 24

Substrate scope of P450 cyclopropanases: p-vinylanisole + EDA.

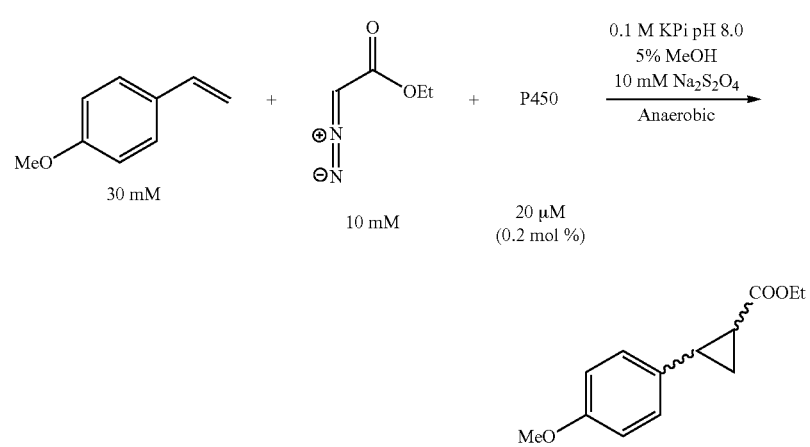

| P450 | % yield | TTN | cis:trans | % ee cis | % ee trans[a] |
|---|---|---|---|---|---|
| 7-11D | 59 | 297 | 70:30 | −27 | N/A |
| H2-5-F10 | 73 | 364 | 11:89 | 38 | N/A |
| C2G9 R1 | 39 | 196 | 10:90 | −1 | N/A |
| H2A10 | 16 | 80 | 40:60 | −75 | N/A |
| 9-10A TS F87V T268A (C3C) | 43 | 214 | 48:52 | −44 | N/A |
| Hemin | 19 | 96 | 7:93 | 0 | N/A |

GC oven temperature = 110° C. for 8 min, 2° C./min to 180° C. then 180° C. for 30 min, 175 kPa. Cyclosil-B column (30 m × 0.25 mm, 0.25 μm film). Elution times: cis-cyclopropanes (38.74 and 39.52 min), trans-cyclopropanes (43.07 min).
[a]Baseline resolution could not be achieved for the trans-enantiomers.

TABLE 25

Substrate scope of P450 cyclopropanases: p-(trifluoromethyl)styrene.

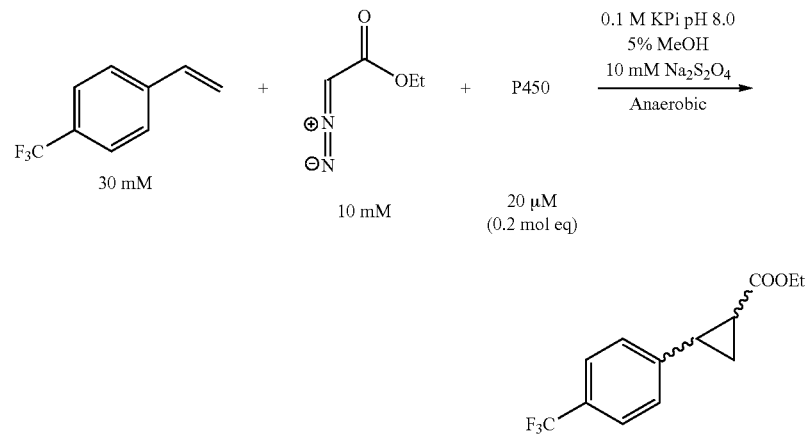

| P450 | % yield[a] | TTN[a] | cis:trans | % ee cis | % ee trans |
|---|---|---|---|---|---|
| 7-11D | 24 | 120 | 76:24 | 31 | 59 |
| H2-5-F10 | 40 | 198 | 26:74 | 72 | −65 |

TABLE 25-continued

| | | | | | |
|---|---|---|---|---|---|
| C2G9 R1 | 18 | 89 | 10:90 | 4 | 0 |
| H2A10 | 9 | 47 | 26:74 | −24 | 22 |
| 9-10A TS F87V T268A (C3C) | 42 | 211 | 39:61 | 54 | −93 |
| Hemin | 2 | 9 | 11:89 | 1 | 1 |

[a]Assumed the same detector response factor as for ethyl 2-(4-methylphenyl)cyclopropane-1-carboxylate. GC (cyclosil-B column 30 m × 0.25 mm, 0.25 μm film): oven temperature = 110° C. for 8 min, 2° C./min to 180° C. for 30 min, 175 kPa. Elution times: cis-cyclopropanes (27.26 and 28.11 min), trans-cyclopropanes (30.78 and 30.99 min).

TABLE 26

Substrate scope of P450 cyclopropanases: α-methyl styrene.

| P450 | % yield | TTN | Z:E | % ee (Z) | % ee (E)[a] |
|---|---|---|---|---|---|
| 7-11D | 31 | 157 | 41:49 | 42 | N/A |
| H2-5-F10 | 66 | 329 | 21:79 | −14 | N/A |
| C2G9 R1 | 77 | 387 | 16:84 | −4 | N/A |
| H2A10 | 34 | 168 | 19:81 | −31 | N/A |
| 9-10A TS F87V T268A (C3C) | 26 | 127 | 16:84 | −6 | N/A |
| WT F87V T268A | 62 | 312 | 7:93 | 3 | N/A |
| Hemin | 15 | 77 | 24:76 | 0 | N/A |

GC oven temperature = 100° C. for 5 min, 1° C./min up to 135° C., 135° C. for 10 min, 10° C./min up to 200° C., 200° C. for 5 min.
Cyclosil-B column (30 m × 0.32 mm, 0.25 μm film).
Elution times: Z-cyclopropanes (34.96 and 35.33 min), E-cyclopropanes (39.34 and 39.61 min).
[a]trans-enantiomers did not separate to baseline resolution.

TABLE 27

Substrate scope of P450 cyclopropanases: t-butyl diazoacetate.

| P450 | % yield[a] | TTN[a] | cis:trans |
|---|---|---|---|
| WT F87V T268A | 1.4 | 7 | 4:96 |
| 7-11D | 11 | 54 | 13:87 |
| H2-5-F10 | 18 | 90 | 3:97 |
| H2A10 | 24 | 120 | 3:97 |
| 9-10A TS F87V T268A (C3C) | 0.3 | 2 | 3:97 |
| Hemin | 20 | 100 | 4:96 |

[a]Assumed the same detector response factor as for ethyl 2-(4-methylphenyl)cyclopropane-1-carboxylate.
GC (cyclosil-B column 30 m × 0.32 mm, 0.25 μm film): oven temperature = 100° C. for 5 min, 5° C./min to 200° C., 20° C./min to 250° C., 250° C. for 5 min.
Elution times: cis-cyclopropanes (21.66 min), trans-cyclopropanes (23.31 min).
Cis- and trans-enantiomers did not resolve.

Designing enzymes that catalyze reactions not observed in nature constitutes a contemporary challenge in protein engineering (J. B. Siegel et al., Science 329, 309 (2010)). Working from a natural enzyme with promiscuous reactivity, this example demonstrates the construction of a cyclopropanase that exhibits kinetics comparable to natural enzymes, albeit with pre-activated reagents. Discovering catalysts for non-natural bond-disconnections by screening natural enzymes against synthetic reagents chosen based on chemical intuition offers a simple strategy for identifying enzymes with basal levels of novel activity. As shown herein, a single mutation can be enough to promote the new activity and achieve synthetically useful stereoselectivities. The established reaction promiscuity of natural enzymes (U. T. Bornscheuer et al., Angew. Chem. Int. Ed. 43, 6032 (2004)) and the ease with which cyclopropanase activity could be installed into $P450_{BM3}$ indicates that this approach will be useful for other synthetically important transformations for which biological counterparts do not yet exist.

Materials and Methods

Unless otherwise noted, all chemicals and reagents for chemical reactions were obtained from commercial suppliers (Sigma-Aldrich, Acros) and used without further purification. The following heme proteins were all purchased from Sigma-Aldrich: myoglobin (from equine heart), peroxidase II (from horseradish), cytochrome c (from bovine heart), catalase (from Corynebacterium glutamicum) and chloroperoxidase (from Caldariomyces fumago). Silica gel chromatography purifications were carried out using AMD Silica Gel 60, 230-400 mesh. $^1$H and $^{13}$C NMR spectra were recorded on either a Varian Mercury 300 spectrometer (300 MHz and 75 MHz, respectively), or a Varian Inova 500 MHz (500 MHz and 125 MHz, respectively), and are internally referenced to residual solvent peak. Data for $^1$H NMR are reported in the conventional form: chemical shift (δ ppm), multiplicity (s=singlet, d=doublet, t=triplet, q=quartet, m=multiplet, br=broad), coupling constant (Hz), integration. Data for $^{13}$C are reported in terms of chemical shift (δ ppm) and multiplicity. High-resolution mass spectra were obtained with a JEOL JMS-600H High Resolution Mass Spectrometer at the California Institute of Technology Mass Spectral Facility. Reactions were monitored using thin layer chromatography (Merck 60 silica gel plates) using an UV-lamp for visualization. Optical rotation was measured using a JASCO P-2000 Polarimeter.

Gas chromatography (GC) analyses were carried out using a Shimadzu GC-17A gas chromatograph, a FID detector, and J&W scientific cyclosil-B columns (30 m×0.32 mm, 0.25 µM film and 30 m×0.25 mm, 0.25 µm film). High-performance liquid chromatography (HPLC) was carried out using an Agilent 1200 series, an UV detector, and an Agilent XDB-C18 column (4.6×150 mm, 5 µm). Cyclopropane product standards for the reaction of ethyl diazoacetate (EDA) with styrene (ethyl 2-phenylcyclopropane-1-carboxylate) and α-methylstyrene (ethyl 2-methyl-2-pehnylcyclopropane-1-carboxylate) were prepared as reported (A. Penoni et al., European Journal of Inorganic Chemistry, 1452 (2003)). These standards were used in co-injection experiments to determine the authenticity of enzyme-catalyzed cyclopropanes. Authentic P450 catalyzed cyclopropane samples were also prepared as described below and were characterized by NMR ($^1$H and $^{13}$C) and mass spectrometry. Azides 5 and 8, and benzosultam standards 6 and 9 were prepared as reported (J. V. Ruppel et al., Org. Lett. 9, 4889 (2007)). Benzosultam 11 was purchased from Sigma. These standards were used in co-injection experiments to determine the authenticity of P450-catalyzed benzosultams. Authentic P450 catalyzed benzosultam samples were also prepared as described below and were characterized by NMR ($^1$H and $^{13}$C) and mass spectrometry.

Plasmids pCWori[BM3] and pET22 were used as cloning vectors. Site-directed mutagenesis was accomplished by standard overlap mutagenesis using primers baring desired mutations (IDT, San Diego, Calif.). Electro-competent Escherichia coli cells were prepared following the protocol of Sambrook et al., Molecular cloning: a laboratory manual. (Cold Spring Harbor Laboratory Press, New York, 1989), vol. 2. Restriction enzymes BamHI, EcoRI, XhoI, Phusion polymerase, and T4 ligase were purchased from New England Biolabs (NEB, Ipswich, Mass.). Alkaline phosphatase was obtained from Roche (Nutley, N.J.). The 1,000× trace metal mix used in expression cultures contained: 50 mM FeCl$_3$, 20 mM CaCl$_2$, 10 mM MnSO$_4$, 10 mM ZnSO$_4$, 2 mM CoSO$_4$, 2 mM CuCl$_2$, 2 mM NiCl$_2$, 2 mM Na$_2$MoO$_4$, and 2 mM H$_3$BO$_3$.

Enzyme Library Screening.

Libraries are stored at −78° C. as glycerol stocks (Luria-Bertani medium (LB$_{amp}$), 150 µL, 25% v/v glycerol with 0.1 mg/mL ampicillin) in 96-well plates. These stocks were used to inoculate 96-shallow-well plates containing 300 µL LB$_{amp}$ medium using a 96-pin stamp. Single colonies from site saturation libraries were picked with toothpicks and used to inoculate 300 µL of LB$_{amp}$. The cells were incubated at 37° C., 250 rpm, and 80% relative humidity overnight. After 16 h, 50 µL aliquots of these over night cultures were transferred into 2 mL deep-well plates containing terrific broth (TB$_{amp}$) (800 µL containing 0.1 mg/mL ampicillin, 1 µL/mL trace metal mix and 20 mg L$^{-1}$ aminolevulinic acid) using a Multimek 96-channel pipetting robot (Beckman Coulter, Fullerton, Calif.). The cultures were incubated at 37° C. for 3 h and 30 min, and 30 min after reducing the incubation temperature to 25° C. (250 rpm, 80% relative humidity), 50 µL isopropyl β-D-1-thiogalactopyranoside (IPTG, 4.5 mM in TB$_{amp}$) was added, and the cultures were allowed to continue for another 24 h at 25° C. (250 rpm, 80% relative humidity). Cells were then pelleted (3,000×g, 15 min, 4° C.) and stored at −20° C. until further use, but at least for 2 h. For cell lysis, plates were allowed to thaw for 30 min at room temperature and then cell pellets were resuspended in 275 µL phosphate buffer (0.1 M, pH=8.0, 0.65 mg/mL lysozyme, 10 mM magnesium chloride and 40 U/mL DNAse I). The lysing cells were incubated at 37° C. for 1 h. Cell debris was separated by centrifugation at 5,000×g and 4° C. for 15 min. The resulting crude lysates were then transferred to 96-well microtiter plates for CO assays and to 2 mL deep well plates for bioconversions.

CO Binding Assay.

P450$_{BM3}$ variants in cell lysate (40 µL) were diluted with 60 µL phosphate buffer (0.1 M, pH=8.0). To this solution was added 160 µL sodium dithionite (0.1 M in phosphate buffer, 0.1 M, pH=8.0). The absorbance at 450 and 490 nm was recorded using a Tecan M1000 UV/Vis plate reader, and the microtiter plates were placed in a vacuum chamber. The chamber was sealed, evacuated to approximately −15 in Hg, purged with CO gas, and incubated for 30 min. The plates were then removed and the absorbance at 450 and 490 nm was again recorded using a plate reader. The difference spectra could then be used to determine the P450 concentration in each well as previously described (C. R. Otey, in Methods in Molecular Biology: Directed Enzyme Evolution, F. H. Arnold, G. Georgiou, Eds. (Humana Press, Totowa, N.J., 2003), vol. 230).

P450 Expression and Purification.

For the enzymatic transformations, P450$_{BM3}$ variants were used in purified form. Enzyme batches were prepared as follows. One liter TB$_{amp}$ was inoculated with an overnight culture (100 mL, LB$_{amp}$) of recombinant E. coli DH5α cells harboring a pCWori plasmid encoding the P450 variant under the control of the tac promoter. After 3.5 h of incubation at 37° C. and 250 rpm shaking (OD$_{600}$ ca. 1.8), the incubation temperature was reduced to 25° C. (30 min), and the cultures were induced by adding IPTG to a final concentration of 0.5 mM. The cultures were allowed to continue for another 24 hours at this temperature. After harvesting the cells by centrifugation (4° C., 15 min, 3,000×g), the cell pellet was stored at −20° C. until further use but at least for 2 h. The cell pellet was resuspended in 25 mM Tris.HCl buffer (pH 7.5 at 25° C.) and cells were lysed by sonication (2×1 min, output control 5, 50% duty cycle; Sonicator, Heat Systems—Ultrasonic, Inc.). Cell debris was removed by centrifugation for 20 min at 4° C. and 27,000×g and the supernatant was subjected to anion exchange chromatography on a Q Sepharose column (Hi-Trap™ Q HP, GE Healthcare, Piscataway, N.J.) using an AKTAxpress purifier FPLC system (GE healthcare). The P450 was eluted from the Q column by running a gradient from 0 to 0.5 M NaCl over 10 column volumes (P450 elutes at 0.35 M NaCl). The P450 fractions were collected and concentrated using a 30 kDa molecular weight cut-off centrifugal filter and buffer-exchanged with 0.1 M phosphate buffer (pH=8.0). The purified protein was flash-frozen on dry ice and stored at −20° C. P450 concentration was determined in triplicate using the CO binding assay described above (10 µL P450 and 190 µL 0.1 M phosphate buffer, pH 8.0, per well).

Thermostability Measurements.

Duplicate measurements were taken for all values reported on Tables 17 and 18. Purified P450 solutions (4 µM, 200 µL) were heated in a thermocycler (Eppendorf) over a range of temperatures (38° C.-65° C.) for 10 min followed by rapid cooling to 4° C. for 1 min. The precipitate was removed by centrifugation. The concentration of folded P450 remaining in the supernatant was measured by CO-difference spectroscopy (as described above). The temperature at which half of the protein was denatured ($T_{50}$) was determined by fitting the data to the equation: $f(T)=100/(1+\exp(a*(T-T_{50})))$.

Typical Procedure for Small-Scale Cyclopropanation Bioconversions Under Anaerobic Conditions.

Small-scale reactions (400 L) were conducted in 2 mL crimp vials (Agilent Technologies, San Diego, Calif.). P450 solution (80 µL, 100 µM) was added to the vial with a small stir bar before crimp sealing with a silicone septum. Phosphate buffer (260 µL, 0.1 M, pH=8.0) and 40 µL of a solution of the reductant (100 mM sodium dithionite, or 20 mM NADPH) were combined in a larger crimp sealed vial and degassed by bubbling argon through the solution for at least 5 min (FIG. 3). In the meantime, the headspace of the 2 mL reaction vial with the P450 solution was made anaerobic by flushing argon over the protein solution (with no bubbling). When multiple reactions were conducted in parallel, up to 8 reaction vials were degassed in series via cannula. The buffer/reductant solution (300 µL) was syringed into the reaction vial, while under argon. The gas lines were disconnected from the reaction vial before placing the vials on a plate stirrer. A 40× styrene solution in MeOH (10 µL, typically 1.2 M) was added to the reaction vial via a glass syringe, and left to stir for about 30 s. A 40×EDA solution in MeOH was then added (10 µlt, typically 400 mM) and the reaction was left stirring for the appropriate time. The final concentrations of the reagents were typically: 30 mM styrene, 10 mM EDA, 10 mM sodium dithionite, 20 µM P450.

The reaction was quenched by adding 30 µL HCl (3M) via syringe to the sealed reaction vial. The vials were opened and 20 µL internal standard (20 mM 2-phenylethanol in MeOH) was added followed by 1 mL ethyl acetate. This mixture was transferred to a 1.8 mL eppendorf tube which was vortexed and centrifuged (16,000×g 1 min). The top organic layer was dried over an anhydrous sodium sulfate plug and analyzed by chiral phase GC.

A slightly modified work-up was implemented for kinetic experiments. The reactions were quenched after the set time by syringing 1 mL EtOAc to the closed vials and immediately vortexing the mixture. The vials were then opened and 20 µL internal standard was added. The mixture was transferred to a 1.8 mL eppendorf tube, vortexed and centrifuged (16,000×g, 1 min). The top organic layer was dried over an anhydrous sodium sulfate plug and analyzed by GC.

Typical Procedure for Preparative-Scale Cyclopropanation Bioconversions Under Anaerobic Conditions.

The P450 solution was added to a Schlenk flask with a stir bar. With the flask kept on ice, the head-space was evacuated and back-filled with argon (4×) with care not to foam the protein solution. Phosphate buffer and reductant were premixed and degassed together in a separate round-bottom-flask by bubbling argon through the solution for 20 min. The buffer/reductant solution was transferred to the Schlenk flask via syringe. Styrene was added under argon and left to mix for 1 min. EDA was added dropwise under argon. The solution was left to stir under argon until reaction completion. The reaction was quenched under argon by adding hydrochloric acid (3 M) to adjust the pH to 4, before opening the Schlenk flask. The reaction mixture was stirred with sodium chloride and dichloromethane ($CH_2Cl_2$). The combined emulsion layers were then filtered through Celite to break the emulsion and the Celite pad was rinsed with 3×20 mL $CH_2Cl_2$. The resulting biphasic mixture was transferred to a separating funnel and the organic phase was removed. The remaining aqueous phase was re-extracted with 3×40 mL $CH_2Cl_2$. The combined organic extracts were dried with sodium sulfate, filtered, and concentrated. The resulting residue was purified by $SiO_2$ chromatography.

Summary of Mutations (with Respect to Wild-Type $P450_{BM3}$) of P450 Cyclopropanases and Aminases.

7-11D (P. Meinhold et al., *Adv. Synth. Catal.* 348, 763 (2006)): R47C, V78A, K94I, P142S, T175I, A184V, F205C, S226R, H236Q, E252G, R255S, A290V, L353V, A82F, A328V 9-10A TS (J. C. Lewis et al., *Chembiochem: A European Journal of Chemical Biology* 11, 2502 (2010)): V78A, P142S, T175I, A184V, S226R, H236Q, E252G, A290V, L353V, I366V, E442K

H2A10: 9-10A TS F87V, L75A, L181A, T268A

H2-5-F10: 9-10A TS F87V, L75A, I263A, T268A, L437A

H2-4-D4: 9-10A TS F87V, L75A, M177A, L181A, T268A, L437A

C3C: 9-10A TS F87V T268A

B1SYN (J. C. Lewis et al., *Proceedings of the National Academy of Sciences USA* 106, 16550 (2009)): R47C, V78A, K94I, P142S, T175I, A184V, F205C, S226R, H236Q, E252G, R255S, A290V, L353V, C47S, N70Y, A78L, F87A, I174N, I94K, V184T, I263M, G315S, A330V Supplementary Data Preliminary Experiments with Heme Proteins The following six heme proteins were initially screened for 'cyclopropanase' activity: catalase, chloroperoxidase (CPO), horseradish peroxidase (HRP), cytochrome C (cyt c), myoglobin (Mb) and $P450_{BM3}$. Small-scale (400 µL) reactions were conducted as described in section II and were analyzed by GC (cyclosil-B 30 m×0.25 mm×0.25 µm): oven temperature=130° C. Table 7 shows heme catalysts under anaerobic conditions with sodium dithionite ($Na_2S_2O_4$). Table 8 shows heme catalysts under anaerobic conditions without $Na_2S_2O_4$. Table 9 shows heme catalysts under aerobic conditions with $Na_2S_2O_4$. Table 10 shows heme catalysts under aerobic conditions without $Na_2S_2O_4$.

Screening P450BM3 Variants for Cyclopropanation Activity
Lysate Screening Under Aerobic Conditions.

The 92 $P450_{BM3}$ variants in the compilation plate (Table 12) represent a diverse selection of $P450_{BM3}$ scaffolds that have previously been engineered for monooxygenase activity on a variety of substrates, including but not limited to short alkane hydroxylation, demethylation of protected monosaccharides and oxidation of lead drug compounds. These $P450_{BM3}$ variants carry various mutations (Table 12) accumulated along sequential rounds of engineering efforts for activity towards the target substrates. The compilation plate was expressed and lysed as described in above (enzyme library screening). 150 µL lysate was transferred (Multimek 96-channel pipetting robot, Beckman Coulter, Fullerton, Calif.) to a 2 mL deep well plate, with 50 µL of 120 mM $Na_2S_2O_4$ in 0.1 M KPi (pH=8.0). 100 µL of a 30 mM styrene, 60 mM EDA mixed solution in 15% MeOH in 0.1 M KPi (pH=8.0) was added to the plate to initiate the reaction. The plate was sealed and was left shaking (300 rpm) for four hours. The plastic seal was removed and 30 µL HCl (3 M) was added to quench the reaction followed by 20 µl, of an internal standard solution (20 mM α-methylstyrene in methanol). The reactions were extracted by adding 500 µL EtOAc and carefully vortexing the plate. The plate was centrifuged (1,700×g)

to separate the biphasic mixture. The top organic layer was transferred (2×150 µL) to a separate deep well plate. The extracts for each of the 92 reactions were dried through 92 separate anhydrous sodium sulfate plugs. The dried extracts were analyzed by GC (cyclosil-B 30 m×0.32 mm×0.25 µm): oven temperature=60° C. 3 min, 7.5° C./min to 160° C., 20° C./min to 250° C., 250° C. 2 min, cis-cyclopropanes (20.3 min and 20.45 min), trans-cyclopropanes (21.8 min).

Determining the Cyclopropanation Activity of the Top 10 Hits in Tables 12-13 Under Anaerobic Conditions.

Small-scale reactions (400 µL total volume) were conducted as described above and were analyzed by GC (cyclosil-B 30 m×0.32 mm×0.25 µm): oven temperature=100° C. 5 min, 1° C./min to 135° C., 135° C. 10 min, 10° C./min to 200° C., 200° C. 5 min, cis-cyclopropanes (39.40 min and 40.20 min), trans-cyclopropanes (44.69 min and 45.00 min). Table 14 shows stereoselective P450BM3 based cyclopropanases.

Experimental Characterization of P450BM3 Cyclopropanases

Controls to Confirm the Enzymatic Cyclopropanation Activity of Variant H2A10.

Small scale reactions (400 µL total volume) were set up and worked-up as described above. For the carbon monoxide (CO) inhibition experiment, the reaction vial and the buffer/reductant vial were purged with CO after having been purged with argon. For the boiled P450 experiment, a 100 µM solution of variant H2A10 was heated at 60° C. for 10 min. For the hemin experiment, hemin (80 µL) was added from a 1 mM solution in 50% DMSO-$H_2O$, such that its final concentration in the reaction was 200 µM. Complete System=10 mM styrene, 20 mM EDA, 20 mM $Na_2S_2O_4$, 20 µM P450 (H2A10) under anaerobic conditions. The dried ethyl acetate extracts were analyzed by chiral phase GC, using 2-phenylethanol as an internal standard (injector temperature=300° C., oven temperature=100° C. for 5 min, 1° C./min ramp up to 135° C., 135° C. for 10 min, 10° C./min ramp up to 200° C., 200° C. for 5 min). Elution time: cis-cyclopropanes (39.40 min and 40.20 min), trans-cyclopropanes (44.69 min and 45.00 min). Table 15 shows controls for P450 based cyclopropanation using variant H2A10.

Optimizing Cyclopropanation Reaction Conditions for Variant H2A10.

Small-scale reactions (400 µL final volume) were set up and worked up as described above. The dried ethyl acetate extracts were analyzed by chiral phase GC, using 2-phenylethanol as an internal standard (injector temperature=300° C., oven temperature=100° C. for 5 min, 5° C./min ramp up to 200° C., 20° C./min ramp up to 250° C., 250° C. for 5 min). Elution time: cis-cyclopropanes (19.20 min and 19.33 min), trans-cyclopropanes (20.44 min). The reaction conditions that gave optimal yields of cyclopropanes (with respect to EDA) were: 30 mM styrene, 10 mM EDA and 20 µM P450 and were used in subsequent experiments.

Styrene Concentration.

FIG. 3 illustrates the effect of styrene concentration on cyclopropane yield.

P450 Concentration.

FIG. 4 illustrates the effect of P450 (H2A10) concentration on cyclopropane yield.

Dithionite Concentration.

Table 16 shows the effect of the concentration of $Na_2S_2O_4$ on cyclopropane yield.

Mutational Analysis of Active Site Alanine Substitutions in 9-10A TS F87V.

Table 17 shows a mutational analysis of alanine substitutions on 9-10A TS F87V.

Sequential Introduction of BM3-CIS Active Site Mutations in Wild-Type $P450_{BM3}$.

Table 18 shows introducing BM3-CIS related active site mutations in wild-type $P450_{BM3}$.

Active Site Saturation Mutagenesis of $C3C_{heme}$

Library Construction.

To simplify library construction and screening, only the C3C heme domain, which comprises residues 1-462 was used. This truncated enzymes lacks the P450 native reductase and exhibits similar activity and stereochemical control to the holo enzyme using dithionite as a reductant, but not NADPH. P450 site-directed mutagenesis and site-saturation libraries were assembled from PCR fragments generated from oligonucleotides containing the desired codon mutation or a degenerate NNK (or for reverse primers, the reverse complement MNN; where N=A,T,G,C,K=G,T and M=A,C) codon, which codes for all 20 amino acids and the TAG stop codon. PCR fragments were assembled using either standard overlap extension PCR or through restriction cloning using the Type IIS restriction enzyme, BsaI, depending on convenience.

Lysate Screening Under Aerobic Conditions.

The compilation plate was expressed and lysed as described above (enzyme library screening). 150 µL lysate was transferred (Multimek 96-channel pipetting robot, Beckman Coulter, Fullerton, Calif.) to a 2 mL deep well plate, with 50 µL of 120 mM $Na_2S_2O_4$ in 0.1 M KPi (pH=8.0). 100 µL of a 90 mM styrene, 30 mM EDA mixed solution in 15% MeOH in 0.1 M KPi (pH=8.0) was added to the plate to initiate the reaction. The plate was sealed and was left shaking (300 rpm) for four hours. The plastic seal was removed and 30 µL HCl (3 M) was added to quench the reaction followed by 20 µL of an internal standard solution (20 mM 2-phenylethanol in methanol). Acetonitrile (400 µL) was added before carefully vortexing the plate. The plate was centrifuged (1,700×g), the supernatant was filtered (1 µm glass, 96 well filter plate, Pall) and transferred (150 µL) to a 96-well microtiter plate (Agilent). Reactions were analyzed by reverse-phase HPLC (210 nm): 50% acetonitrile-water, 1.0 mL min$^{-1}$, cis-cyclopropanes (7.6 min), trans-cyclopropanes (9.7 min). Hits were selected based on enhancement of cis-selectivity over parent C3C.

Determining the Cyclopropanation Activity of Hits from the Site-Saturation Libraries Under Anaerobic Conditions.

Small-scale reactions (400 µL total volume) were conducted as described above and were analyzed by GC (cyclosil-B 30 m×0.25 mm×0.25 µm): oven temperature=130° C., 175 kPa, cis-cyclopropanes (39.40 min and 40.20 min), trans-cyclopropanes (44.69 min and 45.00 min). Table 19 shows the cyclopropanation activity of selected $C3C_{heme}$ active site variants Kinetic Characterization of C3C Determination of initial rates. Both styrene and EDA concentrations were varied in the presence of the P450s expressed as the heme-domain (0.5 or 1.0 µM $C3C_{heme}$). Reactions were set up in phosphate buffer (pH=8.0) with sodium dithionite as the reductant at 298 K, and were worked-up as described above. Three time points were taken and used to determine the rate of product formation by GC (cyclosil-B 30 m×0.32 mm×0.25 µm): oven temperature=100° C. 5 min, 5° C./min to 200° C., 20° C./min to 250° C., 250° C. for 5 min. Elution time: cis-cyclopropanes (19.20 min and 19.33 min), trans-cyclopropanes (20.44 min). Kinetic parameters were determined by fitting the data to the standard Michaelis-Menten model.

FIG. 5 illustrates the initial velocities plot for $C3C_{heme}$. (A) EDA concentration was varied at a saturating concentration of styrene (30 mM). (B) Styrene concentration was varied at a fixed concentration of EDA (20 mM). Table 20 shows the Michaelis-Menten parameters for P450 cyclopropanation catalysts. Table 21 shows kinetic parameters for wild-type cytochrome P450s acting on their native substrates and for an engineered variant of P450$_{BM3}$ (propane monooxygenase, PMO) acting on the non-native substrate propane. Table 22 shows the effect of EDA addition at t=30 min on C3C-catalyzed cyclopropanations.

Substrate Scope of P450 Cyclopropanases

Small-Scale Reactions.

Selected P450 catalysts were surveyed at a small-scale (400 total volume) for each combination of reagents (olefins and diazo esters). The small-scale anaerobic bioconversions were conducted as described above and were analyzed by GC. Table 23 shows the substrate scope of P450 cyclopropanation catalysts: p-methylstyrene+EDA. Table 24 shows the substrate scope of P450 cyclopropanation catalysts: p-vinylanisole+EDA. Table 25 shows the substrate scope of P450 cyclopropanation catalysts: p-(trifluoromethyl)styrene. Table 26 shows the substrate scope of P450 cyclopropanation catalysts: α-methyl styrene. Table 27 shows the substrate scope of P450 cyclopropanation catalysts: t-butyl diazoacetate.

Preparative-Scale Bioconversions.

These reactions were conducted anaerobically as described above.

Cyclopropanation of Styrene with EDA.

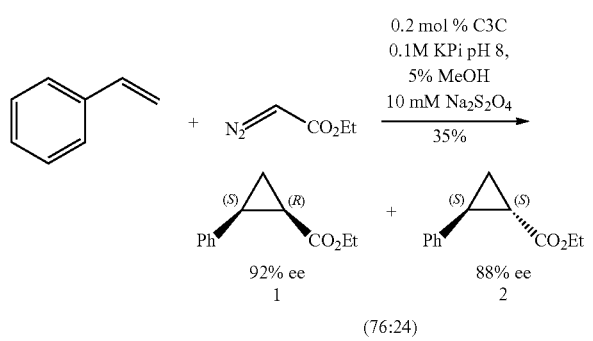

Prepared using 1.5 mmol styrene (3 equiv), 0.5 mmol EDA (1 equiv) and 1 μmol C3C$_{heme}$ (0.002 equiv). The product was purified by SiO$_2$ chromatography (9:1 hexanes-diethyl ether) to give 25 mg of the cis-cyclopropane (1) and 8 mg of a mixture of cyclopropanes with trans (2) in 5:1 excess over cis (C. J. Sanders et al., *Tetrahedron: Asymmetry* 12, 1055 (2001); M. Lenes Rosenberg et al., *Organic Letters* 11, 547 (2009); Y. Chen et al., *Journal of Organic Chemistry* 72, 5931 (2007)). Diagnostic data for the cis-cyclopropane 1: $^1$H NMR (CDCl$_3$, 500 MHz): δ 7.28 (m, 4H), 7.21 (m, 1H), 3.89 (q, J=7.1 Hz, 2H), 2.60 (m, 1H), 2.10 (m, 1H), 1.73 (m, 1H), 1.35 (m, 1H), 0.99 (t, J=7.1 Hz, 3H); $^{13}$C NMR (CDCl$_3$, 125 MHz): δ 170.99, 136.56, 129.31, 127.88, 126.63, 60.18, 25.47, 21.80, 14.02, 11.12; [α]$^{25}$$_D$=−7.056° (c 0.83, CHCl$_3$). Diagnostic data for the trans-cyclopropane 2: $^1$H NMR (CDCl$_3$, 500 MHz): δ 7.20 (m, 3H), 7.03 (m, 2H), 4.10 (q, J=7.1 Hz, 2H), 2.45 (m, 1H), 1.83 (m, 1H), 1.53 (m, 1H), 1.23 (m, 1H), 1.21 (t, J=7.1 Hz, 3H); $^{13}$C NMR (CDCl$_3$, 125 MHz): δ 173.43, 140.13, 128.46, 126.55, 126.16, 60.72, 26.18, 24.20, 17.09, 14.27; [α]$^{25}$$_D$=+199.2° (c 0.50, CHCl$_3$). MS (E1+) m/z: 190 (M$^+$), 162 (PhCH(CH$_2$)CHCO$_2$$^+$), 145 (PhCH(CH$_2$)CHCO$^+$). The absolute configuration of compounds 1 and 2 was determined by comparison of the sign of their optical rotations with that reported (N. Watanabe et al., *Heterocycles* 42, 537 (1996)). The enantiomeric excess was determined to be 92% for the cis-cyclopropane and 88% for the trans-cyclopropane by GC.

Cyclopropanation of p-Methylstyrene with EDA.

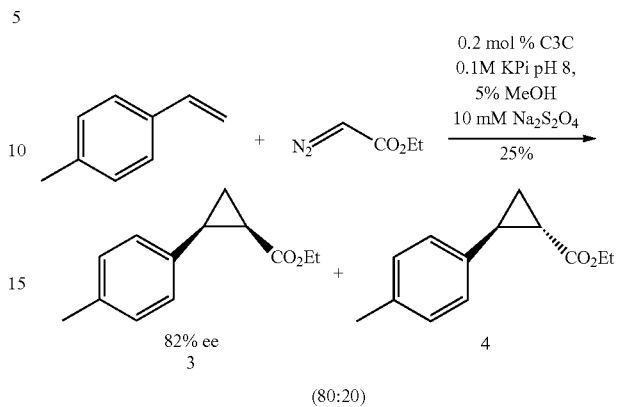

Prepared using 1.5 mmol styrene (3 equiv), 0.5 mmol EDA (1 equiv) and 1 mol C3C$_{heme}$ (0.002 equiv). The product was purified by SiO$_2$ chromatography (9:1 hexanes-diethyl ether) to give 10 mg of the cis-cyclopropane (3) and 16 mg of a mixture of cyclopropanes with trans(4): cis/2:1 (Y. Chen et al., *Journal of Organic Chemistry* 72, 5931 (2007)). Diagnostic data for the cis-cyclopropane 3: $^1$H NMR (CDCl$_3$, 500 MHz): δ 7.17 (d, J=8.0 Hz, 2H), 7.08 (d, J=8.0 Hz, 2H), 3.91 (q, J=7.1 Hz, 2H), 2.56 (m, 1H), 2.32 (s, 3H) 2.06 (m, 1H), 1.69 (m, 1H), 1.32 (m, 1H), 1.02 (t, J=7.1 Hz, 3H); $^{13}$C NMR (CDCl$_3$, 125 MHz): δ 171.12, 136.12, 133.42, 129.14, 128.60, 60.17, 25.23, 21.68, 21.10, 14.08, 11.21. Diagnostic data for the trans-cyclopropane 4: $^1$H NMR (CDCl$_3$, 500 MHz): δ 7.09 (d, J=8.0 Hz, 2H), 7.01 (d, J=8.0 Hz, 2H), 4.19 (q, J=7.1 Hz, 2H), 2.50 (m, 1H), 2.33 (s, 3H), 1.88 (m, 1H), 1.59 (m, 1H), 1.33 (m, 1H), 1.29 (t, J=7.1 Hz, 3H); $^{13}$C NMR (CDCl$_3$, 125 MHz): δ 173.58, 137.04, 136.08, 129.12, 126.10, 60.66, 25.94, 24.06, 21.11, 16.96, 14.28. MS (EI$^+$) m/z: 204 (M$^+$), 175 ([M-Et]$^+$) 131 ([M-COOEt]$^+$). The enantiomeric excess was determined to be 82% for the cis-cyclopropane by GC. Baseline resolution of the trans-enantiomers could not be achieved.

Cyclopropanation of p-Methoxystyrene with EDA.

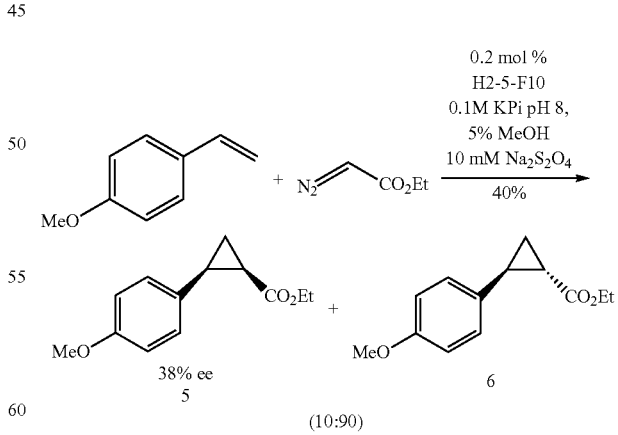

Prepared using 1.5 mmol styrene (3 equiv), 0.5 mmol EDA (1 equiv) and 1 μmol C3C$_{heme}$ (0.002 equiv). The product was purified by SiO$_2$ chromatography (9:1 hexanes-diethyl ether) to give 16 mg of the trans-cyclopropane (6) and 3 mg of a mixture of cyclopropanes with cis:trans/5:1 (Y. Chen et al.,

*Journal of Organic Chemistry* 72, 5931 (2007)). Diagnostic data for the trans-cyclopropane 6: 6.96 (m, 3H), 6.75 (m, 2H), 4.09 (q, J=7.1 Hz, 2H), 3.72 (s, 3H), 2.41 (m, 1H), 1.75 (m, 1H), 1.48 (m, 1H), 1.21 (t, J=7.1 Hz, 3H), 1.18 (m, 1H). MS (EI$^+$) m/z: 220 (M$^+$), 191 ([M-Et]$^+$), 175 ([M-EtO]$^+$), 147 ([M-COOEt]$^+$). The enantiomeric excess was determined to be 38% for the cis-cyclopropane by GC. The trans-enantiomers did not resolve to baseline resolution.

Cyclopropanation of Styrene with t-Butyl Diazo Acetate.

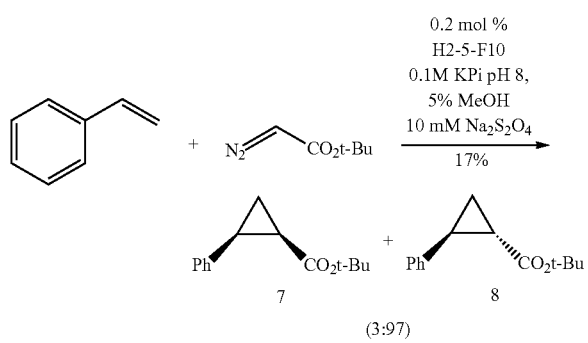

(3:97)

Prepared using 0.75 mmol styrene (3 equiv), 0.24 mmol t-BuDA (1 equiv) and 0.5 μmol C3C$_{heme}$ (0.002 equiv). The product was purified by SiO$_2$ chromatography (9:1 hexanes-diethyl ether) to give 9 mg of the trans-cyclopropane (8) (C. J. Sanders et al., *Tetrahedron: Asymmetry* 12, 1055 (2001); Y. Chen et al., *Journal of Organic Chemistry* 72, 5931 (2007)). Diagnostic data for the trans-cyclopropane 4: $^1$H NMR (CDCl$_3$, 500 MHz): δ 7.20 (m, 2H), 7.12 (m, 1H), 7.02 (m, 2H), 2.36 (m, 1H), 1.76 (m, 1H), 1.45 (m, 1H), 1.40 (s, 9H), 1.16 (m, 1H); $^{13}$C NMR (CDCl$_3$, 125 MHz): δ 172.58, 140.52, 128.42, 126.32, 126.07, 80.57, 28.17, 25.75, 25.31, 17.08. MS (EI$^+$) m/z: 218 (M$^+$), 145 ([M-OtBu]$^+$).

Example 2

In Vivo and In Vitro Olefin Cyclopropanation Catalyzed by Heme Enzymes

This example illustrates the use of heme containing enzymes to catalyze the conversion of olefins to various products containing one or more cyclopropane functional groups. In certain aspects, this example demonstrates novel variants of cytochrome P450$_{BM3}$ (CYP102A1). These variants have an improved ability to use diazo esters as carbene precursors and cyclopropanate various olefins. Preferred variants include cytochrome P450$_{BM3}$ mutants having C400S and T268A amino acid substitutions and engineered variants of other P450s having the equivalent substitutions. Variants with axial serine coordination efficiently catalyze the cyclopropanation reaction in whole cells sustaining over 10,000 total turnovers.

Introduction

The many strategies for functionalizing C=C and C—H bonds that have evolved in Nature have captivated the imaginations of chemists and form the foundation of biomimetic chemistry (J. T. Groves, *Proceedings of the National Academy of Sciences U.S.A.* 100, 3569 (2003); R. Breslow, *Journal of Biological Chemistry* 284, 1337 (2009)). The reverse of this, using inspiration from synthetic chemistry to discover and develop new biocatalysts, is a nascent frontier in molecular engineering whose recent highlights include C—H activation by artificial rhodium enzymes (T. K. Hyster et al., *Science* 338, 500 (2012)) and the de novo design of Diels-Alderases (T. K. Hyster et al., *Science* 338, 500 (2012); J. B. Siegel et al., *Science* 329, 309 (2010)). Synthetic chemists have developed powerful methods for direct C=C and C—H functionalization based on transition metal-catalyzed carbenoid and nitrenoid transfers, reactions that are widely used to synthesize natural product intermediates and pharmaceuticals (H. M. L. Davies et al., *Nature* 451, 417 (2008)). The asymmetric cyclopropanation of olefins with high-energy carbene precursors (e.g., acceptor-substituted diazo reagents) is a hallmark reaction that generates up to 3 stereogenic centers in a single step to make the important cyclopropane motif, featured in many natural products and therapeutic agents (H. Lebel et al., *Chemical Reviews* 103, 977 (2003)). Limited to using physiologically accessible reagents, Nature catalyzes intermolecular cyclopropane formation through wholly different strategies, typically involving olefin addition to the methyl cation of S-adenosyl methionine or through cyclization of dimethylallyl pyrophosphate-derived allylic carbenium ions (L. A. Wessjohann et al., *Chemical Reviews* 103, 1625 (2003)). As a result, the diverse cyclopropanation products that can be formed by metallocarbene chemistry cannot be readily accessed by engineering natural cyclopropanation enzymes. This example describes a natural metalloenzyme, the iron-heme-containing cytochrome P450, engineered to catalyze formal carbenoid transfers, thereby combining the high levels of regio- and stereoselectivity of enzymes with the synthetic versatility of carbene-based strategies. An enzyme is non-toxic, could be used in a primarily aqueous medium at ambient temperatures, and could be significantly less expensive to prepare than current transition metal catalysts.

Results

Members of the cytochrome P450 enzyme family catalyze myriad oxidative transformations, including hydroxylation, epoxidation, oxidative ring coupling, heteroatom release, and heteroatom oxygenation (E. M. Isin et al., *Biochim. Biophys. Acta,* 1770, 314 (2007)). Most transformations encompassed by this broad catalytic scope manifest the reactivity of the same high-valent iron-oxene intermediate (Compound I, FIG. 1). Inspired by the impressive chemo-, regio- and stereoselectivities with which cytochrome P450s can insert oxygen atoms into C—H and C=C bonds, the present inventors investigated whether these enzymes could be engineered to mimic this chemistry for isoelectronic carbene transfer reactions via a high-valent iron-carbenoid species (FIG. 1). This example demonstrates that variants of the cytochrome P450 from *Bacillus megaterium* (CYP102A1, or P450$_{BM3}$) are efficient catalysts for the asymmetric cyclopropanation of styrenes and other olefins.

Because iron porphyrins have been reported to catalyze carbene-based cyclopropanations (J. R. Wolf et al., *J. Am. Chem. Soc.* 117, 9194 (1995); B. Morandi et al., *Science* 335, 1471 (2012)), whether some common heme proteins display measurable levels of cyclopropanation activity in aqueous media (phosphate buffer, 5% methanol co-solvent) was first probed. The reaction between styrene and ethyl diazoacetate (EDA) was chosen (FIG. 2), a well-recognized model system for validating new cyclopropanation catalysts. The experiments showed that optimal formation of the desired cyclopropanation products occurred in the presence of a reducing agent (e.g., sodium dithionite, Na$_2$S$_2$O$_4$) under anaerobic conditions (Tables 7-10). Horseradish peroxidase (HRP), cytochrome c (cyt c), myoglobin (Mb) and P450$_{BM3}$ all displayed multiple turnovers towards the cyclopropane products, with HRP, cyt c and Mb showing negligible enantioinduction and formed the trans cyclopropane with over 90% diastereoselectivity, which is comparable to the diastereoselectivity induced by free hemin (Table 7). P450$_{BM3}$, despite forming the cyclopropane products in low yield, catalyzed the reaction with different diastereoselectivity (cis:trans 37:63) and slight enantioinduction (Table 28), showing that carbene transfer and selectivity are dictated by the heme cofactor bound in the enzyme active site.

TABLE 28

Stereoselective P450$_{BM3}$ cyclopropanation catalysts.
Reactions were run in aqueous phosphate buffer (pH 8.0) and 5% MeOH cosolvent at room temperature under argon with 30 mM styrene, 10 mM EDA, 0.2 mole % catalyst (with respect to EDA), and 10 mM Na$_2$S$_2$O$_4$.

| Catalyst | % yield | TTN | cis:trans | % ee$_{cis}$* | % ee$_{trans}$† |
|---|---|---|---|---|---|
| Hemin | 15 | 73 | 6:94 | −1 | 0 |
| P450$_{BM3}$ | 1 | 5 | 37:63 | −27 | −2 |
| P450$_{BM3}$-T268A | 65 | 323 | 1:99 | −15 | −96 |
| 9-10A-TS-F87V | 1 | 7 | 35:65 | −41 | −8 |
| H2-5-F10 | 59 | 294 | 16:84 | −41 | −63 |
| H2A10 | 33 | 167 | 60:40 | −95 | −78 |
| H2-4-D4 | 41 | 206 | 53:47 | −79 | −33 |
| BM3-CIS | 40 | 199 | 71:29 | −94 | −91 |
| BM3-CIS-I263A | 38 | 190 | 19:81 | −62 | −91 |
| BM3-CIS-A328G | 37 | 186 | 83:17 | 52 | −45 |
| BM3-CIS-T438S | 59 | 293 | 92:8 | −97 | −66 |
| BM3-CIS-C400S | 29 | 150 | 93:7 | −99 | −51 |

Yields, diastereomeric ratios, and enantiomeric excess were determined by GC analysis. Yields based on EDA.
TTN = total turnover number.
*(R,S)-(S,R). † (R,R)-(S,S). See, below for protein sequences indicating mutations from wild type P450$_{BM3}$. Variant 9-10A-TS-F87V-T268A (herein called BM3-CIS).

The activity levels exhibited by the native proteins tested are not suitable for practical synthetic applications. Whether the activity and selectivity of heme-catalyzed cyclopropanation could be enhanced by engineering the protein sequence was therefore explored. P45$_{BM3}$ is a well-studied, soluble, self-sufficient (heme and diflavin reductase domains are fused in a single polypeptide, ~120 KDa), long-chain fatty acid monooxygenase. More than a decade of protein engineering attests to the functional plasticity of this biocatalyst (C. J. C. Whitehouse et al., Chemical Society Reviews 41, 1218 (2012)). Thousands of variants that exhibit monooxygenase activity on a wide range of substrates have been accumulated from the use of engineered cytochrome P450$_{BM3}$ for synthetic applications (J. C. Lewis et al., Chimia 63, 309 (2009)). Some of these variants were tested for altered cyclopropanation diastero- and enantioselectivity by analysis of product distributions using gas chromatography (GC) with a chiral stationary phase. A panel of 92 P450$_{BM3}$ variants, chosen for diversity of activity and protein sequence, was screened in E. coli lysate for the reaction of styrene and EDA under aerobic conditions in the presence of Na$_2$S$_2$O$_4$ (Tables 12 and 13). The ten most promising hits were selected for purification and characterization under standardized anaerobic reaction conditions (Tables 14 and 28).

Five of the ten selected P450s showed improvements in activity compared to wild type (total turnover numbers (TTN) >100), a comprehensive range of diastereoselectivities with cis:trans ratios varying from 9:91 to 60:40, and up to 95% enantioselectivities (Table 14). For example, variant H2-5-F10, which contains 16 amino acid substitutions, catalyzes 294 total turnovers, equivalent to ~58% yield under these conditions (0.2% enzyme loading with respect to EDA). This represents a 50-fold improvement over wild type P450$_{BM3}$. Furthermore, mutations affect both the diastereo- and enantioselectivity of cyclopropanation: H2-5-F10 favors the trans cyclopropanation product (cis:trans 16:84) with 63% ee$_{trans}$, whereas H2A10, with a TTN of 167, shows reversed diastereoselectivity (cis:trans 60:40) with high enantioselectivity (95% ee$_{cis}$).

H2A10 was used to verify the role of the enzyme in catalysis and identify better reaction conditions (Table 15, FIGS. 3 and 4). Heat inactivation produced diastereo- and enantioselectivities similar to those obtained with free hemin, consistent with protein denaturation and release of the cofactor. Complete inhibition was achieved by pre-incubating the reaction mixture with carbon monoxide, which irreversibly binds the reduced P450 heme, confirming that catalysis occurs at the active site. Air inhibited the cyclopropanation reaction by about 50%, showing that dioxygen and EDA compete for reduced Fe$^{II}$. Cyclopropanation was also achieved with NADPH as the reductant, confirming that the activity can also be driven by the endogenous electron transport machinery of the diflavin-containing reductase domain. The presence of a reducing agent in sub-stoichiometric amounts proved essential for cyclopropanation (Table 16), implying that the active species is Fe$^{II}$ rather than the resting state Fe$^{III}$.

Highly active P450$_{BM3}$ variants H2A10, H2-5-F10 and H2-4-D4 have three to five active site alanine substitutions with respect to 9-10A-TS-F87V (12 mutations from P450$_{BM3}$), which itself shows negligible cyclopropanation activity. These variants exhibit a range of TTN, diastereoselectivity, and enantioselectivity (Table 28). To better understand how protein sequence controls P450-mediated cyclopropanation, 12 variants were constructed to assess the contributions of individual alanines to catalysis and stability (Table 17). T268A is key for achieving high cyclopropanation activity, and this mutation alone converts inactive 9-10A-TS-F87V into an active cyclopropanation catalyst. Variant 9-10A-TS-F87V-T268A (herein called BM3-CIS) is a competent cyclopropanation catalyst (199 TTN), displays strong preference for the cis product (cis:trans 71:29), forms both diastereomers with over 90% ee, and is as stable as wild-type P450$_{BM3}$. Other active site alanine mutations tune the product distribution. Notably, the addition of I263A to BM3-CIS reverses diastereoselectivity (cis:trans 19:81). The effects of similar mutations introduced in the poorly active wild type P450$_{BM3}$ were also investigated (Table 18). Impressively, P450$_{BM3}$-T268A, with a single mutation, is an active cyclopropanation catalyst (323 TTN, Table 28) with exquisite trans-selectivity (cis:trans 1:99) and high enantioselectivity for the major diastereomer (−96% ee$_{trans}$, Table 28). Whereas BM3-CIS is a cis-selective cyclopropanation catalyst, identical active site mutations in wild type P450$_{BM3}$ result in a trans-selective enzyme (Table 18), demonstrating that mutations outside of the active site also influence the stereochemical outcome.

Because the design of cis-selective small-molecule catalysts for diazocarbonyl-mediated cyclopropanations has proven more challenging than their trans counterparts (A. Caballero et al., European Journal of Inorganic Chemistry, 1137 (2009)), whether active site engineering of P450$_{BM3}$ could provide robust cis-selective water-compatible catalysts to complement existing organometallic systems was investigated (I. Nicolas et al., Coordination Chemistry Reviews 252, 727 (2008)). Five active site residues (L181, I263, A328, L437, T438) were chosen for individual site-saturation mutagenesis. The A328G, T438A, T438S and T438P variants exhibited enhanced cis-selectivity (Table 19). Notably A328G also reversed the enantioselectivity for the cis-diastereomer (Table 28). BM3-CIS-T438S displayed the highest diastereo- and enantioselectivities (cis:trans 92:8 and −97% ee$_{cis}$) and maintained TTN comparable to BM3-CIS (Table 28).

Variant 9-10A-TS-F87V-T268A (BM3-CIS) exhibits Michaelis-Menten kinetics (FIG. 5 and Table 20) with relatively high K$_M$ values for the olefin (~1.5 mM) and the diazoester (~5 mM), reflecting the lack of evolutionary pressure for this enzyme to bind these substrates. BM3-CIS exhibits a notable C$_{cat}$ for cyclopropanation of 100 min$^{-1}$, comparable to the k$_{cat}$ of many native P450s for hydroxylation, but about fifty times less than P450$_{BM3}$-catalyzed fatty acid hydroxylation (Table 21). Free hemin does not exhibit saturation kinetics and displays slower initial rates than BM3-CIS (only 30 min$^{-1}$ at 10 mM styrene and 15 mM EDA), indicating that the protein scaffold enhances k$_{cat}$ compared to the free cofactor in solution. When used at 0.2 mol % equivalent, BM3-CIS-catalyzed cyclopropanations reached completion after 30 minutes. Adding more EDA enhanced turnovers for cyclopropanes and preserved variant 9-10A-TS-F87V-T268A (BM3-CIS) stereoselectivity (Table 22), confirming catalyst integrity and implying that the reaction stops because of EDA depletion rather than protein inactivation.

This example shows that different variants of this enzyme will accept a wide range of substrates for cyclopropanation. To begin to assess the substrate scope of P450$_{BM3}$-catalyzed cyclopropanation, the activities of six variants were investigated against a panel of olefins and diazo compounds (Tables 29-34).

TABLE 29

Scope of P450 catalyzed cyclopropanation of styrenyl substrates.

| Reagents | P450 catalyst | TTN | Z:E | % ee$_Z$ | % ee$_E$ |
|---|---|---|---|---|---|
| R$_1$ = H, X = Me, R$_2$ = Et | BM3-CIS | 228 | 78:22 | −81 | N/A |
| R$_1$ = H, X = OMe, R$_2$ = Et | H2-5-F10 | 364 | 11:89 | 38 | N/A |
| R$_1$ = H, X = CF$_3$, R$_2$ = Et | 7-11D | 120 | 76:24 | 31 | 59 |
| R$_1$ = Me, X = H, R$_2$ = Et | 7-11D | 157 | 41:49 | 42 | N/A |
| R$_1$ = H, X = H, R$_2$ = t-Bu | H2A10 | 120 | 3:97 | N/A | N/A |

Ar = p-X—C$_6$H$_4$.
Reaction conditions: 20 μM catalyst, 30 mM olefin, 10 mM diazoester, 10 mM Na$_2$S$_2$O$_4$, under argon in aqueous potassium phosphate buffer (pH 8.0) and 5% MeOH cosolvent for 2 hours at 298K.
Enzyme loading is 0.2 mol % with respect to diazoester.
N/A = not available when enantiomers did not separate to baseline resolution.
Variant 9-10A-TS-F87V-T268A (herein called BM3-CIS).

TABLE 30

Substrate scope of P450 cyclopropanation catalysts: p-methylstyrene + EDA.

| P450 | % yield | TTN | cis:trans | % ee cis | % ee trans* |
|---|---|---|---|---|---|
| 7-11D | 21 | 104 | 54:46 | 0.3 | N/A |
| H2-5-F10 | 44 | 222 | 11:89 | 14.9 | N/A |
| C2G9 R1 | 18 | 92 | 10:90 | 8.9 | N/A |
| H2A10 | 10 | 50 | 43:57 | −84.3 | N/A |
| 9-10A-TS-F87V-T268A (BM3-CIS) | 46 | 228 | 78:22 | −81.4 | N/A |
| BM3-CIS-C400S | 32 | 157 | 93:7 | −87.1 | N/A |
| Hemin | 7 | 37 | 6:94 | −1.6 | N/A |

GC (cyclosil-B column 30 m × 0.32 mm, 0.25 μm film): oven temperature = 100° C. for 5 min, 5° C./min to 200° C., 20° C./min to 250° C., 250° C. for 5 min.
Elution times: cis-cyclopropanes (21.03 and 21.18 min), trans-cyclopropanes (22.71 min).
*trans-enantiomers did not resolve.

TABLE 31

Substrate scope of P450 cyclopropanation catalysts: p-vinylanisole + EDA

TABLE 31-continued

| P450 | % yield | TTN | cis:trans | % ee cis | % ee trans* |
|---|---|---|---|---|---|
| 7-11D | 59 | 297 | 70:30 | −27 | N/A |
| H2-5-F10 | 73 | 364 | 11:89 | 38 | N/A |
| C2G9 R1 | 39 | 196 | 10:90 | −1 | N/A |
| H2A10 | 16 | 80 | 40:60 | −75 | N/A |
| 9-10A-TS-F87V-T268A (BM3-CIS) | 43 | 214 | 48:52 | −44 | N/A |
| BM3-CIS-C400S | 47 | 235 | 81:19 | −61 | N/A |
| hemin | 19 | 96 | 7:93 | 0 | N/A |

GC oven temperature = 110° C. for 8 min, 2° C./min to 180° C. then 180° C. for 30 min, 175 kPa.
Cyclosil-B column (30 m × 0.25 mm, 0.25 μm film).
Elution times: cis-cyclopropanes (38.74 and 39.52 min), trans-cyclopropanes (43.07 min).
*Baseline resolution could not be achieved for the trans-enantiomers.

TABLE 32

Substrate scope of P450 cyclopropanation catalysts: p-(trifluoromethyl)styrene.

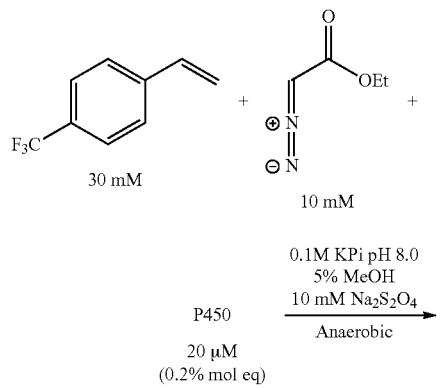

| P450 | % yield* | TTN* | cis:trans | % ee cis | % ee trans |
|---|---|---|---|---|---|
| 7-11D | 24 | 120 | 76:24 | 31 | 59 |
| H2-5-F10 | 40 | 198 | 26:74 | 72 | −65 |
| C2G9 R1 | 18 | 89 | 10:90 | 4 | 0 |
| H2A10 | 9 | 47 | 26:74 | −24 | 22 |
| 9-10A-TS-F87V-T268A (BM3-CIS) | 42 | 211 | 39:61 | 54 | −93 |
| BM3-CIS-C400S | 24 | 121 | 76:24 | 55 | −75 |
| hemin | 2 | 9 | 11:89 | 1 | 1 |

*Assumed the same detector response factor as for ethyl 2-(4-methylphenyl)cyclopropane-1-carboxylate.
GC (cyclosil-B column (30 m × 0.25 mm, 0.25 μm film): oven temperature = 110° C. for 8 min, 2° C./min to 180° C. then 180° C. for 30 min, 175 kPa.
Elution times: cis-cyclopropanes (27.26 and 28.11 min), trans-cyclopropanes (30.78 and 30.99 min).

TABLE 33

Substrate scope of P450 cyclopropanation catalysts: α-methyl styrene.

| P450 | % yield | TTN | Z:E | % ee (Z) | % ee (E)* |
|---|---|---|---|---|---|
| 7-11D | 31 | 157 | 41:49 | 42 | N/A |
| H2-5-F10 | 66 | 329 | 21:79 | −14 | N/A |
| C2G9 R1 | 77 | 387 | 16:84 | −4 | N/A |
| H2A10 | 34 | 168 | 19:81 | −31 | N/A |
| 9-10A-TS-F87V-T268A (BM3-CIS) | 26 | 127 | 16:84 | −6 | N/A |
| WT F87V T268A | 62 | 312 | 7:93 | 3 | N/A |
| BM3-CIS-C400S | 17 | 86 | 30:70 | 34 | N/A |
| hemin | 15 | 77 | 24:76 | 0 | N/A |

GC oven temperature = 100° C. for 5 min, 1° C./min up to 135° C., 135° C. for 10 min, 10° C./min up to 200° C., 200° C. for 5 min.
Cyclosil-B column (30 m × 0.32 mm, 0.25 μm film).
Elution times: Z-cyclopropanes (34.96 and 35.33 min), E-cyclopropanes (39.34 and 39.61 min).
* trans-enantiomers did not separate to baseline resolution.

TABLE 34

Substrate scope of P450 cyclopropanation catalysts: t-butyl diazoacetate.

TABLE 34-continued

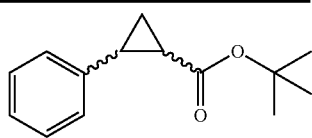

| P450 | % yield* | TTN* | cis:trans |
|---|---|---|---|
| WT F87V T268A | 1.4 | 7 | 4:96 |
| 7-11D | 11 | 54 | 13:87 |
| H2-5-F10 | 18 | 90 | 3:97 |
| H2A10 | 24 | 120 | 3:97 |
| 9-10A-TS-F87V-T268A (BM3-CIS) | 0.3 | 2 | 3:97 |
| BM3-CIS-C400S | 15 | 76 | 8:92 |
| hemin | 20 | 100 | 4:96 |

*Assumed the same detector response factor as for ethyl 2-(4-methylphenyl)cyclopropane-1-carboxylate.
GC (cyclosil-B column (30 m × 0.32 mm, 0.25 μm film): oven temperature = 100° C. for 5 min, 5° C./min to 200° C., 20° C./min to 250° C., 250° C. for 5 min.
Elution times: cis-cyclopropanes (21.66 min), trans-cyclopropanes (23.31 min).
Cis- and trans-enatiomers did not resolve.

P450 cyclopropanation is robust to both electron-donating (p-vinylanisole, p-vinyltoluene) and electron-withdrawing (p-trifluoromethylstyrene) substitutions on styrene, and variant 7-11D showed consistent cis-selectivity for these substrates. The P450s were also active on 1,1-disubstituted olefins (e.g., α-methyl styrene), with chimeric P450 C2G9R1 forming cyclopropanes in 77% yield (with respect to EDA). The P450s were only moderately active with t-butyl diazoacetate as substrate (<30% yield), forming the trans product with >87% selectivity and offering no advantage over free hemin (Table 34). For reactions involving EDA and aryl-substituted olefins, however, the P450s consistently outperformed the free cofactor in both activity and stereoselectivity. An appropriate catalyst for a given substrate can be found by testing the substrate against engineered or native P450s, as demonstrated above. Directed evolution methods well known to those of skill in the art can be used to enhance catalyst activity.

Figure 6:
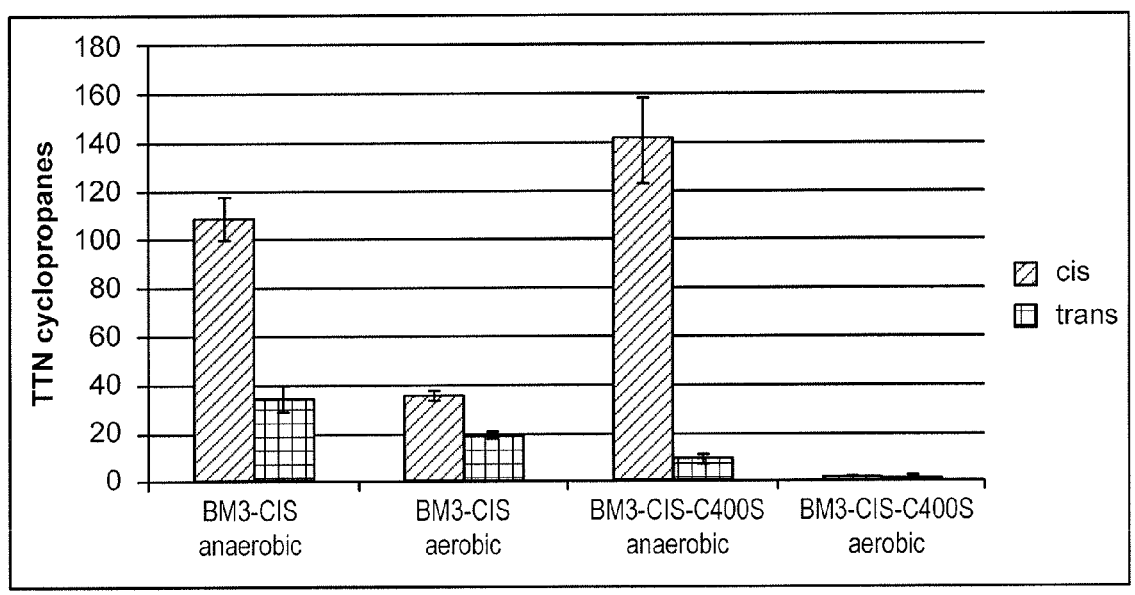
FIG. 6 illustrates the cyclopropanation activities of variant 9-10A-TS-F87V-T268A (also called BM3-CIS or P450$_{BM3}$-CIS) and BM3-CIS-C400S (also called ABC-CIS or P411$_{BM3}$-CIS) driven by sodium dithionite under anaerobic and aerobic conditions. Measurements were taken in triplicate and the error bars represent the standard deviation from the mean value.
Figure 7:
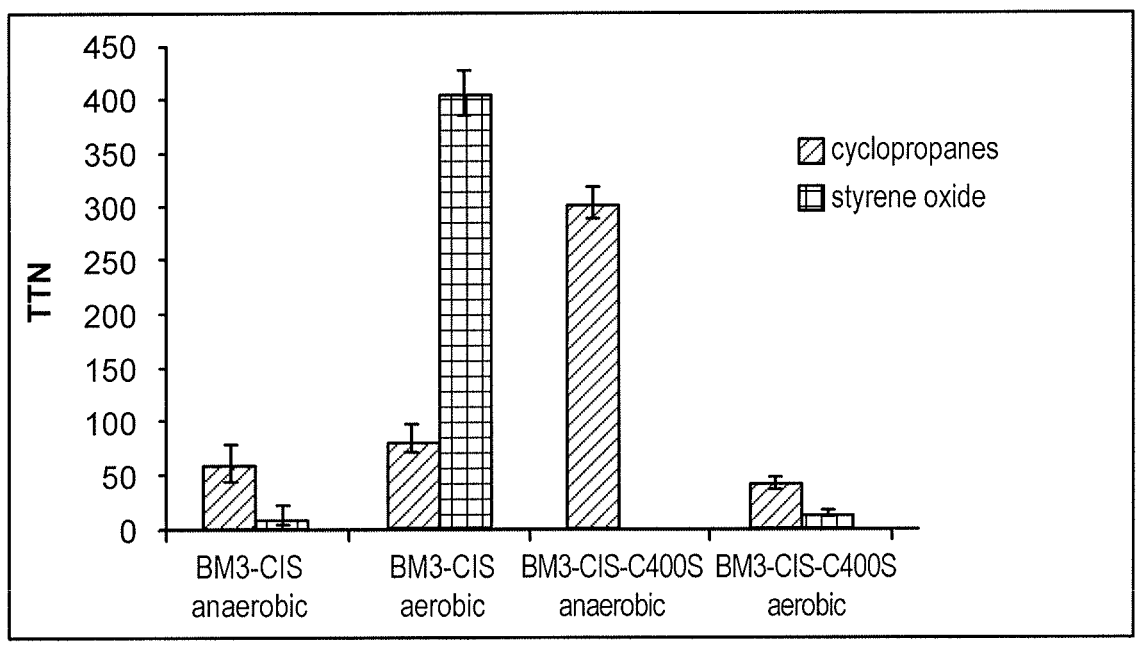
FIG. 7 illustrates the cyclopropanation and epoxidation activities of variant 9-10A-TS-F87V-T268A (also called BM3-CIS or P450$_{BM3}$-CIS) and BM3-CIS-C400S (also called ABC-CIS or P411$_{BM3}$-CIS) driven by NADPH under anaerobic and aerobic conditions. Measurements were taken in triplicate and the error bars represent the standard deviation from the mean value. Reaction conditions: 20 μM catalyst, 30 mM styrene, 10 mM EDA, 0.5 mM NADPH, 25 mM glucose, 2 U ml$^{-1}$ glucose dehydrogenase under argon (or air) in aqueous potassium phosphate buffer (pH 8.0) and 5% MeOH cosolvent for 2 hours at 298 K. Measurements were taken in triplicate and the error bars represent the standard deviation of the measurements.

P450-derived cyclopropanases containing both heme and reductase domains remain competent monooxygenases, preferentially producing styrene oxide in the presence of NADPH under air. The possibility of generating a 'specialist' cyclopropanase that has no promiscuous monooxygenase activity was investigated. It is known that proximal cysteinate ligation (by C400 in P450$_{BM3}$) is important for dioxygen activation and stabilization of compound I during monooxygenation (J. H. Dawson, Science 240, 433 (1988)). As evidenced by the ability of free hemin to catalyze cyclopropanation, this ligand is likely not required for carbene transfer reactions, although it is required for the enzyme to catalyze monooxygenation reactions. Site-saturation mutagenesis of C400 in wild-type P450$_{BM3}$ revealed that only the isosteric C400S mutation led to folded heme-bound protein. Since this mutation has been reported to abolish monooxygenation activity in mammalian P450s (K. P. Vatsis et al., Journal of Inorganic Biochemistry 91, 542 (2002)), BM3-CIS-C400S was created, which remains an active cyclopropanase that is able to initiate the catalytic cycle by utilizing electrons from either dithionite (150 TTN) or NADPH (304 TTN). Unexpectedly, BM3-CIS-C400S displays considerably improved diastereo-(cis:trans/ dithionite 93:7; NADPH 72:28) and enantioselectivity (dithionite –99% ee$_{cis}$; NADPH 94% ee$_{cis}$) compared to its cysteine homologue (Tables 35-36 and FIG. 6) and is a much more active NADPH-driven cyclopropanase (FIG. 7).

TABLE 35

Effect of C400S mutation on BM3-CIS-mediated cyclopropanation driven by Na$_2$S$_2$O$_4$.

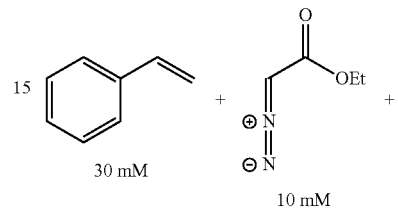

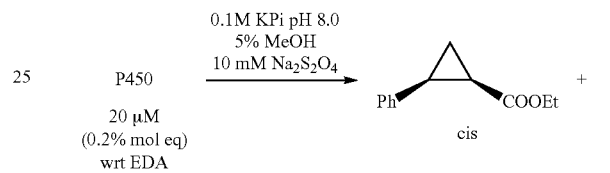

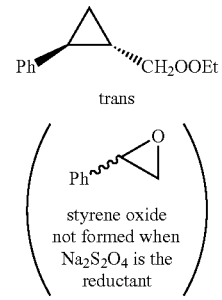

styrene oxide not formed when Na$_2$S$_2$O$_4$ is the reductant

| P450 | Conditions | Yield (%)[a] | TTN | O$_2$ inhibition (%) | cis:trans[b] | % ee cis[c] | % ee trans[d] |
|---|---|---|---|---|---|---|---|
| BM3-CIS$_{heme}$ | Anaerobic | 29 | 143 | — | 77:23 | –94 | –91 |
| BM3-CIS$_{heme}$ | Aerobic | 11 | 55 | –62 | 65:35 | –87 | –86 |
| BM3-CIS-C400S$_{heme}$ | Anaerobic | 30 | 151 | — | 93:7 | –99 | –51 |
| BM3-CIS-C400S$_{heme}$ | Aerobic | 0.6 | 3 | –98 | 45:55 | –79 | –31 |

[a]based on EDA.
[b]Diastereomeric ratios and enantiomeric excess were determined by GC analysis.
[c](R,S) – (S,R).
[d](R,R) – (S,S).
Variant 9-10A-TS-F87V-T268A (herein called BM3-CIS).

TABLE 36

In vitro activities for purified P411$_{BM3}$-CIS vs P450$_{BM3}$-CIS driven by NADPH.

| Cat. | Conditions | TTN cyclopropanes (TTN$_{cyc}$) | TTN styrene oxide (TTN$_{epo}$) | TTN$_{cyc}$/ TTN$_{epo}$ | O$_2$ inhibition (%) | cis:trans$^a$ | % ee cis$^b$ | % ee trans$^c$ |
|---|---|---|---|---|---|---|---|---|
| P450$_{BM3}$-CIS | Anaerobic | 60 ± 18 | 12 ± 10 | 5 | — | 60:40 | −89 | −53 |
| P450$_{BM3}$-CIS | Aerobic | 82 ± 13 | 406 ± 21 | 0.20 | +36 | 56:44 | −88 | −58 |
| P411$_{BM3}$-CIS | Anaerobic | 304 ± 15 | 0 | — | — | 72:28 | −92 | −19 |
| P411$_{BM3}$-CIS | Aerobic | 43 ± 5 | 14 ± 2 | 3.1 | −86 | 49:51 | −74 | −14 |

$^a$Diastereomeric ratios and enantiomeric excess were determined by GC analysis.
$^b$(R,S) − (S,R).
$^c$(R,R) − (S,S).
Small-scale reactions (400 μL total volume) were conducted as described below with the following modifications: glucose dehydrogenase (GDH, 4 μL, 225 U mL$^{-1}$) was added to the reaction vial together with the P450 solution.
Glucose (40 μL, 250 mM) and NADPH (40 μL, 5 mM) were degassed together with the buffer solution.
Measurements were taken in triplicate and the error bars represent the standard deviation from the mean value.
The small amounts of epoxide formed by P450$_{BM3}$-CIS under anaerobic conditions are due to dioxygen contamination in the small-scale reactions in the experiments.
Variant 9-10A-TS-F87V-T268A (herein called BM3-CIS).

Under aerobic conditions in the presence of NADPH, BM3-CIS-C400S forms negligible amounts of styrene oxide and is still able to form cyclopropanes (43 TTN), in marked contrast to BM3-CIS, which forms styrene oxide as the major product (FIG. 7). Cyclopropanation activity in BM3-CIS-C400S remains, however, severely inhibited by dioxygen (FIG. 7). It is noteworthy that Vatsis et al. have shown that the mammalian P450 CYP2B4-C436S which also has its proximal cysteine mutated to a serine is able to use electrons from NADH to reduce dioxygen to hydrogen peroxide. In particular, Vatsis et al. have shown that serine-heme P450s can function as a two-electron oxidase, accepting electrons from NADPH and reducing dioxygen to hydrogen peroxide. This peroxide generation activity can therefore be in competition with cyclopropanation under aerobic conditions.

BM3-CIS-C400S exhibits Michaelis-Menten kinetics (FIG. 8 and Table 37) with similar K$_M$ values for the olefin (~1.5 mM) and the diazocarbene (~5 mM) as variant 9-10A-TS-F87V-T268A (BM3-CIS). Replacement of axial thiolate ligation with serine decreases the k$_{cat}$ to about 20 min$^{-1}$.

TABLE 37

Michaelis-Menten parameters for P450 cyclopropanases.

| Catalyst | k$_{cat}$ (min$^{-1}$) | K$_{M-EDA}$ (mM) | K$_{M-styrene}$ (mM) | k$_{cat}$/K$_{M-EDA}$ (s$^{-1}$ M$^{-1}$) | k$_{cat}$/K$_{M-styrene}$ (s$^{-1}$ M$^{-1}$) | k$_{cat}$/(K$_{M-EDA}$× K$_{M-styrene}$) (s$^{-1}$ M$^{-1}$ M$^{-1}$) |
|---|---|---|---|---|---|---|
| BM3-CIS$_{heme}$ | 100.7 ± 24.1 | 5.2 ± 3.5 | 1.4 ± 0.5 | 321 | 1,111 | 2.1 × 10$^5$ |
| BM3-CIS-C400S | 20.4 | 5.7 | 4.7 | 59.6 | 72.3 | 1.3 × 10$^4$ |

BM3-CIS-C400S demonstrated consistent cis-selectivity for the substrates shown in Tables 30-34. In vitro cyclopropanation reactions catalyzed by BM3-CIS-C400S can be driven by sub-stoichiometric amounts of either NADH or NADPH.

Figure 9:
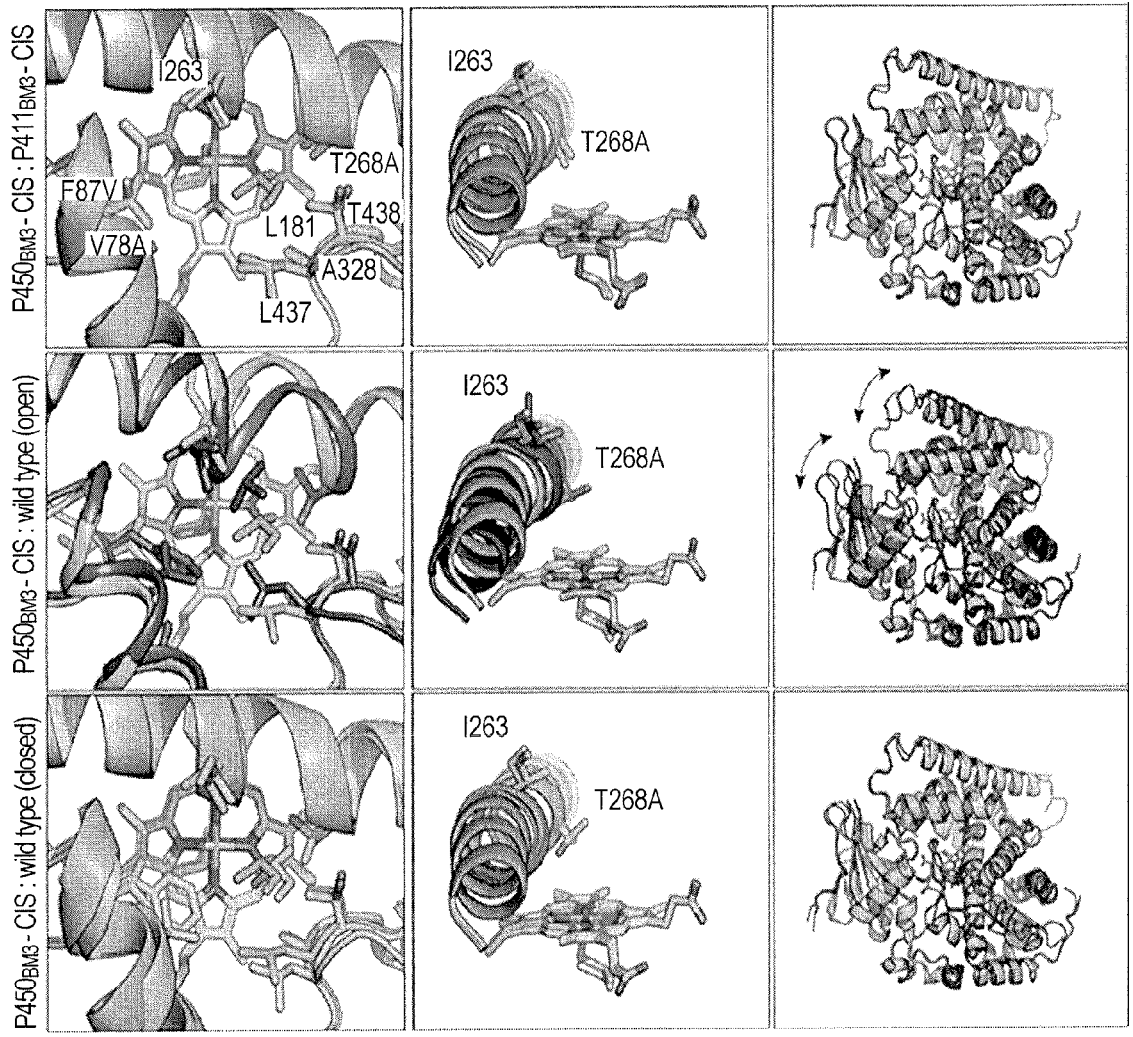
FIG. 9 illustrates the heme domain active site and protein alignments of variant 9-10A-TS-F87V-T268A (also called BM3-CIS or P450$_{BM3}$-CIS) with BM3-CIS-C400S (also called ABC-CIS or P411$_{BM3}$-CIS) and wild type P450$_{BM3}$. Top panels shows alignments of P450$_{BM3}$-CIS (green) and P411$_{BM3}$-CIS (peach) with left, middle and right panels showing active site residues, the active site I-helix, and global protein fold, respectively. No significant structural changes were observed (RMSD 0.52 Å). Middle panels: Large variations are observed upon comparing P411$_{BM3}$-CIS with the open (ligand-free) form of wild type P450$_{BM3}$ (purple, taken from PDB#2IJ2, RMSD 1.2 Å). Pronounced rearrangements are observed in active site side chain residues (left) as well as rotations within the I-helix. Global movements are also observed in the N-terminal beta domain as well as F- and G-helices (right, marked by double headed arrows). These movements are consistent with well-known transitions that occur upon substrate binding and are important for native monooxygenation catalysis. Bottom panels: Alignment of P450$_{BM3}$-CIS with a ligand-bound P450$_{BM3}$ structure (cyan, taken from PDB#1JPZ, RMSD 0.52 Å) demonstrates that P450$_{BM3}$-CIS and P411$_{BM3}$-CIS mimic the closed protein conformation even in the absence of substrate. Protein alignments were carried out using the align tool of PyMol (PyMOL Molecular Graphics System, Version 1.3 Schrödinger, LLC.).

To investigate whether the differences in stereoselectivity and catalytic rates caused by the C400S mutation were caused by changes in active site structure, the crystal structures of BM3-CIS and BM3-CIS-C400S were determined at 2.5 and 3.3 Å, respectively (FIG. 9 and Table 38).

TABLE 38

Data collection and refinement statistics for P450$_{BM3}$ crystals.

| | 9-10A-TS-F87V-T268A (BM3-CIS) | BM3-CIS-C400S |
|---|---|---|
| pdb accession # | 4H23 | 4H24 |
| Data collection* | | |
| Space group | I 1 2 1 | P 2 21 21 |
| wavelength | 1.033 | 1.033 |
| Cell dimensions | | |
| a, b, c (Å) | 187.79, 62.74, 210.28 | 63.16, 124.46, 127.69 |
| αβγ (°) | 90.00, 115.75, 90.00 | 90.00, 90.00, 90.00 |
| Resolution (Å) | 48.6-2.5 (2.5-2.6)** | 44.9-3.3 (3.3-3.5)** |
| R$_{merge}$ | 5.3 (39.5) | 17.6 (51.4) |
| I/σI | 13.4 (3.0) | 11.8 (5.7) |
| Completeness (%) | 98.7 (99.2) | 99.9 (99.9) |
| Redundancy | 2.6 (2.6) | 5.3 (5.4) |
| Refinement | | |
| Resolution (Å) | 48.6-2.5 | 44.9-3.3 |
| No. reflections | 72085 | 14884 |
| R$_{work}$/R$_{free}$ | 0.19/0.25 | 0.18/0.26 |
| No. atoms | | |
| Protein | 14401 | 6890 |
| Ligand/ion | 128 | 86 |
| Water | 196 | 24 |
| B-factors | | |
| Protein | 33.9 | 25.4 |
| Ligand/ion | 25.4 | 19.9 |
| Water | 26.7 | 18.9 |
| R.m.s. deviations | | |
| Bond lengths (Å) | 0.017 | 0.016 |
| Bond angles (°) | 1.70 | 1.65 |
| Ramachandran outliers*** | 0.3% | 0.7% |

*All data sets were collected from single crystals.
**Highest-resolution shell is shown in parentheses.
***Ramachandran outliers lie in regions of protein that are known to be flexible and show similar disorder among P450$_{BM3}$ structures in the literature.

The structures are superimposable (RMSD=0.52 Å), with no significant changes in active site side chain or heme orientation. It is likely that changes in catalytic properties arise from electronic effects of altering the primary heme-ligand sphere. Both cis-selective BM3-CIS and BM3-CIS-C400S closely resemble the ligand-bound 'closed' form of P450$_{BM3}$ (FIG. 9), while trans-selective P450$_{BM3}$-T268A resembles the open apo-form (J. P. Clark et al., *Journal of Inorganic Biochemistry* 100, 1075 (2006)). These large-scale conformational changes may contribute to the different diastereoselectivities observed among proteins that share nearly identical active site sequences.

Figure 10:
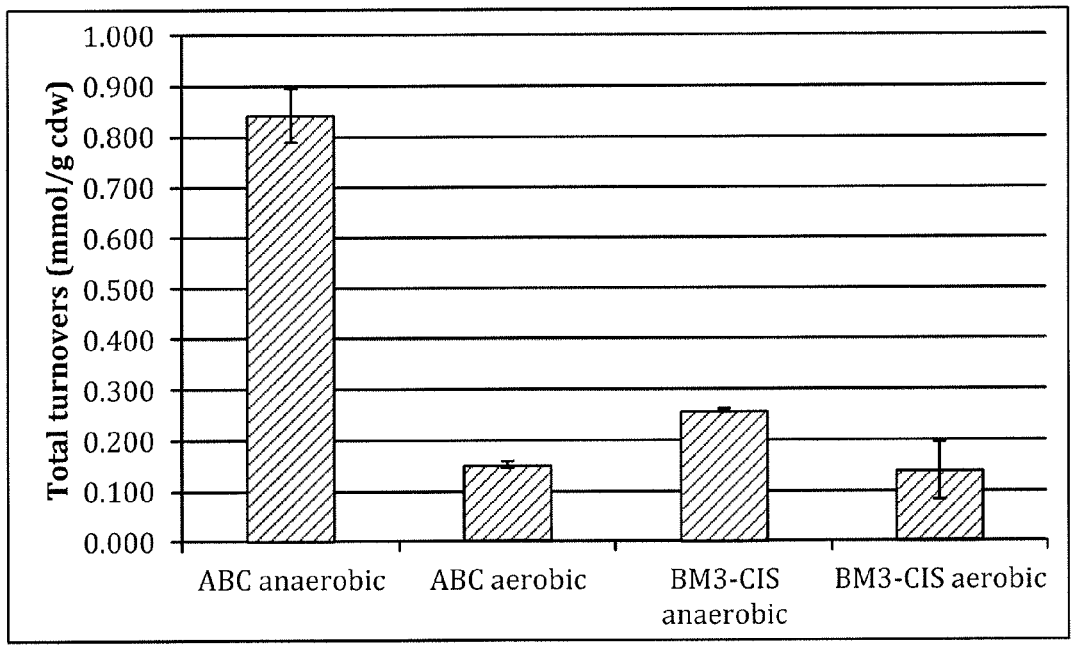
FIG. 10 illustrates that whole-cell cyclopropanation catalysts are inhibited under aerobic conditions. Variant 9-10A-TS-F87V-T268A=BM3-CIS and ABC=BM3+C400S. Reaction conditions: 20 mM styrene, 10 mM EDA, under argon (or air) in nitrogen-free medium and 5% MeOH cosolvent for 2 hours at 298 K ($OD_{600}$~24). Total turnover=concentration of cyclopropanes (mM)/cell density (g cdw/L) in units of mmol/g cdw.

Encouraged by the high turnovers achieved by BM3-CIS-C400S$_{holo}$ in vitro when using NADPH as a reductant (FIG. 7), the catalytic cyclopropanation reaction was investigated using whole cells expressing cytochrome P450 variants. The stability of EDA was first assessed in the presence of *E. coli* cells (OD$_{600}$=30) lacking the P450$_{BM3}$ gene and found no decomposition over the course of two hours. *E. coli* cells expressing BM3-CIS-C400S$_{holo}$ are hereafter referred to as the ABC catalyst. Initial experiments to identify optimal conditions revealed that whole-cell reactions were also significantly inhibited by dioxygen (FIG. 10). The C400S mutation improves in vivo activity by a factor of 3-4 as can be seen in FIG. 10 by comparing the ABC catalyst with whole cells expressing the thiolate-ligated BM3-CIS$_{holo}$. The ABC catalyst also affords higher diastereo- and enantioselectivity compared to BM3-CIS$_{holo}$ (FIG. 10).

Figure 14:
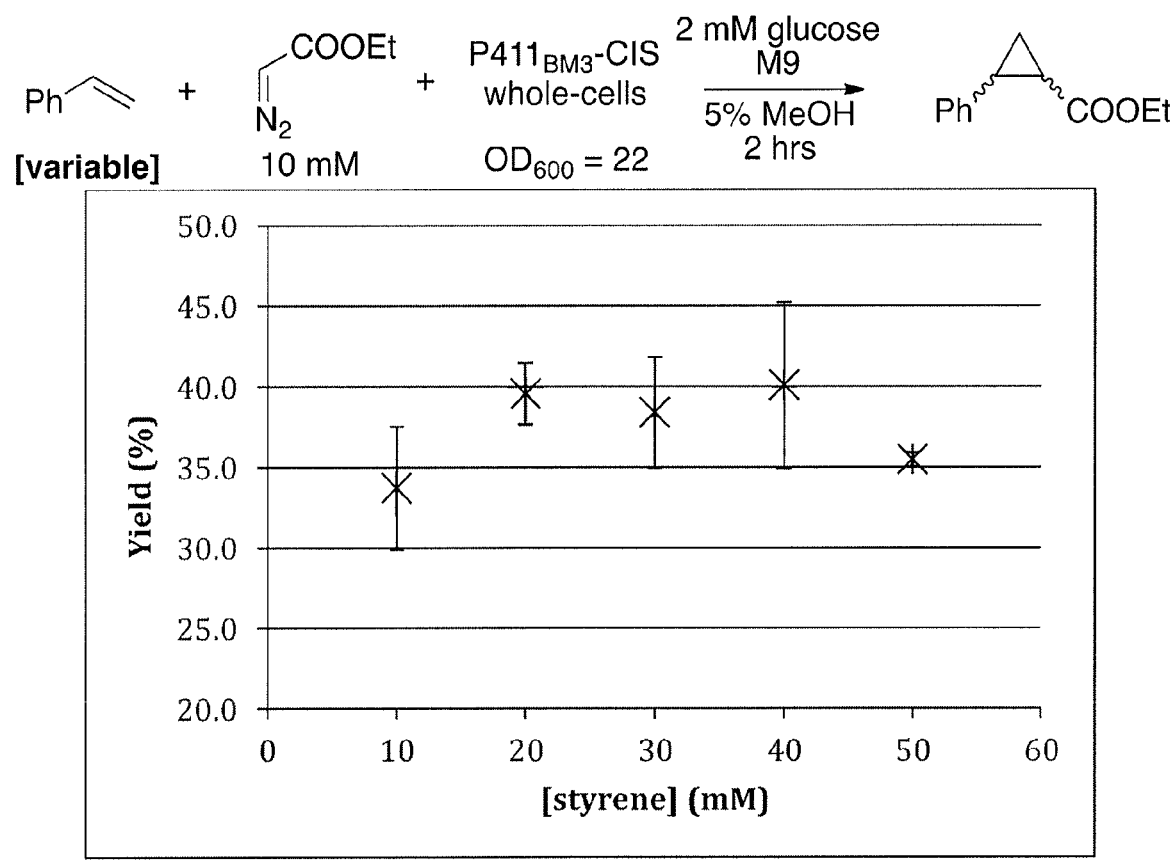
FIG. 14 illustrates the effect of using 1, 2, 3, 4 and 5 equivalents of styrene on reaction yield. Excess styrene gives only small improvements in yield. Measurements were taken in triplicate and the error bars represent the standard deviation from the mean value. ABC (BM3-C400S or $P411_{BM3}$).

Addition of 2 mM glucose gave a consistent increase in cyclopropane yields (FIG. 11), presumably due to increased intracellular concentration of NADH, which is required to reduce the P450 catalyst to the active Fe(II) ferrous state. The ability of the whole cells to catalyze cyclopropanation to moderate yields even in the absence of exogenous glucose implies that some of the P450 is reduced with endogenous amounts of intracellular NAD(P)H. After normalizing for cell density, there are no significant differences in activity for cells grown in M9Y (M9, 1.5% yeast extract) or TB media. M9Y is the preferred growth medium due to its lower cost (FIG. 12). Expressing the holo enzyme gives a slightly higher yield of cyclopropanes compared to the heme domain alone (FIG. 12). Increasing ABC catalyst loading (cell density) increases cyclopropane yield up to approximately 80% at OD$_{600}$=50 (FIG. 13). When EDA is used at 10 mM, a 2:1 excess of styrene affords optimal yields (FIG. 14). Controls for whole cells containing the P450 gene but with no P450 induction and for whole cells devoid of the P450 gene are shown in FIG. 15.

Figure 16:
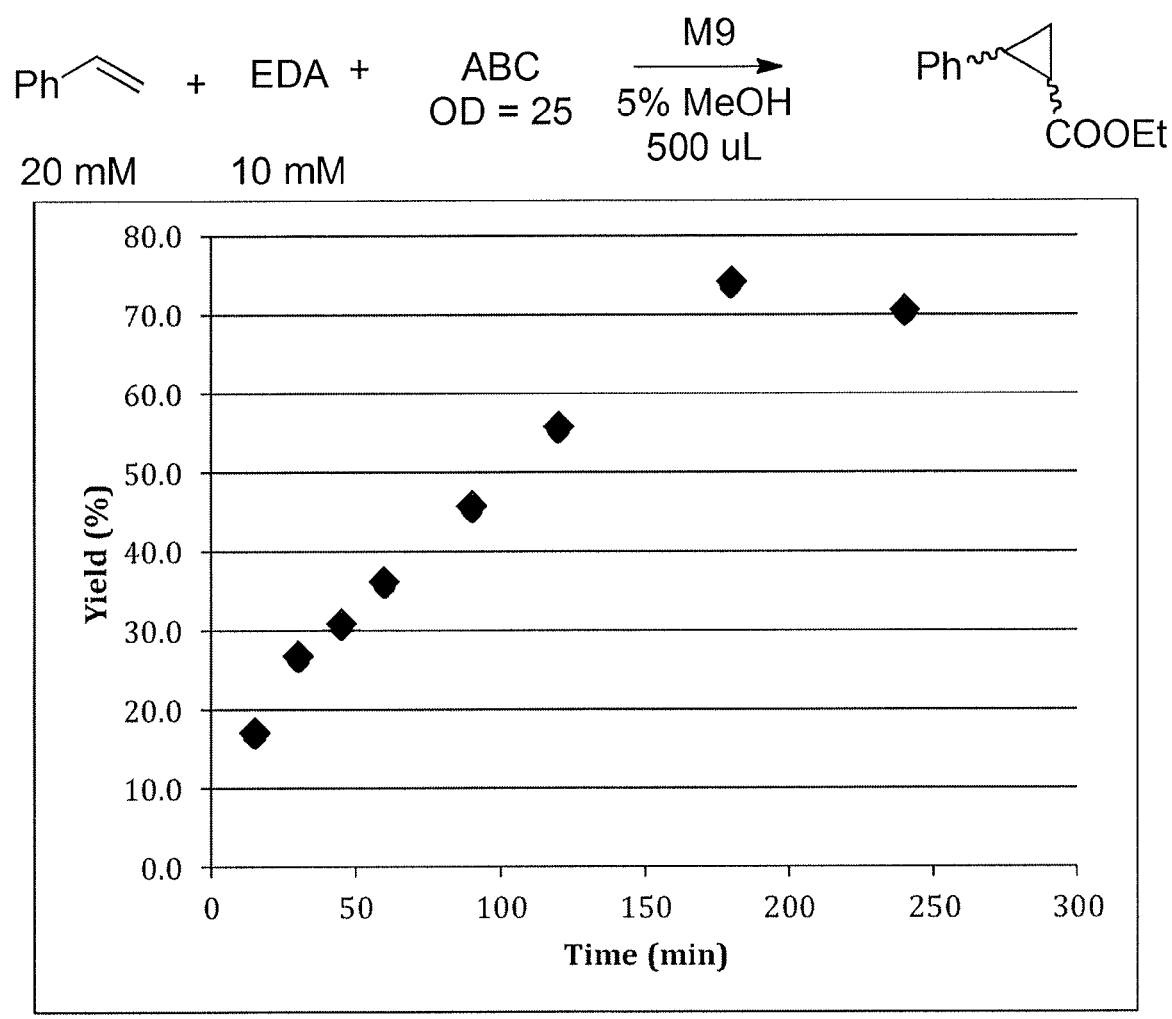
FIG. 16 illustrates that ABC catalyst is active for 3 hours. At $OD_{600}$=25, the P450 concentration in 0.85 µM, such that TTN>8,000. Variant 9-10A-TS-F87V-T268A=BM3-CIS and ABC=BM3-C400S.

The cell seems to stabilize the P450 catalyst, extending its activity for hours, such that the reaction only finishes when EDA is depleted, as shown in FIG. 16. Remarkably, under the conditions in FIG. 16, the in vivo TTN is over 8,000. At high substrate loading (100 mM EDA, 200 mM styrene) the in vivo TTN reaches over 30,000. This is approximately two orders of magnitude higher than the in vitro TTN values reported above for purified enzyme catalyst.

This example also shows that the ABC catalyst can be lyophilized and supplied as a solid that can be resuspended in the desired reaction conditions. It has been observed that the lyophilization process does not compromise the catalyst activity. Thus, this whole cell catalyst can be lyophilized and conveniently stored for long periods of time. It can be packaged, weighed out or otherwise distributed in solid form when needed for a reaction. Because it is genetically encoded in a whole cell, it can also be stored or distributed as a plasmid (to be transformed into live cells) or as the live cells (e.g., in a bacterial stab culture) and then grown to the desired density and volume, using methods well known to those of skill in the art.

In vivo catalysis offers some key advantages over the use of purified enzymes in vitro, such as the lower costs associated with catalyst preparation, the prolonged activity and the ability to incorporate the P450 cyclopropanation reaction into metabolic pathways.

This concept has been demonstrated for a single P450 enzyme, from *Bacillus megaterium*, and for chimeras of the *B. megaterium* enzyme with other, related P450s from *B. subtilis*. Those of skill in the art, however, will recognize that other P450s from other organisms can be engineered to carry out cyclopropanation and ABC whole-cell catalysts can be made using those enzymes. In particular, the equivalent of the C400S mutation will improve the performance of other P450 enzymes for cyclopropanation and other carbene transfer reactions. One of skill in the art knows how to identify the equivalent residue to C400 in other P450s, based on sequence alignments, an example of which is given below. Methods known in the art, such as site-directed mutagenesis or gene synthesis, can be used to alter this residue to serine in any P450. If the resulting enzyme folds properly, it will serve as a catalyst for cyclopropanation. This mutation in a purified protein or whole cell catalyst will improve the activity over the parent enzyme that does not include this mutation.

For example, BLAST alignment (http://blast.ncbi.nlm.nih.gov/Blast.cgi) of the amino acid sequence of P450BM3 (CYP102A1) to other P450s, such as the one from *Pseudomo-* nas putida (CYP101A1, P450CAM) or the mammalian enzyme from Oryctolagus cuniculus (CYP2B4), enables identification of the proximal cysteine residue or of the equivalent T268 (marked in bold), as shown below (SEQ ID NOS:61-69):

```
CYP102A1  380  ENPSAIPQH--------AFKPFGNGQRACIGQQFALHEATLVL              414
               E  +A P H        +    FG+G   C+GQ  A  E   + L
CYP101A1  329  ERENACPMHVDFSRQKVSHTTFGHGSHLCLGQHLARREIIVTL              371

CYP102A1  265  GHETTSGLLSFALYFLVKNPHVLQKAAEEAARVLVDPVPSYKQVKQLKYVGMVLNEALRL  324
               G  +T     LSF++ FL K+P    Q+   E    R      +P+          E LR
CYP101A1  249  GLDTVVNFLSFSMEFLAKSPEHRQELIERPER-----IPA------------ACEELLR-  290

CYP102A1  374  FRPERF--ENPSAIPQHAFKPFGNGQRACIGQQFALHEATLVLGMMLKHFD          422
               F P F   N +       F PF  G+R C+G+  A  E   L      +L++F
CYP2B4    408  FNPGHFLDANGALKRNEGFMPFSLGKRVCLGEGIARTELFLFFTTILQNFS          458

CYP102A1  257  QIITFLIAGHETTSGLLSFALYFLVKNPHVLQKAAEEAARVL-VDPVPSYKQVKQLKYVG  315
                +++    AG ETTS  L +    ++K PHV ++   +E   +V+     P+    ++ Y
CYP2B4    291  TVLSLFFAGTETTSTTLRYGFLLMLKYPHVTERVQKEIEQVIGSHRPPALDDRAKMPYTD  350
```

Therefore, the mutations C357S and T252A in CYP101A1 or C436S and T302A in CYP2B4 are expected to enhance the cyclopropanation activity in these enzymes. The mutation can be introduced into the target gene by using standard cloning techniques or by gene synthesis. The mutated gene can be expressed in the appropriate microbial host under the control of an inducible promoter or by means of chromosomal integration under the control of a constitutive promoter. Cyclopropanation activity can be screened in vivo or in vitro by following product formation by GC or HPLC (see, Materials and Methods).

Because the ABC catalyst is genetically encoded and functions very well in whole cells, this catalyst can be incorporated into multi-enzyme pathways for biological synthesis in vivo, where multiple transformations of a substrate are carried out inside the cell. The EDA or other diazo reagent can be provided exogenously to the medium or generated in situ.

Figure 17A:
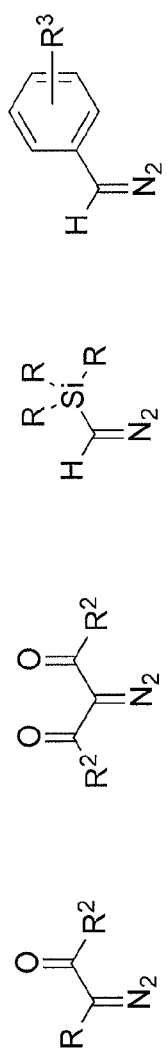
FIGS. 17A-D illustrate the proposed substrate scope of P450-catalyzed cyclopropanation.
Figure 17B:
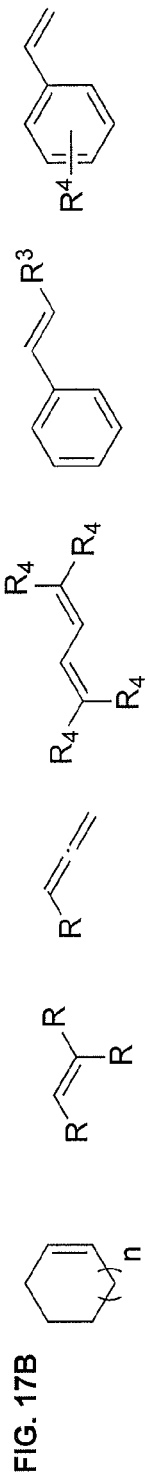
Figure 17C:
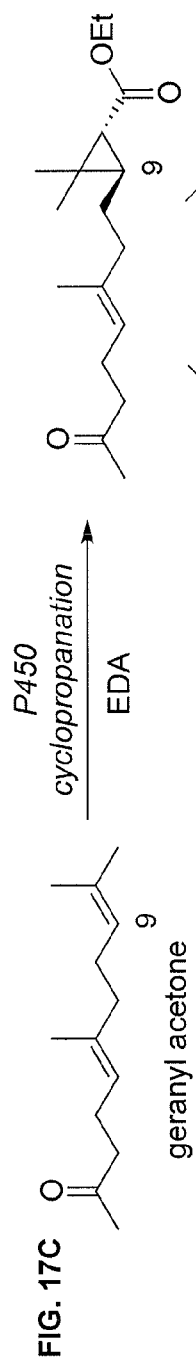
Figure 17D:
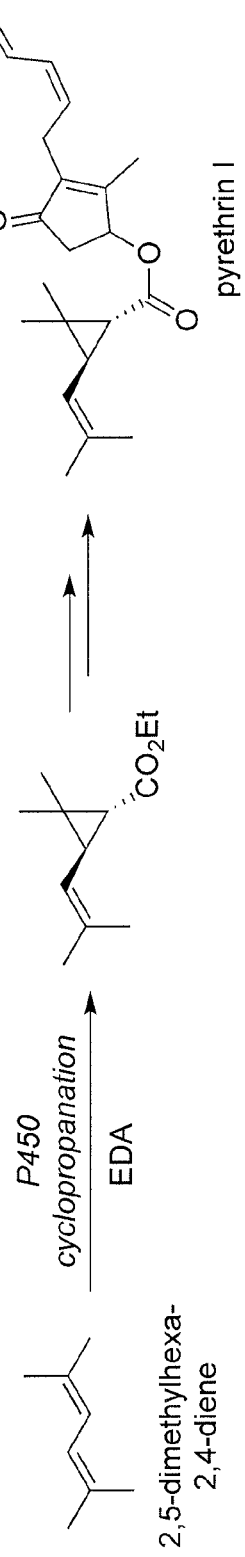

The ability to extend the C400S mutation to other P450 scaffolds allows access to a variety of diazo compounds as carbenoid precursors. These include, but are not limited to, diazo esters (acceptor type), diazo β-keto ester or β-cyano esters (acceptor-acceptor type), and alkyl,aryl, or alkenyl substituted diazo esters (donor-acceptor) (FIG. 17a). These diazo compounds can be reacted inter- and intramolecularly with a variety of styrenes, aliphatic olefins, and allenes to provide biologically active compounds or organic building blocks for further reaction (FIG. 17b). For instance, P450 catalyzed reaction of a diazo ester with aryl or allylic silanes and boronic acids would form cyclopropanes that can then be used in Suzuki or Hiyama cross coupling reactions. Furthermore, cyclopropanation of geranylacetone at the C9 olefin by a trans-selective P450 catalyst and EDA will provide a key precursor to anthroplalone and noranthroplone, marine natural products that exhibit microgram cytotoxicity against B-16 melanoma cells (FIG. 17c) (W. A. Donaldson, Tetrahedron 57, 8589 (2001)). Lastly, treatment of 2,5-dimethylhexα-2,4-diene with a similar catalyst and EDA would provide the ethyl ester of chrysanthemic acid, an important intermediate in the production of pyrethroid insecticides (FIG. 17d).

Materials and Methods

Unless otherwise noted, all chemicals and reagents for chemical reactions were obtained from commercial suppliers (Sigmα-Aldrich, Acros) and used without further purification. The following heme proteins were all purchased from Sigmα-Aldrich: myoglobin (from equine heart), peroxidase II (from horseradish), cytochrome c (from bovine heart), catalase (from *Corynebacterium glutamicum*) and chloroperoxidase (from *Caldariomyces fumago*). Silica gel chromatography purifications were carried out using AMD Silica Gel 60, 230-400 mesh. $^1$H and $^{13}$C NMR spectra were recorded on either a Varian Mercury 300 spectrometer (300 MHz and 75 MHz, respectively), or a Varian Inova 500 MHz (500 MHz and 125 MHz, respectively), and are internally referenced to residual solvent peak. Data for $^1$H NMR are reported in the conventional form: chemical shift (δ ppm), multiplicity (s=singlet, d=doublet, t=triplet, q=quartet, m=multiplet, br=broad), coupling constant (Hz), integration. Data for $^{13}$C are reported in terms of chemical shift (δ ppm) and multiplicity. High-resolution mass spectra were obtained with a JEOL JMS-600H High Resolution Mass Spectrometer at the California Institute of Technology Mass Spectral Facility. Reactions were monitored using thin layer chromatography (Merck 60 silica gel plates) using an UV-lamp for visualization. Optical rotation was measured using a JASCO P-2000 Polarimeter.

Gas chromatography (GC) analyses were carried out using a Shimadzu GC-17A gas chromatograph, a FID detector, and J&W scientific cyclosil-B columns (30 m×0.32 mm, 0.25 μm film and 30 m×0.25 mm, 0.25 μm film). High-performance liquid chromatography (HPLC) was carried out using an Agilent 1200 series, an UV detector, and an Agilent XDB-C18 column (4.6×150 mm, 5 μm). Cyclopropane product standards for the reaction of ethyl diazoacetate (EDA) with styrene (ethyl 2-phenylcyclopropane-1-carboxylate) and α-methylstyrene (ethyl 2-methyl-2-phenylcyclopropane-1-carboxylate) were prepared as reported (A. Penoni et al., *European Journal of Inorganic Chemistry*, 1452 (2003)). These standards and enzyme-prepared cyclopropanes demonstrated identical retention times in gas chromatograms when co-injected, confirming product identity. Absolute stereoconfiguration of cyclopropane enantiomers was determined by measuring optical rotation of purified cyclopropane products from preparative bioconversion reactions using enantioselective P450-BM3 variants and referenced to values taken from reference (N. Watanabe et al., *Heterocycles* 42, 537 (1996)). Authentic P450-catalyzed cyclopropane samples were also prepared as described herein and were characterized by NMR ($^1$H and $^{13}$C) and mass spectrometry.

Plasmids pCWori[BM3] and pET22 were used as cloning vectors. Site-directed mutagenesis was accomplished by standard overlap mutagenesis using primers bearing desired mutations (IDT, San Diego, Calif.). Electrocompetent *Escherichia coli* cells were prepared following the protocol of Sambrook et al., *Molecular cloning: a laboratory manual*. (Cold Spring Harbor Laboratory Press, New York, 1989), vol. 2. Restriction enzymes BamHI, EcoRI, XhoI, Phusion polymerase, and T4 ligase were purchased from New England Biolabs (NEB, Ipswich, Mass.). Alkaline phosphatase was obtained from Roche (Nutley, N.J.). The 1,000× trace metal mix used in expression cultures contained: 50 mM $FeCl_3$, 20 mM $CaCl_2$, 10 mM $MnSO_4$, 10 mM $ZnSO_4$, 2 mM $CoSO_4$, 2 mM $CuCl_2$, 2 mM $NiCl_2$, 2 mM $Na_2MoO_4$, and 2 mM $H_3BO_3$.

Enzyme Library Screening.

Libraries are stored at −78° C. as glycerol stocks (Luria-Bertani medium ($LB_{amp}$), 150 μL, 25% v/v glycerol with 0.1 mg $mL^{-1}$ ampicillin) in 96-well plates. These stocks were used to inoculate 96-shallow-well plates containing 300 μL $LB_{amp}$ medium using a 96-pin stamp. Single colonies from site-saturation libraries were picked with toothpicks and used to inoculate 300 μL of $LB_{amp}$. The cells were incubated at 37° C., 250 rpm shaking, and 80% relative humidity overnight. After 16 h, 50 μL aliquots of these overnight cultures were transferred into 2 mL, deep-well plates containing terrific broth ($TB_{amp}$) (800 μL containing 0.1 mg $mL^{-1}$ ampicillin, 1 μL $mL^{-1}$ trace metal mix and 20 mg $L^{-1}$ aminolevulinic acid) using a Multimek 96-channel pipetting robot (Beckman Coulter, Fullerton, Calif.). The cultures were incubated at 37° C. for 3 h and 30 min, and 30 min after reducing the incubation temperature to 25° C. (250 rpm, 80% relative humidity), 50 μl, isopropyl β-D-1-thiogalactopyranoside (IPTG, 4.5 mM in $TB_{amp}$) was added, and the cultures were allowed to continue for another 24 h at 25° C. (250 rpm, 80% relative humidity). Cells were then pelleted (3,000×g, 15 min, 4° C.) and stored at −20° C. until further use, but at least for 2 h. For cell lysis, plates were allowed to thaw for 30 mM at room temperature and then cell pellets were resuspended in 275 μL phosphate buffer (0.1 M, pH=8.0, 0.65 mg $mL^{-1}$ lysozyme, 10 mM magnesium chloride and 40 U $mL^{-1}$ DNAse I). The lysing cells were incubated at 37° C. for 1 h. Cell debris was separated by centrifugation at 5,000×g and 4° C. for 15 min. The resulting crude lysates were then transferred to 96-well microtiter plates for CO assays and to 2 mL deep-well plates for bioconversions.

CO Binding Assay.

$Na_2S_2O_4$ (160 μL, 0.1 M in phosphate buffer, 0.1 M, pH=8.0) was added to $P450_{BM3}$ variants in cell lysate (40 μL). The absorbance at 450 and 490 nm was recorded using a Tecan M1000 UV/Vis plate reader, and the microtiter plates were placed in a vacuum chamber. The chamber was sealed, evacuated to approximately −15 in Hg, purged with CO gas, and incubated for 30 min. The plates were then removed and the absorbance at 450 and 490 nm was again recorded using a plate reader. The difference spectra could then be used to determine the P450 concentration in each well as previously described (C. R. Otey, in *Methods in Molecular Biology: Directed Enzyme Evolution*, F. H. Arnold, G. Georgiou, Eds. (Humana Press, Totowa, N.J., 2003), vol. 230).

P450 Expression and Purification.

For the enzymatic transformations, $P450_{BM3}$ variants were used in purified form. Enzyme batches were prepared as follows. One liter $TB_{amp}$ was inoculated with an overnight culture (100 mL, $LB_{amp}$) of recombinant *E. coli* DH5α cells harboring a pCWori plasmid encoding the P450 variant under the control of the tac promoter. After 3.5 h of incubation at 37° C. and 250 rpm shaking ($OD_{600}$ ca. 1.8), the incubation temperature was reduced to 25° C. (30 min), and the cultures were induced by adding IPTG to a final concentration of 0.5 mM. The cultures were allowed to continue for another 24 hours at this temperature. After harvesting the cells by centrifugation (4° C., 15 min, 3,000×g), the cell pellet was stored at −20° C. until further use but at least for 2 h. The cell pellet was resuspended in 25 mM Tris.HCl buffer (pH 7.5 at 25° C.) and cells were lysed by sonication (2×1 min, output control 5, 50% duty cycle; Sonicator, Heat Systems—Ultrasonic, Inc.). Cell debris was removed by centrifugation for 20 min at 4° C. and 27,000×g and the supernatant was subjected to anion exchange chromatography on a Q Sepharose column (Hi-Trap™ Q HP, GE Healthcare, Piscataway, N.J.) using an AKTAxpress purifier FPLC system (GE healthcare). The P450 was eluted from the Q column by running a gradient from 0 to 0.5 M NaCl over 10 column volumes (P450 elutes at 0.35 M NaCl). The P450 fractions were collected and concentrated using a 30 kDa molecular weight cut-off centrifugal filter and buffer-exchanged with 0.1 M phosphate buffer (pH=8.0). The purified protein was flash-frozen on dry ice and stored at −20° C. P450 concentration was determined in triplicate using the CO binding assay described above (10 μL P450 and 190 μL 0.1 M phosphate buffer, pH 8.0, per well).

Thermostability Measurements.

Duplicate measurements were taken for all values reported on Tables 17 and 18. Purified P450 solutions (4 μM, 200 μL) were heated in a thermocycler (Eppendorf) over a range of temperatures (38° C.-65° C.) for 10 min followed by rapid cooling to 4° C. for 1 min. The precipitate was removed by centrifugation. The concentration of folded P450 remaining in the supernatant was measured by CO-difference spectroscopy (as described above). The temperature at which half of the protein was denatured ($T_{50}$) was determined by fitting the data to the equation: $f(T)=100/(1+\exp(a*(T-T_{50})))$.

Typical Procedure for Small-Scale Cyclopropanation and Carbene Insertion Bioconversions Under Anaerobic Conditions.

Small-scale reactions (400 μL) were conducted in 2 mL crimp vials (Agilent Technologies, San Diego, Calif.). P450 solution (80 μL, 100 μM) was added to the vial with a small stir bar before crimp sealing with a silicone septum. Phosphate buffer (260 μL, 0.1 M, pH=8.0) and 40 μL of a solution of the reductant (100 mM $Na_2S_2O_4$, or mM NADPH) were combined in a larger crimp-sealed vial and degassed by bubbling argon through the solution for at least 5 min (FIG. 3). In the meantime, the headspace of the 2 mL reaction vial with the P450 solution was made anaerobic by flushing argon over the protein solution (with no bubbling). When multiple reactions were conducted in parallel, up to 8 reaction vials were degassed in series via cannulae. The buffer/reductant solution (300 μL) was syringed into the reaction vial, while under argon. The gas lines were disconnected from the reaction vial before placing the vials on a plate stirrer. A 40× styrene solution in MeOH (10 μL, typically 1.2 M) was added to the reaction vial via a glass syringe, and left to stir for about 30 s. A 40×EDA solution in MeOH was then added (10 μL, typically 400 mM) and the reaction was left stirring for the appropriate time. The final concentrations of the reagents were typically: 30 mM styrene, 10 mM EDA, 10 mM $Na_2S_2O_4$, 20 μM P450.

The reaction was quenched by adding 30 μL HCl (3M) via syringe to the sealed reaction vial. The vials were opened and 20 μL internal standard (20 mM 2-phenylethanol in MeOH) was added followed by 1 mL ethyl acetate. This mixture was transferred to a 1.8 mL eppendorf tube which was vortexed and centrifuged (16,000×g, 1 min). The top organic layer was dried over an anhydrous sodium sulfate plug and analyzed by chiral phase GC.

A slightly modified work-up was implemented for kinetic experiments. The reactions were quenched after the set time by syringing 1 mL EtOAc to the closed vials and immediately vortexing the mixture. The vials were then opened and 20 μL internal standard was added. The mixture was transferred to a 1.8 mL eppendorf tube, vortexed and centrifuged (16,000×g, 1 min). The top organic layer was dried over an anhydrous sodium sulfate plug and analyzed by GC.

Typical Procedure for Preparative-Scale Cyclopropanation Bioconversions Under Anaerobic Conditions.

The P450 solution was added to a Schlenk flask with a stir bar. With the flask kept on ice, the head-space was evacuated and back-filled with argon (4×) with care not to foam the protein solution. Phosphate buffer and reductant were pre-mixed and degassed together in a separate round-bottom-flask by bubbling argon through the solution for 20 min. The buffer/reductant solution was transferred to the Schlenk flask via syringe. Styrene was added under argon and left to mix for 1 min. EDA was added dropwise under argon. The solution was left to stir under argon until reaction completion. The reaction was quenched under argon by adding hydrochloric acid (3 M) to adjust the pH to 4, before opening the Schlenk flask. The reaction mixture was stirred with sodium chloride and dichloromethane ($CH_2Cl_2$). The combined emulsion layers were then filtered through Celite to break the emulsion and the Celite pad was rinsed with 3×20 mL $CH_2Cl_2$. The resulting biphasic mixture was transferred to a separating funnel and the organic phase was removed. The remaining aqueous phase was re-extracted with 3×40 mL $CH_2Cl_2$. The combined organic extracts were dried with sodium sulfate, filtered, and concentrated. The resulting residue was purified by $SiO_2$ chromatography.

Supplementary Data

Preliminary Experiments with Heme Proteins

The following six heme proteins were initially screened for cyclopropanation activity: catalase, chloroperoxidase (CPO), horseradish peroxidase (HRP), cytochrome C (cyt c), myoglobin (Mb) and $P450_{BM3}$. Small-scale (400 µL) reactions were conducted as described above and were analyzed by GC (cyclosil-B 30 m×0.25 mm×0.25 µm): oven temperature=130° C. Table 7 shows heme catalysts under anaerobic conditions with sodium dithionite ($Na_2S_2O_4$). Table 8 shows heme catalysts under anaerobic conditions without $Na_2S_2O_4$. Table 9 shows heme catalysts under aerobic conditions with $Na_2S_2O_4$. Table 10 shows heme catalysts under aerobic conditions without $Na_2S_2O_4$.

Screening $P450_{BM3}$ Variants for Cyclopropanation Activity

Lysate screening under aerobic conditions. The 92 variants in the compilation plate (Table 12) represent a diverse selection of $P450_{BM3}$ variants that have previously been engineered for monooxygenase activity on a variety of substrates, including but not limited to short alkane hydroxylation, demethylation of protected monosaccharides, and oxidation of lead drug compounds. These $P450_{BM3}$ variants carry various mutations accumulated along sequential rounds of engineering efforts for activity towards the target substrates (Table 12) or were generated by recombination with homologous enzymes (Table 13). The compilation plate was expressed and lysed as described above. 150 µL lysate was transferred (Multimek 96-channel pipetting robot, Beckman Coulter, Fullerton, Calif.) to a 2 mL deep-well plate, with 50 µl, of 120 mM $Na_2S_2O_4$ in 0.1 M KPi (pH=8.0). 100 µL of a 30 mM styrene, 60 mM EDA mixed solution in 15% MeOH in 0.1 M KPi (pH=8.0) was added to the plate to initiate the reaction. The plate was sealed and was left shaking (300 rpm) for four hours. The plastic seal was removed and 30 µL HCl (3 M) was added to quench the reaction followed by 20 µL of an internal standard solution (20 mM α-methylstyrene in methanol). The reactions were extracted by adding 500 µL EtOAc and carefully vortexing the plate. The plate was centrifuged (1,700×g) to separate the biphasic mixture. The top organic layer was transferred (2×150 µL) to a separate deep-well plate. The extracts for each of the 92 reactions were dried through 92 separate anhydrous sodium sulfate plugs. The dried extracts were analyzed by GC (cyclosil-B 30 m×0.32 mm×0.25 µm): oven temperature=60° C. 3 min, 7.5° C./min to 160° C., 20° C./min to 250° C., 250° C. 2 min, cis-cyclopropanes (20.3 min and 20.45 min), trans-cyclopropanes (21.8 min). The top 10 protein variants of importance with respect to this report are highlighted in Tables 12 and 13.

Determining the Cyclopropanation Activity of the Top 10 Hits (Highlighted on Tables 12 and 13) Under Anaerobic Conditions.

Small-scale reactions (400 µL total volume) were conducted as described above and were analyzed by GC (cyclosil-B 30 m×0.32 mm×0.25 µm): oven temperature=100° C. 5 min, 1° C./min to 135° C., 135° C. 10 min, 10° C./min to 200° C., 200° C. 5 min, cis-cyclopropanes (39.40 min and 40.20 min), trans-cyclopropanes (44.69 min and 45.00 min). Table 14 shows stereoselective $P450_{BM3}$-based cyclopropanation catalysts.

Experimental Characterization of $P450_{BM3}$ Cyclopropanation Catalysts

Controls to Confirm the Enzymatic Cyclopropanation Activity of Variant H2A10.

Small-scale reactions (400 µL total volume) were set up and worked up as described above. For the carbon monoxide (CO) inhibition experiment, the reaction vial and the buffer/reductant vial were purged with CO after having been purged with argon. For the boiled P450 experiment, a 100 µM solution of variant H2A10 was heated at 60° C. for 10 min. For the hemin experiment, hemin (80 µL) was added from a 1 mM solution in 50% DMSO-H2O, such that its final concentration in the reaction was 200 µM. Complete System=10 mM styrene, 20 mM EDA, 20 mM $Na_2S_2O_4$, 20 µM P450 (H2A10) under anaerobic conditions. The dried ethyl acetate extracts were analyzed by chiral phase GC, using 2-phenylethanol as an internal standard (injector temperature=300° C., oven temperature=100° C. for 5 min, 1° C./min ramp up to 135° C., 135° C. for 10 min, 10° C./min ramp up to 200° C., 200° C. for 5 min). Elution time: cis-cyclopropanes (39.40 min and 40.20 min), trans-cyclopropanes (44.69 min and 45.00 min). Table 15 shows controls for P450 based cyclopropanation using variant H2A1.

Optimizing Cyclopropanation Reaction Conditions for Variant H2A10.

Small-scale reactions (400 µL final volume) were set up and worked up as described above. The dried ethyl acetate extracts were analyzed by chiral phase GC, using 2-phenylethanol as an internal standard (injector temperature=300° C., oven temperature=100° C. for 5 min, 5° C./min ramp up to 200° C., 20° C./min ramp up to 250° C., 250° C. for 5 min). Elution time: cis-cyclopropanes (19.20 min and 19.33 min), trans-cyclopropanes (20.44 min). The reaction conditions that gave optimal yields of cyclopropanes (with respect to EDA) were: 30 mM styrene, 10 mM EDA and 20 µM P450 and were used in subsequent experiments.

Styrene Concentration.

FIG. 3 illustrates the effect of styrene concentration on cyclopropane yield.

P450 Concentration.

FIG. 4 illustrates the effect of P450 (H2A10) concentration on cyclopropane yield.

Dithionite Concentration.

Table 16 shows the effect of the concentration of $Na_2S_2O_4$ on cyclopropane yield.

Mutational Analysis of Active Site Alanine Substitutions in 9-10A TS F87V.

Table 17 shows a mutational analysis of alanine substitutions on 9-10A TS F87V.

Sequential Introduction of BM3-CIS Active Site Mutations in Wild-Type $P450_{BM3}$.

Table 18 shows introducing BM3-CIS related active site mutations in wild-type $P450_{BM3}$.

Active Site Saturation Mutagenesis of BM3-CIS$_{heme}$

Library Construction.

To simplify library construction and screening, only the BM3-CIS heme domain, which comprises residues 1-462 was used. This truncated enzymes lacks the P450 native reductase and exhibits similar activity and stereochemical control to the full length enzyme using $Na_2S_2O_4$ as a reductant, but not NADPH. P450 site-directed mutagenesis and site-saturation libraries were assembled from PCR fragments generated from oligonucleotides containing the desired codon mutation or a degenerate NNK (or for reverse primers, the reverse complement MNN; where N=A,T,G,C,K=G,T and M=A,C) codon, which codes for all 20 amino acids and the TAG stop codon. PCR fragments were assembled using either standard overlap extension PCR or through restriction cloning using the Type IIS restriction enzyme, BsaI, depending on convenience.

Lysate screening under aerobic conditions. The compilation plate was expressed and lysed as described above. 150 µL lysate was transferred (Multimek 96-channel pipetting robot, Beckman Coulter, Fullerton, Calif.) to a 2 mL deep-well plate, with 50 µL of 120 mM $Na_2S_2O_4$ in 0.1 M KPi (pH=8.0). 100 µL of a 90 mM styrene, 30 mM EDA mixed solution in 15% MeOH in 0.1 M KPi (pH=8.0) was added to the plate to initiate the reaction. The plate was sealed and was left shaking (300 rpm) for four hours. The plastic seal was removed and 30 µL HCl (3 M) was added to quench the reaction followed by 20 µL of an internal standard solution (20 mM 2-phenylethanol in methanol). Acetonitrile (400 µL) was added before carefully vortexing the plate. The plate was centrifuged (1,700×g), the supernatant was filtered (1 µm glass, 96 well filter plate, Pall) and transferred (150 µL) to a 96-well microtiter plate (Agilent). Reactions were analyzed by reverse-phase HPLC (210 nm): 50% acetonitrile-water, 1.0 mL min$^{-1}$, cis-cyclopropanes (7.6 min), trans-cyclopropanes (9.7 min). Hits were selected based on enhancement of cis-selectivity over parent BM3-CIS.

Determining the Cyclopropanation Activity of Hits from the Site-Saturation Libraries Under Anaerobic Conditions.

Small-scale reactions (400 µL total volume) were conducted as described above and were analyzed by GC (cyclosil-B 30 m×0.25 mm×0.25 µm): oven temperature=130° C., 175 kPa, cis-cyclopropanes (39.40 min and 40.20 min), trans-cyclopropanes (44.69 min and 45.00 min). Table 19 shows the cyclopropanation activity of selected BM3-CIS$_{heme}$ active site variants.

Kinetic Characterization of BM3-CIS

Determination of Initial Rates.

Both styrene and EDA concentrations were varied in the presence of the P450s expressed as the heme-domain (0.5 or 1.0 µM BM3-CIS$_{heme}$). Reactions were set up in phosphate buffer (pH=8.0) with $Na_2S_2O_4$ as the reductant at 298 K, and were worked-up as described above. Three time points were taken and used to determine the rate of product formation by GC (cyclosil-B 30 m×0.32 mm×0.25 µm): oven temperature=100° C. 5 min, 5° C./min to 200° C., 20° C./min to 250° C., 250° C. for 5 min. Elution time: cis-cyclopropanes (19.20 min and 19.33 min), trans-cyclopropanes (20.44 min). Kinetic parameters were determined by fitting the data to the standard Michaelis-Menten model.

FIG. 5 illustrates the initial velocities plot for BM3-CIS$_{heme}$. (A) EDA concentration was varied at a saturating concentration of styrene (30 mM). (B) Styrene concentration was varied at a fixed concentration of EDA (20 mM). Initial rates were computed as the slope of a zero-intercept linear fit of three different time points from independent reactions. Error bars correspond to 1-σ (68.3%) confidence intervals for the slope. Table 20 shows the Michaelis-Menten parameters for P450 cyclopropanation catalysts. Table 21 shows kinetic parameters for wild-type cytochrome P450s acting on their native substrates and for an engineered variant of $P450_{BM3}$ (propane monooxygenase, PMO) acting on the non-native substrate propane. Table 22 shows the effect of EDA addition at t=30 min on BM3-CIS-catalyzed cyclopropanations.

Substrate Scope of P450 Cyclopropanation Catalysts

Small-Scale Reactions.

Selected P450 catalysts were surveyed at a small-scale (400 µL total volume) for each combination of reagents (olefins and diazo esters). The small-scale anaerobic bioconversions were conducted as described above and were analyzed by GC. Table 30 shows the substrate scope of P450 cyclopropanation catalysts: p-methylstyrene+EDA. Table 31 shows the substrate scope of P450 cyclopropanation catalysts: p-vinylanisole+EDA. Table 32 shows the substrate scope of P450 cyclopropanation catalysts: p-(trifluoromethyl)styrene. Table 33 shows the substrate scope of P450 cyclopropanation catalysts: α-methyl styrene. Table 34 shows the substrate scope of P450 cyclopropanation catalysts: t-butyl diazoacetate.

Preparative-Scale Bioconversions.

These reactions were conducted anaerobically as described above.

Cyclopropanation of Styrene with EDA.

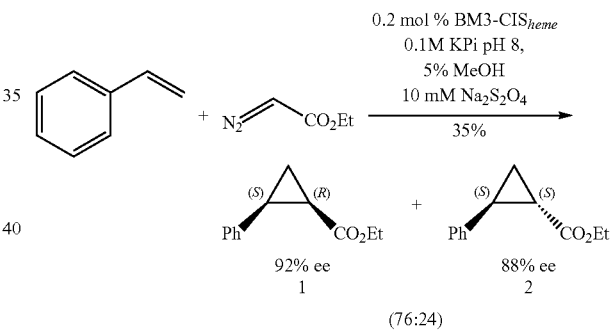

Prepared using 1.5 mmol styrene (3 equiv), 0.5 mmol EDA (1 equiv) and 1 µmol BM3-CIS$_{heme}$ (0.002 equiv). The product was purified by $SiO_2$ chromatography (9:1 hexanes-diethyl ether) to give 25 mg of the cis-cyclopropane (1) and 8 mg of a mixture of cyclopropanes with trans (2) in 5:1 excess over cis (Y. Chen et al., *Journal of Organic Chemistry* 72, 5931 (2007); C. J. Sanders et al., *Tetrahedron: Asymmetry* 12, 1055 (2001); M. Lenes Rosenberg et al., *Organic Letters* 11, 547 (2009)). Diagnostic data for the cis-cyclopropane 1: $^1$H NMR (CDCl$_3$, 500 MHz): δ 7.28 (m, 4H), 7.21 (m, 1H), 3.89 (q, J=7.1 Hz, 2H), 2.60 (m, 1H), 2.10 (m, 1H), 1.73 (m, 1H), 1.35 (m, 1H), 0.99 (t, J=7.1 Hz, 3H); $^{13}$C NMR (CDCl$_3$, 125 MHz): δ 170.99, 136.56, 129.31, 127.88, 126.63, 60.18, 25.47, 21.80, 14.02, 11.12; $[\alpha]^{25}_D$=−7.056° (c 0.83, CHCl$_3$). Diagnostic data for the trans-cyclopropane 2: $^1$H NMR (CDCl$_3$, 500 MHz): δ 7.20 (m, 3H), 7.03 (m, 2H), 4.10 (q, J=7.1 Hz, 2H), 2.45 (m, 1H), 1.83 (m, 1H), 1.53 (m, 1H), 1.23 (m, 1H), 1.21 (t, J=7.1 Hz, 3H); $^{13}$C NMR (CDCl$_3$, 125 MHz): δ 173.43, 140.13, 128.46, 126.55, 126.16, 60.72, 26.18, 24.20, 17.09, 14.27; $[\alpha]^{25}_D$=+199.2° (c 0.50, CHCl$_3$). MS (EI$^+$) m/z: 190 (M$^+$), 162 (PhCH(CH$_2$)CHCO$_2$$^+$), 145 (PhCH(CH$_2$)CHCO$^+$). The absolute configuration of compounds 1 and 2 was determined by comparison of the sign of their optical rotations with that reported (N. Watanabe et al., *Heterocycles* 42, 537 (1996)). The enantiomeric excess was determined to be 92% for the cis-cyclopropane and 88% for the trans-cyclopropane by GC.

Cyclopropanation of p-Methylstyrene with EDA.

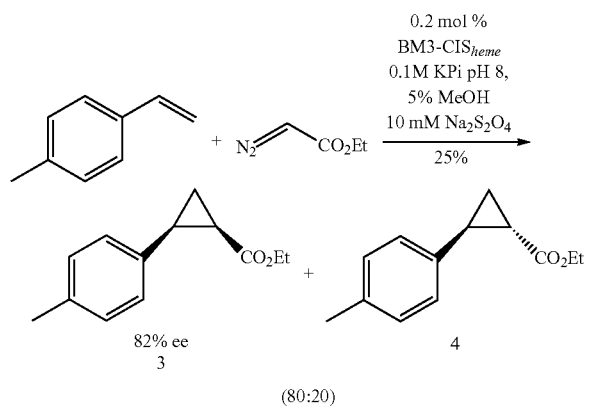

Prepared using 1.5 mmol styrene (3 equiv), 0.5 mmol EDA (1 equiv) and 1 µmol BM3-CIS$_{heme}$ (0.002 equiv). The product was purified by SiO$_2$ chromatography (9:1 hexanes-diethyl ether) to give 10 mg of the cis-cyclopropane (3) and 16 mg of a mixture of cyclopropanes with trans(4):cis/2:1 (Y. Chen et al., *Journal of Organic Chemistry* 72, 5931 (2007)). Diagnostic data for the cis-cyclopropane 3: $^1$H NMR (CDCl$_3$, 500 MHz): δ 7.17 (d, J=8.0 Hz, 2H), 7.08 (d, J=8.0 Hz, 2H), 3.91 (q, J=7.1 Hz, 2H), 2.56 (m, 1H), 2.32 (s, 3H) 2.06 (m, 1H), 1.69 (m, 1H), 1.32 (m, 1H), 1.02 (t, J=7.1 Hz, 3H); $^{13}$C NMR (CDCl$_3$, 125 MHz): δ 171.12, 136.12, 133.42, 129.14, 128.60, 60.17, 25.23, 21.68, 21.10, 14.08, 11.21. Diagnostic data for the trans-cyclopropane 4: $^1$H NMR (CDCl$_3$, 500 MHz): δ 7.09 (d, J=8.0 Hz, 2H), 7.01 (d, J=8.0 Hz, 2H), 4.19 (q, J=7.1 Hz, 2H), 2.50 (m, 1H), 2.33 (s, 3H), 1.88 (m, 1H), 1.59 (m, 1H), 1.33 (m, 1H), 1.29 (t, J=7.1 Hz, 3H); $^{13}$C NMR (CDCl$_3$, 125 MHz): δ 173.58, 137.04, 136.08, 129.12, 126.10, 60.66, 25.94, 24.06, 21.11, 16.96, 14.28. MS (Er) m/z: 204 (M$^+$), 175 ([M-Et]$^+$) 131 ([M-COOEt]$^+$). The enantiomeric excess was determined to be 82% for the cis-cyclopropane by GC. Baseline resolution of the trans-enantiomers could not be achieved.

Cyclopropanation of p-Methoxystyrene with EDA.

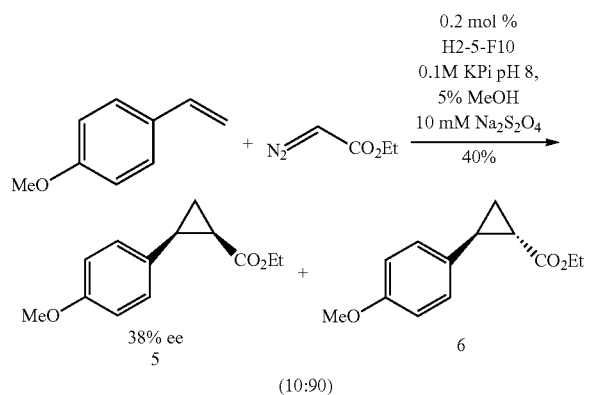

Prepared using 1.5 mmol styrene (3 equiv), 0.5 mmol EDA (1 equiv) and 1 µmol BM3-CIS$_{heme}$ (0.002 equiv). The product was purified by SiO$_2$ chromatography (9:1 hexanes-diethyl ether) to give 16 mg of the trans-cyclopropane (6) and 3 mg of a mixture of cyclopropanes with cis:trans 15:1 (Y. Chen et al., *Journal of Organic Chemistry* 72, 5931 (2007)). Diagnostic data for the trans-cyclopropane 6: 6.96 (m, 3H), 6.75 (m, 2H), 4.09 (q, J=7.1 Hz, 2H), 3.72 (s, 3H), 2.41 (m, 1H), 1.75 (m, 1H), 1.48 (m, 1H), 1.21 (t, J=7.1 Hz, 3H), 1.18 (m, 1H). MS (EI$^+$) m/z: 220 (M$^+$), 191 ([M-Et]$^+$), 175 ([M-EtO]$^+$), 147 ([M-COOEt]$^+$). The enantiomeric excess was determined to be 38% for the cis-cyclopropane by GC. The trans-enantiomers did not resolve to baseline resolution.

Cyclopropanation of Styrene with t-Butyl Diazo Acetate.

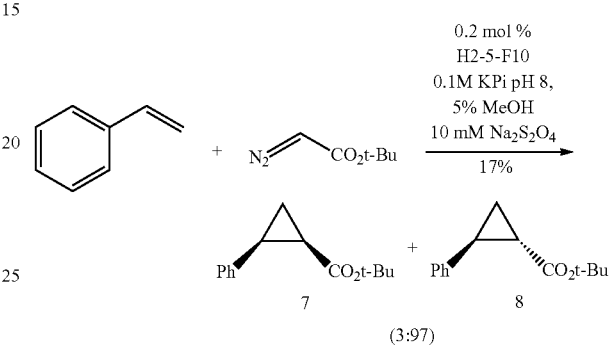

Prepared using 0.75 mmol styrene (3 equiv), 0.24 mmol t-BuDA (1 equiv) and 0.5 µmol BM3-CIS$_{heme}$ (0.002 equiv). The product was purified by SiO$_2$ chromatography (9:1 hexanes-diethyl ether) to give 9 mg of the trans-cyclopropane (8) (Y. Chen et al., *Journal of Organic Chemistry* 72, 5931 (2007); C. J. Sanders et al., *Tetrahedron: Asymmetry* 12, 1055 (2001)). Diagnostic data for the trans-cyclopropane 4: $^1$H NMR (CDCl$_3$, 500 MHz): δ 7.20 (m, 2H), 7.12 (m, 1H), 7.02 (m, 2H), 2.36 (m, 1H), 1.76 (m, 1H), 1.45 (m, 1H), 1.40 (s, 9H), 1.16 (m, 1H); $^{13}$C NMR (CDCl$_3$, 125 MHz): δ 172.58, 140.52, 128.42, 126.32, 126.07, 80.57, 28.17, 25.75, 25.31, 17.08. MS (Er) m/z: 218 (M$^+$), 145 ([M-OtBu]$^+$).

Orthogonalization of Cyclopropanation and Monooxygenation Activities

Figure 18:
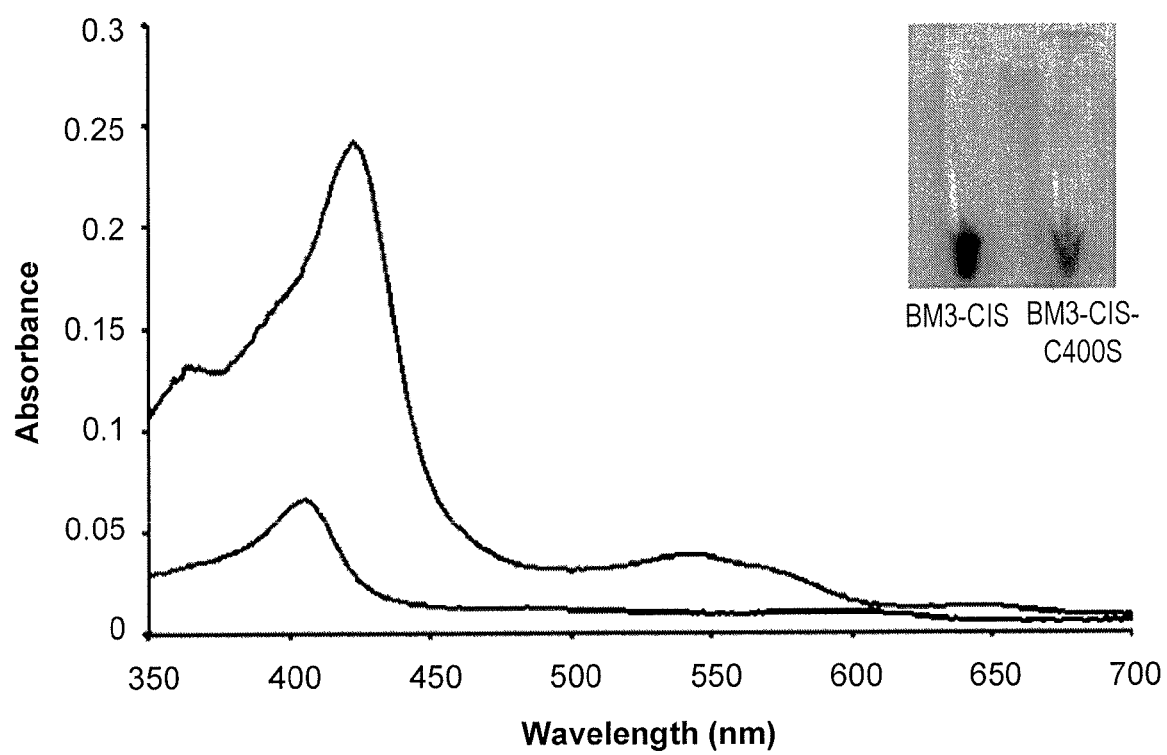
FIG. 18 illustrates UV-Vis absorption spectra of purified BM3-$CIS_{heme}$ (3 µM, red line) and BM3-CIS-$C400S_{heme}$ (2 µM, green line). Insert shows solutions of both proteins at approximately 1 mM.

FIG. 18 illustrates the UV-Vis absorption spectra of purified BM3-CIS$_{heme}$ (3 µM, upper line) and BM3-CIS-C400S$_{heme}$ (2 µM, lower line). Insert shows solutions of both proteins at approximately 1 mM.

Concentration of BM3-CIS-C400S was determined by the micro BCA™ assay (Thermo Scientific) using BM3-CIS as a standard. The serine-ligated cytochrome P450 displays a lower extinction coefficient (~5× lower) and a Soret band that is blue-shifted by 14 nm. Magnetic circular dichroism and electronic absorption spectra of the substrate-free ferric, ferrous and CO-bound ferrous serine-ligated P450 has been reported elsewhere (R. Perera et al., *Archives of Biochemistry and Biophysics* 507, 119 (2011)).

Activity Under Anaerobic Vs Aerobic Conditions with Sodium Dithionite as the Reductant.

Table 35 shows the effect of C400S mutation on BM3-CIS-mediated cyclopropanation driven by Na$_2$S$_2$O$_4$. FIG. 6 shows the cyclopropanation activities of BM3-CIS and BM3-CIS-C400S driven by sodium dithionite under anaerobic and aerobic conditions. Measurements were taken in triplicate and the error bars represent the standard deviation from the mean value.

Activity Under Anaerobic Vs Aerobic Conditions with NADPH as the Reductant.

Small-scale reactions (400 µL total volume) were conducted as described above with the following modifications: glucose dehydrogenase (GDH, 4 µL, 225 U mL$^{-1}$) was added to the reaction vial together with the P450 solution. Glucose (40 µL, 250 mM) and NADPH (40 µL, 5 mM) were degassed together with the buffer solution. Measurements were taken in triplicate and the error bars represent the standard deviation from the mean value. Table 36 shows the effect of C400S mutation on BM3-CIS-mediated cyclopropanation driven by NADPH.

Determination of Initial Rates.

Both styrene and EDA concentrations were varied in the presence of the P450s expressed as the heme-domain (3.5 µM BM3-CIS-C400S$_{heme}$). Reactions were set-up in phosphate buffer (pH=8.0) with sodium dithionite as the reductant at 298 K, and were worked-up as described above. Three time points were taken and used to determine the rate of product formation by GC (cyclosil-B 30 m×0.32 mm×0.25 µm): oven temperature=100° C. 5 min, 5° C./min to 200° C., 20° C./mM to 250° C., 250° C. for 5 min. Elution time: cis-cyclopropanes (19.20 min and 19.33 min), trans-cyclopropanes (20.44 min). Kinetic parameters were determined by fitting the data to the standard Michaelis-Menten model. FIG. 8 shows the initial velocities plot for BM3-CIS-C400S$_{heme}$. (A) EDA concentration was varied at a saturating concentration of styrene (30 mM). (B) Styrene concentration was varied at a fixed concentration of EDA (20 mM). Table 37 shows the Michaelis-Menten parameters for P450 cyclopropanases.

X-Ray Crystallography Statistics

FIG. 9 shows active site and protein alignments of BM3-CIS with BM3-CIS-C400S and wild type P450$_{BM3}$.

To investigate the nature of enhanced stereoselectivity in BM3-CIS-C400S, crystal structures of both proteins were determined to assess any structural changes that may have occurred due to the axial Cys→Ser mutation. The top panels shows alignments of BM3-CIS (green) and BM3-CIS-C400S (peach) with left, middle and right panels showing active site residues, the active site I-helix, and global protein fold, respectively. No significant structural changes were observed (RMSD 0.52 Å). Middle panels: Large variations are observed upon comparing BM3-CIS with the open (ligand-free) form of wild type BM3 (purple, taken from PDB#2IJ2, RMSD 1.2 Å). Pronounced rearrangements are observed in active site side chain residues (left) as well as rotations within the I-helix. Global movements are also observed in the N-terminal rich beta domain as well as F- and G-helices (right, marked by double headed arrows). These movements are consistent with well-known transitions that occur upon substrate binding and are important for native monooxygenation catalysis. Bottom panels: Alignment of BM3-CIS with a ligand-bound BM3 structure (cyan, taken from PDB#1JPZ, RMSD 0.52 Å) demonstrates that BM3-CIS and BM3-CIS-C400S mimic the closed protein conformation even in the absence of substrate.

Table 38 shows data collection and refinement statistics for P450$_{BM3}$ crystals.

Summary of Mutations in P450$_{BM3}$ Variants

Mutations in variant P450 cyclopropanation catalysts are reported with respect to wild-type P450$_{BM3}$.

7-11D (P. Meinhold et al., *Adv. Synth. Catal.* 348, 763 (2006)): R47C, V78A, K94I, P142S, T175I, A184V, F205C, S226R, H236Q, E252G, R255S, A290V, L353V, A82F, A328V 9-10A TS (J. C. Lewis et al., *Chembiochem: A European Journal of Chemical Biology* 11, 2502 (2010)): V78A, P142S, T175I, A184V, S226R, H236Q, E252G, A290V, L353V, I366V, E442K

H2A10: 9-10A TS+F87V, L75A, L181A, T268A

H2-5-F10: 9-10A TS+F87V, L75A, I263A, T268A, L437A

H2-4-D4: 9-10A TS+F87V, L75A, M177A, L181A, T268A, L437A

BM3-CIS: 9-10A TS+F87V, T268A

Whole Cell Catalysts for In Vivo Cyclopropanation

Media and Cell Cultures.

*E. coli* cells were grown from glycerol stock overnight (37° C., 250 rpm) in 5 ml M9Y medium (1 L: 31 g Na$_2$HPO$_4$, 15 g KH$_2$PO$_4$, 2.5 g NaCl, 5.0 g NH$_4$Cl, 0.24 g MgSO$_4$, 0.01 g CaCl$_2$, 1.5% yeast extract, 1 mL micronutrients, 0.1 mg mL$^{-1}$ ampicillin). The pre-culture was used to inoculate 45 mL of M9Y medium and this culture was incubated at 37° C., 250 rpm for 2 h and 30 min. At OD$_{600}$=1.2, the cultures were cooled to 25° C. and induced with IPTG (0.25 mM) and δ-aminolevulinic acid (0.25 mM). Cultures were harvested after 20 h and resuspended (OD$_{600}$=30) in nitrogen-free M9 medium (1 L: 31 g Na$_2$HPO$_4$, 15 g KH$_2$PO$_4$, 2.5 g NaCl, 0.24 g MgSO$_4$, 0.01 g CaCl$_2$, 1 mL micronutrients). The micronutrient solution contains 0.15 mM (NH$_4$)$_6$MO$_7$O$_{24}$, 20.0 mM H$_3$BO$_3$, 1.5 mM CoCl$_2$, 0.5 mM CuSO$_4$, 4.0 mM MnCl$_2$, and 0.5 mM ZnSO$_4$. Aliquots of the cell suspension were used for determination of the cell dry weight (cdw, 2 mL) and P450 expression level (4 mL).

Small-Scale Whole Cell Bioconversions.

*E. coli* cells (OD$_{600}$=30, 425 µL) were made anaerobic by bubbling argon through the cell suspension in a crimped 2 mL vial. A degassed solution of glucose (50 µL, 20 mM) was added to the cells before adding EDA (12.5 µL of a 400 mM solution in MeOH) and olefin (12.5 µL of a 1.2 M solution in MeOH). The reactions were stirred at room temperature for the appropriate and were worked up by adding 20 µL of the internal standard (20 mM 2-phenylethanol) and extracting with 1 mL ethyl acetate. The organic layer was dried over Na$_2$SO$_4$ before analyzing the product mixture by chiral phase gas chromatography.

Figure 11:
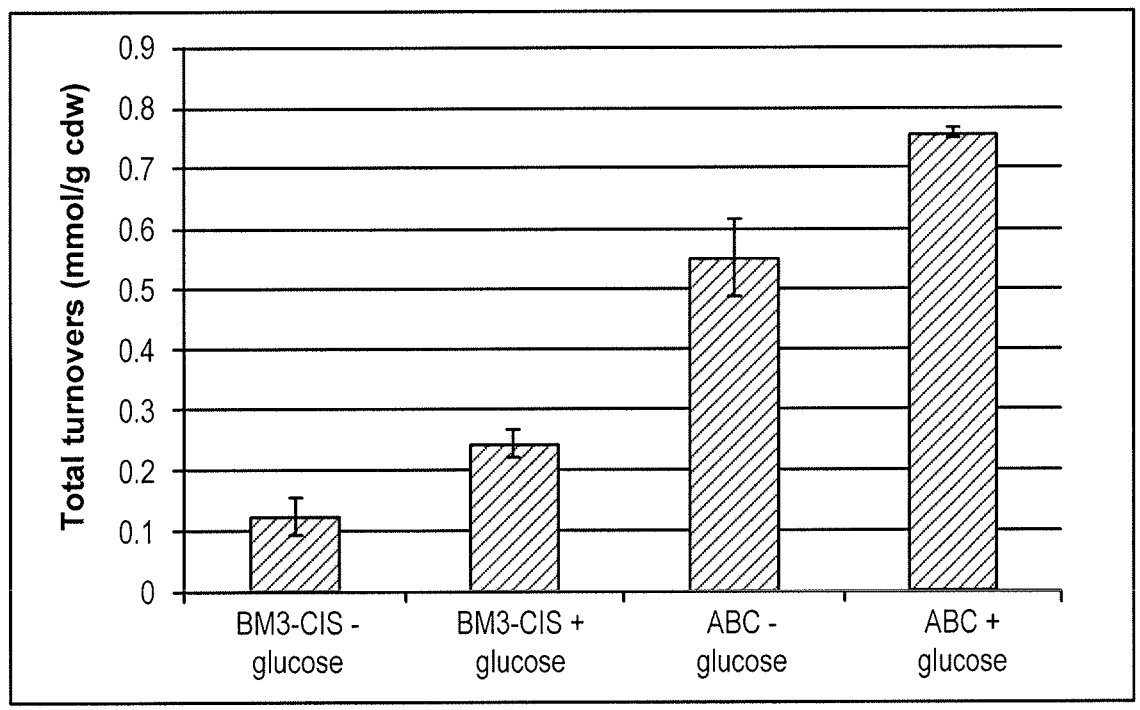
FIG. 11 illustrates the effect of glucose addition on in vivo cyclopropanation of styrene. Reaction conditions: 20 mM styrene, 10 mM EDA, under argon in nitrogen-free medium and 5% MeOH cosolvent for 2 hours at 298 K ($OD_{600}$~24). Total turnover=concentration of cyclopropanes (mM)/cell density (g cdw/L) in units of mmol/g cdw. Variant 9-10A-TS-F87V-T268A=BM3-CIS and ABC=BM3+C400S.
Figure 12:
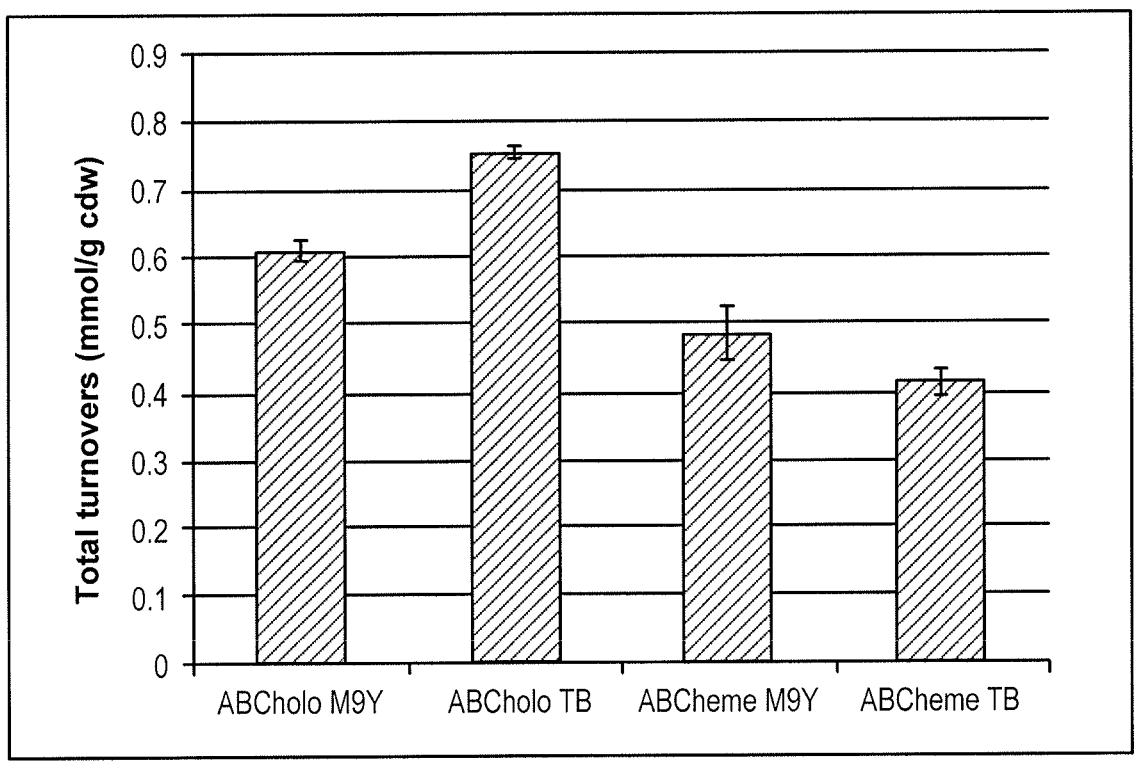
FIG. 12 illustrates the effect of media and comparison of holo vs. heme forms of BM3-CIS-C400S on in vivo cyclopropanation of styrene. Reaction conditions: 20 mM styrene, 10 mM EDA, 2 mM glucose under argon in nitrogen-free medium and 5% MeOH cosolvent for 2 hours at 298 K ($OD_{600}$~24). Variant 9-10A-TS-F87V-T268A=BM3-CIS and ABC=BM3+C400S.

FIG. 11 illustrates the effect of glucose addition on in vivo cyclopropanation of styrene. Reaction conditions: 20 mM styrene, 10 mM EDA, under argon in nitrogen-free medium and 5% MeOH cosolvent for 2 hours at 298 K (OD$_{600}$~24). Total turnover=concentration of cyclopropanes (mM)/cell density (g cdw/L) in units of mmol/g cdw.

FIG. 12 illustrates the effect of media and comparison of holo vs heme forms of BM3-CIS-C400S on in vivo cyclopropanation of styrene. Reaction conditions: 20 mM styrene, 10 mM EDA, 2 mM glucose under argon in nitrogen-free medium and 5% MeOH cosolvent for 2 hours at 298 K (OD$_{600}$~24).

FIG. 13 illustrates that increasing ABC catalyst loading (cell density) increases cyclopropanes yield up to approximately 80% at OD$_{600}$=50.

FIG. 14 illustrates the effect of styrene concentration on cyclopropane yield.

FIG. 15 illustrates controls for ABC catalyzed cyclopropanation.

FIG. 16 illustrates that ABC catalyst is active for 3 hours. At OD$_{600}$=25, the P450 concentration in 0.85 µM, such that TTN>8,000.

Example 3

In Vivo and In Vitro Olefin Cyclopropanation Catalyzed by Heme Enzymes

This example illustrates the use of heme containing enzymes to catalyze the conversion of olefins to various products containing one or more cyclopropane functional groups. In certain aspects, this example demonstrates novel variants of cytochrome P450$_{BM3}$ (CYP102A1 or BM3) having an improved ability to catalyze the formal transfer of carbene equivalents from diazo esters to various olefins, making cyclopropane products with high stereoselectivity. Preferred variants include, but are not limited to, cytochrome P450$_{BM3}$ mutants having C400S and T268A amino acid substitutions and engineered variants of other P450s having the equivalent substitutions. Axial serine heme ligation (C400S in BM3) in cytochrome P450s creates the homologous "cytochrome P411" family. Cytochrome P411s catalyze the cyclopropanation reaction in whole cells, sustaining over 10,000 total turnovers with high stereoselectivity, making the cyclopropane product with titers of over 20 g L$^{-1}$.

Introduction

Genetically programmed whole-cell biocatalysts are readily produced in simple growth media, do not require further purification or isolation and can be engineered with metabolic pathways for the elaboration of complex molecules (P. K. Ajikumar et al., *Science* 330, 70 (2010); P. J. Westfall et al., *Proc. Natl. Acad. Sci. U.S.A.* 109, E111 (2012); M. Kataoka et al., *Appl Microbiol. Biotechnol.* 62, 437 (2003)). The range of accessible transformations, however, is currently limited to the chemical repertoire of natural enzymes. Designing enzymes for non-natural reactions in vivo has been challenging due to the requirements for assembly of the functional catalyst, the compatibility of synthetic reagents in the cellular milieu, and cell permeability to allow substrate influx and product release. The catalysis of non-natural transformations inside cells will enable alternative metabolic routes to natural and artificial products, bio-based production of chemicals currently made using synthetic reactions, and will expand the chemical toolbox available for in vivo studies of cellular function (M. Boyce, C. R. Bertozzi, *Nature Methods* 8, 638 (2011)).

The preceding examples demonstrate that a few amino acid mutations in a bacterial cytochrome P450 monooxygenase can unlock significant cyclopropanation activity in vitro. Variants of P450$_{BM3}$ from *Bacillus megaterium* (BM3) catalyze hundreds of turnovers of formal carbene transfers from diazoesters (e.g., ethyl diazoacetate, EDA) to olefins (e.g., styrene) in the presence of a reductant, forming cyclopropane products with high levels of diastereo- and enantioselectivity (P. S. Coelho et al., *Science* 339, 307 (2013)). Olefin cyclopropanation is widely used in the synthesis of fine chemicals (H. Lebel et al., *Chem. Rev.* 103, 977 (2003)), and state-of-the-art asymmetric organometallic catalysts are able to catalyze thousands to tens of thousands of turnovers (D. A. Evans et al., *J. Am. Chem. Soc.* 113, 726 (1991); H. M. L. Davies, C. Venkataramani, *Org. Lett.* 5, 1403 (2003); G. Maas, *Chem. Soc. Rev.* 33, 183 (2004)). BM3 variants may be suitable for in vivo catalysis because they are readily expressed in functional form and can catalyze non-natural carbene transfers without requiring artificial cofactors or posttranslational modifications. To initiate the catalytic cycle inside a cell, it is necessary to reduce the enzyme to the catalytically active ferrous-P450 with an endogenous reducing agent such as NAD(P)H. Based on consideration of heme ligation control of the P450 Fe$^{III}$/Fe$^{II}$ reduction potential, a genetically-encoded "ABC" catalyst that catalyzes efficient and selective olefin cyclopropanation in intact cells was designed.

Results

Figure 19A:
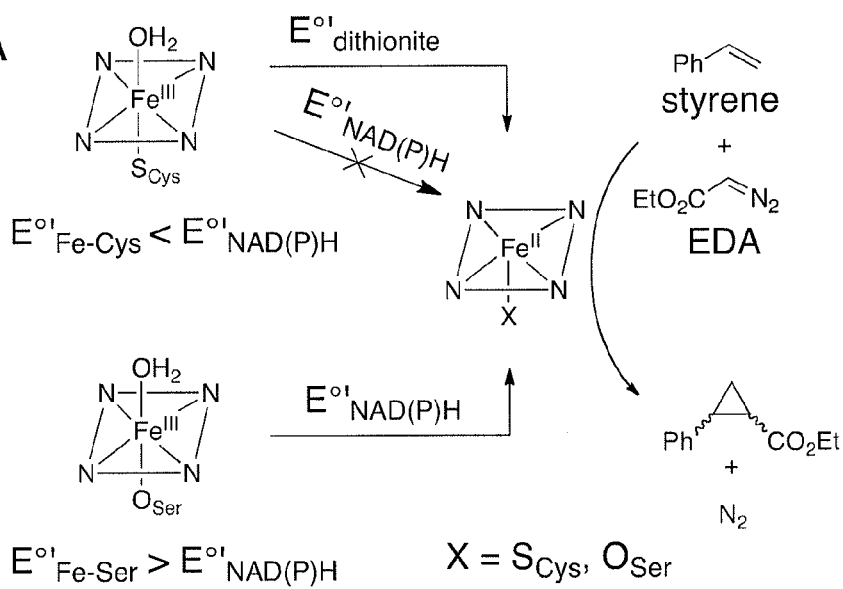
FIGS. 19A-C illustrate (FIG. 19A) Cytochrome P450s inefficiently catalyze cyclopropanation using NAD(P)H as a reductant because the $Fe^{III}/Fe^{II}$ redox potential for the low-spin resting state ($E^{o'}_{Fe-Cys}$=−430 mV) is lower than that of $NAD(P)^+/NAD(P)H$ ($E^{o'}_1$=−320 mV). Replacement of the heme-cysteine ligand (Fe-Cys) with serine (Fe-Ser) increased the resting state reduction potential and allowed reduction by NAD(P)H to the active $Fe^{II}$ species in vivo.

Cytochrome P450-catalyzed cyclopropanations require substoichiometric (with respect to diazoester and olefin) reductant and proceed optimally under anaerobic conditions (P. S. Coelho et al., *Science* 339, 307 (2013)). This indicates that diazoester activation and carbene transfer involve a reduced P450-bound Fe$^{II}$-heme cofactor as opposed to the resting state Fe$^{III}$-heme (FIG. 19A). Active P450-derived cyclopropanation catalysts show marked preference for strong reducing agents such as sodium dithionite (E$^{o'}$=−660 mV, all potentials vs SHE) over native NAD(P)H (E$^{o'}$=−320 mV) (P. S. Coelho et al., *Science* 339, 307 (2013)). This indicates a limited substrate-induced low-spin (E$^{o'}$ Fe$^{III/II}$=−430 mV) to high-spin (E$^{o'}$ Fe$^{III/II}$=−290 mV) transition of the P450 heme-iron (T. W. B. Ost et al., *Biochemistry* 40, 13421 (2001)), which, while essential for monooxygenation, may not be achievable in this engineered system due to the poor affinity for the non-natural substrates (K$_M$~5 mM) (P. S. Coelho et al., *Science* 339, 307 (2013)). It was hypothesized that raising the reduction potential of the resting state enzyme to facilitate NAD(P)H reduction would be important for enhancing Fe$^{II}$ catalysis in vivo. Because the reduction potential of heme proteins can be tuned by axial ligand mutations (D. S. Wuttke, H. B. Gray, *Curr. Opin. Struct. Biol.* 3, 555 (1993); C. J. Reedy et al., *Nucleic Acids Res.* 36, D307 (2008)), the Fe$^{III/II}$ potential was raised by substituting the axial cysteine thiolate in BM3 with the weakly donating serine alcohol (FIG. 19A). Furthermore, axial cysteinate ligation is essential for dioxygen activation and stabilization of the active ferryl-porphyrin cation radical oxidant (compound I, FIG. 1) during monooxygenation (J. H. Dawson, *Science* 240, 433 (1988)), and axial cysteine to serine substitutions abolish monooxygenation activity in mammalian P450s (K. P. Vatsis et al., *J. Inorg. Biochem.* 91, 542 (2002)). Because free hemin is also a (poor) cyclopropanation catalyst (P. S. Coelho et al., *Science* 339, 307 (2013)), an axial cysteine to serine mutation (C400S in BM3) maintains carbene transfer activity while eliminating monooxygenation activity.

Figure 19B:
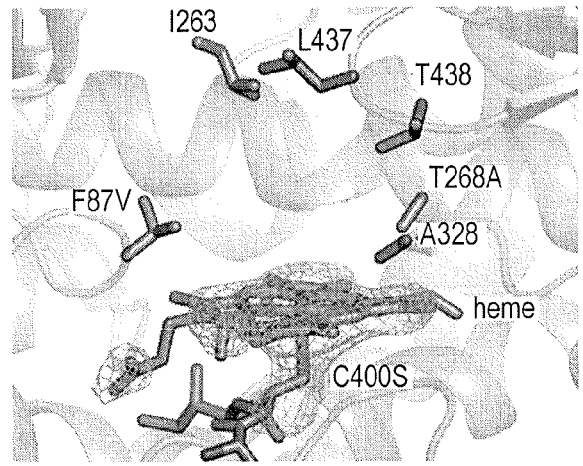
Figure 19C:
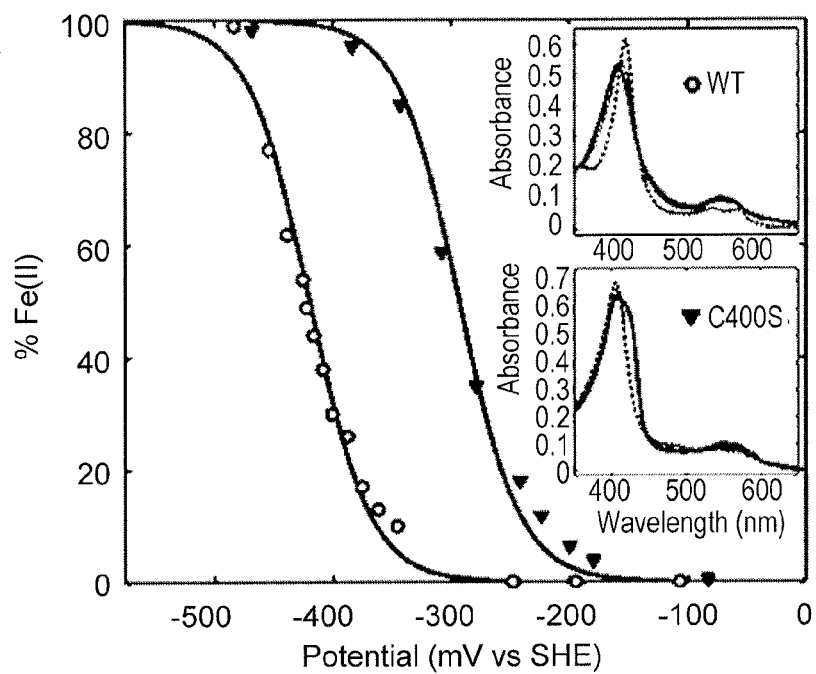
Figure 20A:
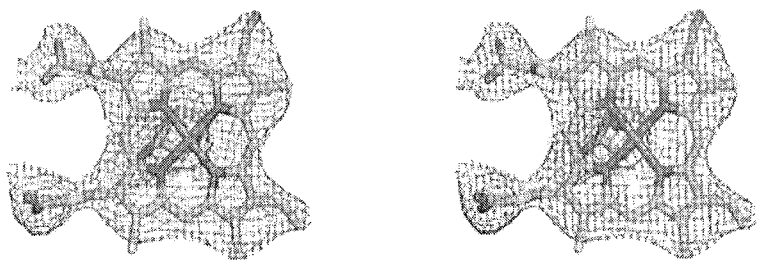
FIGS. 20A-B illustrate the heme electron density of BM3-CIS-C400S (also called ABC-CIS or $P411_{BM3}$-CIS). Maximum likelihood weighted electron density maps of serine-ligated heme in $P411_{BM3}$-CIS.
Figure 20B:
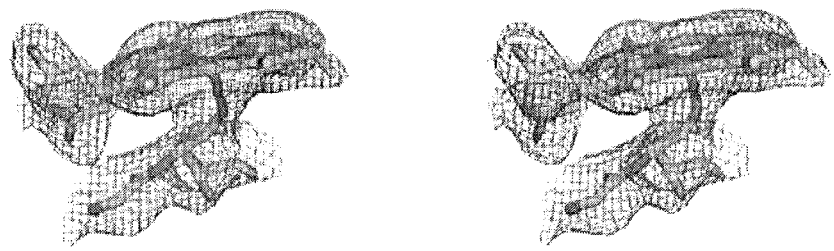

The C400S mutation was introduced into a cis-selective cyclopropanation catalyst of the present invention, BM3-CIS (13 mutations from BM3; P. S. Coelho et al., *Science* 339, 307 (2013)), to contrast with the trans-selectivity observed with iron-porphyrins (J. R. Wolf et al., *J. Am. Chem. Soc.* 117, 9194 (1995)). BM3-CIS catalyzes hundreds of turnovers in the presence of dithionite in vitro and forms the ethyl 2-phenyl-cyclopropane-1-carboxylate product with 71% cis-selectivity and −94% enantiomeric excess (ee$_{cis}$) (P. S. Coelho et al., *Science* 339, 307 (2013)). Heme-serine ligation in BM3-CIS-C400S (hereafter called ABC-CIS) was confirmed by determining the crystal structures of the BM3-CIS and ABC-CIS heme domains at 2.5 and 3.3 Å, respectively (FIG. 9 and Table 38, PDB: 4H23 and 4H24); the structures are superimposable (RMSD=0.52 Å, FIG. 9). Despite the limited resolution of the ABC-CIS structure, simulated annealing omit maps generated in the absence of modeled heme and C400S show density consistent with heme coordination by a proximal amino acid side chain (FIGS. 19B and 20). UV-vis spectra for the green-brown ABC-CIS (FIGS. 21-23) provide further evidence for heme-serine ligation and are consistent with those reported for a Ser-ligated mammalian P450 (K. P. Vatsis et al., *J. Inorg. Biochem.* 91, 542 (2002); R. Perera et al., *Arch. Biochem. Biophys.* 507, 119 (2011)) (Table 39), marked by a ferrous carbon monoxide-bound complex at 411 nm.

TABLE 39

Comparison of λmax for ABC-CISheme and CYP2B4-C436S (Vatsis et al.).

| | ABC-CIS$_{heme}$ (nm) | CYP2B4-C436S (nm) |
|---|---|---|
| Ferric resting state | 404 | 405 |
| Ferrous | 425 | 422 |
| Ferrous-CO | 411 | 413 |

Potentiometric redox titrations using the truncated heme domains of wild-type BM3, its C400S variant (referred to herein as "ABC"), BM3-CIS and ABC-CIS (FIGS. 19C and 24-27) showed that the C400S mutation raises the reduction potential of the resting state enzyme by +127 mV ($E^{o\prime}$ Fe$^{III/II}_{ser}$=−293 mV and −265 mV for ABC and ABC-CIS, respectively). This shift is similar in magnitude to that which occurs in BM3 upon substrate binding (T. W. B. Ost et al., *Biochemistry* 40, 13421 (2001)), and therefore allows ABC-CIS to be reduced by NAD(P)H even in the absence of substrate.

ABC-CIS (P411$_{BM3-heme}$-CIS) is an active dithionite-driven cyclopropanation catalyst in vitro, with Michaelis-Menten parameters ($k_{cat}$=82 min$^{-1}$, $K_{M\text{-}styrene}$=4.6 mM, $K_{M\text{-}EDA}$=5.7 mM, FIG. 8), comparable to those of BM3-CIS (P450$_{BM3-heme}$-CIS) Table 40).

TABLE 40

Michaelis-Menten parameters for P450 cyclopropanation catalysts. Error bars correspond to 99% confidence intervals for the fitted parameters.

| Catalyst | $k_{cat}$ (min$^{-1}$) | $K_{M\text{-}EDA}$ (mM) | $K_{M\text{-}styrene}$ (mM) | $k_{cat}/K_{M\text{-}EDA}$ (s$^{-1}$ M$^{-1}$) | $k_{cat}/K_{M\text{-}styrene}$ (s$^{-1}$ M$^{-1}$) | $k_{cat}/(K_{M\text{-}EDA} \times K_{M\text{-}styrene})$ (s$^{-1}$ M$^{-1}$) |
|---|---|---|---|---|---|---|
| P450$_{BM3-heme}$-CIS (5) | 100 ± 24 | 5.2 ± 3.5 | 1.4 ± 0.5 | 320 | 1,100 | 2.1 × 10$^5$ |
| P411$_{BM3-heme}$-CIS | 82 ± 15 | 5.7 ± 2.9 | 4.6 ± 2.4 | 240 | 300 | 5.5 × 10$^4$ |

ABC-CIS displays considerably improved diastereoselectivity (cis:trans 93:7) and enantioselectivity (−99% ee$_{cis}$) compared to its cysteine homologue (FIG. 28), an unexpected result given the similar active site geometries of the two catalysts (FIG. 9). For a variety of styrenyl substrates, ABC-CIS (P411$_{BM3}$-CIS) showed superior cis-selectivity relative to BM3-CIS (Table 41).

TABLE 41

Enhanced Z selectivity for ABC-CIS (P411$_{BM3}$-CIS) over BM3-CIS (P450$_{BM3}$-CIS).

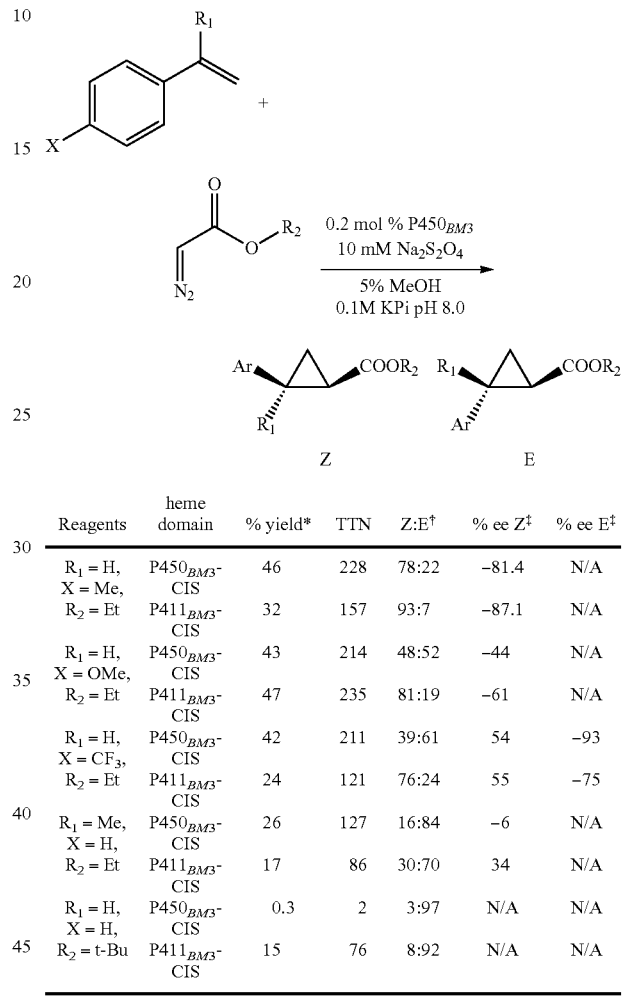

| Reagents | heme domain | % yield* | TTN | Z:E$^\dagger$ | % ee Z$^\ddagger$ | % ee E$^\ddagger$ |
|---|---|---|---|---|---|---|
| R$_1$ = H, X = Me, R$_2$ = Et | P450$_{BM3}$-CIS | 46 | 228 | 78:22 | −81.4 | N/A |
| | P411$_{BM3}$-CIS | 32 | 157 | 93:7 | −87.1 | N/A |
| R$_1$ = H, X = OMe, R$_2$ = Et | P450$_{BM3}$-CIS | 43 | 214 | 48:52 | −44 | N/A |
| | P411$_{BM3}$-CIS | 47 | 235 | 81:19 | −61 | N/A |
| R$_1$ = H, X = CF$_3$, R$_2$ = Et | P450$_{BM3}$-CIS | 42 | 211 | 39:61 | 54 | −93 |
| | P411$_{BM3}$-CIS | 24 | 121 | 76:24 | 55 | −75 |
| R$_1$ = Me, X = H, R$_2$ = Et | P450$_{BM3}$-CIS | 26 | 127 | 16:84 | −6 | N/A |
| | P411$_{BM3}$-CIS | 17 | 86 | 30:70 | 34 | N/A |
| R$_1$ = H, X = H, R$_2$ = t-Bu | P450$_{BM3}$-CIS | 0.3 | 2 | 3:97 | N/A | N/A |
| | P411$_{BM3}$-CIS | 15 | 76 | 8:92 | N/A | N/A |

*Based on EDA.
$^\dagger$Diastereomeric ratios and enantiomeric excess were determined by GC analysis.
$^\ddagger$Enantiomeric excess is only reported when the enantiomers resolved to baseline resolution.

ABC-CIS shows increased activity compared to BM3-CIS when NADPH is used as the reductant under anaerobic conditions (FIG. 7 and Table 36). BM3-CIS only forms small amounts of cyclopropanes when NADPH is used and forms styrene oxide via monooxygenation as the major product under aerobic conditions. In contrast, ABC-CIS produces negligible amounts of styrene oxide and is still able to form cyclopropanes under aerobic conditions, albeit with lower yields (43 TTN) due to oxygen inhibition (FIG. 7). Dioxygen inhibition could be due to a two-electron oxidase activity as reported for CYP2B4-C436S (K. P. Vatsis et al., *J. Inorg. Biochem.* 91, 542 (2002)). NADH drives ABC-CIS-mediated cyclopropanation as efficiently as NADPH (Table 42), indicating that ABC-CIS is well suited for in vivo catalysis under anaerobic conditions where NADPH biosynthesis in *E. coli* does not take place.

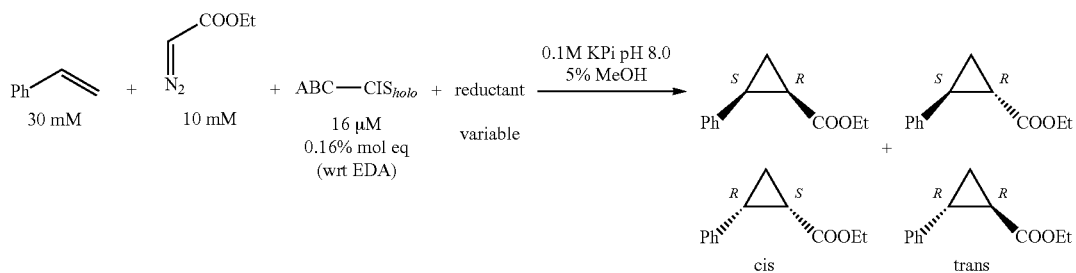

TABLE 42

In vitro BM3-CIS-C400S (also called ABC-CIS or P411$_{BM3}$-CIS) cyclopropanation driven by Na$_2$S$_2$O$_4$, NADPH and NADH.

| [NADPH]/ mM | [NADH]/ mM | [Na$_2$S$_2$O$_4$]/ mM | Yield (%)* | TTN | cis: trans† | % ee cis‡ | % ee trans§ |
|---|---|---|---|---|---|---|---|
| 0 | 0 | 0 | 1 | 3 | 54:46 | — | — |
| 0 | 0 | 10 | 35 | 218 | 94:6 | −99 | −43 |
| 1 | 0 | 0 | 47 | 294 | 93:7 | −98 | −40 |
| 5 | 0 | 0 | 58 | 364 | 90:10 | −97 | −28 |
| 10 | 0 | 0 | 49 | 305 | 91:9 | −98 | −26 |
| 0 | 1 | 0 | 70 | 437 | 93:7 | −98 | −38 |
| 0 | 5 | 0 | 68 | 428 | 93:7 | −98 | −34 |
| 0 | 10 | 0 | 47 | 295 | 93:7 | −98 | −34 |

*Based on EDA.
†Diastereomeric ratios and enantiomeric excess were determined by GC analysis.
‡(2R, 1S) − (2S, 1R).
§(2R, 1R) − (2S, 1S).

The efficiency of cyclopropanation using resting *Escherichia coli* [BL21(DE3)] cells grown in M9Y media [M9, 1.5% yeast extract] expressing variant 9-10A-TS-F87V-T268A (also called BM3-CIS or P450$_{BM3}$-CIS) and BM3-CIS-C400S (also called ABC-CIS or P411$_{BM3}$-CIS) was next investigated. Addition of glucose under anaerobic conditions significantly increased product yield (FIG. 29), presumably due to enhanced intracellular production of NADH. ABC-CIS catalyzes thousands of turnovers in vivo, is about four times more active than BM3-CIS in whole-cells, and provides the cyclopropane products with enhanced cis-enantioselectivity (Table 43, entries 1 and 2).

TABLE 43

Cyclopropanation activities for intact *E. coli* cells expressing engineered enzymes.

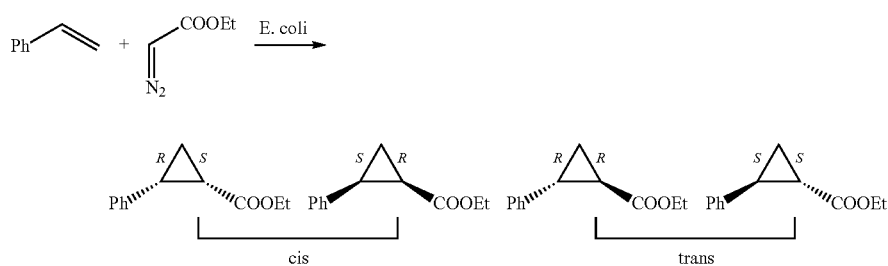

| Entry | Catalyst | [EDA] (mM) | Cell Density (g$_{cdw}$/L) | [P450] (μM) | Yield (%) | TTN | cis:trans | ee$_{cis}$ (%)* | ee$_{trans}$ (%)† |
|---|---|---|---|---|---|---|---|---|---|
| 1 | BM3-CIS (P450$_{BM3}$-CIS) | 8.5 | 7.7 | 3.7 | 42 | 950 | 22:78 | −60 | −22 |
| 2 | ABC-CIS (P411$_{BM3}$-CIS) | 8.5 | 7.7 | 1.3 | 55 | 3,700 | 76:24 | −96 | −25 |
| 3 | ABC-CIS$_{heme}$ (P411$_{BM3-heme}$-CIS) | 8.5 | 7.7 | 3.6 | 67 | 1,600 | 71:29 | −95 | −17 |
| 4 | BM3 (P450$_{BM3}$) | 8.5 | 13.4 | 4.8 | 0.9 | 15 | 25:75 | −24 | −21 |
| 5 | ABC (P411$_{BM3}$) | 8.5 | 8.1 | 1.5 | 50 | 2,900 | 13:87 | −12 | −8 |
| 6 | ABC-CIS (P411$_{BM3}$-CIS) + CO | 8.5 | 8.4 | 1.8 | 0.6 | 30 | 20:80 | −35 | −20 |
| 7 | ABC-CIS (P411$_{BM3}$-CIS)‡ | 170 | 8.4 | 1.8 | 72 | 67,800 | 90:10 | −99 | −43 |

TABLE 43-continued

| 8 | ABC-CIS (P411$_{BM3}$-CIS)[‡] | 200 | 20 | 3.2 | 78[§] | 48,800 | 88:12 | −99 | −35 |

P411$_{BM3}$ = P450$_{BM3}$-C400S.
Reaction conditions were as follows: 2 eq styrene, 1 eq EDA, 0.2 eq glucose, *E. coli* whole-cells in aqueous nitrogen-free M9 minimal medium and 5% MeOH cosolvent under anaerobic conditions for twelve hours at 298K.
Yields, diastereomeric ratios, and enantiomeric excess were determined by GC analysis.
Yields based on EDA.
TTN = total turnover number.
*(2R,1S) − (2S,1R).
[†](2R,1R) − (2S,1S).
[‡]Neat reagents were used without addition of MeOH; reactions were left for 24 h.
[§]Isolated yield (1.63 g cyclopropanes).
The data represent the averages of triplicate experiments.
Standard errors are within 20% of the reported average.

The C400S mutation compromises protein expression such that ABC-CIS accounts for 2% of dry cell mass compared to 6% for BM3-CIS. The reduced expression is not due to decreased protein stability, as C400S contributes to increased thermostability in the purified ABC-CIS heme domain (ABC-CIS$_{heme}$, FIG. 30). The holo enzyme, which contains both heme and diflavin reductase domains, is over two times more active on a molar basis than the heme domain alone (Table 43, entry 3), confirming that reduction to the ferrous state in vivo is important, but also showing that the reducing intracellular environment achieves heme reduction even in the absence of the reductase domain. The C400S mutation (ABC) improves the in vivo cyclopropanation activity of BM3 by over two orders of magnitude (Table 43, entries 4 and 5). Purified ABC is also an efficient NADH-driven cyclopropanation catalyst in vitro, whereas BM3 is barely active (Table 44).

TABLE 44

In vitro cyclopropanation activities of BM3 and ABC driven by NADH.

Ph–CH=CH$_2$ + N$_2$=CHCOOEt
30 mM        10 mM

Catalyst + NADH  →  0.1M KPi pH 8.0, 5% MeOH
10 μM        1.6 mM
0.1% mol eq
(wrt EDA)

Products: cis and trans cyclopropanes (Ph, COOEt)

| Catalyst | Yield (%)* | TTN | cis:trans[†] | % ee cis[‡] | % ee trans[§] |
|---|---|---|---|---|---|
| BM3 (P450$_{BM3}$) | 0.2 | 2 ± 0.5 | 17:83 | −29 | −21 |
| ABC (P411$_{BM3}$) | 36 | 364 ± 50 | 12:88 | −5 | −1 |

*Based on EDA.
[†]Diastereomeric ratios and enantiomeric excess were determined by GC analysis.
[‡](2R,1S) − (2S,1R).
[§](2R,1R) − (2S,1S).
Small-scale (500 μL) reactions were conducted as described herein with purified P450$_{BM3}$ and P411$_{BM3}$ catalysts.
Measurements were taken in triplicate and the error bars represent the standard deviation from the mean value.

Both ABC-CIS and BM3-CIS whole cells are significantly inhibited by dioxygen (FIG. 31). Whole-cells containing the ABC-CIS gene but with no induction and whole cells devoid of the ABC-CIS gene are able to form small amounts of cyclopropanes, but do so with stereoselectivity similar to that of free hemin (FIG. 32) since free hemin and other heme proteins present in cells are also able to catalyze styrene cyclopropanation at low levels (P. S. Coelho et al., *Science* 339, 307 (2013)). Whole-cell ABC-CIS catalysts are as stereoselective as purified ABC-CIS in vitro at equivalent catalyst loading (vide infra), demonstrating that the overexpressed P411 enzyme favorably outcompetes background catalysis. In vivo cyclopropanation is strongly inhibited by carbon monoxide (Table 43, entry 6), which irreversibly binds ferrous heme, confirming that catalysis occurs in the enzyme active site. Yields could be increased to 80% by increasing the cell density up to OD$_{600}$=50 (FIG. 33). Reaction yield was only slightly improved by using excess styrene (FIG. 14). Lysate of cells expressing ABC-CIS and with NADH added retain only about 30% of the activity of the intact whole-cells and are not active in the absence of exogenous reductant (Table 45).

TABLE 45

Lysate activity compared to in vivo activity.

| Catalyst | Conditions | [P411] (μM) | Yield (%)* | TTN | cis: trans[†] | % ee cis[‡] |
|---|---|---|---|---|---|---|
| ABC-CIS (P411$_{BM3}$-CIS) | In vivo | 1.0 | 44 | 5120 | 80:20 | −96 |
| ABC-CIS (P411$_{BM3}$-CIS) | Lysate, no reductant | 1.0 | 0.6 | 55 | 67:33 | −92 |
| ABC-CIS (P411$_{BM3}$-CIS) | Lysate + NADH | 1.0 | 18 | 1780 | 80:20 | −97 |
| ABC-CIS (P411$_{BM3}$-CIS) | Lysate + dithionite | 1.0 | 0.8 | 79 | 64:36 | −86 |

*Based on EDA.
[†]Diastereomeric ratios and enantiomeric excess were determined by GC analysis.
[‡](2R, 1S) − (2S, 1R).

Addition of dithionite inhibited ABC-CIS whole-cell reactions and was less efficient than NADH in driving the reaction in cell lysate (FIG. 15 and Table 45).

Figure 34:
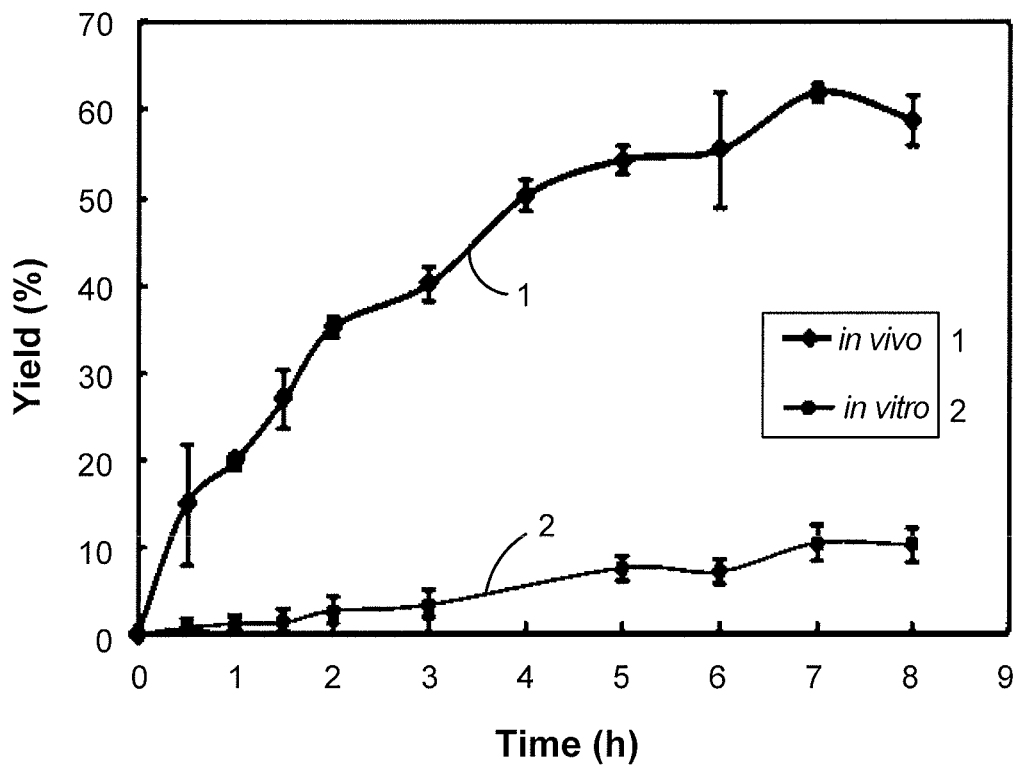
FIG. 34 illustrates the time-course for in vivo and in vitro ABC-CIS (P411$_{BM3}$-CIS)-catalyzed reaction at P411 loading of 1.6 μM [$\epsilon_{411-490}$=103 cm$^{-1}$ for the ferrous-CO complex (K. P. Vatsis et al., J. Inorg. Biochem. 91, 542 (2002))]. Reaction conditions were as follows: 40 mM styrene, 20 mM EDA, 2 mM glucose, 10.2 g$_{cdw}$ L$^{-1}$ whole-cell ABC-CIS (in vivo), 1.6 μM purified ABC-CIS (in vitro) in aqueous nitrogen-free M9 minimal medium and 5% MeOH cosolvent under anaerobic conditions at 298 K. Yields at each time point are reported as averages of two independent reactions.

In order to provide a direct comparison of enzyme activity in vivo versus in vitro, both reactions were monitored at the same enzyme concentration over 8 hours (FIG. 34). On a molar basis, the in vivo catalyst showed almost 6 times higher TTN than the purified enzyme after 8 hours and retained the same stereoselectivity (75:25 cis:trans, −95% ee$_{cis}$). Both catalysts remained active over 6 hrs, indicating that the observed differences in yield and TTN are due to improved activity rather than enhanced catalyst stability in vivo. Gradual addition of EDA did not improve the reaction yield.

At high substrate loading (170 mM EDA, 400 mM styrene, added as neat reagents), more than 60,000 catalytic turnovers were observed in the in vivo reaction with ABC-CIS (Table 43, entry 7). ABC-CIS whole-cell reactions are readily scalable to make gram quantities of cyclopropanes with high stereoselectivity, product titer (27 g $L^{-1}$) and yield (78%, Table 46). No organic cosolvents are necessary, and the cyclopropane products can be readily obtained by extraction with organic solvent at the end of the reaction. Furthermore, the cells can be lyophilized with a cryoprotectant such as sucrose and stored as a powder for weeks at 4° C. without degradation of catalytic activity or diastereo- and enantioselectivity (Table 47).

bolic pathways to complement nature's existing strategies for making cyclopropanes (L. A. Wessjohann et al., Chem. Rev. 103, 1625 (2003).

This concept has been demonstrated for a single P450 enzyme, from Bacillus megaterium, and for chimeras of the B. megaterium enzyme with other, related P450s from B. subtilis. Those of skill in the art, however, will recognize that other P450s from other organisms can be engineered to carry out cyclopropanation and ABC whole-cell catalysts can be made using those enzymes. In particular, the equivalent of the C400S mutation will improve the performance of other P450 enzymes for cyclopropanation and other carbene transfer reactions. One of skill in the art knows how to identify the equivalent residue to C400 in other P450s, based on sequence alignments, an example of which is given below. Methods

TABLE 46

Cyclopropanation activities for intact E. coli cells expressing ABC-CIS (P411$_{BM3}$-CIS).

| $c_{(substrate)}$ [mM] | $c_{(carbene)}$ [mM] | $c_{(cells)}$ [g/L] | $c_{(product)}$ [mM] | $c_{(product)}$ [g/L] | Yield[1] [%] | time [h] | vol. productivity [g/L/h] | sp. Productivity [g/g/h] |
|---|---|---|---|---|---|---|---|---|
| 400 | 170 | 20 | 142 | 27 | 84% | 12[2] | 2.3[2] | 0.19[2] |

Reaction conditions are those described in Table 43 except where noted.
[1]Yield is calculated based on carbene conversion.
[2]Reaction was run overnight; actual reaction time may be shorter and hence productivity numbers are the worst possible scenario.

TABLE 47

Cyclopropanation activity of lyophilized ABC-CIS (P411$_{BM3}$-CIS) whole-cell catalysts.

| Catalyst | [Cell density] ($g_{cdw} L^{-1}$) | [P411] (µM) | Yield (%)* | Total Turnover (mmol $g_{cdw}^{-1}$) | TTN | cis: trans[†] | % ee cis[‡] | % ee trans[§] |
|---|---|---|---|---|---|---|---|---|
| ABC-CIS (P411$_{BM3}$-CIS) | 6.0 | 0.8 | 43 | 0.710 ± 0.08 | 5300 ± 600 | 67:33 | −93 | −25 |

*Based on EDA.
[†]Diastereomeric ratios and enantiomeric excess were determined by GC analysis.
[‡](2R, 1S) − (2S, 1R).
[§](2R, 1R) − (2S, 1S).
Cells were lyophilized in 10% sucrose (m/V) and were stored at 4° C. for two weeks. An appropriate mass of the resulting powder was transferred to a 2 mL glass vial, which was crimp sealed and purged with argon. Degassed solutions of nitrogen-free M9 medium and glucose (20 mM) were added via syringe. Cells were resuspended to OD$_{600}$ = 25 and 2 mM final concentration of glucose. Measurements were taken in triplicate and the error bars represent the standard deviation from the mean value.

The lyophilized cells can be readily packaged and distributed. These features render the whole cell process attractive for facile benchtop synthesis.

ABC catalysts based on a Ser-ligated cytochrome-P411 are spectroscopically, electrochemically and catalytically distinct from cytochrome P450s. Whole-cell ABC catalysts are easy to use and deliver high conversion, optical purity and yield for substrate input in the tens of grams per liter. The ability to catalyze this non-natural C—C bond forming reaction in vivo expands the scope of transformations accessible to microbial organic synthesis and provides artificial metaknown in the art, such as site-directed mutagenesis or gene synthesis, can be used to alter this residue to serine in any P450. If the resulting enzyme folds properly, it will serve as a catalyst for cyclopropanation. This mutation in a purified protein or whole cell catalyst will improve the activity over the parent enzyme that does not include this mutation.

For example, BLAST alignment (http://blast.ncbi.nlm.nih.gov/Blast.cgi) of the amino acid sequence of P450$_{BM3}$ (CYP102A1) to other P450s, such as the one from Pseudomonas putida (CYP101A1, P450$_{CAM}$) or the mammalian enzyme from Oryctolagus cuniculus (CYP2B4), enables identification of the proximal cysteine residue or of the equivalent T268 (marked in bold), as shown below (SEQ ID NOS:61-69):

```
CYP102A1  380  ENPSAIPQH--------AFKPFGNGQRACIGQQFALHEATLVL                         414
               E  +A P H          +    FG+G   C+GQ   A  E   + L
CYP101A1  329  ERENACPMHVDFSRQKVSHTTFGHGSHLCLGQHLARREIIVTL                         371

CYP102A1  265  GHETTSGLLSFALYFLVKNPHVLQKAAEEAARVLVDPVPSYKQVKQLKYVGMVLNEALRL        324
               G  +T      LSF++  FL K+P    Q+   E    R       +P+              E LR
CYP101A1  249  GLDTVVNFLSFSMEFLAKSPEHRQELIERPER-----IPA------------ACEELLR-       290

CYP102A1  374  FRPERF--ENPSAIPQHAFKPFGNGQRACIGQQFALHEATLVLGMMLKHFD                 422
               F P F   N +      F PF  G+R C+G+   A E   L       +L++F
CYP2B4    408  FNPGHFLDANGALKRNEGFMPFSLGKRVCLGEGIARTELFLFFTTILQNFS                 458

CYP102A1  257  QIITFLIAGHETTSGLLSFALYFLVKNPHVLQKAAEEAARVL-VDPVPSYKQVKQLKYVG        315
               +++      AG ETTS  L  +    ++K PHV ++   +E   +V+    P+        ++ Y
CYP2B4    291  TVLSLFFAGTETTSTTLRYGFLLMLKYPHVTERVQKEIEQVIGSHRPPALDDRAKMPYTD        350
```

Therefore, the mutations C357S and T252A in CYP101A1 or C436S and T302A in CYP2B4 are expected to enhance the cyclopropanation activity in these enzymes. The mutation can be introduced into the target gene by using standard cloning techniques or by gene synthesis. The mutated gene can be expressed in the appropriate microbial host under the control of an inducible promoter or by means of chromosomal integration under the control of a constitutive promoter. Cyclopropanation activity can be screened in vivo or in vitro by following product formation by GC or HPLC (see, Materials and Methods).

Because the ABC catalyst is genetically encoded and functions very well in whole cells, this catalyst can be incorporated into multi-enzyme pathways for biological synthesis in vivo, where multiple transformations of a substrate are carried out inside the cell. In particular embodiments, the EDA or other diazo reagent is provided exogenously to the medium and/or generated in situ.

The ability to extend the C400S mutation to other P450 scaffolds provides access to a variety of diazo compounds as carbenoid precursors. These include, but are not limited to, diazo esters (acceptor type), diazo β-keto ester or β-cyano esters (acceptor-acceptor type), and alkyl, aryl, or alkenyl substituted diazo esters (donor-acceptor) (FIG. 17A). These diazo compounds can be reacted inter- and intramolecularly with a variety of styrenes, aliphatic olefins, and allenes to provide biologically active compounds or organic building blocks for further reaction (FIG. 17B). For instance, P450 catalyzed reaction of a diazo ester with aryl or allylic silanes and boronic acids would form cyclopropanes that can then be used in Suzuki or Hiyama cross coupling reactions. Furthermore, cyclopropanation of geranylacetone at the C9 olefin by a trans selective P450 catalyst and EDA provides a key precursor to anthroplalone and noranthroplone, marine natural products that exhibit microgram cytotoxicity against B-16 melanoma cells (FIG. 17C). Lastly, treatment of 2,5-dimethylhexα-2,4-diene with a similar catalyst and EDA provides the ethyl ester of chrysanthemic acid, an important intermediate in the production of pyrethroid insecticides (FIG. 17D).

Materials and Methods

Unless otherwise noted, all chemicals and reagents for chemical reactions were obtained from commercial suppliers (Sigma-Aldrich, Acros) and used without further purification. Silica gel chromatography purifications were carried out using AMD Silica Gel 60, 230-400 mesh. $^1$H and $^{13}$C NMR spectra were recorded on either a Varian Mercury 300 spectrometer (300 MHz and 75 MHz, respectively), or a Varian Inova 500 MHz (500 MHz and 125 MHz, respectively), and are internally referenced to residual solvent peak. Data for $^1$H NMR are reported in the conventional form: chemical shift (δ ppm), multiplicity (s=singlet, d=doublet, t=triplet, q=quartet, m=multiplet, br=broad), coupling constant (Hz), integration. Data for $^{13}$C are reported in terms of chemical shift (δ ppm) and multiplicity. High-resolution mass spectra were obtained with a JEOL JMS-600H High Resolution Mass Spectrometer at the California Institute of Technology Mass Spectral Facility. Reactions were monitored using thin layer chromatography (Merck 60 silica gel plates) using an UV-lamp for visualization.

Gas chromatography (GC) analyses were carried out using a Shimadzu GC-17A gas chromatograph, a FID detector, and an Agilent J&W cyclosil-B column (30 m×0.25 mm, 0.25 μm film) and 2-phenylethanol as an internal standard. Injector temperature=300° C., oven temperature=130° C. for 30 min, pressure=175 kPa. Elution time: cis-cyclopropanes [19.7 min (2R,1S) and 21.0 min (2S,1R)], trans-cyclopropanes [25.8 min (2R,1R) and 26.4 min (2S,1S)]. Cyclopropane product standards for the reaction of ethyl diazoacetate (EDA) with styrene (ethyl 2-phenylcyclopropane-1-carboxylate) and α-methylstyrene (ethyl 2-methyl-2-phenylcyclopropane-1-carboxylate) were prepared as reported (A. Penoni et al., Eur. J. Inorg. Chem. 2003, 1452 (2003)). These standards and enzyme-prepared cyclopropanes demonstrated identical retention times in gas chromatograms when co-injected, confirming product identity. Absolute stereoconfiguration of cyclopropane enantiomers was determined by measuring optical rotation of purified cyclopropane products from preparative bioconversion reactions using enantioselective BM3 variants and referenced to values taken from reference (N. Watanabe et al., Heterocycles 42, 537 (1996)). Authentic P450-catalyzed cyclopropane samples were also prepared as described herein and were characterized by NMR ($^1$H and $^{13}$C) and mass spectrometry.

Plasmids pCWori[BM3] and pET22 were used as cloning vectors. Site-directed mutagenesis was accomplished by standard overlap mutagenesis using primers bearing desired mutations (IDT, San Diego, Calif.). Electrocompetent Escherichia coli cells were prepared following the protocol of Sambrook et al., Molecular cloning: a laboratory manual. (Cold Spring Harbor Laboratory Press, New York, 1989), vol. 2. Restriction enzymes BamHI, EcoRI, XhoI, Phusion polymerase, and T4 ligase were purchased from New England Biolabs (NEB, Ipswich, Mass.). Alkaline phosphatase was obtained from Roche (Nutley, N.J.). The 1,000× trace metal mix used in expression cultures contained: 50 mM FeCl$_3$, 20 mM CaCl$_2$, 10 mM MnSO$_4$, 10 mM ZnSO$_4$, 2 mM CoSO$_4$, 2 mM CuCl$_2$, 2 mM NiCl$_2$, 2 mM Na$_2$MoO$_4$, and 2 mM H$_3$BO$_3$.

CO Binding Assay.

P450 concentration was determined from ferrous CO binding difference spectra using extinction coefficients of $\epsilon_{450-490}=91$ mM$^{-1}$ cm$^{-1}$ for cysteine-ligated BM3 (T. Omura, R. Sato, *J. Biol. Chem.* 239, 2370 (1964)) and $\epsilon_{411-490}=103$ mM$^{-1}$ cm$^{-1}$ for serine ligated ABC (K. P. Vatsis et al., *J. Inorg. Biochem.* 91, 542 (2002)).

P450 Expression and Purification.

For in vitro cyclopropanation reactions, BM3 variants were used in purified form. Enzyme batches were prepared as follows. One liter TB$_{amp}$ was inoculated with an overnight culture (100 mL, LB$_{amp}$) of recombinant *E. coli* BL21(DE3) cells harboring a pCWori plasmid encoding the P450 variant under the control of the tac promoter. After 3.5 h of incubation at 37° C. and 250 rpm shaking (OD$_{600}$ ca. 1.8), the incubation temperature was reduced to 25° C. (30 min), and the cultures were induced by adding IPTG to a final concentration of 0.5 mM. The cultures were allowed to continue for another 24 hours at this temperature. After harvesting the cells by centrifugation (4° C., 15 min, 3,000×g), the cell pellet was stored at −20° C. until further use but at least for 2 h. The cell pellet was resuspended in 25 mM Tris.HCl buffer (pH 7.5 at 25° C.) and cells were lysed by sonication (2×1 min, output control 5, 50% duty cycle; Sonicator, Heat Systems—Ultrasonic, Inc.). Cell debris was removed by centrifugation for 20 min at 4° C. and 27,000×g and the supernatant was subjected to anion exchange chromatography on a Q Sepharose column (Hi-Trap™ Q HP, GE Healthcare, Piscataway, N.J.) using an AKTAxpress purifier FPLC system (GE healthcare). The P450 (or P411) was eluted from the Q column by running a gradient from 0 to 0.5 M NaCl over 10 column volumes (P450 elutes at 0.35 M NaCl). The P450 (or P411) fractions were collected and concentrated using a 30 kDa molecular weight cut-off centrifugal filter and buffer-exchanged with 0.1 M phosphate buffer (pH=8.0). The purified protein was flash-frozen on dry ice and stored at −20° C. P450 and P411 concentrations were determined in triplicate using the CO binding assay described above (10 μL P450 and 190 μL 0.1 M phosphate buffer, pH 8.0, per well).

For crystallization experiments, a two-step purification was performed using the AKTAxpress purifier FPLC system. Frozen cell pellets containing expressed, 6×His tagged heme domains were resuspended in Ni-NTA buffer A (25 mM Tris.HCl, 200 mM NaCl, 25 mM imidazole, pH 8.0, 0.5 mL/gcw) and lysed by sonication (2×1 min, output control 5, 50% duty cycle). The lysate was centrifuged at 27,000×g for 20 min at 4° C. to remove cell debris. The collected supernatant was first subjected to a Ni-NTA chromatography step using a Ni sepharose column (HisTrap-HP, GE healthcare, Piscataway, N.J.). The P450 (or P411) was eluted from the Ni sepharose column using 25 mM Tris.HCl, 200 mM NaCl, 300 mM imidazole, pH 8.0. Ni-purified protein was buffer exchanged into 25 mM Tris.HCl pH 7.5 using a 30 kDa molecular weight cut-off centrifugal filter and subsequently loaded onto a Q sepharose column (HiTrap™ Q HP, GE healthcare, Piscataway, N.J.) and purified to homogeneity by anion exchange. The P450 (or P411) was eluted from the Q column by running a gradient from 0 to 0.5 M NaCl over 10 column volumes. P450 (or P411) fractions were collected and buffer exchanged into 25 mM Tris.HCl pH 7.5, 25 mM NaCl. The purified protein was concentrated with a 30 kDa molecular weight cut-off centrifugal filter to approximately 10 mg/mL. 50 μL aliquots were flash frozen on dry ice and stored at −80° C. until needed.

Protein Crystallography.

BM3-CIS and ABC-CIS were crystallized by vapor diffusion. A 1:1 mixture of protein stock (10 mg/mL in 25 mM Tris.HCl pH 7.5, 25 mM NaCl) and mother liquor was combined in 24 well sitting drop plates (Hampton Research). Optimal crystallization conditions for BM3-CIS were found in 0.1 M sodium cacadolyte, pH 5.7, 0.14 MgCl$_2$ and 17% PEG 3350. BM3-CIS crystals typically grew over a span of 7-14 days. ABC-CIS crystals optimally formed in 0.1 M Bis-Tris, pH 5.3, 0.2 M sodium formate and 18% PEG 3350. Initial ABC-CIS drops are marked with a dense layer of protein precipitate; however, after 36-48 hours, noticeable protein crystals were observed underneath the precipitate layer.

X-Ray Data Collection and Protein Structure Determination.

X-ray diffraction data were collected at the General Medical Sciences and Cancer Institutes Structural Biology Facility (GM/CA) at the Advanced Photon Source (APS, Argonne National Laboratory) using beamline ID23-D and a MAR300 CCD detector. Data were collected at 100K and a wavelength 0f 1.033 Å. Data collections statistics are listed in Table 38. Diffraction datasets were integrated with XDS (W. Kabsch, *Acta Crystallogr.* D66, 133 (2010)) and scaled using SCALA (P. Evans, *Acta Crystallogr.* D62, 72 (2006)). Initial phases were determined by molecular replacement against the closed form of wild type BM3$_{heme}$ structure taken from PDB 1JPZ (D. C. Haines et al., *Biochemistry* 40, 13456 (2001)), chain B using MOLREP software (A. Vagin, A. Teplyakov, *J. App. Crystallogr.* 30, 1022 (1997)), a component of the CCP4 crystallography software suite (S. Bailey, *Acta Crystallogr.* D50, 760 (1994)). Refinement was accomplished by iterative cycles of manual model building within COOT (P. Emsley, K. Cowtan, Coot: *Acta Crystallogr.* D60, 2126 (2004)) and automated refinement using REFMAC (G. N. Murshudov, A. A. Vagin, E. J. Dodson, *Acta Crystallogr.* D53, 240 (1997)) within CCP4. Final cycles of REFMAC refinement included TLS parameters. Non-crystallographic symmetry constraints were not used during refinement. Model quality was assessed using the 'complete validation' tool inside of the PHENIX software suite (P. D. Adams et al., *Acta Crystallogr.* D66, 213 (2010)). Simulated annealing omit maps were also calculated using Phenix. Ramachandran outliers generally lie in poorly structured loops connecting BM3 F and G helices. These residues are often missing or marked by poor density in these and other BM3 structures within the protein database. All protein structure figures and alignments were generated using PyMol software (The PyMOL Molecular Graphics System, Version 1.3, Schrödinger, LLC.).

Thermostability Measurements.

Figure 30:
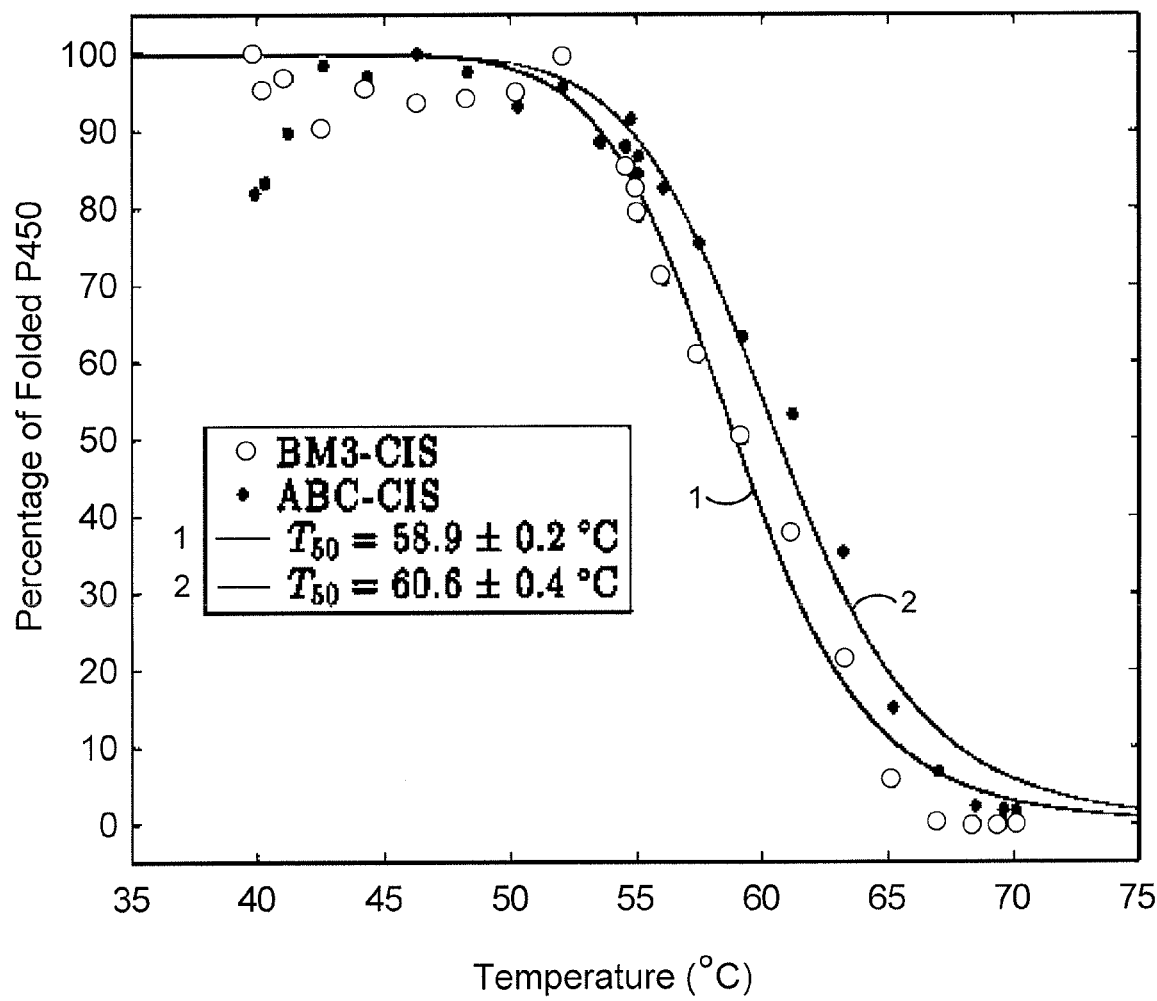
FIG. 30 illustrates the thermostabilities of heme domains of BM3-CIS (P450$_{BM3}$-CIS in blue) and ABC-CIS (P411$_{BM3}$-CIS in red). The C400S mutation stabilizes the heme domain by +1.7° C. The T$_{50}$ is the temperature at which half of the enzyme population has unfolded. Error bars correspond to 1-6 (68.3%) confidence intervals for the T$_{50}$.

Duplicate measurements were taken for all values reported in FIG. 30. Purified P450 (or P411) solutions (4 μM, 200 μL) were heated in a thermocycler (Eppendorf) over a range of temperatures (40° C.-70° C.) for 10 min followed by rapid cooling to 4° C. for 1 min. The precipitate was removed by centrifugation. The concentration of folded P450 (or P411) remaining in the supernatant was measured by CO-difference spectroscopy (as described above). The temperature at which half of the protein was denatured ($T_{50}$) was determined by fitting the data to the equation:

$$f(T) = \frac{100}{1+e^{-a\left(\frac{1}{T}-\frac{1}{T_{50}}\right)}}$$

(J. D. Bloom et al., *Proc. Natl. Acad. Sci. U.S.A.* 103, 5869 (2006)).

Typical Procedure for In Vitro Small-Scale Cyclopropanation Bioconversions Under Anaerobic Conditions.

Small-scale reactions (400 μL) were conducted in 2 mL crimp vials (Agilent Technologies, San Diego, Calif.). P450 solution (80 µL, 100 µM) was added to the vial with a small stir bar before crimp sealing with a silicone septum. Phosphate buffer (260 µL, 0.1 M, pH=8.0) and 40 µl, of a solution of the reductant (100 mM $Na_2S_2O_4$, or 20 mM NADPH) were combined in a larger crimp-sealed vial and degassed by bubbling argon through the solution for at least 5 min (Fig S1). In the meantime, the headspace of the 2 mL reaction vial with the P450 (or P411) solution was made anaerobic by flushing argon over the protein solution (with no bubbling). When multiple reactions were conducted in parallel, up to 8 reaction vials were degassed in series via cannulae. The buffer/reductant solution (300 µL) was syringed into the reaction vial, while under argon. The gas lines were disconnected from the reaction vial before placing the vials on a plate stirrer. A 40× styrene solution in MeOH (10 µL, typically 1.2 M) was added to the reaction vial via a glass syringe, and left to stir for about 30 s. A 40×EDA solution in MeOH was then added (10 µL, typically 400 mM) and the reaction was left stirring for the appropriate time. The final concentrations of the reagents were typically: 30 mM styrene, 10 mM EDA, 10 mM $Na_2S_2O_4$, 20 µM P450.

The reaction was quenched by adding 30 µL HCl (3M) via syringe to the sealed reaction vial. The vials were opened and 20 µL internal standard (20 mM 2-phenylethanol in MeOH) was added followed by 1 mL ethyl acetate. This mixture was transferred to a 1.8 mL eppendorf tube which was vortexed and centrifuged (16,000×g, 1 min). The top organic layer was dried over an anhydrous sodium sulfate plug and analyzed by chiral phase GC.

A slightly modified work-up was implemented for kinetic experiments. The reactions were quenched after the set time by syringing 1 mL EtOAc to the closed vials and immediately vortexing the mixture. The vials were then opened and 20 µL internal standard was added. The mixture was transferred to a 1.8 mL eppendorf tube, vortexed and centrifuged (16,000×g, 1 min). The top organic layer was dried over an anhydrous sodium sulfate plug and analyzed by GC.

Media and Cell Cultures for In Vivo Cyclopropanation.

*E. coli* [BL21(DE3)] cells were grown from glycerol stock overnight (37° C., 250 rpm) in 5 ml M9Y medium (1 L: 31 g $Na_2HPO_4$, 15 g $KH_2PO_4$, 2.5 g NaCl, 5.0 g $NH_4Cl$, 0.24 g $MgSO_4$, 0.01 g $CaCl_2$, 1.5% yeast extract, 1 mL micronutrients, 0.1 mg $mL^{-1}$ ampicillin). The pre-culture was used to inoculate 45 mL of M9Y medium in a 125 mL Erlenmeyer flask and this culture was incubated at 37° C., 250 rpm for 2 h and 30 min. At $OD_{600}$=1.2, the cultures were cooled to 25° C. and the shaking was reduced to 160 rpm before inducing with IPTG (0.25 mM) and δ-aminolevulinic acid (0.25 mM). Cultures were harvested after 20 h and resuspended ($OD_{600}$=30) in nitrogen-free M9 medium (1 L: 31 g $Na_2HPO_4$, 15 g $KH_2PO_4$, 2.5 g NaCl, 0.24 g $MgSO_4$, 0.01 g $CaCl_2$, 1 mL micronutrients). The micronutrient solution contains 0.15 mM $(NH_4)_6MO_7O_{24}$, 20.0 mM $H_3BO_3$, 1.5 mM $CoCl_2$, 0.5 mM $CuSO_4$, 4.0 mM $MnCl_2$, and 0.5 mM $ZnSO_4$. Aliquots of the cell suspension were used for determination of the cell dry weight (cdw, 2 mL) and P450 (or P411) expression level (4 mL).

Small-Scale Whole-Cell Bioconversions.

*E. coli* cells ($OD_{600}$=30, 425 µL) were made anaerobic by bubbling argon through the cell suspension in a crimped 2 mL vial. A degassed solution of glucose (50 µL, 20 mM) was added to the cells before adding EDA (12.5 µl, of a 400 mM solution in MeOH) and olefin (12.5 µL of a 1.2 M solution in MeOH). The reactions were stirred at room temperature for the appropriate time and were worked up by adding 20 µL of the internal standard (20 mM 2-phenylethanol) and extracting with 1 mL ethyl acetate. The organic layer was dried over $Na_2SO_4$ before analyzing the product mixture by chiral phase GC.

Preparative-Scale Whole-Cell Bioconversions.

*E. coli* [BL21(DE3)] cells were grown from glycerol stock overnight (37° C., 250 rpm) in 50 ml M9Y medium. The pre-culture was used to inoculate 2-475 mL of M9Y medium in 2-1 L Erlenmeyer flask (using 25 mL each) and this culture was incubated at 37° C., 250 rpm for 2 h and 30 min. At $OD_{600}$=1.8, the cultures were cooled to 25° C. and the shaking was reduced to 150 rpm before inducing with IPTG (0.25 mM) and δ-aminolevulinic acid (0.25 mM). Cultures were harvested after 24 h and resuspended ($OD_{600}$=75) in nitrogen-free M9 medium. Aliquots of the cell suspension were used for determination of the cell dry weight (cdw, 2 mL) and P450 (or P411) expression level (2 mL). *E. coli* cells ($OD_{600}$=70, 53.6 mL) were made anaerobic by bubbling argon through the cell suspension in a 500 mL sealed round bottom flask. A degassed solution of glucose (1.4 mL, 500 mM) was added to the cells before adding EDA (1.36 mL, 85% EDA in DCM as packaged by Sigma Aldrich) and styrene (2.5 mL, neat). The reaction was stirred at room temperature under positive argon pressure for 24 h. The crude mixture was poured into 3-50 mL conical tubes and the reaction was quenched by the addition of HCl (1 mL, 3 M) to each tube. The aqueous mixtures were extracted with 1:1 EtOAc: hexanes (20 mL each) and centrifuged (5000 rpm, 5 min). The organics were collected and this extraction sequence was performed two more times. The organics were combined, dried over $Na_2SO_4$ then concentrated. Excess styrene was removed via azeotrope with $H_2O$/benzene and 1.85 g of crude product was isolated. Cis/trans selectivity of the reaction was determined via gas chromatography of this crude mixture. Column chromatography of the crude product with 8% $Et_2O$/hexanes afforded the desired products as a mixture of cis and trans isomers (1.63 g combined, 78% yield). Based on comparison of crude and purified yields, the crude product was approximately 88% pure. NMR of the isolated products were identical to those reported in the literature (P. S. Coelho et al., *Science* 339, 307 (2013)).

Time Course of In Vivo and In Vitro Reactions.

Following the procedure for small scale bioconversions, a series of in vivo and in vitro reactions were set up and EDA was added to each sample at time 0 hours. Time points were taken at 0.5, 1, 1.5, 2, 3, 4, 5, 6, 7, and 8 hours. Each reported yield reflects an average of two independent reactions that were allowed to stir for the indicated amount of time. The error bars shown reflect the two unaveraged data points. Yields of each reaction were determined by GC.

Potentiometric Titrations.

Enzyme samples were buffer-exchanged into 100 mM $KPO_4$, 100 mM KCl, pH 7.4, and deoxygenated via 4×20 gentle pump-backfill cycles with argon, with care taken to avoid bubbling. Potentiometric redox titrations were performed in an anaerobic glove box, using a quartz spectroelectrochemical cell with path length of 1 mm, platinum mesh working electrode, platinum wire counter electrode, and a Ag/AgCl electrode (Bioanalytical Systems, Inc.) was used as the reference (Ag/AgCl vs NHE: +197 mV). Protein solutions consisted of approximately 600 µL of 50-100 µM protein with the following mediators added to ensure electrochemical communication between the protein and electrode: methyl viologen (5 µM), benzyl viologen (10 µM) and 2-hydroxy-1, 4-napthaquinone (20 µM). Enzyme samples were titrated using sodium dithionite (reduction) and potassium ferricyanide (re-oxidation). The open circuit potential of the cell was monitored (WaveNow potentiostat, Pine Research Instrumentation) over a 10 minute equilibration period, and spectra were recorded using a Ocean Optics spectrometer (USB2000+). The reduction potentials ($E^{o\prime}$) were determined by fitting the data to the one-electron Nernst equation.

Summary of P450-Derived Cyclopropanation Catalysts.

Mutations in cyclopropanation catalysts are reported with respect to wild-type BM3. The heme domain comprises the first 462 amino acids in the BM3 sequence.
ABC: BM3+C400S
BM3-CIS: V78A, F87V, P142S, T175I, A184V, S226R, H236Q, E252G, T268A A290V, L353V, I366V, E442K
ABC-CIS: BM3-CIS+C400S Rationale for the C400S Mutation.

The very negative $Fe^{III/II}$ potential of cytochromes P450 relative to other heme proteins has been ascribed to the strong donating character of the axial cysteinate ligand. This effect has been modeled in cytochrome c: substitution of the native axial methionine for cysteine decreases the $Fe^{III/II}$ potential by an impressive 652 mV, from 262 mV vs SHE for the Met/His ligated variant to −390 mV vs SHE for the Cys/His variant (A. L. Raphael, H. B. Gray, *J. Am. Chem. Soc.* 113, 1038 (1991)). Even within cytochrome P450, the reduction potential can be further reduced by increasing the electron donating character of the cysteinate ligand. Removal of a single amide proton proposed to stabilize the cysteinate negative charge shifts the $Fe^{III/II}$ potential negative by 35-45 mV with respect to wild-type (S. Yoshioka et al., *J. Am. Chem. Soc.* 124, 14571 (2002)).

In order to facilitate cyclopropanation activity in vivo, it was necessary to shift the reduction potential sufficiently positive to allow reduction by NADPH. In cytochrome c, it was observed that axial ligation by a weakly donating water molecule raises the reduction potential of the His/$H_2O$ ligated variant ($Fe^{III/II}$: −45 mV vs SHE) by 345 mV compared to the Cys/His variant (A. L. Raphael, H. B. Gray, *J. Am. Chem. Soc.* 113, 1038 (1991)). To that end, it was hypothesized that substitution of the P450 cysteinate axial ligand with the weakly donating serine alcohol would shift the C400S reduction potential positive compared to wild-type. The $pK_a$ of serine (~15) is approximately 7 pH units above that of cysteine (~8), and so while cysteine remains deprotonated as the cysteinate ligand in both ferric and ferrous states of the enzyme, serine would remain protonated in at least the ferrous form. The serine-ligated mammalian P450 mutant has been suggested to be serinate in the ferric form, and serine in the ferrous form based on analysis of absorption spectra and magnetic circular dichroism (R. Perera et al., *Arch. Biochem. Biophys.* 507, 119 (2011)), and it was hypothesized that similar ligation in Ser-P450-BM3 would result in a more positive $Fe^{III/II}$ potential.

Supplementary Data
Physical Characterization of the C400S Mutant
X-Ray Crystallography Statistics.

To confirm heme coordination by an axial C400S mutation and to investigate the nature of enhanced stereoselectivity observed in ABC-CIS, crystal structures of both proteins were determined (Table 38) to assess any structural changes that may have occurred due to the axial Cys→Ser mutation. The top panels of FIG. 9 shows alignments of BM3-CIS (green) and ABC-CIS (peach) with left, middle and right panels showing active site residues, the active site I-helix, and global protein fold, respectively. No significant structural changes were observed (RMSD 0.52 Å). FIG. 9, middle panels: Large variations are observed upon comparing BM3-CIS with the open (ligand-free) form of wild type BM3 (purple, taken from PDB#2IJ2, RMSD 1.2 Å). Pronounced rearrangements are observed in active site side chain residues (left) as well as rotations within the I-helix. Global movements are also observed in the N-terminal beta domain as well as F- and G-helices (right, marked by double headed arrows). These movements are consistent with well-known transitions that occur upon substrate binding and are important for native monooxygenation catalysis. FIG. 9, bottom panels: Alignment of BM3-CIS with a ligand-bound BM3 structure (cyan, taken from PDB#1JPZ, RMSD 0.52 Å) demonstrates that BM3-CIS and ABC-CIS mimic the closed protein conformation even in the absence of substrate. Protein aligments were carried out using the align tool of PyMol (PyMOL Molecular Graphics System, Version 1.3 Schrödinger, LLC.).

UV-Vis Spectroscopy

Figure 21:
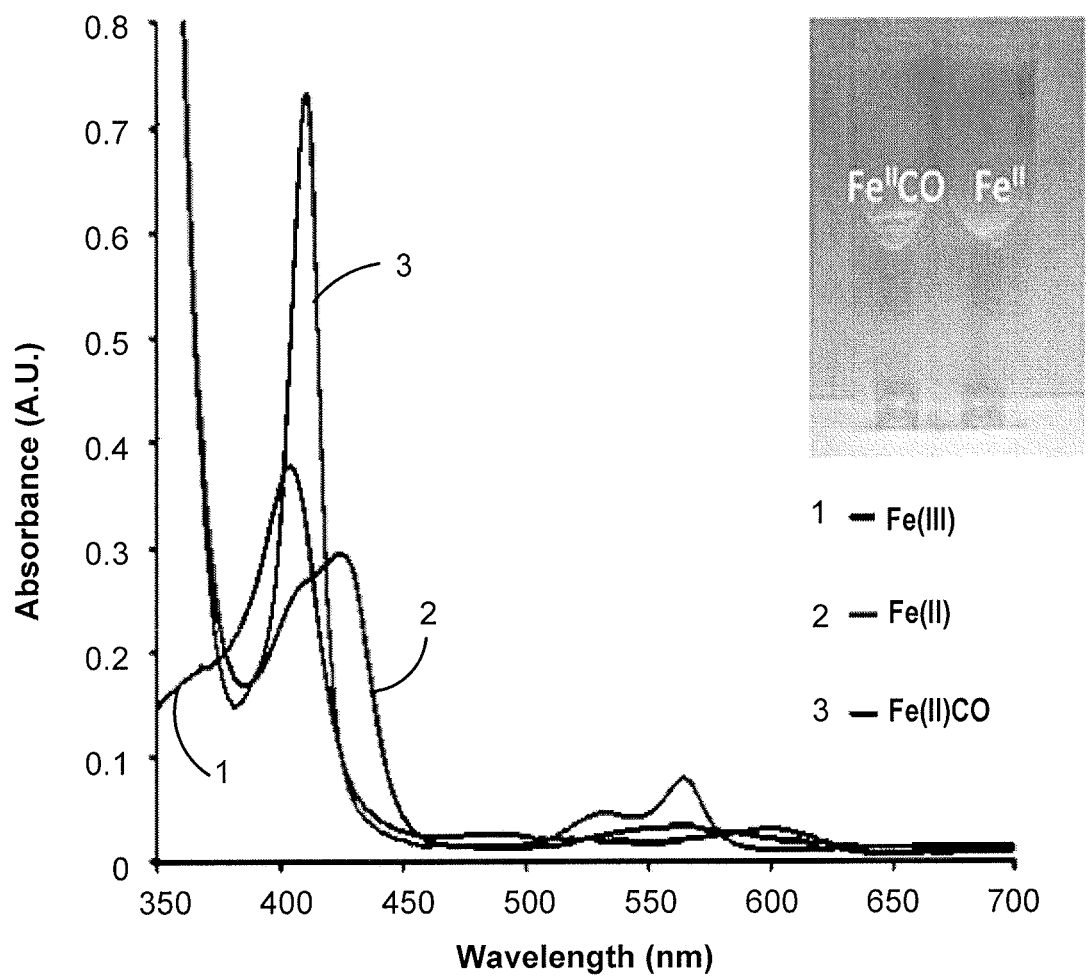
FIG. 21 illustrates the absolute spectra for ferric (blue), dithionite reduced ferrous (red) and carbon monoxide bound ferrous (green) ABC-$CIS_{heme}$. Soret bands (nm): $Fe^{III}$, 404; $Fe^{II}$, 410, 425; $Fe^{II}$-CO, 411. $Fe^{II}$-CO displays α and β bands at 532 and 565 nm. Insert shows the carbon monoxide ferrous (pink) and the dithionite reduced ferrous (yellow) enzymes at 4.5 µM protein concentration.

FIG. 21 illustrates the absolute spectra for ferric (blue), dithionite reduced ferrous (red) and carbon monoxide bound ferrous (green) ABC-CIS$_{heme}$. Soret bands (nm): $Fe^{III}$, 404; $Fe^{II}$, 410, 425; $Fe^{II}$-CO, 411. $Fe^{II}$-CO displays α and β bands at 532 and 565 nm. Insert shows the carbon monoxide ferrous (pink) and the dithionite reduced ferrous (yellow) enzymes at 4.5 µM protein concentration. The shoulder at 410 nm for the ferrous spectrum is due to incomplete reduction to FeII under the aerobic conditions in which these spectra were taken. Reduction of cytochrome P411 under strict anaerobic conditions, as is the case for the redox titrations (FIGS. 25 and 27) gives a single peak at 421 nm.

Figure 22:
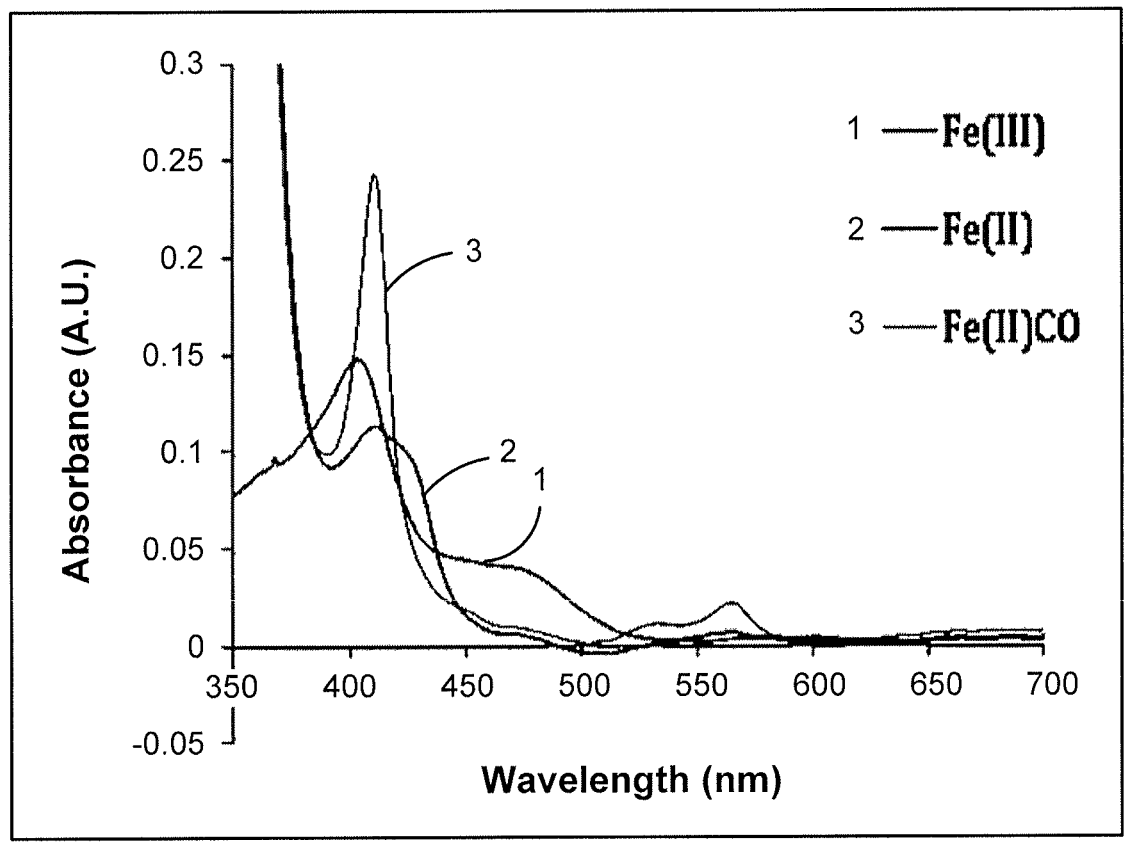
FIG. 22 illustrates the absolute spectra for ferric (blue), dithionite reduced ferrous (red) and carbon monoxide bound ferrous (green) ABC-$CIS_{holo}$. Soret bands (nm): $Fe^{III}$, 404; $Fe^{II}$, 410, 422; $Fe^{II}$-CO, 411. $Fe^{II}$-CO displays α and β bands at 533 and 566 nm. Ferric spectrum displays a broad peak at 465 nm.

FIG. 22 illustrates the absolute spectra for ferric (blue), dithionite reduced ferrous (red) and carbon monoxide bound ferrous (green) ABC-CIS$_{holo}$. Soret bands (nm): $Fe^{III}$, 404; $Fe^{II}$, 410, 422; $Fe^{II}$-CO, 411. $Fe^{II}$-CO displays α and β bands at 533 and 566 nm. Ferric spectrum displays a broad peak at 465 nm.

FIG. 23 illustrates the difference spectra for ferrous carbonyl with respect to ferrous for: (A) ABC-CIS$_{heme}$ and (B) ABC-CIS$_{holo}$.

Redox Titrations

Figure 24:
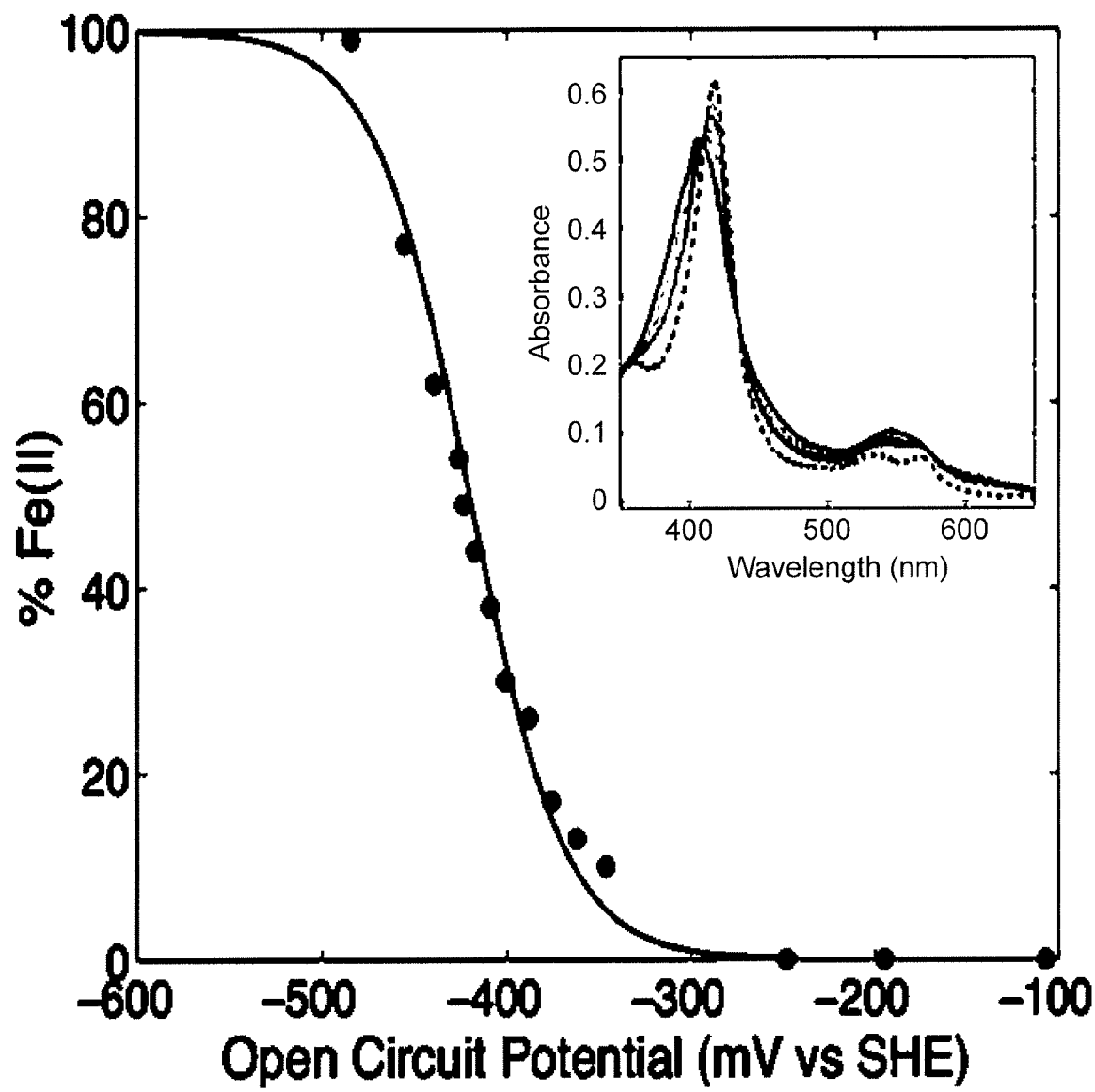
FIG. 24 illustrates the potentiometric redox titration for $P450_{BM3-heme}$ with overlaid Nernst curve fit to $E^{o'}$=~−420 mV. Inset shows spectral changes upon each sub-stoichiometric addition of sodium dithionite (dashed line: fully ferric; solid line: fully ferrous).

FIG. 24 illustrates the potentiometric redox titration for P450$_{BM3-heme}$ with overlaid Nernst curve fit to $E^{o\prime}$=−420 mV. Inset shows spectral changes upon each sub-stoichiometric addition of sodium dithionite (dashed line: fully ferric; solid line: fully ferrous).

Figure 25:
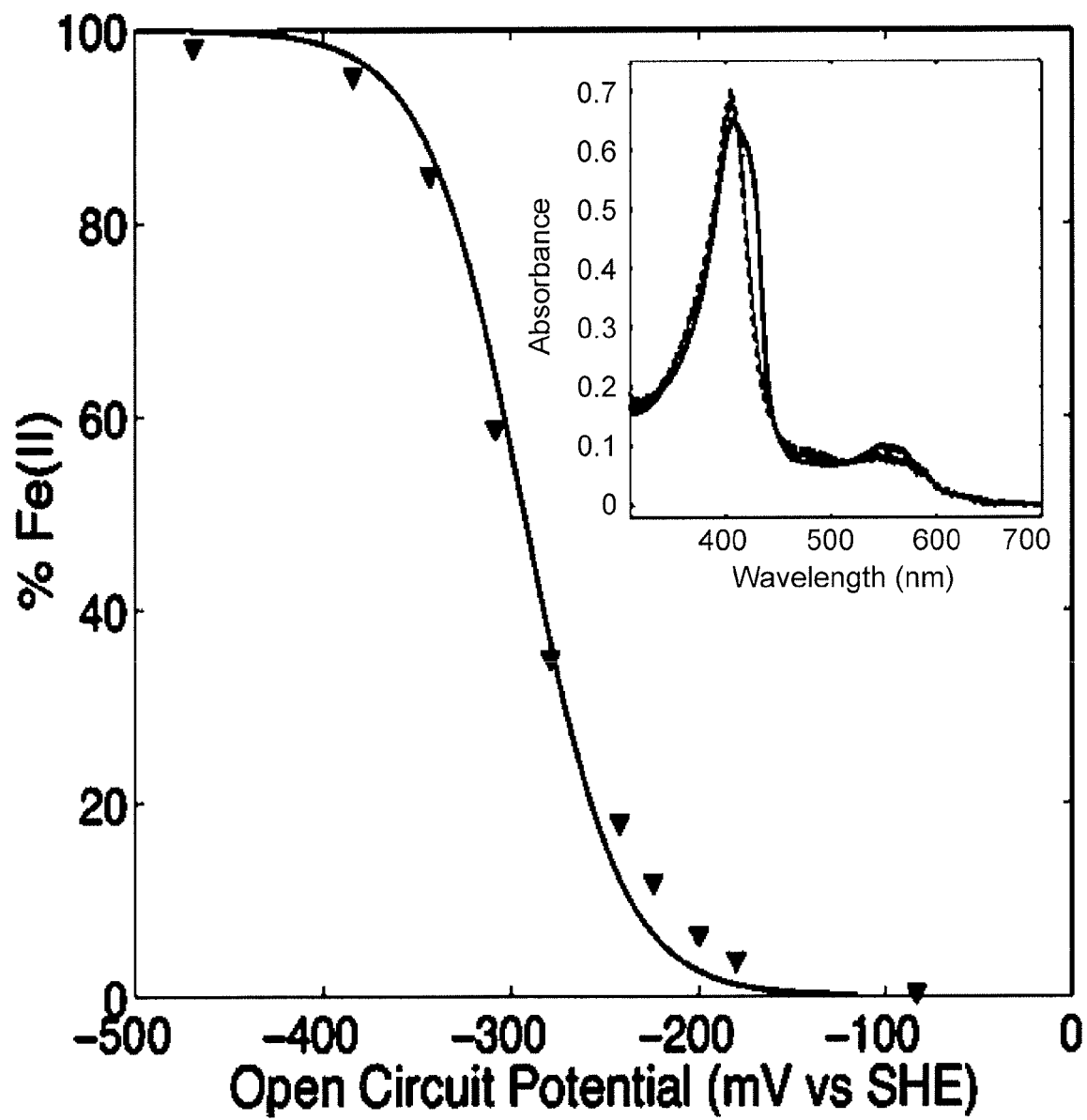
FIG. 25 illustrates the potentiometric redox titration for $P411_{BM3-heme}$ with overlaid Nernst curve fit to $E^{o'}$=−293 mV. Inset shows spectral changes upon each sub-stoichiometric addition of sodium dithionite (dashed line: fully ferric; solid line: fully ferrous).

FIG. 25 illustrates the potentiometric redox titration for P411$_{BM3-heme}$ with overlaid Nernst curve fit to $E^{o\prime}$=−293 mV. Inset shows spectral changes upon each sub-stoichiometric addition of sodium dithionite (dashed line: fully ferric; solid line: fully ferrous).

Figure 26:
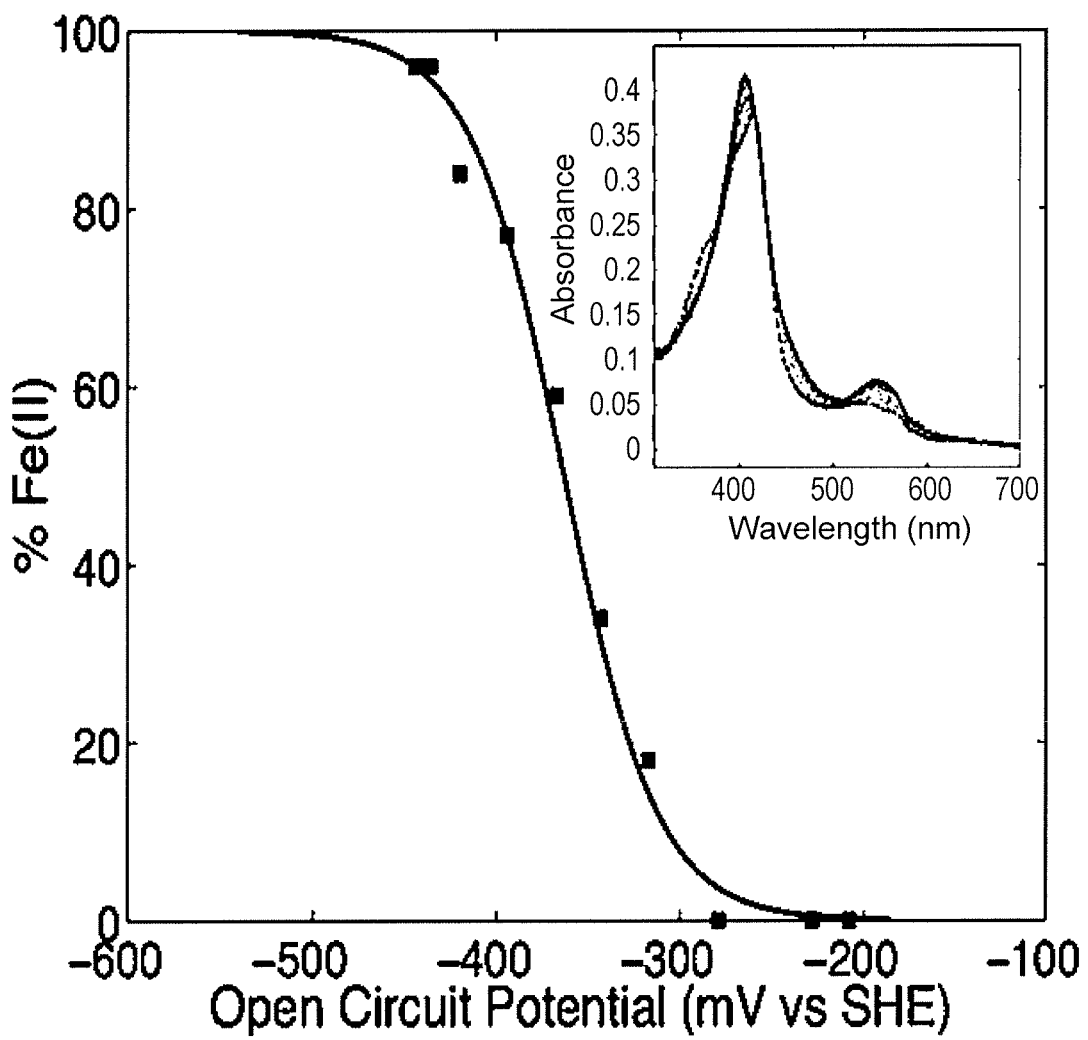
FIG. 26 illustrates the potentiometric redox titration for $P450_{BM3-heme}$-CIS with overlaid Nernst curve fit to $E^{o'}$=−360 mV. Inset shows spectral changes upon each sub-stoichiometric addition of sodium dithionite (dashed line: fully ferric; solid line: fully ferrous).

FIG. 26 illustrates the potentiometric redox titration for P450$_{BM3-heme}$-CIS with overlaid Nernst curve fit to $E^{o\prime}$=−360 mV. Inset shows spectral changes upon each sub-stoichiometric addition of sodium dithionite (dashed line: fully ferric; solid line: fully ferrous).

Figure 27:
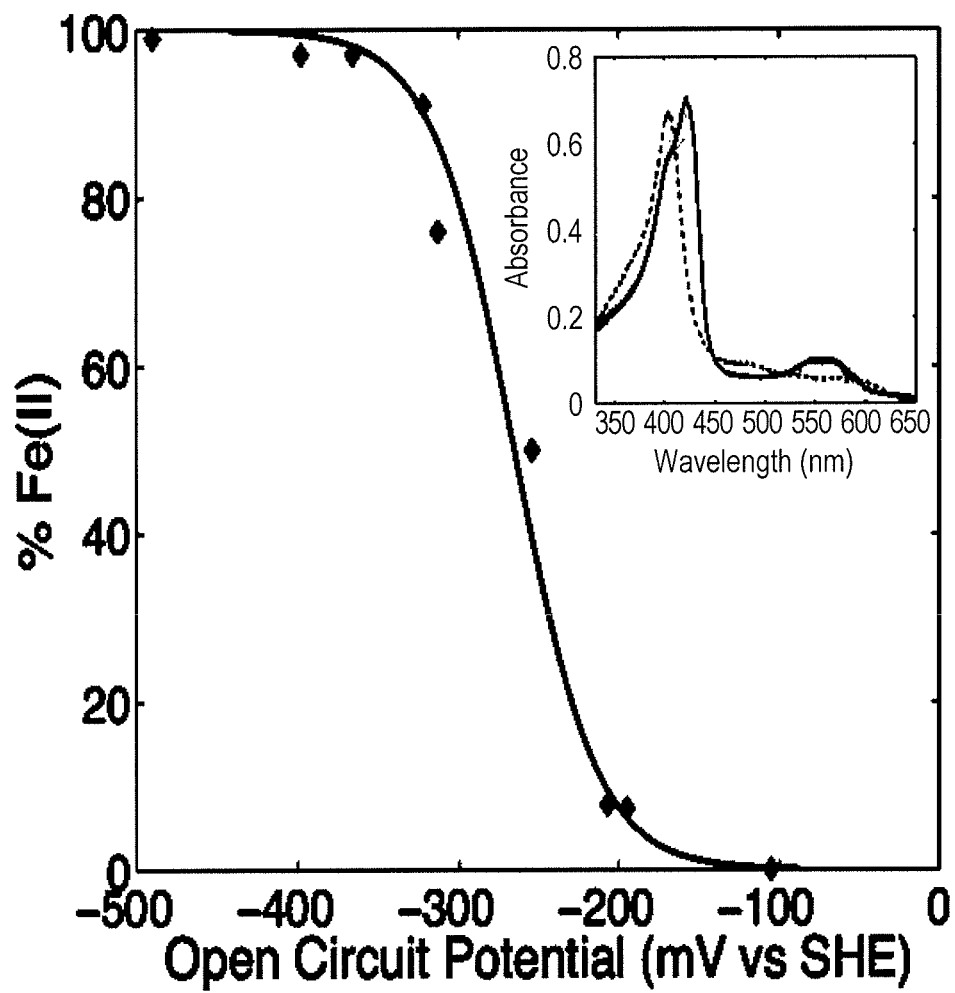
FIG. 27 illustrates the potentiometric redox titration for $P411_{BM3-heme}$-CIS with overlaid Nernst curve fit to $E^{o'}$=−265 mV. Inset shows spectral changes upon each sub-stoichiometric addition of sodium dithionite (dashed line: fully ferric; solid line: fully ferrous).

FIG. 27 illustrates the potentiometric redox titration for P411$_{BM3-heme}$-CIS with overlaid Nernst curve fit to $E^{o\prime}$=−265 mV. Inset shows spectral changes upon each sub-stoichiometric addition of sodium dithionite (dashed line: fully ferric; solid line: fully ferrous).

In vitro Cyclopropanation Activities of ABC-CIS and ABC
Michaelis-Menten Kinetics
Determination of Initial Rates.

Both styrene and EDA concentrations were varied in the presence of the enzymes expressed as the heme-domain (0.5 or 1.0 µM BM3-CIS$_{heme}$). Reactions were set up in phosphate buffer (pH=8.0) with $Na_2S_2O_4$ as the reductant at 298 K, and were worked-up as described above. Three time points were taken and used to determine the rate of product formation by GC (cyclosil-B 30 m×0.32 mm×0.25 µm): oven temperature=100° C. 5 min, 5° C./min to 200° C., 20° C./min to 250° C., 250° C. for 5 min. Elution time: cis-cyclopropanes (19.20 min and 19.33 min), trans-cyclopropanes (20.44 min). Kinetic parameters were determined by fitting the data to the standard Michaelis-Menten model.

Enhanced Cis Selectivity and Substrate Scope

FIG. 28 illustrates the activity under anaerobic vs. aerobic conditions with dithionite for variant 9-10A-TS-F87V-T268A (also called BM3-CIS or P450$_{BM3\text{-}heme}$-CIS) and BM3-CIS-C400S (also called ABC-CIS or P411$_{BM3\text{-}heme}$-CIS).

Small-Scale Reactions.

Selected P450 catalysts were surveyed at a small-scale reaction (400 µL total volume) for each combination of reagents (olefins and diazo esters). The small-scale anaerobic bioconversions were conducted as described above and were analyzed by GC.

GC methods for these products are reported in reference (P. S. Coelho et al *Science* 339, 307 (2013)). Table 41 shows the enhanced Z selectivity for ABC-CIS (P411$_{BM3}$-CIS) over BM3-CIS (P450$_{BM3}$-CIS).

Monooxygenation vs. Cyclopropanation Activities for BM3-CIS and ABC-CIS

Activity Under Anaerobic Vs. Aerobic Conditions with NADPH as the Reductant.

Small-scale reactions (400 µL total volume) were conducted as described above with the following modifications: glucose dehydrogenase (GDH, 4 µL, 225 U mL$^{-1}$) was added to the reaction vial together with the P450 solution. Glucose (40 µL, 250 mM) and NADPH (40 µL, 5 mM) were degassed together with the buffer solution. Measurements were taken in triplicate and the error bars represent the standard deviation from the mean value. Table 36 illustrates in vitro activities for purified P411$_{BM3}$-CIS vs P450$_{BM3}$-CIS driven by NADPH.

Choice of Reductant: NADPH vs NADH

Table 42 illustrates in vitro ABC-CIS$_{holo}$ cyclopropanation driven by Na$_2$S$_2$O$_4$, NADPH and NADH.

In Vitro Cyclopropanation Activities of BM3 and ABC

Small-scale (500 µL) reactions were conducted as described above with purified BM3 and ABC catalysts. Table 44 illustrates in vitro cyclopropanation activities of BM3 and ABC driven by NADH.

Whole-Cell Cyclopropanation Catalysts

All experiments using whole-cells were done in triplicate; the error bars represent the standard deviation of the measurements. 'Total turnovers' is defined herein as the amount of cyclopropane product (mmol) formed per mass of catalyst (g$_{cdw}$).

Effect of Glucose Addition

FIG. 29 illustrates the effect of adding exogenous glucose (2 mM) on olefin cyclopropanation catalyzed by *E. coli* whole cells expressing 9-10A-TS-F87V-T268A (also called BM3-CIS and P450$_{BM3}$-CIS) or BM3-CIS-C400S (also called ABC-CIS and P411$_{BM3}$-CIS).

Effect of C400S on Thermostability

FIG. 30 illustrates thermostabilities of heme domains of BM3-CIS (P450$_{BM3}$-CIS in blue) and ABC-CIS (P411$_{BM3}$-CIS in red). The C400S mutation stabilizes the heme domain by +1.7° C. The T$_{50}$ is the temperature at which half of the enzyme population has unfolded. Error bars correspond to 1-σ (68.3%) confidence intervals for the T$_{50}$.

Anaerobic vs Aerobic Reaction Conditions

FIG. 31 illustrates the effect of dioxygen exposure on whole-cell catalyzed cyclopropanation. ABC-CIS (P411$_{BM3}$-CIS) is strongly inhibited by dioxygen in vivo. All reactions had a cell density equivalent to OD$_{600}$=25. Reactions were conducted in the absence of exogenous glucose. Measurements were taken in triplicate and the error bars represent the standard deviation from the mean value. Product formation is defined as the amount of cyclopropane product (mmol) formed per mass of catalyst (g$_{cdw}$).

Empty Plasmid, No Induction Controls and Dithionite Addition to Whole-Cells

FIG. 32 illustrates empty plasmid, no-induction controls and dithionite addition to whole cells. *E. coli* cells carrying the ABC-CIS (P411$_{BM3}$-CIS) gene but grown without the addition of IPTG (ABC-CIS no induction); *E. coli* cells carrying the pcWori plasmid but not the ABC-CIS gene (empty pcWori); ABC-CIS reaction with the addition of exogenous dithionite instead of glucose (ABC-CIS+dithionite). Reactions were left for two hours at 298 K. Measurements were taken in triplicate and the error bars represent the standard deviation from the mean value. Product formation is defined as the amount of cyclopropane product (mmol) formed per mass of catalyst (g$_{cdw}$).

Effect of Cell Density

FIG. 33 illustrates that increasing cell density increases cyclopropane yields up ~80%. Total turnovers do not increase for cell densities higher than OD$_{600}$=20. Measurements were taken in triplicate and the error bars represent the standard deviation from the mean value. Product formation is defined as the amount of cyclopropane product (mmol) formed per mass of catalyst (g$_{cdw}$).

Effect of Styrene Concentration

FIG. 14 illustrates the effect of using 1, 2, 3, 4 and 5 equivalents of styrene on reaction yield. Excess styrene gives only small improvements in yield.

Lysate Compared to Intact Whole-Cells

Table 45 illustrates lysate activity compared to in vivo activity.

Lyophilization of Whole-Cell Catalysts

Cells were lyophilized in 10% sucrose (m/V) and were stored at 4° C. for two weeks. An appropriate mass of the resulting powder was transferred to a 2 mL glass vial, which was crimp sealed and purged with argon. Degassed solutions of nitrogen-free M9 medium and glucose (20 mM) were added via syringe. Cells were resuspended to OD$_{600}$=25 and 2 mM final concentration of glucose.

Table 47 illustrates the cyclopropanation activity of lyophilized ABC-CIS whole-cell catalysts.

Example 4

A Serine-Substituted P450 Catalyzes Highly Efficient Carbene Transfer to Olefins In Vivo Genetically encoded catalysts for non-natural chemical reactions will open new routes to sustainable production of chemicals. This example illustrates the design of a unique serine-heme ligated cytochrome "P411" that catalyzes efficient and selective carbene transfers from diazoesters to olefins in intact *Escherichia coli* cells. The mutation C400S in cytochrome P450$_{BM3}$ gives a signature ferrous-CO Soret peak at 411 nm, abolishes monooxygenation activity, raises the resting state Fe$^{III/II}$ reduction potential, and significantly improves NAD(P)H-driven cyclopropanation activity.

Introduction

Genetically programmed whole-cell biocatalysts are readily produced in simple growth media, do not require further purification or isolation and can be engineered with biosynthetic pathways for the elaboration of complex molecules (Ajikumar, P. K. et al. *Science* 330, 70-74 (2010); Westfall, P. J. et al. *Proc. Natl. Acad. Sci. U.S.A.* 109, E111-E118 (2012); Kataoka, M. et al. *Appl. Microbiol. Biotechnol.* 62, 437-445 (2003)). The range of accessible transformations, however, is currently limited to the chemical repertoire of natural enzymes. Designing enzymes for non-natural reactions in vivo has been challenging due to the requirements for assembly of the functional catalyst, the compatibility of synthetic reagents in the cellular milieu, and cell permeability to allow substrate influx and product release. The catalysis of non-natural transformations inside cells will enable alternative biosynthetic routes to natural and artificial products, biocatalytic production of chemicals currently made using synthetic reactions, and will expand the chemical toolbox available for in vivo studies of cellular function (Boyce, M. & Bertozzi, C. R. *Nature Methods* 8, 638-642 (2011)).

The preceding examples demonstrate that a few amino acid mutations in a bacterial cytochrome P450 monooxygenase can unlock significant cyclopropanation activity in vitro. Variants of P450$_{BM3}$ from *Bacillus megaterium* catalyze hundreds of turnovers of formal carbene transfers from diazoesters (e.g., ethyl diazoacetate, EDA) to olefins (e.g., styrene) in the presence of a reductant, forming cyclopropane products with high levels of diastereoselectivity and enantioselectivity (Coelho, P. S. et al. *Science* 339, 307-310 (2013)). Olefin cyclopropanation is widely used in the synthesis of fine chemicals (Lebel, H. et al. *Chem. Rev.* 103, 977-1050 (2003)), and state-of-the-art asymmetric organometallic catalysts are able to catalyze thousands to tens of thousands of turnovers (Evans, D. A. et al. *J. Am. Chem. Soc.* 113, 726-728 (1991); Davies, H. M. L. & Venkataramani, C. *Org. Lett.* 5, 1403-1406 (2003); Maas, G. *Chem. Soc. Rev.* 33, 183-190 (2004)). Because P450$_{BM3}$ variants are readily expressed in functional form and can catalyze non-natural carbene transfers without requiring artificial cofactors or posttranslational modifications, this system may be suitable for in vivo catalysis. To initiate the catalytic cycle inside a cell, it is necessary to reduce the enzyme to the catalytically active ferrous-P450 with an endogenous reducing agent such as NAD(P)H. Based on consideration of heme ligation control of the P450 Fe$^{III}$/Fe$^{II}$ reduction potential, genetically encoded cytochrome P411 enzymes have been designed which catalyze efficient and selective olefin cyclopropanation in intact cells.

Results

Cytochrome P450$_{BM3}$-catalyzed cyclopropanations require substoichiometric (with respect to diazoester and olefin) reductant and proceed optimally under anaerobic conditions (Coelho, P. S. et al. *Science* 339, 307-310 (2013)). This suggests that diazoester activation and carbene transfer involve a reduced P450-bound Fe$^{II}$-heme prosthetic group as opposed to the resting state Fe$^{III}$-heme (FIG. 35A). Active cyclopropanation catalysts derived from either full-length P450$_{BM3}$, which contains a catalytic heme domain fused to a NADPH-driven P450-reductase domain, or the isolated heme domain (P450$_{BM3\text{-}heme}$) show marked preference for strong reducing agents such as dithionite (E$^{o\prime}$=−660 mV, all potentials vs SHE) over native NAD(P)H (E$^{o\prime}$=−320 mV) (Coelho, P. S. et al. *Science* 339, 307-310 (2013)). Reduced activity in the presence of NAD(P)H suggests a limited substrate-induced low-spin (E$^{o\prime}$ Fe$^{III/II}$=−430 mV) to high-spin (E$^{o\prime}$ Fe$^{III/II}$=−290 mV) transition of the P450 heme-iron (Ost, T. W. B. et al. *Biochemistry* 40, 13421-13429 (2001)), which, while essential for monooxygenation, may not be achievable in this engineered system due to the poor affinity for the non-natural substrates (K$_M$~5 mM) (Coelho, P. S. et al. *Science* 339, 307-310 (2013)). It was hypothesized that raising the reduction potential of the resting state enzyme to facilitate NAD(P)H-driven reduction would enhance Fe$^{II}$ catalysis in vivo. Aware that the reduction potential of heme proteins can be tuned by axial ligand mutations (Wuttke, D. S. & Gray, H. B. *Curr. Opin. Struct. Biol.* 3, 555-563 (1993); Reedy, C. J. et al. *Nucleic Acids Research* 36, D307-D313 (2008)), it was reasoned that substituting the axial cysteine thiolate in P450$_{BM3}$ with the weakly donating serine alcohol should raise the Fe$^{III/II}$ potential (FIG. 35A). Furthermore, axial cysteinate ligation is essential for dioxygen activation and stabilization of the active ferryl-porphyrin cation radical oxidant (FIG. 1, compound I) during monooxygenation (Dawson, J. H. *Science* 240, 433-439 (1988)), and axial cysteine to serine substitutions have been reported to abolish monooxygenation activity in mammalian P450s (Vatsis, K. P. et al. *J Inorg. Biochem.* 91, 542-553 (2002)). Because free hemin is also a (poor) cyclopropanation catalyst (Coelho, P. S. et al. *Science* 339, 307-310 (2013)), an axial cysteine to serine mutation (C400S in P450$_{BM3}$) would maintain carbene transfer activity while eliminating monooxygenation activity.

The C400S mutation was introduced into a cis-selective cyclopropanation catalyst from the preceding examples, P450$_{BM3}$-CIS (13 mutations from P450$_{BM3}$), to contrast with the trans-selectivity observed with iron-porphyrins (Wolf, J. R. et al. *J. Am. Chem. Soc.* 117, 9194-9199 (1995)). P450$_{BM3}$-CIS catalyzes hundreds of turnovers in the presence of dithionite in vitro and forms the ethyl 2-phenylcyclopropane-1-carboxylate product with 71% cis-selectivity and −94% enantiomeric excess (ee$_{cis}$) (Coelho, P. S. et al. *Science* 339, 307-310 (2013)). UV-vis spectra for the green-brown P450$_{BM3}$-CIS-C400S (P411$_{BM3}$-CIS, FIGS. 21-23), marked by a ferrous carbon monoxide-bound complex at 411 nm, were consistent with those reported for a Ser-ligated mammalian P450 (Vatsis, K. P. et al. *J Inorg. Biochem.* 91, 542-553 (2002); Perera, R. et al. *Arch. Bioch. Bioph.* 507, 119-125 (2011)) (Table 39). Because of this signature Fe$^{II}$-CO band at 411 nm, these new P450-derived Ser-ligated enzymes cytochrome are called "P411s". The C400S P450$_{BM3}$ variants will hereafter be referred to as "P411$_{BM3}$" enzymes. Heme-serine ligation in P411$_{BM3}$-CIS was further confirmed by determining the crystal structures of the P450$_{BM3}$-CIS and P411$_{BM3}$-CIS heme domains at 2.5 and 3.3 Å, respectively (FIG. 9 and Table 38; PDB: 4H23 and 4H24); the structures were superimposable (RMSD=0.52 Å; FIG. 9). Despite the limited resolution of the P411$_{BM3}$-CIS structure, simulated annealing omit maps generated in the absence of modeled heme and C400S showed density consistent with heme coordination by a proximal amino acid side chain (FIG. 35B and FIG. 20).

Potentiometric redox titrations were performed using the truncated heme domains of wild-type P450$_{BM3}$, its C400S variant (P411$_{BM3}$), P450$_{BM3}$-CIS and P411$_{BM3}$-CIS (FIGS. 24-27). The C400S mutation raised the reduction potential of the resting state wild-type P450$_{BM3\text{-}heme}$ by +127 mV (E$^{o\prime}$ Fe$^{III/II}_{ser}$=−293 mV for P411$_{BM3\text{-}heme}$), a shift similar in magnitude to that which occurs in P450$_{BM3}$ upon substrate binding (Ost, T. W. B. et al. *Biochemistry* 40, 13421-13429 (2001)). The 13 amino acid mutations in P450$_{BM3\text{-}heme}$-CIS increased the reduction potential by +60 mV with respect to wild-type P450$_{BM3\text{-}heme}$ (E$^{o\prime}$ Fe$^{III/II}_{cys}$=−360 mV for P450$_{BM3\text{-}heme}$-CIS), but still left P450$_{BM3\text{-}heme}$-CIS with a lower reduction potential than NAD(P)$^+$/NAD(P)H. Introducing the C400S mutation in P450$_{BM3\text{-}heme}$-CIS raised its reduction potential by another +95 mV (E$^{o\prime}$ Fe$^{III/II}_{ser}$=−265 mV for P411$_{BM3\text{-}heme}$-CIS). That the two C400S enzymes have resting state reduction potentials more positive than that of NAD(P)$^+$/NAD(P)H should allow full-length P411s to be reduced by NAD(P)H even in the absence of substrate.

The truncated P411$_{BM3\text{-}heme}$-CIS was an active dithionite-driven cyclopropanation catalyst in vitro, with Michaelis-Menten parameters (k$_{cat}$=82 min$^{-1}$, K$_{M\text{-}styrene}$=4.6 mM, K$_{M\text{-}EDA}$=5.7 mM, FIG. 8), comparable to those of P450$_{BM3\text{-}heme}$-CIS (Table 40). P411$_{BM3\text{-}heme}$-CIS displayed considerably improved diastereo-(cis:trans 93:7) and enantioselectivity (~99% ee$_{cis}$) compared to its cysteine homologue (FIG. 28), an unexpected result given the similar active site geometries of the two catalysts (FIG. 9). For a variety of styrenyl substrates, P411$_{BM3\text{-}heme}$-CIS showed superior cis-selectivity relative to P450$_{BM3\text{-}heme}$-CIS (Table 41). The full-length, reductase-fused P411$_{BM3}$-CIS showed increased activity compared to holo P450$_{BM3}$-CIS when NADPH was used as the reductant under anaerobic conditions (FIG. 35C and Table 36). P450$_{BM3}$-CIS only formed small amounts of cyclopropanes when NADPH was used, and formed styrene oxide, via monooxygenation, as the major product under aerobic conditions. In contrast, P411$_{BM3}$-CIS produced negligible amounts of styrene oxide, confirming removal of monooxygenase activity, and was still able to form cyclopropanes under aerobic conditions, albeit with lower yields (43 TTN) due to oxygen inhibition (FIG. 35C). Dioxygen inhibition could be due to a two-electron oxidase activity as reported for CYP2B4-C436S (Vatsis, K. P. et al. *J. Inorg. Biochem.* 91, 542-553 (2002)). NADH drove P411$_{BM3}$-CIS-mediated cyclopropanation as efficiently as NADPH (Table 42), indicating that P411$_{BM3}$-CIS should be well suited for in vivo catalysis under anaerobic conditions where NADPH biosynthesis in *E. coli* does not take place. The apparent lack of the substoichiometric cofactor preference for cyclopropanation TTN contrasts with P450$_{BM3}$'s reported specificity for NADPH (Dunford, A. J. et al. *Biochim. Bioph. Acta, Proteins and Proteomics* 1794, 1181-1189 (2009)).

The efficiency of cyclopropanation using resting *Escherichia coli* [BL21(DE3)] cells grown in M9Y media (M9, 1.5% yeast extract) expressing full-length P450$_{BM3}$-CIS and P411$_{BM3}$-CIS was next investigated. Addition of glucose under anaerobic conditions significantly increased product yield (FIG. 29), presumably due to enhanced intracellular production of NADH, although other cellular reductants could also be involved in reducing the enzyme in vivo. P411$_{BM3}$-CIS catalyzed thousands of turnovers in vivo, was about four times more active than P450$_{BM3}$-CIS in the whole-cell system, and provided the cyclopropane products with enhanced cis-enantioselectivity (Table 43, entries 1 and 2). The C400S mutation compromises protein expression such that P411$_{BM3}$-CIS accounts for 2% of dry cell mass compared to 6% for BM3-CIS (entries 1 and 2). The reduced expression was not due to decreased protein stability, as C400S contributed to increased thermostability in the purified P411$_{BM3}$-CIS heme domain (P411$_{BM3\text{-}heme}$-CIS, FIG. 10). Full-length P411$_{BM3}$-CIS (entry 2), which contains both heme and diflavin reductase domains, was over two times more active on a molar basis than the truncated heme domain (P411$_{BM3\text{-}heme}$-CIS, entry 3), confirming that reduction to the ferrous state in vivo was important, but also showing that the reducing intracellular environment achieved heme reduction even in the absence of the reductase domain. The single C400S mutation in P411$_{BM3}$ (entry 4) improved the in vivo cyclopropanation activity of wild-type P450$_{BM3}$ (entry 5) by over two orders of magnitude. Purified full-length P411$_{BM3}$ was also an efficient NADH-driven cyclopropanation catalyst in vitro, whereas P450$_{BM3}$ was barely active (Table 44).

Both P411$_{BM3}$-CIS and P450$_{BM3}$-CIS whole cells were significantly inhibited by dioxygen (FIG. 31). Whole cells containing the P411$_{BM3}$-CIS gene but with no induction and whole cells devoid of the P411$_{BM3}$-CIS gene were able to form small amounts of cyclopropanes, but did so with stereoselectivity similar to that of free hemin (FIG. 32). This is not surprising since free hemin and other heme proteins present in cells are also able to catalyze styrene cyclopropanation at low levels (Coelho, P. S. et al. *Science* 339, 307-310 (2013)). Whole-cell P411$_{BM3}$-CIS catalysts were as stereoselective as purified P411$_{BM3}$-CIS in vitro at equivalent catalyst loading (vide infra), demonstrating that the overexpressed P411 enzyme outcompeted background catalysis. In vivo cyclopropanation was strongly inhibited by carbon monoxide (Table 43, entry 6), which irreversibly binds ferrous heme, confirming that catalysis occurs in the enzyme active site. Yield could be increased to 80% by increasing the cell density up to OD$_{600}$=50 (FIG. 33). Using excess styrene only slightly improved reaction yield (FIG. 14). Lysate of cells expressing full-length P411$_{BM3}$-CIS that were supplemented with NADH retained only about 30% of the activity of the intact whole cells and were not active in the absence of exogenous reductant (Table 45). Addition of dithionite inhibited P411$_{BM3}$-CIS whole-cell reactions and was less efficient than NADH in driving the reaction in cell lysate (FIG. 32 and Table 45).

In order to provide a direct comparison of full-length P411$_{BM3}$-CIS activity in vivo versus in vitro, both reactions were monitored at the same enzyme concentration over 8 hours (FIG. 34). On a molar basis, the in vivo catalyst showed almost 6 times higher TTN than the purified enzyme after 6 hours and retained the same stereoselectivity (75:25 cis:trans, ~95% ee$_{cis}$). Both catalysts remained active over this period, indicating that the observed differences in yield and TTN are due to improved activity rather than enhanced catalyst stability in vivo. Gradual addition of EDA did not improve the reaction yield.

At high substrate loading (170 mM EDA, 400 mM styrene, added as neat reagents), more than 60,000 catalytic turnovers were observed in the in vivo reaction with P411$_{BM3}$-CIS (Table 43, entry 7). P411$_{BM3}$-CIS whole-cell reactions were readily scalable to make gram quantities of cyclopropanes with high stereoselectivity, product titer (27 g L$^{-1}$) and yield (78%, entry 8). No organic cosolvent was necessary, and the cyclopropane products were readily obtained by extraction with organic solvent at the end of the reaction. Furthermore, the cells could be lyophilized with a cryoprotectant such as sucrose and stored as a powder for weeks at 4° C. without degradation of catalytic activity or diastereo- and enantioselectivity (Table 47). Lyophilized cells can be readily packaged and distributed. These features render whole-cell P411 catalysts attractive for facile benchtop synthesis.

Cytochrome P411s are spectroscopically, electrochemically, and catalytically distinct from cytochrome P450s, providing a scaffold for engineering orthogonal heme-enzyme catalysis. Whole-cell catalysts based on serine-heme ligated P411s are easy to use and deliver enzymatic cyclopropanation with high conversion, optical purity and yield for substrate input in the tens of grams per liter. The ability to catalyze this non-natural C—C bond forming reaction in vivo expands the scope of transformations accessible to microbial organic synthesis and provides artificial metabolic pathways to complement nature's existing strategies for making cyclopropanes (Wessjohann, L. A. et al. *Chem. Rev.* 103, 1625-1647 (2003)).

Materials and Methods

All reagents were obtained from commercial suppliers (Sigma-Aldrich) and used without further purification. $^1$H and $^{13}$C NMR spectra were recorded on either a Varian Mercury 300 spectrometer (300 MHz and 75 MHz, respectively), or a Varian Inova 500 MHz (500 MHz and 125 MHz, respectively), and are internally referenced to residual solvent peak. High-resolution mass spectra were obtained with a JEOL JMS-600H High Resolution Mass Spectrometer. Gas chromatography (GC) analyses were carried out using a GC-17A gas chromatograph (Shimadzu), a FID detector, and a J&W cyclosil-B column (30 m×0.25 mm, 0.25 µm film, Agilent) and 2-phenylethanol as an internal standard. Injector temperature=300° C., oven temperature=130° C. for 30 min, pressure=175 kPa. Elution time: cis-cyclopropanes [19.7 min (2R,1S) and 21.0 min (2S,1R)], trans-cyclopropanes [25.8 min (2R,1R) and 26.4 min (2S,1S)]. Cyclopropane product standards for the reaction of ethyl diazoacetate (EDA) with styrene (ethyl 2-phenylcyclopropane-1-carboxylate) and α-methylstyrene (ethyl 2-methyl-2-phenylcyclopropane-1-carboxylate) were prepared as reported (Penoni, A. et al. *Eur. J. Inorg. Chem.*, 1452-1460 (2003)). These standards and enzyme-prepared cyclopropanes demonstrated identical retention times in gas chromatograms when co-injected, confirming product identity. Absolute stereoconfiguration of cyclopropane enantiomers was determined by measuring optical rotation of purified cyclopropane products from preparative bioconversion reactions using enantioselective $P450_{BM3}$ variants and referenced to values taken from reference (Watanabe, N. et al. *Heterocycles* 42, 537-542 (1996)). Authentic P450-catalyzed cyclopropane samples were also prepared and were characterized by NMR ($^1H$ and $^{13}C$) and mass spectrometry, which matched literature values.

Plasmids pCWori[$P450_{BM3}$] and pET22 were used as cloning vectors. The C400S mutation was introduced by standard overlap mutagenesis using primers bearing the desired mutation (IDT, San Diego, Calif.).

```
Forward Primers (SEQ ID NOS: 70 and 71):
HF1:
CAGGAAACAGGATCAGCTTACTCCCC

BM3_C400S_F_nheI:
GAAACGGTCAGCGTGCTAGCATCGGTCAGCAGTTCG

Respective Reverse Primers (SEQ ID NOS: 72 and 73):
BM3_C400S_R_nheI:
CGAACTGCTGACCGATGCTAGCACGCTGACCGTTTC pCWori-Rev:
GCGTATCACGAGGCCCTTTCGTCTTCAAGC
```

Electrocompetent *Escherichia coli* cells were prepared following the protocol of Sambrook et al., *Molecular cloning: a laboratory manual*. Vol. 2 (Cold Spring Harbor Laboratory Press, New York, 1989)). Restriction enzymes BamHI, EcoRI, XhoI, Phusion polymerase, and T4 ligase were purchased from New England Biolabs (NEB, Ipswich, Mass.). Alkaline phosphatase was obtained from Roche (Nutley, N.J.). The 1,000× trace metal mix used in expression cultures contained 50 mM $FeCl_3$, 20 mM $CaCl_2$, 10 mM $MnSO_4$, 10 mM $ZnSO_4$, 2 mM $CoSO_4$, 2 mM $CuCl_2$, 2 mM $NiCl_2$, 2 mM $Na_2MoO_4$, and 2 mM $H_3BO_3$.

CO Binding Assay.

P450 concentration was determined from ferrous CO binding difference spectra using extinction coefficients of $\epsilon_{450-490}=91$ $mM^{-1}$ $cm^{-1}$ for cysteine-ligated $P450_{BM3}$ (Omura, T. & Sato, R. *J. Biol. Chem.* 239, 2370-2378 (1964)) and $\epsilon_{411-490}=103$ $mM^{-1}$ $cm^{-1}$ for serine ligated $P411_{BM3}$ (Vatsis, K. P. et al. *J. Inorg. Biochem.* 91, 542-553 (2002)). The in vivo P450 (or P411) concentration was determined by conducting the CO assay in the lysate of an aliquot of cells in the same cell density as used for the whole-cell reactions.

P450 Expression and Purification.

For in vitro cyclopropanation reactions, $P450_{BM3}$ variants were used in purified form. Enzyme batches were prepared as follows. One liter $TB_{amp}$ was inoculated with an overnight culture (100 mL, $LB_{amp}$) of recombinant *E. coli* BL21(DE3) cells harboring a pCWori plasmid encoding the P450 variant under the control of the tac promoter. After 3.5 h of incubation at 37° C. and 250 rpm shaking ($OD_{600}$ ca. 1.8), the incubation temperature was reduced to 25° C. (30 min), and the cultures were induced by adding IPTG to a final concentration of 0.5 mM. The cultures were allowed to continue for another 24 hours at this temperature. After harvesting the cells by centrifugation (4° C., 15 min, 3,000×g), the cell pellet was stored at −20° C. until further use but at least for 2 h. The cell pellet was resuspended in 25 mM Tris.HCl buffer (pH 7.5 at 25° C.) and cells were lysed by sonication (2×1 min, output control 5, 50% duty cycle; Sonicator, Heat Systems—Ultrasonic, Inc.). Cell debris was removed by centrifugation for 20 min at 4° C. and 27,000×g and the supernatant was subjected to anion exchange chromatography on a Q Sepharose column (HiTrap™ Q HP, GE Healthcare, Piscataway, N.J.) using an AKTAxpress purifier FPLC system (GE healthcare). The P450 (or P411) was eluted from the Q column by running a gradient from 0 to 0.5 M NaCl over 10 column volumes. The P450 (or P411) fractions were collected and concentrated using a 30 kDa molecular weight cutoff centrifugal filter and buffer-exchanged with 0.1 M phosphate buffer (pH=8.0). The purified protein was flash-frozen on dry ice and stored at −20° C.

For crystallization experiments, a two-step purification was performed using the AKTAxpress purifier FPLC system. Frozen cell pellets containing expressed, 6×His tagged heme domains were resuspended in Ni-NTA buffer A (25 mM Tris.HCl, 200 mM NaCl, 25 mM imidazole, pH 8.0, 0.5 mL/gcw) and lysed by sonication (2×1 min, output control 5, 50% duty cycle). The lysate was centrifuged at 27,000×g for 20 min at 4° C. to remove cell debris. The collected supernatant was first subjected to a Ni-NTA chromatography step using a Ni sepharose column (HisTrap-HP, GE healthcare, Piscataway, N.J.). The P450 (or P411) was eluted from the Ni sepharose column using 25 mM Tris.HCl, 200 mM NaCl, 300 mM imidazole, pH 8.0. Ni-purified protein was buffer exchanged into 25 mM Tris.HCl pH 7.5 using a 30 kDa molecular weight cutoff centrifugal filter and subsequently loaded onto a Q sepharose column (HiTrap™ Q HP, GE healthcare, Piscataway, N.J.) and purified to homogeneity by anion exchange. The P450 (or P411) was eluted from the Q column by running a gradient from 0 to 0.5 M NaCl over 10 column volumes. P450 (or P411) fractions were collected and buffer exchanged into 25 mM Tris.HCl pH 7.5, 25 mM NaCl. The purified protein was concentrated with a 30 kDa molecular weight cut-off centrifugal filter to approximately 10 mg $mL^{-1}$. Aliquots (50 μL) were flash frozen on dry ice and stored at −80° C. until needed.

Mutations in cyclopropanation catalysts are reported with respect to wild-type $P450_{BM3}$. The heme domain comprises the first 462 amino acids in the $P450_{BM3}$ sequence. $P411_{BM3}=P450_{BM3}+C400S$. $P450_{BM3}$-CIS=$P450_{BM3}$+V78A, F87V, P142S, T175I, A184V, S226R, H236Q, E252G, T268A A290V, L353V, I366V, E442K. $P411_{BM3}$-CIS=$P450_{BM3}$-CIS+C400S.

Protein Crystallography.

$P450_{BM3-heme}$-CIS and $P411_{BM3-heme}$-CIS were crystallized by vapor diffusion. A 1:1 mixture of protein stock (10 mg/mL in 25 mM Tris.HCl pH 7.5, 25 mM NaCl) and mother liquor was combined in 24 well sitting drop plates (Hampton Research). Optimal crystallization conditions for $P450_{BM3-heme}$-CIS were found in 0.1 M sodium cacadolyte, pH 5.7, 0.14 $MgCl_2$ and 17% PEG 3350. $P450_{BM3-heme}$-CIS crystals typically grew over a span of 7-14 days. $P411_{BM3-heme}$-CIS crystals optimally formed in 0.1 M Bis-Tris, pH 5.3, 0.2 M sodium formate and 18% PEG 3350. Initial $P411_{BM3-heme}$-CIS drops are marked with a dense layer of protein precipitate; however, after 36-48 hours, noticeable protein crystals were observed underneath the precipitate layer.

X-Ray Data Collection and Protein Structure Determination.

X-ray diffraction data were collected at the General Medical Sciences and Cancer Institutes Structural Biology Facility (GM/CA) at the Advanced Photon Source (APS, Argonne National Laboratory) using beamline ID23-D and a MAR300CCD detector. Data were collected at 100K and a wavelength of 1.033 Å. Data collection statistics are listed in Table 38. Diffraction datasets were integrated with XDS (Kabsch, W. *Acta Crystallogr., Sect. D: Biol. Crystallogr.* D 66, 133-144 (2010)) and scaled using SCALA (Evans, P. *Acta Crystallogr., Sect. D: Biol. Crystallogr.* D 62, 72-82 (2006)). Initial phases were determined by molecular replacement against the closed form of wild type P450$_{BM3\text{-}heme}$ structure taken from PDB 1JPZ (Haines, D. C. et al. *Biochemistry* 40, 13456-13465 (2001)), chain B using MOLREP software (Vagin, A. & Teplyakov, A. *Journal of Applied Crystallography* 30, 1022-1025 (1997)), a component of the CCP4 crystallography software suite (Bailey, S. *Acta Crystallogr., Sect. D: Biol. Crystallogr.* D 50, 760-763 (1994)). Refinement was accomplished by iterative cycles of manual model building within COOT (Emsley, P. & Cowtan, K. *Acta Crystallogr., Sect. D: Biol. Crystallogr.* D 60, 2126-2132 (2004)) and automated refinement using REFMAC (Murshudov, G. N. et al. *Acta Crystallogr., Sect. D: Biol. Crystallogr.* D 53, 240-255 (1997)) within CCP4. Final cycles of REFMAC refinement included TLS parameters. Non-crystallographic symmetry constraints were not used during refinement. Model quality was assessed using the 'complete validation' tool inside of the PHENIX software suite (Adams, P. D. et al. *Acta Crystallogr., Sect. D: Biol. Crystallogr.* D 66, 213-221 (2010)). Simulated annealing omit maps were also calculated using Phenix. Ramachandran outliers generally lie in poorly structured loops connecting P450$_{BM3\text{-}heme}$ F and G helices. These residues are often missing or marked by poor density in these and other P450$_{BM3\text{-}heme}$ structures within the protein database. All protein structure figures and alignments were generated using PyMol software (The PyMOL Molecular Graphics System, Version 1.3, Schrödinger, LLC.).

Potentiometric Titrations.

Enzyme samples were buffer-exchanged into 100 mM KPO$_4$, 100 mM KCl, pH 7.4, and deoxygenated via 4×20 gentle pump-backfill cycles with argon, with care taken to avoid bubbling. Potentiometric redox titrations were performed in an anaerobic glove box, using a quartz spectroelectrochemical cell with path length of 1 mm, platinum mesh working electrode, platinum wire counter electrode, and a Ag/AgCl electrode (Bioanalytical Systems, Inc.) was used as the reference (Ag/AgCl vs NHE: +197 mV). Protein solutions consisted of approximately 600 µl of 50-100 µM protein with the following mediators added to ensure electrochemical communication between the protein and electrode: methyl viologen (5 µM), benzyl viologen (10 µM) and 2-hydroxy-1,4-napthaquinone (20 µM). Enzyme samples were titrated using sodium dithionite (reduction) and potassium ferricyanide (re-oxidation). The open circuit potential of the cell was monitored (WaveNow potentiostat, Pine Research Instrumentation) over a 10 minute equilibration period, and spectra were recorded using a Ocean Optics spectrometer (USB2000+). The reduction potentials ($E^{o\prime}$) were determined by fitting the data to the one-electron Nernst equation.

Typical Procedure for In Vitro Small-Scale Cyclopropanation Bioconversions Under Anaerobic Conditions.

Small-scale reactions (400 µL) were conducted in 2 mL crimp vials (Agilent Technologies, San Diego, Calif.). P450 solution (80 µL, 100 µM) was added to the vial with a small stir bar before crimp sealing with a silicone septum. Phosphate buffer (260 µL, 0.1 M, pH=8.0) and 40 µL of a solution of the reductant (100 mM Na$_2$S$_2$O$_4$, or 20 mM NADPH) were combined in a larger crimp-sealed vial and degassed by bubbling argon through the solution for at least 5 mM. In the meantime, the headspace of the 2 mL reaction vial with the P450 (or P411) solution was made anaerobic by flushing argon over the protein solution (with no bubbling). When multiple reactions were conducted in parallel, up to 8 reaction vials were degassed in series via cannulae. The buffer/reductant solution (300 µL) was syringed into the reaction vial, while under argon. The gas lines were disconnected from the reaction vial before placing the vials on a plate stirrer. A 40× styrene solution in MeOH (10 µL, typically 1.2 M) was added to the reaction vial via a glass syringe, and left to stir for about 30 s. A 40×EDA solution in MeOH was then added (10 µL, typically 400 mM) and the reaction was left stirring for the appropriate time. The final concentrations of the reagents were typically: 30 mM styrene, 10 mM EDA, 10 mM Na$_2$S$_2$O$_4$, 20 µM P450. The reaction was quenched by adding 30 µL HCl (3M) via syringe to the sealed reaction vial. The vials were opened and 20 µL internal standard (20 mM 2-phenylethanol in MeOH) was added followed by 1 mL ethyl acetate. This mixture was transferred to a 1.8 mL Eppendorf tube which was vortexed and centrifuged (16,000×g, 1 min). The top organic layer was dried over an anhydrous sodium sulfate plug and analyzed by chiral phase GC.

Determination of Initial Rates.

A slightly modified work-up was implemented for kinetic experiments. The reactions were quenched after the set time by syringing 1 mL EtOAc to the closed vials and immediately vortexing the mixture. The vials were then opened and 20 µL internal standard was added. The mixture was transferred to a 1.8 mL Eppendorf tube, vortexed and centrifuged (16,000×g, 1 min). The top organic layer was dried over an anhydrous sodium sulfate plug and analyzed by GC. Both styrene and EDA concentrations were varied in the presence of the enzymes expressed as the heme-domain (0.5 or 1.0 µM BM3-CIS$_{heme}$). Reactions were set up in phosphate buffer (pH=8.0) with Na$_2$S$_2$O$_4$ as the reductant at 298 K, and were worked-up as described herein. Three time points were taken and used to determine the rate of product formation by GC (cyclosil-B 30 m×0.32 mm×0.25 µm): oven temperature=100° C. 5 min, 5° C./min to 200° C., 20° C./min to 250° C., 250° C. for 5 min. Elution time: cis-cyclopropanes (19.20 min and 19.33 min), trans-cyclopropanes (20.44 min). Apparent kinetic constants were determined by fitting the data to the standard Michaelis-Menten model.

Media and Cell Cultures for In Vivo Cyclopropanation.

*E. coli* [BL21(DE3)] cells were grown from glycerol stock overnight (37° C., 250 rpm) in 5 ml M9Y medium [1 L of 5×M9 medium contains 31 g Na$_2$HPO$_4$, 15 g KH$_2$PO$_4$, 2.5 g NaCl, 5.0 g NH$_4$Cl, 0.24 g MgSO$_4$, and 0.01 g CaCl$_2$. 1 L M9Y contains 200 mL 5×M9, 800 mL deionized water, 15 g yeast extract, 1 mL micronutrients, and 0.1 mg mL$^{-1}$ ampicillin). The pre-culture was used to inoculate 45 mL of M9Y medium in a 125 mL Erlenmeyer flask and this culture was incubated at 37° C., 250 rpm for 2 h and 30 min. At OD$_{600}$=1.2, the cultures were cooled to 25° C. and the shaking was reduced to 160 rpm before inducing with IPTG (0.25 mM) and δ-aminolevulinic acid (0.25 mM). Cultures were harvested after 20 h and resuspended (OD$_{600}$=30) in nitrogen-free M9 medium (1 L: 31 g Na$_2$HPO$_4$, 15 g KH$_2$PO$_4$, 2.5 g NaCl, 0.24 g MgSO$_4$, 0.01 g CaCl$_2$, 1 mL micronutrients). The micronutrient solution contains 0.15 mM (NH$_4$)$_6$Mo$_7$O$_{24}$, 20.0 mM H$_3$BO$_3$, 1.5 mM CoCl$_2$, 0.5 mM CuSO$_4$, 4.0 mM MnCl$_2$, and 0.5 mM ZnSO$_4$. Aliquots of the cell suspension were used for determination of the cell dry weight (cdw, 2 mL) and P450 (or P411) expression level (3 mL).

Small-Scale Whole-Cell Bioconversions.

Reaction conditions were as follows: 2 eq styrene, 1 eq EDA, 0.2 eq glucose, *E. coli* whole-cells in aqueous nitrogen-free M9 minimal medium and 5% MeOH cosolvent under anaerobic conditions for twelve hours at 298 K. *E. coli* cells ($OD_{600}$=30, 425 µL) were made anaerobic by bubbling argon through the cell suspension in a crimped 2 mL vial. A degassed solution of glucose (50 µL, 20 mM) was added to the cells before adding EDA (12.5 µL of a 400 mM solution in MeOH) and olefin (12.5 µL of a 800 mM solution in MeOH). The reactions were stirred at room temperature for the appropriate and were worked up by adding 20 µL of the internal standard (20 mM 2-phenylethanol) and extracting with 1 mL ethyl acetate. The organic layer was dried over $Na_2SO_4$ before analyzing the product mixture by chiral phase GC. Yields, diastereomeric ratios, and enantiomeric excess were determined by GC analysis. Yields based on EDA.

Preparative-Scale Whole-Cell Bioconversions.

*E. coli* [BL21(DE3)] cells were grown from glycerol stock overnight (37° C., 250 rpm) in 50 ml M9Y medium. The pre-culture was used to inoculate two 475 mL of M9Y medium in two 1 L Erlenmeyer flask (using 25 mL each) and this culture was incubated at 37° C., 250 rpm for 2 h and 30 min. At ($OD_{600}$=1.8, the cultures were cooled to 25° C. and the shaking was reduced to 150 rpm before inducing with IPTG (0.25 mM) and δ-aminolevulinic acid (0.25 mM). Cultures were harvested after 24 h and resuspended ($OD_{600}$=75) in nitrogen-free M9 medium. *E. coli* cells ($OD_{600}$=70, 53.6 mL) were made anaerobic by bubbling argon through the cell suspension in a 500 mL sealed round bottom flask. A degassed solution of glucose (1.4 mL, 500 mM) was added to the cells before adding EDA (1.36 mL, 85% EDA in DCM as packaged by Sigma Aldrich) and styrene (2.5 mL, neat). The reaction was stirred at room temperature under positive argon pressure for 24 h. The crude mixture was poured into three 50 mL conical tubes and the reaction was quenched by the addition of HCl (1 mL, 3 M) to each tube. The aqueous mixtures were extracted with 1:1 EtOAc:hexanes (20 mL each) and centrifuged (5000 rpm, 5 min). The organics were collected and this extraction sequence was performed two more times. The organics were combined, dried over $Na_2SO_4$ then concentrated. Excess styrene was removed via azeotrope with $H_2O$/benzene and 1.85 g of crude product was isolated. Cis/trans selectivity of the reaction was determined via gas chromatography of this crude mixture. Column chromatography of the crude product with 8% $Et_2O$/hexanes afforded the desired products as a mixture of cis and trans isomers (1.63 g combined, 78% yield). Based on comparison of crude and purified yields, the crude product was approximately 88% pure. NMR of the isolated products were identical to those reported in the literature (Coelho, P. S. et al. *Science* 339, 307-310 (2013)).

Time Course of In Vivo and In Vitro Reactions.

Following the procedure for small scale bioconversions, a series of in vivo and in vitro reactions were set up and EDA was added to each sample at time 0 hours. Time points were taken at 0.5, 1, 1.5, 2, 3, 4, 5, 6, 7, and 8 hours. Each reported yield reflects an average of two independent reactions that were allowed to stir for the indicated amount of time. The error bars shown reflect the two unaveraged data points. Yields of each reaction were determined by GC.

Thermostability Measurements.

Duplicate measurements were taken for all values reported in FIG. 30. Purified P450 (or P411) solutions (4 µM, 200 µL) were heated in a thermocycler (Eppendorf) over a range of temperatures (40-70° C.) for 10 min followed by rapid cooling to 4° C. for 1 min. The precipitate was removed by centrifugation. The concentration of folded P450 (or P411) remaining in the supernatant was measured by CO-difference spectroscopy. The temperature at which half of the protein was denatured ($T_{50}$) was determined by fitting the data to the equation:

$$f(T) = \frac{100}{1+e^{-a\left(\frac{1}{T}-\frac{1}{T_{50}}\right)}}.$$

Accession Codes:

Atomic coordinates and structure factors have been deposited with the PDB (accession codes: 4H23 and 4H24).

Example 5

Enzymatic Synthesis of Milnacipran and Levomilnacipran

Variants of cytochrome $P450_{BM3}$ (CYP102A1 or BM3) and whole cells expressing these enzymes have previously been used for the cyclopropanation of alpha-substituted styrenes with ethyl diazoacetate (EDA) (Coelho, P. S. et al. *Science* 339:307-310 (2013); Coelho, P. S. et al., *Nat. Chem. Bio.*, 9:485-487 (2013)). This example illustrates the application of this method to the concise and stereoselective synthesis of milnacipran [racemic Z-2-(aminomethyl)-N,N-diethyl-1-phenylcyclopropanecarboxamide] and levomilnacipran [(1S,2R)-milnacipran] via both intermolecular and intramolecular olefin cyclopropanation. This example also illustrates the use of the method described herein to prepare aryl and amide derivatives of levomilnacipran as well as other drugs with similar chemical structure, such as bicifadine and DOV-216,303.

Background

Milnacipran is a drug used to treat major depressive disorder (MDD) and fibromyalgia (a long-lasting condition that may cause pain, muscle stiffness and tenderness, tiredness, and difficulty falling asleep or staying asleep). Milnacipran is a selective serotonin (5-HT) and norepinephrine (NE) reuptake inhibitor (SSNRI) that works by blocking the 5-HT and NE transporters, thus increasing the extracellular levels of these two monoamine neurotransmitters in the brain. Levomilnacipran, the most psychoactive stereoisomer of milnacipran, is currently in phase III clinical trials for the treatment of major depressive disorders.

Several strategies have been developed for the synthesis of milnacipran (Pineiro-Nunez, M. in The Art of Drug Synthesis (ed J. J. Li D. S. Johnson) Ch. 14, 205-207 (Wiley, 2007)). Because the commercial drug is a racemate, the synthetic routes are simply concerned with the relative stereochemistry around the cyclopropane ring. The original synthesis of milnacipran employed an alkylation and epoxide ring-opening sequence starting from 2-phenylacetonitrile and 2-(chloromethyl)oxirane (FIG. 36A) (Bonnaud, B. et al., European Patent No. 0200638B1; Bonnaud, B. et al., *J. Medicinal Chemistry* 30, 318-325 (1987)), which yielded a mixture of Z and E cyclopropanes. Lactonization of the resulting products under thermal conditions yielded key intermediate 1 ((1S, 5R)-1-phenyl-3-oxabicyclo[3.1.0]hexan-2-one), which contained the requisite Z-geometry at stereocenters 1 and 2. This intermediate has been converted to milnacipran using three routes outlined in FIG. 36B. In Route A, phthalimide ring opening yielded 2, which was readily converted to milnacipran after amidation and pthalimide deprotection. In Route B, 1 was opened with hydrobromic acid and treated with thionyl chloride to generate doubly functionalized intermediate 3 (Mouzin, G. et al., Synthesis, 4, 304-305 (1978)). Stepwise treatment with diethylamine and potassium phtalimide generated an intermediate, which was common to the synthesis in Route A. In Route C, direct amide formation using n-BuLi and HNEt$_2$ yielded 4 which could be converted to milnacipran after azide nucleophilic substitution followed by hydrogenation (Shuto, S. et al., J. Med. Chem. 38, 2964-2968 (1995)). FIG. 36C shows an entirely different approach to milnacipran synthesis. The general strategy is based on position selective deprotonation of the commercially available cyclopropane carboxamide 5 (Zhang, M.-X. et al., Angew. Chem. Int. Ed., 41, 2169-2170 (2002)).

Enantioselective syntheses of levomilnacipran have focused on asymmetric methods for formation of the key intermediate 1. FIG. 37A shows the first route which employed a chiral dirhodium(II) tetrakis[methyl 2-oxaazetidine-4(S)-carboxylate], Rh2(4S-MEAZ)$_4$ complex for intramolecular cyclopropanation of 6 and produced 1 in 68% enantioselectivity (Doyle, M. P. et al., Org. Lett. 2, 1145 (2000)). More recently, Alliot et al. prepared 1 from 2-phenylacetic acid using asymmetric alkylation using a chiral tetramine auxiliary (Alliot, J. et al., Chem. Commun. 48, 8111-8113 (2012)) (FIG. 37B). Treatment of the alkylation product with I$_2$ produced a masked halohydrin 7, which underwent esterification and epoxide ring formation under basic conditions. The overall sequence produced 1 in 41% yield and 88% ee.

Results

In certain aspects, this example describes the formal synthesis of levomilnacipran via direct enantioselective cyclopropanation of N,N-diethyl-2-phenylacrylamide by diazoacetonitrile or ethyl diazoacetate (EDA). Selective nitrile hydrogenation or ester to alcohol reduction then provides levomilnacipran or product 8 (FIG. 38), which is converted to levomilnacipran following previously published amination protocols (Alliot, J. et al., Chem. Commun. 48, 8111-8113 (2012)). Alternatively, an intramolecular cyclopropanation route such as the one shown in FIG. 37A is employed for synthesis of intermediate 1 using P450 enzymes. In both strategies, all stereocenters in the final product would be constructed via enzymatic cyclopropanation.

Figure 38:
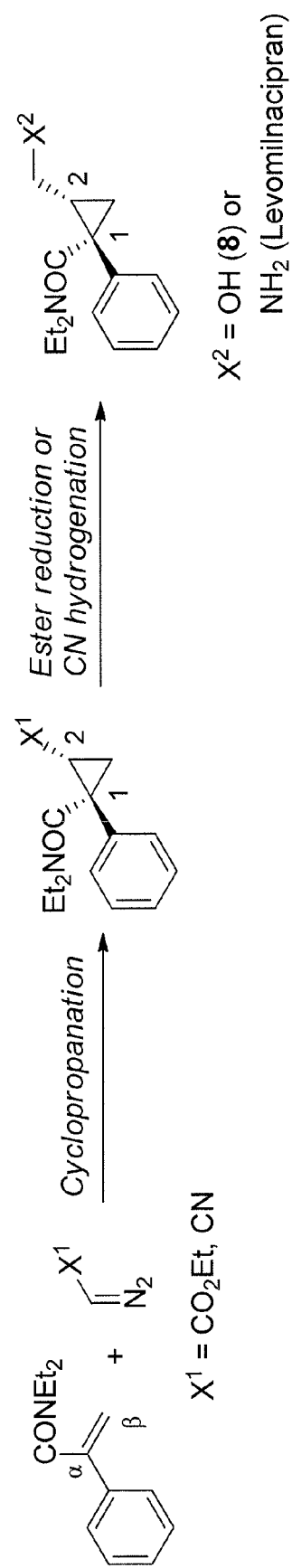
FIG. 38 illustrates the synthesis of levomilnacipran via carbene cyclopropanation by cytochrome P450$_{BM3}$ variants.

These methods are an improvement over previous racemic synthesis because the proposed routes advantageously provide the more psychoactive isomer of milnacipran. Furthermore, the intermolecular route proposed in FIG. 38 is the first route to employ late stage cyclopropanation for synthesis of milnacipran and is highly convergent as the amide moiety is installed prior to cyclopropanation. The intramolecular route is advantageous over previously reported routes because it is concise and enables the use of P450$_{BM3}$ or whole cells expressing these proteins in place of costly rhodium complexes with highly designed synthetic ligands.

The preceding examples show that P450 are excellent catalysts for carbene transfer from diazo compounds to olefins to form cyclopropanes. This reaction has been explored for a variety of substituted olefins and in particular, the present examples show that cyclopropanation can be performed on mono- and disubstituted styrenes. Additionally, functional groups and substitution on the aryl ring of styrene is also well-tolerated by this reaction including electron donating groups such as methoxy and electron withdrawing groups such as trifluoromethyl. This example demonstrates that 1) amide and ester functionalities are compatible with P450-mediated cyclopropanation and 2) significant steric bulk can be tolerated in the alpha position of styrene.

This example shows that P450s are competent catalysts for the cyclopropanation of substituted styrenes of the general form 9, where R=ester or amide. Treatment of the acrylate ester 9a (20 mM) and EDA (8.5 mM) with WT-T268A-C400S (2 mutations from wild-type BM3, herein called P411-T268A, 10 µM, where "P411" denotes the C400S mutation) and sodium dithionite (10 mM) yielded appreciable amounts of the corresponding product 10a. BM3-CIS-C400S (14 mutations from wild-type, herein called P411-CIS) was also able to catalyze the cyclopropanation of the acrylamide 9b, albeit at very low conversions (<1%). A screen of axial mutants at position C400 in BM3-CIS yielded variant BM3-CIS-AxH (where "AxH" denotes a Cys to His substitution in the 400 position of BM3), which exhibited high activity in the reaction of 9b and EDA to provide 10b at 91% yield, 93:7 Z:E diastereoselectivity, and 42% enantioselectivity after 16 h at 25° C. (Table 48).

TABLE 48

P450-screen for cyclopropanation of milnacipran precursors.

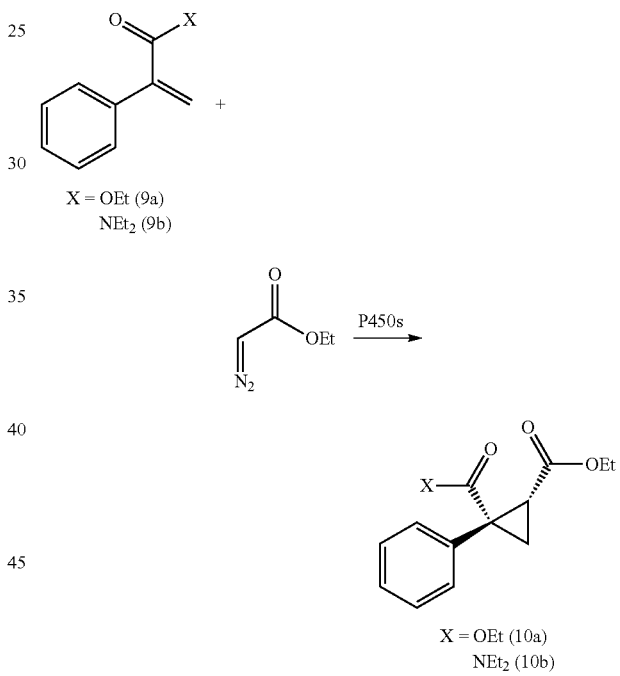

X = OEt (9a)
NEt$_2$ (9b)

X = OEt (10a)
NEt$_2$ (10b)

| Entry | Catalyst | Substrate | Yield (%) | E/Z Ratio |
|---|---|---|---|---|
| 1 | BM3-CIS | 9a | <5 | N/A |
| 2 | P411-T268A | 9a | >80 | 43:57 |
| 3 | P411-T268A | 9b | 1 | N/A |
| 4 | BM3-CIS | 9b | 0 | N/A |
| 5 | P411-CIS | 9b | 0 | N/A |
| 6 | BM3-CIS-AxD | 9b | 44 | 13:87 |
| 7 | BM3-CIS-AxY | 9b | 38 | 16:84 |
| 8 | BM3-CIS-AxK | 9b | 45 | 17:83 |
| 9 | BM3-CIS-AxH | 9b | 91 | 7:93 |
| 10 | BM3-CIS-AxM | 9b | 46 | 17:83 |
| 11 | Hemin | 9b | 3 | 18:82 |

"P411" denotes the C400S mutation and "Ax" denotes a mutation to all other amino acid at the axial position (position 400 in BM3).
Reactions were carried out under anaerobic conditions with 8.5 mM EDA, 20 mM 9a or 10 mM 9b, 10 µM P450, and 10 mM Na$_2$S$_2$O$_4$.

Intact whole cells expressing BM3-CIS-AxH can also be used for the cyclopropanation of 9b. E. coli cells expressing P450 were grown in Hyperbroth then resuspended in nitrogen-free M9 minimal media at pH 7 to $OD_{600}$=30 (7.8 $g_{CDW}$/L). Reaction of 9b and EDA in the presence of these cells and glucose under anaerobic conditions provided 10b in 82% yield. Optimization of BM3-CIS-AxD by site saturation mutagenesis at position T438 yielded BM3-CIS-AxH-T438W, which catalyzed the reaction to 52% yield and 78% enantioselectivity in vivo.

Figure 40:
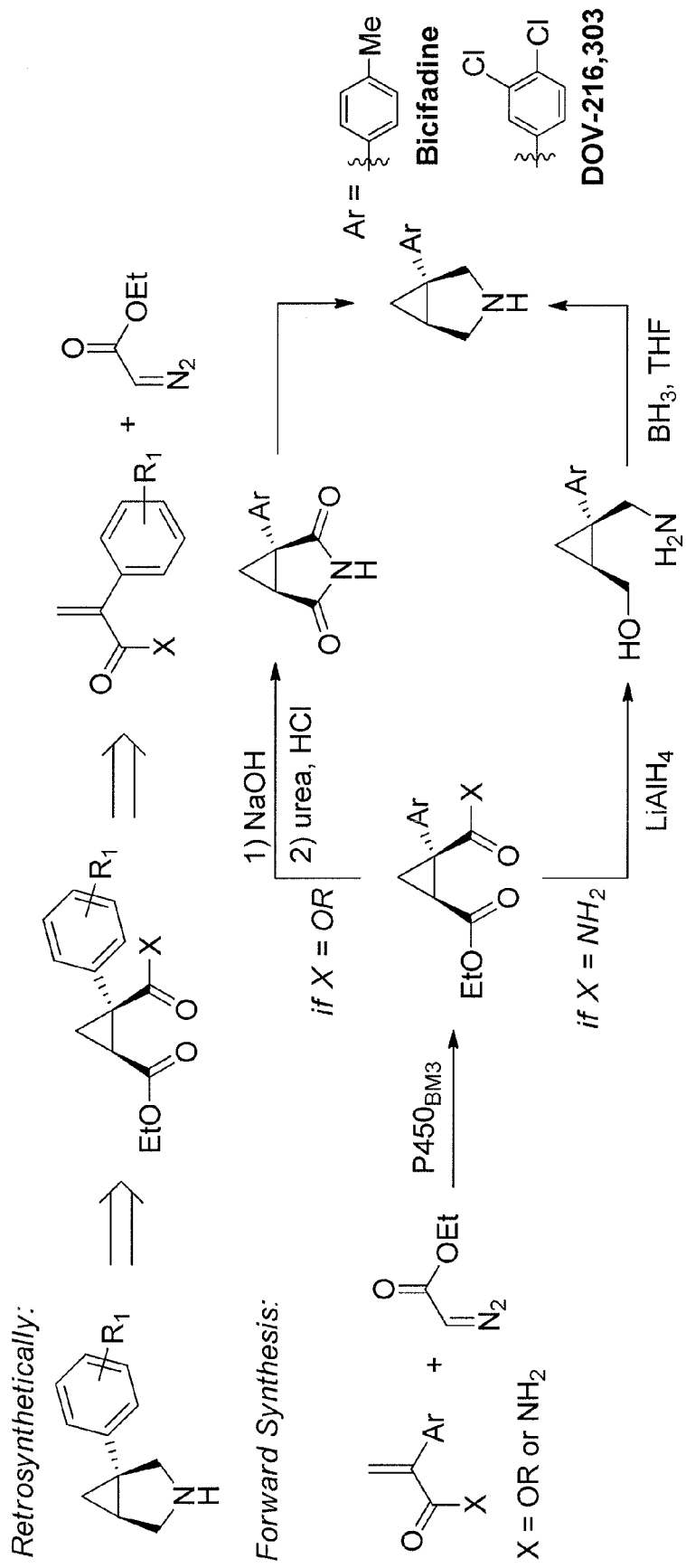
FIG. 40 illustrates the proposed synthesis of bicifadine, DOV-216,303 and derivatives using P450-catalyzed cyclopropanation.

The preceding examples demonstrate that aryl substitution and alpha substitution on styrene are well tolerated by P450 cyclopropanation. Thus, the method described herein may also be used to prepare aryl and amide derivatives of levomilnacipran as well as other drugs with similar chemical structure, such as bicifadine and DOV-216,303 (FIG. 40). For instance, bicifadine and DOV-216,303 can both be prepared using alpha-styrenyl amides and esters similar to the substrates shown herein. Again, cyclopropanation constructs both stereocenters and subsequent functional group manipulation and cyclization would yield bicifadine or DOV-216,303.

Materials and Methods

Procedure for Reactions with Isolated Enzymes:

Small-scale reactions (400 µL) were conducted in 2 mL crimp vials (Agilent Technologies, San Diego, Calif.). P450 solution (60 µL, 67 µM) was added to the vial before crimp sealing with a silicone septum. A solution of $Na_2S_2O_4$ (12.5 mM) in phosphate buffer (0.1 M, pH=8.0) was prepared and sealed in a larger crimp-sealed vial and degassed by bubbling argon through the solution for 5 min. In the meantime, the headspace of the 2 mL reaction vial with the protein solution was made anaerobic by flushing argon over the vial headspace (with no bubbling). When multiple reactions were conducted in parallel, up to 8 reaction vials were degassed in series via cannulae. The buffer/reductant solution (320 µL) was syringed into the reaction vial, while under argon. A 40× styrene solution in EtOH (10 µL, 400 mM) was added to the reaction vial via a glass syringe followed by a 40×EDA solution in EtOH (10 µL, 400 mM). The reactions were shaken on a shake plate at 350 rpm for 16-20 h. The final concentrations of the reagents were typically: 10 mM styrene, 8.5 mM EDA, 10 mM $Na_2S_2O_4$, 10 µM protein. The reaction was quenched by adding 30 µL HCl (3M) via syringe to the sealed reaction vial. The vials were opened and 20 µL internal standard (20 mM 2-phenylethanol in EtOH) was added followed by 1 mL cyclohexane. This mixture was transferred to an eppendorf tube which was vortexed and centrifuged (13,000×g, 1 min). The top organic layer was dried over an anhydrous sodium sulfate plug and analyzed for yield and enantioselectivity.

Procedure for Whole Cell Reactions:

E. coli cells ($OD_{600}$=30, 425 µL) were made anaerobic by bubbling argon through the cell suspension in a crimped 2 mL vial. A degassed solution of glucose (50 µL, 200 mM) was added to the cells before adding EDA (12.5 µL of a 400 mM solution in EtOH) and olefin (12.5 µL of a 400 mM solution in EtOH). The final concentrations of the reagents were typically: 10 mM styrene, 8.5 mM EDA, and 20 mM glucose. The reactions were shaken at room temperature for 16-20 h and were worked up by adding 20 µL of the internal standard (20 mM 2-phenylethanol) and extracting with 1 mL cyclohexane. The organic layer was dried over $Na_2SO_4$ then analyzed for yield and enantioselectivity.

Figure 39:
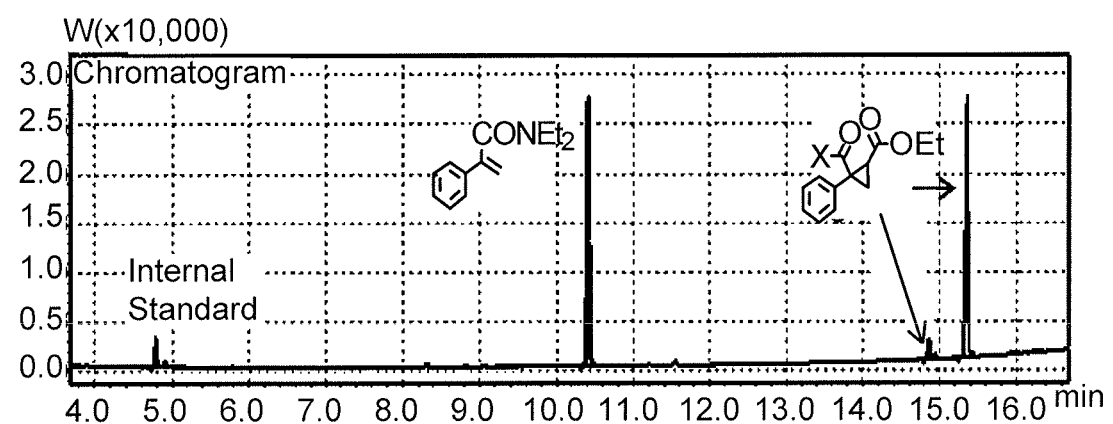
FIG. 39 illustrates the gas chromatography trace of reaction of 9b and EDA mediated by BM3-CIS-AxH, using Agilent cycloSil-B column, 30 m×0.25 um×0.32 mm, method: 90° C. (hold 2 min), 90-110 (6° C./min), 110-190 (40° C./min), and 190-280 (20° C./min). Internal standard at 4.8 min, starting material at 10.4 min, and product at 14.8 min (E-isomer) and 15.4 min (Z-isomer).

Determination of Yield, Enantioselectivity and Absolute Chirality:

Yield for purified enzyme and whole cell reactions were determined via gas chromatography using a flame ionization detector, relative to phenethyl alcohol as internal standard (FIG. 39). Gas chromatography was performed using Agilent cycloSil-B column, 30 m×0.25 µm×0.32 mm, method: 90° C. (hold 2 min), 90-110 (6° C./min), 110-190 (40° C./min), and 190-280 (20° C./min): internal standard at 4.8 min, starting material at 10.4 min, and product at 14.8 min (E-isomer) and 15.4 min (Z-isomer). Independently synthesized product 10b was used to generate a GC calibration curve. Identity of the product was confirmed by proton NMR and relative stereochemistry of the major diastereomer was determined by Nuclear Overhauser effect spectroscopy (NOESY). Enantioselectivity was established by chiral HPLC (on ChiralPak AS column, eluting with 4% IPA/supercritical $CO_2$), using a racemic sample of 10b prepared from 9b, EDA, and hemin as reference. The absolute stereochemistry of 10b was established by polarimetry after reduction of 10b to 8 using $LiBH_4$. Comparison of the optical rotation of product to published specific rotation of 8 (Alliot, J. et al., Chem. Commun. 48, 8111-8113 (2012)) allowed assignment of stereocenters in position 1 and 2 (FIG. 38) as 1S, 2R, in agreement with levomilnacipran.

Amino Acid Sequences:

BM3-CIS contains the following mutations from wild type: V78A F87V P142S T175I A184V S226R H236Q E252G T268A A290V L353V I366V E442K. P411-CIS contains BM3-CIS and Cys to Ser at position 400 of BM3. BM3-CIS-AxX (where X=H, D, A, M, etc.) mutants contains Cys to X mutation at position 400 of BM3. The complete $P450_{BM3}$ sequence is set forth in SEQ ID NO:1.

Example 6

Enzymatic Synthesis of Pyrethroid and Pyrethrin Insecticides

This example illustrates the synthesis of ethyl chrysanthemate using the cytochrome P450 catalysts of the present invention. The resulting ethyl chrysanthemate can be converted chemically or enzymatically to pyrethroid and pyrethrin insecticides.

Figure 41:
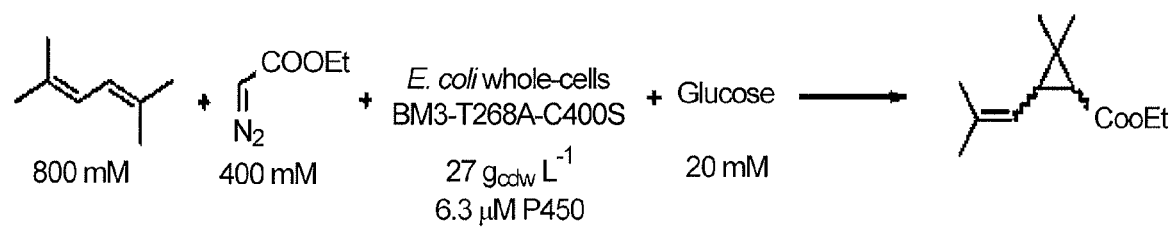
FIG. 41 illustrates that resting E. coli cells (425 μL) were purged with argon, before adding glucose (50 μL), 2,5-dimethyl-2,4-hexadiene (12.5 μL), and EDA (12.5 μL). The reaction was carried out in nitrogen free M9 minimal media with 5% methanol co-solvent for 24 hours at 298 K.

Cytochrome P450 derived cyclopropanation catalysts show a measurable promiscuous activity towards the synthesis of pyrethric acids from ethyl diazoacetate (EDA) and diolefins. This example illustrates that P450 catalysts can make ethyl chrysanthemate from EDA and 2,5-dimethyl-2,4-hexadiene. Intact E. coli cells expressing a double mutant of wild-type cytochrome $P450_{BM3}$(CYP102A1), BM3-T268A-C400S, displayed measurable activity for the synthesis of ethyl chrysanthemate as shown in FIG. 41. Purified BM3-T268A-C400S was also capable of making chrysanthemate in vitro.

Figure 42:
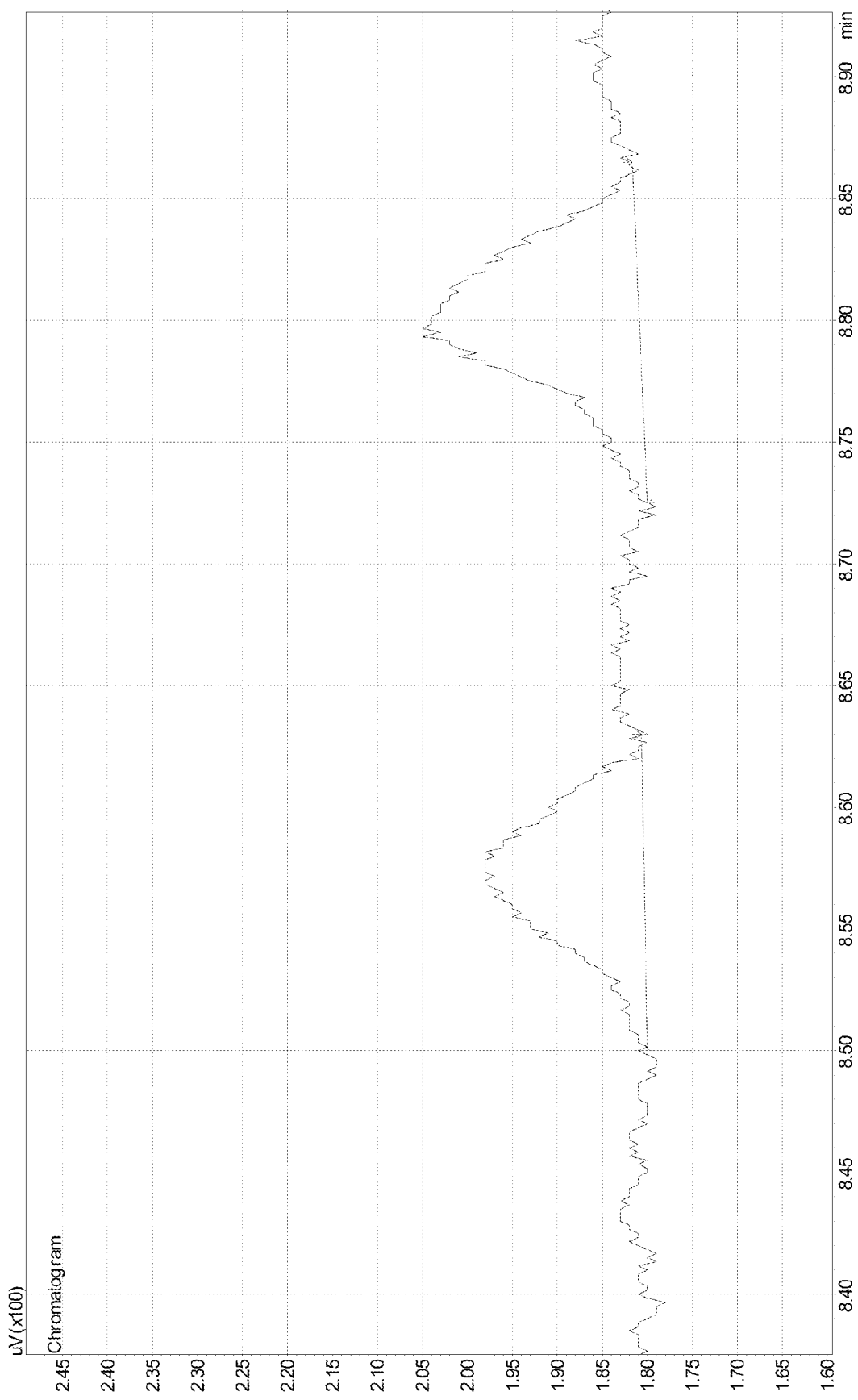
FIG. 42 illustrates a GC-FID chromatogram showing the two ethyl chrysanthemate diastereomers produced by BM3-T268A-C400S. Oven temperature: 90° C. for 2 min, then 2° C./min to 110° C., then 30° C./min to 230° C. HP-5 column (Agilent) 30 m×0.32 mm×0.25 μm.

The reaction solution was quenched with acid (final concentration of 1% HCL) and extracted with ethyl acetate. 2-Phenylethanol was used an internal standard for analysis by gas-chromatography. An authentic sample of ethyl chrysanthemate was purchased from Sigma-Aldrich. Enzymatic production of chrysanthemate was confirmed by GC-FID and GC-MS (FIGS. 42 and 43).

Figure 44:
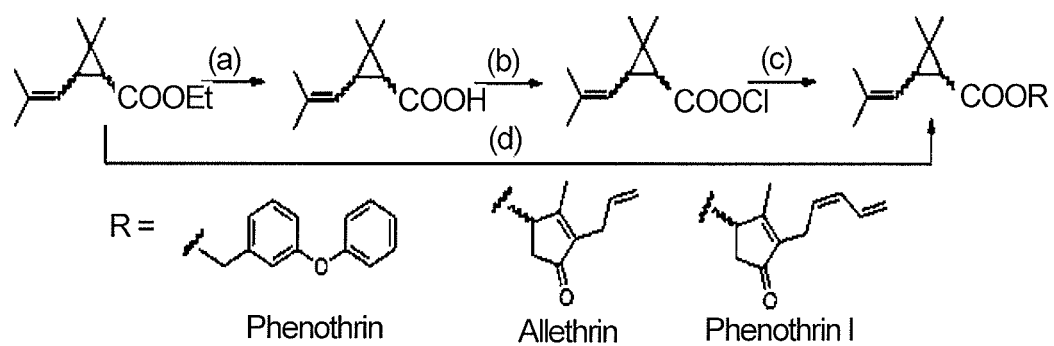
FIG. 44 illustrates the chemical or enzymatic conversion of ethyl chrysanthemate to pyretroid and pyrethrin insecticides. (a) Hydrolysis; (b) activation to the acid chloride; (c) coupling of the pyrethrolone alcohol (ROH) to the acid chloride; (d) transesterification.

The resulting ethyl chrysanthemate can be converted chemically or enzymatically to pyrethroid and pyrethrin insecticides as shown in FIG. 44. For example, a lipase enzyme can be used to catalyze the transesterification reaction shown in FIG. 44(d).

Example 7

Cytochrome P450-Cam Catalyzed Cyclopropanation of Styrene

This example illustrates that cytochrome P450-Cam (Cyp101A1, SEQ ID NO:25) and its cis-axial C357S variant (P411-Cam, wherein the variant has a C357S substitution at the axial position in SEQ ID NO:25) are capable of catalyzing the cyclopropanation of styrene using ethyl diazoacetate (EDA) as the carbene precursor, thereby resulting in ethyl 2-phenylcyclopropane-1-carboxylate, E. coli BL21 (DE3) cells expressing cytochrome P450-Cam and P411-Cam from plasmid pET22 were grown from glycerol stock overnight (37° C., 250 rpm) in 5 ml Hyperbroth medium (54.0 g/L Hyperbroth mix as purchased from Athena Enzyme Systems, 0.1 µg/L ampicillin). The pre-culture was used to inoculate 45 mL of M9Y medium (per 1 L: 31 g $Na_2HPO_4$, 15 g $KH_2PO_4$, 2.5 g NaCl, 5.0 g $NH_4Cl$, 0.24 g $MgSO_4$, 0.01 g $CaCl_2$, 1.5% yeast extract, 1 mL micronutrients (0.15 mM $(NH_4)_6Mo_7O_{24}$, 20.0 mM $H_3BO_3$, 1.5 mM $CoCl_2$, 0.5 mM $CuSO_4$, 4.0 mM $MnCl_2$, and 0.5 mM $ZnSO_4$), 0.1 mg mL$^{-1}$ ampicillin) in a 125 mL Erlenmeyer flask and this culture was incubated at 37° C., 250 rpm for 2 h and 30 min. At $OD_{600}$~1.2, the cultures were cooled to 25° C. and the shaking was reduced to 160 rpm before inducing with IPTG (0.25 mM) and δ-aminolevulinic acid (0.25 mM). Cultures were harvested after 20 h and resuspended ($OD_{600}$=30) in nitrogen-free M9 medium (per 1 L: 31 g $Na_2HPO_4$, 15 g $KH_2PO_4$, 2.5 g NaCl, 0.24 g $MgSO_4$, 0.01 g $CaCl_2$, 1 mL micronutrients (0.15 mM $(NH_4)_6Mo_7O_{24}$, 20.0 mM $H_3BO_3$, 1.5 mM $CoCl_2$, 0.5 mM $CuSO_4$, 4.0 mM $MnCl_2$, and 0.5 mM $ZnSO_4$)). The micronutrient solution contains 0.15 mM $(NH_4)_6Mo_7O_{24}$, 20.0 mM $H_3BO_3$, 1.5 mM $CoCl_2$, 0.5 mM $CuSO_4$, 4.0 mM $MnCl_2$, and 0.5 mM $ZnSO_4$. Aliquots of the cell suspension were used for determination of the cell dry weight (2 mL) and P450 (or P411) expression level (4 mL).

Prior the styrene cyclopropanation using ethyl diazoacetate as the carbene precursor, the cells at specified cell density (see, Table 49) were made anaerobic by bubbling argon through the cell suspension in a crimped 2 mL vial. A degassed solution of glucose (50 µL, 20 mM) was added to the cells before adding EDA (12.5 µL of a 400 mM solution in MeOH) and styrene (12.5 µL, of a 1.2 M solution in MeOH). The reactions were shaken at room temperature for 16 h and were worked up by adding 204 of the internal standard (20 mM 2-phenylethanol) and extracting with 1 mL cyclohexane. The organic layer was analyzed by chiral phase GC.

Gas chromatography (GC) analyses were carried out using a Shimadzu GC-17A gas chromatograph, a FID detector, and an Agilent J&W cyclosil-B column (30 m×0.25 mm, 0.25 µm film) and 2-phenylethanol as an internal standard. Injector temperature=300° C., oven temperature=130° C. for 30 min, pressure=175 kPa. Elution time: cis-cyclopropanes [19.7 min (2R,1S) and 21.0 min (2S,1R)], trans-cyclopropanes [25.8 min (2R,1R) and 26.4 min (2S,1S)]. The ethyl 2-phenylcyclopropane-1-carboxylate product standard for the reaction of ethyl diazoacetate (EDA) with styrene was prepared as reported (A. Penoni et al., Eur. J. Inorg. Chem. 2003, 1452 (2003)). These standards and enzyme-prepared cyclopropanes demonstrated identical retention times in gas chromatograms when co-injected, confirming product identity. Absolute stereoconfiguration of cyclopropane enantiomers was determined by measuring optical rotation of purified cyclopropane products from preparative bioconversion reactions using enantioselective BM3 variants and referenced to values taken from reference (N. Watanabe et al., Heterocycles 42, 537 (1996)).

The cytochrome P450 concentration was determined from ferrous CO binding difference spectra of lysate using extinction coefficients of $\epsilon_{450\text{-}490}$=91 mM$^{-1}$ cm$^{-1}$ for cysteine-ligated P450-Cam (T. Omura, R. Sato, J. Biol. Chem. 239, 2370 (1964)) and $\epsilon_{411\text{-}490}$=103 mM$^{-1}$ cm$^{-1}$ for serine ligated P411-Cam (K. P. Vatsis et al., J. Inorg. Biochem. 91, 542 (2002)).

Results are shown in Table 49 and demonstrate that both P450-Cam and P411-Cam catalyze cyclopropanation of styrene with EDA.

TABLE 49

P450-Cam and P411-Cam catalyzed cyclopropanation of styrene

| Enzyme | $c_{(styrene)}$ [mM] | $c_{(EDA)}$ [mM] | $c_{(P450\ or\ P411)}$ [µM] | $c_{(cells)}$ [g/L] | $c_{(product)}$ [mM] | Yield [%] | TTN | Cis:Trans | ee$_{cis}$ [%] | ee$_{trans}$ [%] |
|---|---|---|---|---|---|---|---|---|---|---|
| P450-Cam | 20 | 8.5 | 9.6 | 5.4 | 4.8 | 56 | 480 | 82:18 | 43% | 0 |
| P411-Cam | 20 | 8.5 | 1.0 | 8 | 2.4 | 28 | 2400 | 13:87 | <5% | <5% |

Example 8

Cyclopropanation by Axial Mutants of P450-BM3

This example illustrates that cytochrome variants of P450-BM3 containing mutations at position 400, the axial heme coordination site, from Cys to Ala, Asp, His, Lys, Asn, Met, Thr, or Tyr, are capable of catalyzing the cyclopranation of styrene using ethyl diazoacetate (EDA) as the carbene precursor, resulting in ethyl 2-phenylcyclopropane-1-carboxylate. The convention "AxX", wherein X is the single letter amino acid code of the amino acid at the axial position, can be used to describe this series of enzymes.

P450 were used as isolated and purified proteins. One liter $TB_{amp}$ was inoculated with an overnight culture (25 mL, $TB_{amp}$) of recombinant E. coli BL21 cells harboring pET22 plasmid encoding the His6 (SEQ ID NO:74) tagged P450 variants under the control of the tac promoter. The cultures were shaken at 200 rpm at 37° C. for roughly 3.5 h or until an optical of density of 1.2-1.8 was reached. The temperature was reduced to 25° C. and the shake rate was reduced to 180 rpm for 20 min, then the cultures were induced by adding IPTG and aminolevulinic acid to a final concentration of 0.5 mM. The cultures were allowed to continue for another 20 hours at this temperature. Cells were harvested by centrifugation (4° C., 15 min, 3,000×g), and the cell pellet was stored at −20° C. for at least 2 h.

For the purification of His6 (SEQ ID NO:74) tagged P450s, the thawed cell pellet was resuspended in Ni-NTA buffer A (25 mM Tris.HCl, 200 mM NaCl, 25 mM imidazole, pH 8.0, 0.5 mL/gcw) and lysed by sonication (2×1 min, output control 5, 50% duty cycle). The lysate was centrifuged at 27,000×g for 20 min at 4° C. to remove cell debris. The collected supernatant was first subjected to a Ni-NTA chromatography step using a Ni Sepharose column (HisTrap-HP, GE healthcare, Piscataway, N.J.). The P450 was eluted from the Ni Sepharose column using 25 mM Tris.HCl, 200 mM NaCl, 300 mM imidazole, pH 8.0. Ni-purified protein was buffer exchanged into 0.1 M phosphate buffer (pH=8.0) using a 30 kDa molecular weight cut-off centrifugal filter. Protein concentrations were determined by CO-assay as described above. For storage, proteins were portioned into 300 uL aliquots and stored at −80° C.

Reactions (400 μL) were conducted in 2 mL crimp vials (Agilent Technologies, San Diego, Calif.). P450 solution (80 μL, 100 μM) was added to the vial with a small stir bar before crimp sealing with a silicone septum. Phosphate buffer (260 μL, 0.1 M, pH=8.0) and 40 μL of a solution of the reductant (100 mM Na$_2$S$_2$O$_4$) were combined in a larger crimp-sealed vial and degassed by bubbling argon through the solution for at least 5 min. In the meantime, the headspace of the 2 mL reaction vial with the P450 solution was made anaerobic by flushing argon over the protein solution (with no bubbling). When multiple reactions were conducted in parallel, up to 8 reaction vials were degassed in series via cannulae. The buffer/reductant solution (300 μL) was syringed into the reaction vial, while under argon. The gas lines were disconnected from the reaction vial before placing the vials on a plate stirrer. A styrene solution in MeOH (10 pt, 800 mM) was added to the reaction vial via a glass syringe, and left to stir for about 30 s. A EDA solution in MeOH was then added (10 μL, 340 mM) and the reaction was left shaking for 16 h at room temperature. The final concentrations of the reagents were: 20 mM styrene, 8.5 mM EDA, 10 mM Na$_2$S$_2$O$_4$, 20 μM P450.

After 16 h, the vials were opened and 20 μL internal standard (20 mM 2-phenylethanol in MeOH) was added followed by 1 mL cyclohexane. This mixture was transferred to a 1.8 mL eppendorf tube which was vortexed and centrifuged (16,000×g, 1 min). The top organic layer was analyzed by chiral phase GC.

Gas chromatography (GC) analyses were carried out using a Shimadzu GC-17A gas chromatograph, a FID detector, and an Agilent J&W cyclosil-B column (30 m×0.25 mm, 0.25 μm film) and 2-phenylethanol as an internal standard. Injector temperature=300° C., oven temperature=130° C. for 30 min, pressure=175 kPa. Elution time: cis-cyclopropanes [19.7 min (2R,1S) and 21.0 min (2S,1R)], trans-cyclopropanes [25.8 min (2R,1R) and 26.4 min (2S,1S)]. The ethyl 2-phenylcyclopropane-1-carboxylate product standard for the reaction of ethyl diazoacetate (EDA) with styrene was prepared as reported (A. Penoni et al., *Eur. J. Inorg. Chem.* 2003, 1452 (2003)). These standards and enzyme-prepared cyclopropanes demonstrated identical retention times in gas chromatograms when co-injected, confirming product identity. Absolute stereoconfiguration of cyclopropane enantiomers was determined by measuring optical rotation of purified cyclopropane products from preparative bioconversion reactions using enantioselective BM3 variants and referenced to values taken from reference (N. Watanabe et al., *Heterocycles* 42, 537 (1996)).

The cytochrome P450 concentration was determined from hemechrome assay of purified protein using extinction coefficients of $\epsilon_{418}$=196 mM$^{-1}$ cm$^{-1}$ for the hemechrome complex (J. E. Falk, *Porphyrins and Metalloporphyrins*, Elsevier: Amsterdam, 1975. p 801-807).

Results are shown in Table 50 and demonstrate that axial mutants are active cyclopropanation catalysts.

TABLE 50

Cyclopropanation of styrene catalyzed by P450-BM3 axial mutants (5 uM)

| Enzyme name | Backbone | AA at position 400 | $c_{(styrene)}$ [mM] | $c_{(EDA)}$ [mM] | $c_{(product)}$ [mM] | Yield [%] | TTN | Cis:Trans | SEQ ID NO: |
|---|---|---|---|---|---|---|---|---|---|
| WT-AxA (heme) | WT | Ala | 20 | 8.5 | 3.9 | 56 | 780 | 12:88 | 50 |
| WT-AxD (heme) | WT | Asp | 20 | 8.5 | 3.4 | 28 | 670 | 13:87 | 51 |
| WT-AxH (heme) | WT | His | 20 | 8.5 | 3.9 | 46 | 780 | 8:92 | 52 |
| WT-AxK (heme) | WT | Lys | 20 | 8.5 | 3.8 | 45 | 760 | 13:87 | 53 |
| WT-AxM (heme) | WT | Met | 20 | 8.5 | 3.3 | 39 | 650 | 11:89 | 54 |
| WT-AxN (heme) | WT | Asn | 20 | 8.5 | 4.3 | 51 | 870 | 13:87 | 55 |
| BM3-CIS-T438S-AxA | BM3-CIS-T438S | Ala | 20 | 8.5 | 2.8 | 33 | 560 | 10:90 | 56 |
| BM3-CIS-T438S-AxD | BM3-CIS-T438S | Asp | 20 | 8.5 | 2.2 | 26 | 430 | 16:84 | 57 |
| BM3-CIS-T438S-AxM | BM3-CIS-T438S | Met | 20 | 8.5 | 5.4 | 63 | 1070 | 69:31 | 58 |
| BM3-CIS-T438S-AxY | BM3-CIS-T438S | Tyr | 20 | 8.5 | 2.0 | 23 | 390 | 21:79 | 59 |
| BM3-CIS-T438S-AxT | BM3-CIS-T438S | Thr | 20 | 8.5 | 3.0 | 35 | 590 | 15:85 | 60 |

The term "(heme)" refers to a truncated variant of wild-type (WT) P450-BM3 comprising amino acids 1-463 of SEQ ID NO: 1 and the indicated point mutation at amino acid position 400, the axial heme coordination site.
The term "BM3-CIS-T438S" refers to a full-length variant of WT P450-BM3 comprising the following amino acid substitutions in SEQ ID NO: 1: V78A, F87V, P142S, T175I, A184V, S226R, H236Q, E252G, T268A, A290V, L353V, I366V, T438S, and E442K.

Example 9

Identification of Cys Axial Ligand in Cytochromes P450

This example illustrates how to identify the conserved cysteine residue in cytochrome P450 enzymes that serves as the heme axial ligand via sequence alignment.

The known cytochrome P450-BM3 axial ligand was used to identify the axial ligand in a new P450, CYP2D7 from *Homo sapiens*, GenBank accession number AAO49806.1. To identify the axial ligand in this enzyme, a protein alignment algorithm provided by the National Institute of Health's NCBI BLASTp suite, version 2.2.28+ (http://blast.ncbi.nlm.nih.gov/Blast.cgi; S. F. Altschul, et al. (1997), Nucleic Acids Res. 25:3389-3402; S. F. Altschul, et al. (2005) FEBS J. 272:5101-5109) was used using the following parameters: E value=10, word size=3, Matrix=Blosum62, and Gap opening=11 and gap extension=1, and conditional compositional score matrix adjustment. Upon entering the protein sequences for P450-BM3 (SEQ ID NO:1) as subject and CYP2D7 (SEQ ID NO:22) as query and requesting an alignment between the two sequences, BLASTp returned a proposed alignment that included the BM3 C400 site (FIG. 45A). On the last row of this alignment, a semi-conserved region including a cysteine was apparent. The cysteine on the lower subject line is BM3's C400 axial ligand. Accordingly, the C461 above in the query line can be identified as the axial ligand in the CYP2D7 protein.

As a second example, the known P450-BM3 axial ligand was used to identify the axial ligand in P450C27, a mitochondrial P450 from *Rattus norvegicus*, GenBank accession number AAB02287.1. Upon entering the protein sequences for P450-BM3 (SEQ ID NO:1) as subject and P450C27 (SEQ ID NO:23) as query into BLASTp and requesting an alignment between the two sequences using the parameters described above, a proposed alignment that included the BM3 C400 site (FIG. 45B) was returned.

On the second to last row of this alignment, a semi-conserved region including a cysteine was apparent. The cysteine on the lower subject line is BM3's C400 axial ligand. Accordingly, the C478 above in the query line can be identified as the axial ligand in the P450C27 protein.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A reaction mixture for producing a cyclopropanation product, the reaction mixture comprising an olefinic substrate, a carbene precursor, and a heme enzyme.

2. The reaction mixture of claim 1, wherein the cyclopropanation product is a compound according to Formula I:

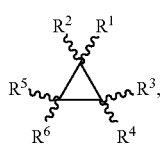

wherein:
R$^1$ is independently selected from the group consisting of H, optionally substituted C$_{1-18}$ alkyl, optionally substituted C$_{6-10}$ aryl, optionally substituted 6- to 10-membered heteroaryl, halo, cyano, C(O)OR$^{1a}$, C(O)N(R$^7$)$_2$, C(O)R$^8$, C(O)C(O)OR$^8$, and Si(R$^8$)$_3$;

R$^2$ is independently selected from the group consisting of H, optionally substituted C$_{1-18}$ alkyl, optionally substituted C$_{6-10}$ aryl, optionally substituted 6- to 10-membered heteroaryl, halo, cyano, C(O)OR$^{2a}$, C(O)N(R$^7$)$_2$, C(O)R$^8$, C(O)C(O)OR$^8$, and Si(R$^8$)$_3$;

wherein
R$^{1a}$ and R$^{2a}$ are independently selected from the group consisting of H, optionally substituted C$_{1-18}$ alkyl and -L-R$^c$, wherein each L is selected from the group consisting of a bond, —C(R$^L$)$_2$—, and —NR$^L$—C(R$^L$)$_2$—, each R$^L$ is independently selected from the group consisting of H, C$_{1-6}$ alkyl, halo, —CN, and —SO$_2$, and each R$^C$ is selected from the group consisting of optionally substituted C$_{6-10}$ aryl, optionally substituted 6- to 10-membered heteroraryl, and optionally substituted 6- to 10-membered heterocyclyl; and R$^3$, R$^4$, R$^5$, and R$^6$ are independently selected from the group consisting of H, C$_{1-18}$ alkyl, C$_{2-18}$ alkenyl, C$_{2-18}$ alkynyl, optionally substituted C$_{6-10}$ aryl, optionally substituted C$_1$-C$_6$ alkoxy, halo, hydroxy, cyano, C(O)N(R$^7$)$_2$, NR$^7$C(O)R$^8$, C(O)R$^8$, C(O)OR$^8$, and N(R$^9$)$_2$, wherein
each R$^7$ and R$^8$ is independently selected from the group consisting of H, optionally substituted C$_{1-12}$ alkyl, optionally substituted C$_{2-12}$ alkenyl, and optionally substituted C$_{6-10}$ aryl; and each R$^9$ is independently selected from the group consisting of H, optionally substituted C$_{6-10}$ aryl, and optionally substituted 6- to 10-membered heteroaryl, or two R$^9$ moieties, together with the nitrogen atom to which they are attached, can form 6- to 18-membered heterocyclyl;

or R$^3$ forms an optionally substituted 3- to 18-membered ring with R$^4$;

or R$^5$ forms an optionally substituted 3- to 18-membered ring with R$^6$;

or R$^3$ or R$^4$ forms a double bond with R$^5$ or R$^6$;

or R$^3$ or R$^4$ forms an optionally substituted 5- to 6-membered ring with R$^5$ or R$^6$.

3. The reaction mixture of claim 2, wherein:
R$^1$ is C(O)O-LR$^c$;
R$^2$ is selected from the group consisting of H and optionally substituted C$_{6-10}$ aryl; and
R$^3$, R$^4$, R$^5$, and R$^6$ are independently selected from the group consisting of H, optionally substituted C$_{1-6}$ alkyl, optionally substituted C$_{2-6}$ alkenyl, optionally substituted C$_{2-6}$ alkynyl, optionally substituted C$_{6-10}$ aryl and halo,
or R$^3$ forms an optionally substituted 3- to 18-membered ring with R$^4$;
or R$^5$ forms an optionally substituted 3- to 18-membered ring with R$^6$.

4. The reaction mixture of claim 2, wherein the cyclopropanation product is a compound according to Formula II:

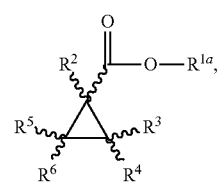

wherein R$^{1a}$ is C$_{1-6}$ alkyl and R$^2$ is selected from the group consisting of H and optionally substituted C$_{6-10}$ aryl.

5. The reaction mixture of claim 4, wherein the cyclopropanation product is selected from the group consisting of:

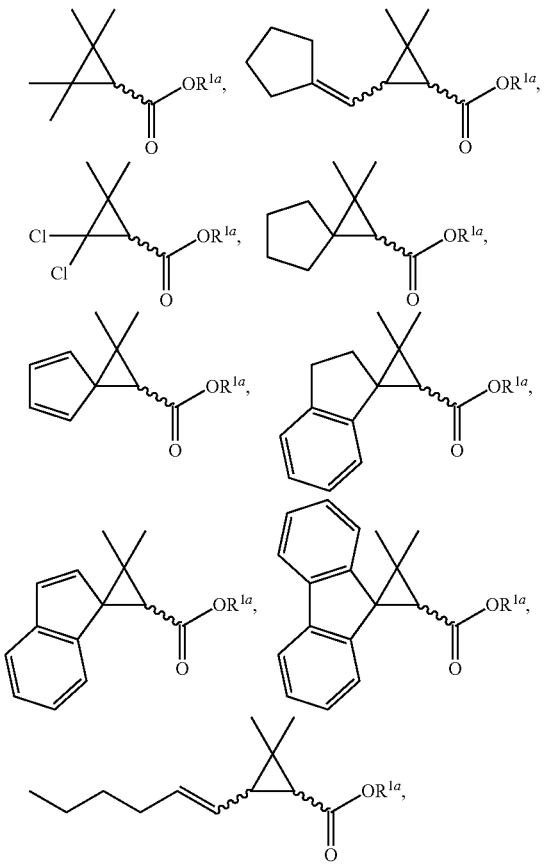

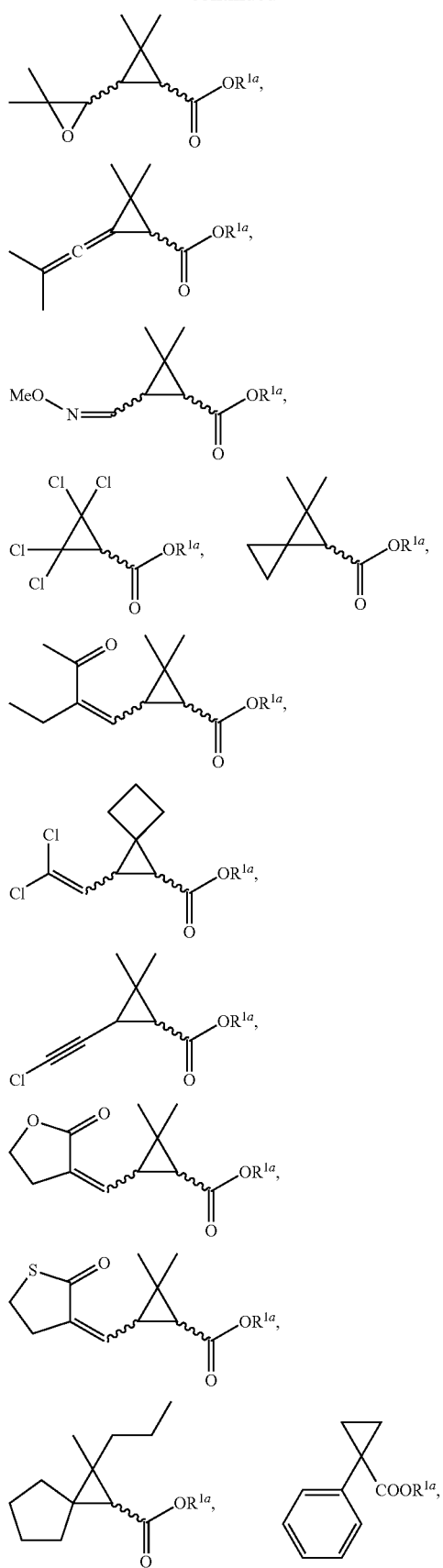
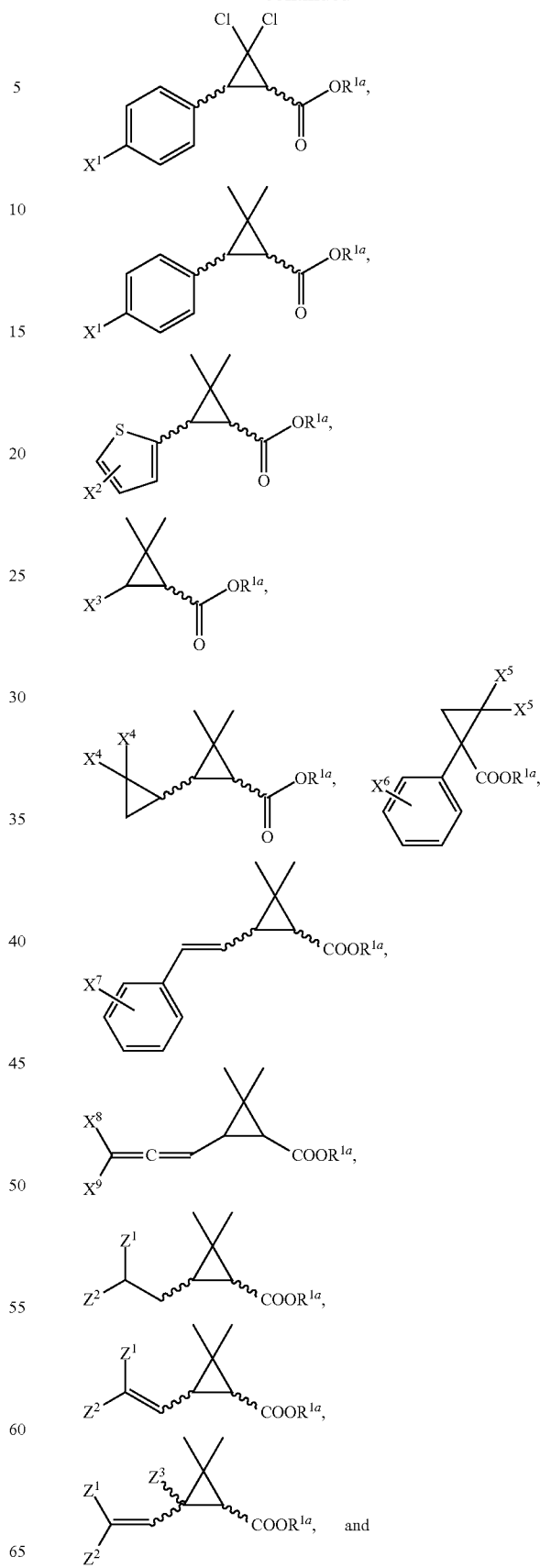

-continued

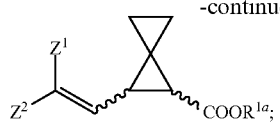

wherein:
X$^1$ is selected from the group consisting of H, optionally substituted C$_{1-6}$ alkyl, haloC$_{1-6}$ alkyl, optionally substituted C$_{1-6}$ alkoxy, optionally substituted C$_{1-6}$ alkylthio, C$_{1-6}$ alkylsilyl, halo, and cyano;
X$^2$ is selected from the group consisting of H, chloro, and methyl;
X$^3$ is selected from the group consisting of H, methyl, halo, and CN;
each X$^4$ is independently halo;
each X$^5$ is independently selected from the group consisting of methyl and halo,
X$^6$ is selected from the group consisting of halo, optionally substituted C$_{1-6}$ alkyl, and optionally substituted C$_{1-6}$ alkoxy;
X$^7$ is selected from the group consisting of H, methyl, and halo;
X$^8$ is selected from the group consisting of H, halo, and optionally substituted C$_{1-6}$ alkyl;
X$^9$ is selected from the group consisting of H, halo, optionally substituted C$_{1-6}$ alkyl, C(O)O—(C$_{1-6}$ alkyl), C(O)—N(C$_{1-6}$ alkyl)$_2$, and cyano; and
Z$^1$, Z$^2$, and Z$^3$ are independently selected from the group consisting of H, halo, optionally substituted C$_{1-6}$ alkyl, and optionally substituted C$_{6-10}$ aryl; or
Z$^1$ and Z$^2$ are taken together to form an optionally substituted 5- to 6-membered cycloalkyl or heterocyclyl group.

6. The reaction mixture of claim 4, wherein the cyclopropanation product is an intermediate of a compound according to Formula III:

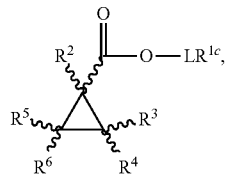

(III)

wherein:
L is selected from the group consisting of a bond, —C(R$^L$)$_2$—, and —NR$^L$—C(R$^L$)$_2$—,
each R$^L$ is independently selected from the group consisting of H, —CN, and —SO$_2$, and
R$^{1c}$ is selected from the group consisting of optionally substituted C$_{6-10}$ aryl, optionally substituted 6- to 10-membered heteroaryl, and optionally substituted 6- to 10-membered heterocyclyl.

7. The reaction mixture of claim 6, wherein the moiety L-R$^{1c}$ has a structure selected from the group consisting of:

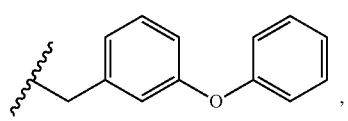

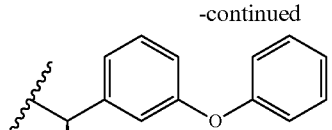

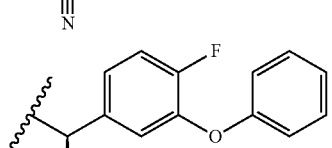

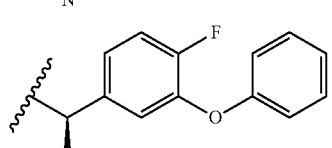

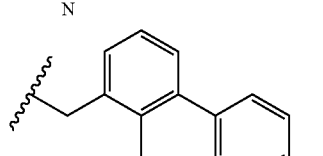

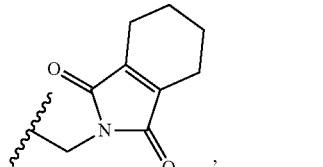

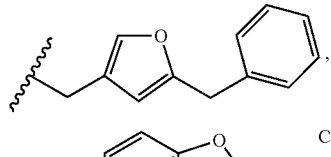

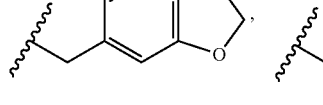

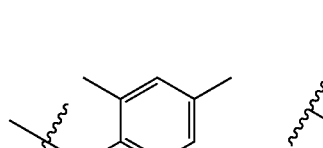

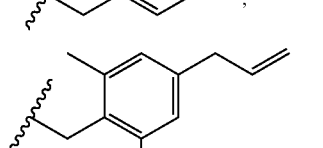

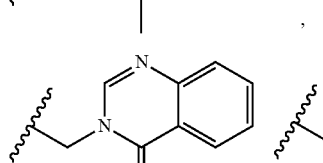

-continued

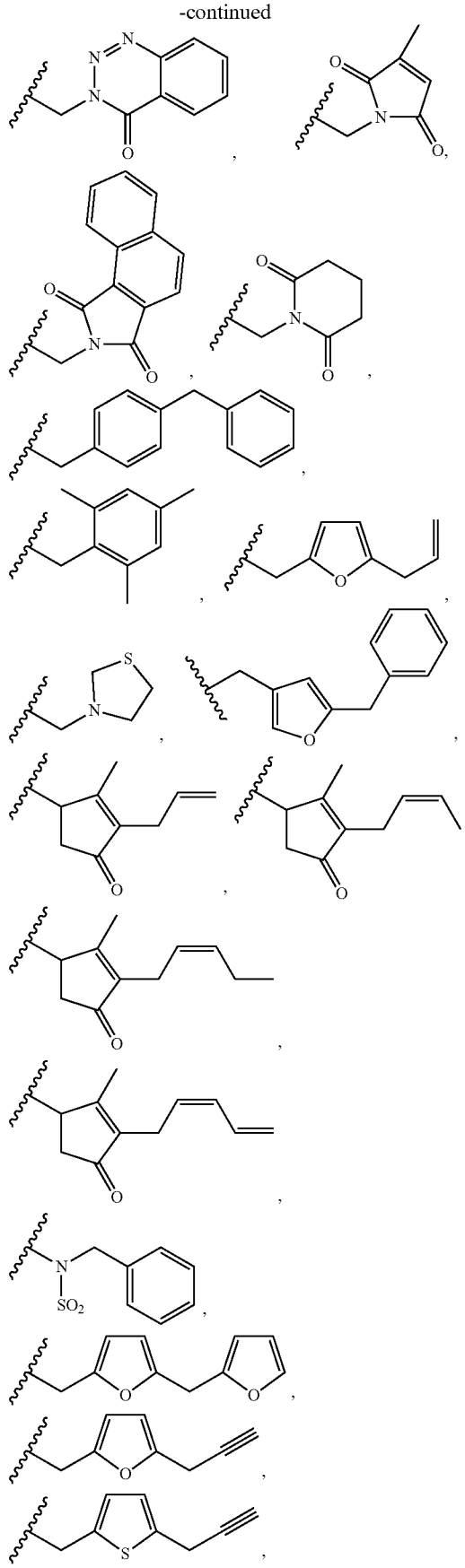

-continued

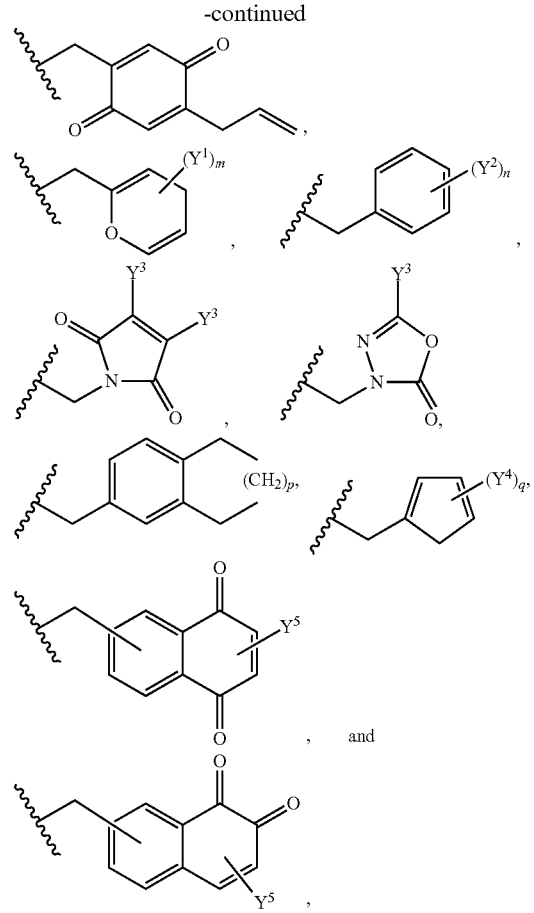

wherein:
each $Y^1$ is independently selected from the group consisting of optionally substituted $C_{1-6}$ alkyl, optionally substituted $C_{2-6}$ alkenyl, optionally substituted $C_{2-6}$ alkynyl, phenyl, and (phenyl)$C_{1-6}$ alkoxy;
each $Y^2$ is independently selected from the group consisting of halo, optionally substituted $C_{1-6}$ alkyl, optionally substituted $C_{2-6}$ alkenyl, optionally substituted $C_{1-6}$ alkoxy, and nitro;
each $Y^3$ is independently optionally substituted $C_{1-6}$ alkyl;
each $Y^4$ is independently selected from the group consisting of optionally substituted $C_{1-6}$ alkyl, optionally substituted $C_{2-6}$ alkenyl, optionally substituted $C_{2-6}$ alkynyl, $C_{6-10}$ aryl-$C_{1-6}$ alkyl, furfuryl, $C_{1-6}$ alkoxy, ($C_{2-6}$ alkenyl)oxy, $C_{1-12}$ acyl, and halo;
$Y^5$ is selected from the group consisting of optionally substituted $C_{1-6}$ alkyl, optionally substituted $C_{1-6}$ alkoxy, and halo,
the subscript m is an integer from 1 to 3,
the subscript n is an integer from 1 to 5,
the subscript p is an integer from 1 to 4,
the subscript q is an integer from 0 to 3,
and the wavy line at the left of the structure represents the point of connection between the moiety -L-$R^{16}$ and the rest of the compound according to Formula III.

8. The reaction mixture of claim 1, wherein the cyclopropanation product is a compound having a structure according to the formula:

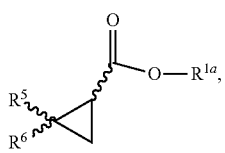

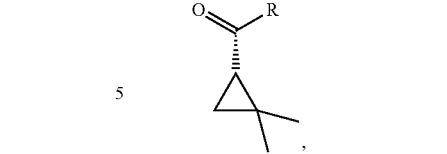

wherein:

$R^{1a}$ is optionally substituted $C_{1-6}$ alkyl, and $R^5$ and $R^6$ are independently selected from the group consisting of H, optionally substituted $C_{1-6}$ alkyl, optionally substituted $C_{6-10}$ aryl, $C(O)N(R^7)_2$, $C(O)OR^8$ and $NR^7C(O)R^8$, and wherein each $R^7$ and $R^8$ is independently selected from the group consisting of H, optionally substituted $C_{1-12}$ alkyl, optionally substituted $C_{2-12}$ alkenyl, and optionally substituted $C_{6-10}$ aryl.

9. The reaction mixture of claim 8, wherein the cyclopanation product has a structure selected from the group consisting of:

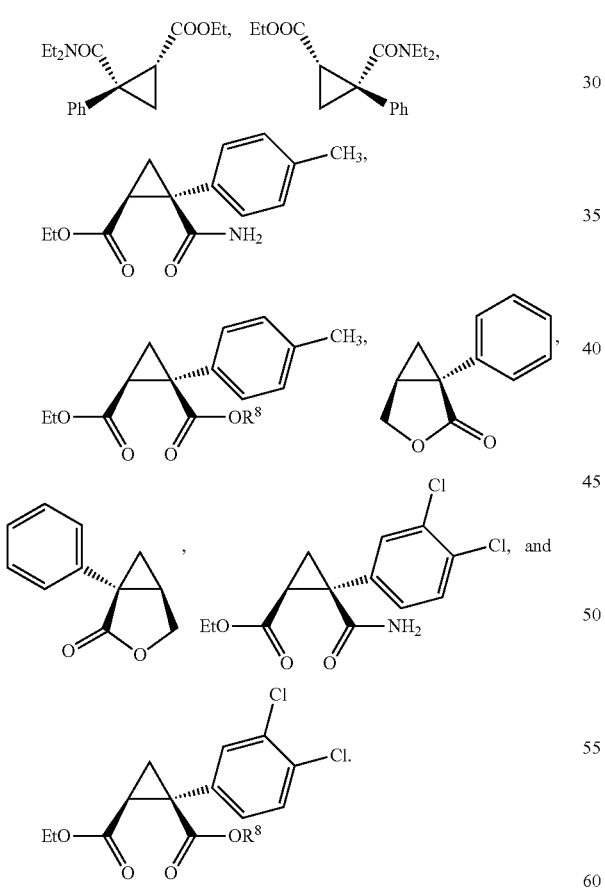

10. The reaction mixture of claim 1, wherein the cyclopanation product is an intermediate of milnacipran, levomilnacipran, cilastain, or sitafloxacin.

11. The reaction mixture of claim 10, wherein the intermediate of cilastain has a structure according to the formula:

wherein:

R is $OR^{1a}$ or $N(R^7)_2$, wherein $R^{1a}$ is selected from the group consisting of H, optionally substituted $C_{1-18}$ alkyl and $-L-R^C$, wherein each L is selected from the group consisting of a bond, $-C(R^L)_2-$, and $-NR^L-C(R^L)_2-$, each $R^L$ is independently selected from the group consisting of H, $C_{1-6}$ alkyl, halo, $-CN$, and $-SO_2$, and each $R^C$ is selected from the group consisting of optionally substituted $C_{6-10}$ aryl, optionally substituted 6- to 10-membered heteroraryl, and optionally substituted 6- to 10-membered heterocyclyl; and $R^7$ is selected from the group consisting of H, optionally substituted $C_{1-12}$ alkyl, optionally substituted $C_{2-12}$ alkenyl, and optionally substituted $C_{6-10}$ aryl.

12. The reaction mixture of claim 1, wherein the olefinic substrate is selected from the group consisting of an alkene, a cycloalkene, and an arylalkene.

13. The reaction mixture of claim 12, wherein the arylalkene is a styrene.

14. The reaction mixture of claim 13, wherein the styrene has the formula:

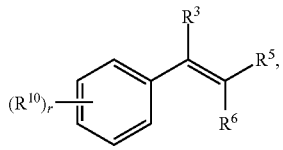

wherein:

$R^3$ is selected from the group consisting of H, optionally substituted $C_1$-$C_6$ alkyl, optionally substituted $C_1$-$C_6$ alkoxy, $C(O)N(R^7)_2$, $C(O)OR^8$, $N(R^9)_2$, halo, hydroxy, and cyano;

wherein each $R^7$ and $R^8$ is independently selected from the group consisting of H, optionally substituted $C_{1-12}$ alkyl, optionally substituted $C_{2-12}$ alkenyl, and optionally substituted $C_{6-10}$ aryl; and each $R^9$ is independently selected from the group consisting of H, optionally substituted $C_{6-10}$ aryl, and optionally substituted 6- to 10-membered heteroaryl, or two $R^9$ moieties, together with the nitrogen atom to which they are attached, can form 6- to 18-membered heterocyclyl;

$R^5$ and $R^6$ are independently selected from the group consisting of H, optionally substituted $C_{1-6}$ alkyl, and halo;

$R^{10}$ is selected from the group consisting of optionally substituted $C_1$-$C_6$ alkyl, optionally substituted $C_1$-$C_6$ alkoxy, halo, and haloalkyl; and the subscript r is an integer from 0 to 2.

15. The reaction mixture of claim 1, wherein the carbene precursor is a diazo reagent having a structure according to the formula:

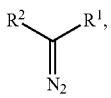

wherein:
R$^1$ is independently selected from the group consisting of H, optionally substituted C$_{1-18}$ alkyl, optionally substituted C$_{6-10}$ aryl, optionally substituted 6- to 10-membered heteroaryl, halo, cyano, C(O)OR$^{1a}$, C(O)N(R$^7$)$_2$, C(O)R$^8$, C(O)C(O)OR$^8$, and Si(R$^8$)$_3$; and
R$^2$ is independently selected from the group consisting of H, optionally substituted C$_{1-18}$ alkyl, optionally substituted C$_{6-10}$ aryl, optionally substituted 6- to 10-membered heteroaryl, halo, cyano, C(O)OR$^{2a}$, C(O)N(R$^7$)$_2$, C(O)R$^8$, C(O)C(O)OR$^8$, and Si(R$^8$)$_3$; wherein
  R$^{1a}$ and R$^{2a}$ are independently selected from the group consisting of H, optionally substituted C$_{1-18}$ alkyl and -L-R$^C$, wherein
  each L is selected from the group consisting of a bond, —C(R$^L$)$_2$—, and —NR$^L$—C(R$^L$)$_2$—,
  each R$^L$ is independently selected from the group consisting of H, C$_{1-6}$ alkyl, halo, —CN, and —SO$_2$, and
  each R$^C$ is selected from the group consisting of optionally substituted C$_{6-10}$ aryl, optionally substituted 6- to 10-membered heteroraryl, and optionally substituted 6- to 10-membered heterocyclyl; and
  each R$^7$ and R$^8$ is independently selected from the group consisting of H, optionally substituted C$_{1-12}$ alkyl, optionally substituted C$_{2-12}$ alkenyl, and optionally substituted C$_{6-10}$ aryl.

16. The reaction mixture of claim 15, wherein R$^1$ and R$^2$ are both C$_1$ alkyl.

17. The reaction mixture of claim 15, wherein the diazo reagent is selected from the group consisting of an α-diazoester, an α-diazoamide, an α-diazonitrile, an α-diazoketone, an α-diazoaldehyde, and an α-diazosilane.

18. The reaction mixture of claim 17, wherein the diazo reagent has a formula selected from the group consisting of:

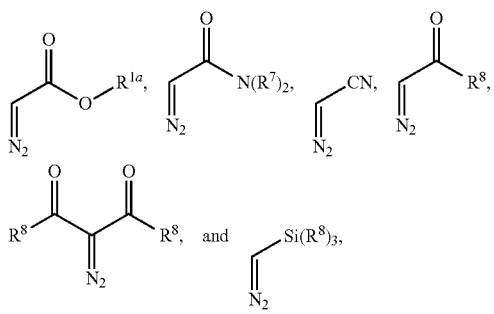

wherein
R$^{1a}$ is selected from the group consisting of H and optionally substituted C$_1$-C$_6$ alkyl; and
each R$^7$ and R$^8$ is independently selected from the group consisting of H, optionally substituted C$_{1-12}$ alkyl, optionally substituted C$_{2-12}$ alkenyl, and optionally substituted C$_{6-10}$ aryl.

19. The reaction mixture of claim 15, wherein the diazo reagent is selected from the group consisting of diazomethane, ethyl diazoacetate, and (trimethylsilyl)diazomethane.

20. The reaction mixture of claim 1, wherein the olefinic substrate and the carbene precursor are part of the same substrate.

21. The reaction mixture of claim 1, wherein the cyclopropanation product is produced in vitro.

22. The reaction mixture of claim 1, wherein the reaction mixture further comprises a reducing agent.

23. The reaction mixture of claim 1, wherein the heme enzyme is localized within a whole cell and the cyclopropanation product is produced in vivo.

24. The reaction mixture of claim 1, wherein the cyclopropanation product is produced under anaerobic conditions.

25. The reaction mixture of claim 1, wherein the heme enzyme is a variant thereof comprising a mutation at the axial position of the heme coordination site.

26. The reaction mixture of claim 1, wherein the heme enzyme is a cyclochrome P450 enzyme or a variant thereof.

27. The reaction mixture of claim 26, wherein the cyclochrome P450 enzyme is a P450 BM3 enzyme or a variant thereof.

28. The reaction mixture of claim 27, wherein the P450 BM3 enzyme comprises the amino acid sequence set forth in SEQ ID NO:1.

29. A method for producing a cyclopropanation product, the method comprising:
  (a) providing an olefinic substrate, a carbene precursor, and a heme enzyme; and
  (b) admixing the components of step (a) in a reaction for a time sufficient to produce a cyclopropanation product.

30. The method of claim 29, wherein the cyclopropanation product is a compound according to Formula I:

wherein:
R$^1$ is independently selected from the group consisting of H, optionally substituted C$_{1-18}$ alkyl, optionally substituted C$_{6-10}$ aryl, optionally substituted 6- to 10-membered heteroaryl, halo, cyano, C(O)OR$^{1a}$, C(O)N(R$^7$)$_2$, C(O)R$^8$, C(O)C(O)OR$^8$, and Si(R$^8$)$_3$;
R$^2$ is independently selected from the group consisting of H, optionally substituted C$_{1-18}$ alkyl, optionally substituted C$_{6-10}$ aryl, optionally substituted 6- to 10-membered heteroaryl, halo, cyano, C(O)OR$^{2a}$, C(O)N(R$^7$)$_2$, C(O)R$^8$, C(O)C(O)OR$^8$, and Si(R$^8$)$_3$;
wherein
  R$^{1a}$ and R$^{2a}$ are independently selected from the group consisting of H, optionally substituted C$_{1-18}$ alkyl and -L-R$^C$, wherein
  each L is selected from the group consisting of a bond, —C(R$^L$)$_2$—, and —NR$^L$—C(R$^L$)$_2$—, each $R^L$ is independently selected from the group consisting of H, $C_{1-6}$ alkyl, halo, —CN, and —SO$_2$, and each $R^C$ is selected from the group consisting of optionally substituted $C_{6-10}$ aryl, optionally substituted 6- to 10-membered heteroraryl, and optionally substituted 6- to 10-membered heterocyclyl; and $R^3$, $R^4$, $R^5$, and $R^6$ are independently selected from the group consisting of H, $C_{1-18}$ alkyl, $C_{2-18}$ alkenyl, $C_{2-18}$ alkynyl, optionally substituted $C_{6-10}$ aryl, optionally substituted $C_1$-$C_6$ alkoxy, halo, hydroxy, cyano, $C(O)N(R^7)_2$, $NR^7C(O)R^8$, $C(O)R^8$, $C(O)OR^8$, and $N(R^9)_2$, wherein
  each $R^7$ and $R^8$ is independently selected from the group consisting of H, optionally substituted $C_{1-12}$ alkyl, optionally substituted $C_{2-12}$ alkenyl, and optionally substituted $C_{6-10}$ aryl; and each $R^9$ is independently selected from the group consisting of H, optionally substituted $C_{6-10}$ aryl, and optionally substituted 6- to 10-membered heteroaryl, or two $R^9$ moieties, together with the nitrogen atom to which they are attached, can form 6- to 18-membered heterocyclyl;

or $R^3$ forms an optionally substituted 3- to 18-membered ring with $R^4$;

or $R^5$ forms an optionally substituted 3- to 18-membered ring with $R^6$;

or $R^3$ or $R^4$ forms a double bond with $R^5$ or $R^6$;

or $R^3$ or $R^4$ forms an optionally substituted 5- to 6-membered ring with $R^5$ or $R^6$.

* * * * *